(12) United States Patent
Baum et al.

(10) Patent No.: US 11,179,473 B2
(45) Date of Patent: Nov. 23, 2021

(54) NECTIN-4 ANTIBODY CONJUGATES AND USES THEREOF

(71) Applicant: Silverback Therapeutics, Inc., Seattle, WA (US)

(72) Inventors: Peter R. Baum, Seattle, WA (US); Robert Dubose, Seattle, WA (US); Valerie Odegard, Seattle, WA (US); Brenda Stevens, Seattle, WA (US); Philip Tan, Seattle, WA (US)

(73) Assignee: Silverback Therapeutics, Inc., Seattle, WA (US)

( * ) Notice: Subject to any disclaimer, the term of this patent is extended or adjusted under 35 U.S.C. 154(b) by 0 days.

(21) Appl. No.: 17/180,110

(22) Filed: Feb. 19, 2021

(65) Prior Publication Data

US 2021/0275683 A1 Sep. 9, 2021

Related U.S. Application Data

(60) Provisional application No. 62/979,755, filed on Feb. 21, 2020, provisional application No. 63/047,124, filed on Jul. 1, 2020, provisional application No. 63/092,714, filed on Oct. 16, 2020.

(51) Int. Cl.
| | |
|---|---|
| *A61K 47/68* | (2017.01) |
| *C07K 16/28* | (2006.01) |
| *A61K 31/55* | (2006.01) |
| *A61P 35/00* | (2006.01) |
| *A61K 47/65* | (2017.01) |
| *A61K 39/00* | (2006.01) |

(52) U.S. Cl.
CPC .......... *A61K 47/6803* (2017.08); *A61K 31/55* (2013.01); *A61K 47/65* (2017.08); *A61K 47/6849* (2017.08); *A61P 35/00* (2018.01); *C07K 16/2803* (2013.01); *C07K 16/2818* (2013.01); *C07K 16/2827* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,846,514 A | 12/1998 | Foster et al. |
| 6,043,238 A | 3/2000 | Cooper et al. |
| 6,334,997 B1 | 1/2002 | Foster et al. |
| 6,942,972 B2 | 9/2005 | Farooqui et al. |
| 7,387,271 B2 | 6/2008 | Noelle et al. |
| 7,923,560 B2 | 4/2011 | Wightman et al. |
| 8,236,318 B2 | 8/2012 | Keler et al. |
| 8,357,374 B2 | 1/2013 | Carson et al. |
| 8,729,088 B2 | 5/2014 | Carson et al. |
| 8,951,528 B2 | 2/2015 | Stoermer et al. |
| 9,556,167 B2 | 1/2017 | Spiegel et al. |
| 9,655,964 B2 | 5/2017 | Perez et al. |
| 9,670,272 B2 | 6/2017 | Nitsch et al. |
| 9,670,276 B2 | 6/2017 | Lacy et al. |
| 9,676,845 B2 | 6/2017 | Imhof-Jung et al. |
| 9,695,233 B2 | 7/2017 | Duerr et al. |
| 9,827,329 B2 | 11/2017 | Li |
| 9,856,319 B2 | 1/2018 | Ghayur et al. |
| 9,878,052 B2 | 1/2018 | Li |
| 9,914,776 B2 | 3/2018 | Ast et al. |
| 9,926,379 B2 | 3/2018 | Bruenker et al. |
| 9,943,416 B2 | 4/2018 | Arramon et al. |
| 9,944,573 B2 | 4/2018 | Radaelli et al. |
| 9,956,091 B2 | 5/2018 | de Villiers et al. |
| 10,035,853 B2 | 7/2018 | Arathoon et al. |
| 10,233,184 B2 | 3/2019 | Gao et al. |
| 10,239,862 B2 | 3/2019 | Coburn et al. |
| 10,253,003 B2 | 4/2019 | Last et al. |
| 10,428,045 B2 | 10/2019 | Coburn et al. |
| 10,442,790 B2 | 10/2019 | Coburn et al. |
| 10,472,420 B2 | 11/2019 | Stoermer et al. |
| 10,519,131 B2 | 12/2019 | Coburn et al. |
| 2004/0091491 A1 | 5/2004 | Kedl et al. |
| 2004/0141950 A1 | 7/2004 | Noelle et al. |
| 2004/0213797 A1 | 10/2004 | Bodmer et al. |
| 2006/0135459 A1 | 6/2006 | Epstein et al. |
| 2006/0142202 A1 | 6/2006 | Alkan et al. |
| 2007/0092940 A1 | 4/2007 | Eigenbrot et al. |
| 2008/0234251 A1 | 9/2008 | Doherty et al. |
| 2008/0306050 A1 | 12/2008 | Doherty et al. |
| 2009/0004194 A1 | 1/2009 | Kedl |

(Continued)

FOREIGN PATENT DOCUMENTS

| | | |
|---|---|---|
| CA | 3085424 A1 | 6/2019 |
| CN | 102753542 A | 10/2012 |

(Continued)

OTHER PUBLICATIONS

U.S. Appl. No. 16/620,437, filed Dec. 6, 2019.
U.S. Appl. No. 17/275,528, filed Mar. 11, 2021.
U.S. Appl. No. 17/275,542, filed Mar. 11, 2021.
Altschul et al., "Gapped BLAST and PSI-BLAST: a new generation of protein database search programs," *Nucleic Acids Res.* 25(17):3389-3402, 1997.
Alves, "Antibody conjugation and formulation," *Antibody Therapeutics* 2(1):33-39, 2019.
Anonymous "Silverback Therapeutics," URL: https://www.sec.gov/Archives/edgar/data/1671858/000119312520290236/d67046dsl.htm, download date Aug. 19, 2021. (279 pages).

(Continued)

*Primary Examiner* — Nelson B Moseley, II
(74) *Attorney, Agent, or Firm* — Seed IP Law Group LLP

(57) ABSTRACT

The present disclosure provides conjugates of anti-Nectin-4 antibodies or antigen binding fragments thereof to a myeloid cell agonist, compositions comprising the conjugates, and methods of treating cancer with the conjugates. The present disclosure also provides for anti-Nectin-4 antibodies or antigen binding fragments thereof and method for using the antibodies or antigen binding fragments thereof in treating cancer.

30 Claims, 15 Drawing Sheets

Specification includes a Sequence Listing.

(56) References Cited

U.S. PATENT DOCUMENTS

| | | |
|---|---|---|
| 2009/0035323 A1 | 2/2009 | Stoermer et al. |
| 2009/0047249 A1 | 2/2009 | Graupe et al. |
| 2009/0074711 A1 | 3/2009 | Glennie |
| 2009/0087440 A1 | 4/2009 | Vicari et al. |
| 2009/0123467 A1 | 5/2009 | Bedi et al. |
| 2010/0000295 A1 | 2/2010 | Howbert et al. |
| 2010/0143301 A1 | 6/2010 | Desai et al. |
| 2010/0291109 A1 | 11/2010 | Kedl |
| 2011/0033383 A1 | 2/2011 | Spencer et al. |
| 2011/0092485 A1 | 4/2011 | Howbert et al. |
| 2011/0098248 A1 | 4/2011 | Halcomb et al. |
| 2011/0117013 A1 | 5/2011 | Mack et al. |
| 2011/0118235 A1 | 5/2011 | Howbert et al. |
| 2011/0214206 A1 | 9/2011 | La Rosa et al. |
| 2011/0274653 A1 | 11/2011 | Banchereau et al. |
| 2011/0287038 A1 | 11/2011 | Slawin et al. |
| 2011/0301056 A1* | 12/2011 | Nakamura ............... A61P 35/00 506/9 |
| 2012/0039916 A1 | 2/2012 | Zurawski et al. |
| 2012/0078028 A1 | 3/2012 | Satpayev et al. |
| 2012/0082658 A1 | 4/2012 | Hershberg |
| 2012/0151504 A1 | 6/2012 | Schwalbe et al. |
| 2012/0219615 A1 | 8/2012 | Hershberg et al. |
| 2012/0231023 A1 | 9/2012 | Zurawski et al. |
| 2012/0263732 A1 | 10/2012 | Gladue et al. |
| 2013/0129729 A1 | 5/2013 | Kischel et al. |
| 2013/0171152 A1 | 7/2013 | Spriggs et al. |
| 2013/0251673 A1 | 9/2013 | Hartman et al. |
| 2013/0295091 A1 | 11/2013 | Esslinger et al. |
| 2013/0295110 A1 | 11/2013 | Binder et al. |
| 2013/0309256 A1 | 11/2013 | Lyon et al. |
| 2014/0045849 A1 | 2/2014 | McGowan et al. |
| 2014/0066432 A1 | 3/2014 | Howbert et al. |
| 2014/0073642 A1 | 3/2014 | McGowan et al. |
| 2014/0088085 A1 | 3/2014 | Burgess et al. |
| 2014/0154252 A1 | 6/2014 | Thompson et al. |
| 2014/0187501 A1 | 7/2014 | Bilodeau et al. |
| 2014/0205653 A1 | 7/2014 | Dubensky, Jr. et al. |
| 2014/0275167 A1 | 9/2014 | Hartman |
| 2014/0341976 A1 | 11/2014 | Dubensky, Jr. et al. |
| 2014/0350031 A1 | 11/2014 | Gowan et al. |
| 2015/0044279 A1 | 2/2015 | Miller et al. |
| 2015/0141625 A1 | 5/2015 | Stoermer et al. |
| 2015/0174268 A1 | 6/2015 | Li |
| 2015/0299194 A1 | 10/2015 | Hoves et al. |
| 2016/0015803 A1 | 1/2016 | Kedl |
| 2016/0108045 A1 | 4/2016 | Andres et al. |
| 2016/0129095 A1 | 5/2016 | Noelle et al. |
| 2016/0130358 A1 | 5/2016 | Bhakta et al. |
| 2016/0159904 A1 | 6/2016 | Yamazaki et al. |
| 2016/0168164 A1 | 6/2016 | McGowan et al. |
| 2016/0199510 A1 | 7/2016 | Mcdonald et al. |
| 2016/0250223 A1 | 9/2016 | Smith et al. |
| 2016/0257653 A1 | 9/2016 | Hoves et al. |
| 2016/0289341 A1 | 10/2016 | Wu |
| 2016/0289343 A1 | 10/2016 | Wu |
| 2016/0375148 A1 | 12/2016 | Ui |
| 2017/0014423 A1 | 1/2017 | Hoves et al. |
| 2017/0028079 A1 | 2/2017 | Li |
| 2017/0071944 A1 | 3/2017 | Geleziunas et al. |
| 2017/0088613 A1* | 3/2017 | Grogan ................... A61P 37/02 |
| 2017/0121421 A1 | 5/2017 | Cortez et al. |
| 2017/0145087 A1 | 5/2017 | Krause et al. |
| 2017/0145116 A1 | 5/2017 | Regula et al. |
| 2017/0151329 A1 | 6/2017 | Krause et al. |
| 2017/0158758 A1 | 6/2017 | Ramasubramanyan et al. |
| 2017/0158759 A1 | 6/2017 | Krause et al. |
| 2017/0158772 A1 | 6/2017 | Thompson et al. |
| 2017/0174786 A1 | 6/2017 | Bacac et al. |
| 2017/0190783 A1 | 7/2017 | Bacac et al. |
| 2017/0253670 A1 | 9/2017 | Klein et al. |
| 2017/0298139 A1 | 10/2017 | Thompson et al. |
| 2017/0342169 A1 | 11/2017 | Akamatsu et al. |
| 2017/0349669 A1 | 12/2017 | Imhof-Jung et al. |
| 2018/0065938 A1 | 3/2018 | Chin et al. |
| 2018/0079805 A1 | 3/2018 | Imhof-Jung et al. |
| 2018/0086755 A1 | 3/2018 | Chin et al. |
| 2018/0112004 A1 | 4/2018 | Liu et al. |
| 2018/0258048 A1 | 9/2018 | Coburn et al. |
| 2018/0263985 A1 | 9/2018 | Geleziunas et al. |
| 2019/0015516 A1 | 1/2019 | Jackson et al. |
| 2019/0016808 A1 | 1/2019 | Li |
| 2019/0055247 A1 | 2/2019 | He et al. |
| 2019/0076547 A1 | 3/2019 | Alonso et al. |
| 2019/0107537 A1 | 4/2019 | Chaudhary |
| 2019/0112380 A1 | 4/2019 | Chaudhary |
| 2019/0153471 A1 | 5/2019 | Paul et al. |
| 2019/0194713 A1 | 6/2019 | Mandell et al. |
| 2019/0336615 A1 | 11/2019 | Thompson et al. |
| 2020/0031798 A1 | 1/2020 | Coburn et al. |
| 2020/0101142 A1 | 4/2020 | Suri et al. |
| 2020/0113912 A1 | 4/2020 | Odegard et al. |
| 2020/0199242 A1 | 6/2020 | Thompson |
| 2020/0231670 A1 | 7/2020 | Morrison et al. |
| 2021/0077632 A1* | 3/2021 | Smith ................. A61K 47/6851 |
| 2021/0115109 A1 | 4/2021 | Thompson et al. |
| 2021/0139477 A1 | 5/2021 | Smith et al. |
| 2021/0139604 A1 | 5/2021 | Thompson et al. |
| 2021/0154317 A1 | 5/2021 | Thompson et al. |

FOREIGN PATENT DOCUMENTS

| | | |
|---|---|---|
| CN | 102781933 A | 11/2012 |
| CN | 103562186 A | 2/2014 |
| EP | 2436696 A1 | 4/2012 |
| EP | 2604625 A1 | 6/2013 |
| EP | 2787005 A1 | 10/2014 |
| EP | 2663580 B1 | 12/2016 |
| EP | 2817338 B1 | 7/2017 |
| EP | 2747781 B1 | 11/2017 |
| EP | 3589654 A1 | 1/2020 |
| EP | 3603671 A2 | 2/2020 |
| EP | 3635013 A1 | 4/2020 |
| WO | 00/76505 A1 | 12/2000 |
| WO | 03/094836 A2 | 11/2003 |
| WO | 2004/091658 A1 | 10/2004 |
| WO | 2005/065678 A1 | 7/2005 |
| WO | 2006/052900 A2 | 5/2006 |
| WO | 2007/005874 A2 | 1/2007 |
| WO | 2007/024612 A2 | 3/2007 |
| WO | 2009/018500 A1 | 2/2009 |
| WO | 2009/084659 A1 | 7/2009 |
| WO | 2011/012637 A2 | 2/2011 |
| WO | 2011/017070 A1 | 2/2011 |
| WO | 2011/022508 A2 | 2/2011 |
| WO | 2011/022509 A2 | 2/2011 |
| WO | 2011/090088 A1 | 7/2011 |
| WO | 2011/104381 A2 | 9/2011 |
| WO | 2011/147921 A1 | 12/2011 |
| WO | 2012/021834 A1 | 2/2012 |
| WO | 2012/078688 A2 | 6/2012 |
| WO | 2012/095412 A1 | 7/2012 |
| WO | 2012/097173 A2 | 7/2012 |
| WO | 2012/097177 A2 | 7/2012 |
| WO | 2012/122396 A1 | 9/2012 |
| WO | 2012/151199 A1 | 11/2012 |
| WO | 2013/093465 A2 | 6/2013 |
| WO | 2013/096835 A1 | 6/2013 |
| WO | 2013/173687 A1 | 11/2013 |
| WO | 2014/012479 A1 | 1/2014 |
| WO | 2014/023813 A1 | 2/2014 |
| WO | 2014/052828 A1 | 4/2014 |
| WO | 2014/056953 A1 | 4/2014 |
| WO | 2014/076221 A1 | 5/2014 |
| WO | 2014/122144 A1 | 8/2014 |
| WO | 2014/128189 A1 | 8/2014 |
| WO | 2014/172532 A2 | 10/2014 |
| WO | 2015/103987 A1 | 7/2015 |
| WO | 2015/103989 A1 | 7/2015 |
| WO | 2015/103990 A1 | 7/2015 |
| WO | 2015/108595 A1 | 7/2015 |
| WO | 2015/112749 A2 | 7/2015 |
| WO | 2015/162293 A1 | 10/2015 |
| WO | 2016/004875 A1 | 1/2016 |

(56) References Cited

FOREIGN PATENT DOCUMENTS

| | | |
|---|---|---|
| WO | 2016/004876 A1 | 1/2016 |
| WO | 2016/016299 A1 | 2/2016 |
| WO | 2016/036678 A1 | 3/2016 |
| WO | 2016/040856 A2 | 3/2016 |
| WO | 2016/064899 A1 | 4/2016 |
| WO | 2016/075670 A1 | 5/2016 |
| WO | 2016/096174 A1 | 6/2016 |
| WO | 2016/096778 A1 | 6/2016 |
| WO | 2016/100302 A2 | 6/2016 |
| WO | 2016/120305 A1 | 8/2016 |
| WO | 2016/142250 A1 | 9/2016 |
| WO | 2017/023779 A1 | 2/2017 |
| WO | 2017/024296 A1 | 2/2017 |
| WO | 2017/027645 A1 | 2/2017 |
| WO | 2017/027646 A1 | 2/2017 |
| WO | 2017/046112 A1 | 3/2017 |
| WO | 2017/072662 A1 | 5/2017 |
| WO | 2017/091745 A1 | 6/2017 |
| WO | 2017/093404 A1 | 6/2017 |
| WO | 2017/093406 A1 | 6/2017 |
| WO | 2017/100305 A2 | 6/2017 |
| WO | 2017/117269 A1 | 7/2017 |
| WO | 2017/118405 A1 | 7/2017 |
| WO | 2017/123657 A1 | 7/2017 |
| WO | 2017/123669 A1 | 7/2017 |
| WO | 2017/139623 A1 | 8/2017 |
| WO | 2017/147368 A1 | 8/2017 |
| WO | 2017/161349 A1 | 9/2017 |
| WO | 2017/190669 A1 | 11/2017 |
| WO | 2017/202703 A1 | 11/2017 |
| WO | 2017/202704 A1 | 11/2017 |
| WO | 2017/216054 A1 | 12/2017 |
| WO | 2018/002358 A1 | 1/2018 |
| WO | 2018/009466 A1 | 1/2018 |
| WO | 2018/009916 A1 | 1/2018 |
| WO | 2018/045204 A1 | 3/2018 |
| WO | 2018/060323 A1 | 4/2018 |
| WO | 2018/065360 A1 | 4/2018 |
| WO | 2018/098203 A1 | 5/2018 |
| WO | 2018/100558 A2 | 6/2018 |
| WO | 2018/102795 A2 | 6/2018 |
| WO | 2018/112108 A1 | 6/2018 |
| WO | 2018/119118 A1 | 6/2018 |
| WO | 2018/136412 A2 | 7/2018 |
| WO | 2018/138685 A2 | 8/2018 |
| WO | 2018/140831 A2 | 8/2018 |
| WO | 2018/144955 A1 | 8/2018 |
| WO | 2018/152453 A1 | 8/2018 |
| WO | 2018/156625 A1 | 8/2018 |
| WO | 2018/158398 A1 | 9/2018 |
| WO | 2018/170179 A1 | 9/2018 |
| WO | 2018/191746 A1 | 10/2018 |
| WO | 2018/198091 A1 | 11/2018 |
| WO | 2018/226578 A1 | 12/2018 |
| WO | 2018/227018 A1 | 12/2018 |
| WO | 2018/227023 A1 | 12/2018 |
| WO | 2019/067805 A1 | 4/2019 |
| WO | 2019/084060 A1 | 5/2019 |
| WO | 2019/099412 A1 | 5/2019 |
| WO | 2019/118884 A1 | 6/2019 |
| WO | 2019/215728 A1 | 11/2019 |
| WO | 2019/241315 A1 | 12/2019 |
| WO | 2020/047187 A1 | 3/2020 |
| WO | 2020/056008 A1 | 3/2020 |
| WO | 2020/056192 A1 | 3/2020 |
| WO | 2020/056194 A1 | 3/2020 |
| WO | 2020/056198 A2 | 3/2020 |
| WO | 2020/150702 A1 | 7/2020 |
| WO | 2020/190725 A1 | 9/2020 |
| WO | 2020/190731 A1 | 9/2020 |
| WO | 2020/190734 A1 | 9/2020 |
| WO | 2020/190760 A1 | 9/2020 |
| WO | 2020/190762 A1 | 9/2020 |
| WO | 2020/252254 A1 | 12/2020 |
| WO | 2020/252294 A1 | 12/2020 |
| WO | 2020/257407 A1 | 12/2020 |
| WO | 2021/007428 A2 | 1/2021 |
| WO | 2021/030665 A1 | 2/2021 |
| WO | 2021/067644 A1 | 4/2021 |

OTHER PUBLICATIONS

Berge et al., "Pharmaceutical Salts," *J. Pharm. Sci*, 66(1):1-19, Jan. 1977.
Bolt Biotherapeutics: "A First-in-human Study Using BDC-1001 in Advanced HER2-Expressing Solid Tumors," URL: https://clinicaltrials.gov/ct2/show/record/NCT04278144?term=NCT04278144 &draw=1 &rank=1, download date Jan. 12, 2021. (4 pages).
Capon et al., "Designing CD4 immunoadhesins for AIDS therapy," *Nature* 337:525-531, Feb. 1989.
Challita-Eid et al., "Enfortumab Vedotin Antibody-Drug Conjugate Targeting Nectin-4 Is a Highly Potent Therapeutic Agent in Multiple Preclinical Cancer Models," *Cancer Research* 76(10):3003-3013, Mar. 2016. (12 pages).
Chauvin et al., "TIGIT in cancer immunotherapy," *Journal for ImmunoTherapy of Cancer* 8:e000957, 2020. (7 pages).
Chothia et al., "Canonical Structures for the Hypervariable Regions of Immunoglobulins," *J Mol. Biol.* 796:901-917, 1987. (18 pages).
Co et al., "Chimeric and Humanized Antibodies With Specificity for the CD33 Antigen[1]," *The Journal of Immunology* 148(4):1149-1154, Feb. 1992.
Co et al., "Humanized antibodies for antiviral therapy," *Proc. Natl. Acad. Sci. USA* 88:2869-2873, Apr. 1991.
Database Caplus Chemical Abstracts Service, Columbus, Ohio, US; Database Accession No. 2017:1888322,Abstract of WO 2017202704, F. Hoffmann-La Roche AG, 2017. (19 pages).
Derycke et al., "Nectin 4 Overexpression in Ovarian Cancer Tissues and Serum: Potential Role as a Serum Biomarker," *Am J Clin Pathol.* 134(5):835-845, 2010 (NIH Public Access Author Manuscript, available in PMC Feb. 20, 2011). (17 pages).
Evans, "Synthesis of Radiolabelled Compounds," *Journal of Radioanalytical Chemistry* 64(1-2):9-32, 1981.
Extended European Search Report, dated Mar. 4, 2020, for European Application No. 18767012.0. (4 pages).
Extended European Search Report, dated Sep. 4, 2020, for European Application No. 18744145.6. (9 pages).
Fabre-Lafay et al., "Nectin-4 is a new histological and serological tumor associated marker for breast cancer," *BMC Cancer* 7:73, 2007. (16 pages).
Fedorak et al., "A novel colon-specific steroid prodrug enhances sodium chloride absorption in rat colitis," *Am. J. Physiol.* 269:G210-218, 1995.
Gadd et al., "Targeted Activation of Toll-Like Receptors: Conjugation of a Toll-Like Receptor 7 Agonist to a Monoclonal Antibody Maintains Antigen Binding and Specificity," *Bioconjugate Chemistry* 26:1743-1752, 2015.
Guiducci et al., "RNA recognition by human TLR8 can lead to autoimmune inflammation," *J. Exp. Med.* 210(13):2903-2919, 2013.
Hochhaus et al., "A Selective HPLC/RIA for Dexamethasone and its Prodrug Dexamethasone-21-sulphobenzoate Sodium in Biological Fluids," *Biomed. Chrom.* 6:283-286, 1992.
Honegger et al., "Yet Another Numbering Scheme for Immunoglobulin Variable Domains: An Automatic Modeling and Analysis Tool," *J. Mol. Biol.* 309:657-670, 2001.
International Search Report and Written Opinion, dated Jul. 3, 2018, for International Patent Application No. PCT/US2018/022510. (18 pages).
International Search Report and Written Opinion, dated Jul. 30, 2018, for International Patent Application No. PCT/US2018/015607. (16 pages).
International Search Report, dated Aug. 3, 2017, for International Patent Application No. PCT/CN2017/083031. (7pages).
Jain et al., "Current ADC Linker Chemistry," *Pharm Res* 32:3526-3540, 2015.
Jones et al., "Replacing the complementarity-determining regions in a human antibody with those from a mouse," *Nature* 321:522-525, May 1986.

(56) References Cited

OTHER PUBLICATIONS

Kabalka et al., "The Synthesis of Radiolabeled Compounds Via Organometallic Intermediates," *Tetrahedron* 45(21):6601-6621, 1989.

Kim et al., "High Cleavage Efficiency of a 2A Peptide Derived from Porcine Teschovirus-1 in Human Cell Lines, Zebrafish and Mice," *PLoS One* 6(4):e18556, Apr. 2011. (8 pages).

Larsen et al., "Prodrug forms for the sulfonamide group. I. Evaluation of N-acyl derivatives, N-sulfonylamidines, N-sulfonylsulfilimines and sulfonylureas as possible prodrug derivatives," *Int. J. Pharmaceutics* 37:87-95, 1987.

Larsen et al., "Prodrug forms for the sulfonamide group. II. Water-soluble amino acid derivatives of N-methylsulfonamides as possible prodrugs," *Int. J. Pharmaceutics* 47:103-110, 1988.

Lattanzio et al., "Membranous Nectin-4 expression is a risk factor for distant relapse of T1-T2, N0 luminal-A early breast cancer," *Oncogenesis* 3:e118; 2014. (7 pages).

Leone et al., "Targeting adenosine for cancer immunotherapy," *Journal for ImmunoTherapy of Cancer* 6(57):1-9, 2018.

Ma et al., "Expression and clinical significance of Nectin-4 in hepatocellular carcinoma," *OncoTargets and Therapy* 9:183-190, 2016.

Mark III et al., "Derivation of Therapeutically Active Humanized and Veneered Anti-CD18 Antibodies," in Metcalf et al. (eds.), *Cellular Adhesion: Molecular Definition to Therapeutic Potential*, Plenum Press, New York, New York, USA, 1994, pp. 291-312. (24 pages).

Mcleod et al., "A Glucocorticoid Prodrug Facilitates Normal Mucosal Function in Rat Colitis Without Adrenal Suppression," *Gastroenterol.* 106(2):405-413, Feb. 1994.

Metz et al., "SBT6290, A Systemically Administered NECTIN-4-Directed TLR8 Immunotac (TM) Therapeutic, is a Potent Human Myeloid Cell Agonist for the Treatment of NECTIN-4-Expressing Tumors," *Journal for Immunotherapy of Cancer* 8(Suppl 3):A1-A559:A427, 2020. (1 page).

Moyes et al., "Abstract 3271: A systemically administered, conditionally active TLR8 agonist for the treatment of HER2-expressing tumors," Cancer Research, Proceedings of the American Association for Cancer Research Annual Meeting 2019, URL: https://cancerres.aacrjournals.org/content/79/13_Supplement/3271, download date May 11, 2019. (4 pages).

M-Rabet et al., "Nectin-4: a new prognostic biomarker for efficient therapeutic targeting of primary and metastatic triple-negative breast cancer," *Annals of Oncology* 28(4):769-776, 2017.

Mullins et al., "Intratumoral immunotherapy with TLR7/8 agonist MEDI9197 modulates the tumor microenvironment leading to enhanced activity when combined with other immunotherapies," *Journal of ImmunoTherapy of Cancer* 7:244, 2019. (18 pages).

Nishii et al., "Systemic administration of a TLR7 agonist attenuates regulatory T cells by dendritic cell modification and overcomes resistance to PD-L1 blockade therapy" *Oncotarget* 9(17):13301-13312, 2018.

Nishiwada et al., "Nectin-4 expression contributes to tumor proliferation, angiogenesis and patient prognosis in human pancreatic cancer," *Journal of Experimental & Clinical Cancer Research* 34:30, 2015. (9 pages).

Notice of Allowance, dated Dec. 19, 2018, for U.S. Appl. No. 15/774,262, Coburn, "Benzazepine Compounds, Conjugates, and Uses Thereof," 12 pages.

Notice of Allowance, dated Jun. 14, 2019, for U.S. Appl. No. 15/973,506, Coburn, "Benzazepine Compounds, Conjugates, and Uses Thereof", 7 pages.

Notice of Allowance, dated May 13, 2019, for U.S. Appl. No. 16/274,132, Coburn, "Benzazepine Compounds, Conjugates, and Uses Thereof," 9 pages.

Notice of Allowance, dated May 13, 2019, for U.S. Appl. No. 16/274,130, Coburn, "Benzazepine Compounds, Conjugates, and Uses Thereof," 9 pages.

Notice of Allowance, dated Sep. 5, 2019, for U.S. Appl. No. 15/973,506, Coburn, "Benzazepine Compounds, Conjugates, and Uses Thereof", 7 pages.

Office Action, dated Dec. 6, 2018, for U.S. Appl. No. 15/973,506, Coburn, "Benzazepine Compounds, Conjugates, and Uses Thereof," 12 pages.

Office Action, dated Mar. 11, 2019, for U.S. Appl. No. 16/274,130, Coburn, "Benzazepine Compounds, Conjugates, and Uses Thereof," 14 pages.

Office Action, dated Mar. 11, 2019, for U.S. Appl. No. 16/274,132, Coburn, "Benzazepine Compounds, Conjugates, and Uses Thereof," 15 pages.

Queen et al., "A humanized antibody that binds to the interleukin 2 receptor," *Proc. Natl. Acad. Sci. USA* 86:10029-10033, Dec. 1989.

Reymond et al., "Nectin4/PRR4, a New Afadin-associated Member of the Nectin Family That Trans-interacts with Nectin1/PRR1 through V Domain Interaction," *J. Biol. Chem.* 276(46):43205-43215, 2001.

Riechmann et al., "Reshaping human antibodies for therapy," *Nature* 332:323-321, Mar. 1988.

Sato-Kaneko et al., "Combination immunotherapy with TLR agonists and checkpoint inhibitors suppresses head and neck cancer," *JCT Insight* 2(18):e93397, 2017. (18 pages).

Scholten et al., "Codon modification of T cell receptors allows enhanced functional expression in transgenic human T cells," *Clinical Immunology* 119:135-145, 2006.

Schrama et al., "Antibody targeted drugs as cancer therapeutics," *Nature Reviews* 5:147-159, Feb. 2006.

Silverback Therapeutics, "A Study of SBT6050 Alone and in Combination with Pembrolizumab in Patients with Advanced HER2 Expressing Solid Tumors" URL: https://clinicaltrials.gov/ct2/show/record/NCT04460456, download date Jan. 13, 2021. (4 pages).

Sinkula et al., "Rationale for Design of Biologically Reversible Drug Derivatives: Prodrugs," *J. Pharm. Sci.* 64(2):181-210, Feb. 1975.

Tan et al., ""Superhumanized" Antibodies: Reduction of Immunogenic Potential by Complementarity-Determining Region Grafting with Human Germline Sequences: Application to an Anti-CD28[1]," *J Immuno.* 169:1119-11252, 2002.

Tempest et al., "Reshaping a Human Monoclonal Antibody To Inhibit Human Respiratory Syncytial Virus Infection In Vivo," *Biotechnology* 9(3):266-271, Mar. 1991.

Verhoeyen et al., "Reshaping Human Antibodies: Grafting an Antilysozyme Activity," *Science* 239:1534-1536, 1988.

Wang et al., "The Functional Effects of Physical Interactions among Toll-like Receptors 7, 8, and 9*," *The Journal of Biological Chemistry* 281(49):31421-31434, Dec. 2006.

Warr et al., "The International ImMunoGeneTics Database IMGT," *Developmental and Comparative Immunology* 27(1):1, 2002.

Wu, "Strategies for designing synthetic immune agonists," *Immunology* 148:315-325, 2016.

Zeindler et al., "Nectin-4 Expression Is an Independent Prognostic Biomarker and Associated With Better Survival in Triple-Negative Breast Cancer," *Front. Med.* 6(200):1-7, Sep. 2019.

Zhang et al., "High expression of Nectin-4 is associated with unfavorable prognosis in gastric cancer," *Oncology Letters* 15:8789-8795, 2018.

\* cited by examiner

SEQUENCE LISTING

```
<160> NUMBER OF SEQ ID NOS: 62

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence D6C VH CDR1

<400> SEQUENCE: 1

Asn Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic sequence D6C VH CDR2

<400> SEQUENCE: 2

Thr Ile Ser Ser Gly Gly Ser Tyr Thr Tyr Tyr Val Asp Ser Val Lys
1               5                   10                  15

Gly
```

```
<210> SEQ ID NO 3
<211> LENGTH: 11
<212> TYPE: PRT
<213> ORGANISM: Artificial Sequence
<220> FEATURE:
<223> OTHER INFORMATION: Synthetic sequence D6C VH CDR3

<400> SEQUENCE: 3

Gln Glu Leu Gly Ser Tyr Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic sequence D6C and D6.1C VL CDR1

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic sequence D6.2C and D6.5C VL CDR1

<400> SEQUENCE: 5

Arg Ser Ser Gln Ser Ile Val His Ser Asn Ala Asn Thr Tyr Leu Glu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic sequence D6.3C and D6.4C VL CDR1

<400> SEQUENCE: 6

Arg Ser Ser Gln Ser Ile Val His Ser Gln Gly Asn Thr Tyr Leu Glu
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic sequence D6C VL CDR2

<400> SEQUENCE: 7

Lys Val Ser Asn Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic sequence D6C VL CDR3

<400> SEQUENCE: 8

Phe Gln Gly Ser His Val Pro Tyr Thr
1               5
```

```
<210> SEQ ID NO 9
<211> LENGTH: 120
<212> TYPE: PRT
<213> ORGANISM: Artificial Sequence
<220> FEATURE:
<223> OTHER INFORMATION: Synthetic sequence D6C VH

<400> SEQUENCE: 9

Glu Val Met Leu Val Glu Ser Gly Gly Ala Leu Val Lys Pro Gly Gly
1               5                   10                  15

Ser Leu Lys Leu Ser Cys Val Ala Ser Gly Phe Thr Phe Ser Asn Tyr
            20                  25                  30

Asp Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Val Asp Ser Val
    50                  55                  60

Lys Gly Arg Phe Thr Ile Ser Arg Asp Asn Ala Arg Asn Thr Leu His
65                  70                  75                  80

Leu Gln Met Ser Ser Leu Arg Ser Lys Asp Thr Ala Met Tyr Tyr Cys
                85                  90                  95

Ala Arg Gln Glu Leu Gly Ser Tyr Tyr Ala Met Asp Tyr Trp Gly Gln
            100                 105                 110

Gly Thr Ser Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic sequence hzD6C VH

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Glu Leu Gly Ser Tyr Tyr Ala Met Asp Tyr Trp Gly Gln
            100                 105                 110

Gly Thr Thr Val Thr Val Ser Ser
        115                 120

<210> SEQ ID NO 11
<211> LENGTH: 112
<212> TYPE: PRT
<213> ORGANISM: Artificial Sequence
<220> FEATURE:
<223> OTHER INFORMATION: Synthetic sequence D6C VL

<400> SEQUENCE: 11

Asp Val Val Met Thr Gln Thr Pro Leu Ser Leu Pro Val Ser Leu Gly
1               5                   10                  15
```

```
Asp Gln Ala Ser Ile Ser Cys Arg Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                 85                  90                  95
Ser His Val Pro Tyr Thr Phe Gly Gly Gly Thr Lys Leu Glu Ile Lys
             100                 105                 110
```

<210> SEQ ID NO 12
<211> LENGTH: 112
<212> TYPE: PRT
<213> ORGANISM: Artificial Sequence
<220> FEATURE:
<223> OTHER INFORMATION: Synthetic sequence hzD6C VL

<400> SEQUENCE: 12

```
Asp Ile Val Met Thr Gln Thr Pro Leu Ser Leu Pro Val Thr Pro Gly
 1               5                  10                  15
Glu Pro Ala Ser Ile Ser Cys Arg Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Gln Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Phe Gln Gly
                 85                  90                  95
Ser His Val Pro Tyr Thr Phe Gly Gly Gly Thr Lys Val Glu Ile Lys
             100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: Synthetic sequence hzD6.1C VL

<400> SEQUENCE: 13

```
Asp Val Val Met Thr Gln Thr Pro Leu Ser Leu Pro Val Thr Pro Gly
 1               5                  10                  15
Glu Pro Ala Ser Ile Ser Cys Arg Ser Gln Ser Ile Val His Ser
            20                  25                  30
Asn Gly Asn Thr Tyr Leu Glu Trp Tyr Leu Gln Lys Pro Gly Gln Ser
        35                  40                  45
Pro Gln Leu Leu Ile Tyr Lys Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Phe Gln Gly
                 85                  90                  95
Ser His Val Pro Tyr Thr Phe Gly Gly Gly Thr Lys Val Glu Ile Lys
```

<210> SEQ ID NO 14
<211> LENGTH: 112
<212> TYPE: PRT
<213> ORGANISM: Artificial Sequence
<220> FEATURE:
<223> OTHER INFORMATION: Synthetic sequence hzD6.2C VL

<400> SEQUENCE: 14

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110
```

<210> SEQ ID NO 15
<211> LENGTH: 112
<212> TYPE: PRT
<213> ORGANISM: Artificial Sequence
<220> FEATURE:
<223> OTHER INFORMATION: Synthetic sequence hzD6.3C VL

<400> SEQUENCE: 15

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: Synthetic sequence hzD6.4C VL

<400> SEQUENCE: 16

```
Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30
```

Gln Gly Asn Thr Tyr Leu Glu Trp Tyr Leu Gln Lys Pro Gly Gln Ser
          35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 17
<211> LENGTH: 112
<212> TYPE: PRT
<213> ORGANISM: Artificial Sequence
<220> FEATURE:
<223> OTHER INFORMATION: Synthetic sequence hzD6.5C VL

<400> SEQUENCE: 17

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Ala Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 18
<211> LENGTH: 330
<212> TYPE: PRT
<213> ORGANISM: Artificial Sequence
<220> FEATURE:
<223> OTHER INFORMATION: Synthetic sequence Human IgG1 HC

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 330
<212> TYPE: PRT
<213> ORGANISM: Artificial Sequence
<220> FEATURE:
<223> OTHER INFORMATION: Synthetic sequence Human IgG1null HC

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
            145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Ala Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 107
<212> TYPE: PRT
<213> ORGANISM: Artificial Sequence
<220> FEATURE:
<223> OTHER INFORMATION: Synthetic sequence Human Kappa LC

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
                50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 21
<211> LENGTH: 330
<212> TYPE: PRT
<213> ORGANISM: Artificial Sequence
<220> FEATURE:
<223> OTHER INFORMATION: Synthetic sequence Mouse IgG2a HC

<400> SEQUENCE: 21

Ala Lys Thr Thr Ala Pro Ser Val Tyr Pro Leu Ala Pro Val Cys Gly
1               5                   10                  15
```

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 22
<211> LENGTH: 107
<212> TYPE: PRT
<213> ORGANISM: Artificial Sequence
<220> FEATURE:
<223> OTHER INFORMATION: Synthetic sequence Mouse Kappa LC

<400> SEQUENCE: 22

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Ser Lys Asp Ser
 50                  55                  60

Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105

<210> SEQ ID NO 23
<211> LENGTH: 450
<212> TYPE: PRT
<213> ORGANISM: Artificial Sequence
<220> FEATURE:
<223> OTHER INFORMATION: Synthetic sequence D6C Heavy Chain (VH-IgG1)

<400> SEQUENCE: 23

Glu Val Met Leu Val Glu Ser Gly Gly Ala Leu Val Lys Pro Gly Gly
 1               5                  10                  15

Ser Leu Lys Leu Ser Cys Val Ala Ser Gly Phe Thr Phe Ser Asn Tyr
             20                  25                  30

Asp Met Ser Trp Val Arg Gln Thr Pro Glu Lys Arg Leu Glu Trp Val
         35                  40                  45

Ala Thr Ile Ser Ser Gly Gly Ser Tyr Thr Tyr Tyr Val Asp Ser Val
     50                  55                  60

Lys Gly Arg Phe Thr Ile Ser Arg Asp Asn Ala Arg Asn Thr Leu His
 65                  70                  75                  80

Leu Gln Met Ser Ser Leu Arg Ser Lys Asp Thr Ala Met Tyr Tyr Cys
                 85                  90                  95

Ala Arg Gln Glu Leu Gly Ser Tyr Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 24
<211> LENGTH: 450
<212> TYPE: PRT
<213> ORGANISM: Artificial Sequence
<220> FEATURE:
<223> OTHER INFORMATION: Synthetic sequence hzD6C Heavy Chain (hzVH-
    IgG1)

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
            35                  40                  45

Ala Thr Ile Ser Ser Gly Gly Ser Tyr Thr Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gln Glu Leu Gly Ser Tyr Tyr Ala Met Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 25
<211> LENGTH: 219
<212> TYPE: PRT
<213> ORGANISM: Artificial Sequence
<220> FEATURE:
<223> OTHER INFORMATION: Synthetic sequence D6C Light Chain (VL-kappa)

<400> SEQUENCE: 25

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 26
<211> LENGTH: 219
<212> TYPE: PRT
<213> ORGANISM: Artificial Sequence
<220> FEATURE:
<223> OTHER INFORMATION: Synthetic sequence hzD6C Light Chain (VL-kappa)

<400> SEQUENCE: 26

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 27
<211> LENGTH: 219
<212> TYPE: PRT
<213> ORGANISM: Artificial Sequence
```

```
<220> FEATURE:
<223> OTHER INFORMATION: Synthetic sequence hzD6.1C Light Chain
      (VL.1-kappa)

<400> SEQUENCE: 27

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 28
<211> LENGTH: 219
<212> TYPE: PRT
<213> ORGANISM: Artificial Sequence
<220> FEATURE:
<223> OTHER INFORMATION: Synthetic sequence hzD6.2C Light Chain
      (VL.2-kappa)

<400> SEQUENCE: 28

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 29
<211> LENGTH: 219
<212> TYPE: PRT
<213> ORGANISM: Artificial Sequence
<220> FEATURE:
<223> OTHER INFORMATION: Synthetic sequence hzD6.3C Light Chain
      (VL.3-kappa)

<400> SEQUENCE: 29

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
                100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215

<210> SEQ ID NO 30
<211> LENGTH: 219
<212> TYPE: PRT
```

<213> ORGANISM: Artificial Sequence
<220> FEATURE:
<223> OTHER INFORMATION: Synthetic sequence hzD6.4C Light Chain
      (VL.4-kappa)

<400> SEQUENCE: 30

Asp Val Val Met Thr Gln Thr Pro Leu Ser Leu Pro Val Thr Pro Gly
1               5                   10                  15

Glu Pro Ala Ser Ile Ser Cys Arg Ser Gln Ser Ile Val His Ser
            20                  25                  30

Gln Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 219
<212> TYPE: PRT
<213> ORGANISM: Artificial Sequence
<220> FEATURE:
<223> OTHER INFORMATION: Synthetic sequence hzD6.5C Light Chain
      (VL.5-kappa)

<400> SEQUENCE: 31

Asp Val Val Met Thr Gln Thr Pro Leu Ser Leu Pro Val Thr Pro Gly
1               5                   10                  15

Glu Pro Ala Ser Ile Ser Cys Arg Ser Gln Ser Ile Val His Ser
            20                  25                  30

Asn Ala Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys

```
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 32
<211> LENGTH: 5
<212> TYPE: PRT
<213> ORGANISM: Artificial Sequence
<220> FEATURE:
<223> OTHER INFORMATION: Recognition motif
<220> FEATURE:
<221> NAME/KEY: VARIANT
<222> LOCATION: (1)...(5)
<223> OTHER INFORMATION: Xaa = Any Amino Acid

<400> SEQUENCE: 32

```
Leu Xaa Pro Thr Gly
1               5
```

<210> SEQ ID NO 33
<211> LENGTH: 7
<212> TYPE: PRT
<213> ORGANISM: Artificial Sequence
<220> FEATURE:
<223> OTHER INFORMATION: Synthetic sequence Chothia D6C VH CDR1

<400> SEQUENCE: 33

```
Gly Phe Thr Phe Ser Asn Tyr
1               5
```

<210> SEQ ID NO 34
<211> LENGTH: 6
<212> TYPE: PRT
<213> ORGANISM: Artificial Sequence
<220> FEATURE:
<223> OTHER INFORMATION: Synthetic sequence Chothia D6C VH CDR2

<400> SEQUENCE: 34

```
Ser Ser Gly Gly Ser Tyr
1               5
```

<210> SEQ ID NO 35
<211> LENGTH: 11
<212> TYPE: PRT
<213> ORGANISM: Artificial Sequence
<220> FEATURE:
<223> OTHER INFORMATION: Synthetic sequence Chothia D6C VH CDR3

<400> SEQUENCE: 35

```
Gln Glu Leu Gly Ser Tyr Tyr Ala Met Asp Tyr
1               5                   10
```

<210> SEQ ID NO 36
<211> LENGTH: 16
<212> TYPE: PRT
<213> ORGANISM: Artificial Sequence
<220> FEATURE:
<223> OTHER INFORMATION: Synthetic sequence Chothia D6.2C and D6.5C VL
      CDR1

<400> SEQUENCE: 36

Arg Ser Ser Gln Ser Ile Val His Ser Asn Gly Asn Thr Tyr Leu Glu
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic sequence Chothia D6C VL CDR2

<400> SEQUENCE: 37

Lys Val Ser Asn Arg Phe Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic sequence Chothia D6C VL CDR3

<400> SEQUENCE: 38

Phe Gln Gly Ser His Val Pro Tyr Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic sequence AbM D6C VH CDR1

<400> SEQUENCE: 39

Gly Phe Thr Phe Ser Asn Tyr Asp Met Ser
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic sequence AbM D6C VH CDR2

<400> SEQUENCE: 40

Thr Ile Ser Ser Gly Gly Ser Tyr Thr Tyr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic sequence AbM D6C VH CDR3

<400> SEQUENCE: 41

Gln Glu Leu Gly Ser Tyr Tyr Ala Met Asp Tyr
1               5                   10

-continued

```
<210> SEQ ID NO 42
<211> LENGTH: 16
<212> TYPE: PRT
<213> ORGANISM: Artificial Sequence
<220> FEATURE:
<223> OTHER INFORMATION: Synthetic sequence AbM D6.2C and D6.5C VL CDR1

<400> SEQUENCE: 42

Arg Ser Ser Gln Ser Ile Val His Ser Asn Gly Asn Thr Tyr Leu Glu
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: Synthetic sequence AbM D6C VL CDR2

<400> SEQUENCE: 43

Lys Val Ser Asn Arg Phe Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic sequence AbM D6C VL CDR3

<400> SEQUENCE: 44

Phe Gln Gly Ser His Val Pro Tyr Thr
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic sequence Contact D6C VH CDR1

<400> SEQUENCE: 45

Ser Asn Tyr Asp Met Ser
1               5

<210> SEQ ID NO 46
<211> LENGTH: 13
<212> TYPE: PRT
<213> ORGANISM: Artificial Sequence
<220> FEATURE:
<223> OTHER INFORMATION: Synthetic sequence Contact D6C VH CDR2

<400> SEQUENCE: 46

Trp Val Ala Thr Ile Ser Ser Gly Gly Ser Tyr Thr Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic sequence Contact D6C VH CDR3

<400> SEQUENCE: 47

Ala Arg Gln Glu Leu Gly Ser Tyr Tyr Ala Met Asp
1               5                   10
```

```
<210> SEQ ID NO 48
<211> LENGTH: 12
<212> TYPE: PRT
<213> ORGANISM: Artificial Sequence
<220> FEATURE:
<223> OTHER INFORMATION: Synthetic sequence Contact D6.2C and D6.5C VL
      CDR1

<400> SEQUENCE: 48

Val His Ser Asn Gly Asn Thr Tyr Leu Glu Trp Tyr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic sequence Contact D6C VL CDR2

<400> SEQUENCE: 49

Leu Leu Ile Tyr Lys Val Ser Asn Arg Phe
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Synthetic sequence Contact D6C VL CDR3

<400> SEQUENCE: 50

Phe Gln Gly Ser His Val Pro Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic sequence IMGT D6C VH CDR1

<400> SEQUENCE: 51

Gly Phe Thr Phe Ser Asn Tyr Asp
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic sequence IMGT D6C VH CDR2

<400> SEQUENCE: 52

Ile Ser Ser Gly Gly Ser Tyr Thr
1               5

<210> SEQ ID NO 53
<211> LENGTH: 13
<212> TYPE: PRT
<213> ORGANISM: Artificial Sequence
<220> FEATURE:
<223> OTHER INFORMATION: Synthetic sequence IMGT D6C VH CDR3

<400> SEQUENCE: 53

Ala Arg Gln Glu Leu Gly Ser Tyr Tyr Ala Met Asp Tyr
1               5                   10
```

```
<210> SEQ ID NO 54
<211> LENGTH: 11
<212> TYPE: PRT
<213> ORGANISM: Artificial Sequence
<220> FEATURE:
<223> OTHER INFORMATION: Synthetic sequence IMGT D6.2C and D6.5C VL CDR1

<400> SEQUENCE: 54

Gln Ser Ile Val His Ser Asn Gly Asn Thr Tyr
1               5                   10

<210> SEQ ID NO 55
<211> LENGTH: 3
<212> TYPE: PRT
<213> ORGANISM: Artificial Sequence
<220> FEATURE:
<223> OTHER INFORMATION: Synthetic sequence IMGT D6C VL CDR2

<400> SEQUENCE: 55

Lys Val Ser
1

<210> SEQ ID NO 56
<211> LENGTH: 9
<212> TYPE: PRT
<213> ORGANISM: Artificial Sequence
<220> FEATURE:
<223> OTHER INFORMATION: Synthetic sequence IMGT D6C VL CDR3

<400> SEQUENCE: 56

Phe Gln Gly Ser His Val Pro Tyr Thr
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic sequence AHo D6C VH CDR1

<400> SEQUENCE: 57

Ser Gly Phe Thr Phe Ser Asn Tyr Asp Met
1               5                   10

<210> SEQ ID NO 58
<211> LENGTH: 17
<212> TYPE: PRT
<213> ORGANISM: Artificial Sequence
<220> FEATURE:
<223> OTHER INFORMATION: Synthetic sequence AHo D6C VH CDR2

<400> SEQUENCE: 58

Ser Ser Gly Gly Ser Tyr Thr Tyr Tyr Val Asp Ser Val Lys Gly Arg
1               5                   10                  15

Phe

<210> SEQ ID NO 59
<211> LENGTH: 10
<212> TYPE: PRT
<213> ORGANISM: Artificial Sequence
<220> FEATURE:
<223> OTHER INFORMATION: Synthetic sequence AHo D6C VH CDR3

<400> SEQUENCE: 59

Glu Leu Gly Ser Tyr Tyr Ala Met Asp Tyr
1               5                   10
```

```
<210> SEQ ID NO 60
<211> LENGTH: 13
<212> TYPE: PRT
<213> ORGANISM: Artificial Sequence
<220> FEATURE:
<223> OTHER INFORMATION: Synthetic sequence AHo D6.2C and D6.5C VL CDR1

<400> SEQUENCE: 60

Ser Ser Gln Ser Ile Val His Ser Asn Gly Asn Thr Tyr
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic sequence AHo D6C VL CDR2

<400> SEQUENCE: 61

Lys Val Ser Asn Arg Phe Ser Gly Val Pro Asp Arg
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Synthetic sequence AHo D6C VL CDR3

<400> SEQUENCE: 62

Gly Ser His Val Pro Tyr Thr Phe
1               5
```

NECTIN-4 ANTIBODY CONJUGATES AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 860234_402_SEQUENCE_LISTING.txt. The text file is 45.6 KB, was created on Feb. 19, 2021, and is being submitted electronically via EFS-Web.

BACKGROUND

One of the leading causes of death in the United States is cancer. Conventional methods of cancer treatment, like chemotherapy, surgery, or radiation therapy, tend to be either highly toxic or nonspecific to a cancer, or both, resulting in limited efficacy and harmful side effects. However, the immune system has the potential to be a powerful, specific tool in fighting cancers. In many cases tumors can specifically express genes whose products are required for inducing or maintaining the malignant state. These proteins may serve as antigen markers for developing more specific anti-cancer treatments that can harness the power of both innate and adaptive immune responses. The activation of these immune responses (e.g., myeloid cell activation) in the tumor microenvironment and lymphoid structures only has the potential to be a powerful anti-cancer treatment that can be more effective than conventional methods of cancer treatment with fewer side effects.

BRIEF SUMMARY

In one aspect, the present disclosure provides a myeloid cell agonist conjugate comprising: (a) an anti-Nectin-4 antibody, or an antigen-binding fragment thereof, comprising a heavy chain variable region (VH) and a light chain variable region (VL), wherein the VH comprises a CDR1 (VH-CDR1) comprising the amino acid sequence of SEQ ID NOT, a VH-CDR2 comprising the amino acid sequence of SEQ ID NO:2, a VH-CDR3 comprising the amino acid sequence of SEQ ID NOG; and the VL comprises a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8; (b) a myeloid cell agonist; and (c) a linker covalently attached to the myeloid cell agonist and the antibody.

In certain embodiments, the conjugate is represented by Formula (I):

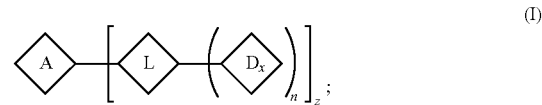

wherein: A is the anti-Nectin-4 antibody or antigen-binding fragment thereof, L is the linker; $D_x$ is the myeloid cell agonist, wherein the myeloid cell agonist is a TLR8 agonist; n is selected from 1 to 20; and z is selected from 1 to 20.

In a related aspect, the present disclosure provides a myeloid cell agonist conjugate or salt thereof represented by the formula:

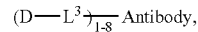

wherein Antibody is an anti-Nectin-4 antibody comprising light chain CDR1, CDR2 and CDR3 set forth in the light chain variable region amino acid sequence of SEQ ID NO:14 or 13, and heavy chain CDR1, CDR2 and CDR3 set forth in the heavy chain variable region amino acid sequence of SEQ ID NO: 10, as determined by the Kabat index, and $L^3$-D is a linker-TLR8 agonist and has the structure:

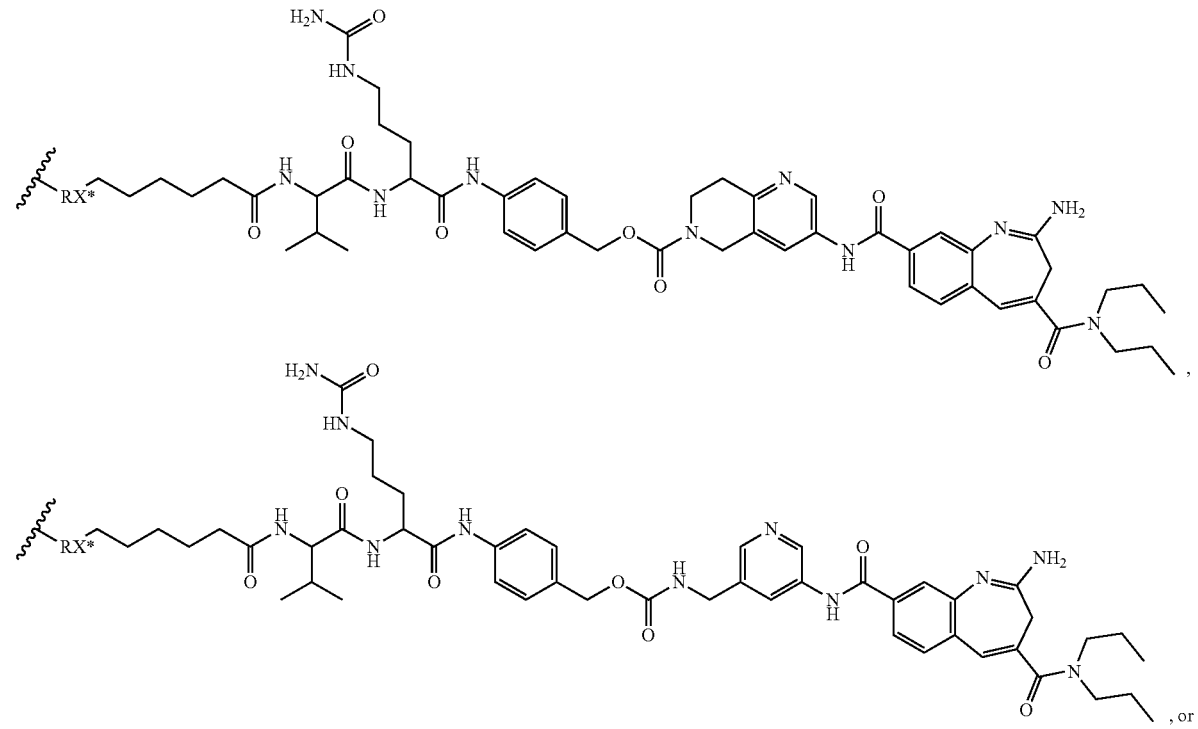

-continued

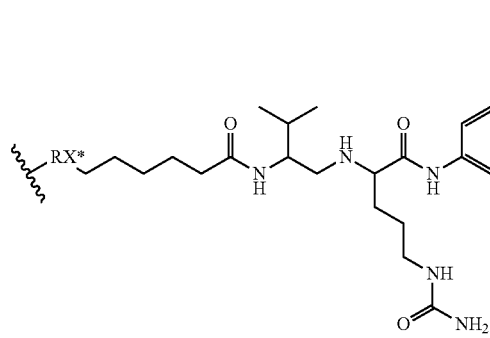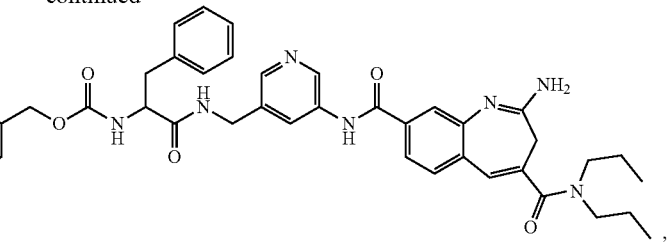

wherein RX* is a bond, a succinimide moiety, or a hydrolyzed succinimide moiety bound to a residue of the antibody construct, wherein

on RX* represents the point of attachment to a cysteine residue of the antibody construct.

In another aspect, the present disclosure provides a pharmaceutical composition comprising a myeloid cell agonist conjugate disclosed herein and a pharmaceutically acceptable excipient.

In a further aspect, the present disclosure provides a method of treating cancer (e.g., a Nectin-4-expressing cancer), comprising administering to a subject in need thereof an effective amount of a myeloid cell agonist conjugate or a pharmaceutical composition disclosed herein.

In certain embodiments, the myeloid cell agonist conjugate or the pharmaceutical composition is subcutaneously administered.

In certain embodiments, the effective amount of the myeloid cell agonist conjugate is about 0.1 to about 100 mg/kg, preferably about 0.1 to about 25 mg/kg, and more preferably about 0.5 to about 20 mg/kg, per treatment cycle or per administration.

In certain embodiments, the myeloid cell agonist conjugate or the pharmaceutical composition is subcutaneously administered, and the effective amount of the myeloid cell agonist conjugate is about 0.1 to about 100 mg/kg, preferably about 0.1 to about 25 mg/kg, and more preferably about 0.5 to about 20 mg/kg, per treatment cycle or per administration.

In another aspect, the present disclosure provides an isolated monoclonal antibody, or an antigen-binding fragment thereof, that specifically binds to Nectin-4, wherein the antibody or antigen-binding fragment thereof comprises a heavy chain variable region (VH) and a light chain variable region (VL), wherein the VH comprises a heavy chain CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3; and the VL comprises a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8.

In a further aspect, the present disclosure provides a conjugate comprising an anti-Nectin-4 antibody disclosed herein and a small molecule drug, such as a TLR8 agonist.

In another aspect, the present disclosure provides a pharmaceutical composition comprising an anti-Nectin-4 antibody disclosed herein or a conjugate comprising such an antibody and a small molecule drug and a pharmaceutically acceptable carrier.

In another aspect, the present disclosure provides an isolated nucleic acid that encodes an anti-Nectin 4 antibody or the heavy chain, the light chain, the heavy chain variable region, or the light chain variable region of the anti-Nectin 4 antibody. The present disclosure also provides a vector comprising the isolated nucleic acid, an isolated host cell comprising the isolated nucleic acid or the vector, an isolated host cell that expresses an anti-Nectin 4 antibody disclosed herein, and a method of producing an anti-Nectin-4 antibody comprising culturing the host cell disclosed herein under conditions suitable for expressing the antibody.

In a further aspect, the present disclosure provides a method of treating a Nectin-4-expressing cancer comprising administering to a subject having a Nectin-4-expressing cancer an effective amount of an anti-Nectin-4 antibody, a conjugate comprising an anti-Nectin-4 antibody and a small molecule drug, or a pharmaceutical composition of comprising the antibody or the conjugate disclosed herein.

In certain embodiments, the conjugate comprising an anti-Nectin-4 antibody and a small molecule drug, or the pharmaceutical composition thereof, is subcutaneously administered.

In certain embodiments, the effective amount of the conjugate is about 0.1 to about 100 mg/kg, preferably about 0.1 to about 25 mg/kg, and more preferably about 0.5 to about 20 mg/kg, per treatment cycle or per administration.

In certain embodiments, the conjugate or the pharmaceutical composition is subcutaneously administered, and the effective amount of the conjugate is about 0.1 to about 100 mg/kg, preferably about 0.1 to about 25 mg/kg, and more preferably about 0.5 to about 20 mg/kg, per treatment cycle or per administration.

DETAILED DESCRIPTION

Figure 1A:
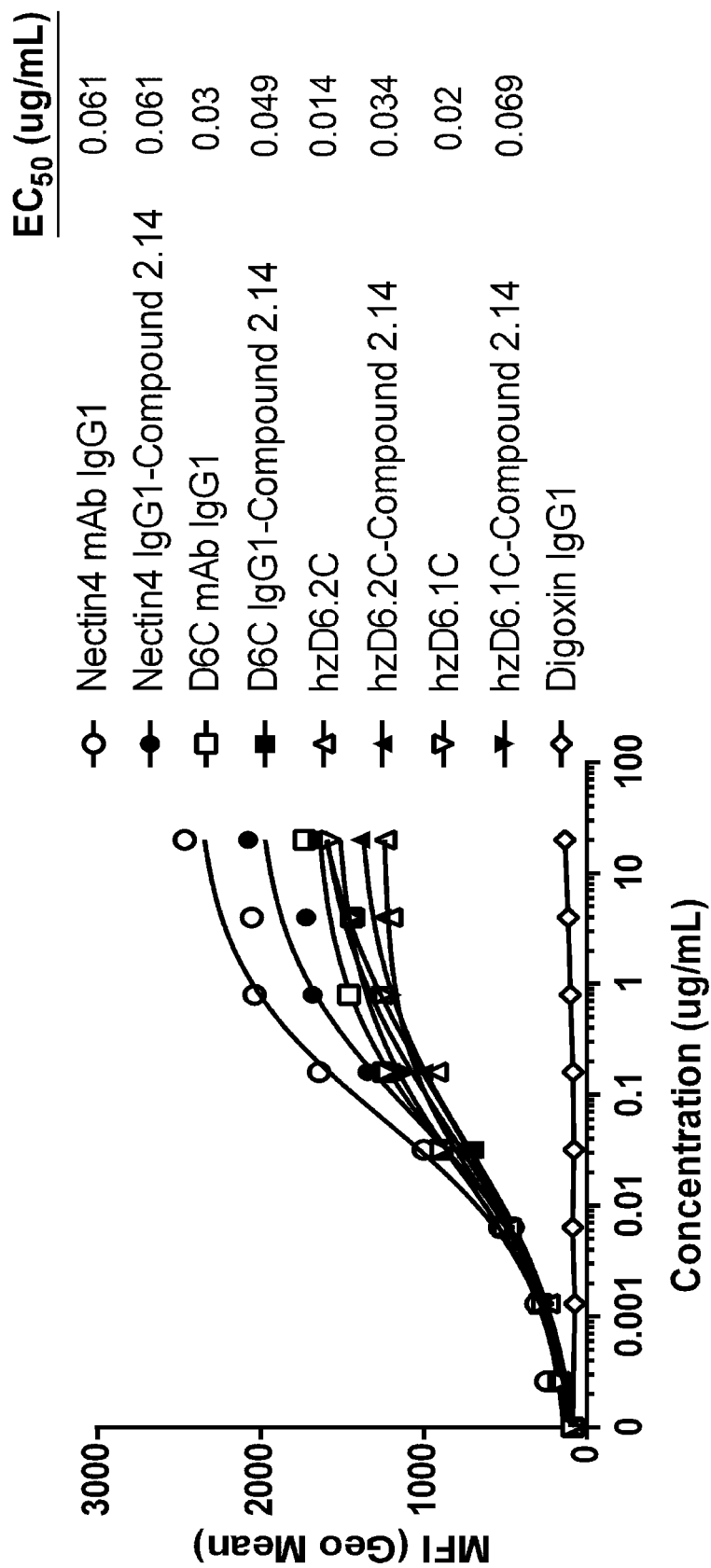
FIGS. 1A-1C show that anti-Nectin-4 antibodies and anti-Nectin-4 antibody-TLR8 agonist immunoconjugates bind to (A) HEK-293 cells transfected with human Nectin-4 (FIG. 1A); (B) HEK-293 cells transfected with cynomolgus Nectin-4 (FIG. 1B); and (C) MDA-MB-175-VII cells (FIG. 1C), which are a Nectin-4 expressing tumor cell line.

The present disclosure provides anti-Nectin-4 antibodies, myeloid cell agonist conjugates comprising anti-Nectin-4 antibodies, and pharmaceutical compositions that comprise such antibodies and conjugates. The antibodies, conjugates and pharmaceutical compositions disclosed herein are useful in treating cancer alone or in combination with other anti-cancer therapeutic agents.

Anti-Nectin-4 antibodies and myeloid cell agonist conjugates comprising such antibodies as provided herein are capable of specifically binding to Nectin-4 expressing cells. The myeloid cell agonist conjugates are also capable of inducing TNF-α production from human peripheral blood mononuclear cells (PBMCs) in the presence of Nectin-4 expressing tumor cells, which indicates that the myeloid cells are being activated by the conjugates of this disclosure. Surprisingly, certain exemplary conjugates comprising humanized anti-Nectin-4 antibodies not only were more potent in inducing TNF-α production from PBMCs, but also reached a higher maximal TNF-α production level compared to conjugates comprising the parent anti-Nectin-4 antibody and compared to conjugates comprising a reference anti-Nectin-4 antibody that cross-blocks the anti-Nectin-4 antibodies of this disclosure.

Anti-Nectin-4 antibodies and myeloid cell agonist conjugates comprising such antibodies as provided herein are also capable of increasing intra-tumoral levels of chemokines and cytokines, indicating that they are capable of enhancing innate immune response driven by myeloid cell activation, which in turn are capable of nucleating an adaptive immune response by indirectly activating T and NK cells with the tumor.

In certain embodiments, anti-Nectin-4 antibodies and myeloid cell agonist conjugates comprising such antibodies as provided herein are capable of blocking the binding of TIGIT to Nectin-4 expressed on tumor cells.

Prior to setting forth this disclosure in more detail, it may be helpful to an understanding thereof to provide definitions of certain terms to be used herein. Additional definitions are set forth throughout this disclosure.

As used in the specification and claims, the singular form "a," "an," and "the" includes plural references unless the context clearly dictates otherwise. It should be understood that the terms "a" and "an" as used herein refer to "one or more" of the enumerated components.

The use of the alternative (e.g., "or") should be understood to mean either one, both, or any combination thereof of the alternatives. As used herein, the terms "include" and "comprise" are used synonymously.

The phrase "at least one of" when followed by a list of items or elements refers to an open ended set of one or more of the elements in the list, which may, but does not necessarily, include more than one of the elements.

The term "about" as used herein in the context of a number refers to a range centered on that number and spanning 15% less than that number and 15% more than that number. The term "about" used in the context of a range refers to an extended range spanning 15% less than that the lowest number listed in the range and 15% more than the greatest number listed in the range.

In the present description, any concentration range, percentage range, ratio range, or integer range is to be understood to include any value (including integers or fractions) or subrange within the recited range unless otherwise indicated.

As used herein, the term "antibody" refers to an immunoglobulin molecule that specifically binds to, or is immunologically reactive toward, a specific antigen. An antibody can include, for example, polyclonal, monoclonal, and genetically engineered antibodies, and antigen binding fragments thereof. An antibody can be, for example, murine, chimeric, humanized, heteroconjugate, bispecific, diabody, triabody, or tetrabody.

As used herein, an "antigen-binding domain" or "antigen-binding fragment refers to a region of a molecule that specifically binds to an antigen. An antigen binding domain can be an antigen-binding portion of an antibody or an antibody fragment. An antigen-binding fragment can include, for example, a Fab', F(ab')$_2$, Fab, Fv, rIgG, scFv, hcAbs (heavy chain antibodies), a single domain antibody, $V_{HH}$, $V_{NAR}$, sdAbs, or nanobody.

As used herein, an "Fc domain" refers to a domain from an Fc portion of an antibody that can specifically bind to an Fc receptor, such as an Fcγ receptor or an FcRn receptor.

As used herein, "identical" or "identity" refer to the similarity between a DNA, RNA, nucleotide, amino acid, or protein sequence to another DNA, RNA, nucleotide, amino acid, or protein sequence. Identity can be expressed in terms of a percentage of sequence identity of a first sequence to a second sequence. Percent (%) sequence identity with respect to a reference DNA sequence can be the percentage of DNA nucleotides in a candidate sequence that are identical with the DNA nucleotides in the reference DNA sequence after aligning the sequences. Percent (%) sequence identity with respect to a reference amino acid sequence can be the percentage of amino acid residues in a candidate sequence that are identical with the amino acid residues in the reference amino acid sequence after aligning the sequences and introducing gaps, if necessary, to achieve the maximum percent sequence identity, and not considering any conservative substitutions as part of the sequence identity. As used herein, the percent sequence identity values is generated using the NCBI BLAST 2.0 software as defined by Altschul et al., "Gapped BLAST and PSI-BLAST: a new generation of protein database search programs," Nucleic Acids Res. 2007, 25, 3389-3402, with the parameters set to default values.

A "small molecule" is an organic compound with a molecular weight of less than 1500, or 100, or 900, or 750, or 600, or 500 Daltons. A "small molecule drug" is a small molecule that has a therapeutic effect such as treating a disease or disorder. In some embodiments, a small molecule drug is a small molecule agonist that has an octanol-water partition coefficient (log P) in the range of from 3 to 6, or from 4 to 5, or from 2 to 4. In some embodiments, a small molecule agonist has a polar surface area of less than 200, or less than 150 Å$^2$. In some embodiments, the small molecule agonist has not more than five, or not more than three, hydrogen bond donors, and not more than 10, or not more than three hydrogen bond acceptors. A small molecule is not a protein, a polysaccharide, or a nucleic acid. A "small molecule inhibitor" is a small molecule that inhibits the activity of another molecule, such as a protein (e.g., PD-L1). Small molecule inhibitors include small molecule antagonists (i.e., small molecules that reduce the effect of an agonist).

As used herein, "specifically binds" and the like refers to the specific association or specific binding between the antigen binding domain and the antigen, as compared with the interaction of the antigen binding domain with a different antigen (i.e., non-specific binding). In some embodiments, an antigen binding domain that recognizes or specifically binds to an antigen has a dissociation constant (KD) of <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M). Specific binding does not require that the antigen binding domain does not associate with or bind to any other antigen, but rather that it preferentially associates with or binds to the antigen, as compared to association with or binding to an unrelated antigen.

As used herein, "Nectin-4," also known as poliovirus receptor-related protein 4 (PVRL4), LNIR, PRIM, and EDSS1, is a member of the nectin subfamily of immunoglobulin-like adhesion molecules that participate in Ca$^{2+}$-independent cell-cell adhesion. Nectins bind to the actin cytoskeleton through the adaptor protein afadin (AFDN) and are key components of adherens junctions. Nectin-4 contains two immunoglobulin-like (Ig-like) C2-type domains and one Ig-like V-type domain. It may be a single-pass type I membrane protein or a soluble form is produced by proteolytic cleavage at the cell surface by the metalloproteinase ADAM17/TACE. Nectin-4 is overexpressed in multiple human cancers, including but not limited to triple negative breast cancer, bladder cancer, urothelial cancer, ovarian cancer, cervical cancer, endometrial cancer, lung cancer, skin cancer, esophageal cancer, and its abnormal expression may associated with cancer progression and poor prognosis. Nectin-4 includes mammalian Nectin-4 proteins, e.g., mouse, rat, rabbit, guinea pig, pig, sheep, dog, non-human primate, and human. In some embodiments, Nectin-4 is a human Nectin-4 (encoded by GenBank accession number AF426163) or a mouse Nectin-4 (see Reymond et al., Journal of Biological Chemistry 276:43205-15, 2001).

As used herein, an "immune cell" refers to a T cell, B cell, NK cell, NKT cell, or an antigen presenting cell. In some embodiments, an immune cell is a T cell, B cell, NK cell, or NKT cell. In some embodiments, an immune cell is an antigen presenting cell. In some embodiments, an immune cell is not an antigen presenting cell.

As used herein, an "immune stimulatory compound" is a compound that activates or stimulates an immune cell, such as a myeloid cell or an APC.

As used herein, a "myeloid cell" refers to a dendritic cell, a macrophage, a monocyte, a myeloid derived suppressor cell (MDSC).

As used herein, a "myeloid cell agonist" refers to a compound that activates or stimulates an immune response by a myeloid cell.

As used herein, a "benzazepine compound" refers to small molecule chemical compound comprising a benzazepine moiety, where the benzazepine moiety is a benzene ring fused to a 7-membered ring that comprises one or two nitrogen ring members. In addition to the bond where the ring is fused to the benzene ring, the 7-membered ring includes two double bonds (e.g., an azepine or diazepine ring), one double bond (e.g., a dihydroazepine or dihydrodiazepine ring), or no double bonds (e.g., a tetrahydrodiazepine, azepane, tetrahydrodiazepine, or diazepane ring). The benzazepine moiety is optionally substituted. In some embodiments, the benzazepine moiety is an optionally substituted 4,5-dihydro-3H-benzo[b]azepine. In some embodiments, the benzazepine moiety has the structure:

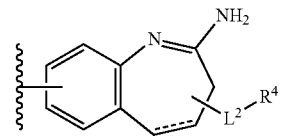

wherein ⸺ is a double bond or a single bond;

$L^2$ is selected from —$X^2$—, —$X^2$—$C_{1-6}$alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$X^2$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$), —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O), —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^{12}$ is independently selected at each occurrence from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$—C(O)O$R^{10}$, —OC(O)$R^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$—C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, C$_{2-6}$alkynyl;

R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^4$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl; and R$^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, —C$_{1-10}$haloalkyl, —O—C$_{1-10}$ alkyl, C$_{2-10}$ alkenyl, C$_{2-10}$ alkynyl, C$_{3-12}$ carbocycle, 3- to 12-membered heterocycle, and haloalkyl; and the moiety is optionally substituted at any position.

The terms "salt" or "pharmaceutically acceptable salt" refer to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, trifluoroacetic acid and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "C$_{x-y}$" when used in conjunction with a chemical moiety, such as alkyl, alkenyl, or alkynyl is meant to include groups that contain from x to y carbons in the chain. For example, the term "C$_{1-6}$alkyl" refers to substituted or unsubstituted saturated hydrocarbon groups, including straight-chain alkyl and branched-chain alkyl groups that contain from 1 to 6 carbons. The term —C$_{x-y}$alkylene- refers to a substituted or unsubstituted alkylene chain with from x to y carbons in the alkylene chain. For example —C$_{1-6}$ alkylene- may be selected from methylene, ethylene, propylene, butylene, pentylene, and hexylene, any one of which is optionally substituted.

The terms "C$_{x-y}$alkenyl" and "C$_{x-y}$alkynyl" refer to substituted or unsubstituted unsaturated aliphatic groups analogous in length and possible substitution to the alkyls described above, but that contain at least one double or triple bond, respectively. The term —C$_{x-y}$alkenylene- refers to a substituted or unsubstituted alkenylene chain with from x to y carbons in the alkenylene chain. For example, —C$_{2-6}$ alkenylene- may be selected from ethenylene, propenylene, butenylene, pentenylene, and hexenylene, any one of which is optionally substituted. An alkenylene chain may have one double bond or more than one double bond in the alkenylene chain. The term —C$_{x-y}$alkynylene- refers to a substituted or unsubstituted alkynylene chain with from x to y carbons in the alkenylene chain. For example, —C$_{2-6}$alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" refers to a divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. In other embodiments, an alkylene comprises one to five carbon atoms (i.e., C$_1$-C$_5$ alkylene). In other embodiments, an alkylene comprises one to four carbon atoms (i.e., C$_1$-C$_4$ alkylene). In other embodiments, an alkylene comprises one to three carbon atoms (i.e., C$_1$-C$_3$ alkylene). In other embodiments, an alkylene comprises one to two carbon atoms (i.e., C$_1$-C$_2$ alkylene). In other embodiments, an alkylene comprises one carbon atom (i.e., C$_1$ alkylene). In other embodiments, an alkylene comprises five to eight carbon atoms (i.e., C$_5$-C$_8$ alkylene). In other embodiments, an alkylene comprises two to five carbon atoms (i.e., C$_2$-C$_5$ alkylene). In other embodiments, an alkylene comprises three to five carbon atoms (i.e., C$_3$-C$_5$ alkylene). Unless stated otherwise specifically in the specification, an alkylene chain is optionally substituted by one or more substituents such as those substituents described herein.

"Alkenylene" refers to a divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atoms (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene). Unless stated otherwise specifically in the specification, an alkenylene chain is optionally substituted by one or more substituents such as those substituents described herein.

"Alkynylene" refers to a divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atoms (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene). Unless stated otherwise specifically in the specification, an alkynylene chain is optionally substituted by one or more substituents such as those substituents described herein.

"Heteroalkylene" refers to a divalent hydrocarbon chain including at least one heteroatom in the chain, containing no unsaturation, and preferably having from one to twelve carbon atoms and from one to 6 heteroatoms, e.g., —O—, —NH—, —S—. The heteroalkylene chain is attached to the rest of the molecule through a single bond and to the radical group through a single bond. The points of attachment of the heteroalkylene chain to the rest of the molecule and to the radical group are through the terminal atoms of the chain. In other embodiments, a heteroalkylene comprises one to five carbon atoms and from one to three heteroatoms. In other embodiments, a heteroalkylene comprises one to four carbon atoms and from one to three heteroatoms. In other embodiments, a heteroalkylene comprises one to three carbon atoms and from one to two heteroatoms. In other embodiments, a heteroalkylene comprises one to two carbon atoms and from one to two heteroatoms. In other embodiments, a heteroalkylene comprises one carbon atom and from one to two heteroatoms. In other embodiments, a heteroalkylene comprises five to eight carbon atoms and from one to four heteroatoms. In other embodiments, a heteroalkylene comprises two to five carbon atoms and from one to three heteroatoms. In other embodiments, a heteroalkylene comprises three to five carbon atoms and from one to three heteroatoms. Unless stated otherwise specifically in the specification, a heteroalkylene chain is optionally substituted by one or more substituents such as those substituents described herein.

The term "carbocycle" as used herein refers to a saturated, unsaturated or aromatic ring in which each atom of the ring is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl. The term "unsaturated carbocycle" refers to carbocycles with at least one degree of unsaturation and excluding aromatic carbocycles. Examples of unsaturated carbocycles include cyclohexadiene, cyclohexene, and cyclopentene.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. The term "unsaturated heterocycle" refers to heterocycles with at least one degree of unsaturation and excluding aromatic heterocycles. Examples of unsaturated heterocycles include dihydropyrrole, dihydrofuran, oxazoline, pyrazoline, and dihydropyridine.

The term "heteroaryl" includes aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more rings in which two or more carbons are common to two adjoining rings wherein at least one of the rings is heteroaromatic, e.g., the other rings can be aromatic or non-aromatic carbocyclic, or heterocyclic. Heteroaryl groups include, for example, pyrrole, furan, thiophene, imidazole, oxazole, thiazole, pyrazole, pyridine, pyrazine, pyridazine, and pyrimidine, and the like.

The term "substituted" refers to moieties having substituents replacing a hydrogen on one or more carbons or substitutable heteroatoms, e.g., —NH—, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants.

In addition, it should be understood that the individual compounds (e.g., proteins), or groups of compounds, derived from the various combinations of the structures and substituents (e.g., domains, regions or peptide components) described herein, are disclosed by the present application to the same extent as if each compound or group of compounds was set forth individually. Thus, selection of particular structures or particular substituents is within the scope of the present disclosure.

Chemical entities having carbon-carbon double bonds or carbon-nitrogen double bonds may exist in Z- or E-form (or cis- or trams-form). Furthermore, some chemical entities may exist in various tautomeric forms. Unless otherwise specified, chemical entities described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

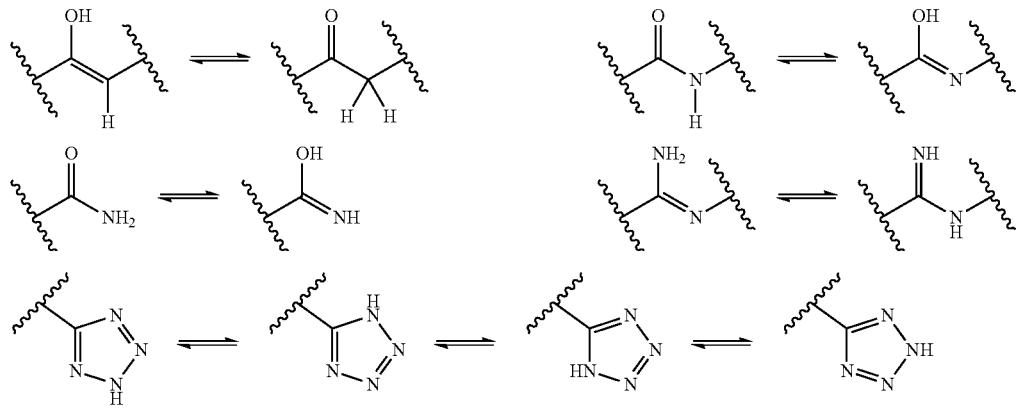

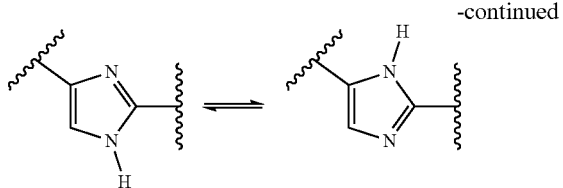 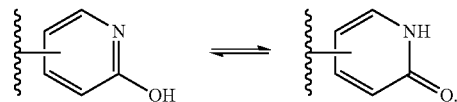

As used herein, a "conjugate" refers to an antibody or antigen binding fragment thereof attached to at least one immune stimulatory compound, optionally via a linker.

The phrases "intravenous administration" and "administered intravenously" as used herein refer to injection or infusion of a conjugate into a vein of a subject.

The phrases "intravenous slow infusion" and "IV slow infusion" as used here refer to an intravenous infusion that results in a T max of about 4 hours or more.

The phrases "subcutaneous administration", "subcutaneously administering" and the like refer to administration of a conjugate into the subcutis of a subject. For clarity, a subcutaneous administration is distinct from an intratumoral injection into a tumor or cancerous lesion located in the subcuta.

The phrase "pharmaceutically acceptable" refers to compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Anti-Nectin-4 Antibodies

In one aspect, antibodies (e.g., isolated monoclonal antibodies) that specifically bind to Nectin-4, also referred to as anti-Nectin-4 antibodies, or antigen-binding fragments thereof, are provided.

In various embodiments, an antibody or antigen binding fragment thereof comprises two light chain polypeptides (light chains) and two heavy chain polypeptides (heavy chains), held together covalently by disulfide linkages.

The heavy chain typically comprises a heavy chain variable region (VH) and a heavy chain constant region. The heavy chain constant region comprises three domains, CH1, CH2, and CH3. Nonlimiting exemplary heavy chain constant regions include human IgG1, human IgG2, human IgG3, and human IgG4 constant regions. In some embodiments, an antibody provided herein comprises an IgG1 constant region.

The light chain typically comprises a light chain variable region (VL) and a light chain constant region. Nonlimiting exemplary light chain constant regions include kappa and lambda constant regions. A nonlimiting exemplary human kappa constant region is shown in SEQ ID NO:20. Another exemplary light chain constant region is mouse kappa constant region shown in SEQ ID NO:22.

The constant domains provide the general framework of the antibody and may not be involved directly in binding the antibody to an antigen, but can be involved in various effector functions, such as participation of the antibody in antibody-dependent cellular cytotoxicity (ADCC), ADCP (antibody-dependent cellular phagocytosis), CDC (complement-dependent cytotoxicity) and complement fixation, binding to Fc receptors (e.g., CD16, CD32, FcRn), greater in vivo half-life relative to a polypeptide lacking an Fc region, protein A binding, and perhaps even placental transfer (see Capon et al., Nature 357:525, 1989). As used herein, "an Fc region constant domain portion" or "Fc region portion" refers to the heavy chain constant region segment of the Fc fragment (the "fragment crystallizable" region or Fc region) from an antibody, which can in include one or more constant domains, such as CH2, CH3, CH4, or any combination thereof. In certain embodiments, an Fc region portion includes the CH2 and CH3 domains of an IgG, IgA, or IgD antibody and any combination thereof, or the CH3 and CH4 domains of an IgM or IgE antibody and any combination thereof.

An Fc region or domain may interact with different types of FcRs. The different types of FcRs may include, for example, FcγRI, FcγRIIA, FcγRIIB, FcγRIIIA, FcγRIIIB, FcαRI, FcμR, FcεRI, FcεRII, and FcRn. FcRs may be located on the membrane of certain immune cells including, for example, B lymphocytes, natural killer cells, macrophages, neutrophils, follicular dendritic cells, eosinophils, basophils, platelets, and mast cells. Once the FcR is engaged by the Fc domain, the FcR may initiate functions including, for example, clearance of an antigen-antibody complex via receptor-mediated endocytosis, antibody-dependent cell-mediated cytotoxicity (ADCC), antibody dependent cell-mediated phagocytosis (ADCP), trogocytosis, trogoptosis, and ligand-triggered transmission of signals across the plasma membrane that can result in alterations in secretion, exocytosis, and cellular metabolism. FcRs may deliver signals when FcRs are aggregated by antibodies and multivalent antigens at the cell surface. The aggregation of FcRs with immunoreceptor tyrosine-based activation motifs (ITAMs) may sequentially activate SRC family tyrosine kinases and SYK family tyrosine kinases. ITAM comprises a twice-repeated YxxL sequence flanking seven variable residues. The SRC and SYK kinases may connect the transduced signals with common activation pathways.

In some embodiments, an Fc region or domain can exhibit reduced binding affinity to one or more Fc receptors. In some embodiments, an Fc region or domain can exhibit reduced binding affinity to one or more Fcγ receptors. In some embodiments, an Fc region or domain can exhibit reduced binding affinity to FcRn receptors. In some embodiments, an Fc region or domain can exhibit reduced binding affinity to Fcγ and FcRn receptors. In some embodiments, an Fc domain is an Fc null domain or region. As used herein, an "Fc null" refers to a domain that exhibits weak to no binding to any of the Fcgamma receptors. In some embodiments, an Fc null domain or region exhibits a reduction in binding affinity (e.g., increase in Kd) to Fcγ receptors of at least about 1000-fold.

The Fc region or domain may have one or more, two or more, three or more, or four or more, or up to five amino acid substitutions that decrease binding of the Fc region or domain to an Fc receptor. In some embodiments, an Fc region or domain exhibits decreased binding to FcγRI (CD64), FcγRIIA (CD32), FcγRIIIA (CD16a), FcγRIIIB (CD16b), or any combination thereof. In order to decrease binding affinity of an Fc region or domain to an Fc receptor, an Fc region or domain may comprise one or more amino acid substitutions that has the effect of reducing the affinity of the Fc domain or region to an Fc receptor. In certain embodiments, the Fc region or domain is an IgG1 and the one or more substitutions in the Fc region or domain comprise any one or more of IgG1 heavy chain mutations corresponding to E233P, L234V, L234A, L235A, L235E, ΔG236, G237A, E318A, K320A, K322A, A327G, A330S, or P331S according to the EU index of Kabat numbering.

In some embodiments, the Fc region or domain can comprise a sequence of the IgG1 isoform that has been modified from the wild-type IgG1 sequence. A modification can comprise a substitution at more than one amino acid residue, such as at 5 different amino acid residues including L235V/F243L/R292P/Y300L/P396L (IgG1VLPLL) according to the EU index of Kabat numbering. A modification can comprise a substitution at more than one amino acid residues, such as at 2 different amino acid residues including S239D/I332E (IgG1DE) according to the EU index of Kabat numbering. A modification can comprise a substitution at more than one amino acid residue, such as at 3 different amino acid residues including S298A/E333A/K334A (IgG1AAA) according to the EU index of Kabat numbering. Non-limiting exemplary IgG1 constant regions are shown in SEQ ID NOs: 18 and 19. In certain other embodiments, an antibody provided herein comprises a mouse IgG2a heavy chain constant region shown in SEQ ID NO:21.

An antibody or Fc domain may be modified to acquire or improve at least one constant region-mediated biological effector function relative to an unmodified antibody or Fc domain, e.g., to enhance FcγR interactions. In certain embodiments, a modification can increase CD32b binding (and support transdelivery in a PBMC assay) comprises a substitution at S267L and E329F (IgG1LF, also known as SELF double mutant) according to the EU index of Kabat numbering. For example, an antibody with a constant region that binds to FcγRIIA, FcγRIIB and/or FcγRIIIA with greater affinity than the corresponding wild type constant region may be produced according to the methods described herein. An Fc domain that binds to FcγRIIA, FcγRIIB and/or FcγRIIIA with greater affinity than the corresponding wild type Fc domain may be produced according to the methods described herein.

In certain embodiments, an Fc region or domain found in an anti-Nectin-4 antibody of the present disclosure will be capable of mediating one or more of these effector functions, or will lack one or more or all of these activities or have one or more of the effector activities increased by way of, for example, one or more mutations as compared to the unmodified Fc region or domain.

The antigen-recognition regions of the antibody variable domains typically comprise six complementarity determining regions (CDRs), or hypervariable regions, that lie within the framework of the heavy chain variable region and light chain variable region at the N-terminal ends of the two heavy and two light chains.

In some embodiments, an antigen binding domain comprises a light chain complementary determining region 1 (LCDR1), a light chain complementary determining region 2 (LCDR2), a light chain complementary determining region 3 (LCDR3), a heavy chain complementary determining region 1 (HCDR1), a heavy chain complementary determining region 2 (HCDR2), and a heavy chain complementary determining region 3 (HCDR3). In some embodiments, an antibody may be a heavy-chain only antibody, in which case the antigen binding domain comprises HCDR1, HCDR2, and HCDR3, and the antibody lacks a light chain.

In some embodiments, an anti-Nectin-4 antibody or antigen binding fragment thereof comprises a heavy chain CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence of SEQ ID NO:4, a VL-CDR2 comprising the amino acid sequence of SEQ ID NO:7, and a VL-CDR3 comprising the amino acid sequence comprising SEQ ID NO:8. In some such embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO:9, and a light chain variable region (VL) comprising an amino acid sequence that is at least 90%, 91%, 92%, 93%, 94%, 95%, 96%, 97%, 98%, or 99% identical to the amino acid sequence of SEQ ID NO: 11, provided that the amino acid sequences of the VH-CDRs (i.e., SEQ ID NOS:1-3) and VL-CDRs (i.e., SEQ ID NOS:4, 7, and 8) are unchanged. In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence selected from SEQ ID NO:23, and a light chain comprising an amino acid sequence that is at least 90%, 91%, 92%, 93%, 94%, 95%, 96%, 97%, 98%, or 99% identical to the amino acid sequence of SEQ ID NO:25, provided that the amino acid sequences of the VH-CDRs and VL-CDRs are unchanged.

In some embodiments, an anti-Nectin-4 antibody or antigen binding fragment thereof comprises a heavy chain CDR1 (VH-CDR1) comprising the amino acid sequence of SEQ ID NO: 1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence selected from SEQ ID NOS:4-6, a VL-CDR2 comprising the amino acid sequence of SEQ ID NO:7, and a VL-CDR3 comprising the amino acid sequence comprising SEQ ID NO:8. In some such embodiments, the antibody or antigen binding fragment thereof comprises a heavy chain variable region (VH) comprising an amino acid sequence that is at least 90%, 91%, 92%, 93%, 94%, 95%, 96%, 97%, 98%, or 99% identical to the amino acid sequence of SEQ ID NO: 10, and a light chain variable region (VL) comprising an amino acid sequence that is at least 90%, 91%, 92%, 93%, 94%, 95%, 96%, 97%, 98%, or 99% identical to the amino acid sequence selected from SEQ ID NOS: 12-17, provided that the amino acid sequences of the VH-CDRs and VL-CDRs are unchanged. In some embodiments, the antibody or antigen binding fragment thereof comprises a heavy chain comprising an amino acid sequence that is at least 90%, 91%, 92%, 93%, 94%, 95%, 96%, 97%, 98%, or 99% identical to the amino acid sequence of SEQ ID NO:24, and a light chain comprising an amino acid sequence that is at least 90%, 91%, 92%, 93%, 94%, 95%, 96%, 97%, 98%, or 99% identical to the amino acid sequence selected from SEQ ID NOS:26-31, provided that the amino acid sequences of the VH-CDRs and VL-CDRs are unchanged.

In some embodiments, an anti-Nectin-4 antibody or antigen binding fragment thereof comprises: a heavy chain CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence of SEQ ID NO:4, a VL-CDR2 comprising the amino acid sequence of SEQ ID NO:7, and a VL-CDR3 comprising the amino acid sequence comprising SEQ ID NO:8. In some such embodiments, the antibody or antigen binding fragment thereof comprises: (a) a heavy chain variable region (VH) comprising an amino acid sequence of SEQ ID NO: 10, (b) a light chain variable region (VL) comprising an amino acid sequence of SEQ ID NO: 12, or both (a) and (b).

In some embodiments, an anti-Nectin-4 antibody or antigen binding fragment thereof comprises: a heavy chain CDR1 (VH-CDR1) comprising the amino acid sequence of SEQ ID NO: 1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence of SEQ ID NO:4, a VL-CDR2 comprising the amino acid sequence of SEQ ID NO:7, and a VL-CDR3 comprising the amino acid sequence comprising SEQ ID NO:8. In certain embodiments, the antibody or antigen binding fragment thereof comprises: (a) a heavy chain variable region (VH) comprising the amino acid sequence of SEQ ID NO: 10, (b) a light chain variable region (VL) comprising the amino acid sequence of SEQ ID NO: 13, or both (a) and (b).

In some embodiments, an anti-Nectin-4 antibody or antigen binding fragment thereof comprises: a heavy chain CDR1 (VH-CDR1) comprising the amino acid sequence of SEQ ID NO: 1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence of SEQ ID NO:5, a VL-CDR2 comprising the amino acid sequence of SEQ ID NO:7, and a VL-CDR3 comprising the amino acid sequence comprising SEQ ID NO:8. In some such embodiments, the antibody or antigen binding fragment thereof comprises: (a) a heavy chain variable region (VH) comprising the amino acid sequence of SEQ ID NO: 10, (b) a light chain variable region (VL) comprising the amino acid sequence of SEQ ID NO: 14, or both (a) and (b).

In some embodiments, an anti-Nectin-4 antibody or antigen binding fragment thereof comprises: a heavy chain CDR1 (VH-CDR1) comprising the amino acid sequence of SEQ ID NO: 1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence of SEQ ID NO:6, a VL-CDR2 comprising the amino acid sequence of SEQ ID NO:7, and a VL-CDR3 comprising the amino acid sequence comprising SEQ ID NO:8. In some such embodiments, the antibody or antigen binding fragment thereof comprises: (a) a heavy chain variable region (VH) comprising the amino acid sequence of SEQ ID NO: 10, (b) a light chain variable region (VL) comprising the amino acid sequence of SEQ ID NO: 15, or both (a) and (b).

In some embodiments, an anti-Nectin-4 antibody or antigen binding fragment thereof comprises: a heavy chain CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence of SEQ ID NO:6, a VL-CDR2 comprising the amino acid sequence of SEQ ID NO:7, and a VL-CDR3 comprising the amino acid sequence comprising SEQ ID NO:8. In some such embodiments, the antibody or antigen binding fragment thereof comprises: (a) a heavy chain variable region (VH) comprising the amino acid sequence of SEQ ID NO: 10, (b) a light chain variable region (VL) comprising the amino acid sequence of SEQ ID NO: 16, or both (a) and (b).

In some embodiments, an anti-Nectin-4 antibody or antigen binding fragment thereof comprises: a heavy chain CDR1 (VH-CDR1) comprising the amino acid sequence of SEQ ID NO: 1, a VH-CDR2 comprising the amino acid sequence of SEQ ID NO:2, a VH-CDR3 comprising the amino acid sequence of SEQ ID NO:3, a light chain CDR1 (VL-CDR1) comprising the amino acid sequence of SEQ ID NO:5, a VL-CDR2 comprising the amino acid sequence of SEQ ID NO:7, and a VL-CDR3 comprising the amino acid sequence comprising SEQ ID NO:8. In some such embodiments, the antibody or antigen binding fragment thereof comprises: (a) a heavy chain variable region (VH) comprising the amino acid sequence of SEQ ID NO: 10, (b) a light chain variable region (VL) comprising the amino acid sequence of SEQ ID NO: 17, or both (a) and (b).

In some embodiments, an anti-Nectin-4 antibody or antigen binding fragment thereof comprises: (a) a heavy chain variable region (VH) comprising the amino acid sequence of SEQ ID NO:9, and a light chain variable region (VL) comprising the amino acid of SEQ ID NO: 11; or (b) a heavy chain variable region (VH) comprising the amino acid sequence of SEQ ID NO: 10, and a light chain variable region (VL) comprising the amino acid sequence selected from SEQ ID NOs:12-17.

In some such embodiments, the antibody or antigen binding fragment thereof comprises a heavy chain variable region (VH) comprising the amino acid sequence of SEQ ID NO: 10 and a light chain variable region (VL) comprising the amino acid sequence of SEQ ID NO: 12.

In some such embodiments, the antibody or antigen binding fragment thereof comprises a heavy chain variable region (VH) comprising the amino acid sequence of SEQ ID NO: 10 and a light chain variable region (VL) comprising the amino acid sequence of SEQ ID NO: 13.

In some such embodiments, the antibody or antigen binding fragment thereof comprises a heavy chain variable region (VH) comprising the amino acid sequence of SEQ ID NO: 10 and a light chain variable region (VL) comprising the amino acid sequence of SEQ ID NO: 14.

In some such embodiments, the antibody or antigen binding fragment thereof comprises a heavy chain variable region (VH) comprising the amino acid sequence of SEQ ID NO: 10 and a light chain variable region (VL) comprising the amino acid sequence of SEQ ID NO: 15.

In some such embodiments, the antibody or antigen binding fragment thereof comprises a heavy chain variable region (VH) comprising the amino acid sequence of SEQ ID NO: 10 and a light chain variable region (VL) comprising the amino acid sequence of SEQ ID NO: 16.

In some such embodiments, the antibody or antigen binding fragment thereof comprises a heavy chain variable region (VH) comprising the amino acid sequence of SEQ ID NO: 10 and a light chain variable region (VL) comprising the amino acid sequence of SEQ ID NO: 17.

In some embodiments, an anti-Nectin-4 antibody comprises: (a) a heavy chain comprising the amino acid sequence of SEQ ID NO:23, and a light chain comprising the amino acid sequence of SEQ ID NO:25; or (b) a heavy chain comprising the amino acid sequence of SEQ ID NO:24, and a light chain comprising the amino acid sequence selected from SEQ ID NOS:26-31.

In some such embodiments, the antibody comprises a heavy chain comprising the amino acid sequence of SEQ ID NO:24 and a light chain comprising the amino acid sequence of SEQ ID NO:26.

In some such embodiments, the antibody comprises a heavy chain comprising the amino acid sequence of SEQ ID NO:24 and a light chain comprising the amino acid sequence of SEQ ID NO:27.

In some such embodiments, the antibody comprises a heavy chain comprising the amino acid sequence of SEQ ID NO:24 and a light chain comprising the amino acid sequence of SEQ ID NO:28.

In some such embodiments, the antibody comprises a heavy chain comprising the amino acid sequence of SEQ ID NO:24 and a light chain comprising the amino acid sequence of SEQ ID NO:29.

In some such embodiments, the antibody comprises a heavy chain comprising the amino acid sequence of SEQ ID NO:24 and a light chain comprising the amino acid sequence of SEQ ID NO:30.

In some such embodiments, the antibody comprises a heavy chain comprising the amino acid sequence of SEQ ID NO:24 and a light chain comprising the amino acid sequence of SEQ ID NO:31.

In any of the aforementioned embodiments, the anti-Nectin-4 antibody or antigen binding fragment thereof is conjugated to a small molecule drug to form an antibody drug conjugate. In certain embodiments, the small molecule drug is a myeloid cell agonist (e.g., TLR8 agonist) as disclosed herein, thus forming a myeloid cell agonist conjugate.

An anti-Nectin-4 antibody or antigen binding fragment thereof can be chimeric or humanized. Chimeric and humanized forms of non-human (e.g., murine) antibodies can be intact (full length) chimeric immunoglobulins, immunoglobulin chains or antigen binding fragments thereof (such as Fv, Fab, Fab', F(ab')₂ or other target-binding subdomains of antibodies), which can contain sequences derived from non-human immunoglobulin. In general, the humanized antibody or antigen binding fragment thereof can comprise substantially all of at least one, and typically two, variable domains, in which all or substantially all of the CDR regions correspond to those of a non-human immunoglobulin and all or substantially all of the framework (FR) regions are those of a human immunoglobulin sequence. A humanized antibody can also comprise at least a portion of an immunoglobulin constant region (Fc), an Fc domain, typically that of a human immunoglobulin sequence.

An anti-Nectin-4 antibody or antigen binding fragment thereof described herein can be a human antibody. As used herein, "human antibodies" can include antibodies having, for example, the amino acid sequence of a human immunoglobulin and include antibodies isolated from human immunoglobulin libraries or from animals transgenic for one or more human immunoglobulins and that typically do not express endogenous immunoglobulins. Human antibodies can be produced using transgenic mice incapable of expressing functional endogenous immunoglobulins, but capable of expressing human immunoglobulin genes. Completely human antibodies that recognize a selected epitope can be generated using guided selection. In this approach, a selected non-human monoclonal antibody, e.g., a mouse antibody, is used to guide the selection of a completely human antibody recognizing the same epitope.

An anti-Nectin-4 antibody or antigen binding fragment thereof described herein can be a bispecific antibody or a dual variable domain antibody (DVD). Bispecific and DVD antibodies are monoclonal, often human or humanized, antibodies that have binding specificities for at least two different antigens, one of which is Nectin-4.

An anti-Nectin-4 antibody or antigen binding fragment thereof described herein can be derivatized or otherwise modified. For example, derivatized antibodies can be modified by glycosylation, acetylation, pegylation, phosphorylation, amidation, derivatization by known protecting/blocking groups, proteolytic cleavage, or the like.

Antibody CDRs

Nectin-4 antibody CDR sequences may be determined by one or more methods, including Kabat, Chothia, AbM, Contact, IMGT and AHo (see Table A below). Unless otherwise specified herein, CDR sequences are determined according to the Kabat method. References to variable region or CDR numbering as in Kabat, amino acid position numbering as in Kabat, or CDR sequences determined according to the Kabat method, and variations thereof, refer to the numbering system used for heavy chain variable regions or light chain variable regions of the compilation of antibodies in Kabat et al. ((1991) *Sequences of Proteins of Immunological Interest*, Fifth Edition, U.S. Department of Health and Human Services, NIH Publication No. 91-3242). Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra).

The "EU numbering system" or "EU index" is generally used when referring to a residue in an immunoglobulin heavy chain constant region (e.g., the EU index reported in Kabat et al., supra). The "EU index, as in Kabat," refers to the residue numbering of the human IgG 1 EU antibody.

Other numbering systems have been described, for example, by AbM (Oxford Molecular's AbM antibody modeling software (see, e.g., *Antibody Engineering Vol. 2* (Kontermann and Dithel eds., 2d ed. 2010)), Chothia (see, Chothia and Lesk, 1987, J. Mol. Biol. 196:901-17), Contact, IMGT (ImMunoGeneTics (IMGT) Information System® (see, Lafranc et al., 2003, Dev. Comp. Immunol. 27(1):55-77)), and AHon (see, Honegger and Plückthun, 2001, J. Mol. Biol. 309: 657-70) and are well understood by a person of ordinary skill in the art.

In certain embodiments, an anti-Nectin-4 antibody of this disclosure is comprised of (a) a heavy chain variable region (VH) comprising a CDR1 (VH-CDR1) comprising the amino acid sequence of SEQ ID NO:1, a VH-CDR2 comprising the amino acid sequence of SEQ ID NO:2, and a VH-CDR3 comprising the amino acid sequence of SEQ ID NO:3; and (b) a light chain variable region (VL) comprising a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8.

In further embodiments, an anti-Nectin-4 antibody of this disclosure is comprised of (a) a VH comprising a CDR1 (VH-CDR1) comprising the amino acid sequence of SEQ ID NO:33, a VH-CDR2 comprising the amino acid sequence of SEQ ID NO:34, and a VH-CDR3 comprising the amino acid sequence of SEQ ID NO:35; and (b) a VL comprising a CDR1 (VL-CDR1) comprising the amino acid sequence of SEQ ID NO:36, a VL-CDR2 comprising the amino acid sequence of SEQ ID NO:37, and a VL-CDR3 comprising the amino acid sequence of SEQ ID NO:38.

In still further embodiments, an anti-Nectin-4 antibody of this disclosure is comprised of (a) a VH comprising a CDR1 (VH-CDR1) comprising the amino acid sequence of SEQ ID NO:39, a VH-CDR2 comprising the amino acid sequence of SEQ ID NO:40, and a VH-CDR3 comprising the amino acid sequence of SEQ ID NO:41; and (b) a VL comprising a CDR1 (VL-CDR1) comprising the amino acid sequence of SEQ ID NO:42, a VL-CDR2 comprising the amino acid sequence of SEQ ID NO:43, and a VL-CDR3 comprising the amino acid sequence of SEQ ID NO:44.

In yet further embodiments, an anti-Nectin-4 antibody of this disclosure is comprised of (a) a VH comprising a CDR1 (VH-CDR1) comprising the amino acid sequence of SEQ ID NO:45, a VH-CDR2 comprising the amino acid sequence of SEQ ID NO:46, and a VH-CDR3 comprising the amino acid sequence of SEQ ID NO:47; and (b) a VL comprising a CDR1 (VL-CDR1) comprising the amino acid sequence of SEQ ID NO:48, a VL-CDR2 comprising the amino acid sequence of SEQ ID NO:49, and a VL-CDR3 comprising the amino acid sequence of SEQ ID NO:50.

In yet further embodiments, an anti-Nectin-4 antibody of this disclosure is comprised of (a) a VH comprising a CDR1 (VH-CDR1) comprising the amino acid sequence of SEQ ID NO:51, a VH-CDR2 comprising the amino acid sequence of SEQ ID NO:52, and a VH-CDR3 comprising the amino acid sequence of SEQ ID NO:53; and (b) a VL comprising a CDR1 (VL-CDR1) comprising the amino acid sequence of SEQ ID NO:54, a VL-CDR2 comprising the amino acid sequence of SEQ ID NO:55, and a VL-CDR3 comprising the amino acid sequence of SEQ ID NO:56.

In yet further embodiments, an anti-Nectin-4 antibody of this disclosure is comprised of (a) a VH comprising a CDR1 (VH-CDR1) comprising the amino acid sequence of SEQ ID NO:57, a VH-CDR2 comprising the amino acid sequence of SEQ ID NO:58, and a VH-CDR3 comprising the amino acid sequence of SEQ ID NO:59; and (b) a VL comprising a CDR1 (VL-CDR1) comprising the amino acid sequence of SEQ ID NO:60, a VL-CDR2 comprising the amino acid sequence of SEQ ID NO:61, and a VL-CDR3 comprising the amino acid sequence of SEQ ID NO:62.

TABLE A

Anti-Nectin4 CDRs

| Antibody CDR Identity | Kabat | Chothia | Abm | Contact | IMGT | AHo |
|---|---|---|---|---|---|---|
| D6C VH CDR1 | NYDMS (SEQ ID NO: 1) | GFTFSNY (SEQ ID NO: 33) | GFTFSNYDMS (SEQ ID NO: 39) | SNYDMS (SEQ ID NO: 45) | GFTFSNYD (SEQ ID NO: 51) | SGFTFSNYDM (SEQ ID NO: 57) |
| D6C VH CDR2 | TISSGGSYTY YVDSVKG (SEQ ID NO: 2) | SSGGSY (SEQ ID NO: 34) | TISSGGSYTY (SEQ ID NO: 40) | WVATISSGG SYTY (SEQ ID NO: 46) | ISSGGSYT (SEQ ID NO: 52) | SSGGSYTYYVDS VKGRF (SEQ ID NO: 58) |
| D6C VH CDR3 | QELGSYYAM DY (SEQ ID NO: 3) | QELGSYYAMD Y (SEQ ID NO: 35) | QELGSYYAMD Y (SEQ ID NO: 41) | ARQELGSYY AMD (SEQ ID NO: 47) | ARQELGSYY AMDY (SEQ ID NO: 53) | ELGSYYAMDY (SEQ ID NO: 59) |
| D6.2C and D6.5C VL CDR1 | RSSQSIVHSN ANTYLE (SEQ ID NO: 5) | RSSQSIVHSNG NTYLE (SEQ ID NO: 36) | RSSQSIVHSNG NTYLE (SEQ ID NO: 42) | VHSNGNTYL EWY (SEQ ID NO: 48) | QSIVHSNGNT Y (SEQ ID NO: 54) | SSQSIVHSNGNT Y (SEQ ID NO: 60) |
| D6C VL CDR2 | KVSNRFS (SEQ ID NO: 7) | KVSNRFS (SEQ ID NO: 37) | KVSNRFS (SEQ ID NO: 43) | LLIYKVSNR F (SEQ ID NO: 49) | KVS (SEQ ID NO: 55) | KVSNRFSGVPDR (SEQ ID NO: 61) |
| D6C VL CDR3 | FQGSHVPYT (SEQ ID NO: 8) | FQGSHVPYT (SEQ ID NO: 38) | FQGSHVPYT (SEQ ID NO: 44) | FQGSHVPY (SEQ ID NO: 50) | FQGSHVPYT (SEQ ID NO: 56) | GSHVPYTF (SEQ ID NO: 62) |

Nucleic Acids. Vectors, and Host Cells

The present disclosure provides an isolated nucleic acid that encodes anti-Nectin-4 antibody or antigen binding fragment thereof as described herein. In some embodiments, the nucleic acid encoding the anti-Nectin-4 antibody or antigen binding fragment thereof is codon optimized to enhance or maximize expression in certain types of cells (e.g., Scholten et al., *Clin. Immunol.* 119: 135-145, 2006). As used herein a "codon optimized" polynucleotide is a heterologous polypeptide having codons modified with silent mutations corresponding to the abundances of host cell tRNA levels.

In some embodiments, a nucleic acid molecule encodes an anti-Nectin-4 antibody or antigen binding fragment thereof (e.g., an antibody heavy and light chains, or an antibody binding domain comprising VH and VL binding regions) as disclosed herein wherein two or more chains or regions are separated by a cleavage site. In some embodiments, the cleavage site is a self-cleaving amino acid sequence comprising a 2A peptide from porcine teschovirus-1 (P2A), equine rhinitis A virus (E2A), *Thosea asigna* virus (T2A), foot-and-mouth disease virus (F2A), or any combination thereof (see, e.g., Kim et al., *PLOS One* 6:e18556, 2011, which 2A nucleic acid and amino acid sequences are incorporated herein by reference in their entirety).

In another aspect, an expression construct comprising a nucleic acid encoding an anti-Nectin-4 antibody or antigen binding fragment thereof as described herein is provided. In some embodiments, a nucleic acid may be operably linked to an expression control sequence. As used herein, "expression construct" refers to a DNA construct containing a nucleic acid molecule that is operably-linked to a suitable control sequence capable of effecting the expression of the nucleic acid molecule in a suitable host. An expression construct may be present in a vector (e.g., a bacterial vector, a viral vector) or may be integrated into a genome. The term "operably linked" refers to the association of two or more nucleic acids on a single polynucleotide fragment so that the function of one is affected by the other. For example, a promoter is operably-linked with a coding sequence when it is capable of affecting the expression of that coding sequence (i.e., the coding sequence is under the transcriptional control of the promoter). The term "expression control sequence" (also called a regulatory sequence) refers to nucleic acid sequences that effect the expression and processing of coding sequences to which they are operably linked. For example, expression control sequences may include transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In some embodiments, a nucleic acid or an expression construct encoding an anti-Nectin-4 antibody or antigen binding fragment thereof is present in a vector. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) or expression of nucleic acids to which they are linked (expression vectors). Exemplary viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996). In some embodiments, a vector is a plasmid. In some other embodiments, a vector is a viral vector. In some such embodiments, the viral vector is a lentiviral vector or a γ-retroviral vector.

In yet another aspect, the disclosure provides an isolated host cell comprising a nucleic acid, expression construct, or vector encoding an anti-Nectin-4 antibody or antigen binding fragment thereof, as described herein. As used herein, the term "host" refers to a cell or microorganism targeted for genetic modification with a heterologous or exogenous nucleic acid molecule to produce a polypeptide of interest (e.g., an anti-Nectin-4 antibody or antigen-binding fragment thereof). In certain embodiments, a host cell may optionally already possess or be modified to include other genetic modifications that confer desired properties related or unrelated to biosynthesis of the heterologous or exogenous protein (e.g., inclusion of a detectable marker). More than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When two or more exogenous nucleic acid molecules are introduced into a host cell, it is understood that the two more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell.

Methods for Producing Ant-Nectin-4 Antibodies

Anti-Nectin-4 antibodies or antigen binding fragments thereof of this disclosure can be produced by any method known in the art for antibody production. As one example, an anti-Nectin-4 antibody or antigen binding fragment can be produced by a method using an isolated nucleic acid sequence encoding an anti-Nectin-4 antibody or antigen binding fragment thereof, vectors and host cells comprising the nucleic acid sequence, and recombinant techniques for the production of the antibody or antigen binding fragment thereof. The nucleic acid sequence encoding the anti-Nectin-4 antibody or antigen binding fragment thereof can be isolated into a replicable DNA vector for further cloning or for expression. DNA encoding an anti-Nectin-4 antibody or antigen binding fragment thereof can be readily isolated and sequenced using conventional procedures (e.g., by using oligonucleotide probes that are capable of binding specifically to genes encoding the heavy and light chains of the antibody). Many vectors known in the art can be used as a vector. The vector components generally can include, but are not limited to, one or more of the following: a signal sequence, an origin of replication, one or more marker genes, an enhancer element, a promoter, and a transcription-termination sequence.

Suitable host cells for cloning or expressing the DNA vectors herein can be prokaryote, yeast, or higher eukaryote cells described herein. Suitable host cells for expression of glycosylated antibody or antigen binding fragment can be derived from multicellular organisms. Examples of invertebrate cells can include, but are not limited to, plant and insect cells. Host cells used to produce an antibody or antigen binding fragment can be cultured in a variety of commercial media. When using recombinant techniques, an antibody or antigen binding fragment can be produced, for example, intracellularly, in the periplasmic space, or directly secreted into the medium. If the antibody or antigen binding fragment is produced intracellularly, the particulate debris, either host cells or lysed fragments, can be removed, for example, by centrifugation or ultrafiltration. Where the antibody or antigen binding fragment is secreted into the medium, supernatants from such expression systems can be concentrated using a commercially available protein concentration filter. A protease inhibitor such as phenylmethylsulphonyl fluoride can be included in any of the foregoing steps to inhibit proteolysis, and antibiotics can be included to prevent the growth of adventitious contaminants.

An anti-Nectin-4 antibody or antigen binding fragment thereof composition prepared from the cells can be purified using, for example, hydroxylapatite chromatography, gel electrophoresis, dialysis, and affinity chromatography. The suitability of a protein A as an affinity ligand can depend on the species and isotype of any immunoglobulin Fc domain that may be present in the antibody or antigen binding fragment. Other techniques for protein purification such as fractionation on the an ion-exchange column, ethanol precipitation, reverse-phase HPLC, chromatography on silica, chromatography on heparin SEPHAROSE™, chromatography on an anion- or cation-exchange resin (such as a polyaspartic acid column), chromatofocusing, SDS-PAGE, and ammonium-sulfate precipitation can also be used to recover the antibody or antigen binding fragment. Following any preliminary purification step(s), the mixture comprising the antibody or antigen binding fragment and contaminants can be subjected to low-pH hydrophobic-interaction chromatography. The methods for humanizing antibodies can include, for example, humanization uses CDR grafting (Jones et al., Nature 15 321:522 (1986)) and variants thereof, including "reshaping" (Verhoeyen, et al., 1988 Science 239: 1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 J Immunol 148:1149-1154), and "veneering" (Mark, et al., B W Metcalf, B J Dalton (Eds.) Cellular adhesion: molecular definition to therapeutic potential. Plenum Press, New York; 1994:291-312). Superhumanization (Tan, et al., 2002 J Immunol 169: 1119-25) is another variant humanization method that can be used to graft non-human CDRs into human germline antibody sequences having similar CDR canonical structures.

In certain embodiments, the anti-Nectin-4 antibodies or antigen binding fragments thereof of this disclosure, or conjugates thereof having a myeloid cell agonist, are humanized.

Immune-Stimulatory Compounds

Anti-Nectin-4 antibodies or antigen binding fragments thereof of this disclosure are attached to immune stimulatory compounds (e.g., TLR8 agonist), generally via a linker(s) to form immune-stimulatory conjugates. An anti-Nectin-4 antibody or antigen binding fragment thereof of this disclosure can be attached to one or more immune-stimulatory compounds, generally from about 1 to about 10 compounds per antibody or antigen binding fragment thereof, and preferably from about 2 to about 4 compounds per antibody or antigen binding fragment thereof.

In some embodiments, an immune stimulatory compound activates human immune cells, such as dendritic cells, macrophages, monocytes, myeloid-derived suppressor cells, NK cells, B cells, T cells, or a combination thereof. In some embodiments, an immune-stimulatory compound is a myeloid cell agonist. A myeloid cell agonist is a compound that activates or stimulates an immune response by a myeloid cell. For example, a myeloid cell agonist can stimulate an immune response by causing the release of cytokines by myeloid cells, which results in the activation of immune cells. The stimulation of an immune response by a myeloid cell agonist can be measured in vitro by co-culturing immune cells (e.g., peripheral blood mononuclear cells (PBMCs)) with cells targeted by the conjugate and measuring cytokine release, chemokine release, proliferation of immune cells, upregulation of immune cell activation markers, ADCP, and/or ADCC. Exemplary assays are described in the Examples. ADCC can be measured by determining the percentage of remaining target cells in the co-culture after administration of the conjugate with the target cells and PBMCs.

For example, an immune stimulatory compound can act on toll like receptors (TLRs), nucleotide-oligomerization domain-like receptors (NOD), RIG-I-Like receptors (RLR), c-type lectin receptors (CLR), or cytosolic DNA Sensors (CDS), or a combination thereof.

In some embodiments, an immune stimulatory compound comprises a ligand of one or more TLRs selected from the group consisting of: TLR2, TLR3, TLR4, TLR5, TLR7, TLR8, TLR9, and TLR10.

In some embodiments, an immune-stimulatory compound is a myeloid cell agonist. In some embodiments, a myeloid cell agonist is a ligand of TLR2 selected from the group consisting of: (a) a heat killed bacteria product, preferably HKAL, HKEB, HKHP, HKLM, HKLP, HKLR, HKMF, HKPA, HKPG, or HKSA, HKSP, and (b) a cell-wall components product, preferably LAM, LM, LPS, LIA, LIA, PGN, FSL, Pam2CSK4, Pam3CSK4, or Zymosan.

In some embodiments, a myeloid cell agonist is a ligand of TLR3 selected from the group consisting of: rintatolimod, poly-ICLC, RIBOXXON®, Apoxxim, RIBOXXIM®, IPH-33, MCT-465, MCT-475, and ND-1.1.

In some embodiments, a myeloid cell agonist is a ligand of TLR4 selected from the group consisting of LPS, MPLA or a pyrimido[5,4-b]indole such as those described in International Publication No. WO 2014/052828 (Regents of the University of California).

In some embodiments, the myeloid cell agonist is a ligand of TLR5 selected from the group consisting of: FLA and Flagellin.

In some embodiments, the myeloid cell agonist is a ligand of TLR6.

In certain embodiments, a myeloid cell agonist is a TLR7 agonist and/or a TLR8 agonist. In certain embodiments, the myeloid cell agonist is a TLR7 agonist. In certain embodiments, the myeloid cell agonist is a TLR8 agonist. In some embodiments, the myeloid cell agonist selectively agonizes TLR7 and not TLR8. In other embodiments, the myeloid cell agonist selectively agonizes TLR8 and not TLR7.

In certain embodiments, a myeloid cell agonist is a TLR7 agonist. In certain embodiments, the TLR7 agonist is selected from an imidazoquinoline, an imidazoquinoline amine, a thiazoquinoline, an aminoquinoline, an aminoquinazoline, a pyrido[3,2-d]pyrimidine-2,4-diamine, a pyrimidine-2,4-diamine, a 2-aminoimidazole, an 1-alkyl-1H-benzimidazol-2-amine, a tetrahydropyridopyrimidine, a heteroarothiadiazide-2,2-dioxide, a benzonaphthyridine, a thieno[3,2-d]pyrimidine, a 4-amino-imidazoquinoline, an imidazo-pyridinone, an imidazo-pyrimidinone, a purine, a fused pyrimidine-lactam, an imidazo[4,5-c]quinoline-4-amine, an imidazo[4,5-c]quinoline, a pyrimidine, a benzazepine, an imidazo-pyridine, a pyrrolo-pyrimidine, a 2-amino-quinazoline, a guanosine analog, an adenosine analog, a thymidine homopolymer, an ssRNA, CpG-A, PolyG10, and PolyG3. In certain embodiments, the TLR7 agonist is selected from an imidazoquinoline, an imidazoquinoline amine, a thiazoquinoline, an aminoquinoline, an aminoquinazoline, a pyrido[3,2-d]pyrimidine-2,4-diamine, a pyrimidine-2,4-diamine, a 2-aminoimidazole, a 1-alkyl-1H-benzimidazol-2-amine, a tetrahydropyridopyrimidine, a heteroarothiadiazide-2,2-dioxide, a benzonaphthyridine, a thieno[3,2-d]pyrimidine, a 4-amino-imidazoquinoline, an imidazo-pyridinone, an imidazo-pyrimidinone, a purine, a fused pyrimidine-lactam, an imidazo[4,5-c]quinoline-4-amine, an imidazo[4,5-c]quinoline, a pyrimidine, a benzazepine, an imidazo-pyridine, a pyrrolo-pyrimidine, and a 2-amino-quinazoline, but is other than a guanosine analog, an adenosine analog, a thymidine homopolymer, an ssRNA, CpG-A, PolyG10, and PolyG3. In some embodiments, a TLR7 agonist is a non-naturally occurring compound. Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the TLR7 modulator compounds disclosed in US Patent Application Publication No. US 2016/0168164 (Janssen, thieno[3,2-d]pyrimidine derivatives), US Patent Application Publication No. US 2015/0299194 (Roche, 4-amino-imidazoquinoline derivatives), US Patent Application Publication No. US 2011/0098248 (Gilead Sciences, imidazo-pyridinone, imidazo-pyrimidinone, and purine derivatives), US Patent Application Publication No. US 2010/0143301 (Gilead Sciences, fused pyrimidine-lactam derivatives), and US Patent Application Publication No. US 20090047249 (Gilead Sciences, purine derivatives), and these publications are incorporated by reference herein. Further examples of TLR7 modulators include compounds disclosed in International Publication No. WO 2018/009916 (Stanford University/Bolt Biotherapeutics, imidazo[4,5-c]quinolin-4-amine derivatives), International Publication No. WO 2018/112108 (Bolt Biotherapeutics, imidazo[4,5-c]quinoline, pyrimidine, benzazepine, imidazo-pyridine, pyrrolo-pyrimidine, and purine derivatives), US Patent Application Publication No. US 2019/0055247 (Bristol-Myers Squibb, purine derivatives), International Publication No. WO 2018/198091 (Novartis, pyrrolo-pyrimidine derivatives), US Patent Application Publication No. US 2017/0121421 (Novartis, pyrrolo-pyrimidine derivatives), U.S. Pat. No. 10,253,003 (Janssen, 2-amino-quinazoline derivatives), and U.S. Pat. No. 10,233,184 (Roche, imidazo-pyrimidinone derivatives), and these publications are incorporated by reference herein. In some embodiments, a TLR7 agonist has an EC50 value of 500 nM or less by PBMC assay measuring TNFalpha or IFNalpha production. In some embodiments, a TLR7 agonist has an EC50 value of 100 nM or less by PBMC assay measuring TNFalpha or IFNalpha production. In some embodiments, a TLR7 agonist has an EC50 value of 50 nM or less by PBMC assay measuring TNFalpha or IFNalpha production. In some embodiments, a TLR7 agonist has an EC50 value of 10 nM or less by PBMC assay measuring TNFalpha or IFNalpha production.

In certain embodiments, the myeloid cell agonist is a TLR8 agonist. In certain embodiments, a TLR8 agonist is selected from the group consisting of a benzazepine, an imidazoquinoline, a thiazoloquinoline, an aminoquinoline, an aminoquinazoline, a pyrido[3,2-d]pyrimidine-2,4-diamine, a pyrimidine-2,4-diamine, a 2-aminoimidazole, an 1-alkyl-1H-benzimidazol-2-amine, a tetrahydropyridopyrimidine, a pyrido[3,2-d]pyrimidine, a dihydropyrimidinyl benzazepine carboxamide, a benzo[b]azepine, benzazepine dicarboxamide derivatives with a tertiary amide, benzazepine dicarboxamide derivatives with a secondary amide, a quinazoline, a pyrido[3,2-d]pyrimidine, a diamino-pyrimidine, an amino-quinazoline, a heterocyclic-substituted 2-amino-quinazoline, a diamino-pyrimidine, a piperidino-pyrimidine, an alkylamino-pyrimidine, an 8-substituted benzoazepine, an amino-diazepine, an amino-benzo-diazepine, an amido-indole, an amido-benzimidazole, a phenyl sulfonamide, a dihydropteridinone, a fused amino-pyrimidine, a quinazoline, a pyrido-pyrimidine, an amino-substituted benzazepine, a pyrrolo-pyridine, an imidazo-pyridine derivatives, and an amino-benzazepine, and is other than a ssRNA. In some embodiments, a TLR8 agonist is a non-naturally occurring compound. Examples of TLR8 agonists include selgantolimod, motolimod, resiquimod, 3M-051, 3M-052, MCT-465, IMO-4200, VTX-763, VTX-1463, and the TLR8 modulator compounds disclosed in US Patent Application Publication No. US 2018/0086755 (Gilead, pyrido[3,2-d]pyrimidine derivatives), International Publication No. WO 2017216054 (Roche, dihydropyrimidinyl benzazepine carboxamide derivatives), International Publication No. WO 2017/190669 (Shanghai De Novo Pharmatech, benzo[b]azepine derivatives), International Publication No. WO 2016/142250 (Roche, benzazepine dicarboxamide derivatives), International Publication No. WO 2017/202704 (Roche, benzazepine dicarboxamide derivatives with a tertiary amide), International Publication No. WO2 017/202703 (Roche, benzazepine dicarboxamide derivatives with a secondary amide), US Patent Application Publication No. US 2017/0071944 (Gilead, quinazoline and pyrido[3,2-d]pyrimdine derivatives), US Patent Application Publication No. US 2014/0045849 (Janssen, diamino-pyrimidine derivatives), US Patent Application Publication No. US 2014/0073642 (Janssen, amino-quinazoline derivatives), International Publication No. WO 2014/056953 (Janssen, pyrrolo[3,2-d]pyrimidine derivatives), International Publication No. WO 2014/076221 (Janssen, heterocyclic substituted 2-amino-quinazoline derivatives), International Publication No. WO 2014/128189 (Janssen, diamino-pyrimidine derivatives), US Patent Application Publication No. 2014/0350031 (Janssen, piperidino-pyrimidine derivatives), International Publication No. WO2014/023813 (Janssen, alkylaminopyrimidine derivatives), US Patent Application Publication No. US 2008/0234251 (Array Biopharma, 8-substituted benzoazepine derivatives), US Patent Application Publication No. US 2008/0306050 (Array Biopharma, amino-diazepine derivatives), US Patent Application Publication No. US 2010/0029585 (VentiRx Pharma, amino-benzazepine derivatives), US Patent Application Publication No. US 2011/0092485 (VentiRx Pharma, amino-benzazepine derivatives), US Patent Application Publication No. US 2011/0118235 (VentiRx Pharma, amino-benzazepine derivatives), US Patent Application Publication No. US 2012/0082658 (VentiRx Pharma, amino-benzazepine VTX-378), US Patent Application Publication No. US 2012/0219615 (VentiRx Pharma), US Patent Application Publication No. US 2014/0066432 (VentiRx Pharma, amino-benzazepine VTX-2337), US Patent Application Publication No. US 2014/0088085 (VentiRx Pharma, amino-benzazepine and amino-benzo-diazepine derivatives), US Patent Application Publication No. US 2014/0275167 (Novira Therapeutics, amido-indole and amido-benzimidazole derivatives), and US Patent Application Publication No. US 2013/0251673 (Novira Therapeutics, phenyl sulfonamide derivatives), and these publications are incorporated by reference herein. Further examples of TLR8 modulators include compounds disclosed in US Patent Application Publication No. US 2016/0108045 (Gilead, dihydropteridinone derivatives), US Patent Application Publication No. US 2018/0065938 (Gilead, fused amino-pyrimidine derivatives), US Patent Application Publication No. US 2018/0263985 (Gilead, quinazoline and pyrido-pyrimidine derivatives), International Publication No. WO 2017/046112 (Roche, amino-substituted benzazepine derivatives), International Publication No. WO 2016/096778 (Roche, amino-substituted benzazepine derivatives), US Patent Application Publication No. 2019/0016808 (Birdie Biopharmaceuticals, pyrrolo- or imidazo-pyridine derivatives or amino-benzazepine derivatives), and these publications are incorporated by reference herein. In some embodiments, the TLR8 agonist comprises the structure:

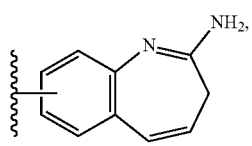

wherein the structure is optionally substituted at any position other than the —NH$_2$ position. In some embodiments, a TLR8 agonist has an EC50 value of 500 nM or less by PBMC assay measuring TNFalpha production. In some embodiments, a TLR8 agonist has an EC50 value of 100 nM or less by PBMC assay measuring TNFalpha production. In some embodiments, a TLR8 agonist has an EC50 value of 50 nM or less by PBMC assay measuring TNFalpha production. In some embodiments, a TLR8 agonist has an EC50 value of 10 nM or less by PBMC assay measuring TNFalpha production.

In some embodiments, a TLR8 agonist is a benzazepine selected from compounds provided herein (e.g., compounds of Category A and Category C).

In some embodiments, a myeloid cell agonist is a ligand of TLR9 selected from the group consisting of: ODN1585, ODN1668, ODN1826, PF-3512676 (ODN2006), ODN2007, ODN2216, ODN2336, ODN2395, BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

In other embodiments, the myeloid agonist selectively agonizes TLR9, TLR3, TLR4, TLR2, TLR5, RIG-I, STING, cGAS, NOD1, NOD2, NOD1/NOD2, NRLP3, ALPK1, MDA5 AIM2, IRE1 and PERK.

In some embodiments, a myeloid cell agonist is a ligand of TLR10.

In some embodiments, a myeloid cell agonist is a ligand of a ligand of nucleotide-oligomerization domain (NOD)-like selected from the group consisting of: NOD1 agonist (C12-iE-DAP, iE-DAP, Tri-DAP), NOD2 agonist (L18-MDP, MDP, M-TriLYS, M-TriLYS-D-ASN, Murabutide, N-Glycolyl-MDP), and NOD1/NOD2 agonists (M-TriDAP, PGN).

In some embodiments, a myeloid cell agonist is a ligand of one or more RIG-I-Like receptors (RLR) selected from the group consisting of: S'ppp-dsRNA, Poly (dA:dT), Poly (dG:dC), and Poly (I:C).

In some embodiments, a myeloid cell agonist is a ligand of one or more C-type lectin receptors (CLR) selected from the group consisting of: Cnrdlan AL, HKCA, HKSC, WGP, Zymosan, and Trehalose-6,6-dibehenate.

In some embodiments, a myeloid cell agonist is a ligand of one or more Cytosolic DNA Sensors (CDS) selected from the group consisting of: ADU-S100, c-GMP, c-G-AMP, c-G-GMP, c-A-AMP, c-di-AMP, c-di-IMP, c-di-GMP, c-di-UMP, HSV-60, ISD, pCpG, Poly (dA:dT), Poly(dG:dC), Poly (dA), VACV-70 and α-mangostin and the compounds disclosed in International Publication No. WO 2018/156625 (U of Texas), International Publication No. WO 2018/152453 (Eisai), International Publication No. WO 2018/138685 (Janssen), International Publication No. WO 2018/100558 (Takeda), International Publication No. WO 2018/098203 (Janssen), International Publication No. WO 2018/065360 (Biolog Life Sciences), International Publication No. WO 2018/060323 (Boehringer Ingelheim), International Publication No. WO 2018/045204 (IFM Therapeutics), International Publication No. WO 2018/009466 (Aduro), International Publication No. WO 2017/161349 (Immune Sensor), International Publication No. WO 2017/123669, International Publication No. WO 2017/123657, International Publication No. WO 2017/027646 (Merck), International Publication No. WO 2017/027645 (Merck), International Publication No. WO2016/120305 (GSK), International Publication No. WO 2016/096174 (InvivoGen), and US Patent Application Publication No. US 2014/0341976 (Aduro).

In some embodiments, the myeloid cell agonist is a ligand of an inflammasome inducer selected from the group consisting of: (a) NLRP3 inflammasome protein complex, preferably alum Crystals, ATP, CPPD Crystals, Hennozoin, MSU Crystals, Nano-Si 02, Nigericin, and (b) AIM2 inflammasome protein complex, such as Poly (dA:dT).

In certain aspects, a TLR8 agonist is selected from Category A or Category C, or a TLR7 agonist is selected from Category B, as further described herein. Variables and Formula of the Compounds of Category A (TLR8 agonists) are described in the section entitled Compounds of Category A; variables and Formula of the Compounds of Category B (TLR7 agonists) are described in section entitled Compounds of Category B; and variables and Formula of the Compounds of Category C (TLR8 agonists) are described in section entitled Compounds of Category C. Formulas and variables of the Compounds of Category A, the Compounds of Category B and the Compounds of Category C may overlap in nomenclature, e.g., Formula IA for Compounds of each of Category A, Category B and Category C; however, variables and Formula descriptions are not intended to be interchangeable between the categories.

Compounds of Category A. TLR8 Agonists

In some aspects, the myeloid cell agonist is a benzazepine-4-carboxamide compound. In certain embodiments, the benzazepine-4-carboxamide compound has the structure of Formula X-1:

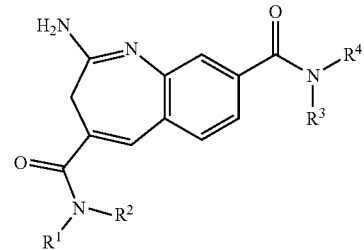

X-1 wherein:
$R^1$ is $C_{3-7}$ alkyl;
$R^2$ is $C_{3-7}$ alkyl or $C_{3-7}$ cycloalkyl-$C_{1-7}$ alkyl;
$R^3$ is hydrogen;
$R^4$ is selected from the group consisting of
$C_{1-7}$ alkyl, said $C_{1-7}$ alkyl being unsubstituted or substituted by one or two groups selected from the group consisting of phenyl and heteroaryl, said heteroaryl being an aromatic 5- or 6-membered ring which comprises one, two, or three atoms selected from nitrogen, oxygen, and/or sulfur;
$C_{3-7}$ cycloalkyl, said $C_{3-7}$ cycloalkyl being unsubstituted or substituted by phenyl or phenylamino-$C_{1-4}$ alkyl, and
heterocyclyl, said heterocyclyl being a saturated 3- to 7-membered ring containing one heteroatom selected from N and O and being unsubstituted or substituted by phenyl. Structures of Formula X-1 are described, for example, in International Publication No. WO 2017/202703.

In some aspects, the myeloid cell agonist is a benzazepine-dicarboxamide compound. In certain embodiments, the benzazepine-dicarboxamide compound has the structure of Formula X-2:

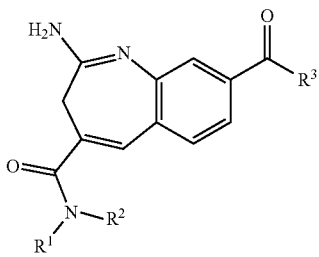

X-2 wherein:
$R^1$ is $C_{3-7}$ alkyl;
$R^2$ is $C_{3-7}$ alkyl or $C_{3-7}$ cycloalkyl-$C_{1-7}$ alkyl;
$R^3$ is a heterocycle selected from

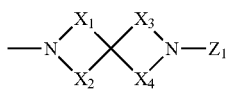

(a)

wherein
$X_1$ is $(CH_2)_m$ wherein m is 1 or 2;
$X_2$ is $(CH_2)_n$ wherein n is 1 or 2;
$X_3$ is $(CH_2)_o$ wherein o is 1 or 2;
$X_4$ is $(CH_2)_p$ wherein p is 1 or 2; and
$Z_1$ is phenyl, wherein phenyl is unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, and di-$C_{1-7}$ alkyl-amino-$C_{1-7}$ alkyl; or

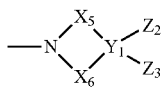

(b)

wherein
$X_5$ is $(CH_2)_q$ wherein q is 1 or 2;
$X_6$ is $(CH_2)_r$ wherein r is 1 or 2;
$Y_1$ is a carbon or nitrogen atom;
$Z_2$ is hydrogen; and
$Z_3$ is selected from the group consisting of hydrogen, $C_{1-7}$ alkoxy, $C_{2-7}$ alkenyloxy, phenyl, phenyl-$C_{1-7}$ alkyl, phenyl-$C_{1-7}$ alkyloxy, phenyl-$C_{1-7}$ alkylamino, phenylamino-$C_{1-7}$ alkyl, phenylamino, wherein phenyl is unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, and di-$C_{1-7}$ alkyl-amino-$C_{1-7}$ alkyl; or

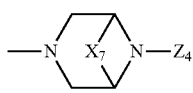

(c)

wherein
$X_7$ is $(CH_2)_s$ wherein s is 1 or 2; and
$Z_4$ is phenyl, wherein phenyl is unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, and di-$C_{1-7}$ alkyl-amino-$C_{1-7}$ alkyl; or

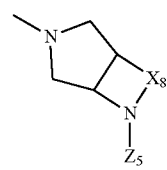

(d)

wherein
$X_8$ is $(CH_2)_t$ wherein t is 1 or 2; and
$Z_5$ is phenyl, wherein phenyl is unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, and di-$C_{1-7}$ alkyl-amino-$C_{1-7}$ alkyl.

Compounds of Formula X-2 are described, for example, in International Publication No. WO 2017/202704.

In some aspects, the myeloid cell agonist is a benzazepine sulfonamide compound. In certain embodiments, the benzazepine sulfonamide compound has the structure of Formula X-3:

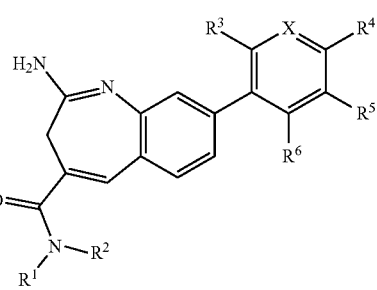

X-3 wherein
$R^1$ and $R^2$ are the same or different and are selected from the group consisting of $C_{1-7}$ alkyl, hydroxy-$C_{2-7}$ alkyl, amino-$C_{2-7}$ alkyl, $C_{2-7}$ alkenyl, and $C_{3-7}$ alkynyl;
$R^3$ is hydrogen or $C_{1-7}$ alkyl;
$R^6$ is hydrogen or $C_{1-7}$ alkyl;
one of $R^4$ and $R^5$ is selected from the group consisting of hydrogen, $C_{1-7}$ alkyl, halogen-$C_{1-7}$ alkyl, and $C_{1-7}$ alkoxy, and the other one of $R^4$ and $R^5$ is

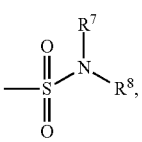

wherein $R^7$ and $R^8$ are the same or different and are selected from the group consisting of hydrogen, $C_{1-7}$ alkyl, halogen-$C_{1-7}$ alkyl, hydroxy-$C_{1-7}$ alkyl, hydroxy-$C_{1-7}$ alkoxy-$C_{1-7}$ alkyl, amino-$C_{1-7}$ alkyl, $C_{1-7}$ alkyl-amino-$C_{1-7}$ alkyl, amino-$C_{1-7}$ alkoxy-$C_{1-7}$ alkyl, $C_{1-7}$ alkyl-amino-$C_{1-7}$ alkoxy-$C_{1-7}$ alkyl, amino-$C_{1-7}$ alkyl-carbonyl, and $C_{1-7}$ alkyl-xamino-$C_{1-7}$ alkyl-carbonyl; or $R^7$ and $R^8$ together with the nitrogen atom they are attached to form a 4- to 6-membered heterocycle which is unsubstituted or substituted with a group selected from the group consisting of amino, $C_{1-7}$ alkyl-amino, hydroxy, and hydroxy-$C_{1-7}$ alkyl, and which may contain an additional N—$R^{10}$ group, wherein $R^{10}$ is selected from the group consisting of hydrogen, amino-$C_{1-7}$ alkyl, and $C_{1-7}$ alkyl-amino-$C_{1-7}$ alkyl; and Y is N or $CR^9$;

wherein $R^9$ is selected from the group consisting of hydrogen, $C_{1-7}$ alkyl, and halogen-$C_{1-7}$ alkyl.

Compounds of Formula X-3 are described, for example, in International Publication No. WO 2016/096778.

In some aspects, the myeloid cell agonist is a dihydropyrimidinyl benzazepine carboxamide compound. In some aspects, the dihydropyrimidinyl benzazepine carboxamide compound has the structure of Formula X-4:

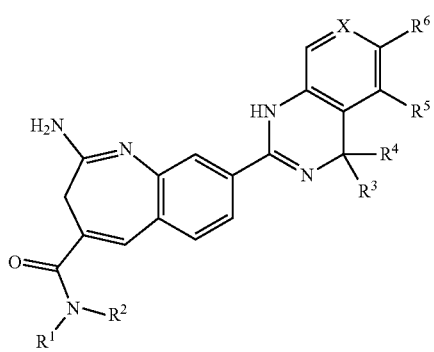

X-4 wherein $R^1$ is $C_{3-7}$ alkyl;

$R^2$ is $C_{3-7}$ alkyl or $C_{3-7}$ cycloalkyl-$C_{1-7}$ alkyl;

$R^3$ is hydrogen or $C_{1-7}$ alkyl;

$R^4$ is hydrogen or $C_{1-7}$ alkyl;

$R^5$ is selected from the group consisting of hydrogen, halogen, $C_{1-7}$ alkyl, and $C_{1-7}$ alkoxy;

$R^6$ is selected from the group consisting of hydrogen, halogen, $C_{1-7}$ alkyl, and $C_{1-7}$ alkoxy; and X is N or $CR^7$, wherein $R^7$ is selected from the group consisting of hydrogen, halogen, $C_{1-7}$ alkyl, and $C_{1-7}$ alkoxy.

Compounds of Formula X-4 are described, for example, in International Publication No. WO2017/216054.

In some aspects, the myeloid cell agonist is a sulfinylphenyl or sulfonimidoylphenyl benzazepine compound. In some aspects, the sulfinylphenyl or sulfonimidoylphenyl benzazepine compound has the structure of Formula X-5:

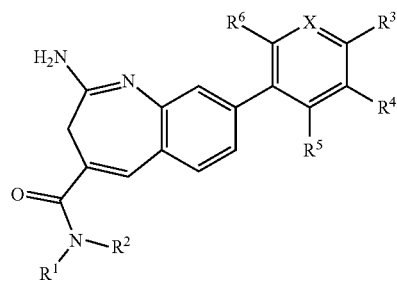

X-5 wherein

X is $CR^7$ or N;

$R^1$ is $C_{3-7}$ alkyl or $C_{3-7}$ cycloalkyl;

$R^2$ is selected from the group consisting of $C_{3-7}$ alkyl, hydroxy-$C_{1-7}$ alkyl, $C_{3-7}$-alkynyl, amino-$C_{1-7}$ alkoxy-$C_{1-7}$ alkoxy-$C_{1-7}$ alkyl, halogen-$C_{1-7}$ alkyl, and $C_{3-7}$ cycloalkyl-$C_{1-7}$ alkyl;

one of $R^3$ and $R^4$ is

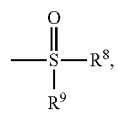

and the other one of $R^3$ and $R^4$ is selected from the group consisting of hydrogen, $C_{1-7}$ alkyl, and halogen;

$R^5$, $R^6$, and $R^7$ are independently from each other selected from hydrogen, $C_{1-7}$ alkyl, and halogen;

$R^8$ is $C_{1-7}$ alkyl; and $R^9$ is absent or is =N—$R^{10}$, wherein $R^{10}$ is selected from the group consisting of hydrogen, $C_{1-7}$ alkyl, halogen-$C_{1-7}$ alkyl, hydroxy-$C_{1-7}$ alkyl, and hydroxy-$C_{1-7}$ alkoxy-$C_{1-7}$ alkyl.

Compounds of Formula X-5 are described, for example, in International Publication No. WO 2017/046112.

In some aspects, the myeloid cell agonist is a TLR modulator compound that has the structure of Formula X-6:

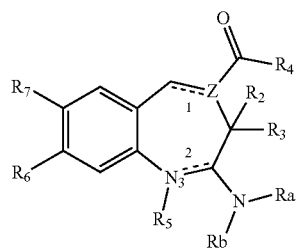

X-6 wherein

--- (1) is a double bond or a single bond;

--- (2) is a single bond or is double bond and $R_1$ is absent;

$R_2$ and $R_3$ are independently selected from H and lower alkyl, or $R_2$ and $R_3$ are connected to form a saturated carbocycle having from 3 to 7 ring members; one of $R_7$ and $R_8$ is —$NR_fR_g$,

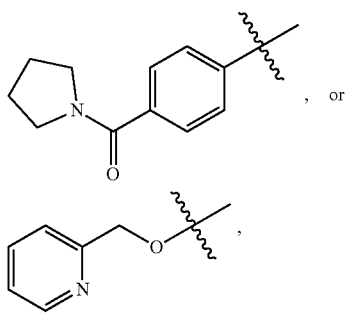

, or

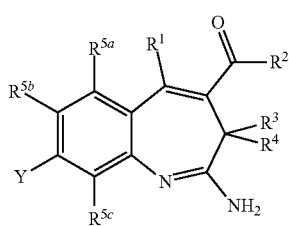

, and
the other is hydrogen;

where $R_f$ and $R_g$ are lower alkyl or $R_f$ and $R_g$ together with the nitrogen to which they are attached form a saturated heterocyclic ring having 4 to 6 ring members;

$R_4$ is —$NR_cR_d$ or —$OR_{10}$;

$R_c$ and $R_d$ are lower alkyl, where the alkyl is optionally substituted with one or more —OH;

$R_{10}$ is alkyl, where the alkyl is optionally substituted with one or more —OH;

Z is C and ≡≡≡ (1) is a double bond, or Z is N and ≡≡≡ (1) is a single bond;

$R_a$ and $R_b$ are independently selected from H, alkyl, alkenyl, alkynyl, and $R^e$, wherein the alkyl is optionally substituted with one or more —$OR^{10}$, or $R^e$;

$R^e$ is selected from —$NH_2$, —NH(alkyl), and —N(alkyl)$_2$;

$R^1$ is absent when ≡≡≡ (2) is a double bond, or when ≡≡≡ (2) is a single bond, $R^1$ and one of $R^a$ or $R^b$ are taken together with the atoms to which they are attached to form a saturated, partially unsaturated, or unsaturated heterocycle having 5-7 ring members, and the other of $R^a$ or $R^b$ is hydrogen or is absent as necessary to accommodate ring unsaturation.

In some aspects, the myeloid cell agonist is a TLR modulator compound that has the structure of Formula X-7:

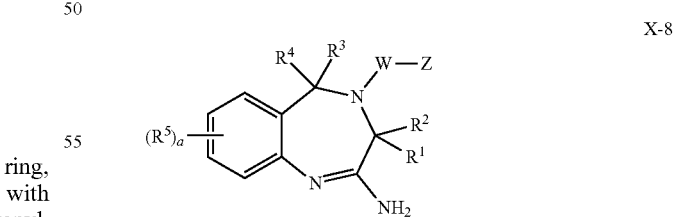

X-7 wherein

Y is $CF_2CF_3$, $CF_2CF_7R^6$, or an aryl or heteroaryl ring, wherein said aryl and heteroaryl rings are substituted with one or more groups independently selected from alkenyl, alkynyl, Br, CN, OH, $NR^6R^7$, C(=O)$R^8$, $NR^6SO_2R^7$, ($C_1$-$C_6$ alkyl)amino, $R^6OC$(=O)CH=$CH_2$—, $SR^6$ and $SO_2R^6$, and wherein the aryl and heteroaryl rings are optionally further substituted with one or more groups independently selected from F, Cl, $CF_3$, $CF_3O$—, $HCF_2O$—, alkyl, heteroalkyl and ArO—;

$R^1$, $R^3$ and $R^4$ are independently selected from H, alkyl, alkenyl, alkynyl, heteroalkyl, cycloalkyl, cycloalkenyl, heterocycloalkyl, aryl and heteroaryl, wherein the alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, C(=O)$R^6$, C(=O)$OR^6$, OC(=O)$R^6$, C(=O)$NR^6R^7$, ($C_1$-$C_6$ alkyl)amino, $CH_3OCH_2O$—, $R^6OC(O)CH=CH_2$—, $NR^6SO_2R^7$, $SR^6$ and $SO_2R^6$, or $R^3$ and $R^4$ together with the atom to which they are attached form a saturated or partially unsaturated carbocyclic ring, wherein the carbocyclic ring is optionally substituted with one or more groups independently selected from alkyl, alkenyl, alkynyl, F, Cl, Br, I, CN, $OR^6$, $NR^6R^7$, C(=O)$R^6$, C(=O)$OR^6$, OC(=O)$R^6$, C(=O)$NR^6R^7$, ($C_1$-$C_6$ alkyl)amino, $CH_3OCH_2O$—, $R^6OC$(=O)CH=$CH_2$—, $NR^6SO_2R^7$, $SR^6$ and $SO_2R^6$;

$R^2$ and $R^8$ are independently selected from H, $OR^6$, $NR^6R^7$, alkyl, alkenyl, alkynyl, heteroalkyl, cycloalkyl, cycloalkenyl, heterocycloalkyl, aryl and heteroaryl, wherein the alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, C(=O)$R^6$, C(=O)$OR^6$, OC(=O)$R^6$, C(O)$NR^6R^7$, ($C_1$-$C_6$ alkyl)amino, $CH_3OCH_2O$—, $R^6OC$(=O)CH=$CH_2$—, $NR^6SO_2R^7$, $SR^6$ and $SO_2R^6$;

$R^{5a}$, $R^{5b}$, and $R^{5c}$ are independently H, F, Cl, Br, I, OMe, $CH_3$, $CH_2F$, $CHF_2$ or CF3; and $R^6$ and $R^7$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl and heteroaryl are optionally substituted with one or more groups independently selected from alkyl, alkenyl, alkynyl, F, Cl, Br, I, CN, $OR^6$, $NR^6R^7$, C(=O)$R^6$, C(=O)$OR^6$, OC(=O)$R^6$, C(=O)$NR^6R^7$, ($C_1$-$C_6$ alkyl)amino, $CH_3OCH_2O$—, $R^6OC(O)CH=CH_2$—, $NR^6SO_2R^7$, $SR^6$ and $SO_2R^6$, or $R^6$ and $R^7$ together with the atom to which they are attached form a saturated or partially unsaturated heterocyclic ring, wherein said heterocyclic ring is optionally substituted with one or more groups independently selected from alkyl, alkenyl, alkynyl, F, Cl, Br, I, CN, $OR^6$, $NR^6R^7$, C(=O)$R^6$, C(=O)$OR^6$, OC(=O)$R^6$, C(=O)$NR^6R^7$, ($C_1$-$C_6$ alkyl)amino, $CH_3OCH_2O$—, $R^6OC$(=O)CH=$CH_2$—, $NR^6SO_2R^7$, $SR^6$ and $SO_2R^6$.

In some aspects, the myeloid cell agonist is a TLR modulator compound that has the structure of Formula X-8:

X-8 wherein

W is —C(O)—;

Z is H, alkyl, alkenyl, alkynyl, heteroalkyl, cycloalkyl, heterocycloalkyl, aryl, heteroaryl, $OR^6$ or $NR^6R^7$, wherein the alkyl, alkenyl, alkynyl, heteroalkyl, cycloalkyl, heterocycloalkyl, aryl and heteroaryl are optionally substituted with one or more groups independently selected from alkyl, alkenyl, alkynyl. F, Cl, Br, I, CN, $OR^6$, $NR^6R^7$, $C(=O)R^6$, $C(=O)OR^6$, $OC(=O)R^6$, $C(=O)NR^6R^7$, $(C_1\text{-}C_6$ alkyl)amino, $CH_3OCH_2O-$, $R^6OCC(=O)CH=CH_2-$, $NR^6SO_2R^7$, $SR^6$ and $SO_2R^6$;

$R^1$, $R^2$, $R^3$ and $R^4$ are independently selected from H, alkyl, alkenyl, alkynyl, heteroalkyl, cycloalkyl, cycloalkenyl, heterocycloalkyl, aryl and heteroaryl, wherein said alkyl, alkenyl, alkynyl, heteroalkyl, cycloalkyl, cycloalkenyl, heterocycloalkyl, aryl, and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1\text{-}C_6$ alkyl)amino, $CH_3OCH_2O-$, $R^6OC(C=O)CH=CH_2-$, $NR^6SO_2R^7$, $SR_6$ and $SO_2R^6$, or $R^1$ and $R^2$ together with the atom to which they are attached form a saturated or partially unsaturated carbocyclic ring, wherein said carbocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1\text{-}C_6$ alkyl)amino, $CH_3OCH_2O-$, $R^6OC(=O)CH=CH_2-$, $NR^6SO_2R^7$, $SR^6$ and $SO_2R^6$, or $R^3$ and $R^4$ together are oxo;

$R^5$ is H, F, Cl, Br, I, OMe, $CH_3$, $CH_2F$, $CHF_2$, $CF_3$ or $CF_2CF_3$;

$R^6$ and $R^7$ are independently selected from H, alkyl, alkenyl, alkynyl, heteroalkyl, cycloalkyl, cycloalkenyl, heterocycloalkyl, aryl, and heteroaryl, wherein said alkyl, alkenyl, alkynyl, heteroalkyl, cycloalkyl cycloalkenyl, heterocycloalkyl, aryl, and heteroaryl are optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1\text{-}C_6$ alkyl)amino, $CH_3OCH_2O-$, $R^6OC(=O)CH=CH_2-$, $NR^6SO_2R^7$, $SR^6$ and $SO_2R^6$;

or $R^6$ and $R^7$ together with the atom to which they are attached form a saturated or partially unsaturated heterocyclic ring, wherein said heterocyclic ring is optionally substituted with one or more groups independently selected from alkyl, alkenyl, alkynyl, F, Cl, Br, I, CN, $OR^6$, $NR^6R^7$, $C(=O)R^6$, $C(=O)OR^6$, $OC(=O)R^6$, $C(=O)NR^6R^7$, $(C_1\text{-}C_6$ alkyl)amino, $CH_3OCH_2O-$, $R^6OC(=O)CH=CH_2-$, $NR^6SO_2R^7$, $SR^6$ and $SO_2R^6$; and n is 0, 1, 2, 3 or 4.

Compounds of Formula X-6, X-7, and X-8 are described, for example, in U.S. Publication Nos. US 2019/0016808 and US 2014/0088085.

In some aspects, the myeloid cell agonist is a TLR modulator compound that has the structure of Formula X-9:

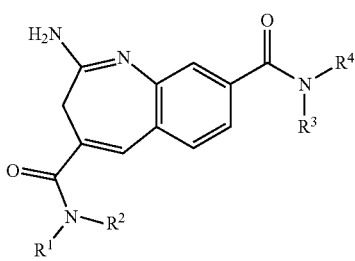

X-9 wherein $R^1$ is $C_{3-7}$ alkyl or $C_{3-7}$ cycloalkyl;

$R^2$ is selected from the group consisting of $C_{1-7}$ alkyl, hydroxy-$C_{1-7}$ alkyl, $C_{2-7}$ alkenyl, $C_{3-7}$ alkynyl, amino-$C_{1-7}$ alkoxy-$C_{1-7}$alkyl, amino-$C_{1-7}$ alkoxy-$C_{1-7}$alkoxy-$C_{1-7}$ alkyl, halogen-$C_{1-7}$ alkyl, $C_{3-7}$ cycloalkyl-$C_{1-7}$ alkyl, and phenyl-$C_{1-7}$ alkyl, wherein phenyl is unsubstituted or substituted by amino-$C_{1-7}$ alkyl;

$R^3$ is hydrogen;

$R^4$ is selected from the group consisting of phenyl, said phenyl being unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, di-$C_{1-7}$ alkyl-amino-$C_{1-7}$ alkyl, amino-$C_{2-7}$ alkenyl, $C_{1-7}$ alkyl-amino-$C_{2-7}$ alkenyl, di-$C_{1-7}$ alkyl-amino-$C_{2-7}$ alkenyl, amino-$C_{2-7}$ alkynyl, $C_{1-7}$ alkyl-amino-$C_{2-7}$ alkynyl, di-$C_{1-7}$ alkyl-amino-$C_{2-7}$ alkynyl, benzyloxycarbonylamino-$C_{1-7}$ alkyl, amino-$C_{1-7}$ alkoxy, amino-$C_{1-7}$ alkoxy-$C_{1-7}$ alkoxy, amino-$C_{1-7}$ alkoxy-$C_{1-7}$ alkyl, amino-$C_{1-7}$ alkoxy-$C_{1-7}$ alkoxy-$C_{1-7}$ alkyl, $C_{1-7}$ alkylsulfonyl, heterocyclylcarbonyl, and phenyl-$C_{1-7}$ alkyl, wherein phenyl is unsubstituted or substituted by $C_{1-7}$ alkoxy or amino-$C_{1-7}$ alkyl; or heteroaryl, said heteroaryl being a 5- or 6-membered aromatic ring containing one, two, or three heteroatoms selected from N, O, or S, and being unsubstituted or substituted by one or two groups selected from the group consisting of $C_{1-7}$ alkyl, halogen, halogen-$C_{1-7}$ alkyl, $C_{1-7}$ alkoxy, hydroxy-$C_{1-7}$ alkyl, amino-$C_{1-7}$ alkyl, $C_{1-7}$ alkyl-amino-$C_{1-7}$ alkyl, di-$C_{1-7}$ alkyl-amino-$C_{1-7}$ alkyl, amino-$C_{2-7}$ alkenyl, $C_{1-7}$ alkyl-amino-$C_{2-7}$ alkenyl, di-$C_{1-7}$ alkyl-amino-$C_{2-7}$ alkenyl, amino-$C_{2-7}$ alkynyl, $C_{1-7}$ alkyl-amino-$C_{2-7}$ alkynyl, di-$C_{1-7}$ alkyl-amino-$C_{2-7}$ alkynyl, benzyloxycarbonylamino-$C_{1-7}$ alkyl, amino-$C_{1-7}$ alkoxy, amino-$C_{1-7}$ alkoxy-$C_{1-7}$ alkoxy, amino-$C_{1-7}$ alkoxy-$C_{1-7}$ alkyl, amino-$C_{1-7}$ alkoxy-$C_{1-7}$ alkoxy-$C_{1-7}$ alkyl, $C_{1-7}$ alkylsulfonyl, heterocyclylcarbonyl, and phenyl-$C_{1-7}$ alkyl, wherein phenyl is unsubstituted or substituted by $C_{1-7}$ alkoxy or amino-$C_{1-7}$ alkyl.

Compounds of Formula X-9 are described, for example, in International Publication No. WO 2016/142250.

In some aspects, the present disclosure provides a TLR8 agonist represented by the structure of Formula (IIA):

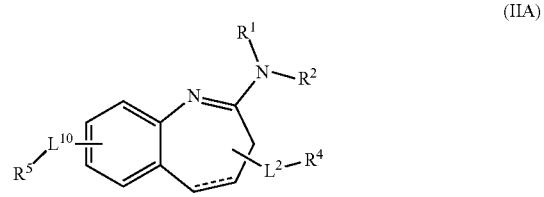

(IIA)

or a pharmaceutically acceptable salt thereof, wherein:

$- - - - -$ represents an optional double bond;

$L^{10}$ is $-X^{10}-$;

$L^2$ is selected from $-X^2-$, $-X^2-C_{1-6}$alkylene-$X^2-$, $-X^2-C_{2-6}$ alkenylene-$X^2-$, and $-X^2-C_{2-6}$ alkynylene-$X^2-$, each of which is optionally substituted on alkylene, alkenylene or alkynylene with one or more $R^{12}$;

$X^{10}$ is selected from $-C(O)-$, and $-C(O)N(R^{10})-*$, wherein * represents where $X^{10}$ is bound to $R^5$;

$X^2$ at each occurrence is independently selected from a bond, $-O-$, $-S-$, $-N(R^{10})-$, $-C(O)-$, $-C(O)O-$, $-OC(O)-$, $-OC(O)O-$, $-C(O)N(R^{10})-$, $-C(O)N(R^{10})C(O)-$, $-C(O)N(R^{10})C(O)N(R^{10})-$, $-N(R^{10})C(O)-$, $-N(R^{10})C(O)N(R^{10})-$, $-N(R^{10})C(O)O-$, $-OC(O)N$ (R$^{10}$)—, —C(NR$^{10}$)—, —N(R$^{10}$)C(NR$^{10}$)—, —C(NR$^{10}$)N(R$^{10}$)—, —N(R$^{10}$)C(NR$^{10}$)N(R$^{10}$)—, —S(O)$_2$—, —OS(O)—, —S(O)O—, —S(O), —OS(O)$_2$—, —S(O)$_2$O, —N(R$^{10}$)S(O)$_2$—, —S(O)$_2$N(R$^{10}$)—, —N(R$^{10}$)S(O)—, —S(O)N(R$^{10}$)—, —N(R$^{10}$)S(O)$_2$N(R$^{10}$)—, and —N(R$^{10}$)S(O)N(R$^{10}$)—;

R$^1$ and R$^2$ are independently selected from hydrogen; and C$_{1-10}$ alkyl, C$_{2-10}$ alkenyl, and C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;

R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^4$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;

R$^5$ is selected from unsaturated C$_{4-8}$ carbocycle; bicyclic carbocycle; and fused 5-5, fused 5-6, and fused 6-6 bicyclic heterocycle, wherein R$^5$ is optionally substituted and wherein substituents are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^5$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$alkynyl;

R$^{10}$ is independently selected at each occurrence from hydrogen, —NH$_2$, —C(O)OCH$_2$C$_6$H$_5$; and C$_{1-10}$ alkyl, C$_2$to alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and haloalkyl; and R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, C$_{2-6}$ alkynyl;

wherein any substitutable carbon on the benzazepine core is optionally substituted by a substituent independently selected from R$^{12}$ or two substituents on a single carbon atom combine to form a 3- to 7-membered carbocycle.

In some embodiments, the compound of Formula (IIA) is represented by Formula (IIB):

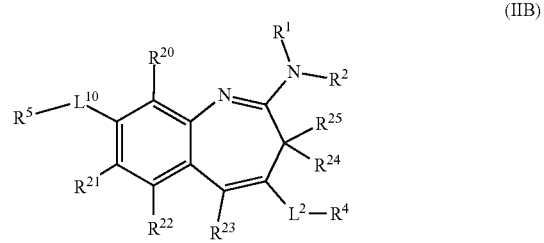

(IIB)

or a pharmaceutically acceptable salt thereof, wherein:

R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and R$^{24}$ and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —OR$^{10}$, —NO$_2$, —CN, and C$_{1-10}$ alkyl. R$^{20}$, R$^{21}$, R$^{22}$, and R$^{23}$ may be each hydrogen. In certain embodiments, R$^{21}$ is halogen. In certain embodiments, R$^{21}$ is hydrogen. In certain embodiments, R$^{21}$ is —OR$^{10}$. For example, R$^{21}$ may be —OCH$_3$.

In some embodiments, R$^{24}$ and R$^{25}$ are independently selected from hydrogen, halogen, —OH, —NO$_2$, —CN, and C$_{1-10}$ alkyl, or R$^{24}$ and R$^{25}$ taken together form an optionally substituted saturated C$_{3-7}$ carbocycle. In certain embodiments, R$^{24}$ and R$^{25}$ are each hydrogen. In other embodiments, R$^{24}$ and R$^{25}$ taken together form an optionally substituted saturated C$_{3-5}$ carbocycle, wherein substituents are selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; and C$_{1-10}$ alkyl, C$_{2-10}$ alkenyl, C$_{2-10}$ alkynyl, each of which is independently optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle.

In some embodiments, R$^1$ is hydrogen. In some embodiments, R$^2$ is hydrogen. In some embodiments, R$^2$ is-C(O)—.

In some embodiments, L$^{10}$ is selected from —C(O)N(R$^{10}$)—*. In certain embodiments, R$^{10}$ of —C(O)N(R$^{10}$)—* is selected from hydrogen and C$_{1-6}$ alkyl. For example, L$^{10}$ may be —C(O)NH—*.

In some embodiments, R$^5$ is an optionally substituted bicyclic carbocycle. In certain embodiments, R$^5$ is an optionally substituted 8- to 12-membered bicyclic carbocycle. R$^5$ may be an optionally substituted 8- to 12-membered bicyclic carbocycle substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. In certain embodiments, R$^5$ is an optionally substituted 8- to 12-membered bicyclic carbocycle substituted with one or more substituents independently selected from —OR$^{10}$, —N(R$^{10}$)$_2$, and =O. In some embodiments, R$^5$ is an optionally substituted indane, and optionally substituted tetrahydronaphthalene. R$^5$ may be selected from:

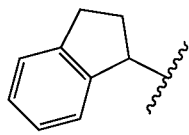 and 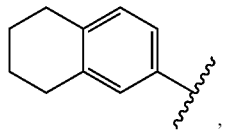, any one of which is optionally substituted. For example, the R$^5$ is selected from:

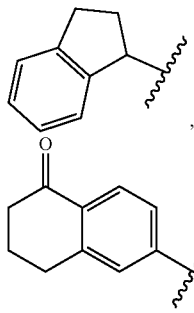,
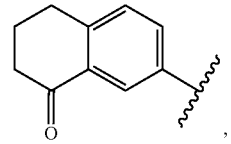,
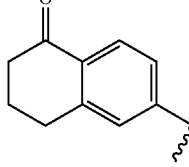,
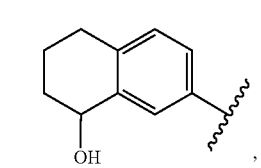,
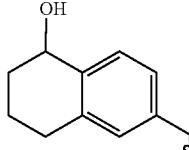,
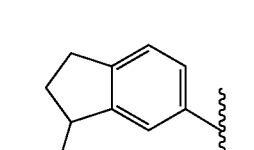,
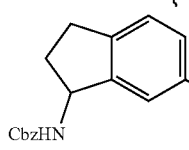, and
.

In some embodiments, R$^5$ is an optionally substituted unsaturated C$_{4-8}$ carbocycle. In certain embodiments, R$^5$ is an optionally substituted unsaturated C$_{4-6}$ carbocycle. In certain embodiments, R$^5$ is an optionally substituted unsaturated C$_{4-6}$ carbocycle with one or more substituents independently selected from optionally substituted C$_{3-12}$ carbocycle, and optionally substituted 3- to 12-membered heterocycle. R$^5$ may be an optionally substituted unsaturated C$_{4-6}$ carbocycle with one or more substituents independently selected from optionally substituted phenyl, optionally substituted 3- to 12-heterocycle, optionally substituted C$_{1-10}$ alkyl, optionally substituted C$_{2-10}$ alkenyl, and halogen.

In some embodiments, R$^5$ is selected from an optionally substituted fused 5-5, fused 5-6, and fused 6-6 bicyclic heterocycle. In certain embodiments, R$^5$ is an optionally substituted fused 5-5, fused 5-6, and fused 6-6 bicyclic heterocycle with one or more substituents independently selected from —C(O)OR$^{10}$, —N(R$^{10}$)$_2$, —OR$^{10}$, and optionally substituted C$_{1-10}$ alkyl. In certain embodiments, R$^5$ is an optionally substituted fused 5-5, fused 5-6, and fused 6-6 bicyclic heterocycle substituted with —C(O)OR$^{10}$. In certain embodiments, R$^5$ is an optionally substituted fused 6-6 bicyclic heterocycle. For example, the fused 6-6 bicyclic heterocycle may be an optionally substituted pyridine-piperidine. In some embodiments, L$^{10}$ is bound to a carbon atom of the pyridine of the fused pyridine-piperidine. In certain embodiments, R$^5$ is selected from tetrahydroquinoline, tetrahydroisoquinoline, tetrahydronaphthyridine, cyclopentapyridine, and dihydrobenzoxaborole, any one of which is optionally substituted. R$^5$ may be an optionally substituted tetrahydronaphthyridine. In some embodiments, R$^5$ is selected from:

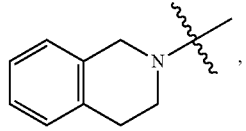,
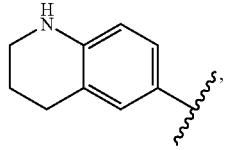, 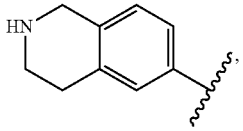,
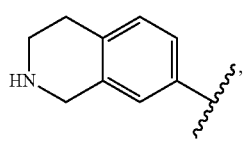,
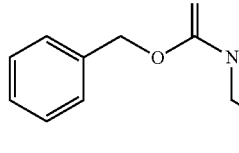,
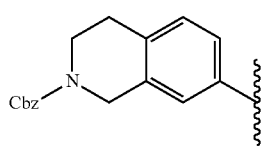,
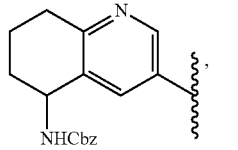

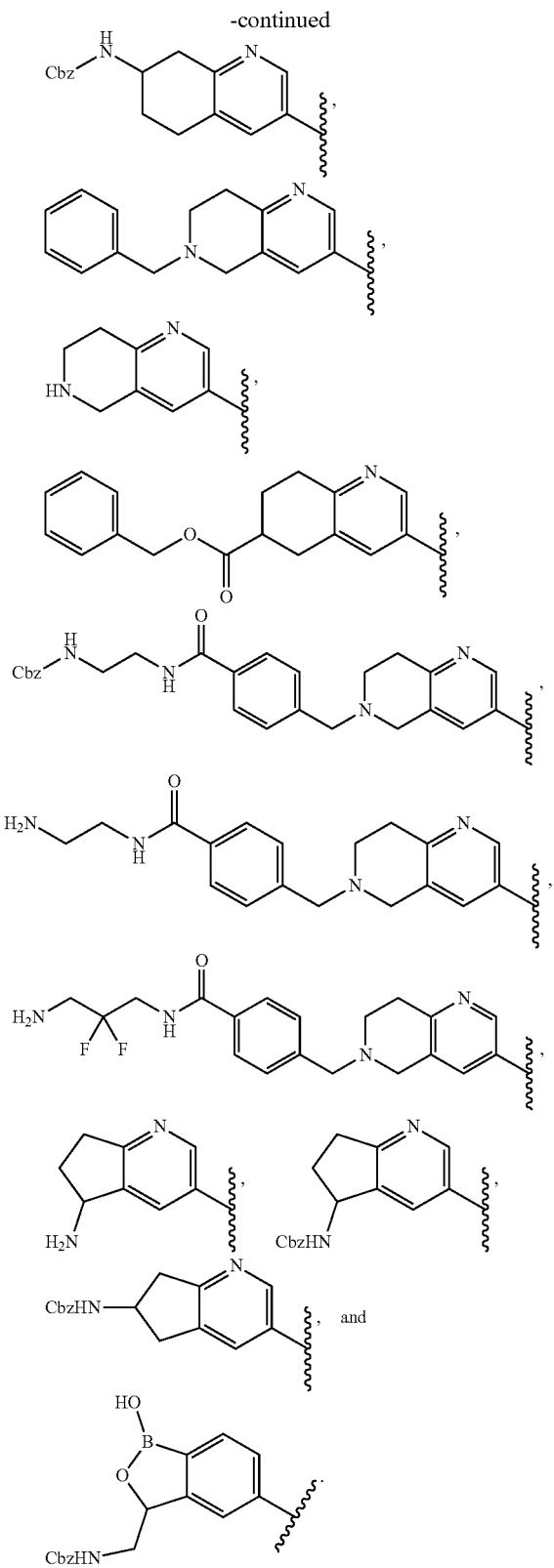

In some embodiments, when $R^5$ is substituted, substituents on $R^5$ are independently selected at each occurrence from: halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, and —CN; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{1-6}$ alkyl, $C_{2-6}$ alkenyl, and $C_{2-6}$alkynyl. In certain embodiments, the substituents on $R^5$ are independently selected at each occurrence from: halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, and —CN; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle. In certain embodiments, the substituents on $R^5$ are independently selected at each occurrence from: halogen, —$OR^{10}$, —$SR^{10}$, —$C(O)N(R^{10})_2$, —$N(R^{10})C(O)R^{10}$, —$N(R^{10})_2$, —$C(O)R^{10}$, —$C(O)OR^{10}$, —$OC(O)R^{10}$, —$NO_2$, =O, and —CN; and $C_{1-10}$ alkyl optionally substituted with one or more substituents independently selected from halogen, —$OR^{10}$, —$SR^{10}$, —$N(R^{10})_2$, —$C(O)R^{10}$, —$C(O)OR^{10}$, —$NO_2$, =O, and —CN. In some embodiments, $R^5$ is not substituted.

In some embodiments, $L^2$ is selected from —C(O)—, and —$C(O)NR^{10}$—. In some embodiments, $L^2$ is —C(O)—. In some embodiments, $L^2$ is —$C(O)NR^{10}$—. $R^{10}$ of —$C(O)NR^{10}$— may be selected from hydrogen and $C_{1-6}$ alkyl. For example, $L^2$ may be —C(O)NH—.

In some embodiments, $R^4$ is selected from: —$OR^{10}$, —$N(R^{10})_2$, —$C(O)N(R_{10})_2$, —$C(O)R^{10}$, —$C(O)OR^{10}$, —$S(O)R^{10}$, and —$S(O)_2R^{10}$; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$C(O)N(R^{10})_2$, —$N(R^{10})C(O)R$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle; and $C_{3-12}$ carbocycle and 3- to 12-membered, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{1-6}$ alkyl, $C_{2-6}$ alkenyl, and $C_{2-6}$ alkynyl. In some embodiments, $R^4$ is selected from: —$OR^{10}$, and —$N(R^{10})_2$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —$OR^{10}$, —$SR^{10}$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl. In certain embodiments, $R^4$ is —$N(R^{10})_2$. $R^{10}$ of —$N(R^{10})_2$ may be independently selected at each occurrence from optionally substituted $C_{1-6}$ alkyl. In certain embodiments, $R^{10}$ of —$N(R^{10})_2$ is independently selected at each occurrence from methyl, ethyl, propyl, and butyl, any one of which is optionally substituted. For example, $R^4$ may be

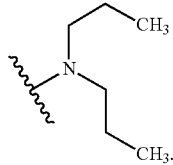

In certain embodiments, -$L^2$-$R^4$ is

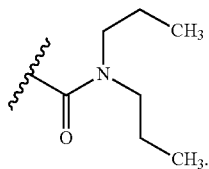

In some embodiments, $R^{12}$ is independently selected at each occurrence from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$C(O)OR^{10}$, —$OC(O)R^{10}$, —$S(O)R^{10}$, —$S(O)_2R^{10}$, —$P(O)(OR^{10})_2$, —$OP(O)(OR^{10})_2$, —$NO_2$, =O, =S, =$N(R^{10})$, and —CN; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$C(O)OR^{10}$, —$OC(O)R^{10}$, —$S(O)R^{10}$, —$S(O)_2R^{10}$, —$P(O)(OR^{10})_2$, —$OP(O)(OR^{10})_2$, —$NO_2$, =O, =S, =$N(R^{10})$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10}$, —$SR^{10}$, —$N(R^{10})_2$, —$C(O)R_{10}$, —$C(O)N(R^{10})_2$, —$N(R^{10})C(O)R^{10}$, —$C(O)OR^{10}$, —$OC(O)R^{10}$, —$S(O)R^{10}$, —$S(O)_2R^{10}$, —$P(O)(OR^{10})_2$, —$OP(O)(OR^{10})_2$, —$NO_2$, =O, =S, =$N(R^{10})$, —CN, $C_{1-6}$ alkyl, $C_{2-6}$ alkenyl, and $C_{2-6}$ alkynyl. In certain embodiments, $R^{12}$ is independently selected at each occurrence from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$C(O)OR^{10}$, —$OC(O)R^{10}$, —$S(O)R^{10}$, —$S(O)_2R^{10}$, —$P(O)(OR^{10})_2$, —$OP(O)(OR^{10})_2$, —$NO_2$, =O, =S, =$N(R^{10})$, and —CN; and $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$N(R^{10})_2$, —$C(O)R^{10}$, —$C(O)N(R^{10})_2$, —$N(R^{10})C(O)R^{10}$, —$C(O)OR^{10}$, —$OC(O)R^{10}$, —$S(O)R^{10}$, —$S(O)_2R^{10}$, —$P(O)(OR^{10})_2$, —$OP(O)(OR^{10})_2$, —$NO_2$, =O, =S, =$N(R^{10})$, —CN, $C_{3-10}$ carbocycle and 3- to 10-membered heterocycle.

In some embodiments, the compound of Formula (IIB) is a compound of Formula (IIC):

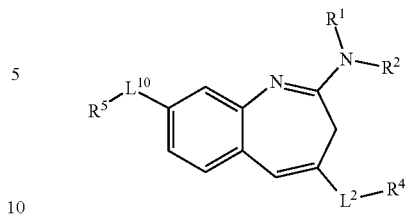

or a pharmaceutically acceptable salt thereof,
wherein:
$R^1$ and $R^2$ are hydrogen;
$L^2$ is —C(O)—;
$R^4$ is —$N(R^{10})_2$;
$R^{10}$ is independently selected at each occurrence from hydrogen, —$NH_2$, —$C(O)OCH_2C_6H_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —$C(O)OCH_2C_6H_5$, —$NHC(O)OCH_2C_6H_5$, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl;
$L^{10}$ is —$C(O)N(R^{10})$—*, wherein * represents where $L^{10}$ is bound to $R^5$; and
$R^5$ is a fused 5-5, fused 5-6, or fused 6-6 bicyclic heterocycle, wherein $R^5$ is optionally substituted and wherein substituents are independently selected at each occurrence from:
halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, and —CN;
$C_{1-10}$ alkyl, $C_{1-10}$ alkenyl, $C_{2-10}$ alkynyl, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle; and
$C_{3-12}$ carbocycle, and 3- to 12-membered heterocycle, each of which is optionally substituted with one or more substituents independently selected from halogen, $OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{1-6}$ alkyl, $C_{2-6}$ alkenyl, and $C_{2-6}$ alkynyl.

In certain embodiments, $R^{10}$ of —$N(R^{10})_2$ is independently selected at each occurrence from methyl, ethyl, propyl, and butyl, any one of which is optionally substituted; and/or $R^{10}$ of —$C(O)N(R^{10})$—* is hydrogen.

In certain embodiments, $R^4$ is

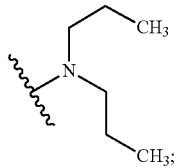 [SMILES: *N(CCC)CCC]

and/or $R^{10}$ of —$C(O)N(R^{10})$—* is hydrogen.

In some embodiments, the compound is selected from:
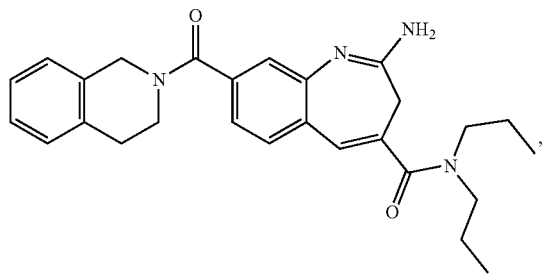
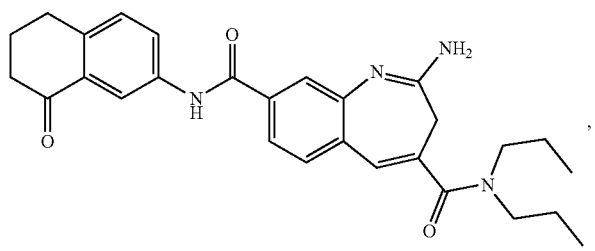
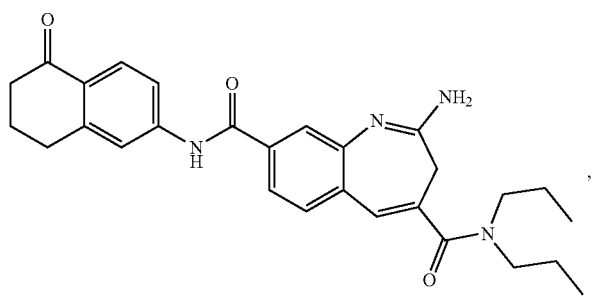
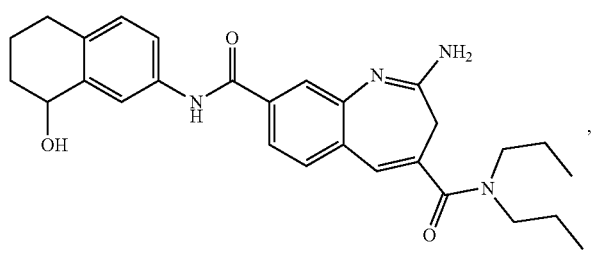
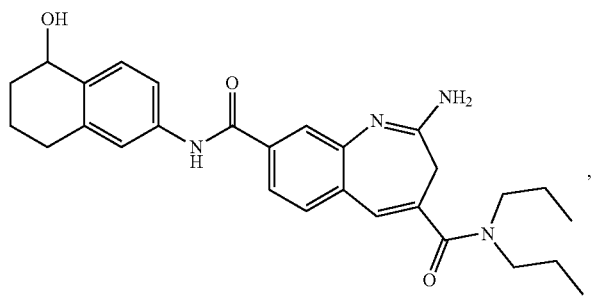
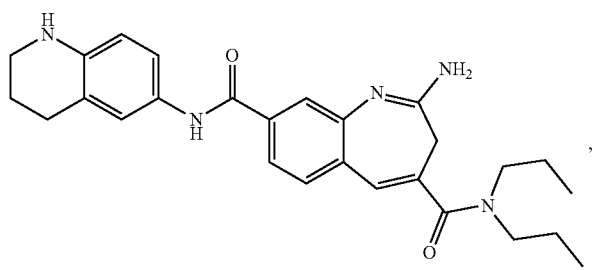

-continued
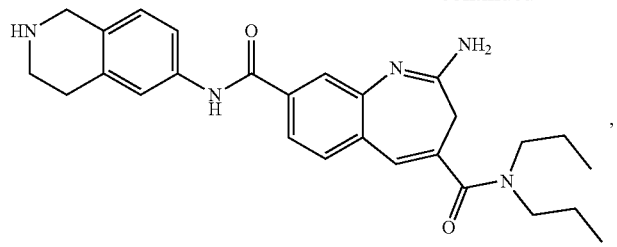
,
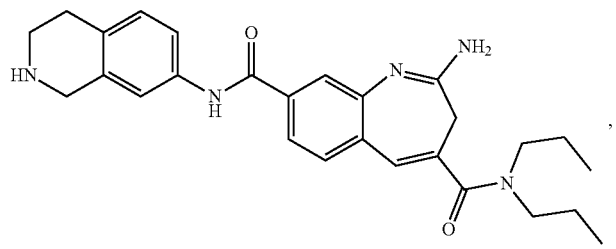
,
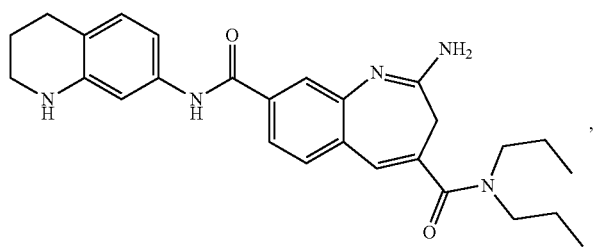
,
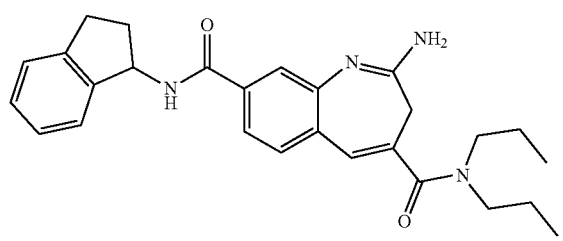
,
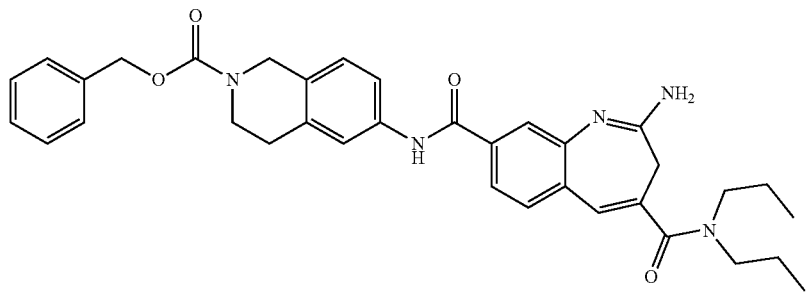
,
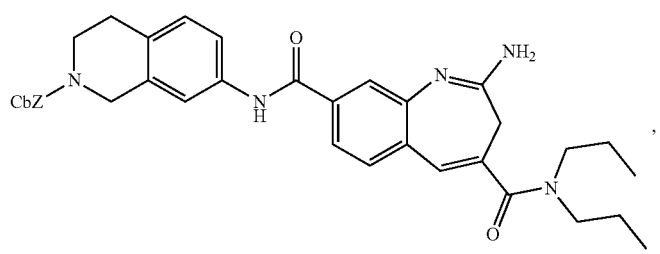
,

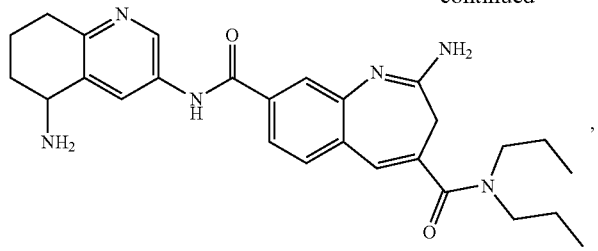
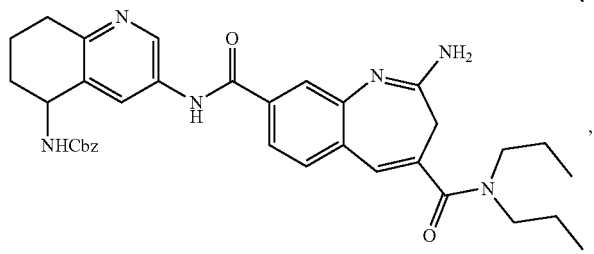
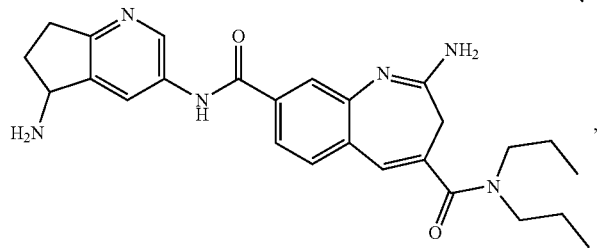
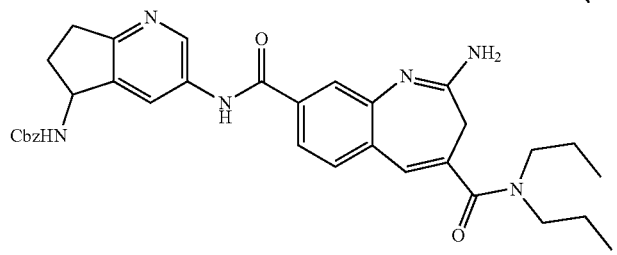
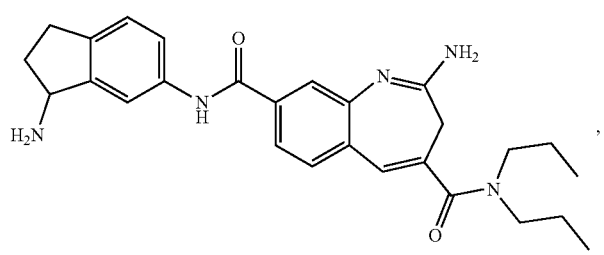
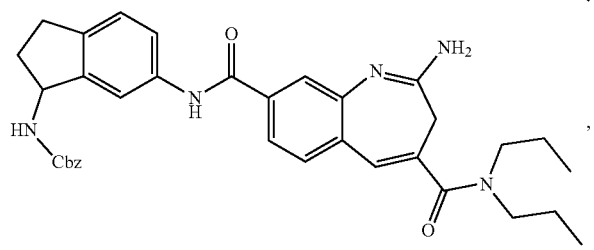
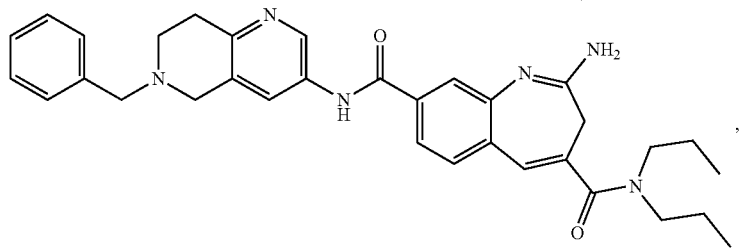

-continued
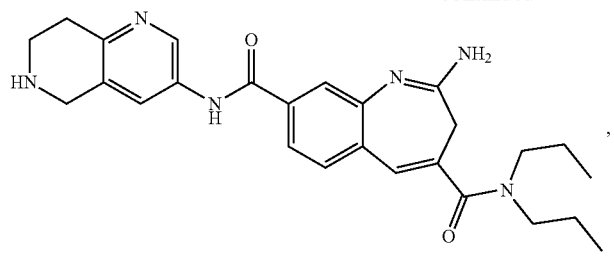
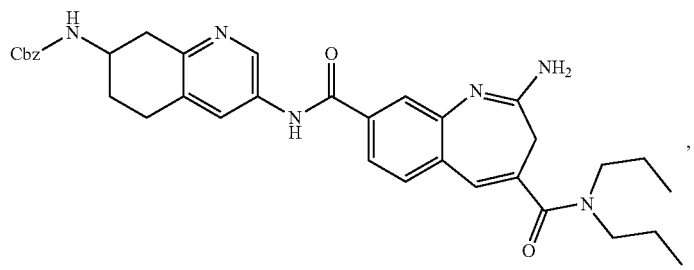
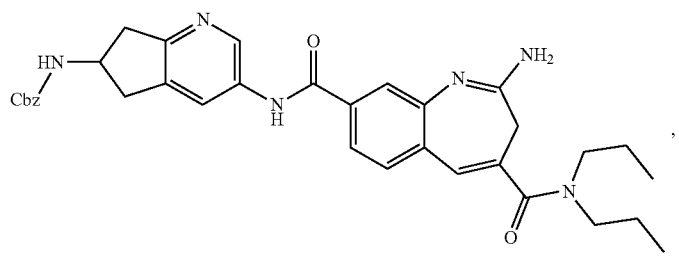
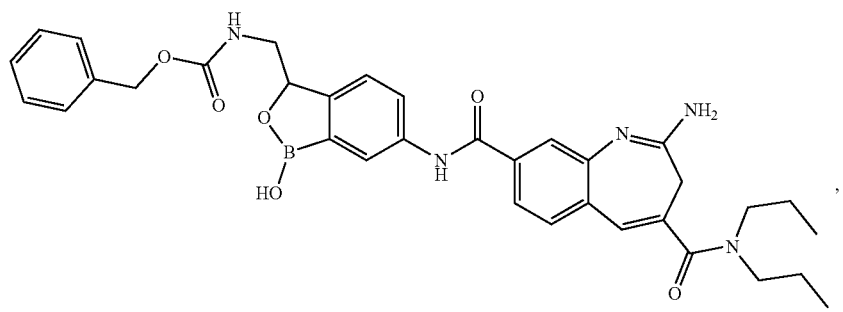
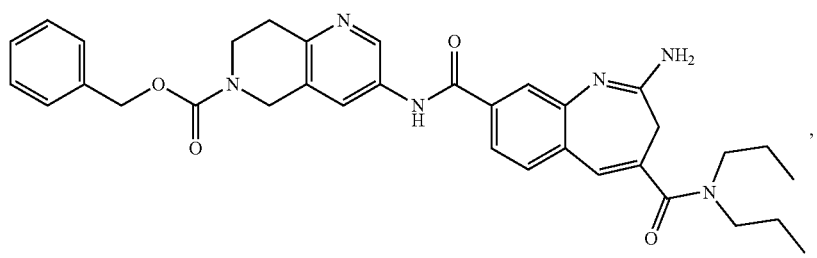
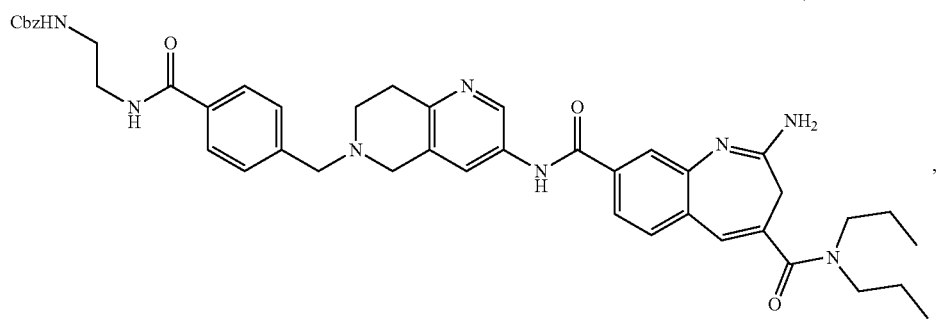

-continued

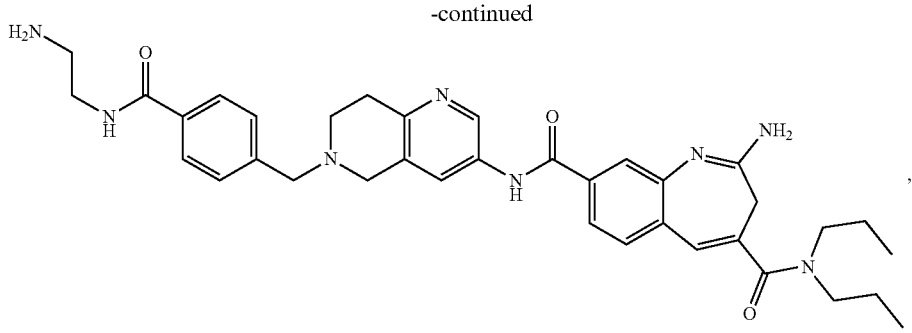

,

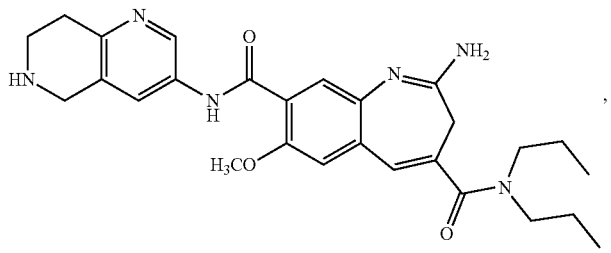

,

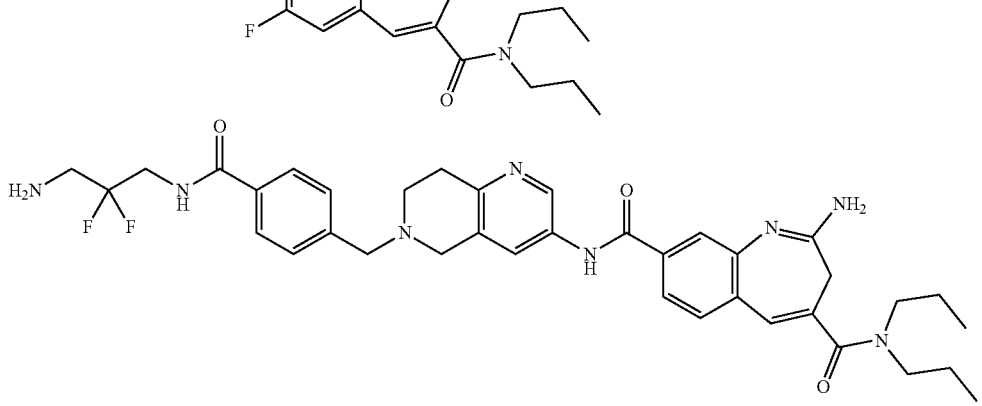

, and

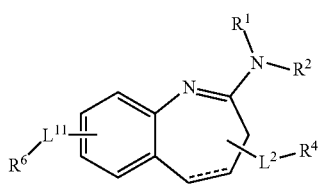

, and a salt of any one thereof.

In some aspects, the present disclosure provides a compound represented by the structure of Formula (IIIA):

$$\text{(IIIA)}$$

or a pharmaceutically acceptable salt thereof, wherein:
- - - - - represents an optional double bond;
$L^{11}$ is —$X^{11}$—;
$L^2$ is selected from —$X^2$—, —$X^2$—$C_{1-6}$alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;
$X^{11}$ is selected from —C(O)— and —C(O)N($R^{10}$)—*, wherein * represents where $X^{11}$ is bound to $R^6$;

$X^2$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O)—, —OS(O)$_2$—, —S(O)$_2$O—, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; $C_{1-10}$ alkyl, $C_{2-10}$ alkenyl, and $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)$_2$, —S(O)R, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^4$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$alkenyl, and C$_{2-6}$ alkynyl;

R$^6$ is selected from phenyl and 5- or 6-membered heteroaryl, any one of which is substituted with one or more substituents selected from R$^7$ and R$^6$ is further optionally substituted by one or more additional substituents independently selected from R$^{12}$;

R$^7$ is selected from —C(O)NHNH$_2$, —C(O)NH—C$_{1-3}$ alkylene-NH(R$^{10}$), —C(O)CH$_3$, —C$_{1-3}$ alkylene-NHC(O)OR$^{11}$, —C$_{1-3}$ alkylene-NHC(O)R$^{10}$, —C$_{1-3}$ alkylene-NHC(O)NHR$^{10}$, —C$_{1-3}$ alkylene-NHC(O)—C$_{1-3}$ alkylene-R$^{10}$, and a 3- to 12-membered heterocycle optionally substituted with one or more substituents independently selected from R$^{12}$;

R$^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, —C$_{1-10}$ alkyl, —C$_{1-10}$haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

R$^{11}$ is selected from C$_{3-12}$ carbocycle and 3- to 12-membered heterocycle, each of which is optionally substituted with one or more substituents independently selected from R$^{12}$; and R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl; and wherein any substitutable carbon on the benzazepine core is optionally substituted by a substituent independently selected from R$^{12}$ or two substituents on a single carbon atom combine to form a 3- to 7-membered carbocycle.

In some embodiments, the compound of Formula (IIIA) is represented by Formula (IIIB):

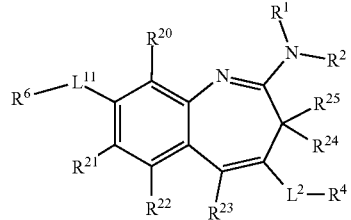

(IIIB)

or a pharmaceutically acceptable salt thereof, wherein:

R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and R$^{24}$ and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —NO$_2$, —CN, and C$_{1-10}$ alkyl. In certain embodiments, R$^{20}$, R$^{21}$, R$^{22}$, and R$^{23}$ are each hydrogen. In some embodiments, R$^{24}$ and R$^{25}$ are independently selected from hydrogen, halogen, —OH, —NO$_2$, —CN, and C$_{1-10}$ alkyl, or R and R taken together form an optionally substituted saturated C$_{3-7}$ carbocycle. In certain embodiments, R$^{24}$ and R$^{25}$ are each hydrogen. In certain embodiments, R$^{24}$ and R$^{25}$ taken together form an optionally substituted saturated C$_{3-5}$ carbocycle.

In some embodiments, R$^1$ is hydrogen. In some embodiments, R$^2$ is hydrogen.

In some embodiments, L$^{11}$ is selected from —C(O)N(R$^{10}$)—*. In some embodiments, R$^{10}$ of —C(O)N(R$^{10}$)—* is selected from hydrogen and C$_{1-6}$ alkyl. For example, L$^{11}$ may be —C(O)NH—*.

In some embodiments, R$^6$ is phenyl substituted with R$^7$ and R$^6$ is further optionally substituted with one or more additional substituents independently selected from R$^{12}$. In some embodiments, R$^6$ is selected from phenyl substituted with one or more substituents independently selected from —C(O)NHNH$_2$, —C(O)NH—C$_{1-3}$ alkylene-NH(R$^{10}$), —C$_{1-3}$ alkylene-NHC(O)R$^{10}$, and —C(O)CH$_3$; and 3- to 12-membered heterocycle, which is optionally substituted with one or more substituents selected from —OH, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)N(R$^{10}$)$_2$, —C(O)$_2$R$^{10}$, and —C$_{1-3}$ alkylene-(R$^{10}$) and R$^6$ is further optionally substituted with one or more additional substituents independently selected from R$^{12}$. For example, R$^6$ may be selected from:

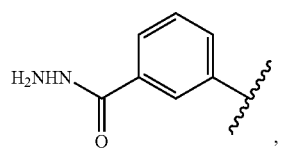

-continued

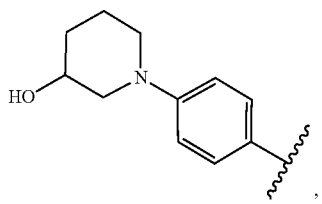

,

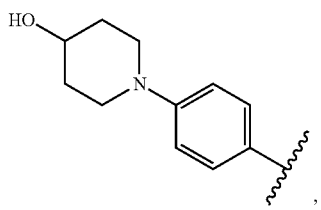

,

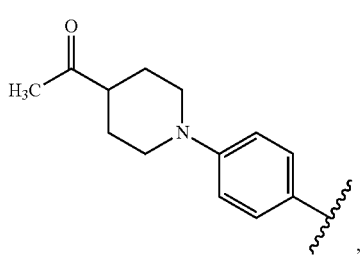

,

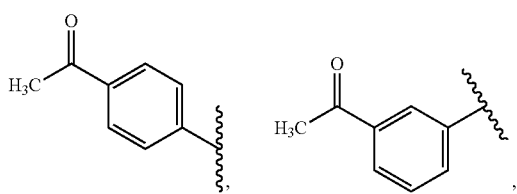

,

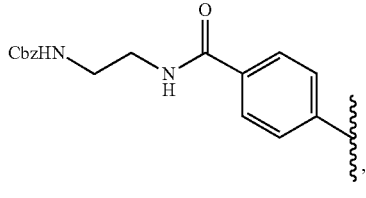

,

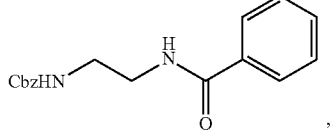

,

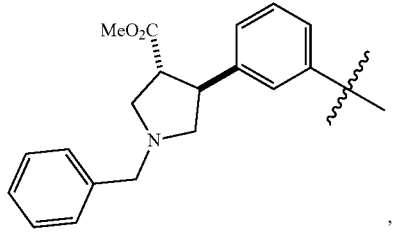

,

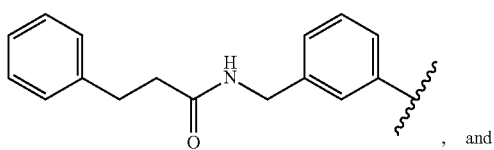

, and

-continued

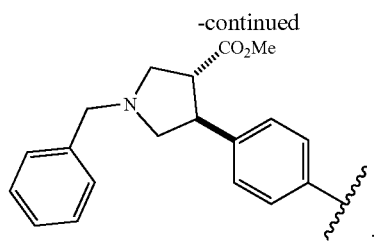

.

In some embodiments, $R^6$ is selected from a 5- and 6-membered heteroaryl substituted with one or more substituents independently selected from $R^7$, and $R^6$ is further optionally substituted with one or more additional substituents selected from $R^{12}$. In certain embodiments, $R^6$ is selected from 5- and 6-membered heteroaryl substituted with one or more substituents independently selected from —C(O)CH$_3$, —C$_{1-3}$ alkylene-NHC(O)OR$^{10}$, —C$_{1-3}$ alkylene-NHC(O)R$^{10}$, —C$_{1-3}$ alkylene-NHC(O)NHR$^{10}$, and —C$_{1-3}$ alkylene-NHC(O)—C$_{1-3}$ alkylene-(R$^{10}$); and 3- to 12-membered heterocycle, which is optionally substituted with one or more substituents selected from —OH, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)N(R$^{10}$)$_2$, —C(O)$_2$R$^{10}$, and —C$_{1-3}$ alkylene-(R$^{10}$), and $R^6$ is optionally further substituted with one or more additional substituents independently selected from $R^{12}$. $R^6$ may be selected from substituted pyridine, pyrazine, pyrimidine, pyridazine, furan, pyran, oxazole, thiazole, imidazole, pyrazole, oxadiazole, oxathiazole, and triazole, and $R^6$ is optionally further substituted with one or more additional substituents independently selected from $R^{12}$. In some embodiments, $R^6$ is substituted pyridine and $R^6$ is optionally further substituted with one or more additional substituents independently selected from $R^{12}$. $R^6$ may be represented as follows:

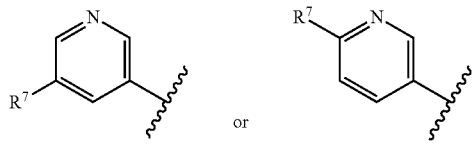

In some embodiments, $R^6$ is substituted pyridine, and wherein $R^7$ is —C$_{1-3}$ alkylene-NHC(O)—C$_{1-3}$ alkylene-R$^{10}$. In certain embodiments, $R^7$ is —C$_1$ alkylene-NHC(O)—C$_1$ alkylene-R$^{10}$. In certain embodiments, $R^7$ is —C$_1$ alkylene-NHC(O)—C$_1$ alkylene-NH$_2$. In some embodiments, $R^6$ is selected from:

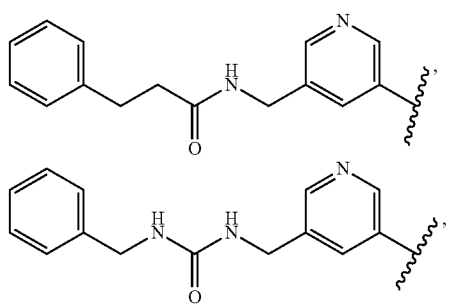

,

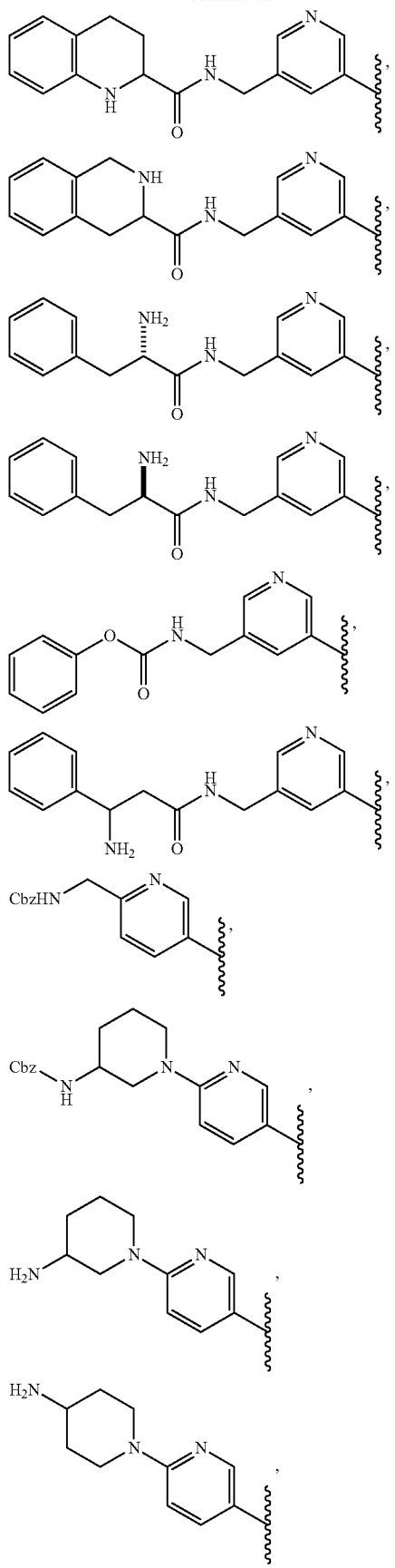
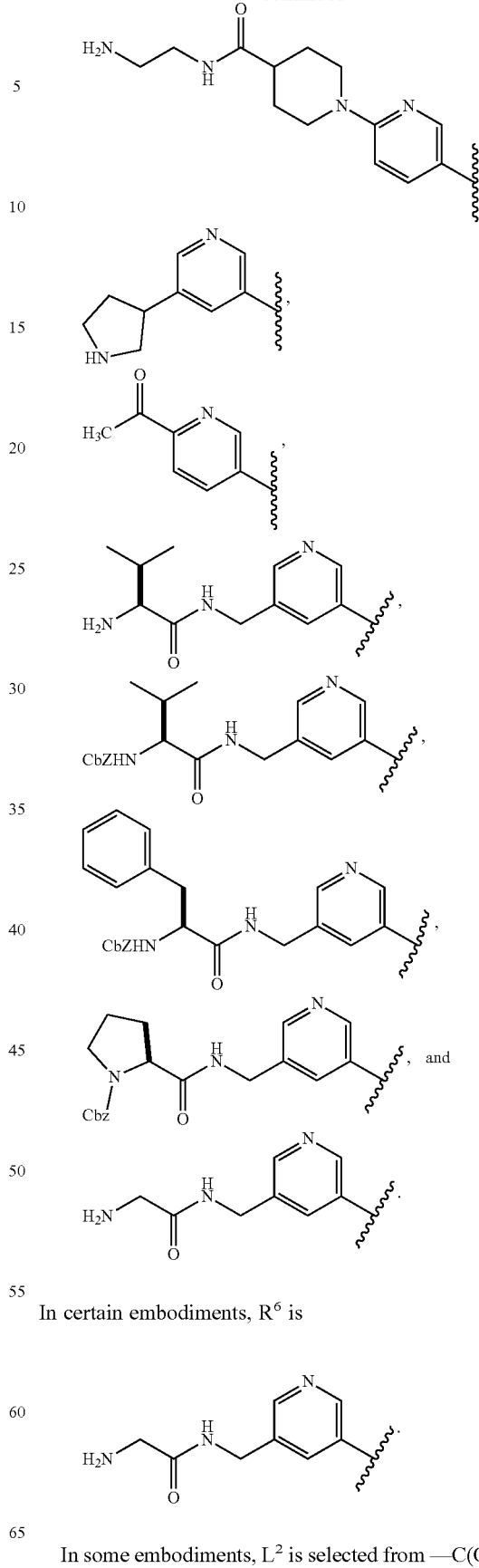
In certain embodiments, R⁶ is
In some embodiments, L² is selected from —C(O)—, and —C(O)NR¹⁰—. In some embodiments, L² is selected from —C(O)NR$^{10}$—. R$^{10}$ of —C(O)NR$^{10}$— may be selected from hydrogen and C$_{1-6}$ alkyl. For example, L$^2$ may be —C(O)NH—. In some embodiments, L$^2$ is —C(O)—.

In some embodiments, R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle and 3- to 12-membered, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl. In some embodiments, R$^4$ is selected from: —OR$^{10}$ and —N(R$^{10}$)$_2$; and C$_{1-10}$ alkyl, C$_{2-10}$ alkenyl, C$_{2-10}$ alkynyl, C$_{3-12}$ carbocycle and 3- to 12-membered heterocycle, each of which is independently optionally substituted at each occurrence with one or more substituents selected from halogen, —OR$^{10}$, —SR$^{10}$, —N(R$^{10}$)$_2$, —S(O)R$^{10}$, —S(O)$_2$R$^{10}$—C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl. In certain embodiments, R$^4$ is —N(R$^{10}$)$_2$. R$^{10}$ of —N(R$^{10}$)$_2$ may be independently selected at each occurrence from optionally substituted C$_{1-6}$ alkyl. In some embodiments, R$^{10}$ of —N(R$^{10}$)$_2$ is independently selected at each occurrence from methyl, ethyl, propyl, and butyl, any of which are optionally substituted. For example, R$^4$ may be

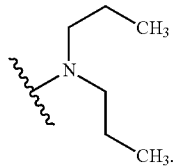

In some embodiments, -L$^2$-R$^4$ is

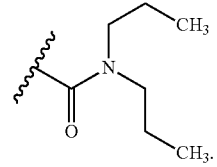 [SMILES: *C(=O)N(CCC)CCC]

In some embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, each of which is independently optionally substituted at each occurrence with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl. In certain embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$—C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle.

In some embodiments, the compound is selected from:

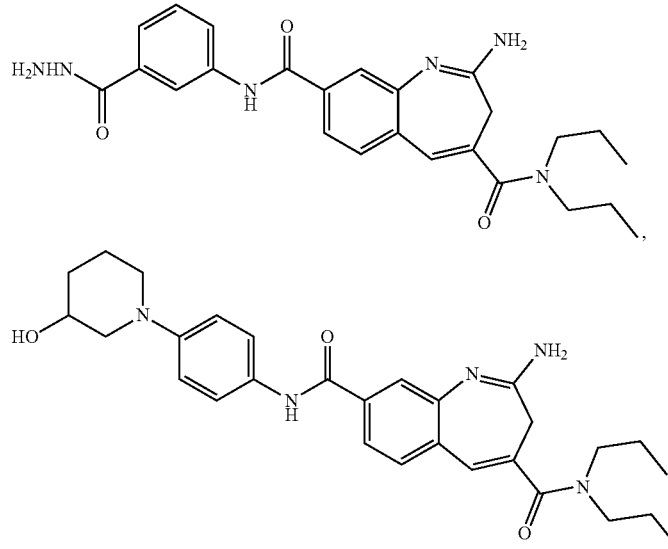

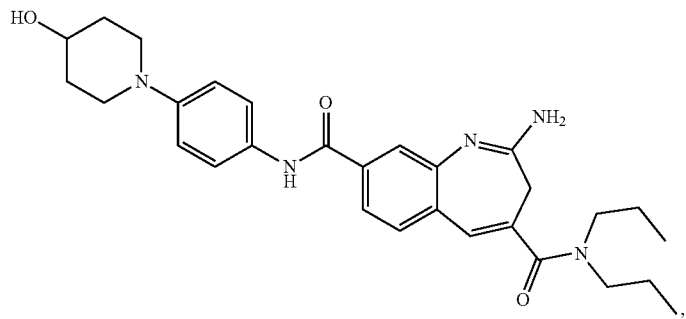
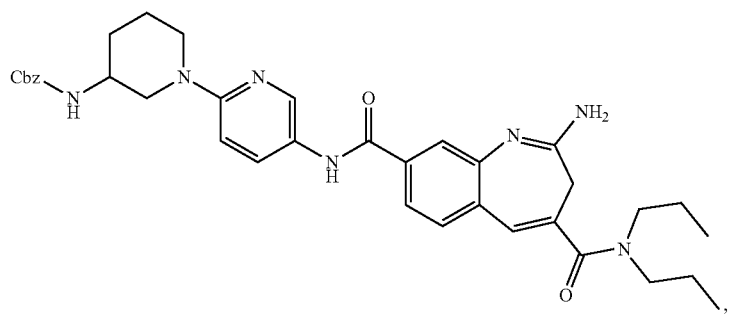
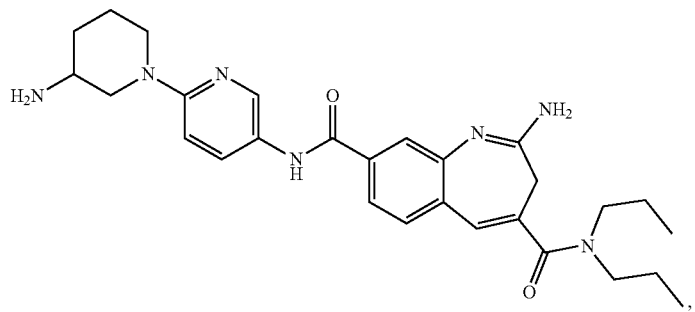
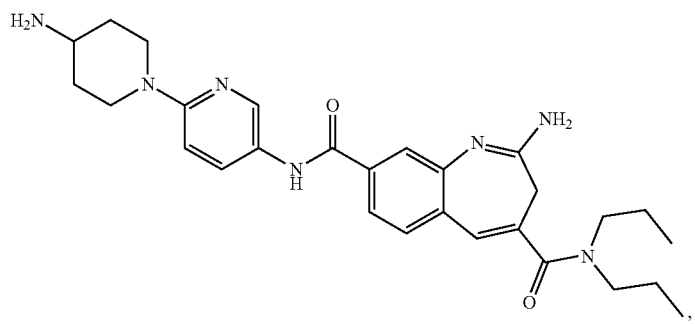
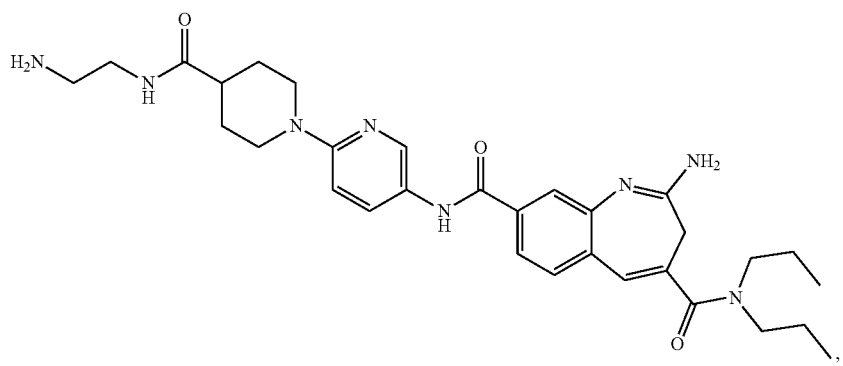

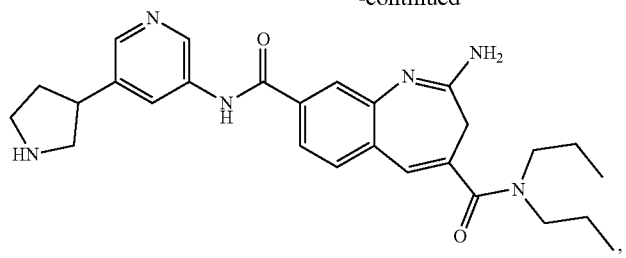
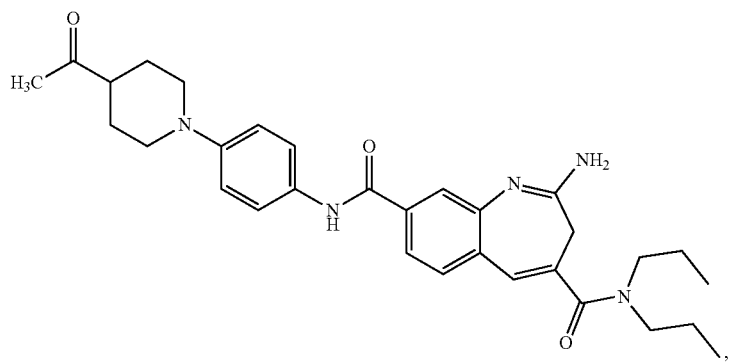
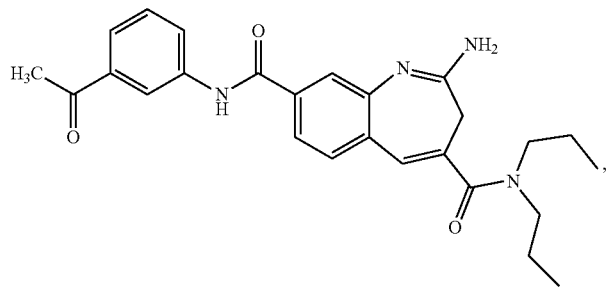
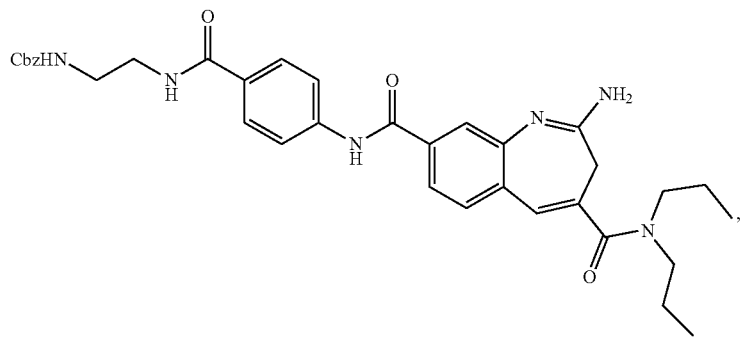
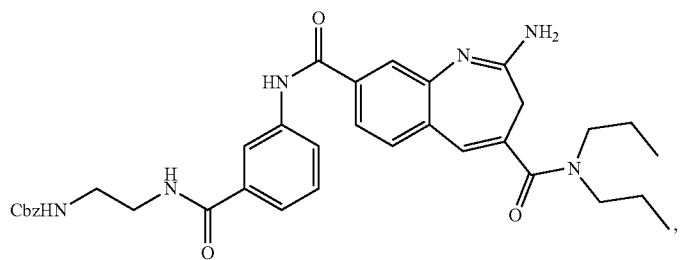

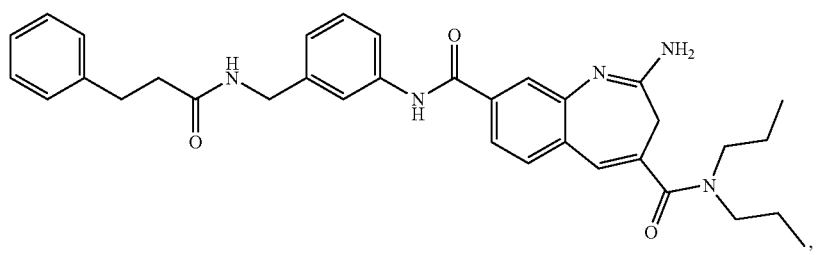
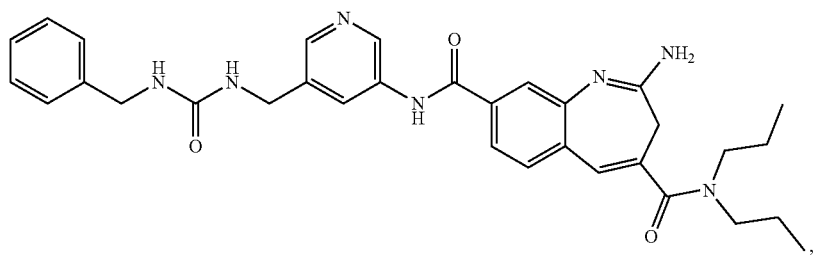
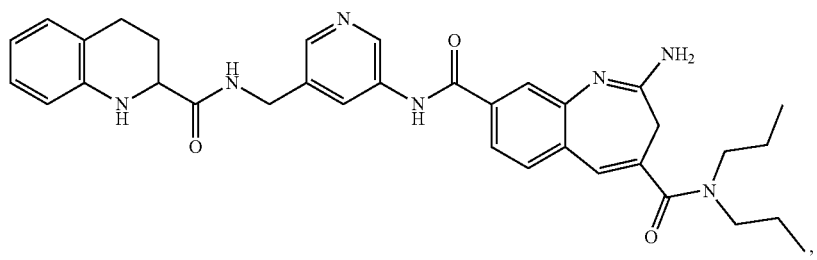
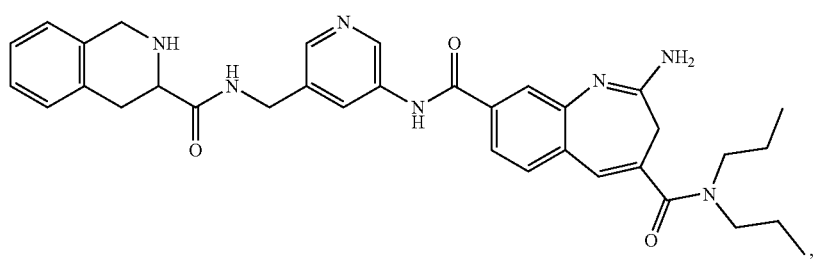
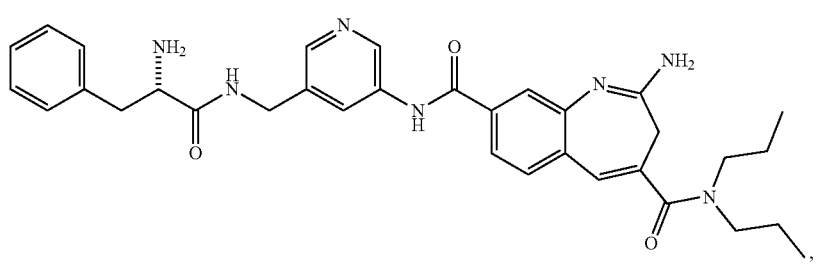
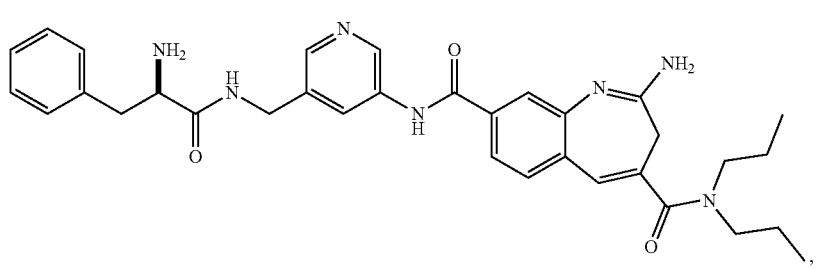

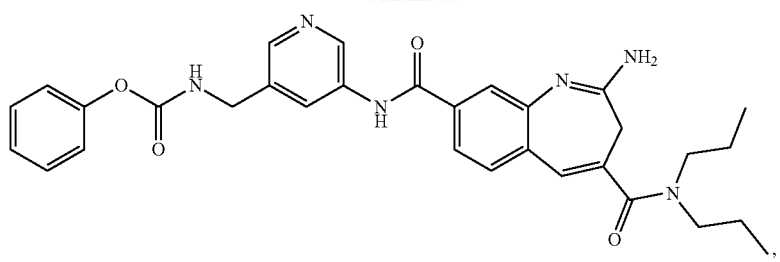
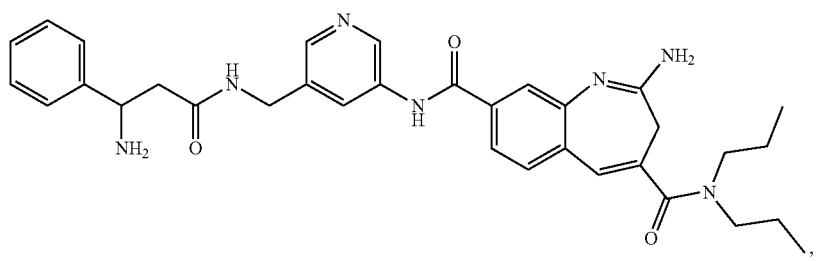
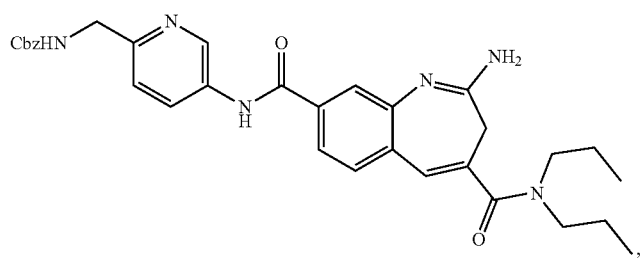
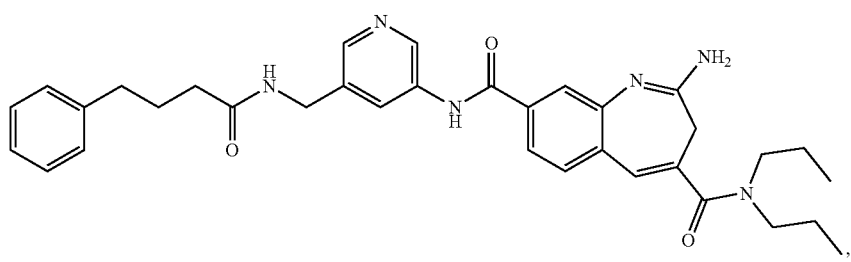
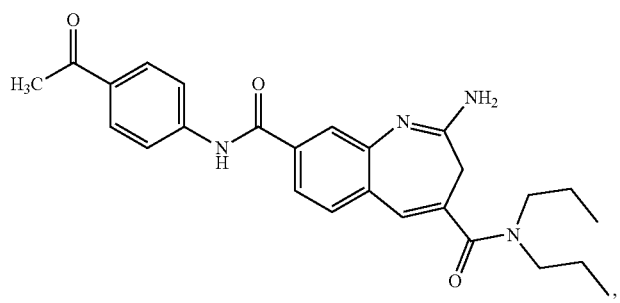
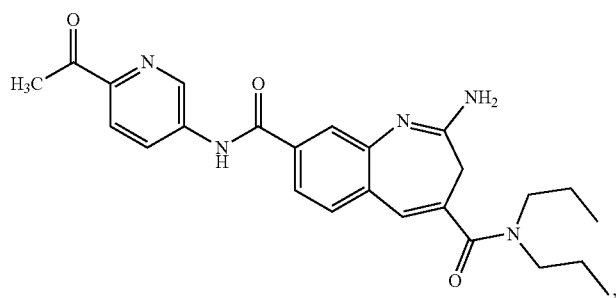

-continued
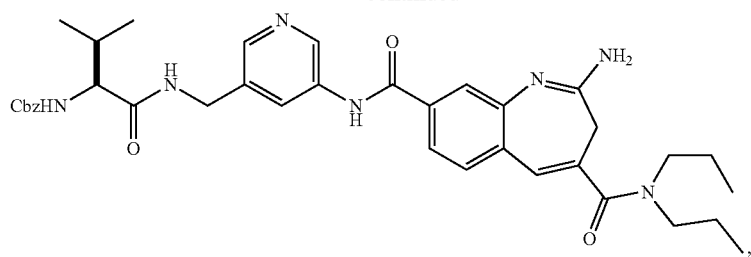
,
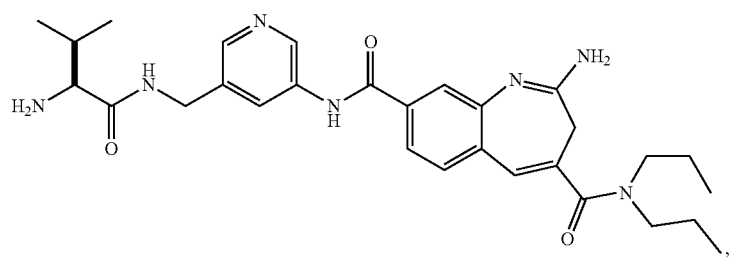
,
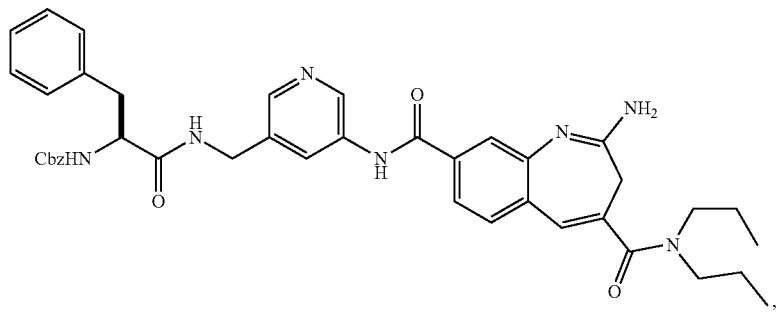
,
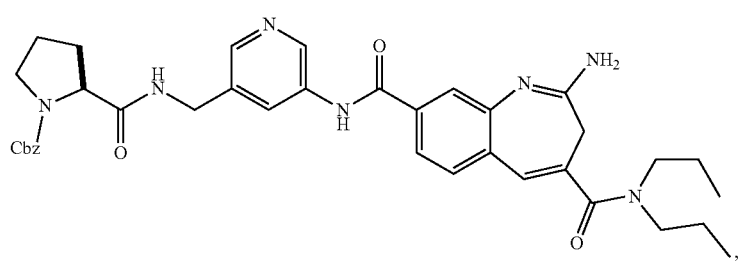
,
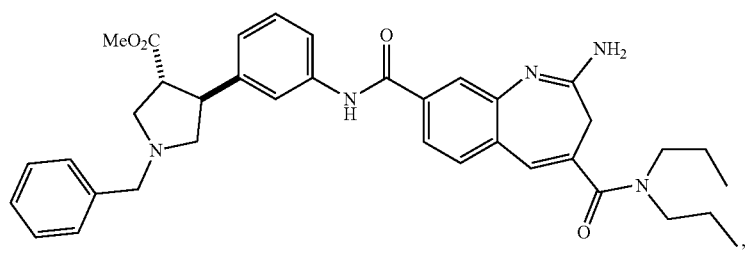
,
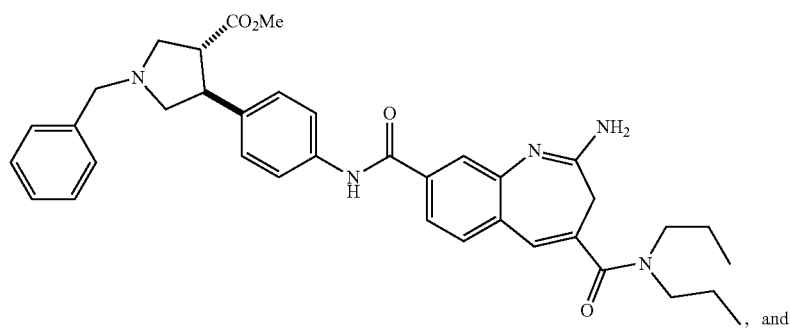
, and -continued

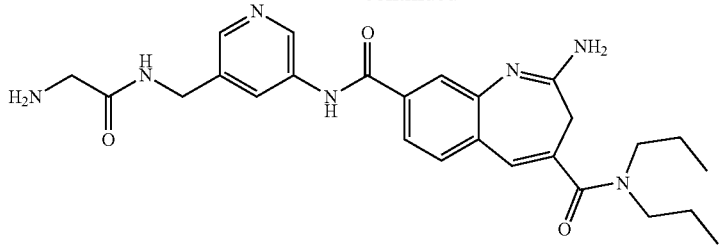

and a salt of any one thereof.

In some aspects, the present disclosure provides a compound represented by the structure of Formula (IA):

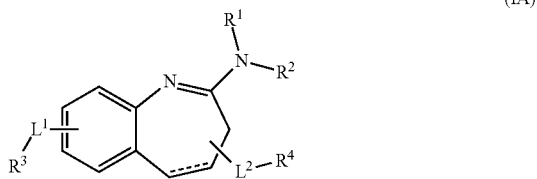

(IA)

or a pharmaceutically acceptable salt thereof, wherein:

------ represents an optional double bond;

$L^1$ is selected from —$X^1$—, —$X^2$—$C_{1-6}$ alkylene-$X^2$—, $C_{1-6}$ alkylene-, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$L^2$ is selected from —$X^2$—, —$X^2$—$C_{1-6}$ alkylene-$X^2$—, —$X^2$—$C_{2-6}$ alkenylene-$X^2$—, and
—$X^2$—$C_{2-6}$ alkynylene-$X^2$—, each of which is optionally substituted on alkylene, alkenylene or alkynylene with one or more $R^{12}$;

$X^1$ is selected from —S—*, —N($R^{10}$)—*, —C(O)O—*, —OC(O)—*, —OC(O)O—*, —C(O)N($R^{10}$)C(O)—*, —C(O)N($R^{10}$)C(O)N($R^{10}$)*, —N($R^{10}$)C(O)—*, —C$R^{10}_2$N($R^{10}$)C(O)—*, —N($R^{10}$)C(O)N($R^{10}$)—*, —N($R^{10}$)C(O)O—*, —OC(O)N($R^{10}$)—*, —C(N$R^{10}$)—*, —N($R^{10}$)C(N$R^{10}$)—*, —C(N$R^{10}$)N($R^{10}$)—*, —N($R^{10}$)C(N$R^{10}$)N($R^{10}$)—*, —S(O)$_2$—*, —OS(O)—*, —S(O)O—*, —S(O)—*, —S(O), —OS(O)$_2$—*, —S(O)$_2$O*, —N($R^{10}$)S(O)$_2$—*, —S(O)$_2$N($R^{10}$)—*, —N($R^{10}$)S(O)—*, —S(O)N($R^{10}$)—*, —N($R^{10}$)S(O)$_2$N($R^{10}$)—*, and —N($R^{10}$)S(O)N($R^{10}$)—*, wherein * represents where $X^1$ is bound to $R^3$;

$X^2$ is independently selected at each occurrence from —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$), —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O), —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; $C_{1-10}$ alkyl, $C_{2-10}$ alkenyl, and $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)$_2$, —S(O)$R^{10}$, —S(O)$_2 R^{10}$, —C(O)$R^{10}$, —C(O)O$R^{10}$, —OC(O)$R^{10}$, —NO$_2$, =O, =S, =N($R^{10}$), and —CN;

$R^3$ is selected from optionally substituted $C_{3-12}$ carbocycle, and optionally substituted 3- to 12-membered heterocycle, wherein substituents on $R^3$ are independently selected at each occurrence from: halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^3$ is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2 R^{10}$; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, Cue alkyl, $C_{2-6}$ alkenyl, and $C_{2-6}$ alkynyl;

$R^{10}$ is independently selected at each occurrence from: hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{1-20}$ alkenyl, $C_{2-10}$ alkynyl, $C_{3-12}$ carbocycle, 3- to 12-membered heterocycle, and haloalkyl; and $R^{12}$ is independently selected at each occurrence from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2 R^{10}$, —P(O)(O$R^{10}$)$_2$, —OP(O)(O$R^{10}$)$_2$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —N($R^{10}$)$_2$, —C(O)$R^{10}$, —C(O)N(R$^{10}$)$_2$, —N(R$^{10}$)C(O)R$^{10}$—C(O)OR$^{10}$, —OC(O) R$^{10}$, —S(O)R$^{10}$, —S(O)$_2$R$^{10}$, —P(O)(OR$^{10}$)$_2$, —OP(O) (OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl; and wherein any substitutable carbon on the benzazepine core is optionally substituted by a substituent independently selected from R$^{12}$ or two substituents on a single carbon atom combine to form a 3- to 7-membered carbocycle.

In some embodiments, the compound of Formula (IA) is represented by Formula (IB):

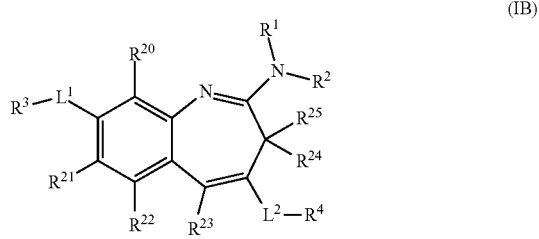

(IB)

or a pharmaceutically acceptable salt thereof, wherein:
R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and
R$^{24}$ and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —NO$_2$, —CN, and C$_{1-10}$ alkyl. In certain embodiments, R$^{20}$, R$^{21}$, R$^{22}$, and R$^{23}$ are each hydrogen.

In some embodiments, R$^{24}$ and R$^{25}$ are independently selected from hydrogen, halogen, —OH, —NO$_2$, —CN, and C$_{1-10}$ alkyl, or R$^{24}$ and R$^{25}$ taken together form an optionally substituted saturated C$_{3-7}$ carbocycle. In some embodiments, R$^{24}$ and R$^{25}$ are each hydrogen. In some embodiments, R$^{24}$ and R$^{25}$ taken together form an optionally substituted saturated C$_{3-5}$ carbocycle.

In some embodiments, R$^1$ is hydrogen. In some embodiments, R$^2$ is hydrogen.

In some embodiments, L$^1$ is selected from —N(R$^{10}$)C(O)—*, —S(O)$_2$N(R$^{10}$)—*, —CR$^{10}$2N(R$^{10}$)C(O)—* and —X$^2$—C$_{1-6}$ alkylene-X$^2$—C$_{1-6}$ alkylene-. In some embodiments, L$^1$ is selected from —N(R$^{10}$)C(O)—*. In certain embodiments, R$^{10}$ of —N(R$^{10}$)C(O)—* is selected from hydrogen and C$_{1-6}$ alkyl. For example, L$^1$ may be —NHC(O)—*. In some embodiments, L$^1$ is selected from —S(O)$_2$N(R$^{10}$)—*. In certain embodiments, R$^{10}$ of —S(O)$_2$N(R$^{10}$)—* is selected from hydrogen and C$_{1-6}$ alkyl. For example, L$^1$ is —S(O)$_2$NH—*. In some embodiments, L$^1$ is —CR$^{10}$$_2$N(R$^{10}$)C(O)—*. In certain embodiments, L$^1$ is selected from —CH$_2$N(H)C(O)—* and —CH(CH$_3$)N(H)C (O)—*.

In some embodiments, R$^3$ is selected from optionally substituted C$_{3-12}$ carbocycle, and optionally substituted 3- to 12-membered heterocycle, wherein substituents on R$^3$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O) OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl. In certain embodiments, R$^3$ is selected from optionally substituted C$_{3-12}$ carbocycle, and optionally substituted 3- to 12-membered heterocycle, wherein substituents on R$^3$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O) OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle.

In some embodiments, R$^3$ is selected from an optionally substituted aryl and an optionally substituted heteroaryl. In some embodiments, R$^3$ is an optionally substituted heteroaryl. R$^3$ may be an optionally substituted heteroaryl substituted with one or more substituents independently selected from halogen, —OR$^{10}$, —SR$^{10}$, —N(R$^{10}$)$_2$, —C(O) R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. In certain embodiments, R$^3$ is selected from an optionally substituted 6-membered heteroaryl. For example, R$^3$ may be an optionally substituted pyridine. In some embodiments, R$^3$ is an optionally substituted aryl. In certain embodiments, R$^3$ is an optionally substituted aryl substituted with one or more substituents independently selected from halogen, —OR$^{10}$, —SR$^{10}$, —N(R$^{10}$)$_2$, —C(O)R$^{10}$, —C(O)OR$^{10}$, —OC(O) R$^{10}$, —NO$_2$, =O, =S, —CN, C$_{1-6}$ alkyl, C$_{2-6}$ alkenyl, and C$_{2-6}$ alkynyl. R$^3$ may be an optionally substituted phenyl. In certain embodiments, R$^3$ is selected from pyridine, phenyl, tetrahydronaphthalene, tetrahydroquinoline, tetrahydroisoquinoline, indane, cyclopropylbenzene, cyclopentapyridine, and dihydrobenzoxaborole, any one of which is optionally substituted. R$^3$ may be selected from:

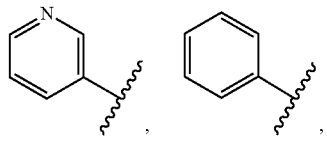

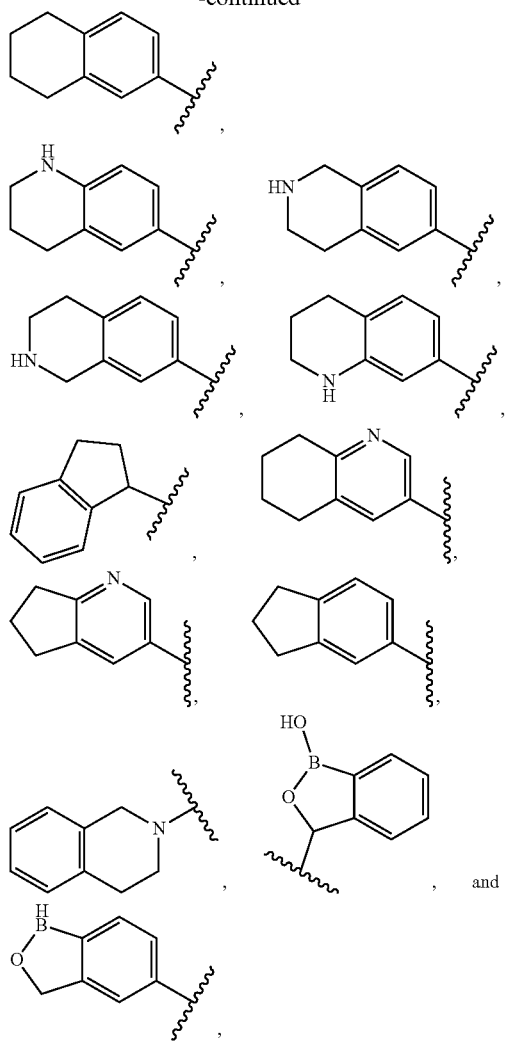
any one of which is optionally substituted. For example, R³ may be selected from:
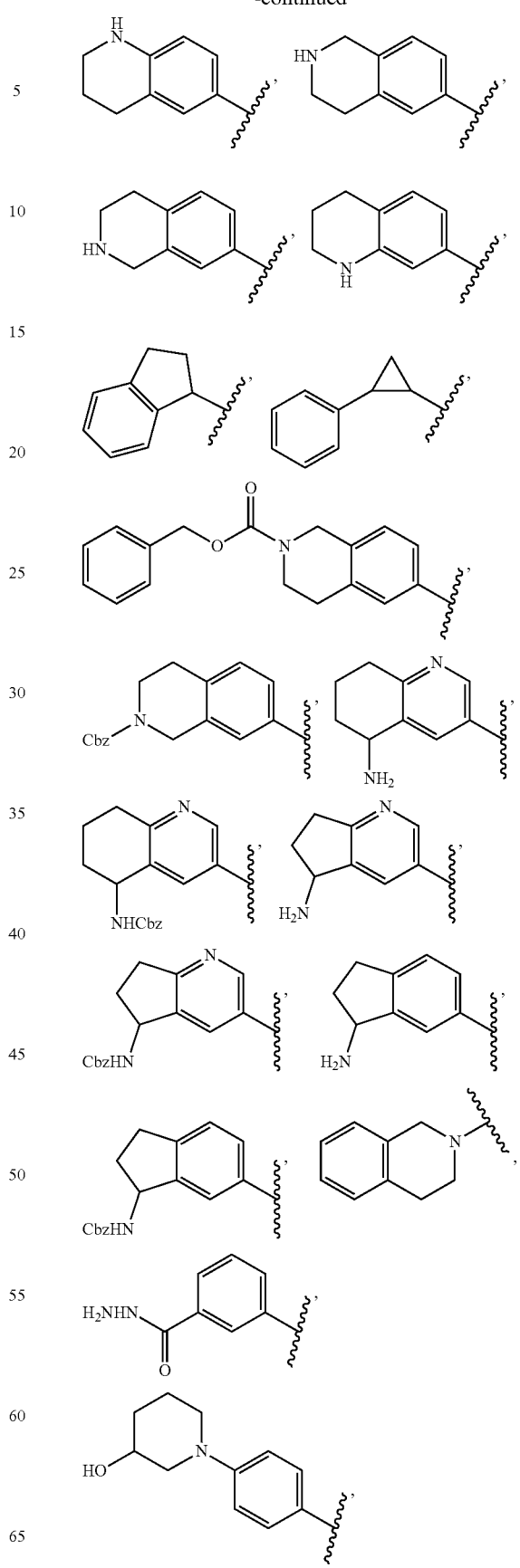

83
-continued
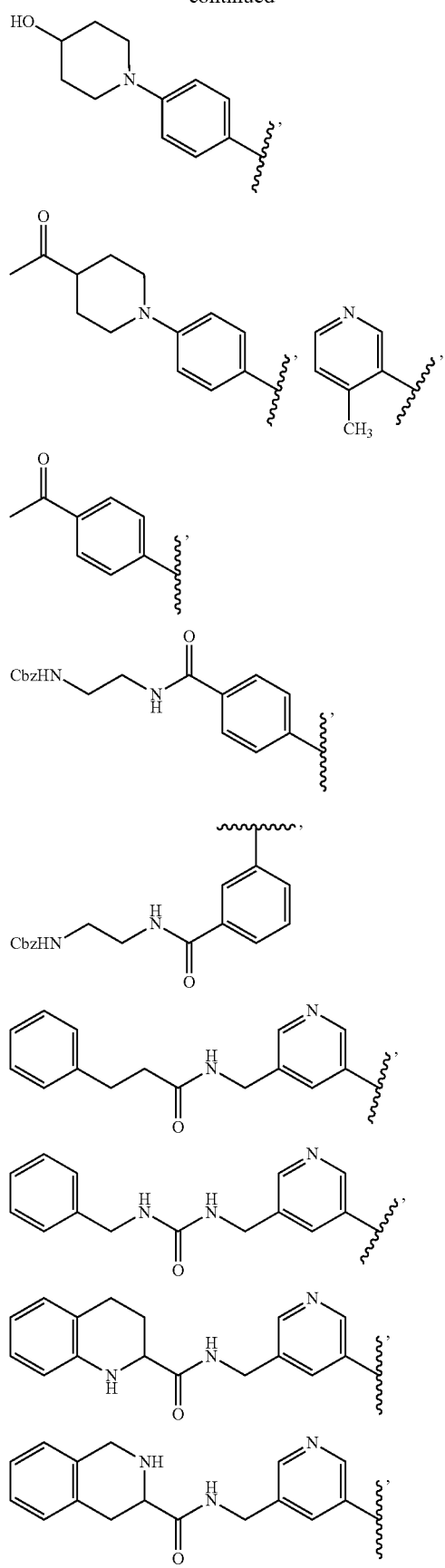
84
-continued
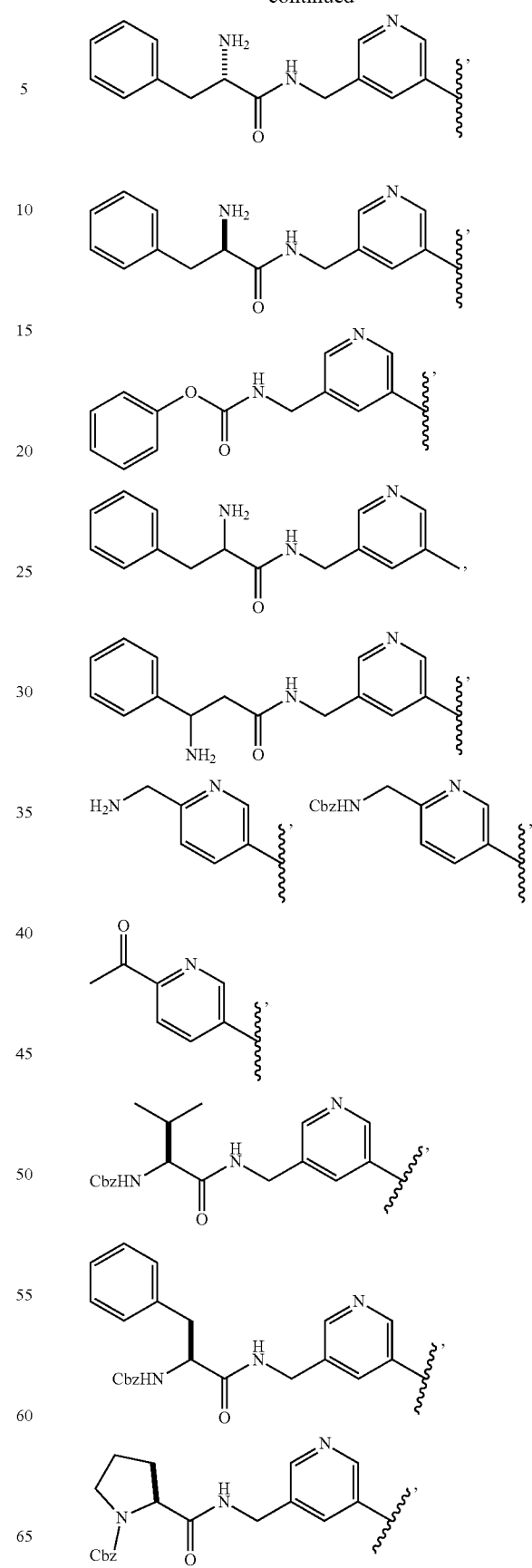

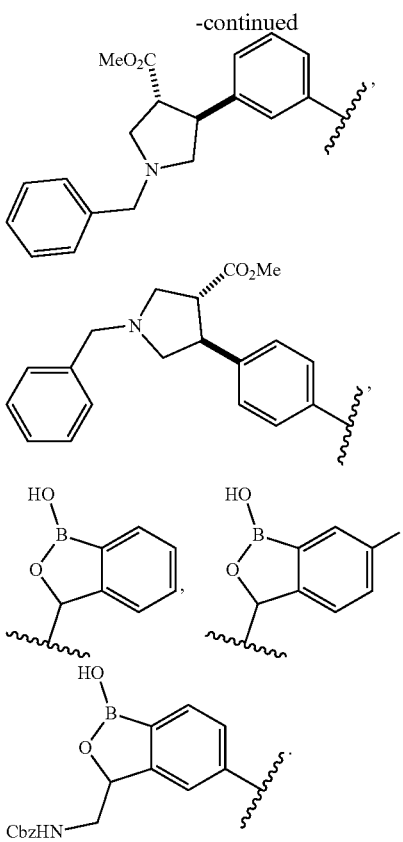

In some embodiments, $L^2$ is selected from —C(O)—, and —C(O)NR$^{10}$—. In certain embodiments, $L^2$ is —C(O)—. In certain embodiments, $L^2$ is selected from —C(O)NR$^{10}$—. R$^{10}$ of —C(O)NR$^{10}$— may be selected from hydrogen and $C_{1-6}$ alkyl. For example, $L^2$ may be —C(O)NH—.

In some embodiments, R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{1-6}$ alkyl, $C_{2-6}$ alkenyl, and $C_{2-6}$ alkynyl.

In some embodiments, R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{3-12}$ carbocycle, and 3- to 12-membered heterocycle. In some embodiments, R$^4$ is selected from: —OR$^{10}$, and —N(R$^{10}$)$_2$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, $C_{1-10}$ alkyl, $C_{2-10}$ alkenyl, and $C_{2-10}$ alkynyl. In certain embodiments, R$^4$ is —N(R$^{10}$)$_2$. R$^{10}$ of —N(R$^{10}$)$_2$ may be independently selected at each occurrence from optionally substituted $C_{1-6}$ alkyl. In certain embodiments, R$^{10}$ of —N(R$^{10}$)$_2$ is independently selected at each occurrence from methyl, ethyl, propyl, and butyl, any one of which is optionally substituted. For example, R$^4$ may be

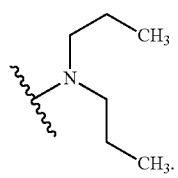

In certain embodiments, $L^2$-R$^4$ is

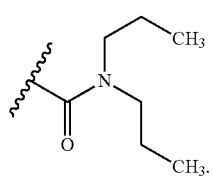

In some embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$—C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{1-6}$alkyl, $C_{2-6}$alkenyl, $C_{2-6}$alkynyl. In some embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$—C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{3-10}$ carbocycle and 3- to 10-membered heterocycle.

In some embodiments, the compound is selected from:

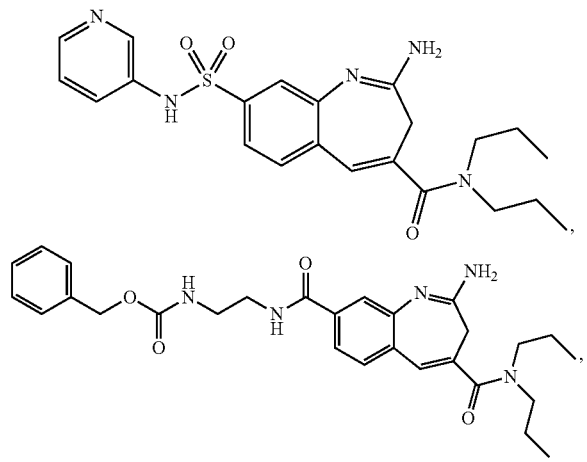

and a salt of any one thereof.

In some aspects, the present disclosure provides a compound represented by the structure of Formula (IVA):

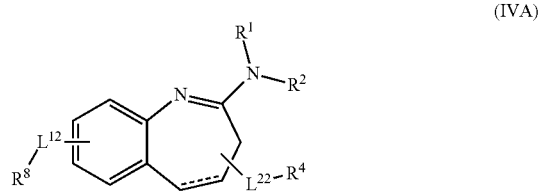

or a pharmaceutically acceptable salt thereof, wherein:

------ represents an optional double bond;

$L^{12}$ is selected from $-X^3-$, $-X^3-C_{1-6}$alkylene-$X^3-$, $-X^3-C_{2-6}$ alkenylene-$X^3-$, and $-X^3-C_{2-6}$ alkynylene-$X^3-$, each of which is optionally substituted on alkylene, alkenylene, or alkynylene with one or more substituents independently selected from $R^{12}$;

$L^{22}$ is independently selected from $-X^4-$, $-X^4-C_{1-6}$ alkylene-$X^4-$, $-X^4-C_{2-6}$ alkenylene-$X^4-$, and $-X^4-C_{2-6}$ alkynylene-$X^4-$, each of which is optionally substituted on alkylene, alkenylene, or alkynylene with one or more substituents independently selected from $R^{10}$;

$X^3$ and $X^4$ are independently selected at each occurrence from a bond, $-O-$, $-S-$, $-N(R^{10})-$, $-C(O)-$, $-C(O)O-$, $-OC(O)-$, $-OC(O)O-$, $-C(O)N(R^{10})-$, $-C(O)N(R^{10})C(O)-$, $-C(O)N(R^{10})C(O)N(R^{10})-$, $-N(R^{10})C(O)-$, $-N(R^{10})C(O)N(R^{10})-$, $-N(R^{10})C(O)O-$, $-OC(O)N(R^{10})-$, $-C(NR^{10})-$, $-N(R^{10})C(NR^{10})-$, $-C(NR^{10})N(R^{10})-$, $-N(R^{10})C(NR^{10})N(R^{10})-$, $-S(O)_2-$, $-OS(O)-$, $-S(O)O-$, $-S(O)-$, $-OS(O)_2-$, $-S(O)_2O-$, $-N(R^{10})S(O)_2-$, $-S(O)_2N(R^{10})-$, $-N(R^{10})S(O)-$, $-S(O)N(R^{10})-$, $-N(R^{10})S(O)_2N(R^{10})-$, and $-N(R^{10})S(O)N(R^{10})-$;

$R^1$ and $R^2$ are independently selected from $L^3$, and hydrogen; and $C_{1-10}$ alkyl, $C_{2-10}$ alkenyl, and $C_{2-10}$ alkynyl, each of which is optionally bound to $L^3$ and each of which is optionally substituted with one or more substituents independently selected from halogen, $-OR^{10}$, $-SR^{10}$, $-C(O)N(R^{10})_2$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, and $-CN$;

$R^4$ and $R^8$ are independently selected from: $-OR^{10}$, $-N(R^{10})_2$, $-C(O)N(R^{10})_2$, $-C(O)R^{10}$, $-C(O)OR^{10}$, $-S(O)R^{10}$, and $-S(O)_2R^{10}$; $C_{1-10}$ alkyl, $C_{2-10}$ alkenyl, $C_{2-10}$ alkynyl, each of which is optionally bound to $L^3$ and each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ and $R^8$ is optionally bound to $L^3$ and each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$alkyl, $C_{2-6}$ alkenyl, and $C_{2-6}$ alkynyl;

$R^{10}$ is independently selected at each occurrence from $L^3$, hydrogen, $-NH_2$, $-C(O)OCH_2C_6H_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, $-CN$, $-NO_2$, $-NH_2$, $=O$, $=S$, $-C(O)OCH_2C_6H_5$, $-NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;

$L^3$ is a linker moiety, wherein there is at least one occurrence of $L^3$; and $R^{12}$ is independently selected at each occurrence from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-P(O)(OR^{10})_2$, $-OP(O)(OR^{10})_2$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-P(O)(OR^{10})_2$, $-OP(O)(OR^{10})_2$, $-NO_2$, $=O$, $=S$, $=N(R^{10})$, $-CN$, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^{12}$ is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $S(O)_2R^{10}$, $-P(O)(OR^{10})_2$, $-OP(O)(OR^{10})_2$, $-NO_2$, $=O$, $=S$, $=N(R^{10})$, $-CN$, $C_{1-6}$ alkyl, $C_{2-6}$ alkenyl, $C_{2-6}$ alkynyl;

wherein any substitutable carbon on the benzazepine core is optionally substituted by a substituent independently selected from $R^{12}$ or two substituents on a single carbon atom combine to form a 3- to 7-membered carbocycle.

In some embodiments, the compound of Formula (IVA) is represented by Formula (IVB):

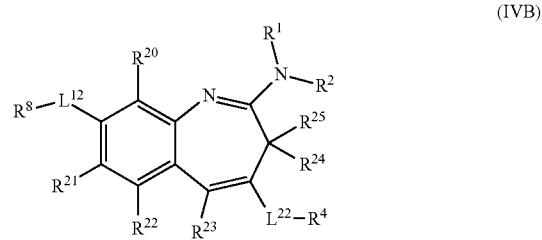

or a pharmaceutically acceptable salt thereof, wherein:

$R^{20}$, $R^{21}$, $R^{22}$, and $R^{23}$ are independently selected from hydrogen, halogen, —$OR^{10}$, —$SR^{10}$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl; and $R^{24}$, and $R^{25}$ are independently selected from hydrogen, halogen, —$OR^{10}$, —$SR^{10}$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl; or $R^{24}$ and $R^{25}$ taken together form an optionally substituted saturated $C_{3-7}$ carbocycle.

In some embodiments, $R^1$ is $L^3$. In some embodiments, $R^2$ is $L^3$.

In some embodiments, $L^{12}$ is —$C(O)N(R^{10})$—. In some embodiments, $R^{10}$ of —$C(O)N(R^{10})$— is selected from hydrogen, $C_{1-6}$ alkyl, and $L^3$. For example, $L^{12}$ may be —C(O)NH—.

In some embodiments, $R^8$ is an optionally substituted 5- or 6-membered heteroaryl. $R^8$ may be an optionally substituted 5- or 6-membered heteroaryl, bound to $L^3$. In some embodiments, $R^8$ is an optionally substituted pyridine, bound to $L^3$.

In some embodiments, $L^{22}$ is selected from —C(O)—, and —$C(O)NR^{10}$—. In certain embodiments, $L^{22}$ is —C(O)—. In certain embodiments, $L^{22}$ is —$C(O)NR^{10}$—. $R^{10}$ of —$C(O)NR^{10}$— may be selected from hydrogen, $C_{1-6}$ alkyl, and -$L^3$. For example, $L^{22}$ may be —C(O)NH—.

In some embodiments, $R^4$ is selected from: —$OR^{10}$, and —$N(R^{10})_2$; and $C_{1-10}$ alkyl, $C_{2-10}$ alkenyl, $C_{2-10}$ alkynyl, $C_{3-12}$ carbocycle, 3- to 12-membered heterocycle, aryl, and heteroaryl, each of which is optionally substituted with one or more substituents independently selected from halogen, —$OR^{10}$, —$SR^{10}$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl and each of which is further optionally bound to $L^3$. In some embodiments, $R^4$ is —$N(R^{10})_2$ and $R^{10}$ of —$N(R^{10})_2$ is selected from $L^3$ and hydrogen, and wherein at least one $R^{10}$ of —$N(R^{10})_2$ is $L^3$.

In some aspects, the compound of Formula (IVB) is a compound of Formula (IVC):

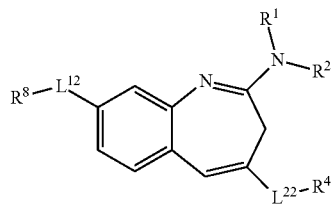

(IVC)

or a pharmaceutically acceptable salt thereof,
wherein:
$R^1$ and $R^2$ are hydrogen;
$L^{22}$ is —C(O)—;
$R^4$—$N(R^{10})_2$;
$R^{10}$ is independently selected at each occurrence from hydrogen, —$NH_2$, —$C(O)OCH_2C_6H_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —CN, —$NO_2$, —$NH_2$, =O, =S, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;

$L^{12}$ is —$C(O)N(R^{10})$—*, wherein * represents where $L^{12}$ is bound to $R^8$;

$R^8$ is an optionally substituted fused 5-5, fused 5-6, or fused 6-6 bicyclic heterocycle bound to linker moiety, $L^3$, and wherein optional substituents are independently selected at each occurrence from:

halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, and —CN;

$C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{1-6}$ alkyl, $C_{2-6}$ alkenyl, and $C_{2-6}$ alkynyl.

In certain embodiments: $R^{10}$ of —$N(R^{10})_2$ is independently selected at each occurrence from methyl, ethyl, propyl, and butyl, any one of which is optionally substituted. In certain embodiments, $R^{10}$ of —$C(O)N(R^{10})$—* is hydrogen.

In some embodiments, the compound is further covalently bound to a linker, $L^3$. In some embodiments, $L^3$ is a noncleavable linker. In some embodiments, $L^3$ is a cleavable linker. $L^3$ may be cleavable by a lysosomal enzyme. In some embodiments, the compound is covalently attached to an antibody or antigen binding fragment thereof.

In some embodiments, $L^3$ is represented by the formula:

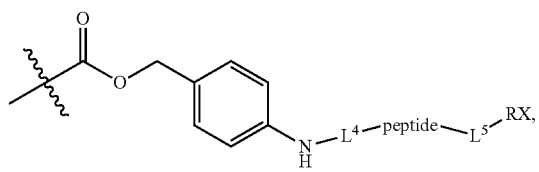

wherein:
$L^4$ represents the C-terminus of the peptide and $L^5$ is selected from a bond, alkylene and heteroalkylene, wherein $L^5$ is optionally substituted with one or more groups independently selected from $R^{32}$, and RX is a reactive moiety; and $R^{32}$ is independently selected at each occurrence from halogen, —OH, —CN, —O— alkyl, —SH, =O, =S, —$NH_2$, —$NO_2$; and $C_{1-10}$ alkyl, $C_{2-10}$ alkenyl, $C_{2-10}$ alkynyl, each of which is optionally substituted with one or more substituents independently selected from halogen, —OH, —CN, —O-alkyl, —SH, =O, =S, —$NH_2$, —$NO_2$.

In some embodiments, RX comprises a leaving group. In some embodiments, RX comprises a maleimide. In some embodiments, $L^3$ is further covalently bound to an antibody or antigen binding fragment thereof.

In some embodiments, $L^3$ is represented by the formula:

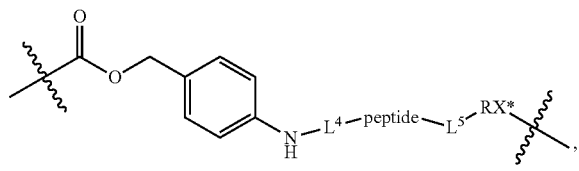

wherein $L^4$ represents the C-terminal of the peptide and $L^5$ is selected from a bond, alkylene and heteroalkylene, wherein $L^5$ is optionally substituted with one or more groups independently selected from $R^{32}$;

RX* comprises a bond, a succinimide moiety, or a hydrolyzed succinimide moiety bound to a residue of an antibody or antigen binding fragment thereof, wherein

on RX* represents the point of attachment to the residue of the antibody or antigen binding fragment thereof; and, $R^{32}$ is independently selected at each occurrence from halogen, —OH, —CN, —O— alkyl, —SH, =O, =S, —NH$_2$, —NO$_2$; and C$_{1-10}$ alkyl, C$_{2-10}$ alkenyl, C$_{2-10}$ alkynyl, each of which is optionally substituted with one or more substituents independently selected from halogen, —OH, —CN, —O-alkyl, —SH, =O, =S, —NH$_2$, —NO$_2$. In some embodiments, the peptide of $L^3$ comprises Val-Cit or Val-Ala.

In some aspects, the present disclosure provides a compound or salt selected from:

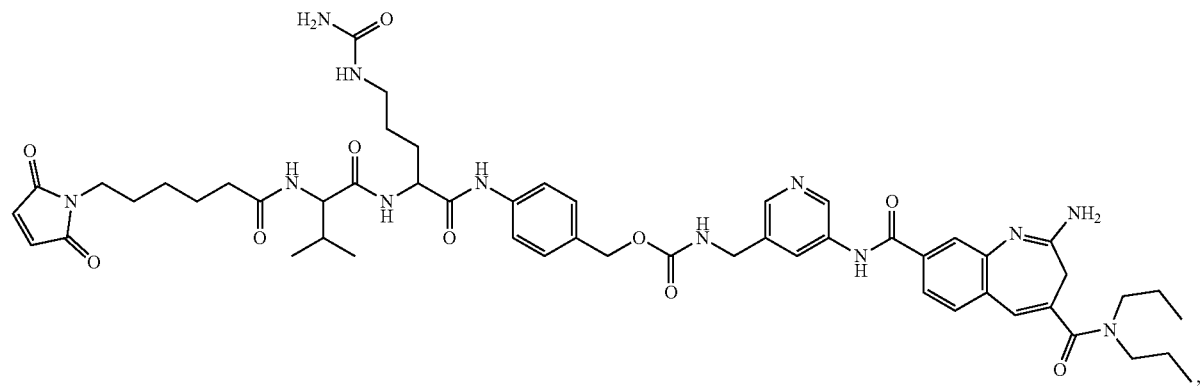

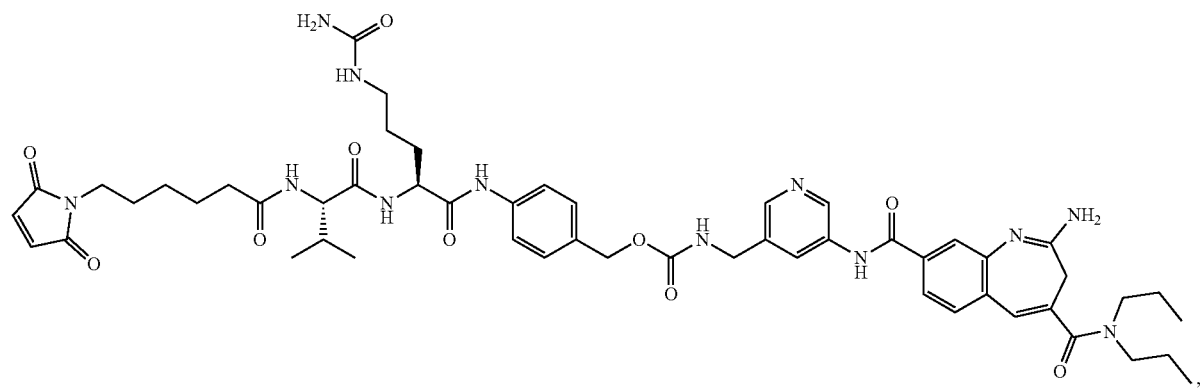

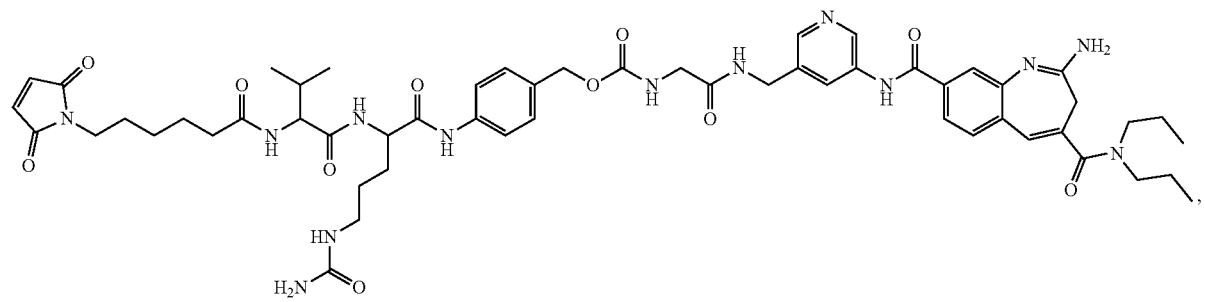

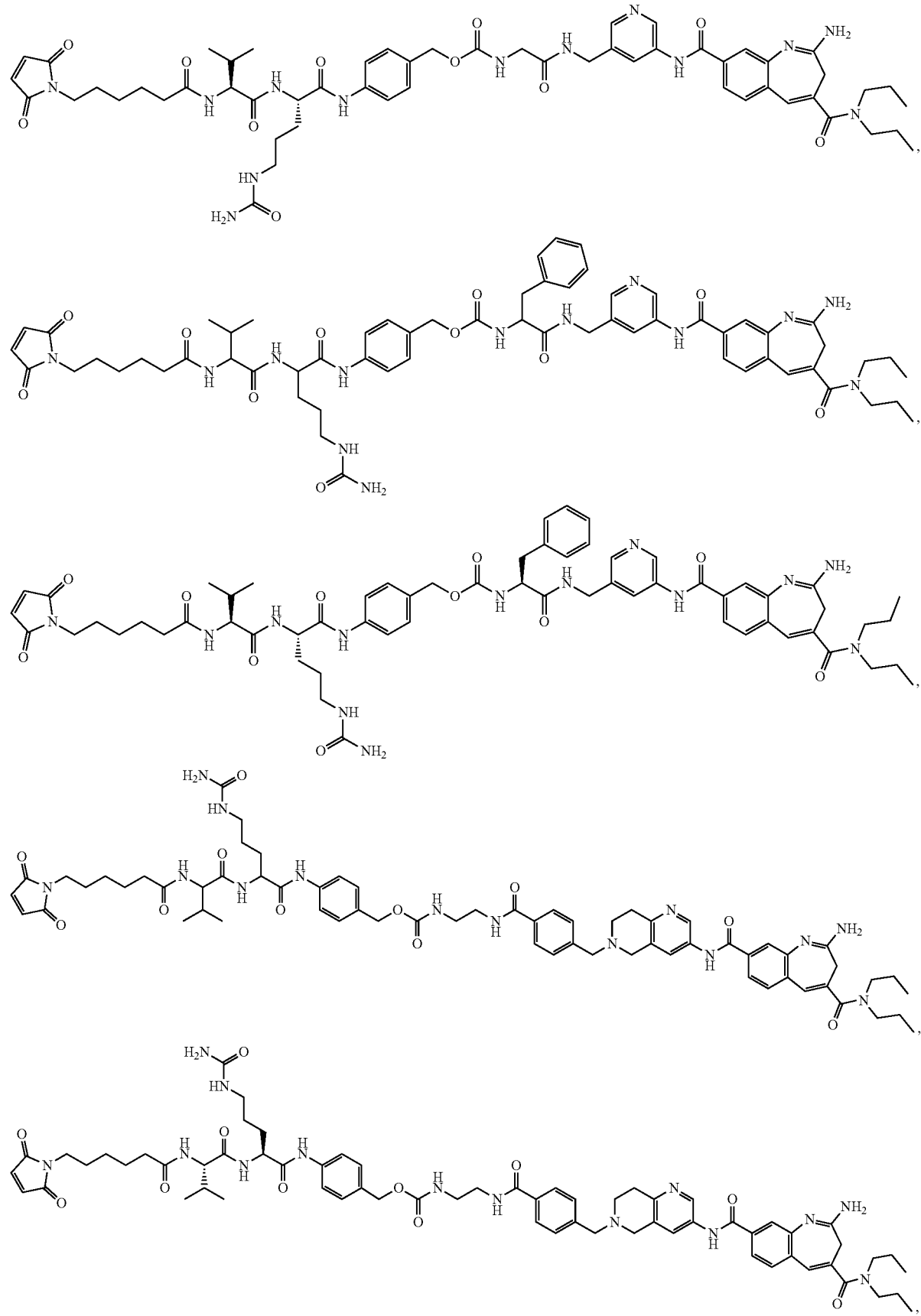

-continued
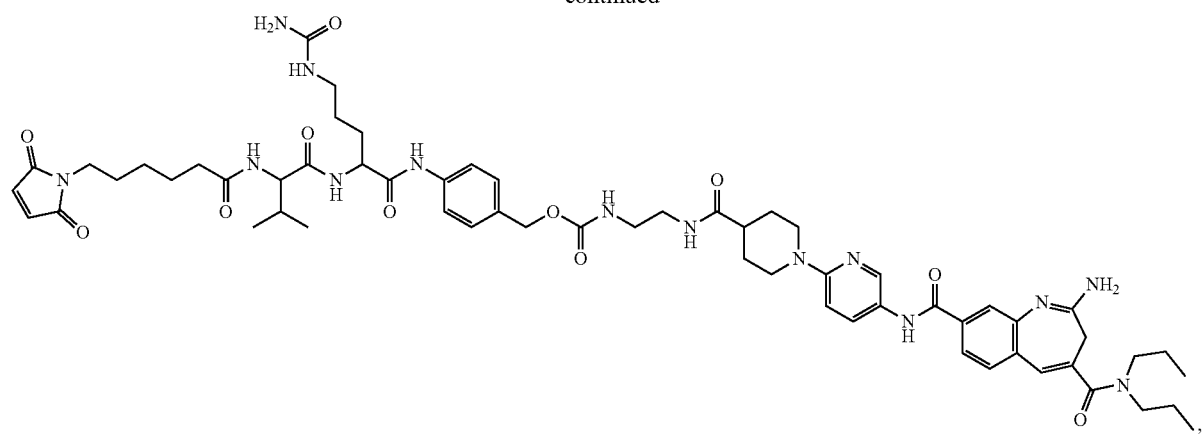
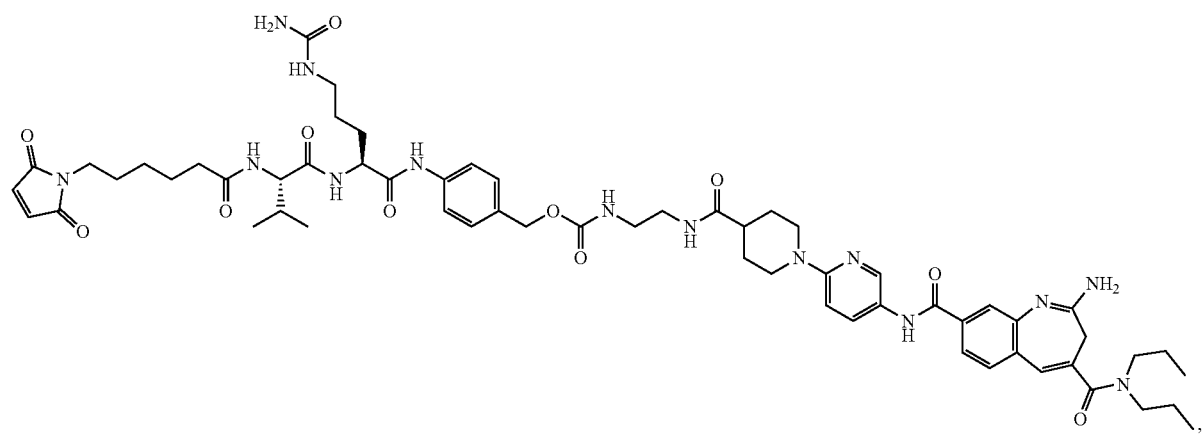
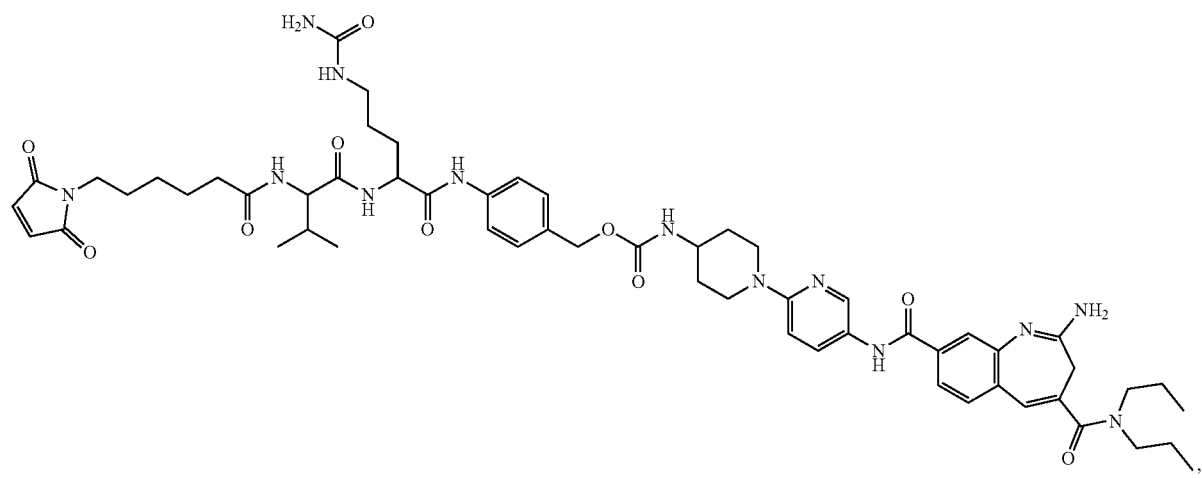

-continued
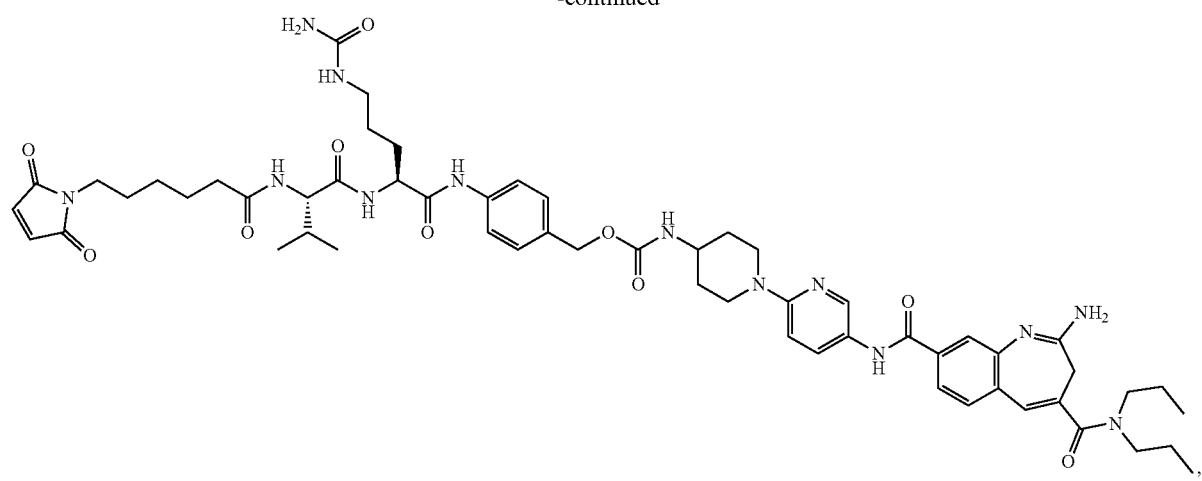
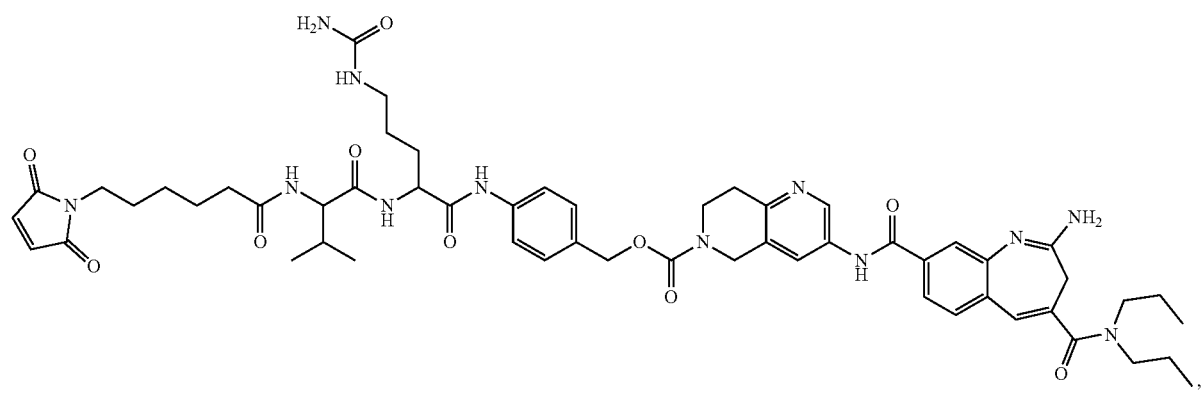
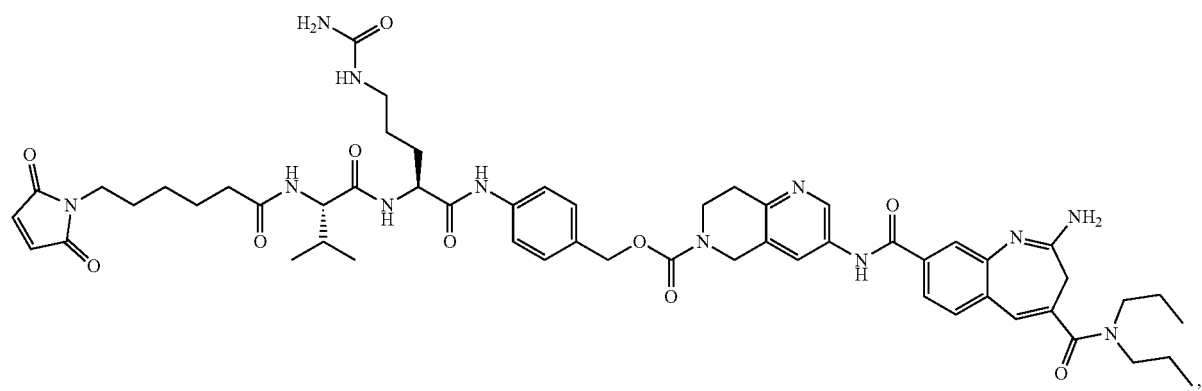
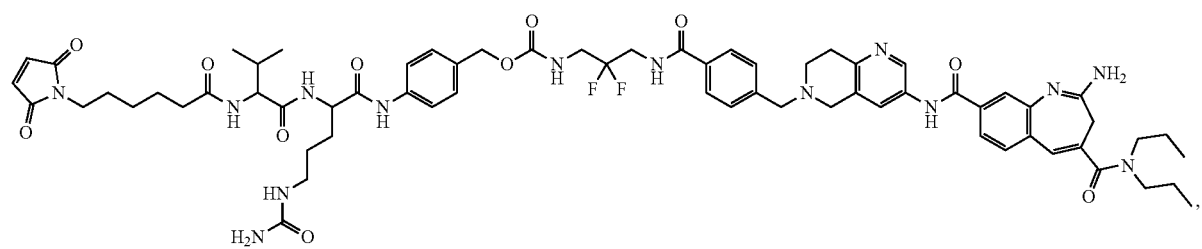

-continued
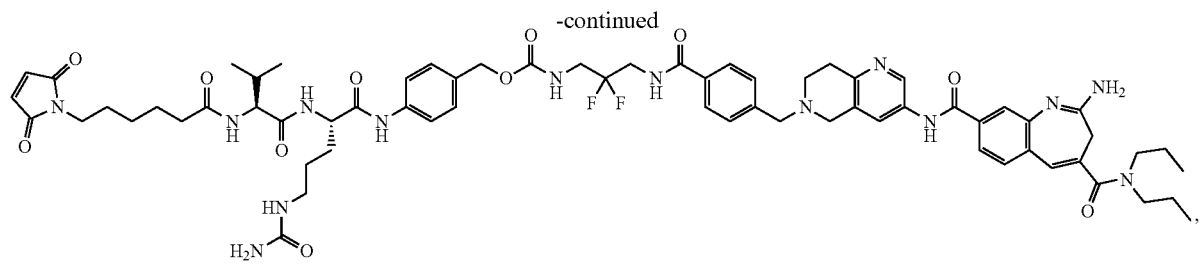
and a salt of any one thereof.
In some aspects, the present disclosure provides a compound or salt selected from:
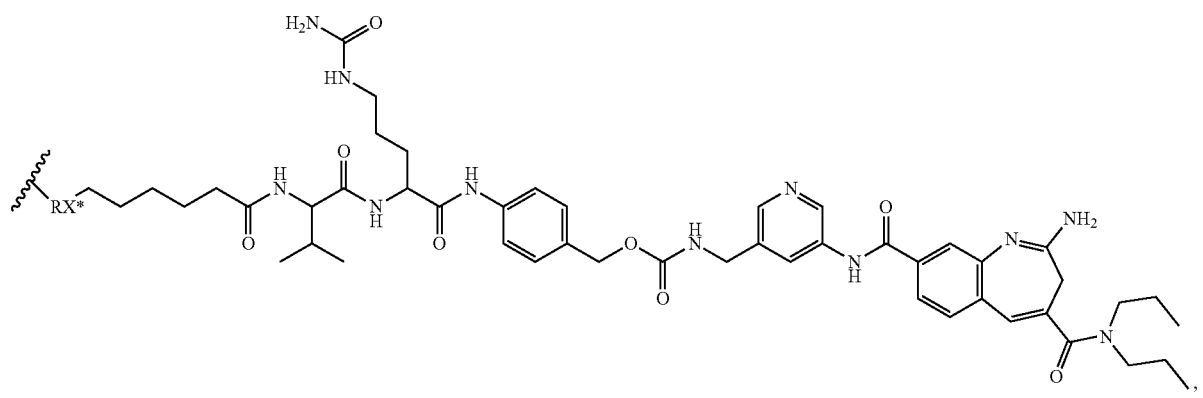
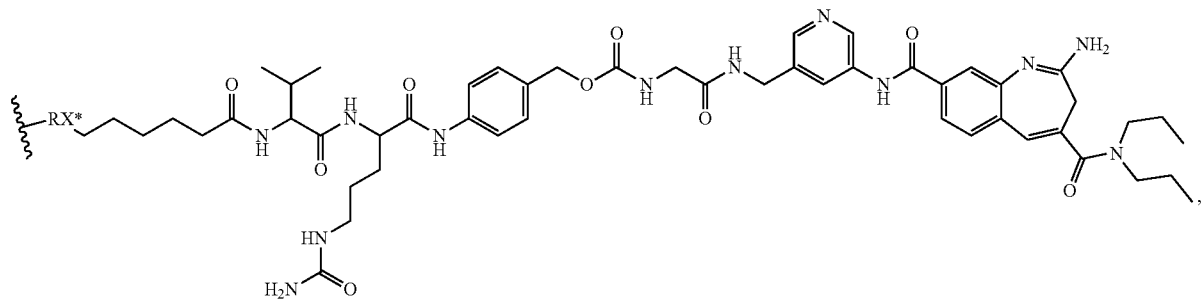

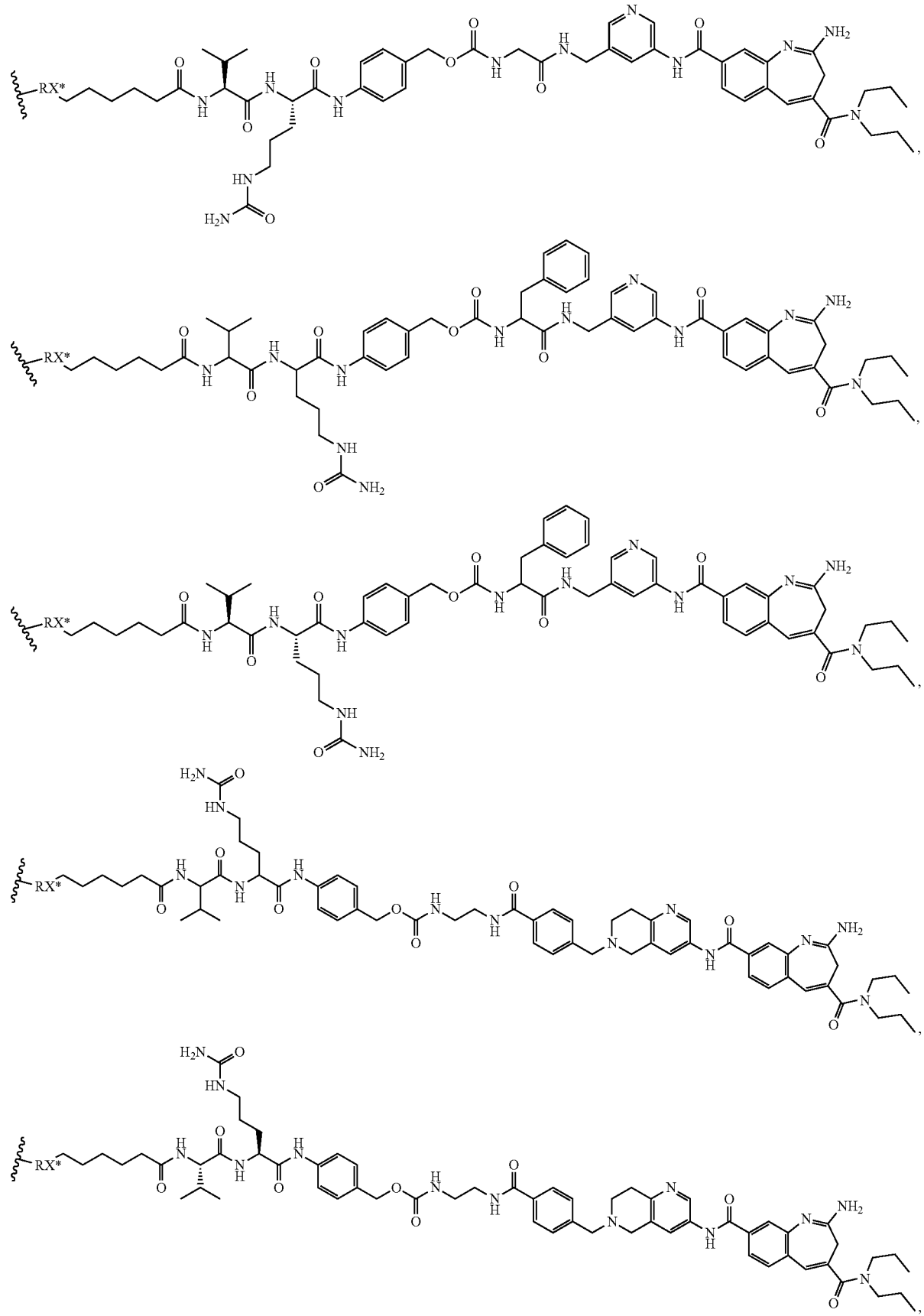

-continued
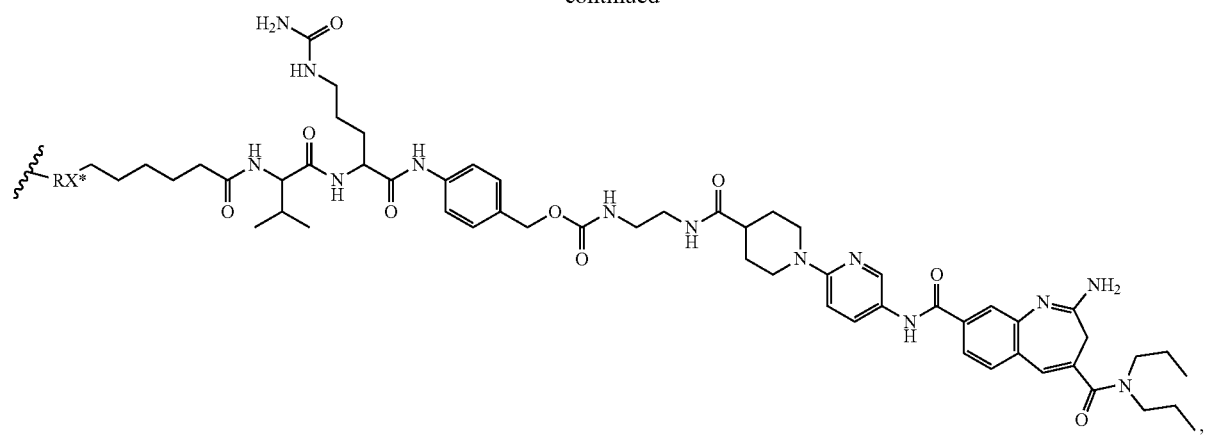
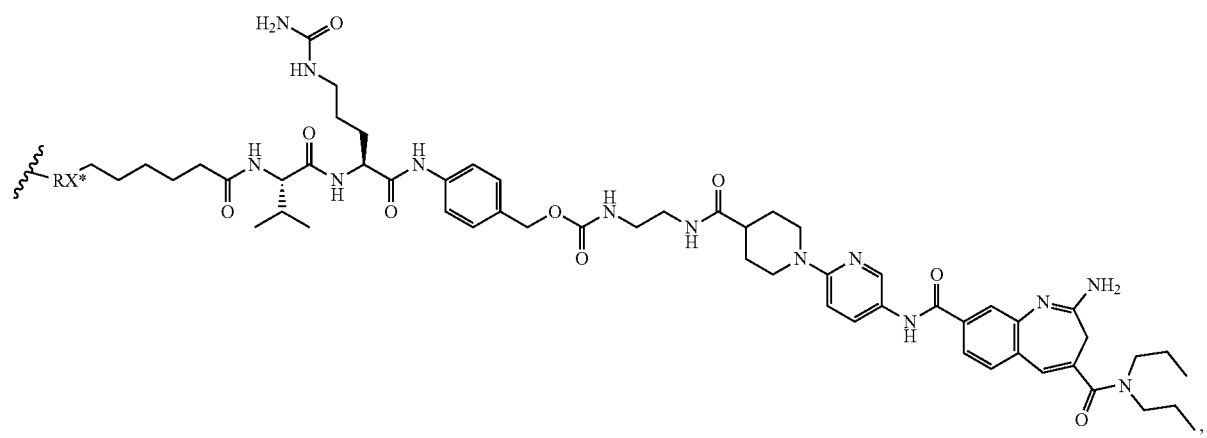
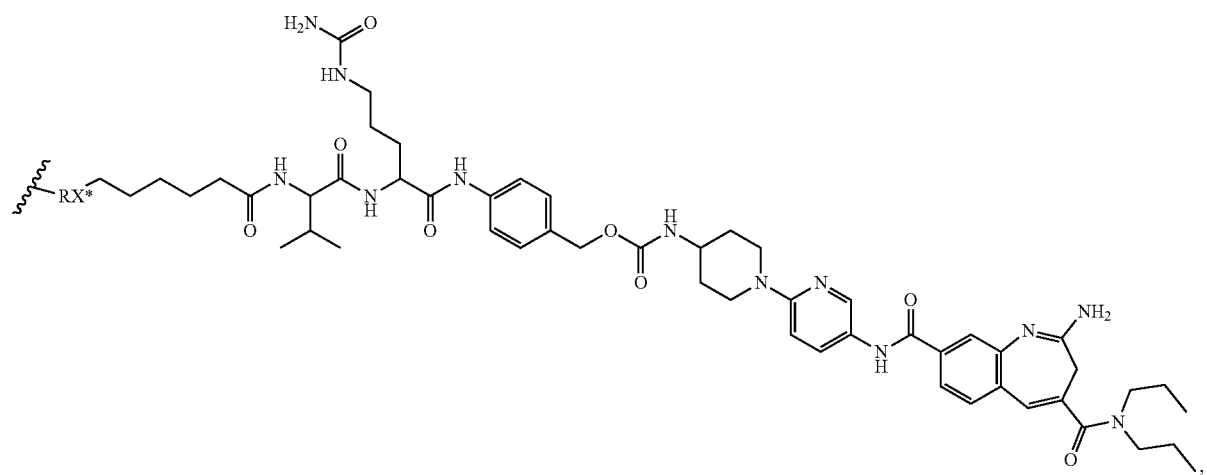

-continued
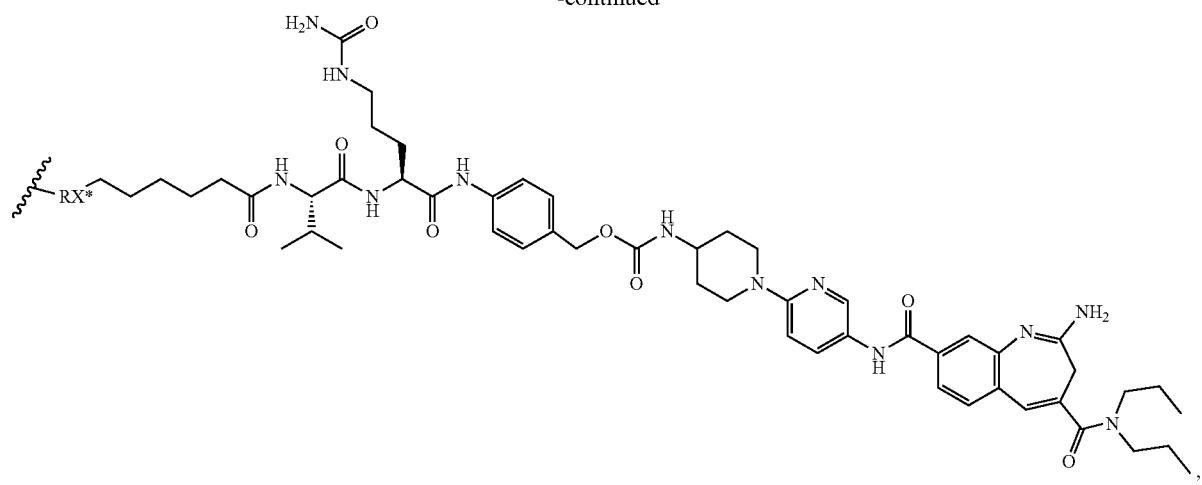
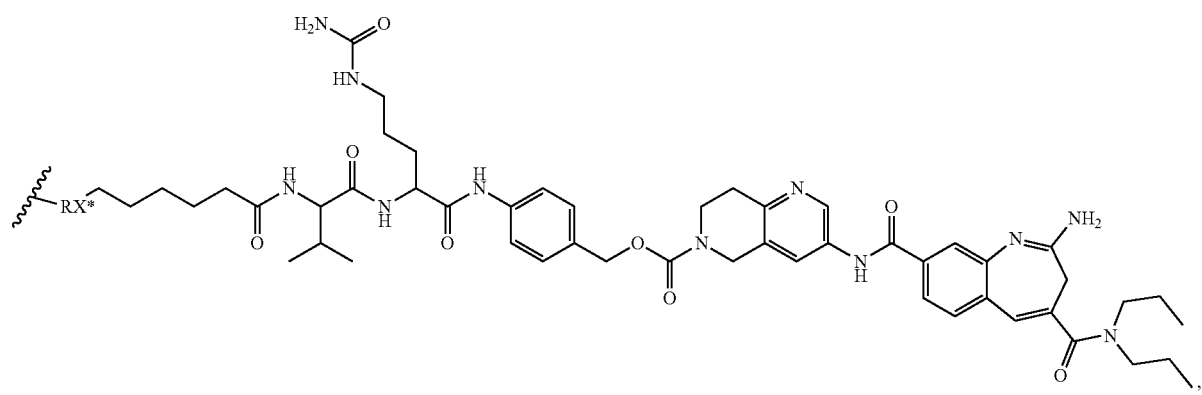
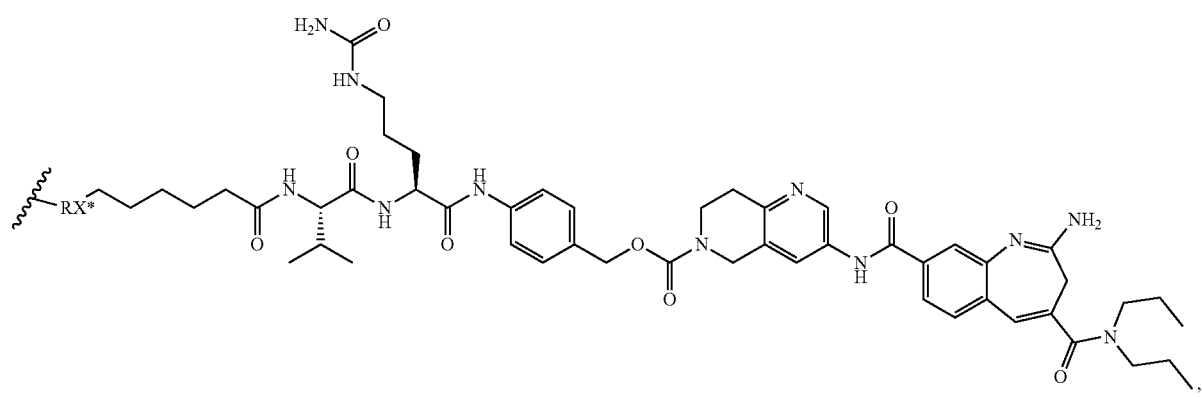
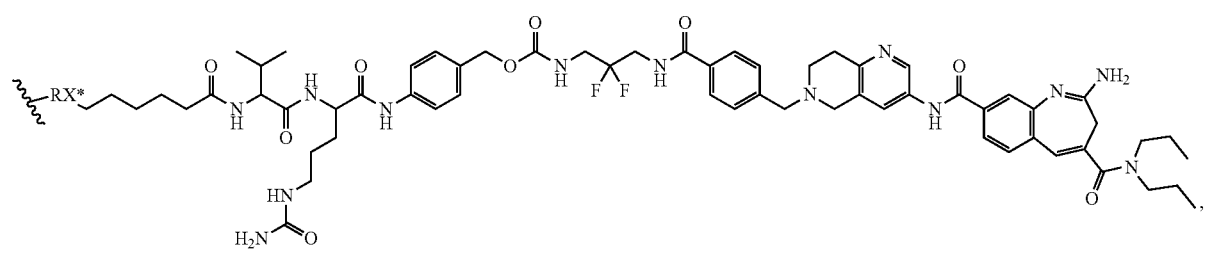

-continued

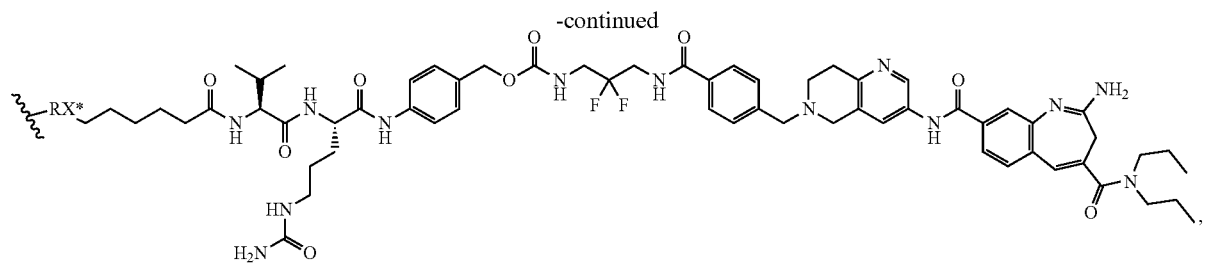

and a salt of any one thereof,
wherein the RX* is a bond, a succinimide moiety, or a hydrolyzed succinimide moiety bound to a residue of an antibody or antigen binding fragment thereof,
wherein

on RX* represents the point of attachment to the residue of the antibody or antigen binding fragment thereof.
In some embodiments, $L^3$ is represented by the formula:

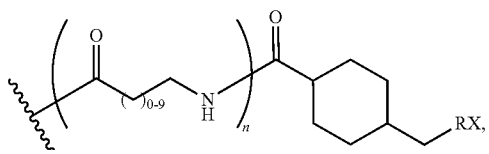

wherein RX comprises a reactive moiety, and n=0-9. In some embodiments, RX comprises a leaving group. In some embodiments, RX comprises a maleimide. In some embodiments. $L^3$ is represented as follows:

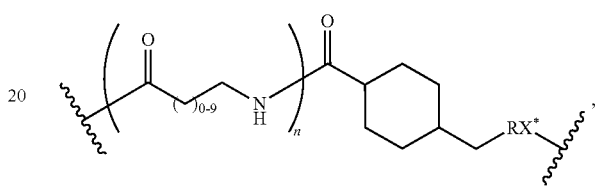

wherein RX* comprises a bond, a succinimide moiety, or a hydrolyzed succinimide moiety bound to a residue of an antibody or antigen binding fragment, wherein

on RX* represents the point of attachment to the residue of the antibody or antigen binding fragment thereof, and n=0-9.
In some aspects, the present disclosure provides a compound or salt selected from:

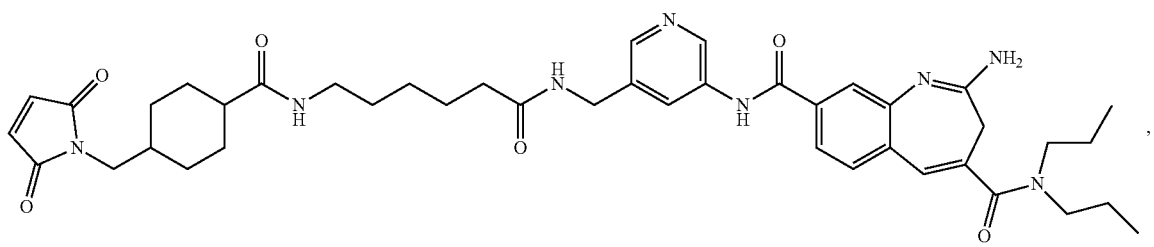

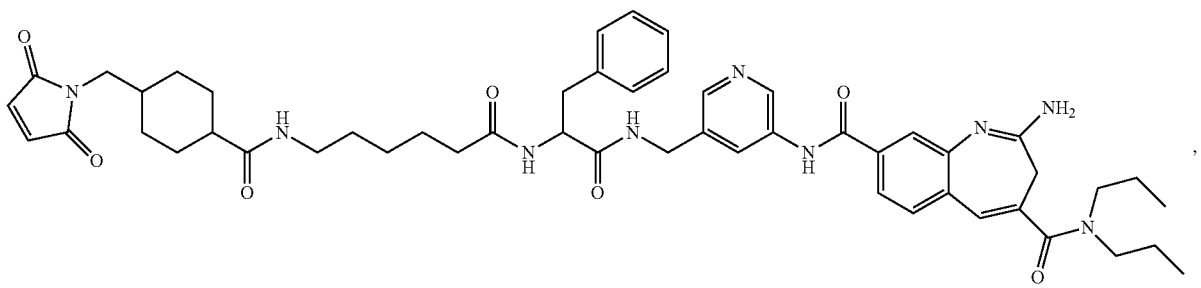

-continued
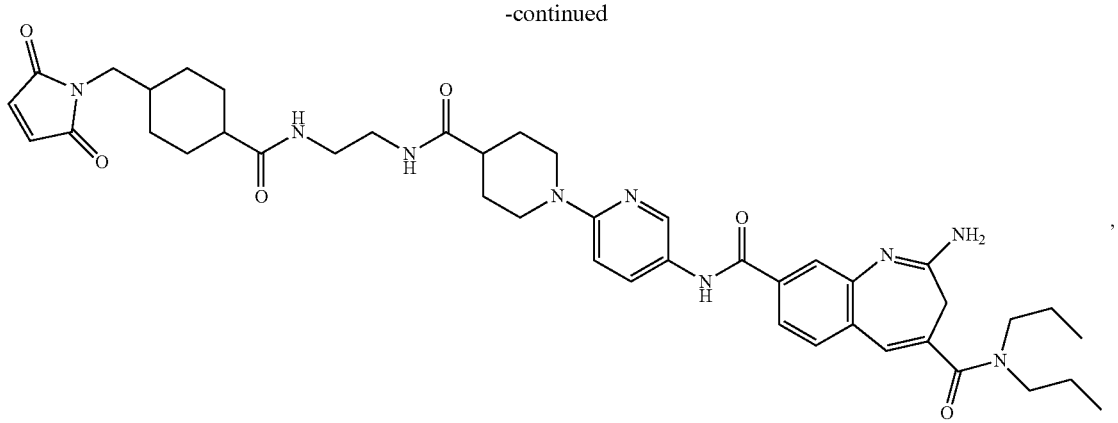
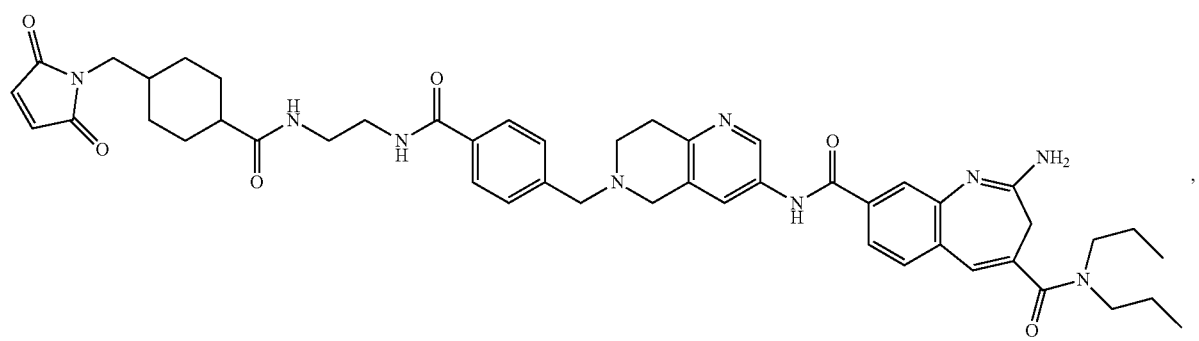
and a salt of any one thereof.
In some aspects, the present disclosure provides a compound or salt selected from:
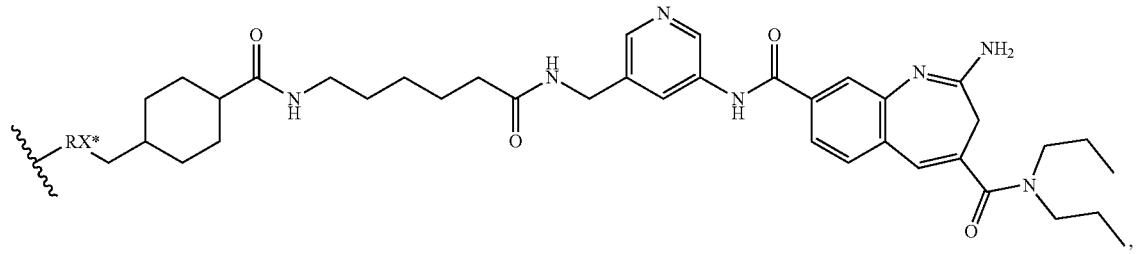
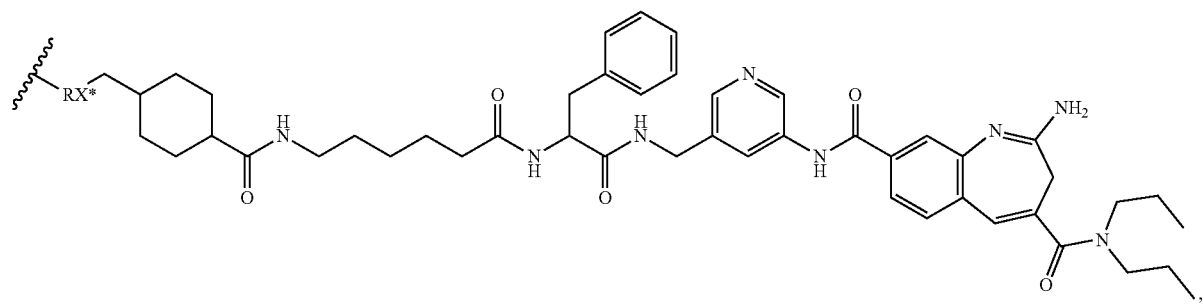

-continued

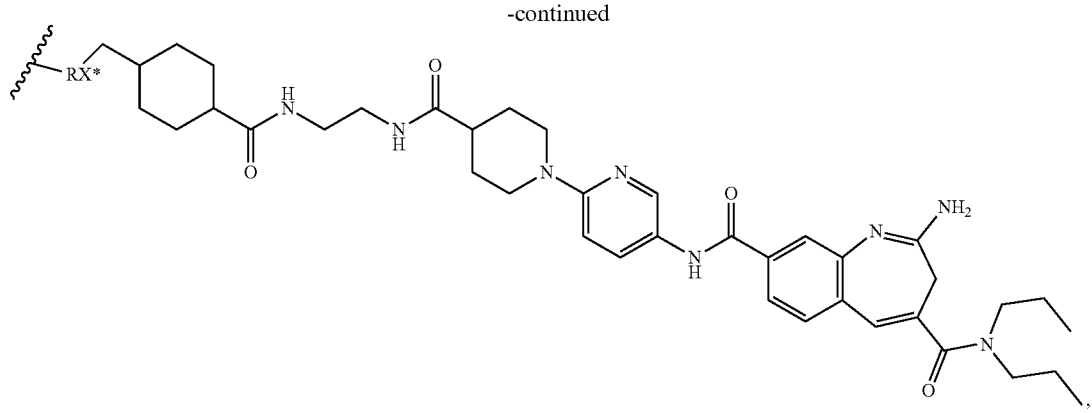

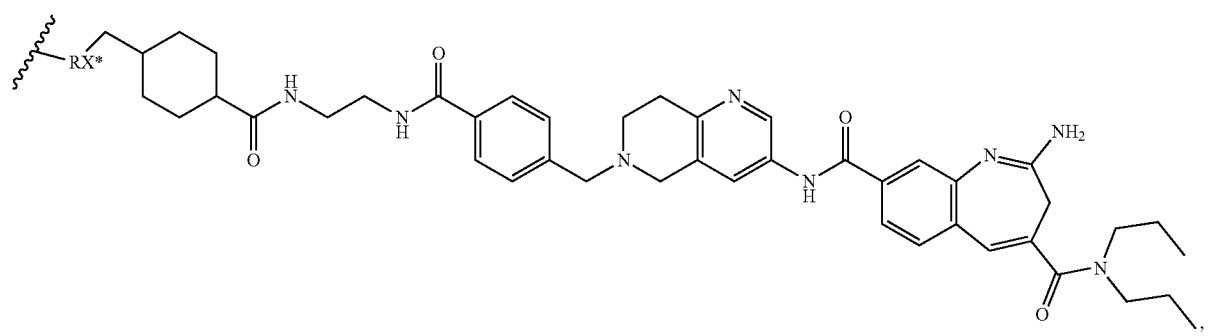

and a salt of any one thereof, wherein the RX* comprises a bond, a succinimide moiety, or a hydrolyzed succinimide moiety bound to a residue of an antibody or antigen binding fragment thereof, wherein

on RX* represents the point of attachment to the residue of the antibody or antigen binding fragment thereof.

In some embodiments, RX* comprises a succinamide moiety and is bound to a cysteine residue of an antibody or antigen binding fragment thereof. In some embodiments, RX* comprises a hydrolyzed succinamide moiety and is bound to a cysteine residue of an antibody or antigen binding fragment thereof.

In some aspects, the present disclosure provides a conjugate represented by the formula:

$$(D-L^3)_{1-8} \text{Antibody},$$

wherein Antibody is an anti-Nectin-4 antibody or antigen binding fragment thereof disclosed herein, D is a Category A compound or salt disclosed herein, and $L^3$ is a linker moiety.

In some aspects, the present disclosure provides a conjugate represented by the formula:

$$(D-L^3)_{1-8} \text{Antibody},$$

wherein Antibody is an anti-Nectin-4 antibody or antigen binding fragment thereof disclosed herein, and D-$L^3$ is a Category A compound or salt disclosed herein.

In some aspects, the present disclosure provides a pharmaceutical composition, comprising the conjugate disclosed herein and at least one pharmaceutically acceptable excipient.

In some embodiments, the average DAR of the conjugate is from about 2 to about 8, or about 1 to about 3, or about 3 to about 5.

Examples of TLR8 agonist compounds according to Category A are provided in Table 1a and their stereoisomers. It is understood that a compound is provided in Table 1a, salts of that compound are envisioned by Table 1a.

TABLE 1a

Compounds 1.1-1.69

| Compound | Structure and IUPAC |
|---|---|
| 1.1 | 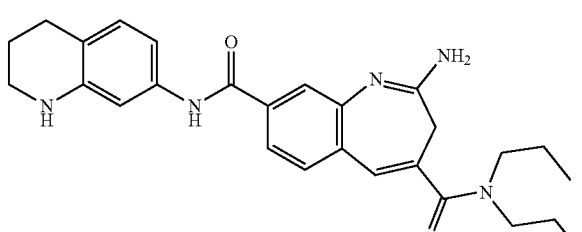

2-amino-N4,N4-dipropyl-N8-(1,2,3,4-tetrahydroquinolin-7-yl)-3H-benzo[b]azepine-4,8-dicarboxamide |
| 1.2 | 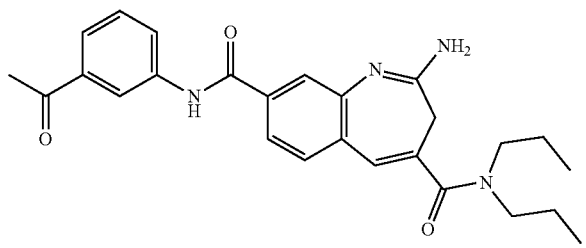 [SMILES: CCCN(CCC)C(=O)C1=Cc2ccc(C(=O)Nc3cccc(C(C)=O)c3)cc2N=C(N)C1]

$N^8$-(3-acetylphenyl)-2-amino-$N^4,N^4$-dipropyl-3H-benzo[b]azepine-4,8-dicarboxamide |
| 1.3 | 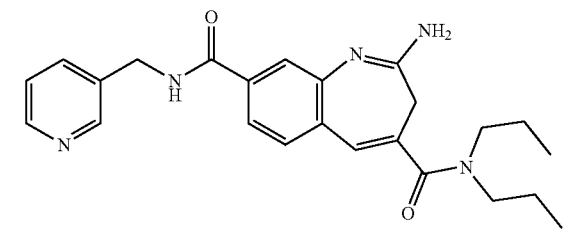 [SMILES: CCCN(CCC)C(=O)C1=Cc2ccc(C(=O)NCc3cccnc3)cc2N=C(N)C1]

2-amino-$N^4,N^4$-dipropyl-$N^8$-(pyridin-3-ylmethyl)-3H-benzo[b]azepine-4,8-dicarboxamide |
| 1.4 | 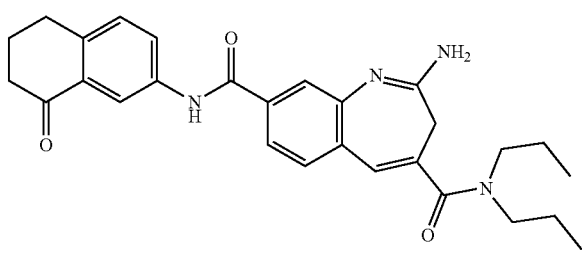 [SMILES: CCCN(CCC)C(=O)C1=Cc2ccc(C(=O)Nc3ccc4c(c3)C(=O)CCC4)cc2N=C(N)C1]

2-amino-$N^8$-(8-oxo-5,6,7,8-tetrahydronaphthalen-2-yl)-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.5 | 2-amino-$N^8$-(5-oxo-5,6,7,8-tetrahydronaphthalen-2-yl)-$N^4,N^4$-dipropyl-3H-benzo[b]azepine-4,8-dicarboxamide |
| 1.6 | 2-amino-$N^8$-(3-(hydrazinecarbonyl)phenyl)-$N^4,N^4$-dipropyl-3H-benzo[b]azepine-4,8-dicarboxamide |
| 1.7 | 2-amino-$N^8$-(8-hydroxy-5,6,7,8-tetrahydronaphthalen-2-yl)-N4,N4-dipropyl-3H-benzo[b]azepine-4,8-dicarboxamide |
| 1.8 | 2-amino-$N^8$-(5-hydroxy-5,6,7,8-tetrahydronaphthalen-2-yl)-$N^4,N^4$-dipropyl-3H-benzo[b]azepine-4,8-dicarboxamide |

TABLE 1a-continued
Compounds 1.1-1.69
| Compound | Structure and IUPAC |
|---|---|
| 1.9 | 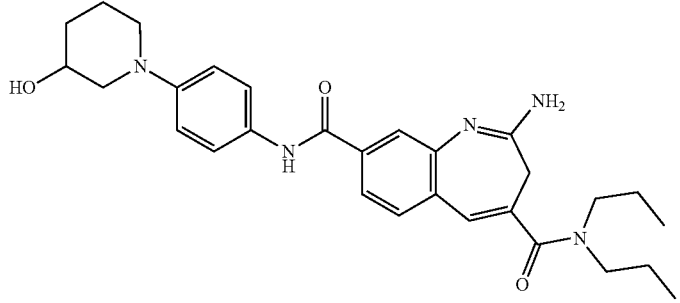 [SMILES: CCCN(CCC)C(=O)C1=Cc2ccc(C(=O)Nc3ccc(N4CCCC(O)C4)cc3)cc2N=C(N)C1]<br>2-amino-$N^8$-(4-(3-hydroxypiperidin-1-yl)phenyl)-<br>$N^4,N^4$-dipropyl-3H-benzo[b]azepine-4,8-<br>dicarboxamide |
| 1.10 | 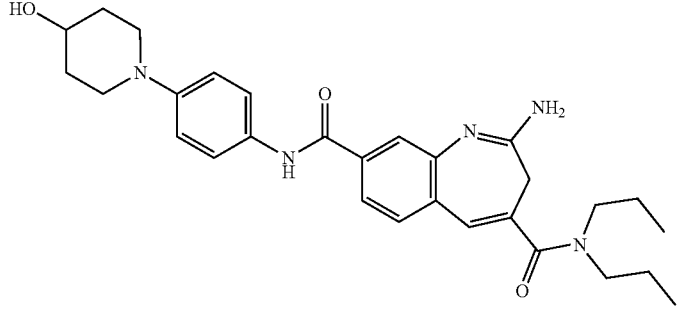 [SMILES: CCCN(CCC)C(=O)C1=Cc2ccc(C(=O)Nc3ccc(N4CCC(O)CC4)cc3)cc2N=C(N)C1]<br>2-amino-$N^8$-(4-(4-hydroxypiperidin-1-yl)phenyl)-<br>$N^4,N^4$-dipropyl-3H-benzo[b]azepine-4,8-<br>dicarboxamide |
| 1.11 | 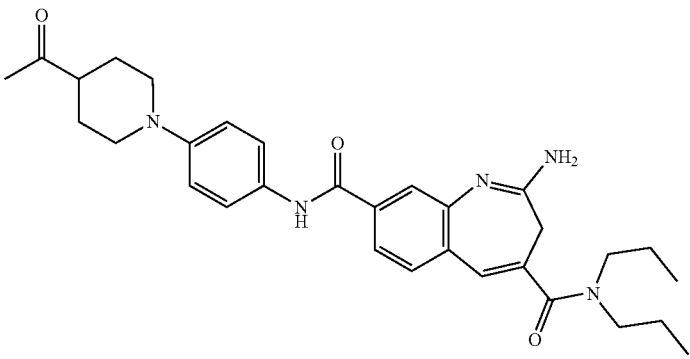 [SMILES: CCCN(CCC)C(=O)C1=Cc2ccc(C(=O)Nc3ccc(N4CCC(C(C)=O)CC4)cc3)cc2N=C(N)C1]<br>$N^8$-(4-(4-acetylpiperidin-1-yl)phenyl)-2-amino-<br>$N^4,N^4$-dipropyl-3H-benzo[b]azepine-4,8-<br>dicarboxamide |

TABLE 1a-continued

Compounds 1.1-1.69

| Compound | Structure and IUPAC |
|---|---|
| 1.12 | 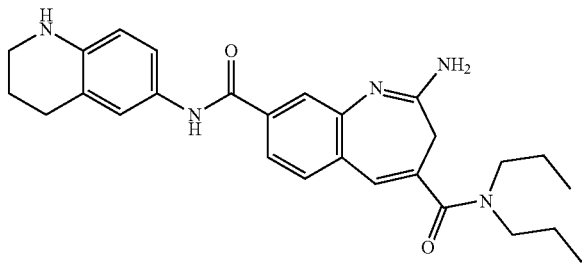 [SMILES: CCCN(CCC)C(=O)C1=Cc2ccc(C(=O)Nc3ccc4c(c3)CCCN4)cc2N=C(N)C1]<br>2-amino-$N^4,N^4$-dipropyl-$N^8$-(1,2,3,4-tetrahydroquinolin-6-yl)-3H-benzo[b]azepine-4,8-dicarboxamide |
| 1.13 | 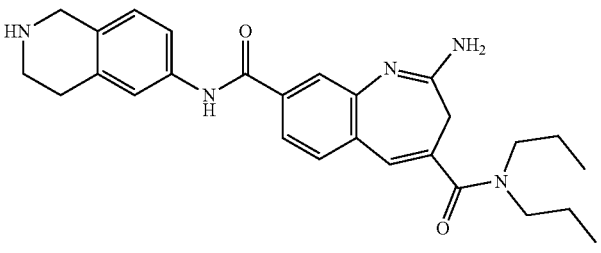 [SMILES: CCCN(CCC)C(=O)C1=Cc2ccc(C(=O)Nc3ccc4c(c3)CCNC4)cc2N=C(N)C1]<br>2-amino-$N^4,N^4$-dipropyl-$N^8$-(1,2,3,4-tetrahydroisoquinolin-6-yl)-3H-benzo[b]azepine-4,8-dicarboxamide |
| 1.14 | 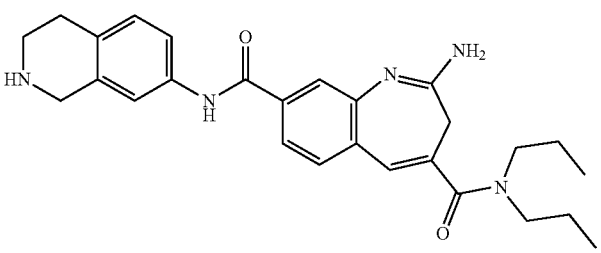 [SMILES: CCCN(CCC)C(=O)C1=Cc2ccc(C(=O)Nc3ccc4c(c3)CNCC4)cc2N=C(N)C1]<br>2-amino-$N^4,N^4$-dipropyl-$N^8$-(1,2,3,4-tetrahydroisoquinolin-7-yl)-3H-benzo[b]azepine-4,8-dicarboxamide trifluoroacetate salt |
| 1.15 | 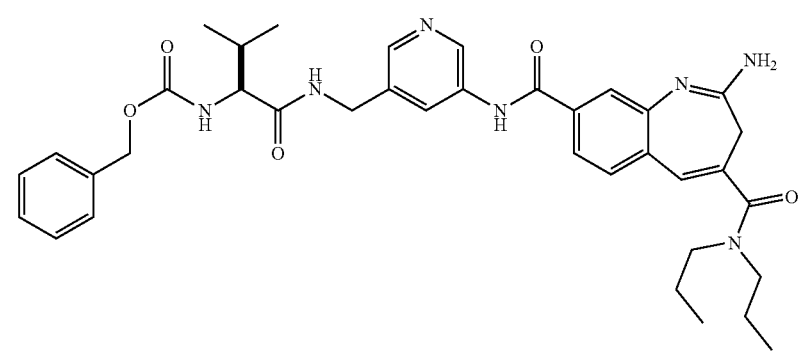 [SMILES: CCCN(CCC)C(=O)C1=Cc2ccc(C(=O)Nc3cncc(CNC(=O)[C@@H](NC(=O)OCc4ccccc4)C(C)C)c3)cc2N=C(N)C1]<br>benzyl (S)-(1-(((5-(2-amino-4-(dipropylcarbamoyl)-3H-benzo[b]azepine-8-carboxamido)pyridin-3-yl)methyl)amino)-3-methyl-1-oxobutan-2-yl)carbamate |

TABLE 1a-continued

Compounds 1.1-1.69

| Compound | Structure and IUPAC |
|---|---|
| 1.16 | 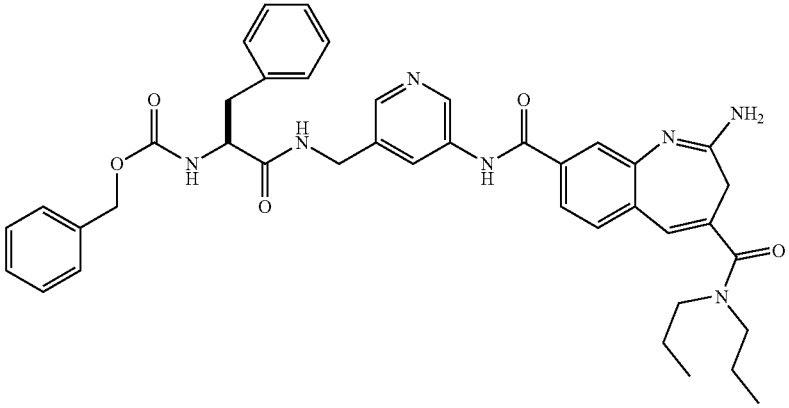 [SMILES: CCCN(CCC)C(=O)C1=Cc2ccc(C(=O)Nc3cncc(CNC(=O)[C@H](Cc4ccccc4)NC(=O)OCc4ccccc4)c3)cc2N=C(N)C1]<br>benzyl (S)-(1-(((5-(2-amino-4-(dipropyl-carbamoyl)-3H-benzo[b]azepine-8-carboxamido)pyridin-3-yl)methyl)amino)-1-oxo-3-phenylpropan-2-yl)carbamate |
| 1.17 | 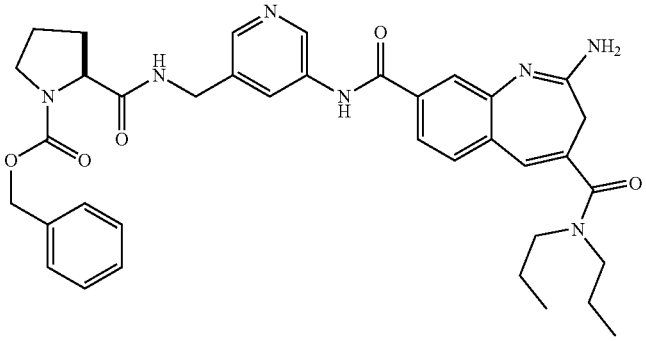 [SMILES: CCCN(CCC)C(=O)C1=Cc2ccc(C(=O)Nc3cncc(CNC(=O)[C@@H]4CCCN4C(=O)OCc4ccccc4)c3)cc2N=C(N)C1]<br>benzyl (S)-2-(((5-(2-amino-4-(dipropyl-carbamoyl)-3H-benzo[b]azepine-8-carboxamido)pyridin-3-yl)methyl)carbamoyl)pyrrolidine-1-carboxylate |
| 1.18 | 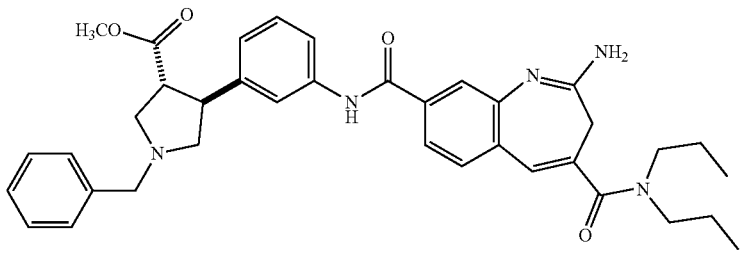 [SMILES: CCCN(CCC)C(=O)C1=Cc2ccc(C(=O)Nc3cccc([C@H]4CN(Cc5ccccc5)C[C@@H]4C(=O)OC)c3)cc2N=C(N)C1]<br>methyl (3R,4S)-4-(3-(2-amino-4-(dipropylcarbamoyl)-3H-benzo[b]azepine-8-carboxamido)phenyl)-1-benzylpyrrolidine-3-carboxylate |

TABLE 1a-continued

Compounds 1.1-1.69

| Compound | Structure and IUPAC |
|---|---|
| 1.19 | 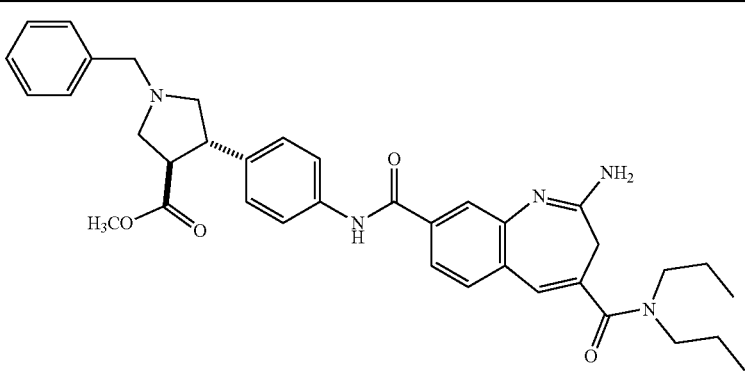<br>methyl (3R,4S)-4-(4-(2-amino-4-(dipropylcarbamoyl)-3H-benzo[b]azepine-8-carboxamido)phenyl)-1-benzylpyrrolidine-3-carboxylate |
| 1.20 | 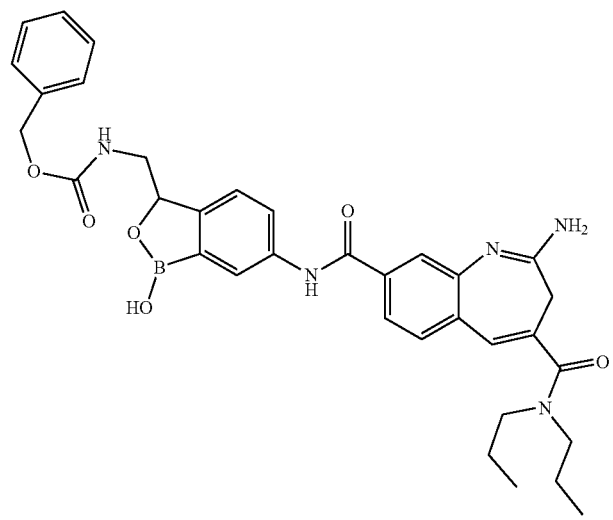 [SMILES: CCCN(CCC)C(=O)C1=Cc2ccc(C(=O)Nc3ccc4c(c3)B(O)OC4CNC(=O)OCc3ccccc3)cc2N=C(N)C1]<br>benzyl ((6-(2-amino-4-(dipropylcarbamoyl)-3H-benzo[b]azepine-8-carboxamido)-1-hydroxy-1,3-dihydrobenzo[c][1,2]oxaborol-3-yl)methyl)carbamate |
| 1.21 | 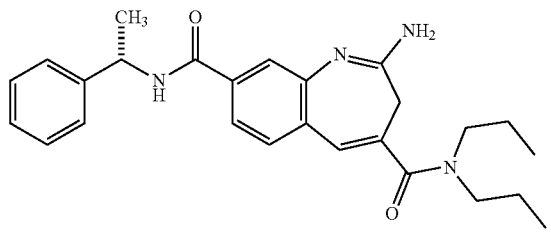 [SMILES: CCCN(CCC)C(=O)C1=Cc2ccc(C(=O)N[C@@H](C)c3ccccc3)cc2N=C(N)C1]<br>(S)-2-amino-$N^8$-(1-phenylethyl)-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.22 | 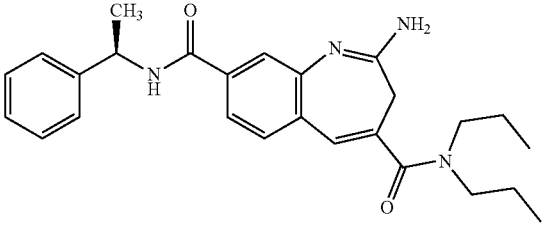 [SMILES: CCCN(CCC)C(=O)C1=Cc2ccc(C(=O)N[C@H](C)c3ccccc3)cc2N=C(N)C1]

(R)-2-amino-$N^8$-(1-phenylethyl)-$N^4$,$N^4$-dipropyl-3H-benzo[b]azepine-4,8-dicarboxamide |
| 1.23 | 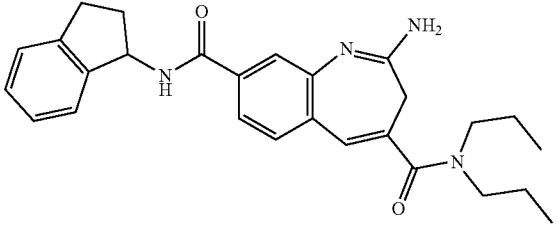 [SMILES: CCCN(CCC)C(=O)C1=Cc2ccc(C(=O)NC3CCc4ccccc43)cc2N=C(N)C1]

2-amino-$N^8$-(2,3-dihydro-1H-inden-1-yl)-$N^4$,$N^4$-dipropyl-3H-benzo[b]azepine-4,8-dicarboxamide |
| 1.24 | 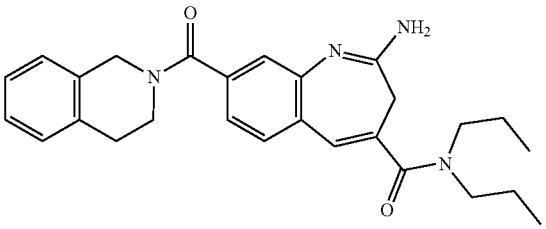 [SMILES: CCCN(CCC)C(=O)C1=Cc2ccc(C(=O)N3CCc4ccccc4C3)cc2N=C(N)C1]

2-amino-N,N-dipropyl-8-(1,2,3,4-tetrahydroisoquinoline-2-carbonyl)-3H-benzo[b]azepine-4-carboxamide |
| 1.25 | 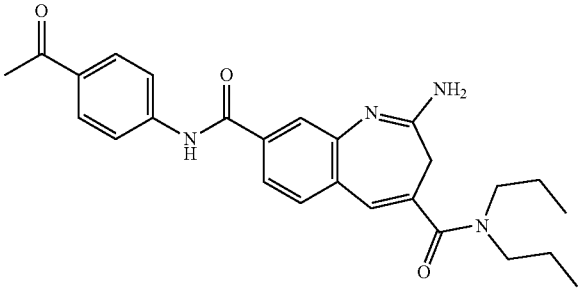 [SMILES: CCCN(CCC)C(=O)C1=Cc2ccc(C(=O)Nc3ccc(C(C)=O)cc3)cc2N=C(N)C1]

$N^8$-(4-acetylphenyl)-2-amino-$N^4$,$N^4$-dipropyl-3H-benzo[b]azepine-4,8-dicarboxamide |

TABLE 1a-continued
Compounds 1.1-1.69
| Compound | Structure and IUPAC |
|---|---|
| 1.26 | 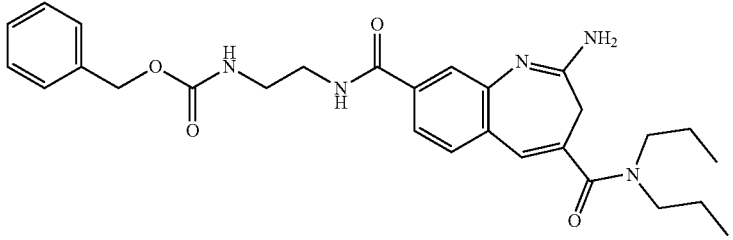 [SMILES: CCCN(CCC)C(=O)C1=Cc2ccc(C(=O)NCCNC(=O)OCc3ccccc3)cc2N=C(N)C1]<br>benzyl (2-(2-amino-4-(dipropylcarbamoyl)-3H-benzo[b]azepine-8-carboxamido)ethyl)carbamate |
| 1.27 | 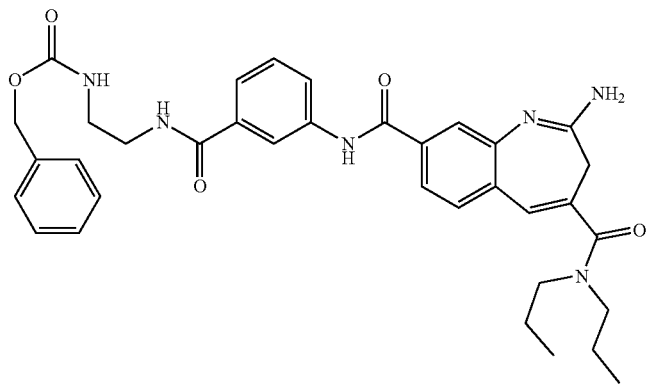 [SMILES: CCCN(CCC)C(=O)C1=Cc2ccc(C(=O)Nc3cccc(C(=O)NCCNC(=O)OCc4ccccc4)c3)cc2N=C(N)C1]<br>benzyl (2-(3-(2-amino-4-(dipropylcarbamoyl)-3H-benzo[b]azepine-8-carboxamido)benzamido)ethyl)carbamate |
| 1.28 | 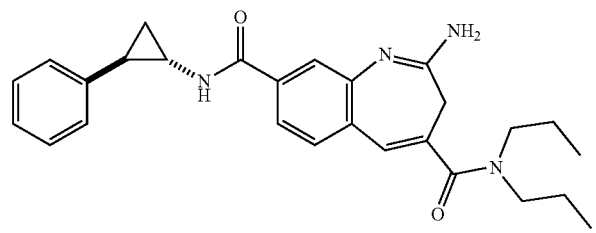<br>2-amino-$N^8$-((1S,2R)-2-phenylcyclopropyl)-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.29 | 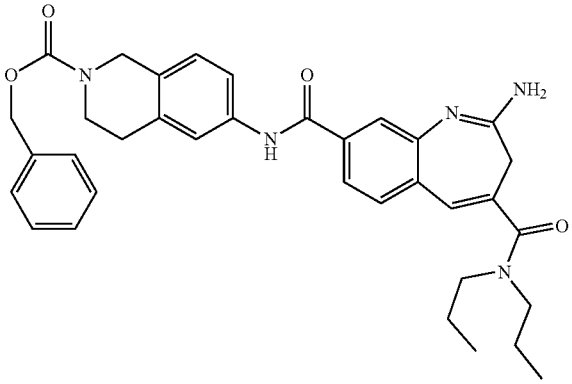 [SMILES: CCCN(CCC)C(=O)C1=Cc2ccc(C(=O)Nc3ccc4c(c3)CCN(C(=O)OCc3ccccc3)C4)cc2N=C(N)C1]<br>benzyl 6-(2-amino-4-(dipropylcarbamoyl)-3H-benzo[b]azepine-8-carboxamido)-3,4-dihydroisoquinoline-2(1H)-carboxylate |
| 1.30 | 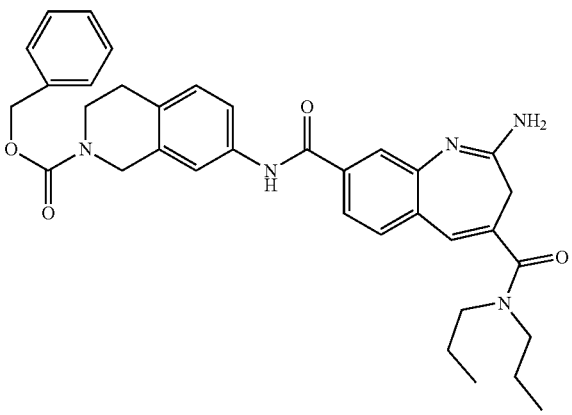 [SMILES: CCCN(CCC)C(=O)C1=Cc2ccc(C(=O)Nc3ccc4c(c3)CN(C(=O)OCc3ccccc3)CC4)cc2N=C(N)C1]<br>benzyl 7-(2-amino-4-(dipropylcarbamoyl)-3H-benzo[b]azepine-8-carboxamido)-3,4-dihydroisoquinoline-2(1H)-carboxylate |
| 1.31 | 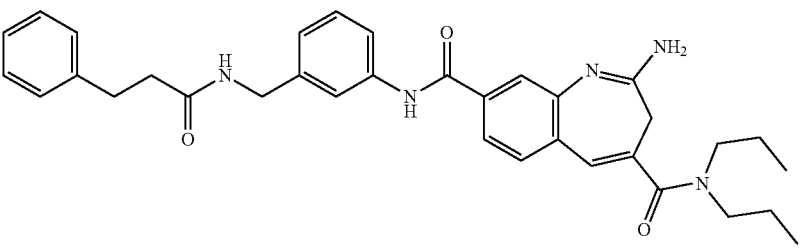 [SMILES: CCCN(CCC)C(=O)C1=Cc2ccc(C(=O)Nc3cccc(CNC(=O)CCc4ccccc4)c3)cc2N=C(N)C1]<br>2-amino-$N^8$-(3-((3-phenylpropanamido)methyl)phenyl)-$N^4$,$N^4$-dipropyl-3H-benzo[b]azepine-4,8-dicarboxamide |

TABLE 1a-continued

Compounds 1.1-1.69

| Compound | Structure and IUPAC |
|---|---|
| 1.32 | 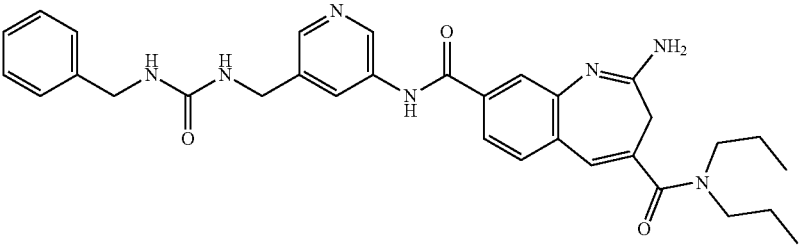 [SMILES: CCCN(CCC)C(=O)C1=Cc2ccc(C(=O)Nc3cncc(CNC(=O)NCc4ccccc4)c3)cc2N=C(N)C1]<br>2-amino-$N^8$-(5-((3-benzylureido)methyl)pyridin-3-yl)-$N^4,N^4$-dipropyl-3H-benzo[b]azepine-4,8-dicarboxamide |
| 1.33 | 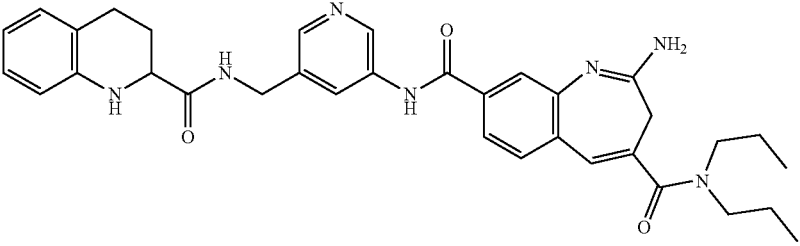 [SMILES: CCCN(CCC)C(=O)C1=Cc2ccc(C(=O)Nc3cncc(CNC(=O)C4CCc5ccccc5N4)c3)cc2N=C(N)C1]<br>2-amino-$N^4,N^4$-dipropyl-$N^8$-(5-((1,2,3,4-tetrahydroquinoline-2-carboxamido)methyl)pyridin-3-yl)-3H-benzo[b]azepine-4,8-dicarboxamide |
| 1.34 | 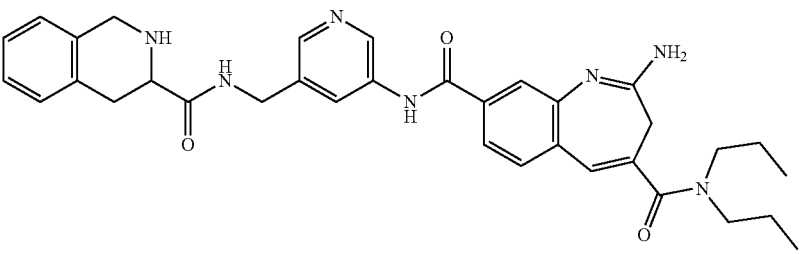 [SMILES: CCCN(CCC)C(=O)C1=Cc2ccc(C(=O)Nc3cncc(CNC(=O)C4Cc5ccccc5CN4)c3)cc2N=C(N)C1]<br>2-amino-$N^4,N^4$-dipropyl-$N^8$-(5-((1,2,3,4-tetrahydroisoquinoline-3-carboxamido)-methyl)pyridin-3-yl)-3H-benzo[b]azepine-4,8-dicarboxamide |
| 1.35 | 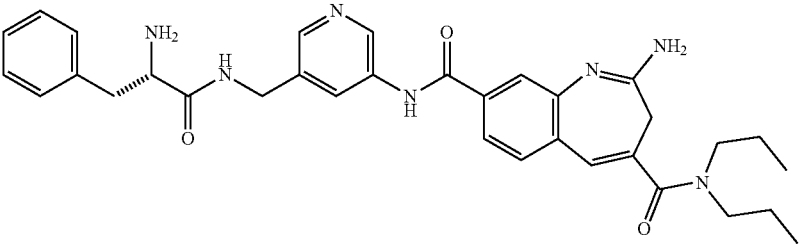<br>(S)-2-amino-$N^8$-(5-((2-amino-3-phenylpropanamido)methyl)pyridin-3-yl)-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.36 | 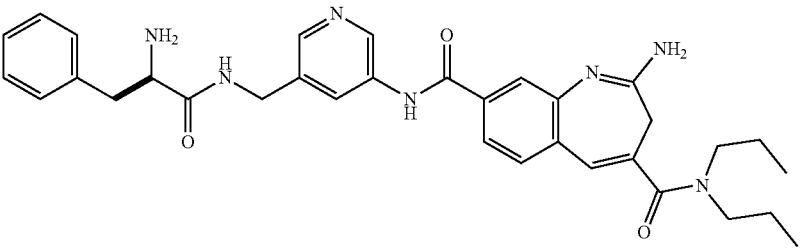<br>(R)-2-amino-$N^8$-(5-((2-amino-3-phenyl-propanamido)-methyl)pyridine-3-yl)-$N^4,N^4$-dipropyl-3H-benzo[b]azepine-4,8-dicarboxamide |
| 1.37 | 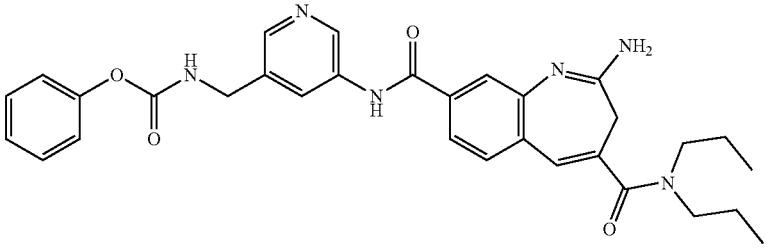 [SMILES: CCCN(CCC)C(=O)C1=Cc2ccc(C(=O)Nc3cncc(CNC(=O)Oc4ccccc4)c3)cc2N=C(N)C1]<br>Phenyl ((5-(2-amino-4-(dipropylcarbamoyl)-3H-benzo[b]azepine-8-carboxamido)pyridin-3-yl)methyl)carbamate |
| 1.38 | 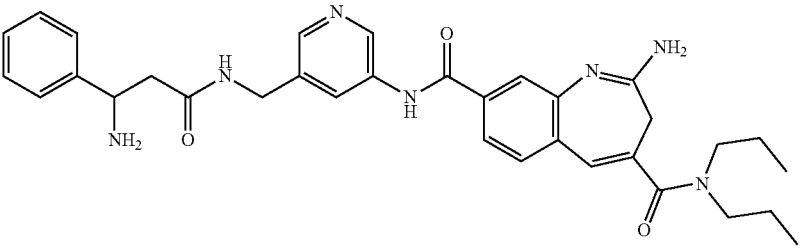 [SMILES: CCCN(CCC)C(=O)C1=Cc2ccc(C(=O)Nc3cncc(CNC(=O)CC(N)c4ccccc4)c3)cc2N=C(N)C1]<br>2-amino-$N^8$-(5-((3-amino-3-phenyl-propanamido)methyl)-pyridin-3-yl)-$N^4,N^4$-dipropyl-3H-benzo[b]azepine-4,8-dicarboxamide |
| 1.39 | 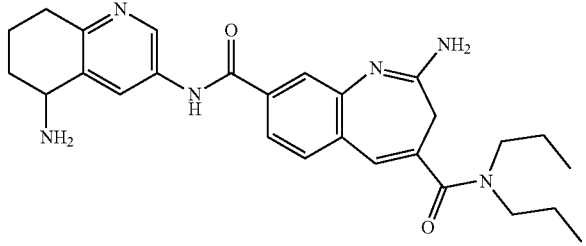 [SMILES: CCCN(CCC)C(=O)C1=Cc2ccc(C(=O)Nc3cnc4c(c3)C(N)CCC4)cc2N=C(N)C1]<br>2-amino-$N^8$-(5-amino-5,6,7,8-tetrahydro-quinolin-3-yl)-$N^4,N^4$-dipropyl-3H-benzo-[b]azepine-4,8-dicarbox-amide |

TABLE 1a-continued

Compounds 1.1-1.69

| Compound | Structure and IUPAC |
|---|---|
| 1.40 | 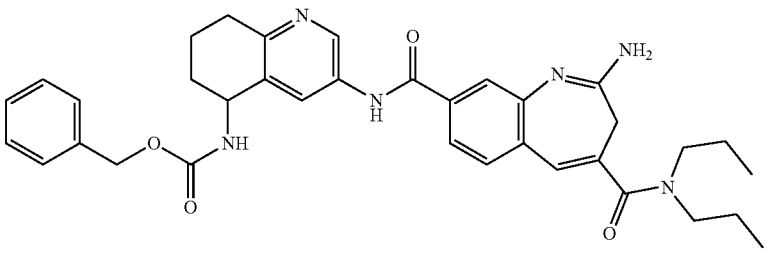 [SMILES: CCCN(CCC)C(=O)C1=Cc2ccc(C(=O)Nc3cnc4c(c3)C(NC(=O)OCc3ccccc3)CCC4)cc2N=C(N)C1]<br>Benzyl (3-(2-amino-4-(dipropylcarbamoyl)-3H-benzo[b]azepine-8-carboxamido)-5,6,7,8-tetrahydroquinolin-5-yl)carbamate |
| 1.41 | 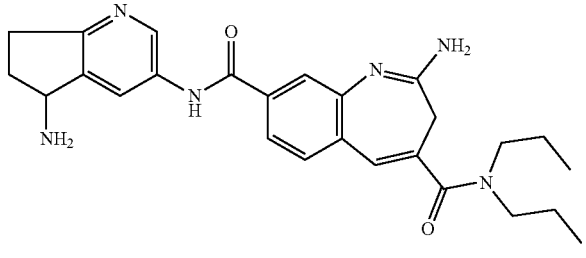 [SMILES: CCCN(CCC)C(=O)C1=Cc2ccc(C(=O)Nc3cnc4c(c3)C(N)CC4)cc2N=C(N)C1]<br>2-amino-$N^8$-(5-amino-6,7-dihydro-5H-cyclopenta[b]pyridin-3-yl)-$N^4,N^4$-dipropyl-3H-benzo[b]azepine-4,8-dicarboxamide |
| 1.42 | 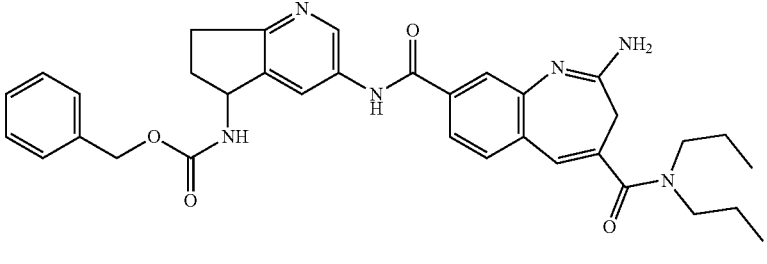 [SMILES: CCCN(CCC)C(=O)C1=Cc2ccc(C(=O)Nc3cnc4c(c3)C(NC(=O)OCc3ccccc3)CC4)cc2N=C(N)C1]<br>Benzyl (3-(2-amino-4-(dipropylcarbamoyl)-3H-benzo[b]azepine-8-carboxamido)-6,7-dihydro-5H-cyclopenta[b]pyridin-5-yl)carbamate |
| 1.43 | 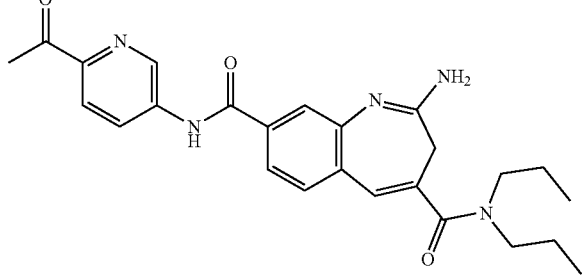<br>$N^8$-(6-acetylpyridin-3-yl)-2-amino-$N^4,N^4$-dipropyl-3H-benzo[b]azepine-4,8-dicarboxamide |

TABLE 1a-continued

Compounds 1.1-1.69

| Compound | Structure and IUPAC |
|---|---|
| 1.44 | 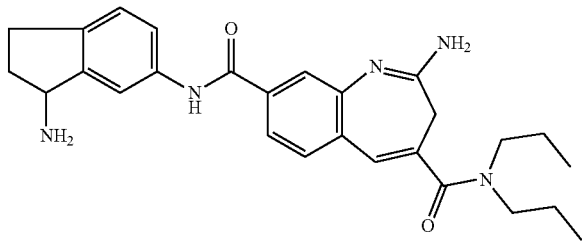 [SMILES: CCCN(CCC)C(=O)C1=Cc2ccc(C(=O)Nc3ccc4c(c3)C(N)CC4)cc2N=C(N)C1]<br>2-amino-$N^8$-(3-amino-2,3-dihydro-1H-inden-5-yl)-$N^4,N^4$-dipropyl-3H-benzo[b]azepine-4,8-dicarboxamide |
| 1.45 | 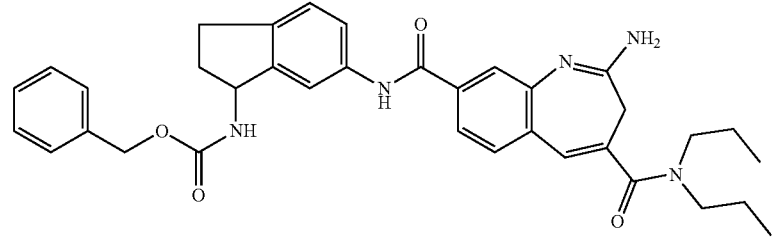 [SMILES: CCCN(CCC)C(=O)C1=Cc2ccc(C(=O)Nc3ccc4c(c3)C(NC(=O)OCc3ccccc3)CC4)cc2N=C(N)C1]<br>Benzyl (6-(2-amino-4-(dipropylcarbamoyl)-3H-benzo[b]azepine-8-carboxamido)-2,3-dihydro-1H-inden-1-yl)carbamate |
| 1.46 | 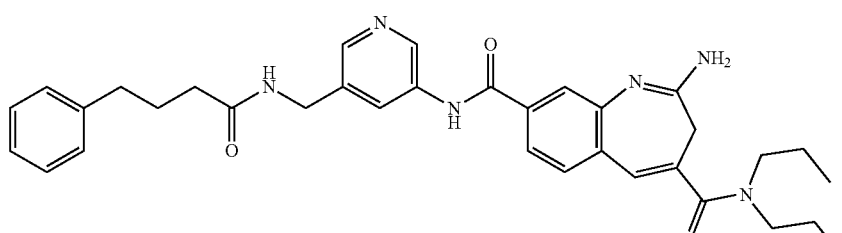<br>2-amino-$N^8$-(5-((4-phenylbutanamido)methyl)pyridin-3-yl)-$N^4,N^4$-dipropyl-3H-benzo[b]azepine-4,8-dicarboxamide |
| 1.47 | 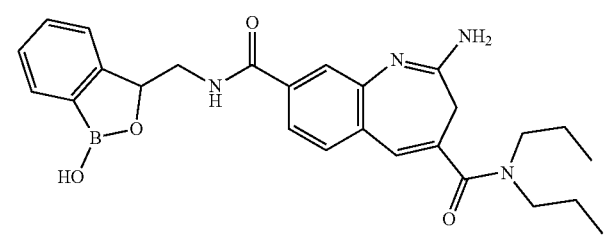 [SMILES: CCCN(CCC)C(=O)C1=Cc2ccc(C(=O)NCC3OB(O)c4ccccc43)cc2N=C(N)C1]<br>2-amino-$N^8$-((1-hydroxy-1,3-dihydro-benzo[c][1,2]oxaborol-3-yl)methyl)-N4,N4-dipropyl-3H-benzo[b]azepine-4,8-dicarboxamide |

TABLE 1a-continued

Compounds 1.1-1.69

| Compound | Structure and IUPAC |
|---|---|
| 1.48 | 2-amino-$N^8$-(6-benzyl-5,6,7,8-tetrahydro-1,6-naphthyridin-3-yl)-$N^4$,$N^4$-dipropyl-3H-benzo[b]azepine-4,8-dicarboxamide |
| 1.49 | benzyl (3-((2-amino-4-(dipropylcarbamoyl)-3H-benzo[b]azepine-8-carboxamido)methyl)-1-hydroxy-1,3-dihydrobenzo[c][1,2]oxaborol-6-yl)carbamate |
| 1.50 | 2-amino-$N^4$,$N^4$-dipropyl-$N^8$-(5,6,7,8-tetrahydro-1,6-naphthyridin-3-yl)-3H-benzo[b]azepine-4,8-dicarboxamide |
| 1.51 | (S)-2-amino-$N^8$-(5-((2-amino-3-methylbutanamido)methyl)pyridin-3-yl)-$N^4$,$N^4$-dipropyl-3H-benzo[b]azepine-4,8-dicarboxamide |

TABLE 1a-continued

Compounds 1.1-1.69

| Compound | Structure and IUPAC |
|---|---|
| 1.52 | benzyl (3-(2-amino-4-(dipropylcarbamoyl)-3H-benzo[b]azepine-8-carboxamido)-5,6,7,8-tetrahydroquinolin-7-yl)carbamate |
| 1.53 | benzyl (3-(2-amino-4-(dipropylcarbamoyl)-3H-benzo[b]azepine-8-carboxamido)-6,7-dihydro-5H-cyclopenta[b]pyridin-6-yl)carbamate |
| 1.54 | benzyl 3-(2-amino-4-(dipropylcarbamoyl)-3H-benzo[b]azepine-8-carboxamido)-7,8-dihydro-1,6-naphthyridine-6(5H)-carboxylate |
| 1.55 | benzyl (1-(5-(2-amino-4-(dipropylcarbamoyl)-3H-benzo[b]azepine-8-carboxamido)pyridin-2-yl)piperidin-3-yl)carbamate |

TABLE 1a-continued

Compounds 1.1-1.69

| Compound | Structure and IUPAC |
|---|---|
| 1.56 | 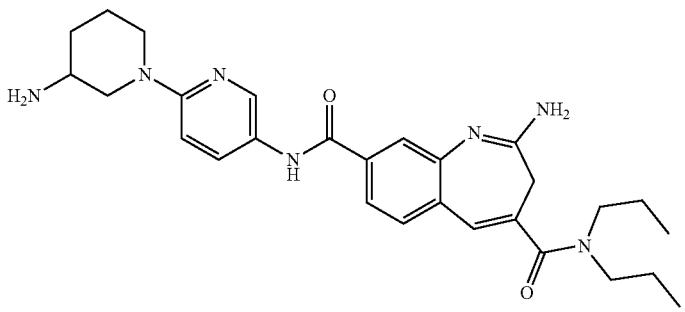 [SMILES: CCCN(CCC)C(=O)C1=Cc2ccc(C(=O)Nc3ccc(N4CCCC(N)C4)nc3)cc2N=C(N)C1]<br>2-amino-$N^8$-(6-(3-aminopiperidin-1-yl)pyridin-3-yl)-$N^4$,$N^4$-dipropyl-3H-benzo[b]azepine-4,8-dicarboxamide |
| 1.57 | 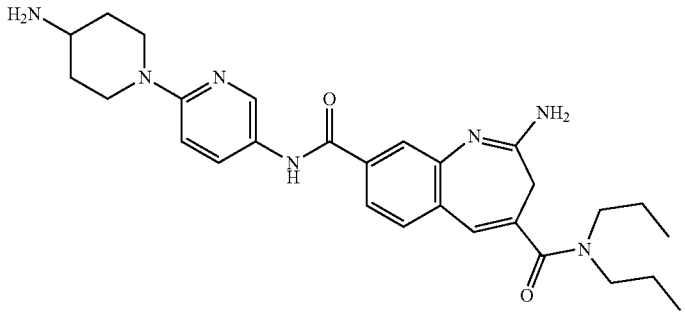 [SMILES: CCCN(CCC)C(=O)C1=Cc2ccc(C(=O)Nc3ccc(N4CCC(N)CC4)nc3)cc2N=C(N)C1]<br>2-amino-$N^8$-(6-(4-aminopiperidin-1-yl)pyridin-3-yl)-$N^4$,$N^4$-dipropyl-3H-benzo[b]azepine-4,8-dicarboxamide |
| 1.58 | 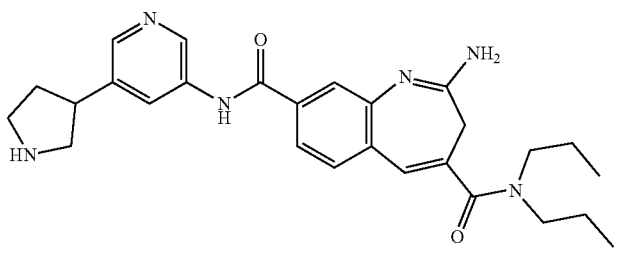 [SMILES: CCCN(CCC)C(=O)C1=Cc2ccc(C(=O)Nc3cncc(C4CCNC4)c3)cc2N=C(N)C1]<br>2-amino-$N^4$,$N^4$-dipropyl-$N^8$-(5-(pyrrolidin-3-yl)pyridin-3-yl)-3H-benzo[b]azepine-4,8-dicarboxamide |
| 1.59 | 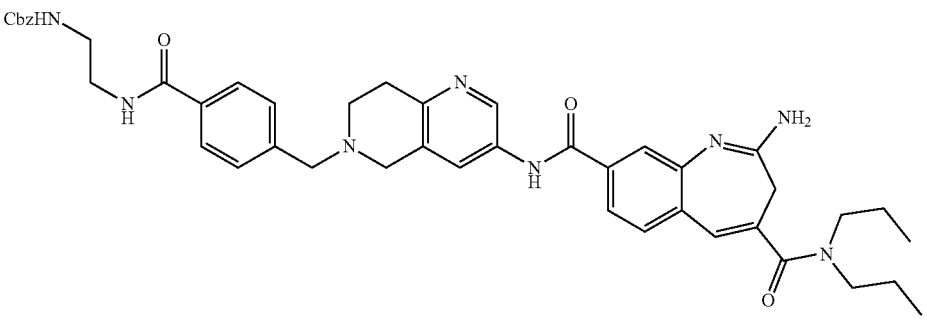 [SMILES: CCCN(CCC)C(=O)C1=Cc2ccc(C(=O)Nc3cnc4c(c3)CN(Cc3ccc(C(=O)NCCNC(=O)OCc5ccccc5)cc3)CC4)cc2N=C(N)C1]<br>benzyl (2-(4-((3-(2-amino-4-(dipropylcarbamoyl)-3H-benzo[b]azepine-8-carboxamido)-7,8-dihydro-1,6-naphthyridin-6(5H)-yl)methyl)benzamido)ethyl)carbamate |

TABLE 1a-continued

Compounds 1.1-1.69

| Compound | Structure and IUPAC |
| --- | --- |
| 1.60 | 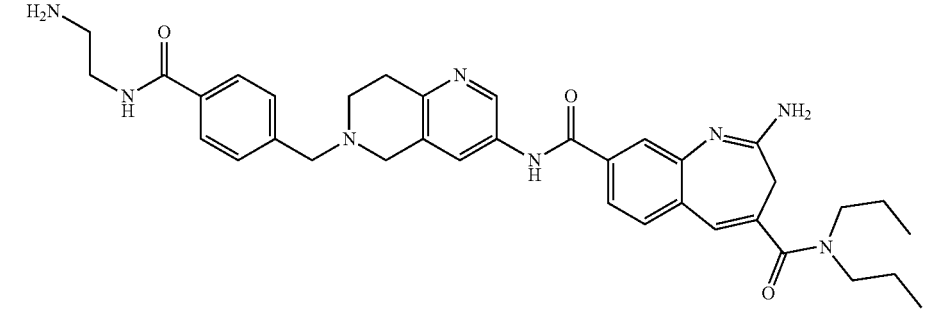 [SMILES: CCCN(CCC)C(=O)C1=Cc2ccc(C(=O)Nc3cnc4c(c3)CN(Cc3ccc(C(=O)NCCN)cc3)CC4)cc2N=C(N)C1]
2-amino-$N^8$-(6-(4-((2-aminoethyl)carbamoyl)benzyl)-5,6,7,8-tetrahydro-1,6-naphthyridin-3-yl)-$N^4$,$N^4$-dipropyl-3H-benzo[b]azepine-4,8-dicarboxamide |
| 1.61 | 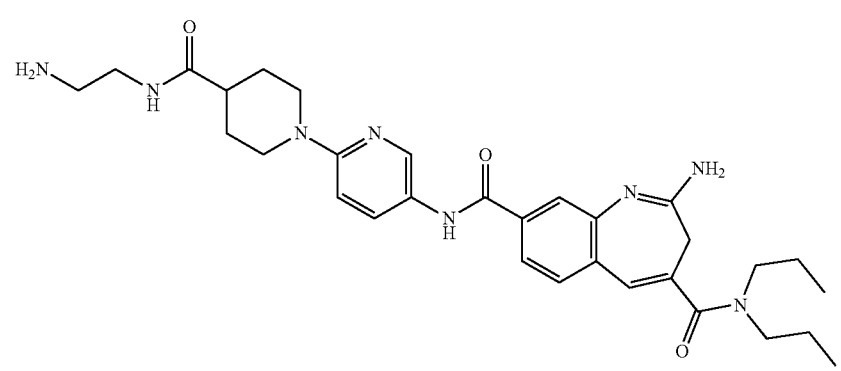 [SMILES: CCCN(CCC)C(=O)C1=Cc2ccc(C(=O)Nc3ccc(N4CCC(C(=O)NCCN)CC4)nc3)cc2N=C(N)C1]
2-amino-$N^8$-(6-(4-((2-aminoethyl)carbamoyl)piperidin-1-yl)pyridin-3-yl)-$N^4$,$N^4$-dipropyl-3H-benzo[b]azepine-4,8-dicarboxamide |
| 1.62 | 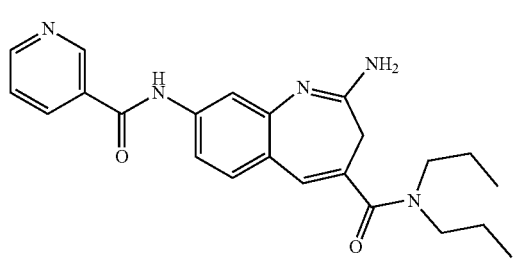 [SMILES: CCCN(CCC)C(=O)C1=Cc2ccc(NC(=O)c3cccnc3)cc2N=C(N)C1]
2-amino-8-(nicotinamido)-N,N-dipropyl-3H-benzo[b]azepine-4-carboxamide |
| 1.63 | 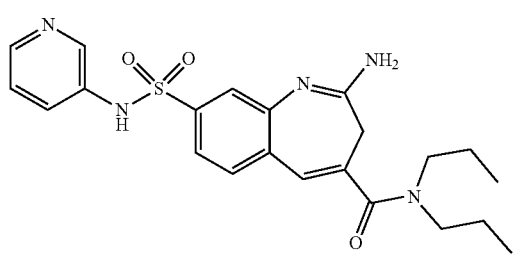 [SMILES: CCCN(CCC)C(=O)C1=Cc2ccc(S(=O)(=O)Nc3cccnc3)cc2N=C(N)C1]
2-amino-N,N-dipropyl-8-(N-(pyridin-3-yl)sulfamoyl)-3H-benzo[b]azepine-4-carboxamide |

TABLE 1a-continued

Compounds 1.1-1.69

| Compound | Structure and IUPAC |
|---|---|
| 1.64 | 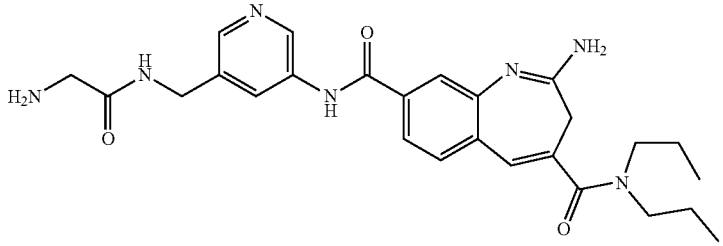 [SMILES: CCCN(CCC)C(=O)C1=Cc2ccc(C(=O)Nc3cncc(CNC(=O)CN)c3)cc2N=C(N)C1]<br>2-amino-N8-(5-((2-aminoacetamido)methyl)pyridin-3-yl)-N4,N4-dipropyl-3H-benzo[b]azepine-4,8-dicarboxamide |
| 1.65 | 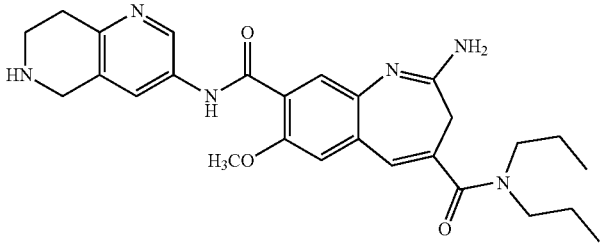 [SMILES: CCCN(CCC)C(=O)C1=Cc2cc(OC)c(C(=O)Nc3cnc4c(c3)CNCC4)cc2N=C(N)C1]<br>2-amino-7-methoxy-N4,N4-dipropyl-N8-(5,6,7,8-tetrahydro-1,6-naphthyridin-3-yl)-3H-benzo[b]azepine-4,8-dicarboxamide |
| 1.66 | 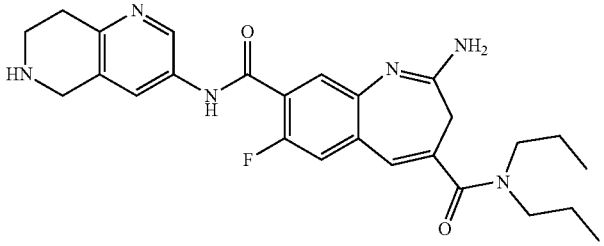 [SMILES: CCCN(CCC)C(=O)C1=Cc2cc(F)c(C(=O)Nc3cnc4c(c3)CNCC4)cc2N=C(N)C1]<br>2-amino-7-fluoro-N4,N4-dipropyl-N8-(5,6,7,8-tetrahydro-1,6-naphthyridin-3-yl)-3H-benzo[b]azepine-4,8-dicarboxamide |
| 1.67 | 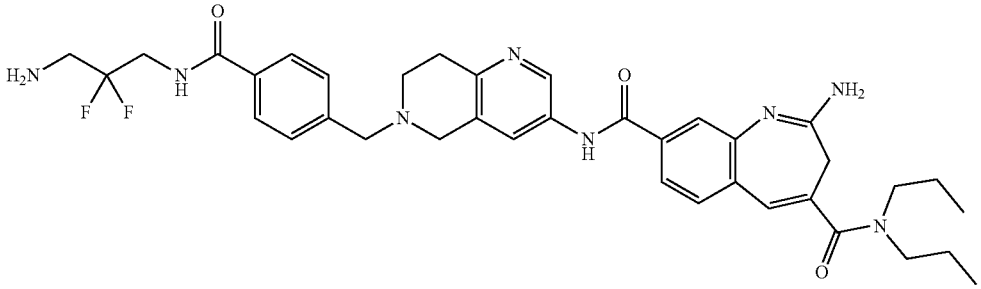 [SMILES: CCCN(CCC)C(=O)C1=Cc2ccc(C(=O)Nc3cnc4c(c3)CN(Cc3ccc(C(=O)NCC(F)(F)CN)cc3)CC4)cc2N=C(N)C1]<br>2-amino-N8-(6-(4-((3-amino-2,2-difluoropropyl)carbamoyl)benzyl)-5,6,7,8-tetrahydro-1,6-naphthyridin-3-yl)-N4,N4-dipropyl-3H-benzo[b]azepine-4,8-dicarboxamide |

TABLE 1a-continued

Compounds 1.1-1.69

| Compound | Structure and IUPAC |
|---|---|
| 1.68 | |
| 1.69 | |

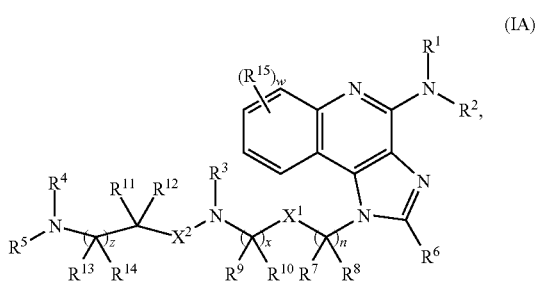

Compounds of Category B, TLR7 Agonists

In some aspects, the present disclosure provides a compound represented by the structure of Formula (IA):

(IA)

or a pharmaceutically acceptable salt thereof, wherein:

$R^1$, $R^2$, $R^3$, $R^4$, and $R^5$ are independently selected from hydrogen; and $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =N($R^{20}$), and —CN; or $R^3$ and $R^{11}$ taken together form a 5- to 10-membered heterocycle optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =N($R^{20}$), and —CN;

$R^6$ is selected from halogen, —$OR^{20}$, —$N(R^{20})_2$, —$C(O)N(R^{20})_2$, —$C(O)R^{20}$, —$C(O)OR^{20}$, —$S(O)R^{20}$, and —$S(O)_2R^{20}$; and $C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =N($R^{20}$), and —CN;

$R^7$, $R^8$, $R^9$, and $R^{10}$ are independently selected at each occurrence from hydrogen and halogen; and $C_{1-6}$ alkyl, $C_{2-6}$ alkenyl, and $C_{2-6}$ alkynyl, each of which is optionally substituted with one or more substituents independently selected from halogen;

$R^{11}$ and $R^{12}$ are independently selected from hydrogen, halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, and —CN; and $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =N($R^{20}$), —CN, $C_{3-12}$ carbocycle, and 3- to 12-membered heterocycle; or $R^{11}$ and $R^{12}$ taken together form a $C_{3-6}$ carbocycle optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =N($R^{20}$), and —CN;

$R^{13}$ and $R^{14}$ are independently selected at each occurrence from hydrogen, halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, and —CN; Cue alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =N($R^{20}$), —CN, $C_{3-12}$ carbocycle, and 3- to 12-membered heterocycle; and $C_{3-12}$ carbocycle and 3- to 12-membered heterocycle, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =N($R^{20}$), —CN, $C_{1-6}$ alkyl, $C_{2-6}$ alkenyl, and $C_{2-6}$ alkynyl;

$R^{15}$ is independently selected at each occurrence from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, —CN, $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —$C_{1-6}$ alkyl, —$C_{1-6}$ haloalkyl, —O—$C_{1-6}$ alkyl, $C_{2-6}$ alkenyl, $C_{2-6}$ alkynyl, $C_{3-12}$ carbocycle, and 3- to 12-membered heterocycle;

$R^{16}$ is selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, $C_{1-6}$alkyl, —$C_{1-6}$ haloalkyl, —O—$C_{1-6}$ alkyl, $C_{2-6}$ alkenyl, $C_{2-6}$alkynyl, $C_{3-12}$ carbocycle, and 3- to 12-membered heterocycle;

$R^{20}$ is independently selected at each occurrence from hydrogen; and $C_{1-6}$ alkyl, $C_{2-6}$ alkenyl, $C_{2-6}$alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —$C(O)OCH_2C_6H_5$, —$NHC(O)OCH_2C_6H_5$, $C_{1-6}$ alkyl, —$C_{1-6}$haloalkyl, —O—$C_{1-6}$ alkyl, $C_{2-6}$ alkenyl, $C_{2-6}$alkynyl, $C_{3-12}$ carbocycle, and 3- to 12-membered heterocycle;

$X^1$ is O, S, or $NR^{16}$;
$X^2$ is C(O) or $S(O)_2$;
n is 1, 2, or 3;
x is 1, 2, or 3;
w is 0, 1, 2, 3, or 4; and
z is 0, 1, or 2.

In certain embodiments, for a compound of Formula (IA), wherein $X^1$ is O. In certain embodiments, for a compound of Formula (IA), n is 2. In certain embodiments, for a compound of Formula (IA), x is 2. In certain embodiments, for a compound of Formula (IA), z is 0. In certain embodiments, for a compound of Formula (IA), z is 1.

In certain embodiments, a compound of Formula (IA) is represented by Formula (IB):

(IB)

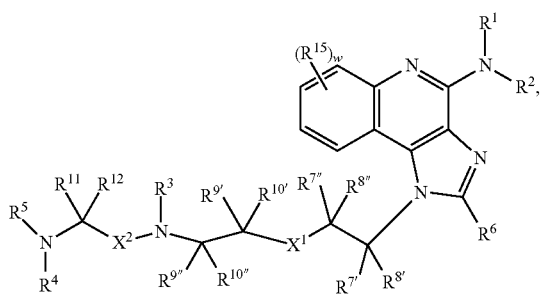

or a pharmaceutically acceptable salt thereof, wherein $R^{7'}$, $R^{7''}$, $R^{8'}$, $R^{8''}$, $R^{9'}$, $R^{9''}$, $R^{10'}$, and $R^{10''}$ are independently selected at each occurrence from hydrogen and halogen; and $C_{1-6}$ alkyl, $C_{2-6}$ alkenyl, and $C_{2-6}$alkynyl, each of which is optionally substituted with one or more substituents independently selected from halogen.

In certain embodiments, a compound of Formula (IA) is represented by Formula (IC):

(IC)

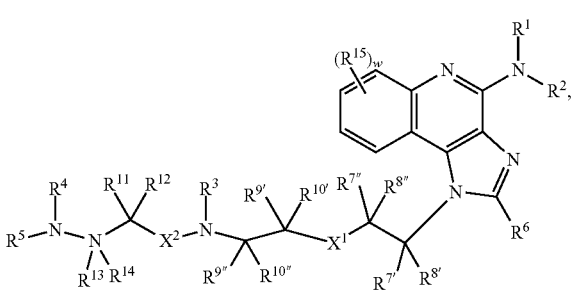

or a pharmaceutically acceptable salt thereof, wherein $R^{7'}$, $R^{7''}$, $R^{8'}$, $R^{8''}$, $R^{9'}$, $R^{9''}$, $R^{10'}$, and $R^{10''}$ are independently selected at each occurrence from hydrogen and halogen; and $C_{1-6}$ alkyl, $C_{2-6}$ alkenyl, and $C_{2-6}$ alkynyl, each of which is optionally substituted with one or more substituents independently selected from halogen.

In certain embodiments, for a compound or salt of any one of Formulas (IA), (IB), or (IC), $R^1$, $R^2$, $R^3$, $R^4$, and $R^5$ are independently selected from hydrogen and $C_{1-6}$ alkyl optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN.

In certain embodiments, for a compound or salt of any one of Formulas (IA), (IB), or (IC), $R^1$ and $R^2$ are independently selected from hydrogen and $C_{1-6}$ alkyl. In certain embodiments, for a compound or salt of any one of Formulas (IA), (IB), or (IC), $R^1$ and $R^2$ are each hydrogen.

In certain embodiments, for a compound or salt of any one of Formulas (IA), (IB), or (IC), $R^3$ is selected from hydrogen and $C_{1-6}$ alkyl optionally substituted with one or more halogens.

In certain embodiments, for a compound or salt of any one of Formulas (IA), (IB), or (IC), $R^3$ is hydrogen.

In certain embodiments, for a compound or salt of any one of Formulas (IA), (IB), or (IC), $R^4$ is selected from hydrogen and $C_{1-6}$ alkyl optionally substituted with one or more halogens.

In certain embodiments, for a compound or salt of any one of Formulas (IA), (IB), or (IC), $R^4$ is hydrogen.

In certain embodiments, for a compound or salt of any one of Formulas (IA), (IB), or (IC), $R^5$ is selected from hydrogen and $C_{1-6}$ alkyl optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN. In certain embodiments, for a compound or salt of any one of Formulas (IA), (IB), or (IC), $R^5$ is hydrogen.

In certain embodiments, for a compound or salt of any one of Formulas (IA), (IB), or (IC), $R^6$ is selected from halogen, —$OR^{20}$, and —$N(R^{20})_2$; and $C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN; and $R^{20}$ is independently selected at each occurrence from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-6}$ alkyl, —C$_{1-6}$haloalkyl, —O—C$_{1-6}$ alkyl, C$_{2-6}$ alkenyl, C$_{2-6}$alkynyl, C$_{3-12}$ carbocycle, and 3- to 12-membered heterocycle.

In certain embodiments, for a compound or salt of any one of Formulas (IA), (IB), or (IC), R$^6$ is C$_{1-6}$ alkyl optionally substituted with one or more substituents independently selected from halogen, —OR$^{20}$, —SR$^{20}$, —C(O)N(R$^{20}$)$_2$, —N(R$^{20}$)$_2$, —S(O)R$^{20}$, —S(O)$_2$R$^{20}$, —C(O)R$^{20}$, —C(O)OR$^{20}$, —OC(O)R$^{20}$; and R$^{20}$ is independently selected at each occurrence from hydrogen; C$_{1-6}$ alkyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-6}$ alkyl, —C$_{1-6}$haloalkyl, —O—C$_{1-6}$ alkyl, C$_{2-6}$ alkenyl, C$_{2-6}$ alkynyl, C$_{3-12}$ carbocycle, and 3- to 12-membered heterocycle.

In certain embodiments, for a compound or salt of any one of Formulas (IA), (IB), or (IC), R$^6$ is C$_{1-6}$ alkyl substituted with —OR$^{20}$, and R$^{20}$ is selected from hydrogen and C$_{1-6}$ alkyl optionally substituted with one or more substituents independently selected from halogen, —OH, and —NH$_2$.

In certain embodiments, for a compound or salt of any one of Formulas (IA), (IB), or (IC), R$^{7'}$, R$^{7''}$, R$^{8'}$, R$^{8''}$, R$^{9'}$, R$^{9''}$, R$^{10'}$, and R$^{10''}$ are independently selected at each occurrence from hydrogen and halogen; and C$_{1-6}$ alkyl, optionally substituted with one or more substituents independently selected from halogen.

In certain embodiments, for a compound or salt of any one of Formulas (IB) or (IC), wherein R$^{7'}$ and R$^{8'}$ are each hydrogen. In certain embodiments, for a compound or salt of any one of Formulas (IB) or (IC), wherein R$^{7''}$ and R$^{8''}$ are each C$_{1-6}$ alkyl. In certain embodiments, for a compound or salt of any one of Formulas (IB) or (IC), R$^{7''}$ and R$^{8''}$ are each methyl.

In certain embodiments, for a compound or salt of any one of Formulas (IB) or (IC), R$^{9'}$, R$^{9''}$, R$^{10'}$, and R$^{10''}$ are independently selected at each occurrence from hydrogen and C$_{1-6}$ alkyl.

In certain embodiments, for a compound or salt of any one of Formulas (IB) or (IC), R$^{9'}$, R$^{9''}$, R$^{10'}$, and R$^{10''}$ are each hydrogen.

In certain embodiments, for a compound or salt of any one of Formulas (IA), (IB), or (IC), R$^{11}$ and R$^{12}$ are independently selected from hydrogen, halogen, —OR$^{20}$, —SR$^{20}$, —C(O)N(R$^{20}$)$_2$, —N(R$^{20}$)$_2$, —C(O)R$^{20}$, —C(O)OR$^{20}$, —OC(O)R$^{20}$; and C$_{1-6}$ alkyl, optionally substituted with one or more substituents independently selected from halogen, —OR$^{20}$, —SR$^{20}$, —C(O)N(R$^{20}$)$_2$, —N(R$^{20}$)$_2$, —C(O)R$^{20}$, —C(O)OR$^{20}$, —OC(O)R$^{20}$, C$_{3-12}$ carbocycle, and 3- to 12-membered heterocycle.

In certain embodiments, for a compound or salt of any one of Formulas (IA) or (IC), R$^{13}$ and R$^{14}$ are independently selected from hydrogen, halogen, —OR$^{20}$, —SR$^{20}$, —C(O)N(R$^{20}$)$_2$, —N(R$^{20}$)$_2$, —C(O)R$^{20}$, —C(O)OR$^{20}$, —OC(O)R$^{20}$; and C$_{1-6}$ alkyl optionally substituted with one or more substituents independently selected from halogen, —OR$^{20}$, —SR$^{20}$, —C(O)N(R$^{20}$)$_2$, —N(R$^{20}$)$_2$, —C(O)R$^{20}$, —C(O)OR$^{20}$, —OC(O)R$^{20}$, C$_{3-12}$ carbocycle, and 3- to 12-membered heterocycle.

In certain embodiments, for a compound or salt of any one of Formulas (IA), (IB), or (IC), R$^3$ and R$^{11}$ taken together form an optionally substituted 5- to 6-membered heterocycle.

In certain embodiments, for a compound or salt of any one of Formulas (IA), (IB), or (IC), R$^{11}$ and R$^{12}$ taken together form an optionally substituted C$_{3-6}$ carbocycle.

In certain embodiments, for a compound or salt of any one of Formulas (IA), (IB), or (IC), X$^2$ is C(O).

In certain embodiments, the compound is represented by:

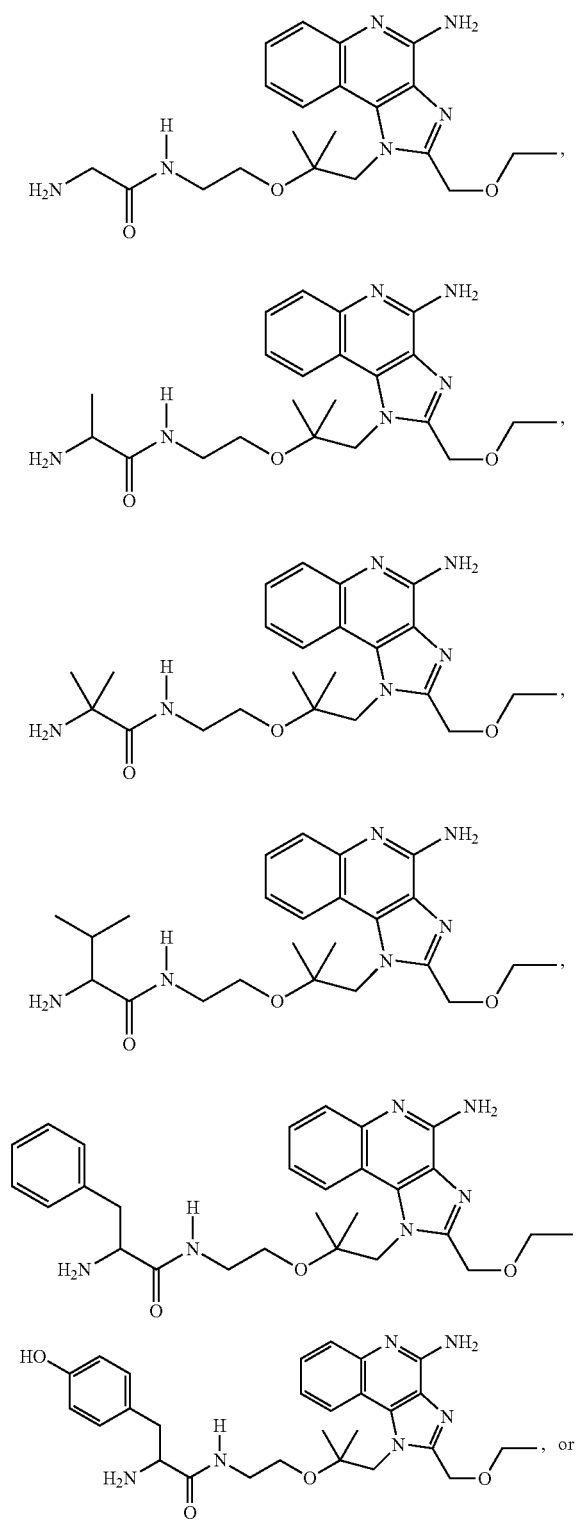

-continued or a pharmaceutically acceptable salt of any one thereof.

In certain aspects, the disclosure provides a pharmaceutical composition of a compound or pharmaceutically acceptable salt of any one of Formulas (IA), (IB), or (IC), and a pharmaceutically acceptable excipient.

In certain embodiments, for a compound or salt of any one of Formulas (IA), (IB), or (IC), the compound or salt is further covalently bound to a linker, $L^3$.

In certain aspects the disclosure provides a compound represented by Formula (IIA):

(IIA)

or a pharmaceutically acceptable salt thereof, wherein:
$R^2$ and $R^4$ are independently selected from hydrogen; and $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{2c}$, —$NO_2$, =O, =S, =$N(R^{20})$, and —CN;
$R^{21}$, $R^{23}$, and $R^{25}$ are independently selected from hydrogen; $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN; and $L^3$; or $R^{23}$ and $R^{11}$ taken together form a 5- to 10-membered heterocycle optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN; and wherein one of $R^{21}$, $R^{23}$, and $R^{25}$ is $L^3$;
$R^6$ is selected from halogen, —$OR^{20}$, —$N(R^{20})_2$, —$C(O)N(R^{20})_2$, —$C(O)R^{20}$, —$C(O)OR^{20}$, —$S(O)R^{20}$, and —$S(O)_2R^{20}$; and $C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN;
$R^7$, $R^8$, $R^9$, and $R^{10}$ are independently selected at each occurrence from hydrogen and halogen; and $C_{1-6}$ alkyl, $C_{2-6}$ alkenyl, and $C_{2-6}$ alkynyl, each of which is optionally substituted with one or more substituents independently selected from halogen;

$R^{11}$ and $R^{12}$ are independently selected from hydrogen, halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, and —CN; and $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, —CN, $C_{3-12}$ carbocycle, and 3- to 12-membered heterocycle; or $R^{11}$ and $R^{12}$ taken together form a $C_{3-6}$ carbocycle optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{29}$, —$OC(O)R^{20}$, —$NO_2$, =O, =S, =$N(R^{20})$, and —CN;
$R^{13}$ and $R^{14}$ are independently selected at each occurrence from hydrogen, halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, —CN, $C_{1-6}$ alkyl, $C_{2-6}$ alkenyl, and $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, —CN, $C_{3-12}$ carbocycle, and 3- to 12-membered heterocycle; and $C_{3-12}$ carbocycle and 3- to 12-membered heterocycle, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, —CN, $C_{1-6}$ alkyl, $C_{2-6}$ alkenyl, and $C_{2-6}$alkynyl;
$R^{15}$ is independently selected at each occurrence from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, —CN, $C_{1-6}$ alkyl, $C_{2-6}$ alkenyl, and $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —$C_{1-6}$alkyl, —$C_{1-6}$haloalkyl, —O—$C_{1-6}$ alkyl, $C_{2-6}$alkenyl, $C_{2-6}$alkynyl, $C_{3-12}$ carbocycle, and 3- to 12-membered heterocycle;
$R^{16}$ is selected from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, $C_{1-6}$ alkyl, —$C_{1-6}$ haloalkyl, —O—$C_{1-6}$ alkyl, $C_{2-6}$ alkenyl, $C_{2-6}$ alkynyl, $C_{3-12}$ carbocycle, and 3- to 12-membered heterocycle;
$R^{20}$ is independently selected at each occurrence from hydrogen; $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —$C(O)OCH_2C_6H_5$, —$NHC(O)$ $OCH_2C_6H_5$, $C_{1-6}$ alkyl, —$C_{1-6}$haloalkyl, —O—$C_{1-6}$ alkyl, $C_{2-6}$ alkenyl, $C_{2-6}$ alkynyl, $C_{3-12}$ carbocycle, and 3- to 12-membered heterocycle;
$L^3$ is a linker;
$X^1$ is O, S, or $NR^{16}$;
$X^2$ is C(O) or $S(O)_2$;
n is 1, 2, or 3;
x is 1, 2, or 3;
w is 0, 1, 2, 3, or 4; and
z is 0, 1, or 2.

In certain embodiments, for a compound or salt of Formula (IIA), $X^1$ is O. In certain embodiments, for a compound or salt of Formula (IIA), n is 2. In certain embodiments, for a compound or salt of Formula (IIA), x is 2. In certain embodiments, for a compound or salt of Formula (IIA), z is 0. In certain embodiments, for a compound or salt of Formula (IIA), z is 1.

In certain embodiments, the compound of Formula (IIA) is represented by (IIB) or (IIC):

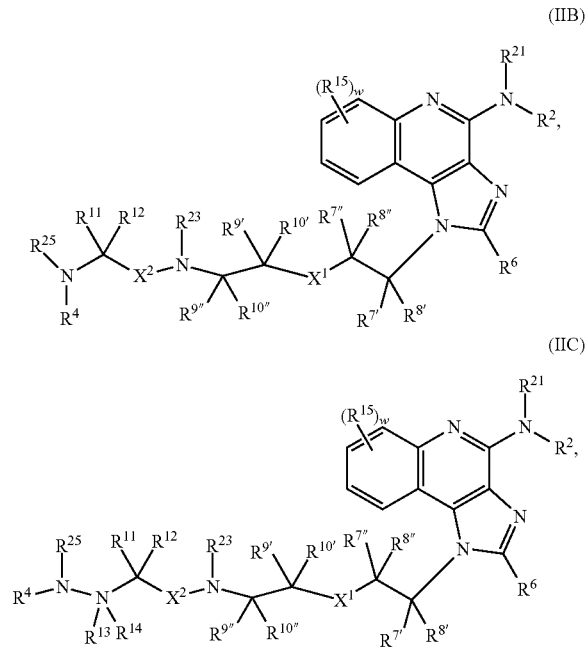

or a pharmaceutically acceptable salt thereof, wherein $R^{7'}$, $R^{7''}$, $R^{8'}$, $R^{8''}$, $R^{9'}$, $R^{9''}$, $R^{10'}$, and $R^{10''}$ are independently selected at each occurrence from hydrogen and halogen; and $C_{1-6}$ alkyl, $C_{2-6}$ alkenyl, and $C_{2-6}$ alkynyl, each of which is optionally substituted with one or more substituents independently selected from halogen.

In certain embodiments, for a compound or salt of any one of Formulas (IIA), (IIB), or (IIC), $R^2$ and $R^4$ are independently selected from hydrogen and $C_{1-6}$ alkyl optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN.

In certain embodiments, for a compound or salt of any one of Formulas (IIA), (IIB), or (IIC), $R^2$ and $R^4$ are independently selected from hydrogen and $C_{1-6}$ alkyl. In certain embodiments, for a compound or salt of any one of Formulas (IIA), (IIB), or (IIC), $R^2$ and $R^4$ are each hydrogen.

In certain embodiments, for a compound or salt of any one of Formulas (IIA), (IIB), or (IIC), $R^{23}$ is selected from hydrogen and $C_{1-6}$ alkyl optionally substituted with one or more halogens. In certain embodiments, for a compound or salt of any one of Formulas (IIA), (IIB), or (IIC), $R^{23}$ is hydrogen.

In certain embodiments, for a compound or salt of any one of Formulas (IIA), (IIB), or (IIC), $R^{21}$ is selected from hydrogen and $C_{1-6}$ alkyl optionally substituted with one or more halogens. In certain embodiments, for a compound or salt of any one of Formulas (IIA), (IIB), or (IIC), $R^{21}$ is hydrogen.

In certain embodiments, for a compound or salt of any one of Formulas (IIA), (IIB), or (IIC), $R^{21}$ is $L^3$.

In certain embodiments, for a compound or salt of any one of Formulas (IIA), (IIB), or (IIC), $R^{25}$ is selected from hydrogen and $C_{1-6}$ alkyl, optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN. In certain embodiments, for a compound or salt of any one of Formulas (IIA), (IIB), or (IIC), $R^{25}$ is hydrogen.

In certain embodiments, for a compound or salt of any one of Formulas (IIA), (IIB), or (IIC), $R^{25}$ is $L^3$.

In certain embodiments, for a compound or salt of any one of Formulas (IIA), (IIB), or (IIC), $R^6$ is selected from halogen, —$OR^{20}$, and —$N(R^{20})_2$; and $C_{1-6}$ alkyl, $C_{2-6}$ alkenyl, $C_{2-6}$ alkynyl, each of which is optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$, —$NO_2$, =O, =S, =$N(R^{20})$, and —CN; and $R^{20}$ is independently selected at each occurrence from hydrogen; and $C_{1-6}$ alkyl, $C_{2-6}$ alkenyl, $C_{2-6}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —$C(O)OCH_2C_6H_5$, —$NHC(O)OCH_2C_6H_5$, $C_{1-6}$ alkyl, —$C_{1-6}$ haloalkyl, —O—$C_{1-6}$ alkyl, $C_{2-6}$ alkenyl, $C_{2-6}$ alkynyl, $C_{3-12}$ carbocycle, and 3- to 12-membered heterocycle.

In certain embodiments, for a compound or salt of any one of Formulas (IIA), (IIB), or (IIC), $R^6$ is $C_{1-6}$ alkyl optionally substituted with one or more substituents independently selected from halogen, —$OR^{20}$, —$SR^{20}$, —$C(O)N(R^{20})_2$, —$N(R^{20})_2$, —$S(O)R^{20}$, —$S(O)_2R^{20}$, —$C(O)R^{20}$, —$C(O)OR^{20}$, —$OC(O)R^{20}$; and $R^{20}$ is independently selected at each occurrence from hydrogen, —$NH_2$, —$C(O)OCH_2C_6H_5$; $C_{1-6}$ alkyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —$C(O)OCH_2C_6H_5$, —$NHC(O)OCH_2C_6H_5$, $C_{1-6}$alkyl, —$C_{1-6}$ haloalkyl, —O—$C_{1-6}$ alkyl, $C_{2-6}$ alkenyl, $C_{2-6}$alkynyl, $C_{3-12}$ carbocycle, and 3- to 12-membered heterocycle.

In certain embodiments, for a compound or salt of any one of Formulas (IIA), (IIB), or (IIC), $R^6$ is $C_{1-6}$ alkyl substituted with —$OR^{20}$, and $R^{20}$ is selected from hydrogen and $C_{1-6}$ alkyl, which is optionally substituted with one or more substituents independently selected from halogen, —OH, and —$NH_2$.

In certain embodiments, for a compound or salt of any one of Formulas (IIB) or (IIC), $R^{7'}$, $R^{7''}$, $R^{8'}$, $R^{8''}$, $R^{9'}$, $R^{9''}$, $R^{10'}$, and $R^{10''}$ are independently selected at each occurrence from hydrogen and halogen; and $C_{1-6}$ alkyl optionally substituted with one or more substituents independently selected from halogen.

In certain embodiments, for a compound or salt of any one of Formulas (IIB) or (IIC), $R^{7'}$ and $R^{8'}$ are hydrogen.

In certain embodiments, for a compound or salt of any one of Formulas (IIB) or (IIC), $R^{7''}$ and $R^{8''}$ are $C_{1-6}$ alkyl.

In certain embodiments, for a compound or salt of any one of Formulas (IIB) or (IIC), $R^{7''}$ and $R^{8''}$ are methyl.

In certain embodiments, for a compound or salt of any one of Formulas (IIB) or (IIC), $R^{9'}$, $R^{9''}$, $R^{10'}$, and $R^{10''}$ are independently selected at each occurrence from hydrogen and $C_{1-6}$ alkyl.

In certain embodiments, for a compound or salt of any one of Formulas (IIB) or (IIC), $R^{9'}$, $R^{9''}$, $R^{10'}$, and $R^{10''}$ are each hydrogen.

In certain embodiments, for a compound or salt of any one of Formulas (IIA), (IIB), or (IIC), $R^{11}$ and $R^{12}$ are independently selected from hydrogen, halogen, —$OR^{20}$, —$SR^{20}$, —$C(O)N(R^{20})_2$, —$N(R^{20})_2$, —$C(O)R^{20}$, —$C(O)OR^{20}$, and —$OC(O)R^{20}$; and $C_{1-6}$ alkyl optionally substituted with one or more substituents independently selected from halogen, —$OR^{20}$, —$SR^{20}$, —$C(O)N(R^{20})_2$, —$N(R^{20})_2$, —$C(O)R^{20}$, —$C(O)OR^{20}$, —$OC(O)R^{20}$, $C_{3-12}$ carbocycle, and 3- to 12-membered heterocycle.

In certain embodiments, for a compound or salt of any one of Formulas (IIA) or (IIC), $R^{13}$ and $R^{14}$ are independently selected from hydrogen, halogen, —$OR^{20}$, —$SR^{20}$, —$C(O)N(R^{20})_2$, —$N(R^{20})_2$, —$C(O)R^{20}$, —$C(O)OR^{20}$, and —$OC(O)R^{20}$; and $C_{1-6}$ alkyl optionally substituted with one or more substituents independently selected from halogen, —$OR^{20}$, —$SR^{20}$, —$C(O)N(R^{20})_2$, —$N(R^{20})_2$, —$C(O)R^{20}$, —$C(O)OR^{20}$, —$OC(O)R^{20}$, $C_{3-12}$ carbocycle, and 3- to 12-membered heterocycle.

In certain embodiments, for a compound or salt of any one of Formulas (IIA), (IIB), or (IIC), $R^{23}$ and $R^{11}$ taken together form an optionally substituted 5- to 6-membered heterocycle.

In certain embodiments, for a compound or salt of any one of Formulas (IIA), (IIB), or (IIC), $R^{11}$ and $R^{12}$ taken together form an optionally substituted $C_{3-6}$ carbocycle.

In certain embodiments, for a compound or salt of any one of Formulas (IIA), (IIB), or (IIC), $X^2$ is C(O).

In certain embodiments, for a compound or salt of any one of Formulas (IIA), (IIB), or (IIC), $L^3$ is a cleavable linker. In certain embodiments, for a compound or salt of any one of Formulas (IIA), (IIB), or (IIC), $L^3$ is cleavable by a lysosomal enzyme.

In certain embodiments, for a compound or salt of any one of Formulas (IIA), (IIB), or (IIC), $L^3$ is represented by the formula:

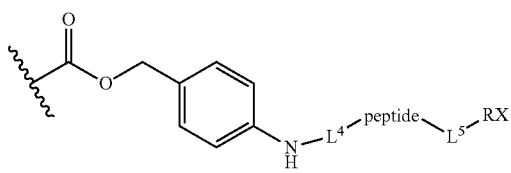

wherein:

$L^4$ represents the C-terminus of the peptide and $L^5$ is selected from a bond, alkylene and heteroalkylene, wherein $L^5$ is optionally substituted with one or more groups independently selected from $R^{30}$, and RX is a reactive moiety; and $R^{30}$ is independently selected at each occurrence from halogen, —OH, —CN, —O— alkyl, —SH, =O, =S, —$NH_2$, —$NO_2$; and $C_1$-$C_{10}$ alkyl, $C_2$-$C_{10}$ alkenyl, and $C_2$-$C_{10}$ alkynyl, each of which is independently optionally substituted at each occurrence with one or more substituents selected from halogen, —OH, —CN, —O-alkyl, —SH, =O, =S, —$NH_2$, and —$NO_2$.

In certain embodiments, for a compound or salt of any one of Formulas (IIA), (IIB), or (IIC), RX comprises a leaving group. In certain embodiments, for a compound or salt of any one of Formulas (IIA), (IIB), or (IIC), RX is a maleimide or an alpha-halo carbonyl. In certain embodiments, for a compound or salt of any one of Formulas (IIA), (IIB), or (IIC), the peptide of $L^3$ comprises Val-Cit or Val-Ala.

In certain embodiments, for a compound or salt of any one of Formulas (IIA), (IIB), or (IIC), $L^3$ is represented by the formula:

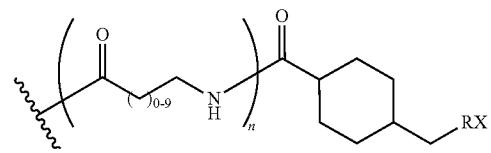

wherein:

RX comprises a reactive moiety; and n is 0-9.

In certain embodiments, for a compound or salt of any one of Formulas (IIA), (IIB), or (IIC), RX comprises a leaving group. In certain embodiments, for a compound or salt of any one of Formulas (IIA), (IIB), or (IIC), RX is a maleimide or an alpha-halo carbonyl. In certain embodiments, for a compound or salt of any one of Formulas (IIA), (IIB), or (IIC), $L^3$ is further covalently bound to an antibody or antigen binding fragment thereof to form a conjugate.

In certain embodiments, the disclosure provides a conjugate represented by the formula:

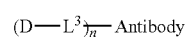

wherein:

Antibody is an anti-Nectin-4 antibody or an antigen-binding fragment thereof disclosed herein;

n is 1 to 20;

D is a compound or salt of any one of a Category B compound of Formulas (IA), (IB), or (IC); and $L^3$ is a linker moiety; or D-$L^3$ is a compound or salt of any one of a Category B compound of Formulas (IIA), (IIB), or (IIC).

In certain embodiments, for a conjugate of a compound or salt of any one of Formulas (IA), (IB), (IC), (IIA), (IIB), and (IIC), n is selected from 1 to 8. In certain embodiments, for a conjugate of a compound or salt of any one of Formulas (IA), (IB), (IC), (IIA), (IIB), and (IIC), n is selected from 2 to 5. In certain embodiments, for a conjugate of a compound or salt of any one of Formulas (IA), (IB), (IC), (IIA), (IIB), and (IIC), n is 2.

In certain embodiments, for a compound or salt of any one of Formulas (IIA), (IIB), and (IIC), -$L^3$ is represented by the formula:

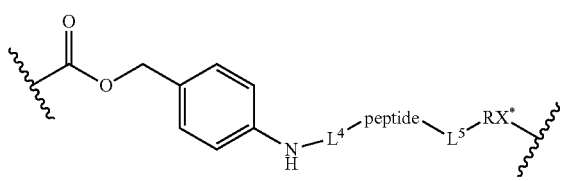

wherein:

L⁴ represents the C-terminus of the peptide and L⁵ is selected from a bond, alkylene and heteroalkylene, wherein L⁵ is optionally substituted with one or more groups independently selected from R³⁰;

RX* is a bond, a succinimide moiety, or a hydrolyzed succinimide moiety bound to a residue of an antibody or antigen binding fragment thereof, wherein

on RX* represents the point of attachment to the residue of the antibody or antigen binding fragment thereof; and R³⁰ is independently selected at each occurrence from halogen, —OH, —CN, —O— alkyl, —SH, =O, =S, —NH₂, —NO₂; and $C_1$-$C_{10}$ alkyl, $C_2$-$C_{10}$ alkenyl, and $C_2$-$C_{10}$ alkynyl, each of which is independently optionally substituted at each occurrence with one or more substituents selected from halogen, —OH, —CN, —O-alkyl, —SH, =O, =S, —NH₂, and —NO₂.

In certain embodiments, for a compound or salt of any one of Formulas (IIA), (IIB), or (IIC), RX* is a succinamide moiety, hydrolyzed succinamide moiety or a mixture thereof and is bound to a cysteine residue of an antibody.

In certain embodiments for a compound of Formulas (IIA), (IIB) and (IIC), -L³ is represented by the formula:

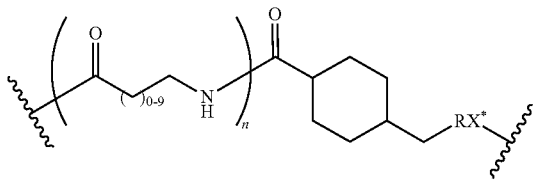

wherein:

RX* is a bond, a succinimide moiety, or a hydrolyzed succinimide moiety bound to a residue of an antibody, wherein

a on RX* represents the point of attachment to the residue of the antibody; and n is 0-9.

Examples of TLR7 agonist compounds according to Category B are provided in Table 3 and their stereoisomers. It is understood that salts of the compounds provided in Table 3 are also envisioned by Table 3.

TABLE 3

| Compounds 3.1-3.14 | |
|---|---|
| Compound | Structure |
| 3.1 | ![structure] benzyl (1-((2-((1-(4-amino-2-(ethoxymethyl)-1H-imidazo[4,5-c]quinolin-1-yl)-2-methylpropan-2-yl)oxy)ethyl)amino)-2-methyl-1-oxopropan-2-yl)carbamate |

TABLE 3-continued

Compounds 3.1-3.14

| Compound | Structure |
|---|---|
| 3.2 | 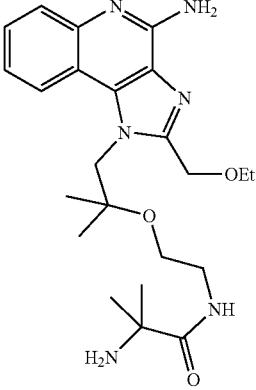 [SMILES: CCOCc1nc2c(N)nc3ccccc3c2n1CC(C)(C)OCCNC(=O)C(C)(C)N] 2-amino-N-(2-((1-(4-amino-2-(ethoxymethyl)-1H-imidazo[4,5-c]quinolin-1-yl)-2-methylpropan-2-yl)oxy)ethyl)-2-methylpropanamide |
| 3.3 | 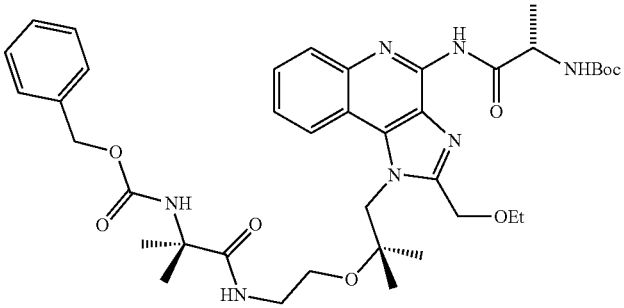 benzyl (S)-(1-((2-(((1-(4-(2-((tert-butoxycarbonyl)amino)propanamido)-2-(ethoxymethyl)-1H-imidazo[4,5-c]quinolin-1-yl)-2-methylpropan-2-yl)oxy)ethyl)amino)-2-methyl-1-oxopropan-2-yl)carbamate |
| 3.4 | 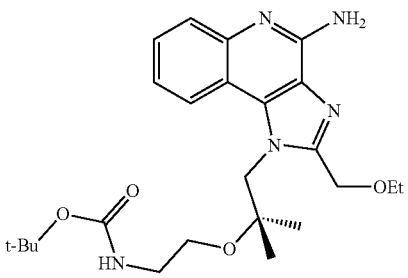 tert-butyl (2-((1-(4-amino-2-(ethoxymethyl)-1H-imidazo[4,5-c]quinolin-1-yl)-2-methylpropan-2-yl)oxy)ethyl)carbamate |

TABLE 3-continued
Compounds 3.1-3.14
| Compound | Structure |
|---|---|
| 3.5 | 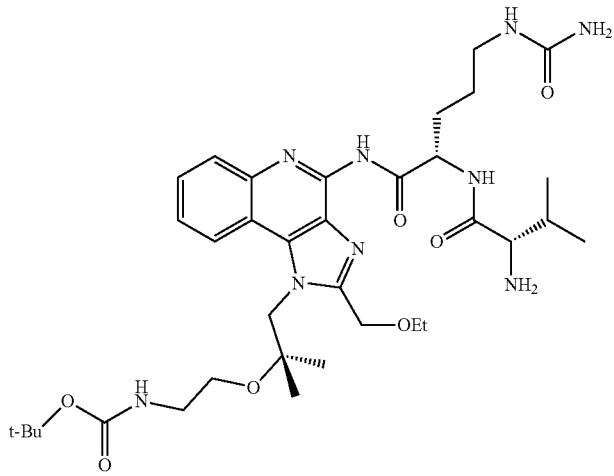<br>tert-butyl (2-((1-(4-((S)-2-((S)-2-amino-3-methylbutanamido)-5-ureidopentanamido)-2-(ethoxymethyl)-1H-imidazo[4,5-c]quinolin-1-yl)-2-methylpropan-2-yl)oxy)ethyl)carbamate |
| 3.6 | 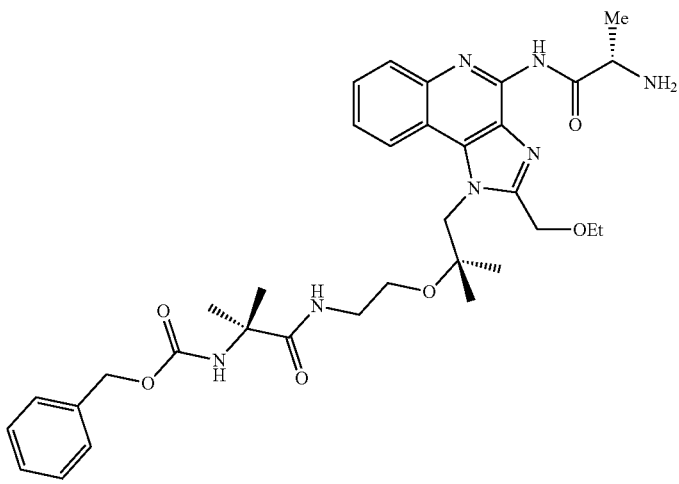<br>benzyl (S)-(1-((2-((1-(4-(2-aminopropanamido)-2-(ethoxymethyl)-1H-imidazo[4,5-c]quinolin-1-yl)-2-methylpropan-2-yl)oxy)ethyl)amino)-2-methyl-1-oxopropan-2-yl)carbamate |

TABLE 3-continued

Compounds 3.1-3.14

| Compound | Structure |
|---|---|
| 3.7 | tert-butyl 2-(((S)-1-((2-(ethoxymethyl)-1-(5,5,11,11-tetramethyl-3,6-dioxo-1-phenyl-2,10-dioxa-4,7-diazadodecan-12-yl)-1H-imidazo[4,5-c]quinolin-4-yl)amino)-1-oxopropan-2-yl)carbamoyl)pyrrolidine-1-carboxylate |
| 3.8 | (9H-fluoren-9-yl)methyl ((S)-1-(((S)-1-((1-(2-(2-((tert-butoxycarbonyl)amino)ethoxy)-2-methylpropyl)-2-(ethoxymethyl)-1H-imidazo[4,5-c]quinolin-4-yl)amino)-1-oxo-5-ureidopentan-2-yl)amino)-3-methyl-1-oxobutan-2-yl)carbamate |
| 3.9 | 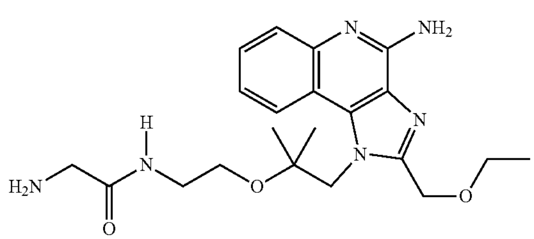 [SMILES: CCOCc1nc2c(N)nc3ccccc3c2n1CC(C)(C)OCCNC(=O)CN] |
| 3.10 | 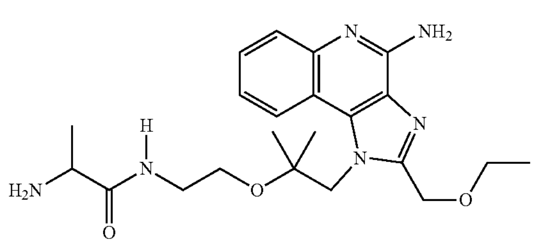 [SMILES: CCOCc1nc2c(N)nc3ccccc3c2n1CC(C)(C)OCCNC(=O)C(C)N] |

TABLE 3-continued
Compounds 3.1-3.14
| Compound | Structure |
|---|---|
| 3.11 | 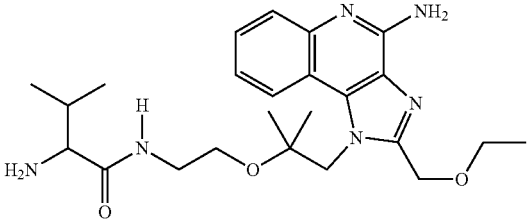 [SMILES: CCOCc1nc2c(N)nc3ccccc3c2n1CC(C)(C)OCCNC(=O)C(N)C(C)C] |
| 3.12 | 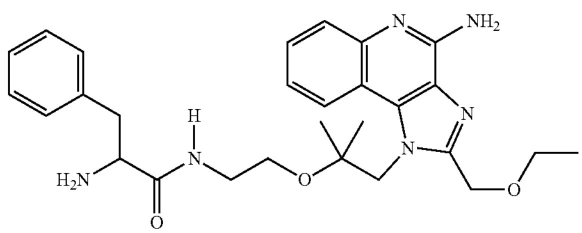 [SMILES: CCOCc1nc2c(N)nc3ccccc3c2n1CC(C)(C)OCCNC(=O)C(N)Cc1ccccc1] |
| 3.13 | 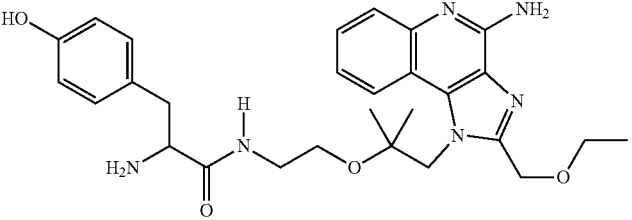 [SMILES: CCOCc1nc2c(N)nc3ccccc3c2n1CC(C)(C)OCCNC(=O)C(N)Cc1ccc(O)cc1] |
| 3.14 | 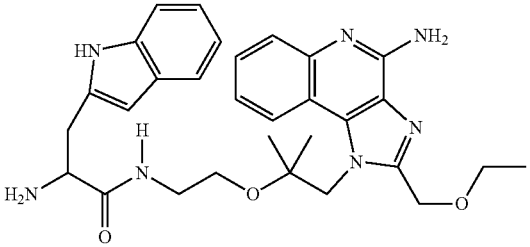 [SMILES: CCOCc1nc2c(N)nc3ccccc3c2n1CC(C)(C)OCCNC(=O)C(N)Cc1cc2ccccc2[nH]1] |

In some aspects, the present disclosure provides a conjugate represented by the following structure:

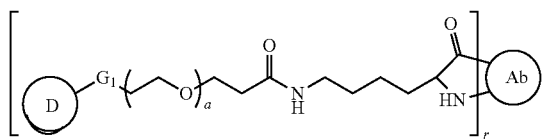

or a pharmaceutically acceptable salt thereof, wherein Ab comprises an anti-Nectin-4 antibody or an antigen-binding fragment thereof disclosed herein, D is a compound or salt of a Category B compound of Formula (IID):

(IID)

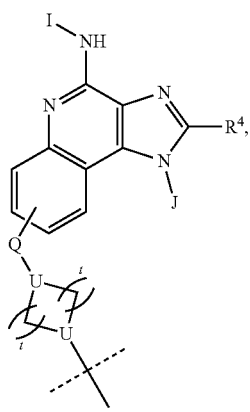

wherein $R^4$ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript r is an integer from 1 to 10.

In certain embodiments, D has the following structure:

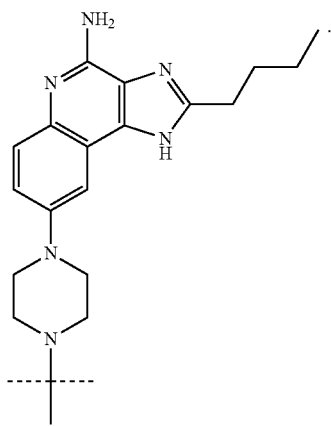

In further embodiments, the conjugate has the following structure:

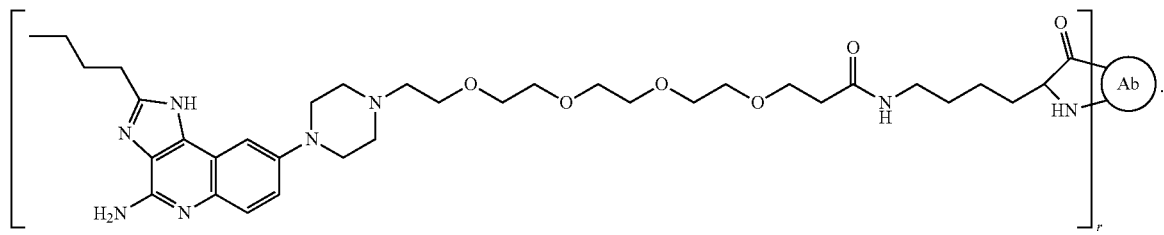

In any of the aforementioned embodiments having a conjugate structure of:

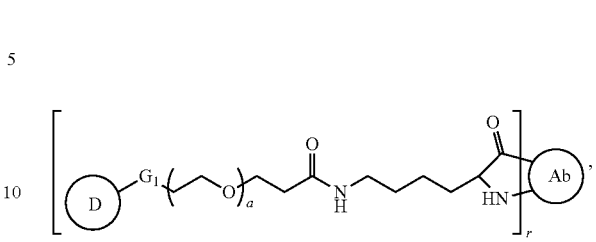

wherein D is a compound or salt of a Category B compound of Formula (IID):

(IID)

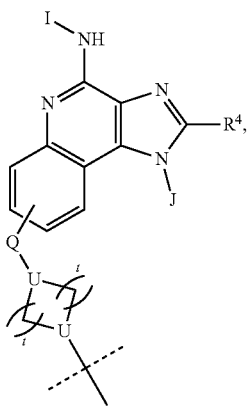

wherein $R^4$ is alkyl, heteroalkyl, cycloalkyl, heterocycloalkyl, aryl, heteroaryl, arylalkyl, or heteroarylalkyl group comprising from 1 to 8 carbons, each J is hydrogen, each U is N, each t is 2, Q is not present, the dashed line represents a point of attachment of the adjuvant to $G_1$, and $G_1$ is a bond; subscript a is an integer from 1 to 40; and subscript t r is an integer from 1 to 10; or

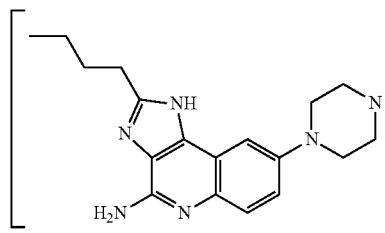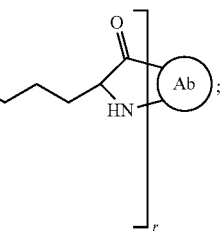

the antibody of the conjugate comprises a heavy chain variable region (VH) and a light chain variable region (VL), (1) wherein the VH comprises a CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3; and the VL comprises a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8;

(2) wherein the VH comprises a CDR1 (VH-CDR1) comprising the amino acid sequence of SEQ ID NO:33, a VH-CDR2 comprising the amino acid sequence of SEQ ID NO:34, a VH-CDR3 comprising the amino acid sequence of SEQ ID NO:35; and the VL comprises a CDR1 (VL-CDR1) comprising the amino acid sequence of SEQ ID NO:36, a VL-CDR2 comprising the amino acid sequence of SEQ ID NO:37, and a VL-CDR3 comprising the amino acid sequence of SEQ ID NO:38;

(3) wherein the VH comprises a CDR1 (VH-CDR1) comprising the amino acid sequence of SEQ ID NO:39, a VH-CDR2 comprising the amino acid sequence of SEQ ID NO:40, a VH-CDR3 comprising the amino acid sequence of SEQ ID NO:41; and the VL comprises a CDR1 (VL-CDR1) comprising the amino acid sequence of SEQ ID NO:42, a VL-CDR2 comprising the amino acid sequence of SEQ ID NO:43, and a VL-CDR3 comprising the amino acid sequence of SEQ ID NO:44;

(4) wherein the VH comprises a CDR1 (VH-CDR1) comprising the amino acid sequence of SEQ ID NO:45, a VH-CDR2 comprising the amino acid sequence of SEQ ID NO:46, a VH-CDR3 comprising the amino acid sequence of SEQ ID NO:47; and the VL comprises a CDR1 (VL-CDR1) comprising the amino acid sequence of SEQ ID NO:48, a VL-CDR2 comprising the amino acid sequence of SEQ ID NO:49, and a VL-CDR3 comprising the amino acid sequence of SEQ ID NO:50;

(5) wherein the VH comprises a CDR1 (VH-CDR1) comprising the amino acid sequence of SEQ ID NO:51, a VH-CDR2 comprising the amino acid sequence of SEQ ID NO:52, a VH-CDR3 comprising the amino acid sequence of SEQ ID NO:53; and the VL comprises a CDR1 (VL-CDR1) comprising the amino acid sequence of SEQ ID NO:54, a VL-CDR2 comprising the amino acid sequence of SEQ ID NO:55, and a VL-CDR3 comprising the amino acid sequence of SEQ ID NO:56;

(6) wherein the VH comprises a CDR1 (VH-CDR1) comprising the amino acid sequence of SEQ ID NO:57, a VH-CDR2 comprising the amino acid sequence of SEQ ID NO:58, a VH-CDR3 comprising the amino acid sequence of SEQ ID NO:59; and the VL comprises a CDR1 (VL-CDR1) comprising the amino acid sequence of SEQ ID NO:60, a VL-CDR2 comprising the amino acid sequence of SEQ ID NO:61, and a VL-CDR3 comprising the amino acid sequence of SEQ ID NO:62;

(7) wherein VH comprises the amino acid sequence of SEQ ID NO: 10, and VL comprises the amino acid sequence selected from any one of SEQ ID NOS: 12-17; or (8) wherein VH comprises the amino acid of SEQ ID NO:24, and VL comprises the amino acid sequence selected from any one of SEQ ID NOS:26-31.

In another aspect, the present disclosure provides a conjugate represented by the following structure:

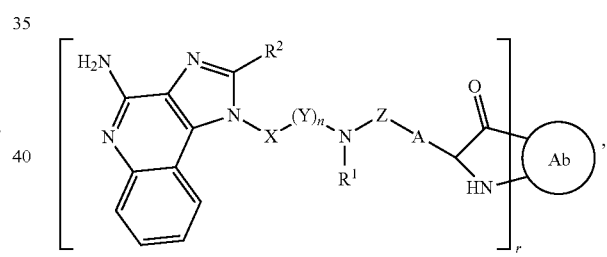

or a pharmaceutically acceptable salt thereof, wherein Ab comprises an anti-Nectin-4 antibody or an antigen-binding fragment thereof disclosed herein; A is an unmodified amino acid sidechain in the antibody or a modified amino acid sidechain in the antibody; Z is a linking moiety; $R^1$ is selected from H and $C_{1-4}$ alkyl; or Z, $R^1$, and the nitrogen atom to which they are attached form a linking moiety comprising a 5- to 8-membered heterocycle; each Y is independently $CHR^2$, wherein $R^2$ is selected from H, OH, and $NH_2$, $R^3$ is selected from $C_{1-6}$ alkyl and 2- to 6-membered heteroalkyl, each of which is optionally substituted with one or more members selected from the group consisting of halo, hydroxy, amino, oxo (=O), alkylamino, amido, acyl, nitro, cyano, and alkoxy; X is selected from O and $CH_2$; subscript n is an integer from 1 to 12; and subscript r is an integer from 1 to 10.

In certain embodiments, the conjugate is represented by the following structure:

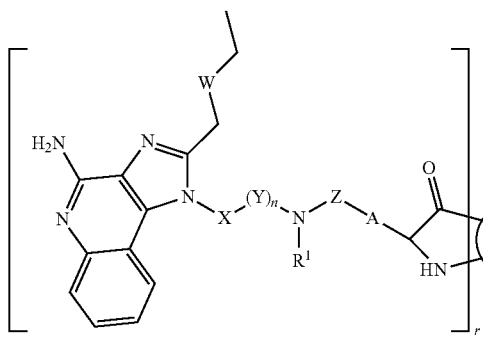

or a pharmaceutically acceptable salt thereof, wherein Ab comprises an anti-Nectin-4 antibody or an antigen-binding fragment thereof disclosed herein; A is an unmodified amino acid sidechain in the antibody or a modified amino acid sidechain in the antibody; Z is a linking moiety; $R^1$ is selected from H and $C_{1-4}$ alkyl; or Z, $R^1$, and the nitrogen atom to which they are attached form a linking moiety comprising a 5- to 8-membered heterocycle; each Y is independently $CHR^2$, wherein $R^2$ is selected from H, OH, and $NH_2$; X is selected from O and $CH_2$; subscript n is an integer from 1 to 12; and W is selected from the group consisting of O and $CH_2$.

In further embodiments, the conjugate is represented by the following structure:

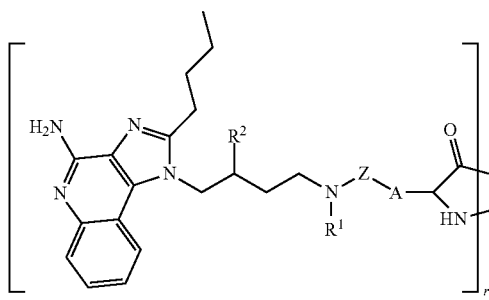

or a pharmaceutically acceptable salt thereof, wherein Ab comprises an anti-Nectin-4 antibody or antigen-binding fragment thereof disclosed herein; subscript r is an integer from 1 to 10; A is an unmodified amino acid sidechain in the antibody or a modified amino acid sidechain in the antibody; Z is a linking moiety; and $R^1$ is selected from H and $C_{1-4}$ alkyl; or Z, $R^1$, and the nitrogen atom to which they are attached form a linking moiety comprising a 5- to 8-membered heterocycle; and $R^2$ is selected from H, OH, and $NH_2$.

In yet further embodiments, the conjugate is represented by the following structure:

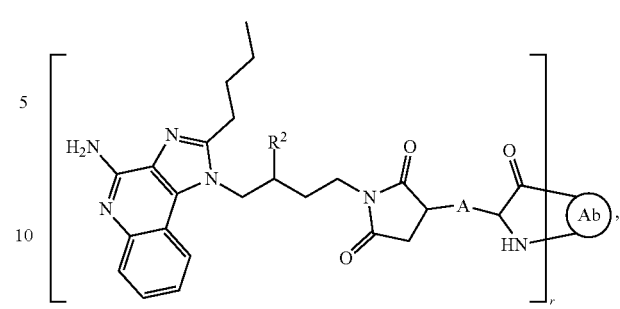

or a pharmaceutically acceptable salt thereof, wherein Ab comprises an anti-Nectin-4 antibody or antigen-binding fragment thereof disclosed herein; A is an unmodified amino acid sidechain in the antibody or a modified amino acid sidechain in the antibody; $R^2$ is selected from H, OH, and $NH_2$; and subscript r is an integer from 1 to 10.

In any of the aforementioned embodiments having a conjugate structure of:

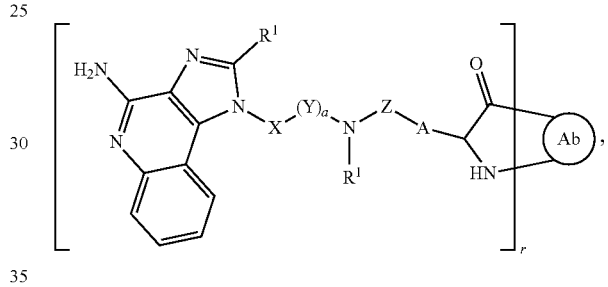

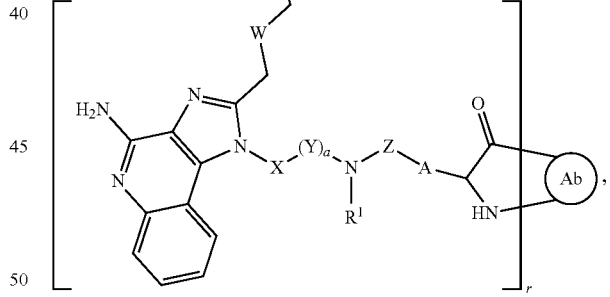

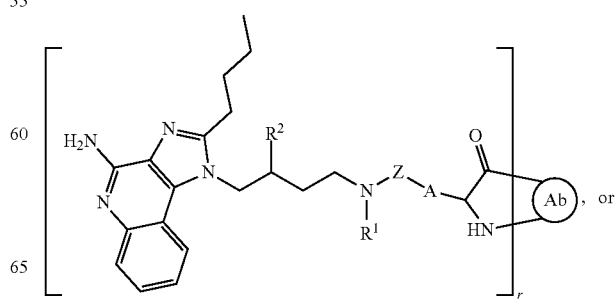

or

-continued

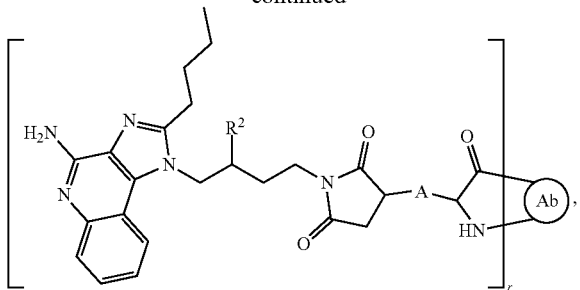

the antibody of the conjugate comprises a heavy chain variable region (VH) and a light chain variable region (VL), (1) wherein the VH comprises a CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3; and the VL comprises a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8;

(2) wherein the VH comprises a CDR1 (VH-CDR1) comprising the amino acid sequence of SEQ ID NO:33, a VH-CDR2 comprising the amino acid sequence of SEQ ID NO:34, a VH-CDR3 comprising the amino acid sequence of SEQ ID NO:35; and the VL comprises a CDR1 (VL-CDR1) comprising the amino acid sequence of SEQ ID NO:36, a VL-CDR2 comprising the amino acid sequence of SEQ ID NO:37, and a VL-CDR3 comprising the amino acid sequence of SEQ ID NO:38;

(3) wherein the VH comprises a CDR1 (VH-CDR1) comprising the amino acid sequence of SEQ ID NO:39, a VH-CDR2 comprising the amino acid sequence of SEQ ID NO:40, a VH-CDR3 comprising the amino acid sequence of SEQ ID NO:41; and the VL comprises a CDR1 (VL-CDR1) comprising the amino acid sequence of SEQ ID NO:42, a VL-CDR2 comprising the amino acid sequence of SEQ ID NO:43, and a VL-CDR3 comprising the amino acid sequence of SEQ ID NO:44;

(4) wherein the VH comprises a CDR1 (VH-CDR1) comprising the amino acid sequence of SEQ ID NO:45, a VH-CDR2 comprising the amino acid sequence of SEQ ID NO:46, a VH-CDR3 comprising the amino acid sequence of SEQ ID NO:47; and the VL comprises a CDR1 (VL-CDR1) comprising the amino acid sequence of SEQ ID NO:48, a VL-CDR2 comprising the amino acid sequence of SEQ ID NO:49, and a VL-CDR3 comprising the amino acid sequence of SEQ ID NO:50;

(5) wherein the VH comprises a CDR1 (VH-CDR1) comprising the amino acid sequence of SEQ ID NO:51, a VH-CDR2 comprising the amino acid sequence of SEQ ID NO:52, a VH-CDR3 comprising the amino acid sequence of SEQ ID NO:53; and the VL comprises a CDR1 (VL-CDR1) comprising the amino acid sequence of SEQ ID NO:54, a VL-CDR2 comprising the amino acid sequence of SEQ ID NO:55, and a VL-CDR3 comprising the amino acid sequence of SEQ ID NO:56;

(6) wherein the VH comprises a CDR1 (VH-CDR1) comprising the amino acid sequence of SEQ ID NO:57, a VH-CDR2 comprising the amino acid sequence of SEQ ID NO:58, a VH-CDR3 comprising the amino acid sequence of SEQ ID NO:59; and the VL comprises a CDR1 (VL-CDR1) comprising the amino acid sequence of SEQ ID NO:60, a VL-CDR2 comprising the amino acid sequence of SEQ ID NO:61, and a VL-CDR3 comprising the amino acid sequence of SEQ ID NO:62;

(7) wherein VH comprises the amino acid sequence of SEQ ID NO: 10, and VL comprises the amino acid sequence selected from any one of SEQ ID NOS:12-17; or (8) wherein VH comprises the amino acid of SEQ ID NO:24, and VL comprises the amino acid sequence selected from any one of SEQ ID NOS:26-31.

Compounds of Category C, TLR8 Agonists

In some aspects, the myeloid cell agonist is a benzazepine compound (Bza). In some aspects, the present disclosure provides a conjugate represented by Formula I:

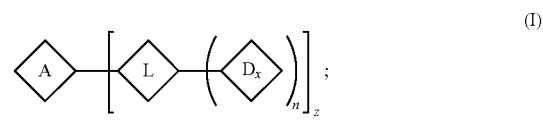

(I)

wherein: A is an anti-Nectin-4 antibody or an antigen-binding fragment thereof, L is a linker; $D_x$ is an immune-stimulatory compound; n is selected from 1 to 20; and z is selected from 1 to 20.

In certain embodiments of the conjugates of the disclosure, $D_x$ is selected from a compound or salt of a compound of the disclosure, including, but not limited to Category C (e.g., Formulas (Ia), (Ib), (Ic), (Id), (Ie), (If), (Ig) and (Ih)).

In certain embodiments, L is represented by the formula:

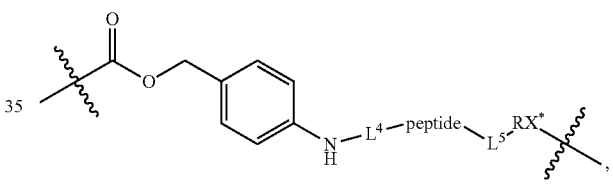

wherein
$L^4$ represents the C-terminal of the peptide and
$L^5$ is selected from a bond, alkylene and heteroalkylene, wherein $L^5$ is optionally substituted with one or more groups independently selected from $R^{32}$;
RX* comprises a bond, a succinimide moiety, or a hydrolyzed succinimide moiety bound to a residue of an antibody or antigen binding fragment thereof,
wherein

on RX* represents the point of attachment to the residue of the antibody or antigen binding fragment thereof; and,
$R^{32}$ is independently selected at each occurrence from halogen, —OH, —CN, —O— alkyl, —SH, =O, =S, —NH₂, —NO₂; and $C_{1-10}$ alkyl, $C_{2-10}$ alkenyl, $C_{2-10}$ alkynyl, each of which is optionally substituted with one or more substituents independently selected from halogen, —OH, —CN, —O-alkyl, —SH, =O, =S, —NH₂, —NO₂. In some embodiments, the peptide of L comprises Val-Cit or Val-Ala.

In certain embodiments of the Category C compounds of the disclosure, $D_x$ comprises an aminobenzazepine moiety having the formula:

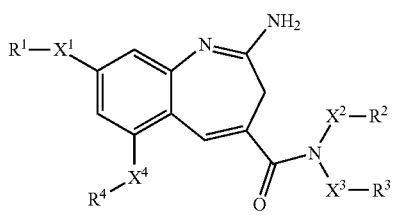

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from: —($C_1$-$C_{12}$ alkyldiyl)-N($R^5$)—*; —($C_1$-$C_{12}$ alkyldiyl)-N($R^5$)$_2$; —($C_3$-$C_{12}$ carbocyclyl); —($C_3$-$C_{12}$ carbocyclyl)-*; —($C_3$-$C_{12}$ carbocyclyl)-($C_1$-$C_{12}$ alkyldiyl)-N$R^5$—*; —($C_3$-$C_{12}$ carbocyclyl)-($C_1$-$C_{12}$ alkyldiyl)-N($R^5$)$_2$; —($C_3$-$C_{12}$ carbocyclyl)-N$R^5$—C(=N$R^5$)N$R^5$—*; —($C_6$-$C_{20}$ aryl); —($C_6$-$C_{20}$ aryl)-*; —($C_6$-$C_{20}$ aryldiyl)-N($R^5$)—*; —($C_6$-$C_{20}$ aryldiyl)-($C_1$-$C_{12}$ alkyldiyl)-N($R^5$)—*; —($C_6$-$C_{20}$ aryldiyl)-($C_1$-$C_{12}$ alkyldiyl)-N($R^5$)$_2$; —($C_6$-$C_{20}$ aryldiyl)-($C_1$-$C_{12}$ alkyldiyl)-N$R^5$—C(=N$R^{5a}$)N($R^5$)—*; —($C_2$-$C_{20}$ heterocyclyl); —($C_2$-$C_{20}$ heterocyclyl)-*; —($C_2$-$C_9$ heterocyclyl)-($C_1$-$C_{12}$ alkyldiyl)-N$R_5$—*; —($C_2$-$C_9$ heterocyclyl)-($C_1$-$C_{12}$ alkyldiyl)-N($R^5$)$_2$; —($C_2$-$C_9$ heterocyclyl)-N$R^5$—C(=N$R^{5a}$)N$R^5$—*; —($C_1$-$C_{20}$ heteroaryl); —($C_1$-$C_{20}$ heteroaryl)-*; —($C_1$-$C_{20}$ heteroaryl)-($C_1$-$C_{12}$ alkyldiyl)-N($R^5$)—*; —($C_1$-$C_{20}$ heteroaryl)-($C_1$-$C_{12}$ alkyldiyl)-N($R^5$)$_2$; —($C_1$-$C_{20}$ heteroaryl)-N$R^5$—C(=N$R^{5a}$)N($R^5$)—*; —C(=O)—*; —C(=O)—($C_2$-$C_{20}$ heterocyclyldiyl)-*; —C(=O)N($R^5$)$_2$; —C(=O)N($R^5$)—*; —C(=O)N($R^5$)—($C_1$-$C_{12}$ alkyldiyl)-N($R^5$)C(=O)$R^5$; —C(=O)N($R^5$)—($C_1$-$C_{12}$ alkyldiyl)-N($R^5$)C(=O)N($R^5$)$_2$; —C(=O)N$R^5$—($C_1$-$C_{12}$ alkyldiyl)-N($R^5$)CO$_2R^5$; —C(=O)N$R^5$—($C_1$-$C_{12}$ alkyldiyl)-N($R^5$)C(=NR5a)N($R^5$)$_2$; —C(=O)N$R^5$—($C_1$-$C_{12}$ alkyldiyl)-N$R^5$C(=N$R^{5a}$)$R^5$; —C(=O)N$R^5$—($C_1$-$C_5$ alkyldiyl)-N$R^5$ ($C_2$-$C_5$ heteroaryl); —C(=O)N$R^5$—($C_1$-$C_{20}$ heteroaryldiyl)-N($R^5$)—*; —C(=O)N$R^5$—($C_1$-$C_{20}$ heteroaryldiyl)-*; —C(=O)N$R^5$—($C_1$-$C_{20}$ heteroaryldiyl)-($C_1$-$C_{12}$ alkyldiyl)-N($R^5$)$_2$; —C(=O)N$R^5$—($C_1$-$C_{20}$ heteroaryldiyl)-($C_2$-$C_{20}$ heterocyclyldiyl)-C(=O)N$R^5$—($C_1$-$C_{12}$ alkyldiyl)-N$R^5$*; —N($R^5$)$_2$; —N($R^5$)—*; —N($R^5$)C(=O) $R^5$; —N($R^5$)C(=O)—*; —N($R^5$)C(=O)N($R^5$)$_2$; —N($R^5$)C(=O)N($R^5$)—*; —N($R^5$)CO$_2R^5$; —N$R^5$C(=N$R^{5a}$)N($R^5$)$_2$; —N$R^5$C(=N$R^{5a}$)N($R^5$)—*; —N$R^5$C(=N$R^{5a}$) $R^5$; —N($R^5$)—($C_2$-$C_5$ heteroaryl); —O—($C_1$-$C_{12}$ alkyl); —O—($C_1$-$C_{12}$ alkyldiyl)-N($R^5$)$_2$; —O—($C_1$-$C_{12}$ alkyldiyl)-N($R^5$)—*; —S(=O)$_2$—($C_2$-$C_{20}$ heterocyclyldiyl)-*; —S(=O)$_2$—($C_2$-$C_{20}$ heterocyclyldiyl)-($C_1$-$C_{12}$ alkyldiyl)-N($R^5$)$_2$; —S(=O)$_2$—($C_2$-$C_{20}$ heterocyclyldiyl)-($C_1$-$C_{12}$ alkyldiyl)-N$R^5$*; and —S(=O)$_2$—($C_2$-$C_{20}$ heterocyclyldiyl)-($C_1$-$C_{12}$ alkyldiyl)-OH; or $R^2$ and $R^3$ together form a 5- or 6-membered heterocyclyl ring;

$X^1$, $X^2$, $X^3$, and $X^4$ are independently selected from the group consisting of a bond, C(=O), C(=O)N($R^5$), O, N($R^5$), S, S(O)$_2$, and S(O)$_2$N($R^5$); $R^5$ is selected from the group consisting of H, $C_6$-$C_{20}$ aryl, $C_6$-$C_{20}$ aryldiyl, $C_1$-$C_{12}$ alkyl, and $C_1$-$C_{12}$ alkyldiyl, or two Rs groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk* indicates the attachment site of L, and where one of $R^1$, $R^2$, $R^3$ and $R^4$ is attached to L;

L is the linker selected from the group consisting of: —C(=O)-(PEG)-; —C(=O)-(PEG)-C(=O)—; —C(=O)-(PEG)-O—; —C(=O)-(PEG)-C(=O)-(PEP)-; —C(=O)-(PEG)-C(=O)N($R^5$)—($C_1$-$C_{12}$ alkyldiyl)-; —C(=O)-(PEG)-C(=O)N($R^5$)—($C_1$-$C_{12}$ alkyldiyl)-N($R^5$)C(=O)—($C_2$-$C_5$ monoheterocyclyldiyl)-; —C(=O)-(PEG)-C(=O)N($R^5$)—($C_1$-$C_{12}$ alkyldiyl)-(MCgluc)-; —C(=O)-(PEG)-C(=O)-(MCgluc)-; —C(=O)-(PEG)-C(=O)-(PEP)-N($R^5$)—($C_1$-$C_{12}$ alkyldiyl)-; —C(=O)-(PEG)-C(=O)-(PEP)-N($R^5$)—($C_1$-$C_{12}$ alkyldiyl)-N($R^5$)C(=O)—($C_2$-$C_5$ monoheterocyclyldiyl)-; —C(=O)-(PEG)-N($R^5$)—; —C(=O)-(PEG)-N($R^5$)—(PEG)-C(=O)-(PEP)-; —C(=O)-(PEG)-N+($R^5$)$_2$-(PEG)-C(=O)-(PEP)-; —C(=O)-(PEG)-C(=O)—N($R^5$)CH(AA$_1$)C(=O)-(PEG)-C(=O)-(PEP)-; —C(=O)-(PEG)-C(=O)—N($R^5$)CH(AAI)C(=O)—N($R^5$)—($C_1$-$C_{12}$ alkyldiyl)-; —C(=O)-(PEG)-SS—($C_1$-$C_{12}$ alkyldiyl)-OC(=O)—; —C(=O)-(PEG)-SS—($C_1$-$C_{12}$ alkyldiyl)-C(=O)—; —C(=O)—($C_1$-$C_{12}$ alkyldiyl)-C(=O)-(PEP)-; —C(=O)—($C_1$-$C_{12}$ alkyldiyl)-C(=O)-(PEP)-N($R^5$)—($C_1$-$C_{12}$ alkyldiyl)-; —C(=O)—($C_1$-$C_{12}$ alkyldiyl)-C(=O)-(PEP)-N($R^5$)—($C_1$-$C_{12}$ alkyldiyl)-N($R^5$)—C(=O); —C(=O)—($C_1$-$C_{12}$alkyldiyl)-C(=O)-(PEP)-N($R^5$)—($C_1$-$C_{12}$alkyldiyl)-N($R^5$)C(=O)—($C_2$-$C_5$ monoheterocyclyldiyl)-; —C(=O)—CH$_2$CH$_2$OCH$_2$CH$_2$—($C_1$-$C_{20}$ heteroaryldiyl)-CH$_2$O—(PEG)-C(=O)(MCgluc)-; —C(=O)—CH$_2$CH$_2$OCH$_2$CH$_2$—($C_1$-$C_{20}$ heteroaryldiyl)-CH$_2$O—(PEG)-C(=O)(MCgluc)-N($R^5$)—($C_1$-$C_{12}$ alkyldiyl)-N($R^5$)C(=O)—($C_2$-$C_5$ monoheterocyclyldiyl)-; and -(succinimidyl)-(CH$_2$)$_m$—C(=O)-(PEP)-N($R^5$)—($C_1$-$C_{12}$ alkyldiyl)-N($R^5$)C(=O)—($C_2$-$C_5$ monoheterocyclyldiyl)-;

PEG has the formula: —(CH$_2$CH$_2$O)$_n$—(CH$_2$)$_m$—; m is an integer from 1 to 5, and n is an integer from 2 to 50;

PEP has the formula:

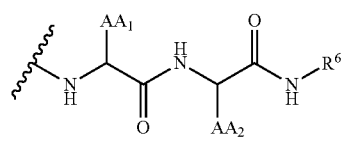

where AA$_1$ and AA$_2$ are independently selected from an amino acid side chain, or AA$_1$ or AA$_2$ and an adjacent nitrogen atom form a 5-membered ring praline amino acid, and the wavy line indicates a point of attachment;

$R^6$ is selected from the group consisting of $C_6$-$C_{20}$ aryldiyl and $C_1$-$C_{20}$ heteroaryldiyl, substituted with —CH$_2$O—C(=O)— and optionally with:

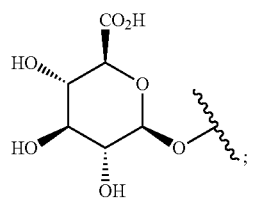 [SMILES: *O[C@@H]1O[C@H](C(=O)O)[C@@H](O)[C@H](O)[C@H]1O]

and

MCgluc is selected from the groups:

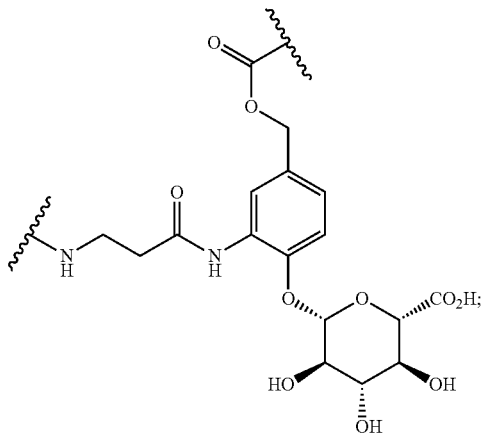

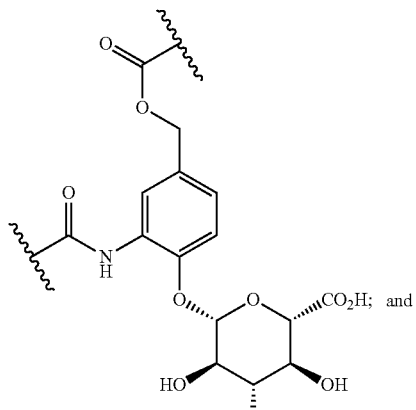

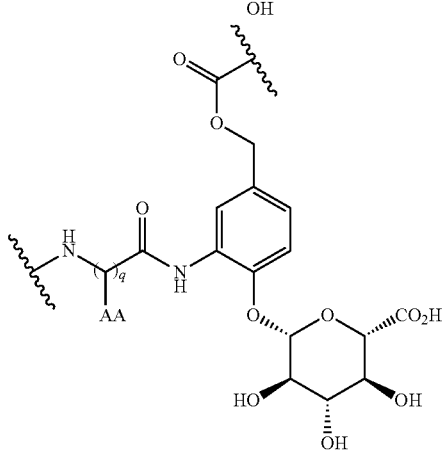

where q is 1 to 8, and AA is an amino acid side chain; and alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —CH$_3$, —CH$_2$CH$_3$, —CH=CH$_2$, —C≡CH, —C≡CCH$_3$, —CH$_2$CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CH$_2$NH$_2$, —CH$_2$NHSO$_2$CH$_3$, —CH$_2$NHCH$_3$, —CH$_2$N(CH$_3$)$_2$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NHC(=NH)H, —NHC(=NH)CH$_3$, —NHC(=NH)NH$_2$, —NHC(=O)NH$_2$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —O(CH$_2$CH$_2$O)n-(CH$_2$)mCO$_2$H, —O(CH2CH2O)$_n$H, —OP(O)(OH)$_2$, —S(O)$_2$N(CH$_3$)$_2$, —SCH$_3$, —S(O)$_2$CH$_3$, and —S(O)$_3$H.

In certain embodiments, the PEP is selected from the groups:

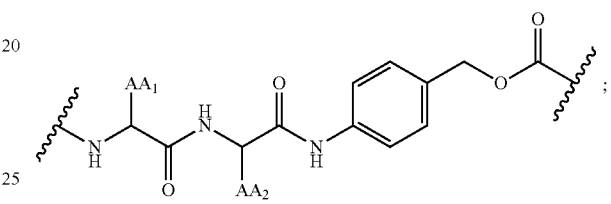

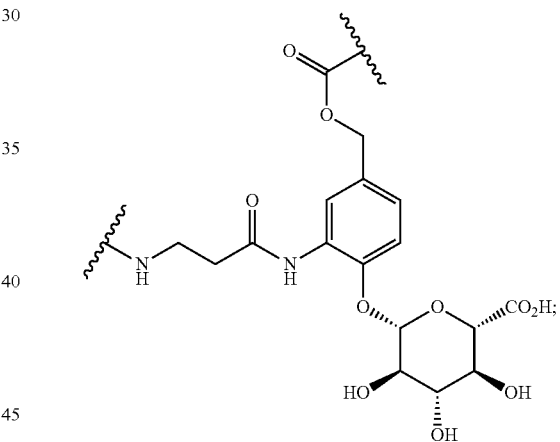

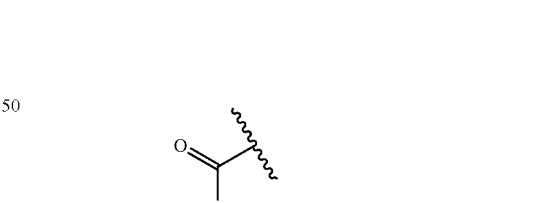

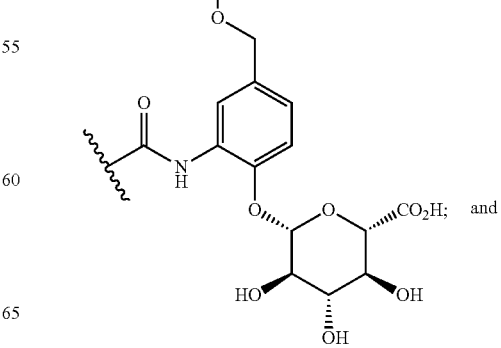

-continued

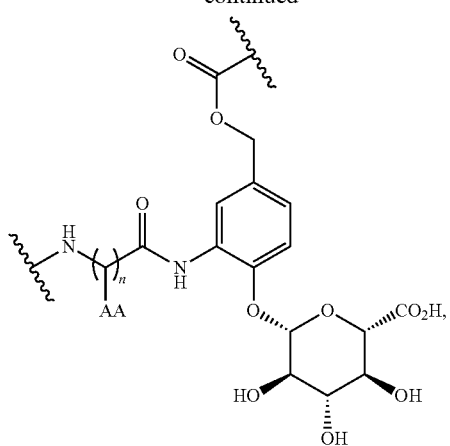

wherein n is 1 or more and AA is an amino acid side chain. In certain embodiments of Formula I, each of $AA_1$ and $AA_2$ are independently selected from a side chain of a naturally-occurring amino acid. In certain embodiments of Formula I, each of $AA_1$ and $AA_2$ are independently selected from H, —$CH_3$, —$CH(CH_3)_2$, —$CH_2(C_6H_5)$, —$CH_2CH_2CH_2CH_2NH_2$, —$CH_2CH_2CH_2NHC(NH)NH_2$, —$CH_2CH(CH_3)_2$, —$CH_2SO_3H$, and —$CH_2CH_2CH_2NHC(O)NH_2$. In certain embodiments of Formula I, $AA_1$ is —$CH(CH_3)_2$ and $AA_2$ is —$CH_2CH_2CH_2NHC(O)NH_2$. In certain embodiments of Formula I, each of $AA_1$ and $AA_2$ are independently selected from GlcNAc, aspartic acid, —$CH_2SO_3H$ and —$CH_2OPO_3H$.

In certain embodiments of the formulas of the disclosure, including Formula I of Category C, L-$D_x$ is selected from Formulas Ia-Id:

Ia
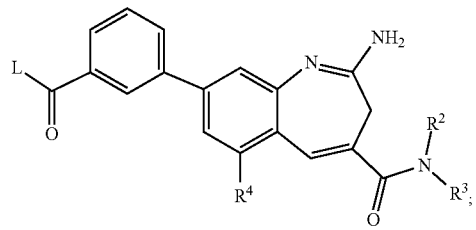

Ib
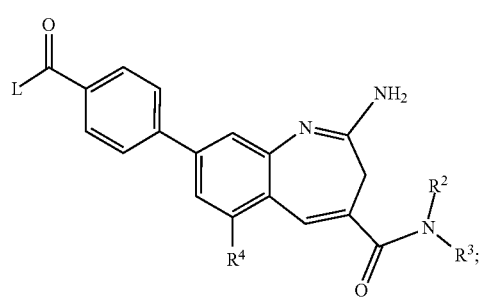

Ic
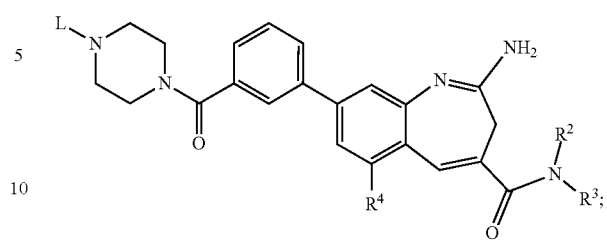

Id
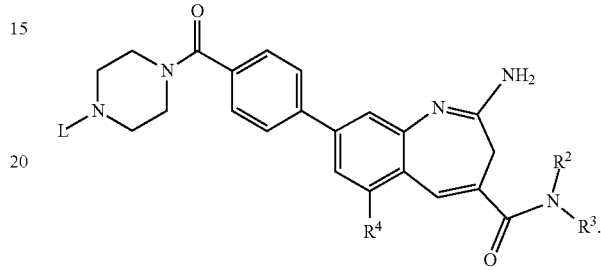

In certain embodiments of the formulas of the disclosure, including Formula I of Category C, L is —C(=O)-(PEG)- or —C(=O)-(PEG)-C(=O)—. In certain embodiments of the formulas of the disclosure, including Formula I of Category C, L-$D_x$ is selected from Formulas Ie and If:

Ie
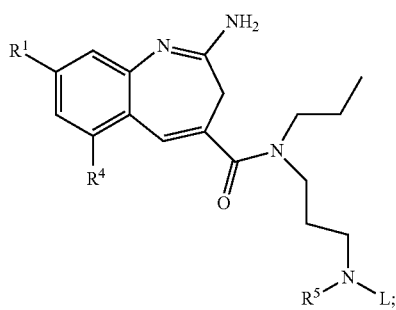

If
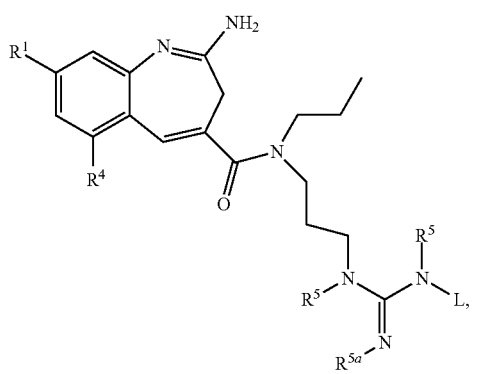

wherein $R^{5a}$ of Formula If is phenyl, optionally substituted with one or more groups selected from F, Cl, Br, I, —CN, and —$NO_2$. In certain embodiments of the formulas of the disclosure, including Formula I of Category C, L-$D_x$ is selected from Formulas Ig and Ih:

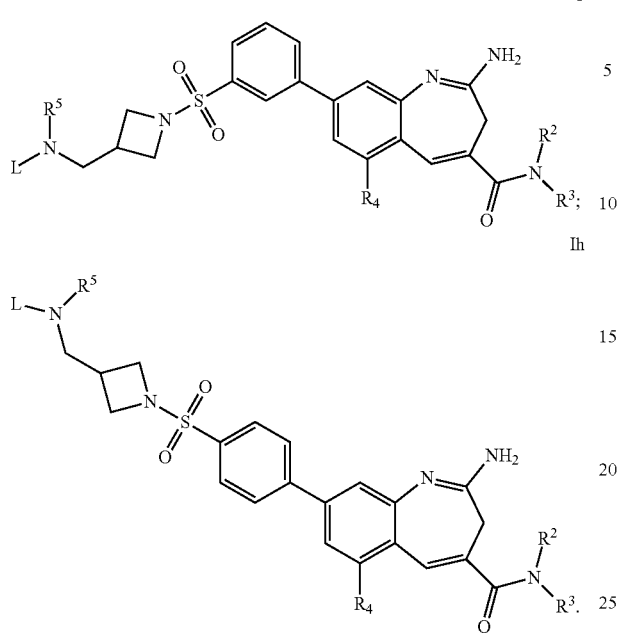

In certain embodiments of the formulas of the disclosure, including Formula I of Category C, L is —C(=O)-(PEG)-C(=O)-(PEP)-.

In certain embodiments of the formulas of the disclosure, including Formula I of Category C, $R^2$ and $R^3$ are each $C_1$-$C_5$ alkyl.

In certain embodiments of the formulas of the disclosure, including Formula I of Category C, $R^2$ and $R^3$ are each —$CH_2CH_2CH_3$.

In certain embodiments of the formulas of the disclosure, including Formula I of Category C, $X^2$ and $X^3$ are each a bond, and $R^2$ or $R^3$ is —O—($C_1$-$C_{12}$ alkyl).

In certain embodiments of the formulas of the disclosure, including Formula I of Category C, $X^2$ and $X^3$ are each a bond, and $R^2$ or $R^3$ is —$OCH_2CH_3$.

In certain embodiments of the formulas of the disclosure, including Formula I of Category C, one of R1 and R4 is selected from: —($C_1$-$C_{12}$ alkyldiyl)-N($R^5$)—*; —($C_1$-$C_{12}$ alkyldiyl)-N($R^5$)C(=N$R^5$)N($R^5$)—*; —($C_6$-$C_{20}$ aryldiyl)-S(=O)$_2$—($C_2$-$C_{20}$ heterocyclyldiyl)-($C_6$-$C_{20}$ aryldiyl)-S(=O)$_2$—($C_2$-$C_{20}$ heterocyclyldiyl)-($C_1$-$C_{12}$ alkyldiyl)-N($R^5$)—*; —($C_6$-$C_{20}$aryldiyl)-C(=O)—*; —($C_6$-$C_{20}$ aryldiyl)-($C_1$-$C_{12}$ alkyldiyl)-N($R^5$)—*; —($C_6$-$C_{20}$ aryldiyl)-C(=O)—($C_2$-$C_{20}$ heterocyclyldiyl)-*; —C(=O)N$R^5$—($C_1$-$C_2$O heteroaryldiyl)-*; and —C(=O)N$R^5$—($C_1$-$C_2$O heteroaryldiyl)-($C_2$-$C_{20}$ heterocyclyldiyl)-C(=O)N$R^5$—($C_1$-$C_{12}$ alkyldiyl)-N$R^5$—*.

In certain embodiments of the formulas of the disclosure, including Formula I of Category C, one of $R^2$ and $R^3$ is selected from: —($C_1$-$C_{12}$ alkyldiyl)-N($R^5$)—*; —($C_1$-$C_{12}$ alkyldiyl)-O—($C_1$-$C_{12}$ alkyldiyl)-N($R^5$)—*; —($C_1$-$C_{12}$ alkyldiyl)-N($R^5$)C(=N$R^5$)—N($R^5$)—*; —($C_1$-$C_{12}$ alkyldiyl)-($C_6$-$C_{20}$ aryldiyl)-($C_1$-$C_{12}$ alkyldiyl)-N($R^5$)—*; —($C_1$-$C_{12}$ alkyldiyl)-($C_6$-$C_{20}$ aryldiyl)-($C_1$-$C_{12}$ alkyldiyl)-N($R^5$)—C(=N$R^5$)N($R^5$)—*; —($C_2$-$C_6$ alkynyldiyl)-N($R^5$)—*; and —($C_2$-$C_6$ alkynyldiyl)-N($R^5$)C(=N$R^5$)N($R^5$)—*; $X^2$ and $X^3$ are a bond, and where the asterisk* indicates the attachment site of L.

In certain embodiments of the formulas of the disclosure, including Formula I of Category C, one of $R^1$ and $R^4$ is selected from —($C_6$-$C_{20}$ aryldiyl)-S(=O)$_2$—($C_2$-$C_{20}$ heterocyclyldiyl)-($C_1$-$C_{12}$ alkyldiyl)-N($R^5$)$_2$ and —($C_6$-$C_{20}$ aryldiyl)-S(=O)$_2$—($C_2$-$C_{20}$ heterocyclyldiyl)-($C_1$-$C_{12}$ alkyldiyl)-OH.

In certain embodiments of the formulas of the disclosure, including Formula I of Category C, $C_6$-$C_{20}$ aryldiyl is phenyldiyl and $C_2$-$C_{20}$ heterocyclyldiyl is azetidindiyl.

In certain embodiments of the formulas of the disclosure, including Formula I of Category C, one of $R^1$ and $R^4$ is selected from the formulas:

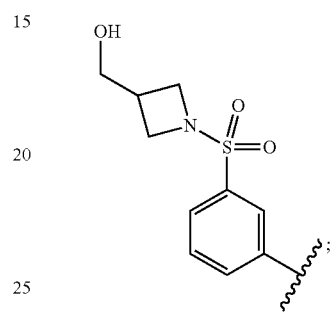

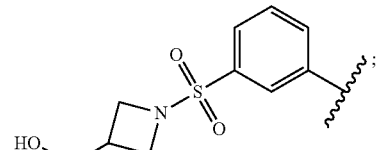

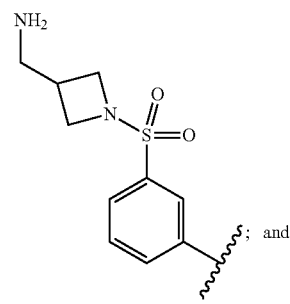

and

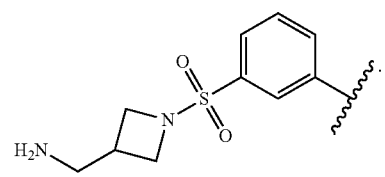

In certain embodiments of the formulas of the disclosure, including Formula I of Category C, one of $R^1$ and $R^4$ is —C(=O)N$R^5$—($C_1$-$C_{20}$ heteroaryldiyl)-($C_2$-$C_{20}$ heterocyclyldiyl)-C(=O)N$R^5$—($C_1$-$C_{12}$ alkyldiyl)-N$R^5$-L.

In certain embodiments of the formulas of the disclosure, including Formula I of Category C, $C_1$-$C_{20}$ heteroaryldiyl is pyridindiyl and $C_2$-$C_{20}$ heterocyclyldiyl is piperidiyl.

In some aspects, the disclosure provides a conjugate comprising a benzazepine according to Formula (II):

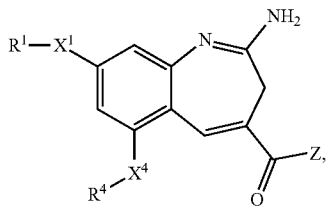

(II)

wherein

Z is selected from H, —O($C_1$-$C_8$ alkyl), and N($X^2R^2$)($X^3R^3$); $R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from: —($C_1$-$C_{12}$ alkyldiyl)-N($R^5$)—*; —($C_1$-$C_{12}$ alkyldiyl)-N($R^5$)$_2$; —($C_3$-$C_{12}$ carbocyclyl); —($C_3$-$C_{12}$ carbocyclyl)-*; —($C_3$-$C_{12}$ carbocyclyl)-($C_1$-$C_{12}$ alkyldiyl)-NR$^5$—*; —($C_3$-$C_{12}$ carbocyclyl)-($C_1$-$C_{12}$ alkyldiyl)-N($R^5$)$_2$; —($C_3$-$C_{12}$ carbocyclyl)-NR$^5$—C(=NR$^5$)NR$^5$—*; —($C_6$-$C_{20}$ aryl); —($C_6$-$C_{20}$ aryl)-*; —($C_6$-$C_{20}$ aryldiyl)-N($R^5$)—*; —($C_6$-$C_{20}$ aryldiyl)-($C_1$-$C_{12}$ alkyldiyl)-N($R^5$)—*; —($C_6$-$C_{20}$ aryldiyl)-($C_1$-$C_{12}$ alkyldiyl)-N($R^5$)$_2$; —($C_6$-$C_{20}$aryldiyl)-($C_1$-$C_{12}$ alkyldiyl)-NR$^5$—C(=NR$^{5a}$)N($R^5$)—*; —($C_2$-$C_{20}$ heterocyclyl); —($C_2$-$C_{20}$ heterocyclyl)-*; —($C_2$-$C_9$ heterocyclyl)-($C_1$-$C_{12}$ alkyldiyl)-NR$^5$—*; —($C_2$-$C_9$ heterocyclyl)-($C_1$-$C_{12}$ alkyldiyl)-N($R^5$)$_2$; —($C_2$-$C_9$ heterocyclyl)-NR$^5$—C(=NR$^{5a}$)NR$^5$—*; —($C_1$-$C_{20}$ heteroaryl); —($C_1$-$C_{20}$ heteroaryl)-*; —($C_1$-$C_{20}$ heteroaryl)-($C_1$-$C_{12}$ alkyldiyl)-N($R^5$)—*; —($C_1$-$C_{20}$ heteroaryl)-($C_1$-$C_{12}$ alkyldiyl)-N($R^5$)$_2$; —($C_1$-$C_{20}$ heteroaryl)-NR$^5$—C(=NR$^{5a}$)N($R^5$)—*; —C(=O)—*; —C(=O)—($C_2$-$C_{20}$ heterocyclyldiyl)-*; —C(=O)N($R^5$)$_2$; —C(=O)N($R^5$)—*; —C(=O)N($R^5$)—($C_1$-$C_{12}$ alkyldiyl)-N($R^5$)C(=O)R$^5$; —C(=O)N($R^5$)—($C_1$-$C_{12}$ alkyldiyl)-N($R^5$)C(=O)N($R^5$)$_2$; —C(=O)NR$^5$—($C_1$-$C_{12}$ alkyldiyl)-N($R^5$)CO$_2$R$^5$; —C(=O)NR$^5$—($C_1$-$C_{12}$ alkyldiyl)-N($R^5$)C(=NR$^{5a}$)N($R^5$)$_2$; —C(=O)NR$^5$—($C_1$-$C_{12}$ alkyldiyl)-NR$^5$C(=NR$^{5a}$a)R$^5$; —C(=O)NR$^5$—($C_1$-$C_8$ alkyldiyl)-NR$^5$ ($C_2$-$C_8$ heteroaryl); —C(=O)NR$^5$—($C_1$-$C_2$O heteroaryldiyl)-N($R^5$)—*; —C(=O)NR$^5$—($C_1$-$C_{20}$ heteroaryldiyl)-*; —C(=O)NR$^5$—($C_1$-$C_2$O heteroaryldiyl)-($C_1$-$C_{12}$ alkyldiyl)-N($R^5$)$_2$; —C(=O)NR$^5$—($C_1$-$C_{20}$ heteroaryldiyl)-($C_2$-$C_{20}$ heterocyclyldiyl)-C(=O)NR$^5$—($C_1$-$C_{12}$ alkydiyl)-NR$^5$; —N($R^5$)$_2$; —N($R^5$)—*; —N($R^5$)C(=O)R$^5$; —N($R^5$)C(=O)—*; —N($R^5$)C(=O)N($R^5$)$_2$; —N($R^5$)C(=O)N($R^5$)—*; —N($R^5$)CO$_2$R$^5$; —NR$^5$C(=NR$^{5a}$)N($R^5$)$_2$; —NR$^5$C(=NR$^{5a}$)N($R^5$)—*; —NR$^5$C(=NR$^{5a}$)R$^5$; —N($R^5$)—($C_2$-$C_8$ heteroaryl); —O—($C_1$-$C_{12}$ alkyl); —O—($C_1$-$C_{12}$ alkyldiyl)-N($R^5$)$_2$; —O—($C_1$-$C_{12}$ alkyldiyl)-N($R^5$)—*; —S(=O)$_2$—($C_2$-$C_{20}$ heterocyclyldiyl)-*; —S(=O)$_2$—($C_2$-$C_{20}$ heterocyclyldiyl)-($C_1$-$C_{12}$ alkyldiyl)-N($R^5$)$_2$; —S(=O)$_2$—($C_2$-$C_{20}$ heterocyclyldiyl)-($C_1$-$C_{12}$ alkyldiyl)-NR$^5$—*; and —S(=O)$_2$—($C_2$-$C_{20}$ heterocyclyldiyl)-($C_1$-$C_{12}$ alkyldiyl)-OH; or $R^2$ and $R^3$ together form a 5- or 6-membered heterocyclyl ring;

$X^1$, $X^2$, $X^3$, and $X^4$ are independently selected from the group consisting of a bond, C(=O), C(=O)N($R^5$), O, N($R^5$), S, S(O)$_2$, and S(O)$_2$N($R^5$);

$R^5$ is selected from the group consisting of H, $C_6$-$C_{20}$ aryl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk* indicates the attachment site of L, and where one of $R^1$, $R^2$, $R^3$ and $R^4$ is attached to L;

L is the linker selected from the group consisting of: Q-C(=O)-(PEG)-; Q-C(=O)-(PEG)-C(=O)—; Q-C(=O)-(PEG)-O—; Q-C(=O)-(PEG)-C(=O)-(PEP)-; Q-C(=O)-(PEG)-C(=O)N($R^5$)—($C_1$-$C_{12}$ alkyldiyl)-; Q-C(=O)-(PEG)-C(=O)N($R^5$)—($C_1$-$C_{12}$ alkyldiyl)-N($R^5$)C(=O)—($C_2$-$C_8$ monoheterocyclyldiyl)-; Q-C(=O)-(PEG)-C(=O)N($R^5$)—($C_1$-$C_{12}$ alkyldiyl)-(MCgluc)-; Q-C(=O)-(PEG)-C(=O)-(MCgluc)-; Q-C(=O)-(PEG)-C(=O)-(PEP)-N($R^5$)—($C_1$-$C_{12}$ alkyldiyl)-; Q-C(=O)-(PEG)-C(=O)-(PEP)-N($R^5$)—($C_1$-$C_{12}$ alkyldiyl)-N($R^5$)C(=O)—($C_2$-$C_8$ monoheterocyclyldiyl)-; Q-C(=O)-(PEG)-N($R^5$)—; Q-C(=O)-(PEG)-N($R^5$)—(PEG)-C(=O)-(PEP)-; Q-C(=O)-(PEG)-N$^+$($R^5$)$_2$-(PEG)-C(=O)-(PEP)-; Q-C(=O)-(PEG)-C(=O)—N($R^5$)CH(AA$_1$)C(=O)-(PEG)-C(=O)-(PEP)-; Q-C(=O)-(PEG)-C(=O)—N($R^5$)CH(AAl)C(=O)—N($R^5$)—($C_1$-$C_{12}$ alkyldiyl)-; Q-C(=O)-(PEG)-SS—($C_1$-$C_{12}$ alkyldiyl)-OC(=O)—; Q-C(=O)-(PEG)-SS—($C_1$-$C_{12}$ alkyldiyl)-C(=O)—; Q-C(=O)—($C_1$-$C_{12}$ alkyldiyl)-C(=O)-(PEP)-; Q-C(=O)—($C_1$-$C_{12}$ alkyldiyl)-C(=O)-(PEP)-N($R^5$)—($C_1$-$C_{12}$ alkyldiyl)-; Q-C(=O)—($C_1$-$C_{12}$ alkyldiyl)-C(=O)-(PEP)-N($R^5$)—($C_1$-$C_{12}$ alkyldiyl)-N($R^5$)—C(=O); Q-C(=O)—($C_1$-$C_{12}$ alkyldiyl)-C(=O)-(PEP)-N($R^5$)—($C_1$-$C_{12}$ alkyldiyl)-N($R^5$)C(=O)($C_2$-$C_5$ monoheterocyclyldiyl)-; Q-C(=O)—CH$_2$CH$_2$OCH$_2$CH$_2$—($C_1$-$C_{20}$ heteroaryldiyl)-CH$_2$O—(PEG)-C(=O)(MCgluc)-; Q-C(=O)—CH$_2$CH$_2$OCH$_2$CH$_2$—($C_1$-$C_2$O heteroaryldiyl)-CH$_2$O—(PEG)-C(=O)(MCgluc)-N($R^5$)—($C_1$-$C_{12}$ alkyldiyl)-N($R^5$)C(=O)—($C_2$-$C_5$ monoheterocyclyldiyl)-; and Q-(CH$_2$)$_m$—C(=O)-(PEP)-N($R^5$)—($C_1$-$C_{12}$ alkyldiyl)-N($R^5$)C(=O)—($C_2$-$C_5$ monoheterocyclyldiyl)-;

where PEG has the formula: —(CH$_2$CH$_2$O)$_n$—(CH$_2$)$_m$—;
m is an integer from 1 to 5, and
n is an integer from 2 to 50;
PEP has the formula:

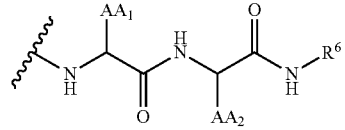

where AA$_1$ and AA$_2$ are independently selected from an amino acid side chain, or
AA$_1$ or AA$_2$ and an adjacent nitrogen atom form a 5-membered ring praline amino acid, and the wavy line indicates a point of attachment and;
$R^6$ is selected from the group consisting of $C_6$-$C_{20}$ aryldiyl and $C_1$-$C_{20}$ heteroaryldiyl, substituted with —CH$_2$O—C(=O)— and optionally with:

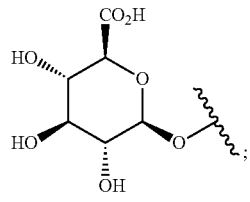 [SMILES: *O[C@@H]1O[C@H](C(=O)O)[C@@H](O)[C@H](O)[C@H]1O]

and

MCgluc is selected from the groups:

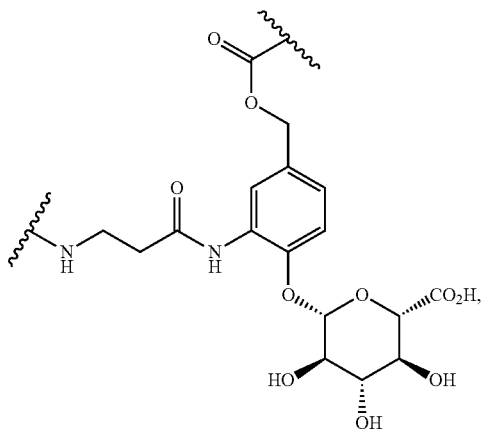

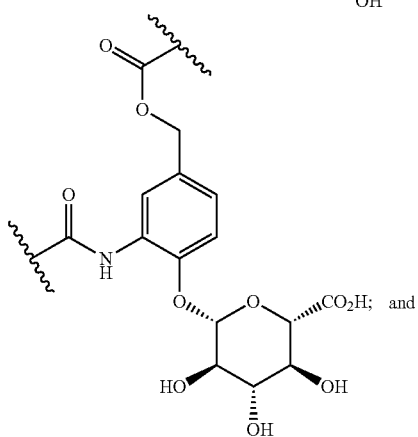

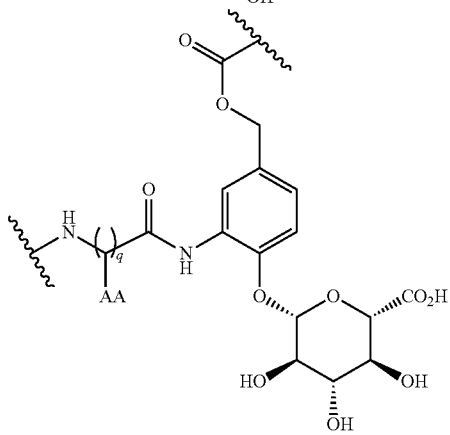

where q is 1 to 8, and AA is an amino acid side chain; and

Q is selected from the group consisting of N-hydroxysuccinimidyl, N-hydroxysulfosuccinimidyl, maleimide, and phenoxy substituted with one or more groups independently selected from F, Cl, $NO_2$, and $SO_3^-$;

where alkyl, alkyldiyl, alkenyl, alkenyldiyl, alkynyl, alkynyldiyl, aryl, aryldiyl carbocyclyl, carbocyclyldiyl, heterocyclyl, heterocyclyldiyl, heteroaryl, and heteroaryldiyl are optionally substituted with one or more groups independently selected from F, Cl, Br, I, —CN, —$CH_3$, —$CH_2CH_3$, —CH=$CH_2$, —C≡CH, —C≡$CCH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —CH2CF3, —$CH_2CHF_2$, —$CH(CH_3)CN$, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —NHC(=NH)H, —NHC(=NH)$CH_3$, —NHC(=NH)$NH_2$, —NHC(=O)$NH_2$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$O(CH_2CH_2O)_n$—$(CH_2)_mCO_2H$, —$O(CH_2CH_2O)_nH$, —$OP(O)(OH)_2$, —$S(O)_2N(CH_3)_2$, —$SCH_3$, —$S(O)_2CH_3$, and —$S(O)_3H$.

In certain embodiments of the formulas of the disclosure, including Formula (II) of Category C, PEP is selected from the groups:

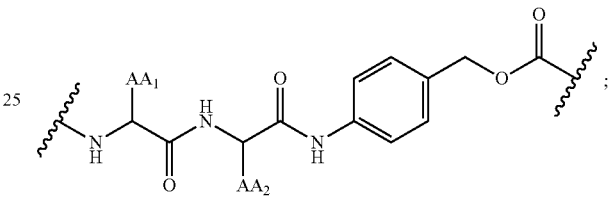

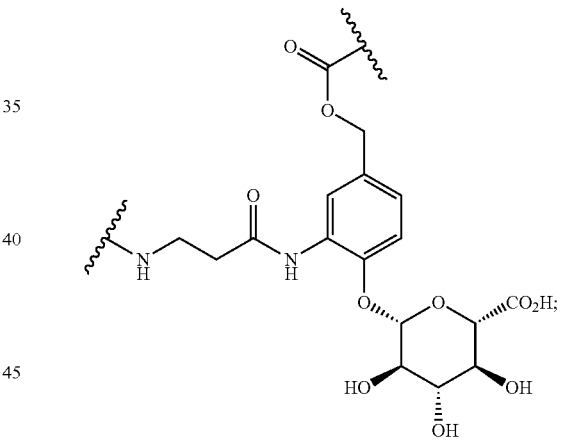

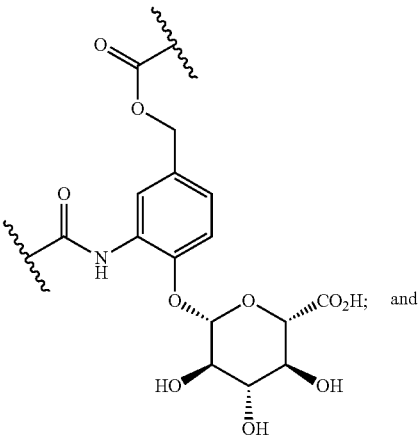

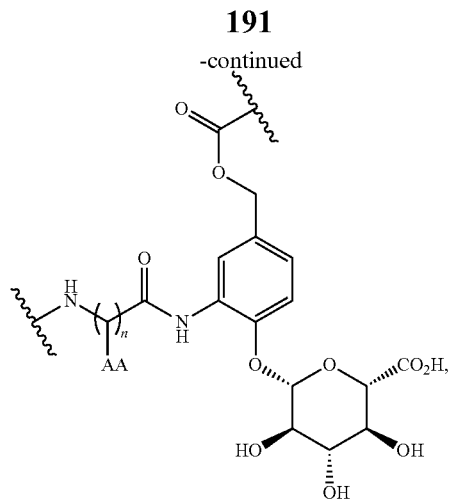

wherein n is 1 or more and AA is an amino acid side chain.

In certain embodiments of the formulas of the disclosure, including Formula (II) of Category C, each $AA_1$ and $AA_2$ are independently selected from a side chain of a naturally-occurring amino acid.

In certain embodiments of the formulas of the disclosure, including Formula (II) of Category C, $AA_1$ and $AA_2$ are independently selected from H, —$CH_3$, —$CH(CH_3)_2$, —$CH_2(C_6H_5)$, —$CH_2CH_2CH_2CH_2NH_2$, —$CH_2CH_2CH_2NHC(NH)NH_2$, —$CH_2CH(CH_3)_2$, —$CH_2SO_3H$, and —$CH_2CH_2CH_2NHC(O)NH_2$.

In certain embodiments of the formulas of the disclosure, including Formula (II) of Category C, each $AA_1$ is —$CH(CH_3)_2$, and $AA_2$ is —$CH_2CH_2CH_2NHC(O)NH_2$.

In certain embodiments of the formulas of the disclosure, including Formula (II) of Category C, each $AA_1$ and $AA_2$ are independently selected from GlcNAc aspartic acid, —$CH_2SO_3H$, and —$CH_2OPO_3H$.

In certain embodiments of the formulas of the disclosure, including Formula II of Category C, the aminobenzazepine-linker compound of Formula (II) is selected from Formulas IIa-IId:

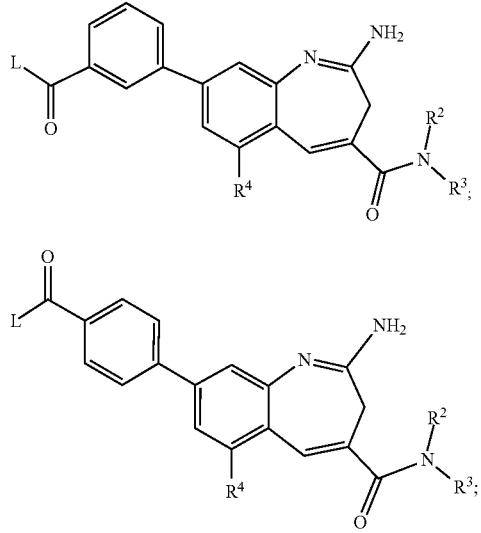

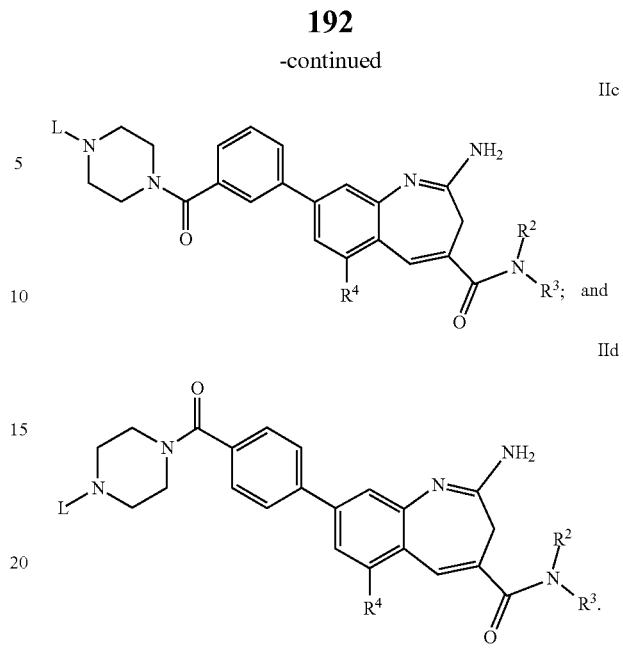

In certain embodiments of the formulas of the disclosure, including Formula II of Category C, the aminobenzazepine-linker compound of Formula (II) is selected from Formulas IIe and IIf:

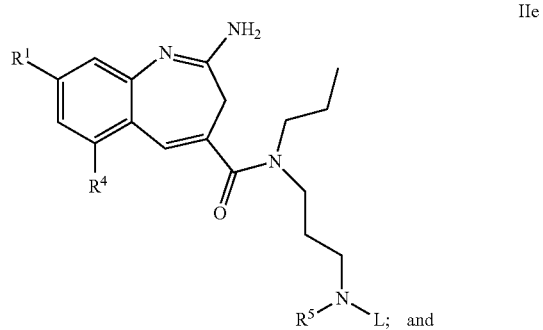

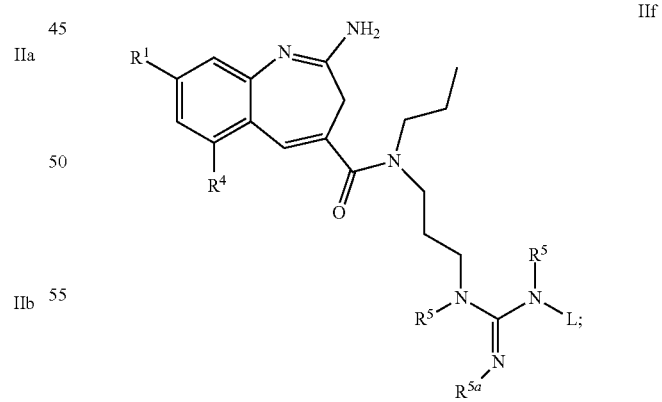

wherein $R^{5a}$ of formula IIf is phenyl, optionally substituted with one or more groups selected from F, Cl, Br, I, —CN, and —$NO_2$.

In certain embodiments of the formulas of the disclosure, including Formula II of Category C, L is Q-C(═O)-(PEG)- or Q-C(═O)-(PEG)-C(═O)—.

In certain embodiments of the formulas of the disclosure, including Formula II of Category C, the aminobenzazepine-linker compound of Formula II is selected from Formulas IIg and IIh:

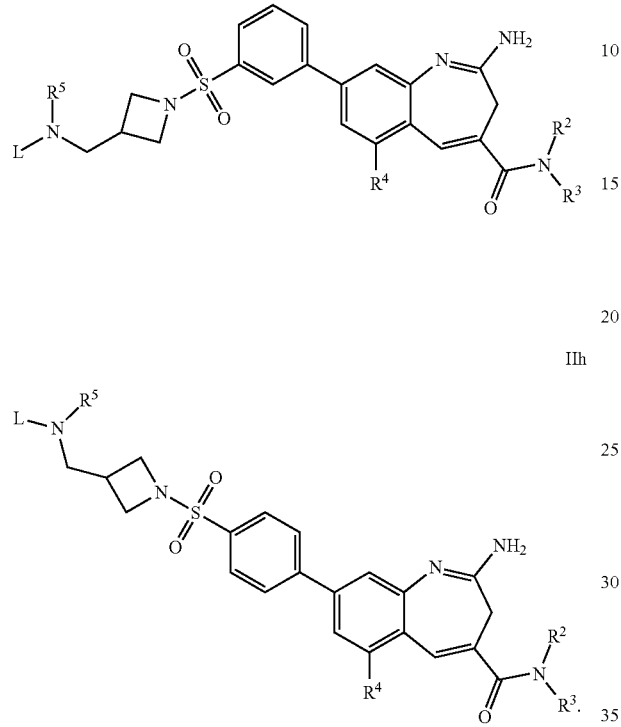

In certain embodiments of the formulas of the disclosure, including Formula II of Category C, L is —C(=O)-(PEG)-C(=O)-(PEP)-.

In certain embodiments of the formulas of the disclosure, including Formula II of Category C, $R^2$ and $R^3$ are each $C_1$-$C_8$ alkyl.

In certain embodiments of the formulas of the disclosure, including Formula II of Category C, $R^2$ and $R^3$ are each —CH$_2$CH$_2$CH$_3$.

In certain embodiments of the formulas of the disclosure, including Formula II of Category C, $X^2$ and $X^3$ are each a bond, and $R^2$ and $R^3$ is —O—($C_1$-$C_{12}$ alkyl).

In certain embodiments of the formulas of the disclosure, including Formula II of Category C, $X^2$ and $X^3$ are each a bond, and $R^2$ and $R^3$ is —OCH$_2$CH$_3$.

In certain embodiments of the formulas of the disclosure, including Formula II of Category C, one of $R^1$ and $R^4$ is selected from —($C_6$-$C_{20}$ aryldiyl)-S(=O)$_2$—($C_2$-$C_{20}$ heterocyclyldiyl)-($C_1$-$C_{12}$ alkyldiyl)-N($R^5$)$_2$ and —($C_6$-$C_{20}$ aryldiyl)-S(=O)$_2$—($C_2$-$C_{20}$ heterocyclyldiyl)-($C_1$-$C_{12}$ alkyldiyl)-OH.

In certain embodiments of the formulas of the disclosure, including Formula II of Category C, $C_6$-$C_{20}$ aryldiyl is phenyldiyl and $C_2$-$C_{20}$ heterocyclyldiyl is azetidindiyl.

In certain embodiments of the formulas of the disclosure, including Formula II of Category C, the aminobenzazepine-linker compound of Formula II is selected from Formulas:

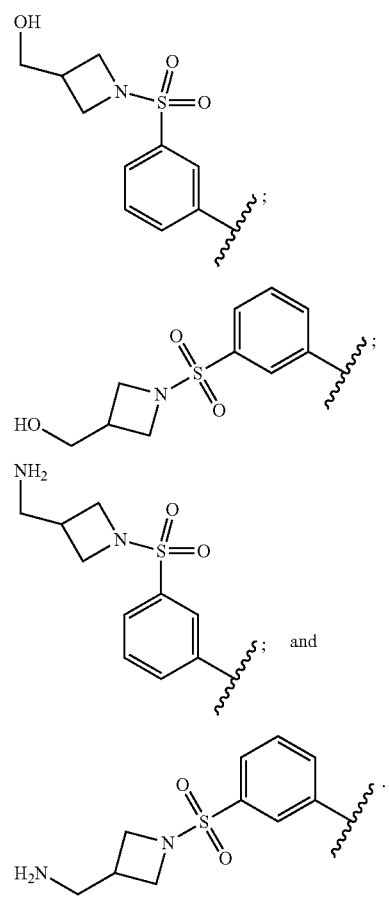

In certain embodiments of the formulas of the disclosure, including Formula II of Category C, one of $R^1$ and $R^4$ is —C(=O)NR$^5$—($C_1$-$C_{20}$ heteroaryldiyl)-($C_2$-$C_{20}$ heterocyclyldiyl)-C(=O)NR$^5$—($C_1$-$C_{12}$ alkyldiyl)-NR$^5$-L.

In certain embodiments of the formulas of the disclosure, including Formula II of Category C, $C_1$-$C_{20}$ heteroaryldiyl is pyridindiyl and $C_2$-$C_{20}$ heterocyclyldiyl is piperidiyl.

In certain embodiments of the formulas of the disclosure, including Formula II of Category C, Q is selected from:

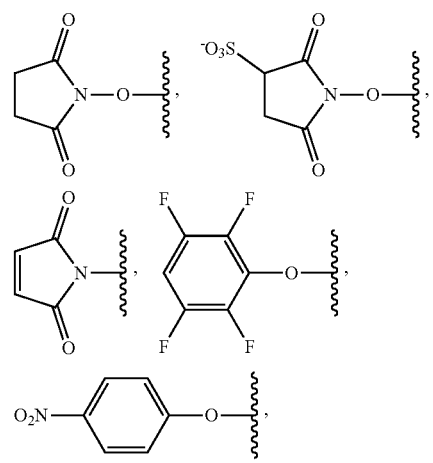

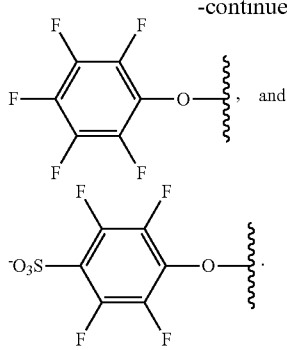, and

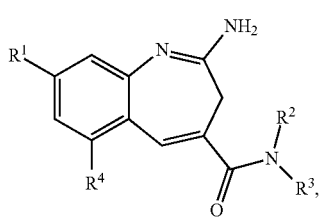

In some aspects, the disclosure provides a conjugate comprising a benzazepine according to Formula III:

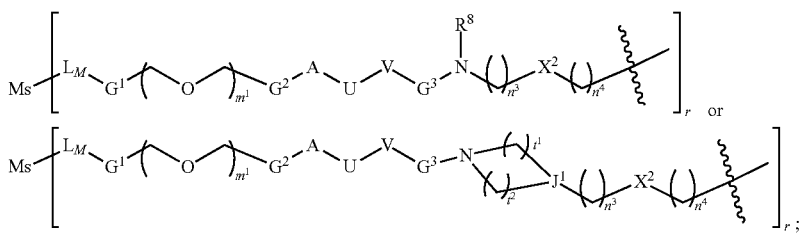

a pharmaceutically acceptable salt thereof, or a quaternary ammonium salt thereof, wherein $R^1$, $R^2$, $R^3$, and $R^4$ are independently Y or Z, wherein one of $R^1$, $R^2$, $R^3$, and $R^4$ is Y, having the formula:

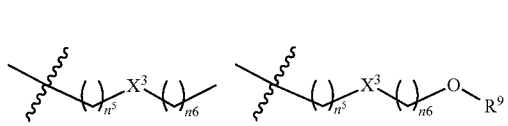

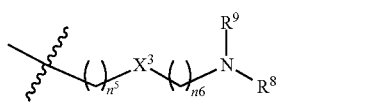

independently is hydrogen or selected from the formulas:

U is optionally present and is $CH_2$, $C(=O)$, $CH_2C(=O)$, or $C(=O)CH_2$,

A is optionally present and is $NR^{10}$ or selected from the formulas:

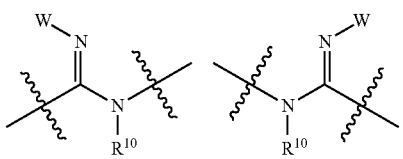

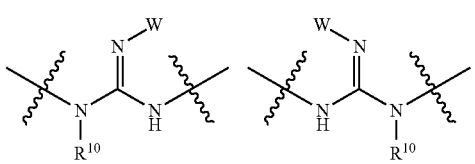

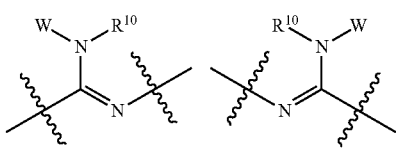

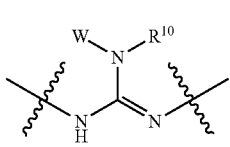

$R^{10}$ and W independently are hydrogen, $Ar^1$, or of formula:

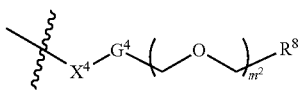

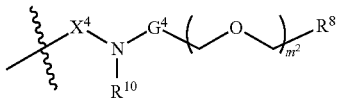

V is optionally present and is of formula:

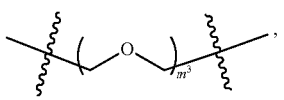

-continued

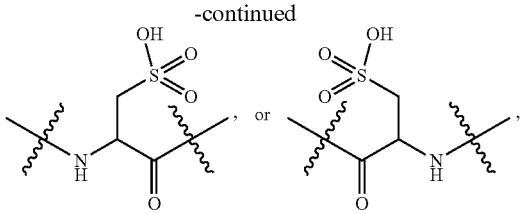

J¹ and J² independently are CH or N, m¹, m², and m³ independently are an integer from 0 to 25, except that at least one of m¹, m², and m³ is a non-zero integer, n¹, n², n³, n⁴, n⁵, and n⁶ independently are an integer from 0 to 10, t₁ and t₂ independently are an integer from 1 to 3, G₁, G₂, G₃, and G₄ independently are CH₂, C(=O), CH₂C(=O), C(=O)CH₂, or a bond, X¹, X², X³, and X⁴ are each optionally present and independently are O, NR⁷, CHR⁷, SO₂, S, or one or two cycloalkyldiyl, heterocycloalkyldiyl, aryldiyl, or heteroaryldiyl groups, and when more than one cycloalkyldiyl, heterocycloalkyldiyl, aryldiyl, or heteroaryldiyl group is present, the more than one cycloalkyldiyl, heterocycloalkyldiyl, aryldiyl, or heteroaryldiyl groups are linked or fused, wherein linked cycloalkyldiyl, heterocycloalkyldiyl, aryldiyl, or heteroaryldiyl groups are linked through a bond or —CO—, R⁹ is hydrogen, C₁-C₄ alkyl, or selected from the formulas:

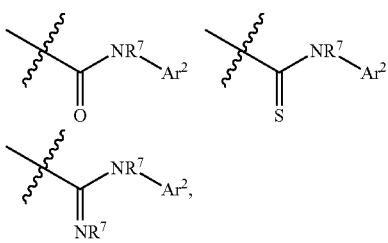

R⁸ is independently hydrogen or C₁-C₄ alkyl,

Ar¹ and Ar² independently are an aryl or heteroaryl group, optionally substituted with one or more halogens (e.g., fluorine, chlorine, bromine, or iodine), nitriles, hydroxyls, C₁-C₄ alkyl groups, or a combination thereof, L_M is a linking moiety that comprises a functional group selected from an amide, amine, ester, carbamate, urea, thioether, thiocarbamate, thiocarbonate, and thiourea, r is an integer from 1 to 50, "Ms" is a macromolecular support, and each wavy line (~) represents a point of attachment.

Nonlimiting examples of TLR8 agonist compounds of Category C are provided in Table 1b.

TABLE 1b

Compounds 1.70-1.74

| Compound | Structure |
|---|---|
| 1.70 | 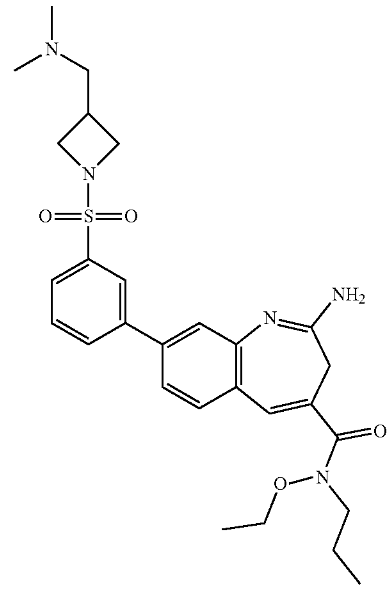 [SMILES: CCCN(OCC)C(=O)C1=Cc2ccc(-c3cccc(S(=O)(=O)N4CC(CN(C)C)C4)c3)cc2N=C(N)C1] |
| 1.71 | 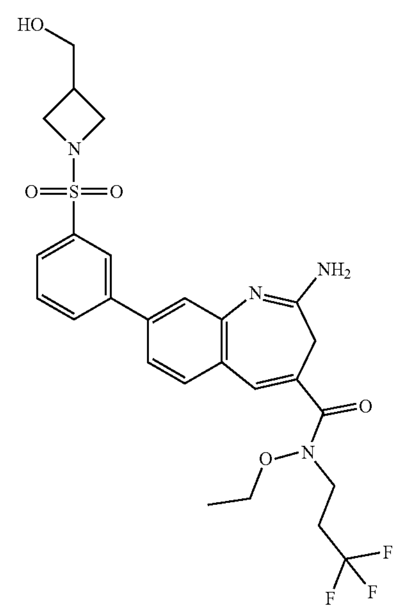 [SMILES: CCON(CCC(F)(F)F)C(=O)C1=Cc2ccc(-c3cccc(S(=O)(=O)N4CC(CO)C4)c3)cc2N=C(N)C1] |

TABLE 1b-continued

Compounds 1.70-1.74

| Compound | Structure |
|---|---|
| 1.72 | 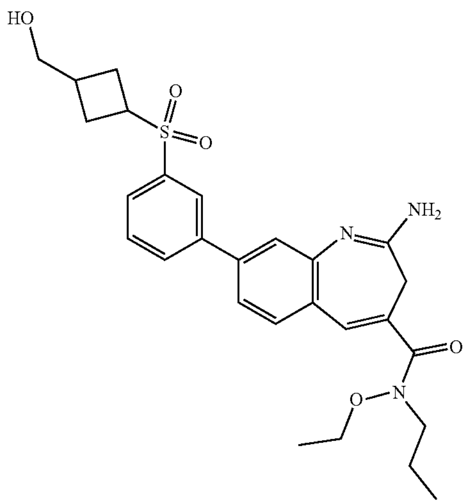 [SMILES: CCCN(OCC)C(=O)C1=Cc2ccc(-c3cccc(S(=O)(=O)C4CC(CO)C4)c3)cc2N=C(N)C1] |
| 1.73 | 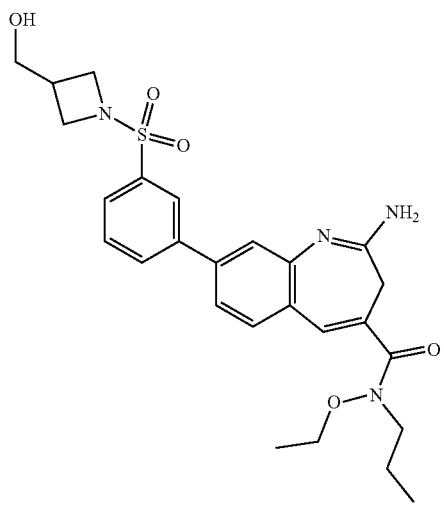 [SMILES: CCCN(OCC)C(=O)C1=Cc2ccc(-c3cccc(S(=O)(=O)N4CC(CO)C4)c3)cc2N=C(N)C1] |
| 1.74 | |

Linkers

The conjugates include a linker(s) that attaches an anti-Nectin-4 antibody or antigen-binding fragment thereof to at least one immune-stimulatory compound, such as a myeloid cell agonist. A linker can be, for example, a cleavable or a non-cleavable linker. A conjugate can comprise multiple linkers. The linkers in a conjugate can be the same linkers or different linkers.

As will be appreciated by skilled artisans, a linker connects an immune-stimulatory compound(s), such as a myeloid cell agonist, to the antibody or antigen-binding fragment thereof by forming a covalent linkage to the compound at one location and a covalent linkage to the antibody or antigen-binding fragment thereof at another location. The covalent linkages can be formed by reaction between functional groups on the linker and functional groups on the immune-stimulatory compound and on the antibody or antigen-binding fragment thereof. As used herein, the expression "linker" can include (i) unattached forms of the linker that can include a functional group capable of covalently attaching the linker to an immune-stimulatory compound and a functional group capable of covalently attached the linker to an antibody or antigen-binding fragment thereof; (ii) partially attached forms of the linker that can include a functional group capable of covalently attaching the linker to an antibody or antigen-binding fragment thereof and that can be covalently attached to an immune-stimulatory compound, or vice versa; and (iii) fully attached forms of the linker that can be covalently attached to both an immune stimulatory compound and to an antibody or antigen-binding fragment thereof. In some specific embodiments, the functional groups on a linker and covalent linkages formed between the linker and an antibody or antigen-binding fragment thereof can be specifically illustrated as Rx and Rx', respectively.

A linker can be short or long, and cleavable or non-cleavable. A linker can contain segments that have different characteristics, such as segments of flexibility or segments of rigidity, segments of hydrophilicity, and/or segments of hydrophobicity. A linker can be chemically stable to extracellular environments, for example, chemically stable in the blood stream, and/or may include linkages that are not stable. A linker can include linkages that are designed to cleave and/or immolate or otherwise breakdown specifically or non-specifically inside cells. A cleavable linker can be sensitive to enzymes at a specific site, such as the lysosome or the extracellar space adjacent cancer cells.

A cleavable linker can include a valine-citrulline peptide, a valine-alanine peptide, a phenylalanine-lysine or other peptide, such as a peptide that forms a protease recognition and cleavage site. Such a peptide-containing linker can contain a pentafluorophenyl group. A peptide-containing linker can include a succimide or a maleimide group. A peptide-containing linker can include a para aminobenzoic acid (PABA) group. A peptide-containing linker can include an aminobenzyloxycarbonyl (PABC) group. A peptide-containing linker can include a PABA or PABC group and a pentafluorophenyl group. A peptide-containing linker can include a PABA or PABC group and a succinimide group. A peptide-containing linker can include a PABA or PABC group and a maleimide group.

A non-cleavable linker is generally protease-insensitive and insensitive to intracellular processes. A non-cleavable linker can include a maleimide group. A non-cleavable linker can include a succinimide group. A non-cleavable linker can be maleimido-alkyl-C(O)— linker. A non-cleavable linker can be maleimidocaproyl linker. A maleimidocaproyl linker can be N-maleimidomethylcyclohexane-1-carboxylate. A maleimidocaproyl linker can include a succinimide group. A maleimidocaproyl linker can include pentafluorophenyl group.

A linker can be a combination of a maleimidocaproyl group and one or more polyethylene glycol molecules. A linker can be a maleimide-PEG4 linker. A linker can be a combination of a maleimidocaproyl linker containing a succinimide group and one or more polyethylene glycol molecules. A linker can be a combination of a maleimidocaproyl linker containing a pentafluorophenyl group and one or more polyethylene glycol molecules. A linker can contain a maleimide(s) linked to polyethylene glycol molecules in which the polyethylene glycol can allow for more linker flexibility or can be used lengthen the linker.

A linker can be a (maleimidocaproyl)-(valine-alanine)-(para-aminobenzyloxycarbonyl) linker. A linker can be a (maleimidocaproyl)-(valine-citrulline)-(para-aminobenzyloxycarbonyl) linker. A linker can be a (maleimidocaproyl)-(phenylalanine-lysine)-(para-aminobenzyloxycarbonyl) linker.

A linker can also contain segments of alkylene, alkenylene, alkynylene, polyether, polyester, polyamide, polyamino acids, peptides, polypeptides, cleavable peptides, and/or aminobenzyl-carbamates. A linker can contain a maleimide at one end and an N-hydroxysuccinimidyl ester at the other end. A linker can contain a lysine with an N-terminal amine acetylated, and a valine-citrulline, valine-alanine or phenylalanine-lysine cleavage site. A linker can be a link created by a microbial transglutaminase, wherein the link can be created between an amine-containing moiety and a moiety engineered to contain glutamine as a result of the enzyme catalyzing a bond formation between the acyl group of a glutamine side chain and the primary amine of a lysine chain. A linker can contain a reactive primary amine. A linker can be a Sortase A linker. A Sortase A linker can be created by a Sortase A enzyme fusing an LXPTG recognition motif (SEQ ID NO:32) to an N-terminal GGG motif to regenerate a native amide bond. The linker created can therefore link to a moiety attached to the LXPTG recognition motif (SEQ ID NO:32) with a moiety attached to the N-terminal GGG motif. A linker can be a link created between an unnatural amino acid on one moiety reacting with oxime bond that was formed by modifying a ketone group with an alkoxyamine on another moiety. A moiety can be part of a conjugate. A moiety can be part of an antibody, such as an antibody. A moiety can be part of an immune-stimulatory compound, such as a myeloid cell agonist. A moiety can be part of a binding domain. A linker can be unsubstituted or substituted, for example, with a substituent. A substituent can include, for example, hydroxyl groups, amino groups, nitro groups, cyano groups, azido groups, carboxyl groups, carboxaldehyde groups, imine groups, alkyl groups, alkenyl groups, alkynyl groups, alkoxy groups, acyl groups, acyloxy groups, amide groups, and ester groups.

A linker can be polyvalent such that it covalently links more than one immune-stimulatory compound to a single site on the antibody or antigen-binding fragment thereof, or monovalent such that it covalently links a single immune-stimulatory compound to a single site on the antibody or antigen-binding fragment thereof.

Exemplary polyvalent linkers that may be used to attach many immune-stimulatory compounds to an antibody or antigen-binding fragment thereof of the conjugate are described. For example, Fleximer® linker technology has the potential to enable high-DAR conjugate with good physicochemical properties. As shown below, the Fleximer® linker technology is based on incorporating molecules into a solubilizing poly-acetal backbone via a sequence of ester bonds. The methodology renders highly-loaded conjugates (DAR up to 20) whilst maintaining good physicochemical properties.

This methodology can be utilized with an immune-stimulatory compound as shown in the scheme below, where Drug' refers to the immune-stimulatory compound.

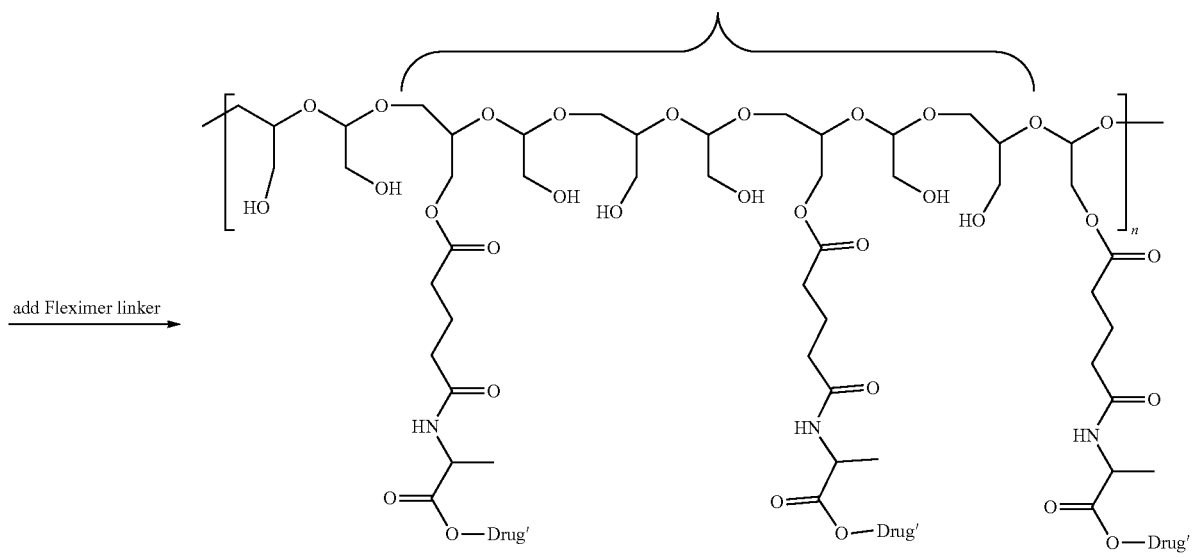

add Fleximer linker →

To utilize the Fleximer® linker technology depicted in the scheme above, an aliphatic alcohol can be present or introduced into the immune-stimulatory compound. The alcohol moiety is then attached to an alanine moiety, which is then synthetically incorporated into the Fleximer® linker. Liposomal processing of the conjugate in vitro releases the parent alcohol-containing drug.

By way of example and not limitation, some cleavable and noncleavable linkers that may be included in the conjugates described herein are described below.

Cleavable linkers can be cleavable in vitro and in vivo. Cleavable linkers can include chemically or enzymatically unstable or degradable linkages. Cleavable linkers can rely on processes inside the cell to liberate an immune-stimulatory compound, such as reduction in the cytoplasm, exposure to acidic conditions in the lysosome, or cleavage by specific proteases or other enzymes within the cell. Cleavable linkers can incorporate one or more chemical bonds that are chemically or enzymatically cleavable while the remainder of the linker can be non-cleavable.

A linker can contain a chemically labile group such as hydrazone and/or disulfide group. Linkers comprising chemically labile groups can exploit differential properties between the plasma and some cytoplasmic compartments. The intracellular conditions that can facilitate immune-stimulatory compound release for hydrazine-containing linkers can be the acidic environment of endosomes and lysosomes, while disulfide-containing linkers can be reduced in the cytosol, which can contain high thiol concentrations, e.g., glutathione. The plasma stability of a linker containing a chemically labile group can be increased by introducing steric hindrance using substituents near the chemically labile group.

Acid-labile groups, such as hydrazones, can remain intact during systemic circulation in the blood's neutral pH environment (pH 7.3-7.5) and can undergo hydrolysis and can release an immune-stimulatory compound once the conjugate is internalized into mildly acidic endosomal (pH 5.0-6.5) and lysosomal (pH 4.5-5.0) compartments of the cell. This pH dependent release mechanism can be associated with nonspecific release of the immune-stimulatory compound. To increase the stability of the hydrazone group of the linker, the linker can be varied by chemical modification, e.g., substitution, allowing tuning to achieve more efficient release in the lysosome with a minimized loss in circulation.

Hydrazone-containing linkers can contain additional cleavage sites, such as additional acid-labile cleavage sites and/or enzymatically labile cleavage sites. Conjugates including exemplary hydrazone-containing linkers can include, for example, the following structures:

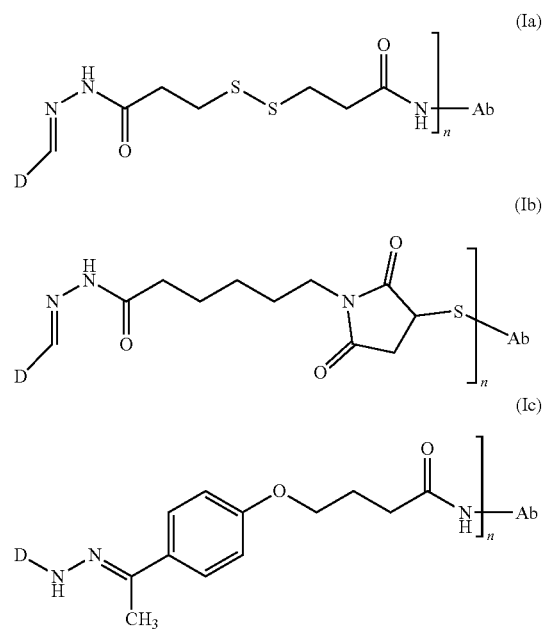

wherein D is an immune-stimulatory compound and Ab is an antibody or antigen-binding fragment thereof, respectively, and n represents the number of compound-bound linkers (LP) bound to the antibody or antigen-binding fragment thereof. In certain linkers, such as linker (Ia), the linker can comprise two cleavable groups, a disulfide and a hydrazone moiety. For such linkers, effective release of the unmodified free immune-stimulatory compound can require acidic pH or disulfide reduction and acidic pH. Linkers such as (Ib) and (Ic) can be effective with a single hydrazone cleavage site.

Other acid-labile groups that can be included in linkers include cis-aconityl-containing linkers. cis-Aconityl chemistry can use a carboxylic acid juxtaposed to an amide bond to accelerate amide hydrolysis under acidic conditions.

Cleavable linkers can also include a disulfide group. Disulfides can be thermodynamically stable at physiological pH and can be designed to release an immune-stimulatory compound upon internalization inside cells, wherein the cytosol can provide a significantly more reducing environment compared to the extracellular environment. Scission of disulfide bonds can require the presence of a cytoplasmic thiol cofactor, such as (reduced) glutathione (GSH), such that disulfide-containing linkers can be reasonably stable in circulation, selectively releasing the immune-stimulatory compound in the cytosol. The intracellular enzyme protein disulfide isomerase, or similar enzymes capable of cleaving disulfide bonds, can also contribute to the preferential cleavage of disulfide bonds inside cells. GSH can be present in cells in the concentration range of 0.5-10 mM compared with a significantly lower concentration of GSH or cysteine, the most abundant low-molecular weight thiol, in circulation at approximately 5 µM. Tumor cells, where irregular blood flow can lead to a hypoxic state, can result in enhanced activity of reductive enzymes and therefore even higher glutathione concentrations. The in vivo stability of a disulfide-containing linker can be enhanced by chemical modification of the linker, e.g., use of steric hindrance adjacent to the disulfide bond.

Immune-stimulatory conjugates including disulfide-containing linkers can include the following structures:

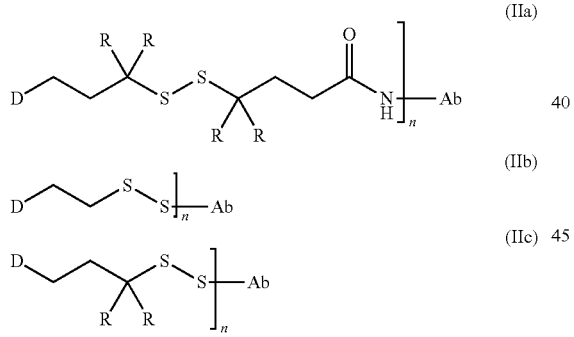

wherein D is an immune-stimulatory compound and Ab is an antibody or antigen-binding fragment thereof, respectively, n represents the number of compounds bound to linkers bound to the antibody or antigen-binding fragment thereof and R is independently selected at each occurrence from hydrogen or alkyl, for example. Increasing steric hindrance adjacent to the disulfide bond can increase the stability of the linker. Structures such as (IIa) and (IIe) can show increased in vivo stability when one or more R groups is selected from a lower alkyl such as methyl.

Another type of linker that can be used is a linker that is specifically cleaved by an enzyme. For example, the linker can be cleaved by a lysosomal enzyme. Such linkers can be peptide-based or can include peptidic regions that can act as substrates for enzymes. Peptide based linkers can be more stable in plasma and extracellular milieu than chemically labile linkers.

Peptide bonds can have good serum stability, as lysosomal proteolytic enzymes can have very low activity in blood due to endogenous inhibitors and the unfavorable pH value of blood compared to lysosomes. Release of an immune-stimulatory compound from an antibody or antigen-binding fragment thereof can occur due to the action of lysosomal proteases, e.g., cathepsin and plasmin. These proteases can be present at elevated levels in certain tumor tissues. A linker can be cleavable by a lysosomal enzyme. The lysosomal enzyme can be, for example, cathepsin B, cathepsin S, β-glucuronidase, or β-galactosidase.

The cleavable peptide can be selected from tetrapeptides such as Gly-Phe-Leu-Gly, Ala-Leu-Ala-Leu, dipeptides such as Val-Cit, Val-Ala, and Phe-Lys, or other peptides. Dipeptides can have lower hydrophobicity compared to longer peptides, depending on the composition of the peptide.

A variety of dipeptide-based cleavable linkers can be used in the immune-stimulatory conjugates described herein.

Enzymatically cleavable linkers can include a self-immolative spacer to spatially separate the immune-stimulatory compound from the site of enzymatic cleavage. The direct attachment of an immune-stimulatory compound to a peptide linker can result in proteolytic release of the immune-stimulatory compound or of an amino acid adduct of the immune-stimulatory compound, thereby impairing its activity. The use of a self-immolative spacer can allow for the elimination of the fully active, chemically unmodified immune-stimulatory compound upon amide bond hydrolysis.

One self-immolative spacer can be a bifunctional para-aminobenzyl alcohol group (PABA), which can link to the peptide through the amino group, forming an amide bond, while amine containing immune-stimulatory compounds can be attached through carbamate functionalities to the benzylic hydroxyl group of the linker (to give a p-amidobenzylcarbamate, PABC). The resulting pro-immune-stimulatory compound can be activated upon protease-mediated cleavage, leading to a 1,6-elimination reaction releasing the unmodified immune-stimulatory compound, carbon dioxide, and remnants of the linker. The following scheme depicts the fragmentation of p-amidobenzyl carbamate and release of the immune-stimulatory compound:

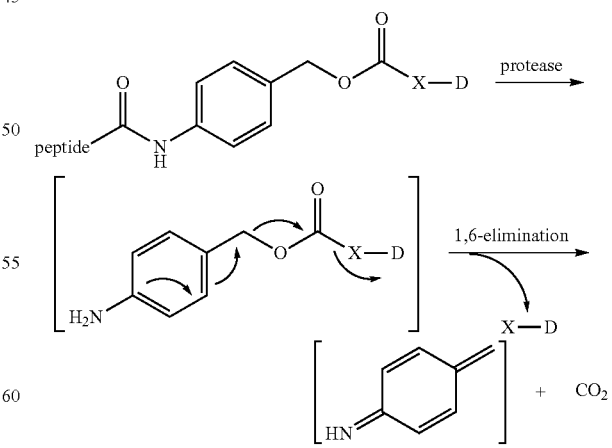

wherein X-D represents the unmodified immune-stimulatory compound and the carbonyl group adjacent "peptide" is part of the peptide. Heterocyclic variants of this self-immolative group have also been described.

An enzymatically cleavable linker can be a ß-glucuronic acid-based linker. Facile release of an immune-stimulatory compound can be realized through cleavage of the ß-glucuronide glycosidic bond by the lysosomal enzyme ß-glucuronidase. This enzyme can be abundantly present within lysosomes and can be overexpressed in some tumor types, while the enzyme activity outside cells can be low. ß-Glucuronic acid-based linkers can be used to circumvent the tendency of an immune-stimulatory conjugate to undergo aggregation due to the hydrophilic nature of ß-glucuronides. In certain embodiments, ß-glucuronic acid-based linkers can link an antibody or antigen-binding fragment thereof to a hydrophobic immune-stimulatory compound. The following scheme depicts the release of an immune-stimulatory compound (D) from an immune-stimulatory conjugate containing a β-glucuronic acid-based linker shown below, wherein Ab indicates the antibody or antigen-binding fragment thereof.

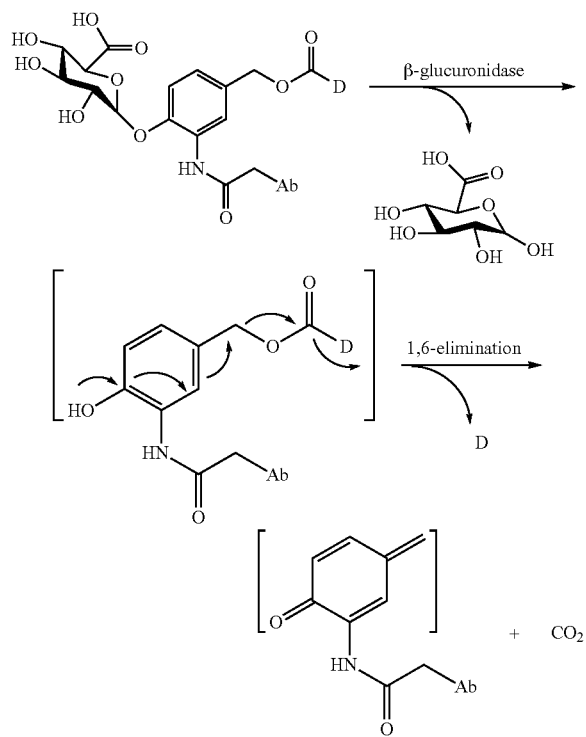

A variety of cleavable ß-glucuronic acid-based linkers useful for linking drugs such as auristatins, camptothecin and doxorubicin analogues, CBI minor-groove binders, and psymberin to antibodies have been described. These ß-glucuronic acid-based linkers may be used in the conjugates described herein. In certain embodiments, the enzymatically cleavable linker is a ß-galactoside-based linker. ß-Galactoside is present abundantly within lysosomes, while the enzyme activity outside cells is low.

Additionally, immune-stimulatory compounds containing a phenol group can be covalently bonded to a linker through the phenolic oxygen. One such linker relies on a methodology in which a diamino-ethane "Space Link" is used in conjunction with traditional "PABO"-based self-immolative groups to deliver phenols.

Cleavable linkers can include non-cleavable portions or segments, and/or cleavable segments or portions can be included in an otherwise non-cleavable linker to render it cleavable. By way of example only, polyethylene glycol (PEG) and related polymers can include cleavable groups in the polymer backbone. For example, a polyethylene glycol or polymer linker can include one or more cleavable groups such as a disulfide, a hydrazone or a dipeptide.

Other degradable linkages that can be included in linkers can include ester linkages formed by the reaction of PEG carboxylic acids or activated PEG carboxylic acids with alcohol groups on an immune-stimulatory compound, wherein such ester groups can hydrolyze under physiological conditions to release the immune-stimulatory compound. Hydrolytically degradable linkages can include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

A linker can contain an enzymatically cleavable peptide moiety, for example, a linker comprising structural formula (IIIa), (IIIb), (IIIc), or (IIId):

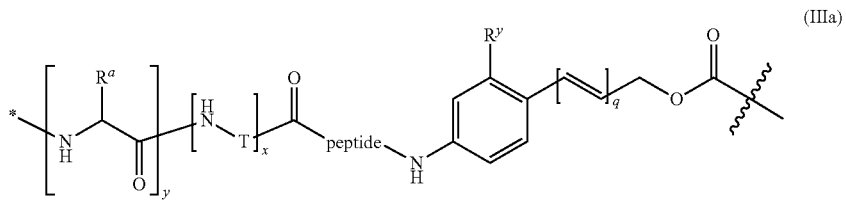

(IIIa)

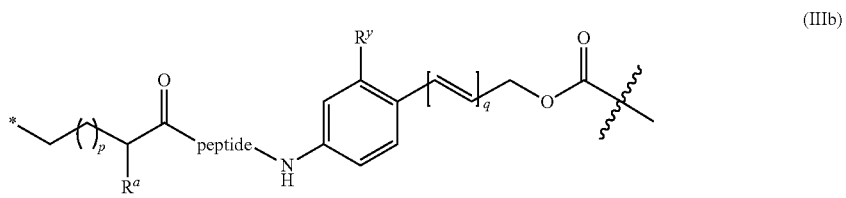

(IIIb)

-continued (IIIc)
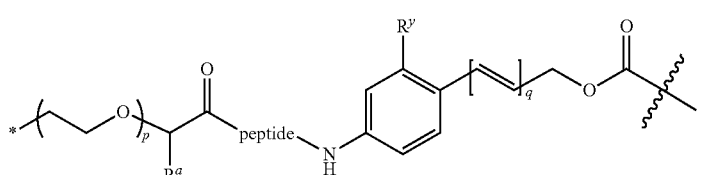

(IIId)
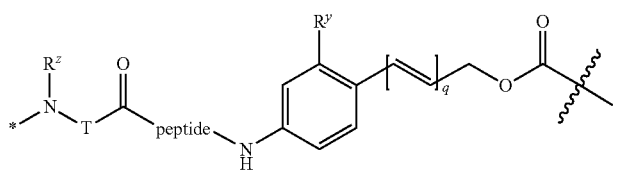

or a pharmaceutically acceptable salt thereof, wherein: "peptide" represents a peptide (illustrated in N→C orientation, wherein peptide includes the amino and carboxy "termini") that is cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; $R^y$ is hydrogen or $C_{1-4}$ alkyl-$(O)_r$—$(C_{1-4}$ alkylene$)_s$-$G^1$ or $C_{1-4}$ alkyl-(N)—[($C_{1-4}$ alkylene)-$G^1$]$_2$; $R^z$ is $C_{1-4}$ alkyl-$(O)_r$—$(C_{1-4}$ alkylene$)_s$-$G^2$; $G^1$ is $SO_3H$, $CO_2H$, PEG 4-32, or a sugar moiety; $G^2$ is $SO_3H$, $CO_2H$, or a PEG 4-32 moiety; r is 0 or 1; s is 0 or 1; p is an integer ranging from 0 to 5; q is 0 or 1; x is 0 or 1; y is 0 or 1; ⌇ represents the point of attachment of the linker to an immune-stimulatory compound; and * represents the point of attachment to the remainder of the linker.

In certain embodiments, the peptide can be selected from natural amino acids, unnatural amino acids or combinations thereof. In certain embodiments, the peptide can be selected from a tripeptide or a dipeptide. In particular embodiments, the dipeptide can comprise L-amino acids and be selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Lys-Phe; Val-Lys; Lys-Val; Ala-Lys; Lys-Ala; Phe-Cit; Cit-Phe; Leu-Cit; Cit-Leu; Ile-Cit; Cit-Ile; Phe-Arg; Arg-Phe; Cit-Trp; and Trp-Cit, or salts thereof.

Exemplary embodiments of linkers according to structural formula (IIIa) are illustrated below (as illustrated, the linkers include a reactive group suitable for covalently linking the linker to an antibody or antigen-binding fragment thereof):

(IIIa.1)
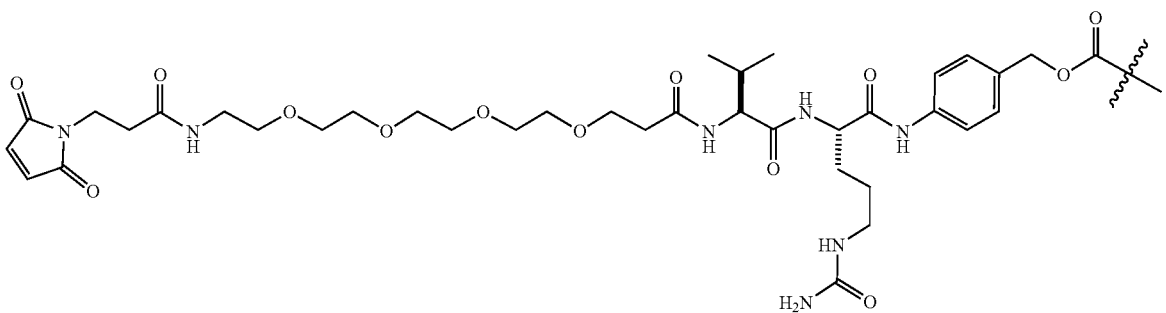

(IIIa.2)
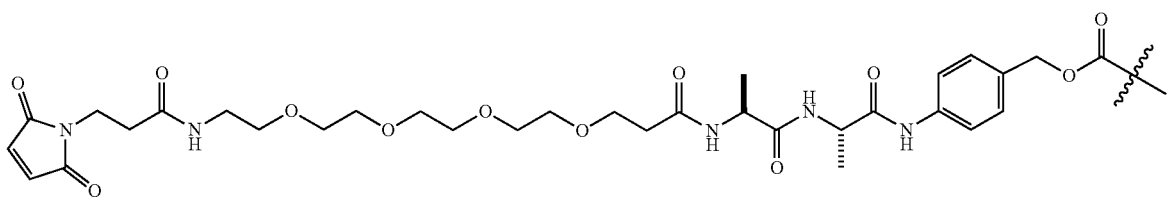

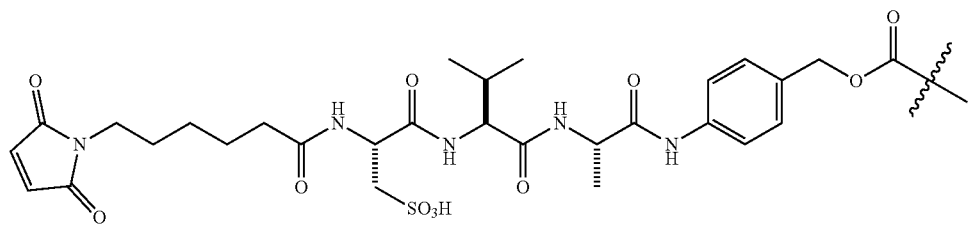
(IIIa.3)
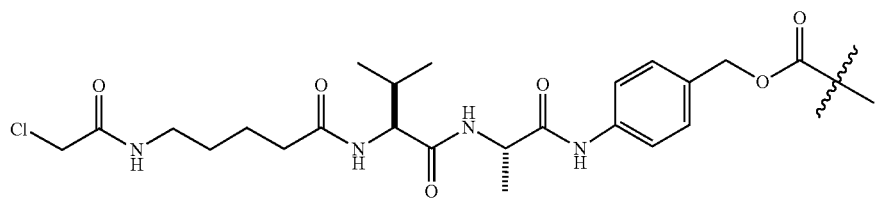
(IIIa.4)
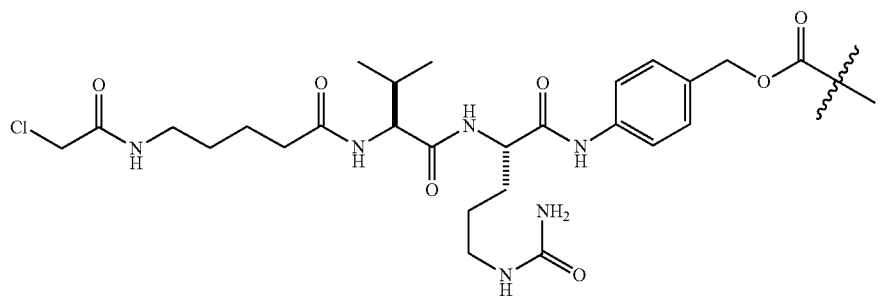
(IIIa.5)
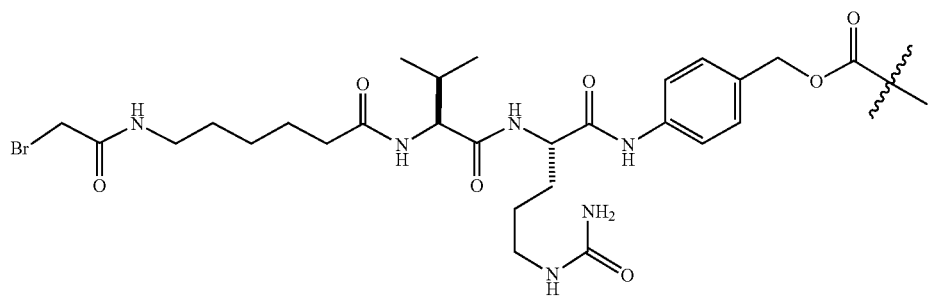
(IIIa.6)
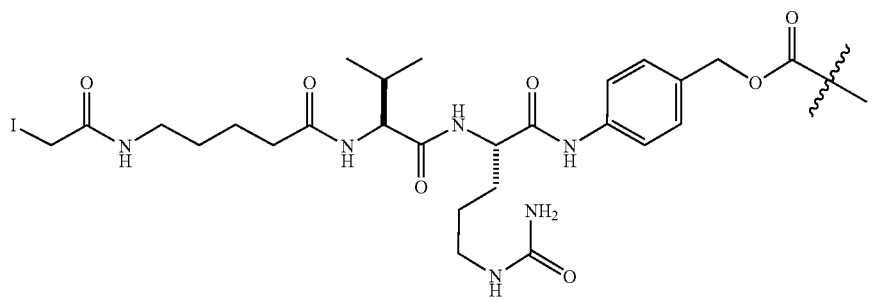
(IIIa.7)

(IIIa.8)

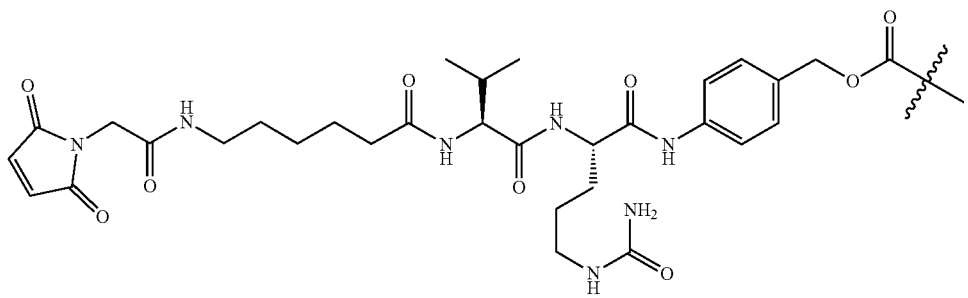

wherein ⌇ indicates an attachment site of a linker to an immune-stimulatory compound.

Exemplary embodiments of linkers according to structural formula (IIIb), (IIIc), or (IIId) that can be included in the conjugates described herein can include the linkers illustrated below (as illustrated, the linkers can include a reactive group suitable for covalently linking the linker to an antibody or antigen-binding fragment thereof):

(IIIb.1)

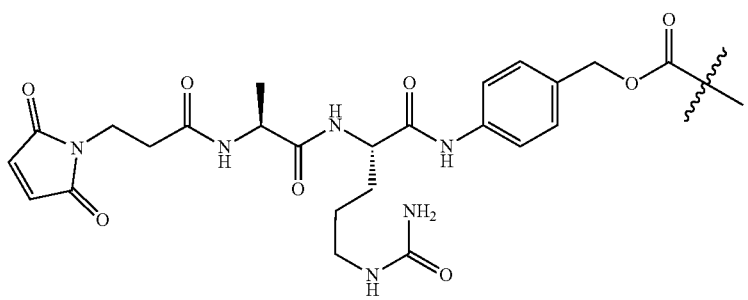

(IIIb.2)

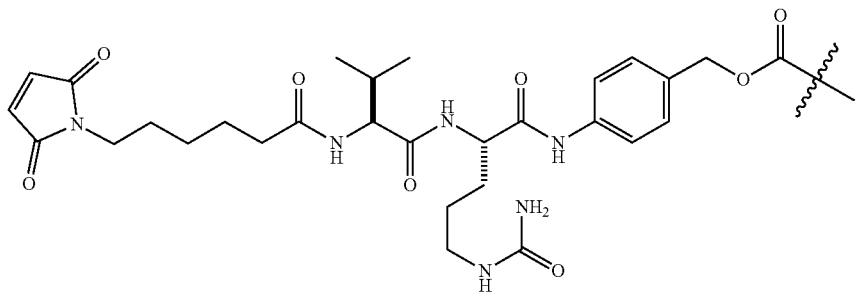

(IIIb.3)

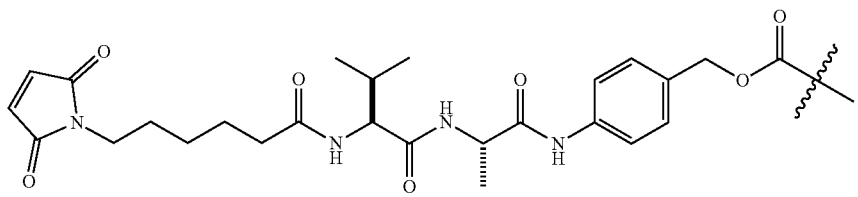

(IIIb.4)

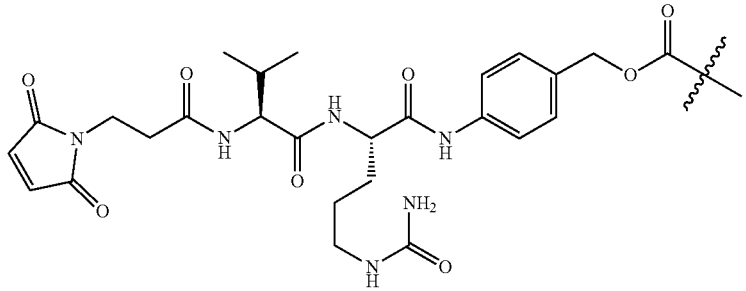

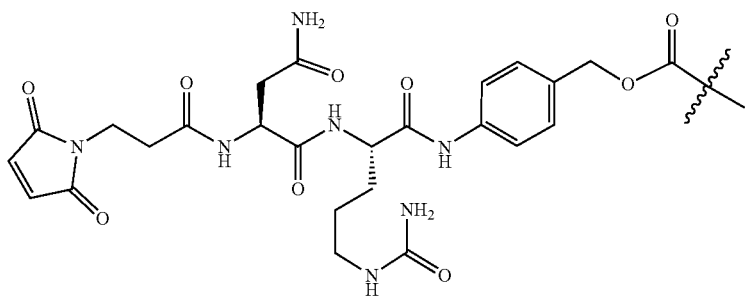
(IIIb.5)
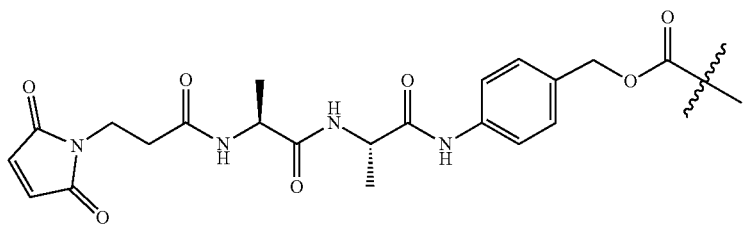
(IIIb.6)
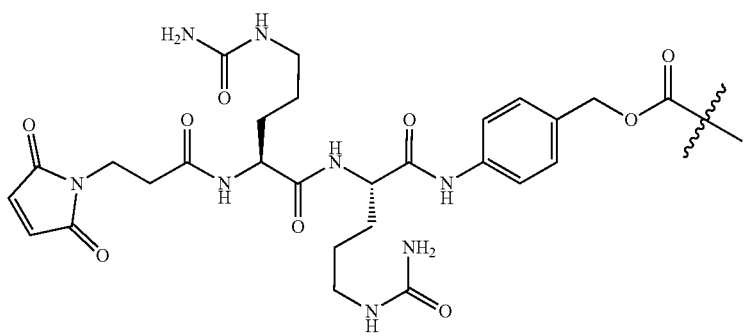
(IIIb.7)
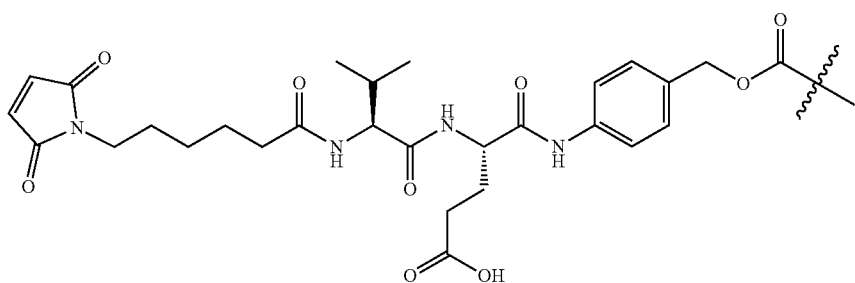
(IIIb.8)
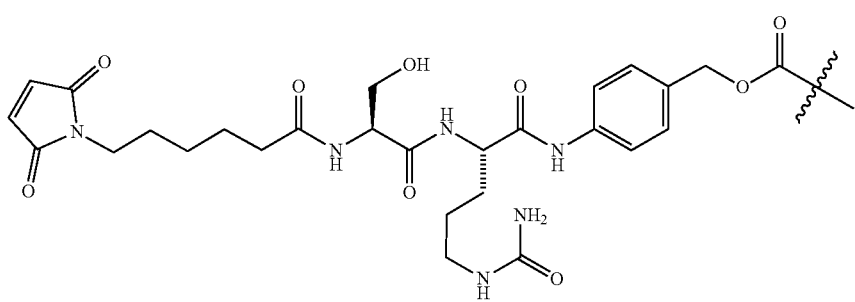
(IIIb.9)

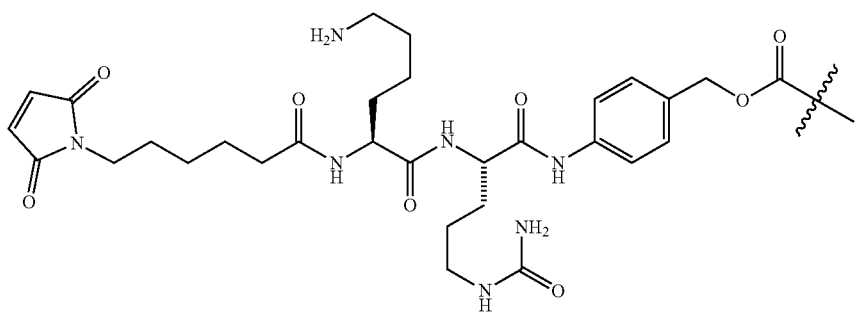
(IIIb.10)
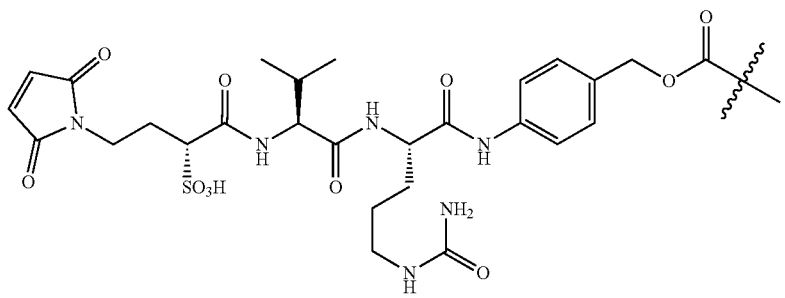
(IIIb.11)
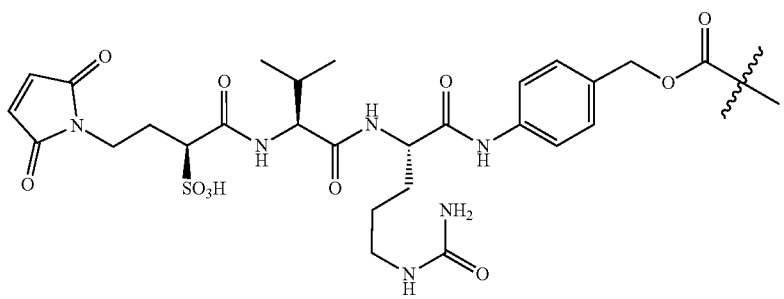
(IIIb.12)
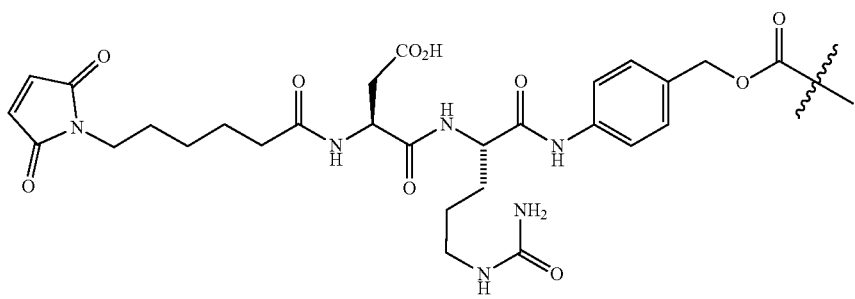
(IIIb.13)
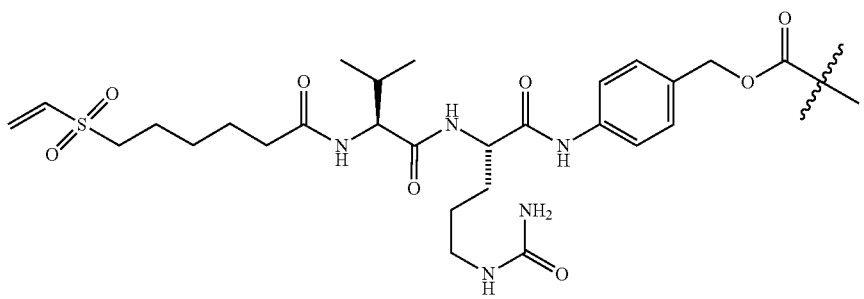
(IIIb.14)

-continued
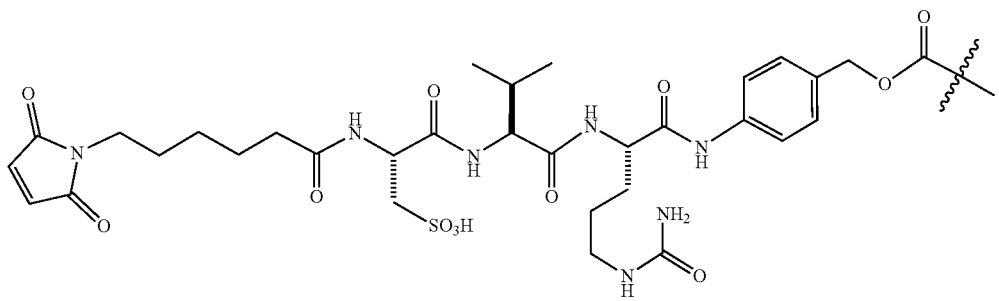
(IIIb.15)
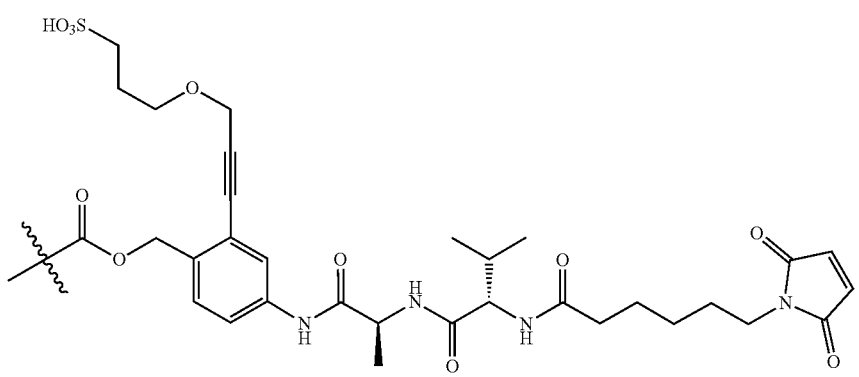
(IIIb.16)
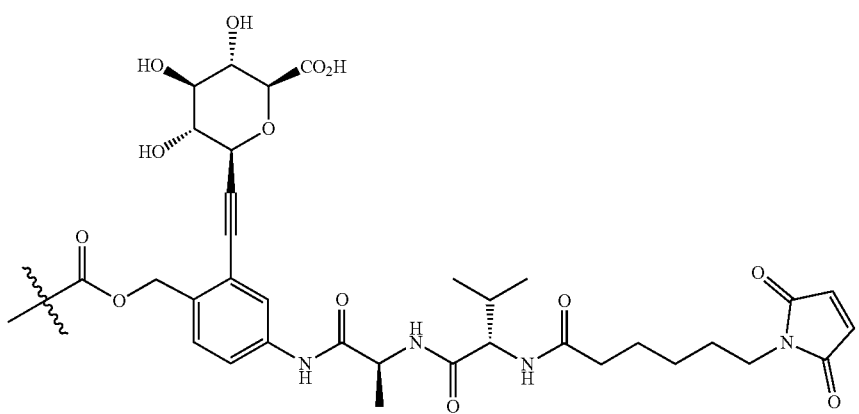
(IIIb.17)
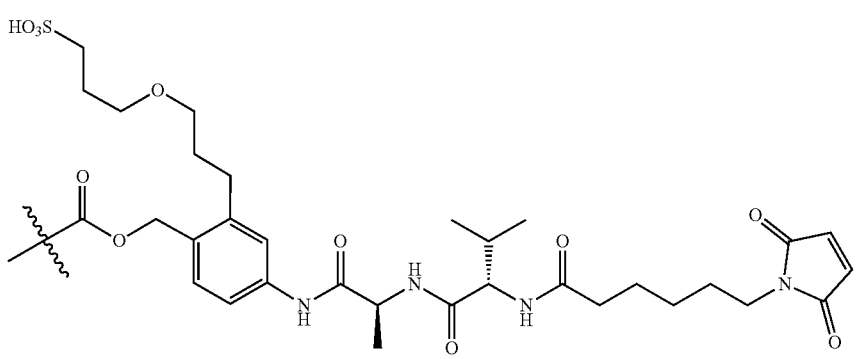
(IIIb.18)

(IIIb.19)
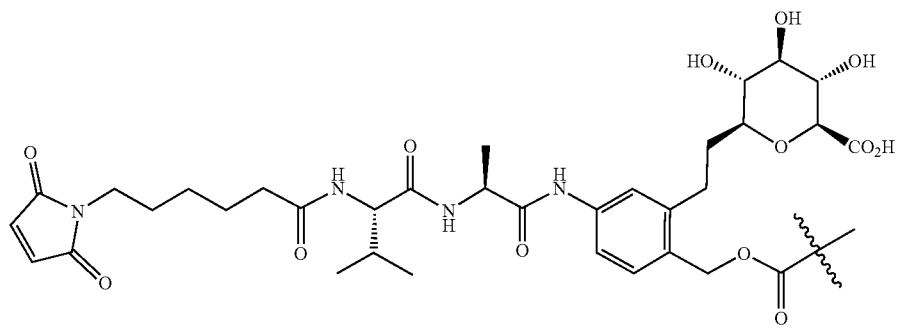
(IIIc.1)
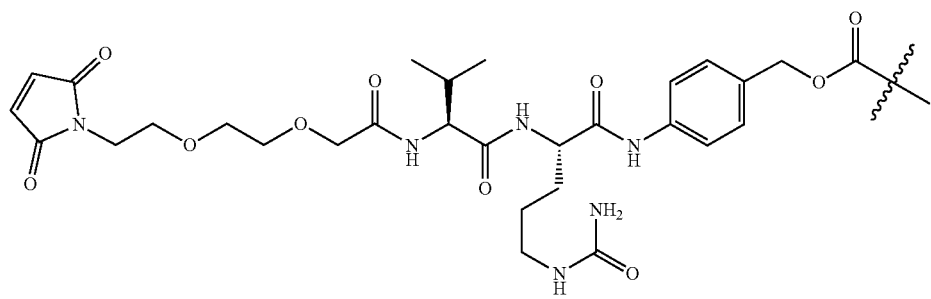
(IIIc.2)
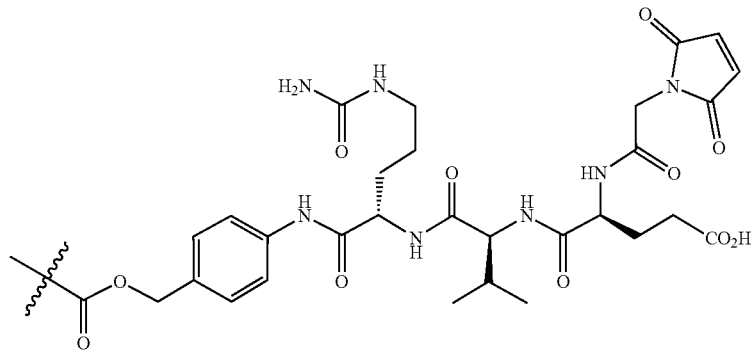
(IIIc.3)
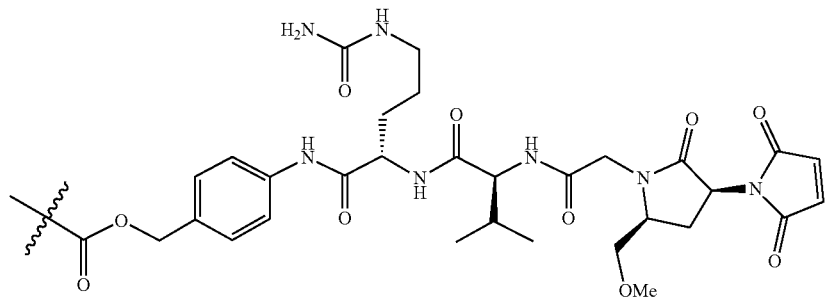

-continued
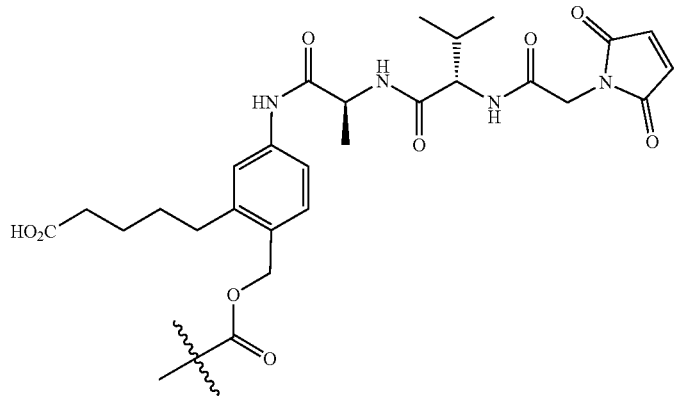
(IIIc.4)
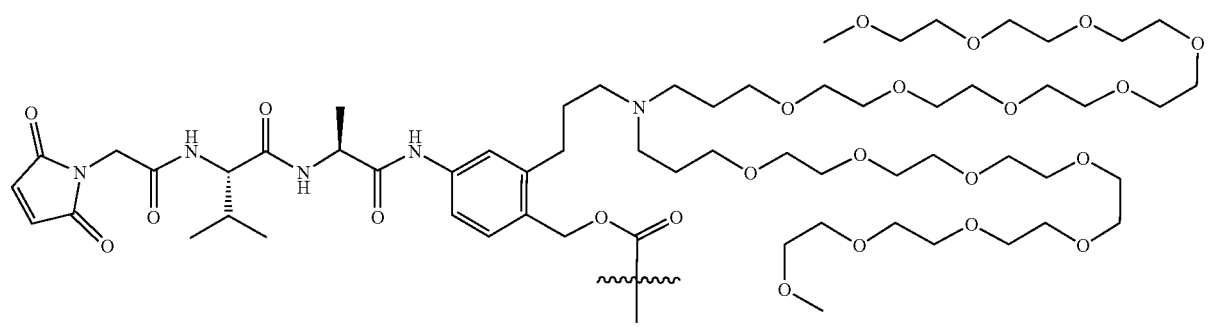
(IIIc.5)
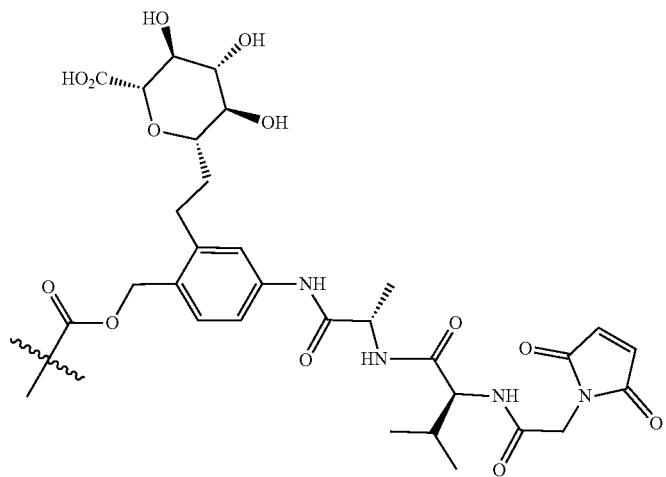
(IIIc.6)
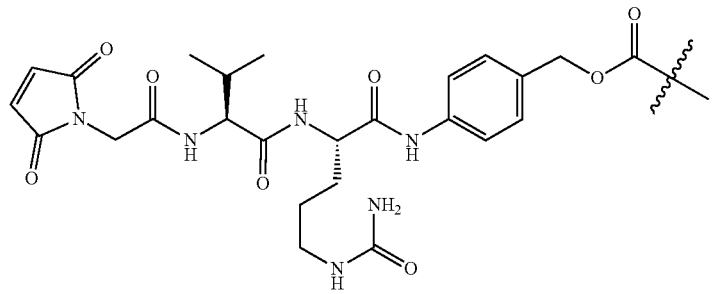
(IIIc.7)

(IIId.1)
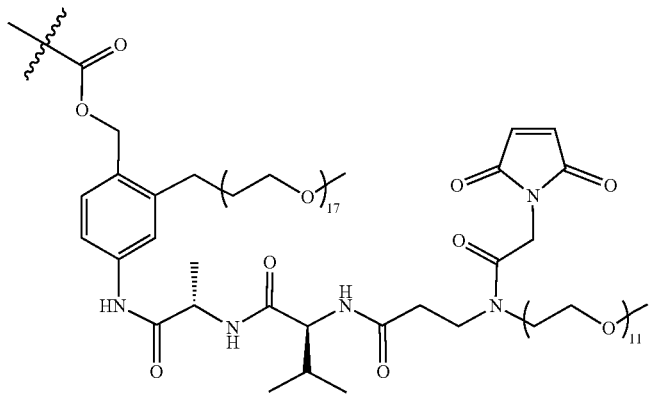
(IIId.2)
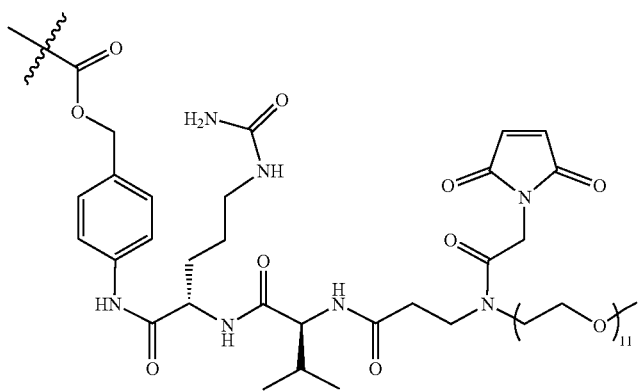
(IIId.3)
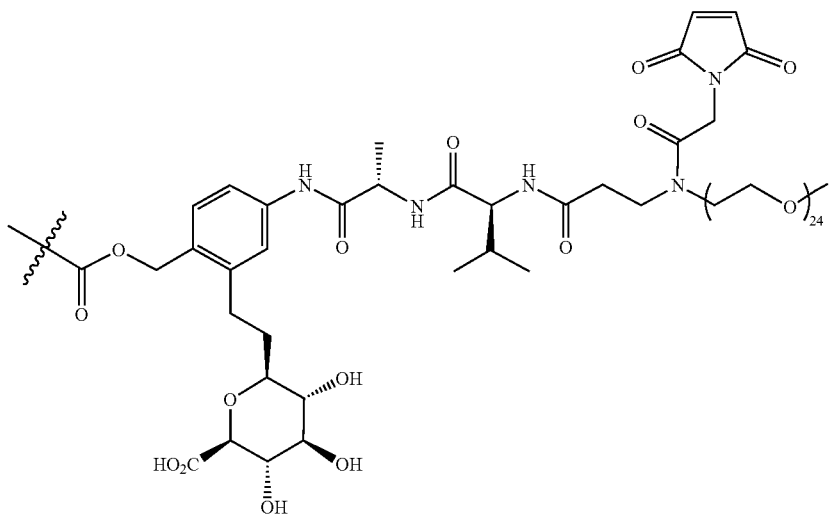

(IIId.4)

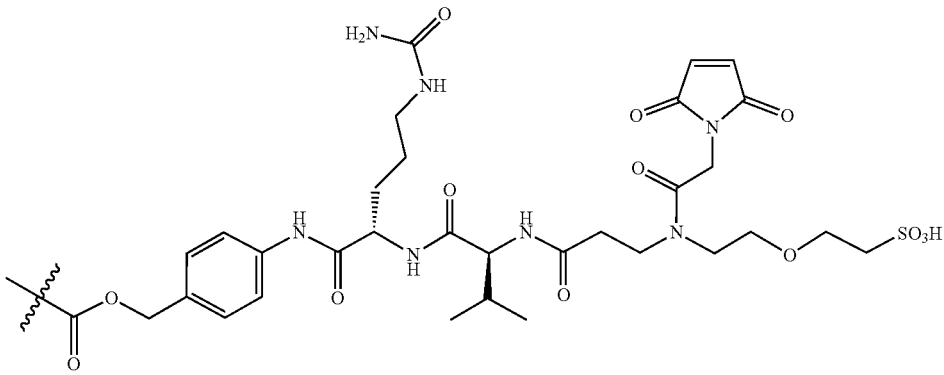

wherein ⁓ indicates an attachment site to an immune-stimulatory compound

The linker can contain an enzymatically cleavable sugar moiety, for example, a linker comprising structural formula (IVa), (IVb), (IVc), (IVd), or (IVe):

(IVa)

(IVb)

(IVc)

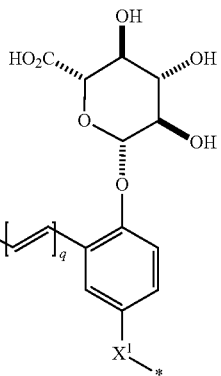

(IVd)

(IVe)

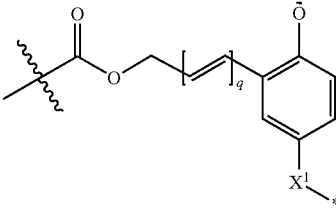

or a pharmaceutically acceptable salt thereof, wherein: q is 0 or 1; r is 0 or 1; $X^1$ is $CH_2$, O or NH; ⁋ represents the point of attachment of the linker to an immune-stimulatory compound; and * represents the point of attachment to the remainder of the linker.

Exemplary embodiments of linkers according to structural formula (IVa) that may be included in the immune-stimulatory conjugates described herein can include the linkers illustrated below (as illustrated, the linkers include a group suitable for covalently linking the linker to an antibody or antigen-binding fragment thereof):

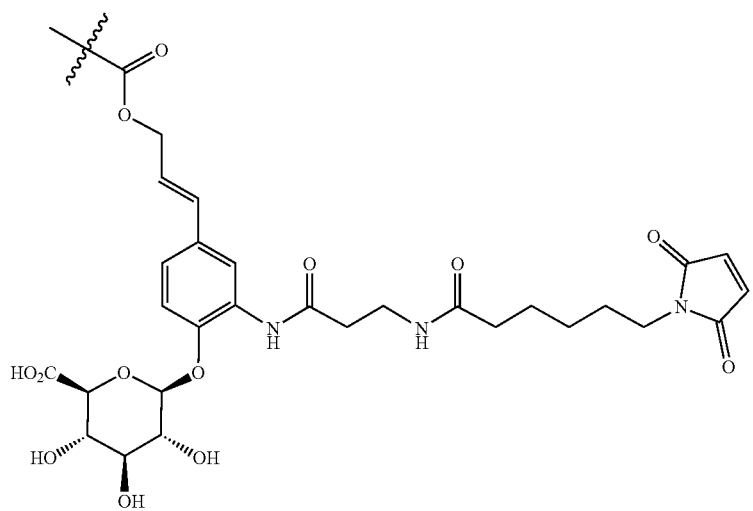
(IVa.1)
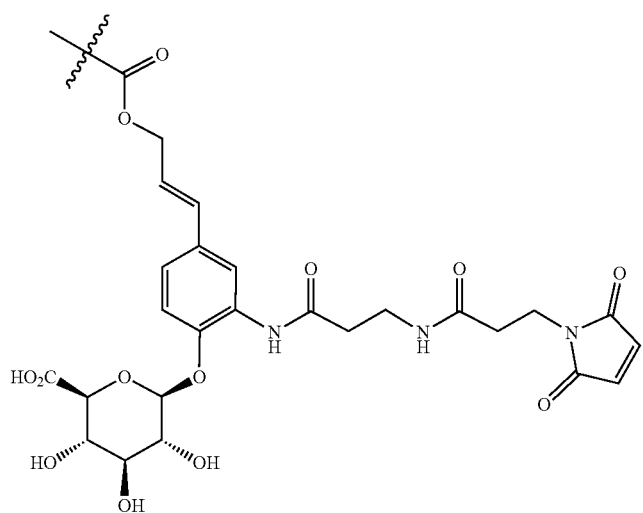
(IVa.2)
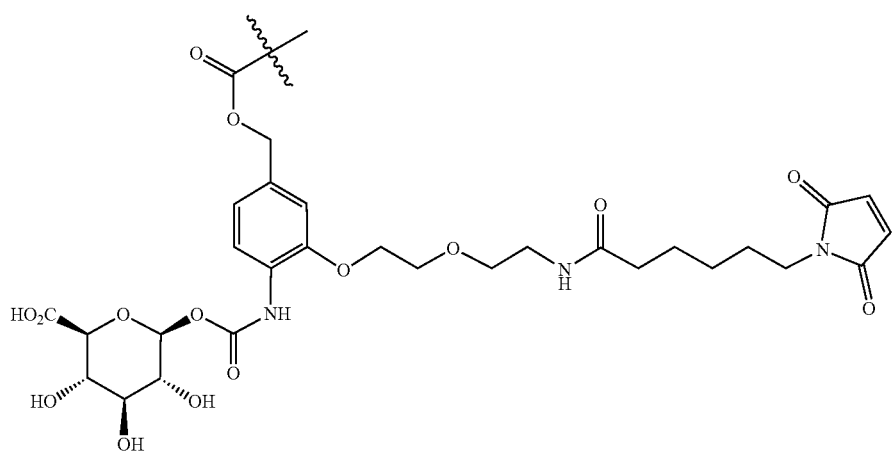
(IVa.3)

(IVa.4)
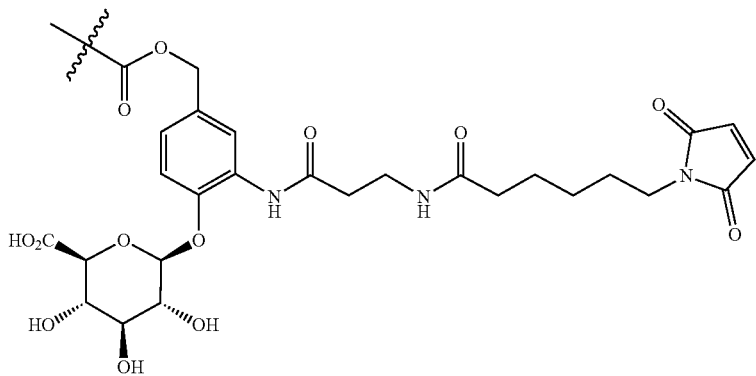
(IVa.5)
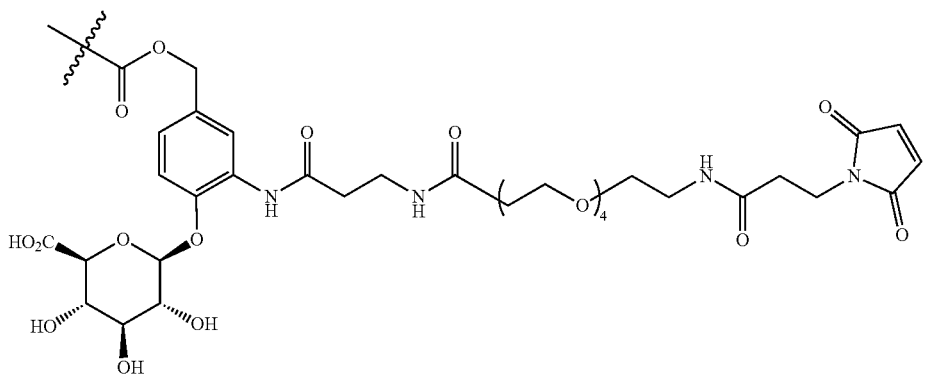
(IVa.6)
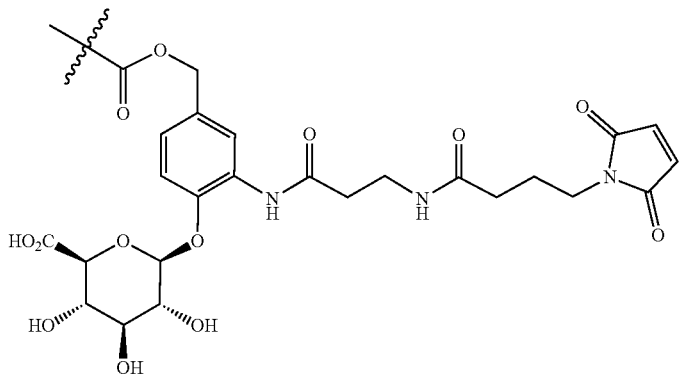
(IVa.7)
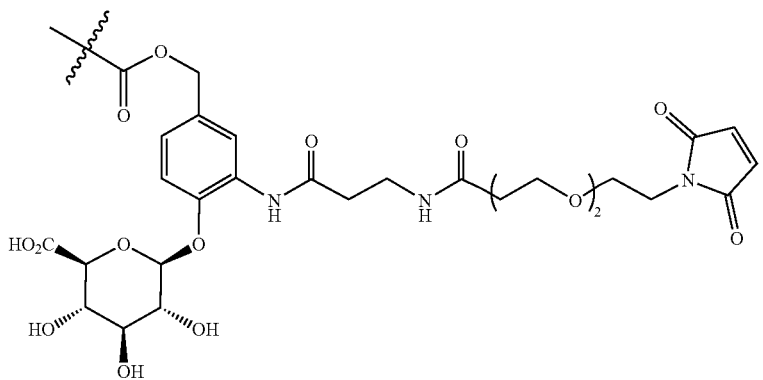

(IVa.8)
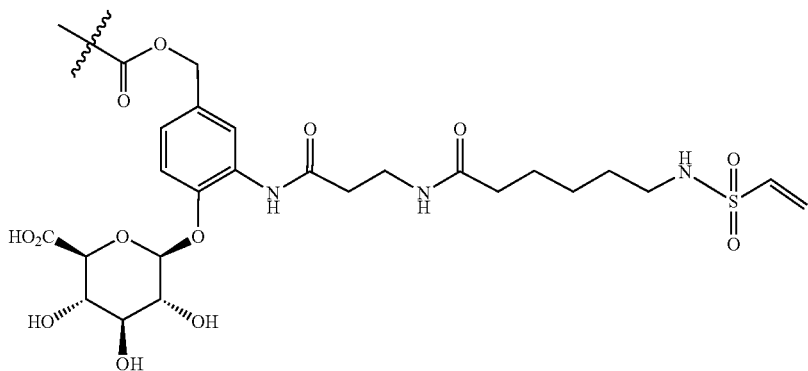
(IVa.9)
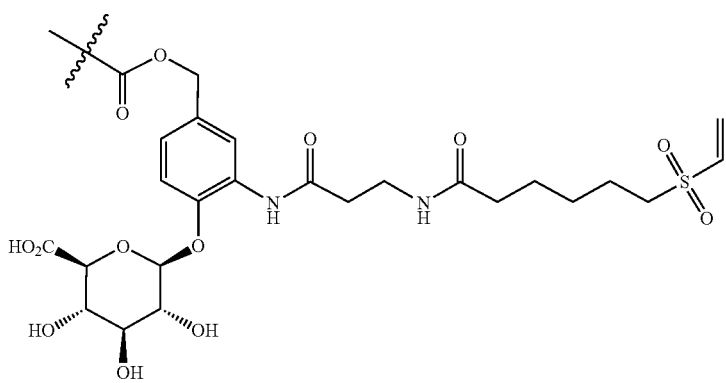
(IVa.10)
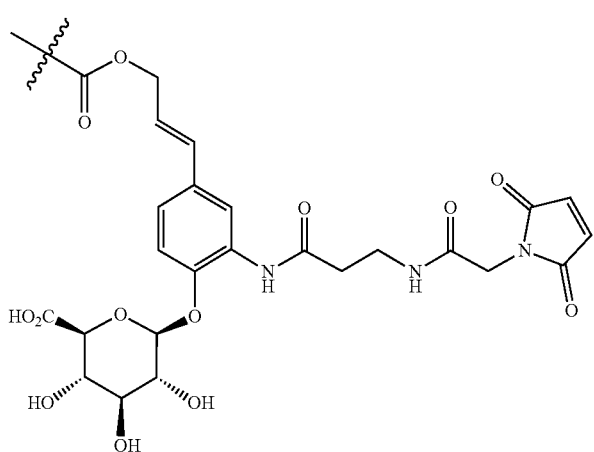
(IVa.11)
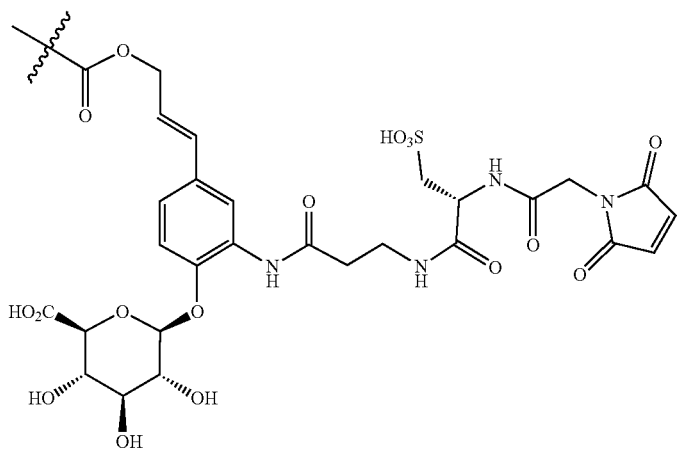

(IVa.12)

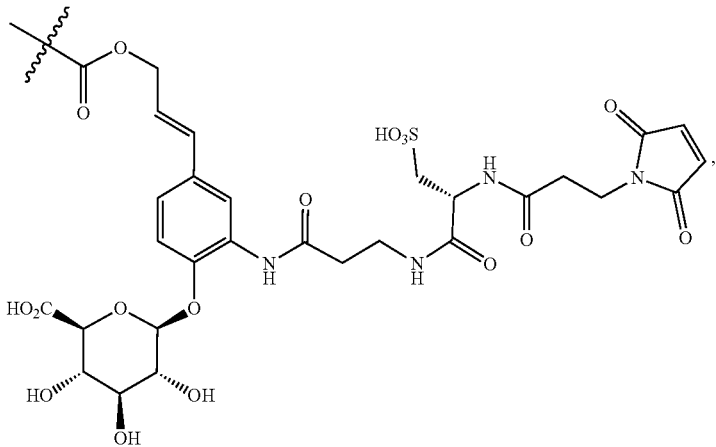

wherein ⌇ represents the point of attachment of a linker to an immune-stimulatory.

Exemplary embodiments of linkers according to structural formula (IVb) that may be included in the conjugates described herein include the linkers illustrated below (as illustrated, the linkers include a group suitable for covalently linking the linker to an antibody or antigen-binding fragment thereof):

(IVb.1)

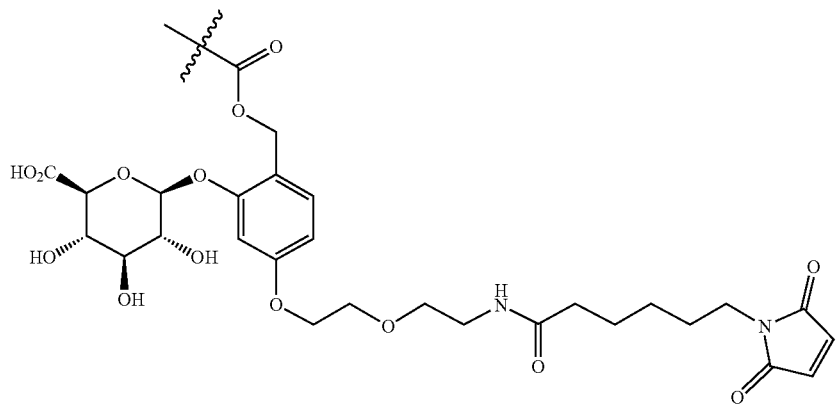

(IVb.1)

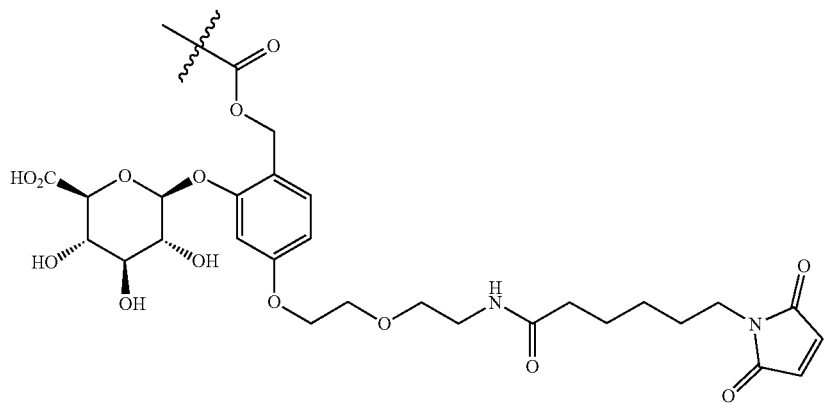

(IVb.2)
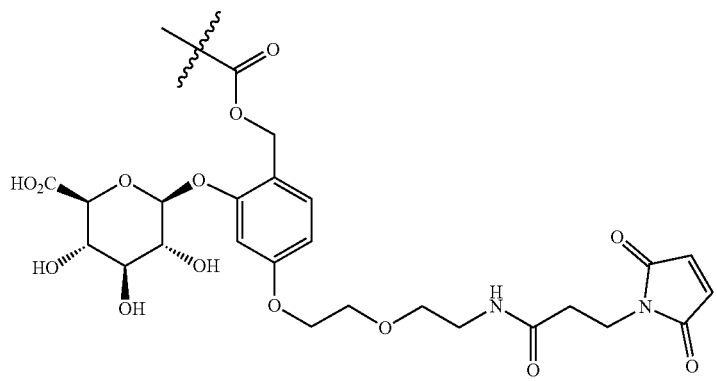
(IVb.3)
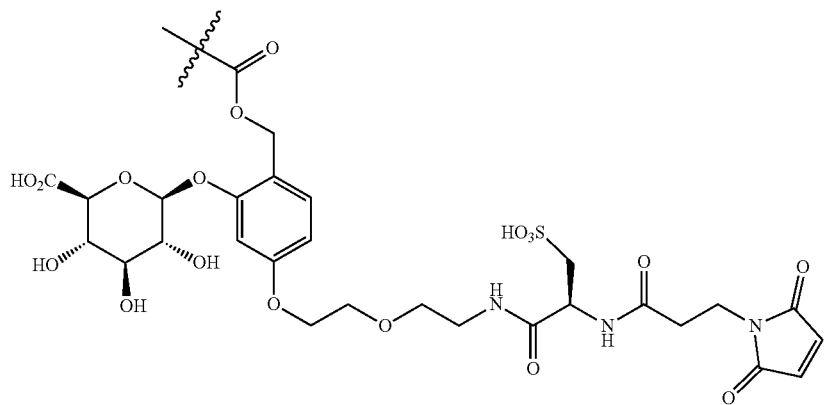
(IVb.4)
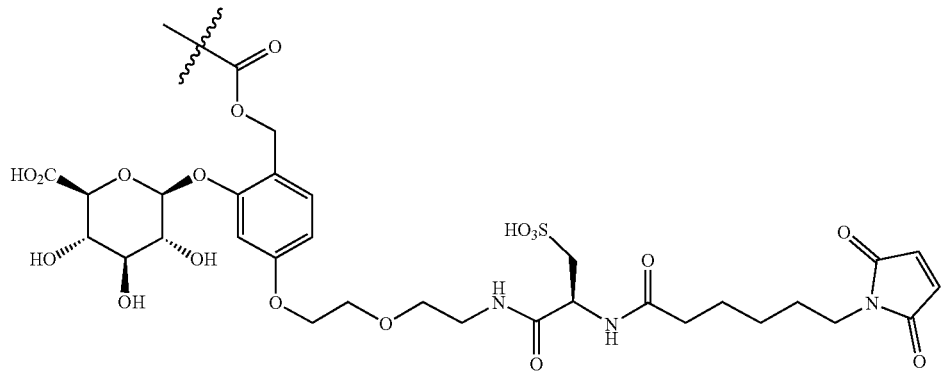
(IVb.5)
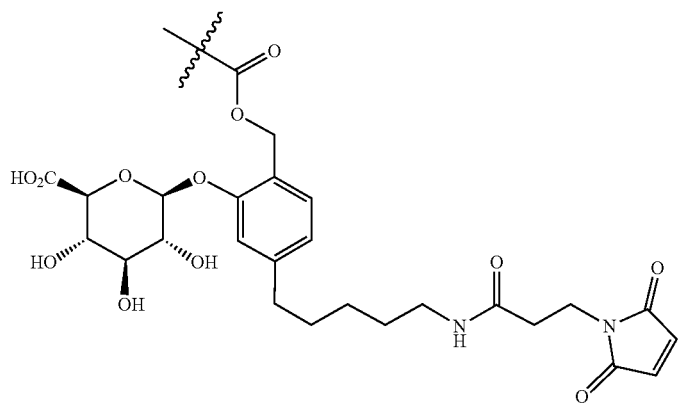

(IVb.6)
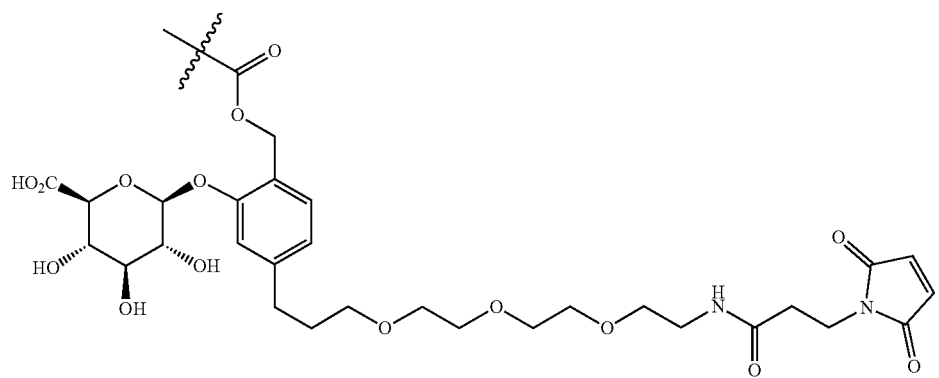
(IVb.7)
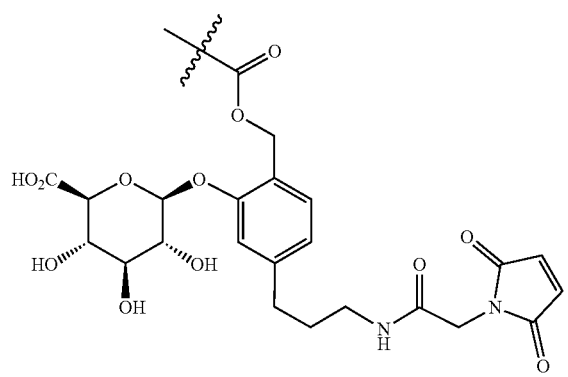
(IVb.8)
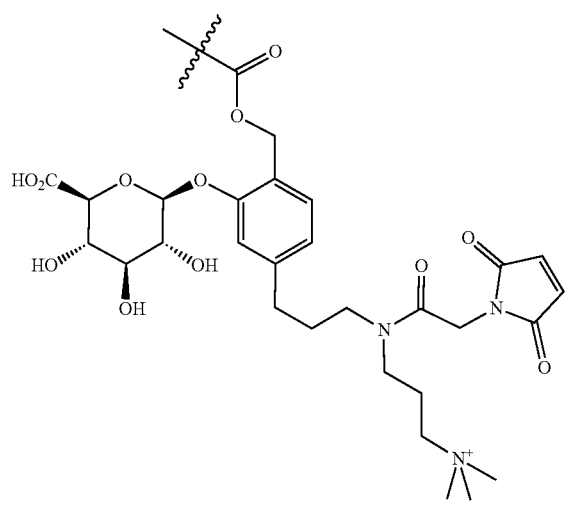
(IVb.9)
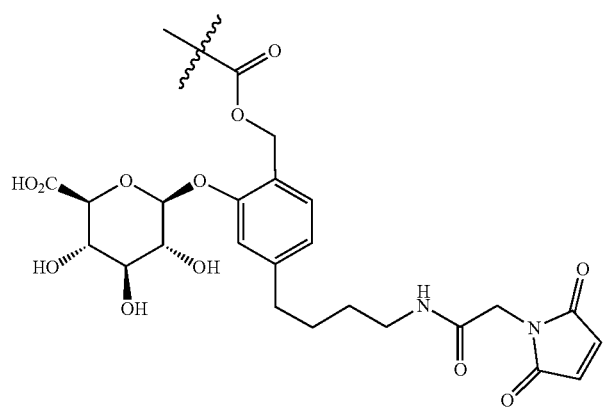

(IVb.10)

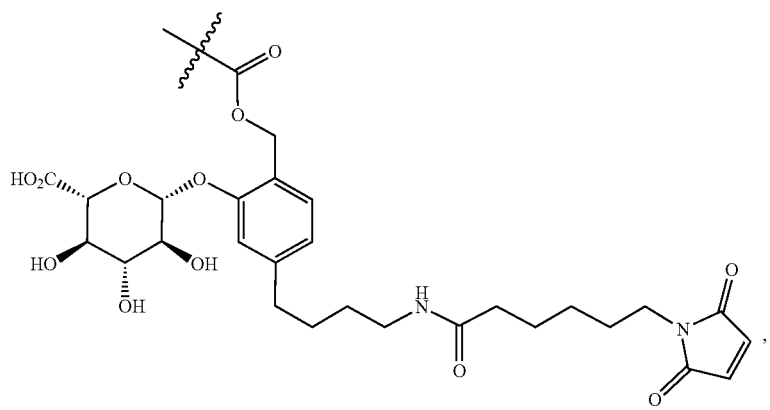

wherein ⌇ represents the point of attachment of a linker to an immune-stimulatory compound.

Exemplary embodiments of linkers according to structural formula (IVc) that may be included in the conjugates described herein include the linkers illustrated below (as illustrated, the linkers include a group suitable for covalently linking the linker to an antibody or antigen-binding fragment thereof):

(IVc.1)

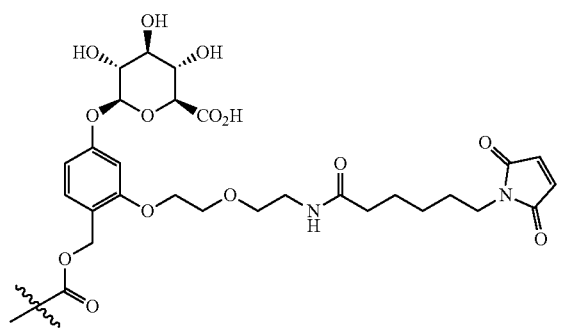

(IVc.2)

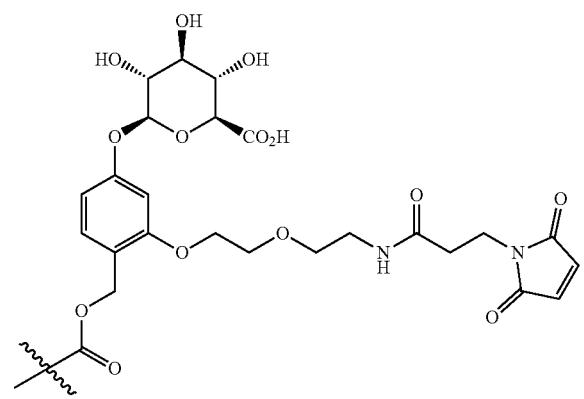

(IVc.3)

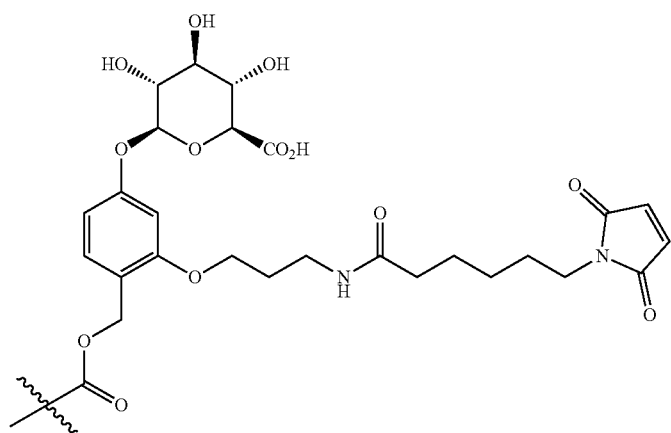

-continued
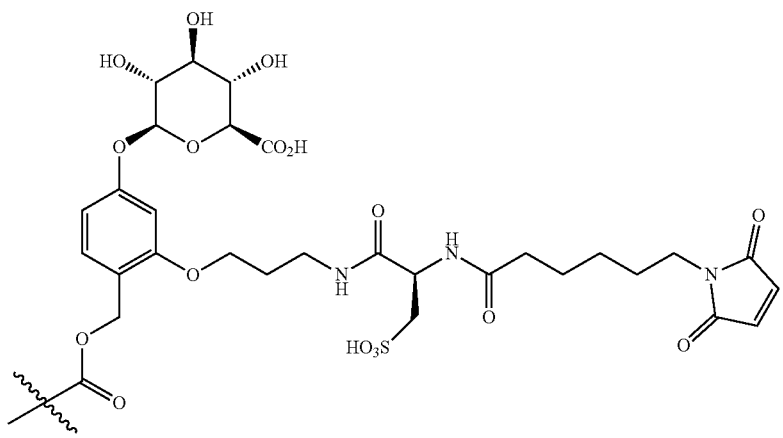
(IVc.4)
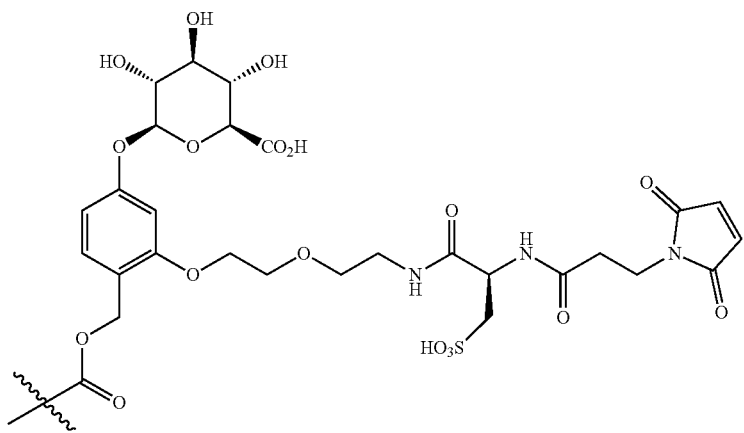
(IVc.5)
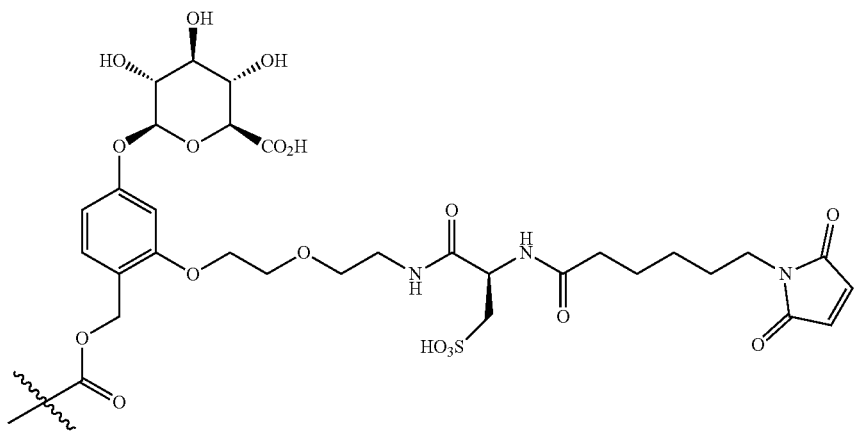
(IVc.6)

-continued
(IVc.7)
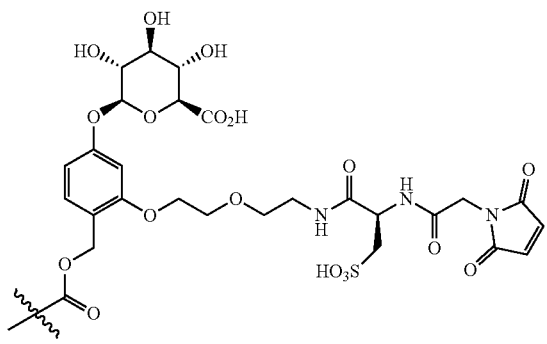
(IVc.8)
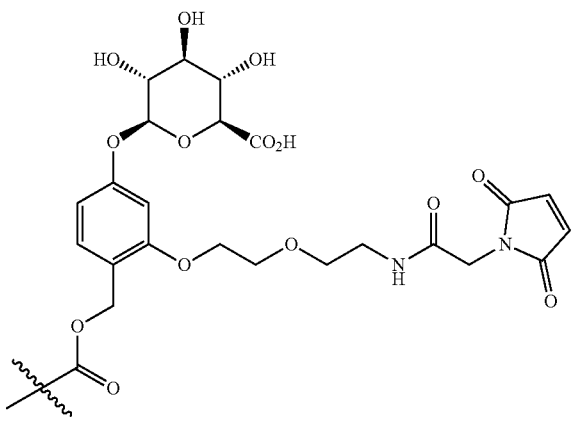
(IVc.9)
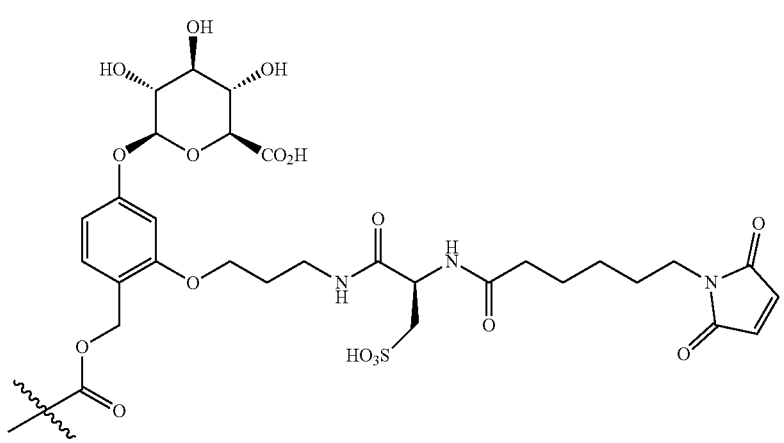
(IVc.10)
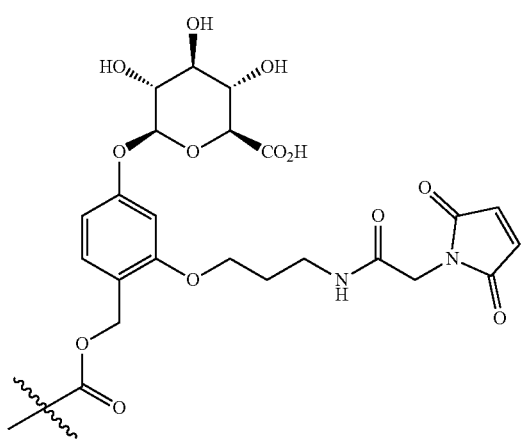

(IVc.11)

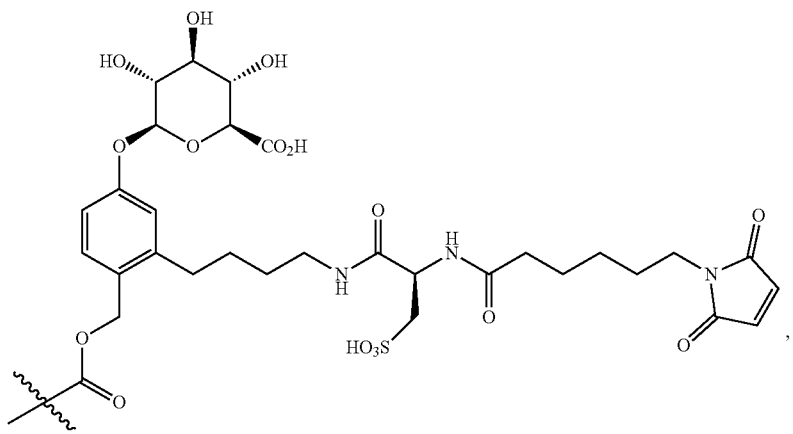

wherein ⌇ represents the point of attachment of a linker to an immune-stimulatory compound.

Exemplary embodiments of linkers according to structural formula (IVd) that may be included in the conjugates described herein include the linkers illustrated below (as illustrated, the linkers include a group suitable for covalently linking the linker to an antibody or antigen-binding fragment thereof):

(IVd.1)

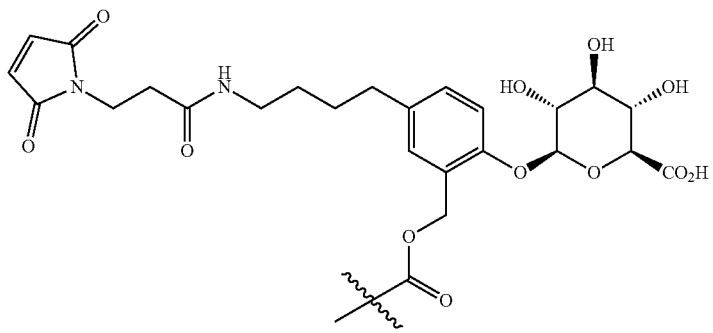

(IVd.2)

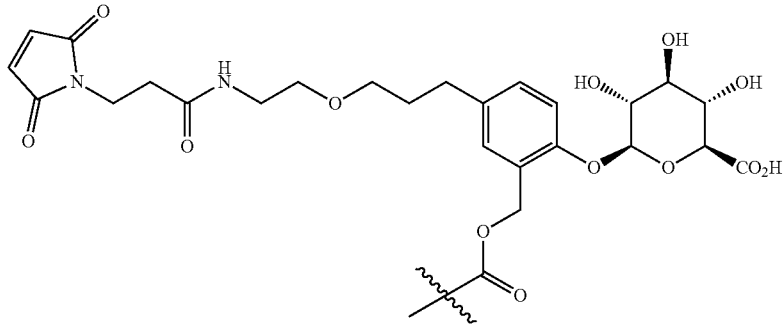

(IVd.3)

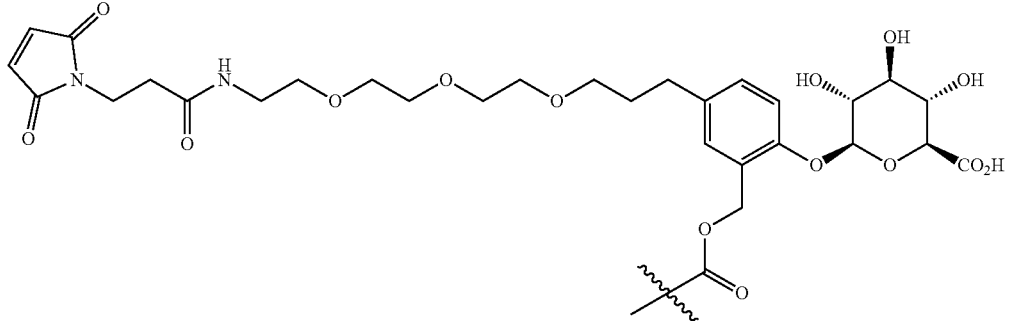

-continued (IVd.4)
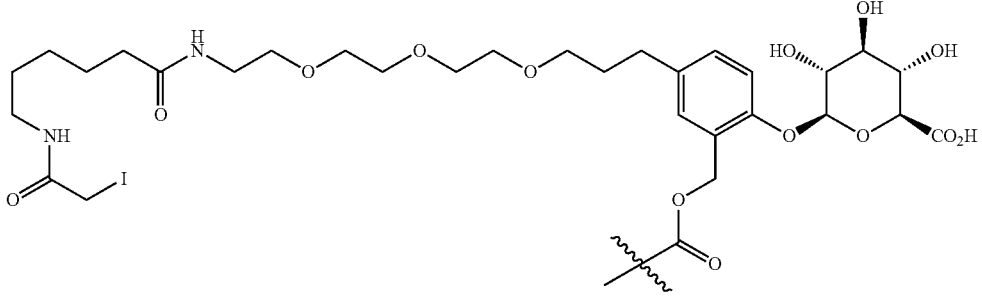

(IVd.5)
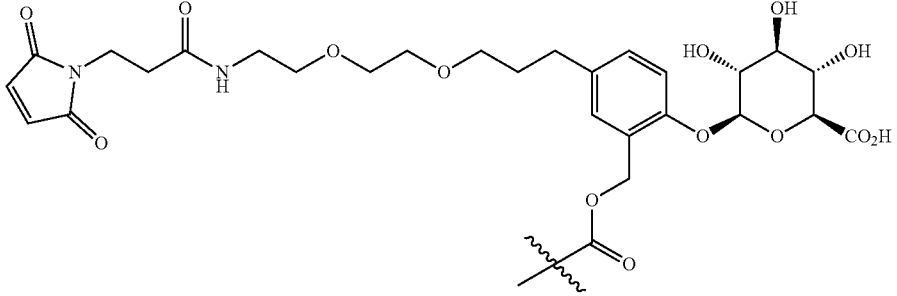

(IVd.6)
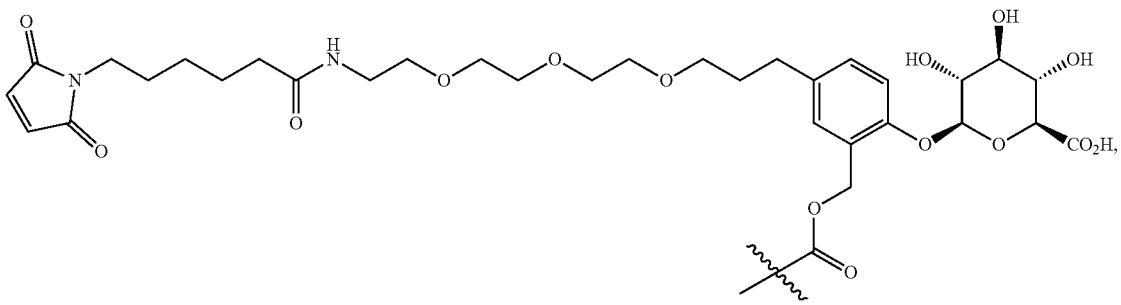

wherein ⌇ represents the point of attachment of a linker to an immune-stimulatory compound.

Exemplary embodiments of linkers according to structural formula (IVe) that may be included in the conjugates described herein include the linkers illustrated below (as illustrated, the linkers include a group suitable for covalently linking the linker to an antibody or antigen-binding fragment thereof):

(IVe.1)
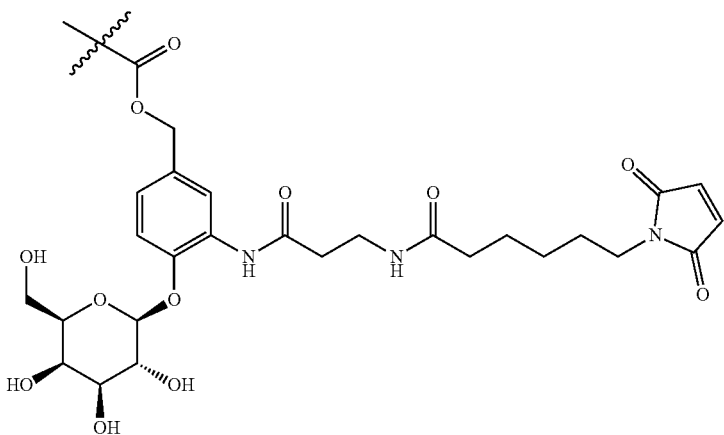

(IVe.2)

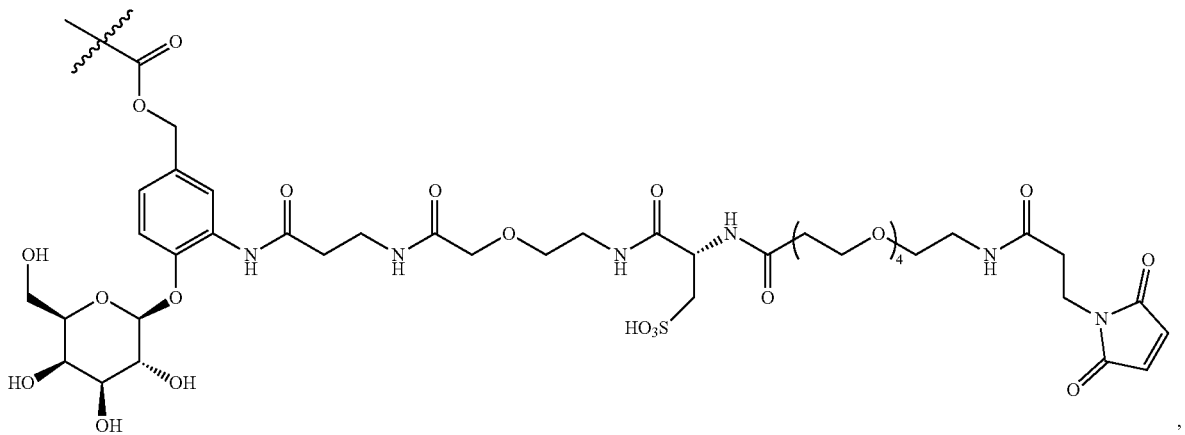

wherein ⌇ represents the point of attachment of a linker to an immune-stimulatory compound.

Although cleavable linkers can provide certain advantages, the linkers comprising the conjugate described herein need not be cleavable. For non-cleavable linkers, the immune-stimulatory compound release may not depend on the differential properties between the plasma and some cytoplasmic compartments. The release of the immune-stimulatory compound can occur after internalization of the immune-stimulatory conjugate via antigen-mediated endocytosis and delivery to lysosomal compartment, where the antibody or antigen-binding fragment thereof can be degraded to the level of amino acids through intracellular proteolytic degradation. This process can release an immune-stimulatory compound derivative, which is formed by the immune-stimulatory compound, the linker, and the amino acid residue or residues to which the linker was covalently attached. The immune-stimulatory compound derivative from immune-stimulatory conjugates with non-cleavable linkers can be more hydrophilic and less membrane permeable, which can lead to less bystander effects and less nonspecific toxicities compared to immune-stimulatory conjugates with a cleavable linker. Immune-stimulatory conjugates with non-cleavable linkers can have greater stability in circulation than immune-stimulatory conjugates with cleavable linkers. Non-cleavable linkers can include alkylene chains, or can be polymeric, such as, for example, based upon polyalkylene glycol polymers, amide polymers, or can include segments of alkylene chains, polyalkylene glycols and/or amide polymers. The linker can contain a polyethylene glycol segment having from 1 to 6 ethylene glycol units.

The linker can be non-cleavable in vivo, for example, a linker according to the formulations below:

(Va)

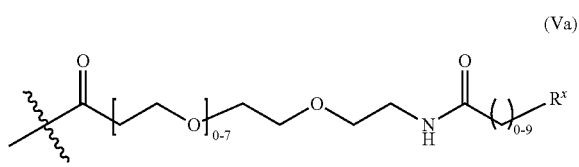

(Vb)

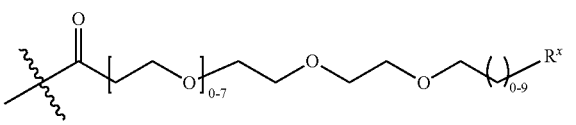

(Vc)

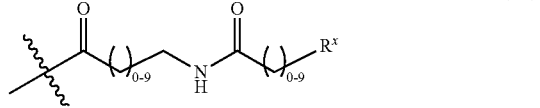

(Vd)

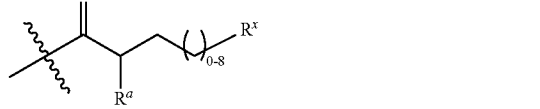

(Ve)

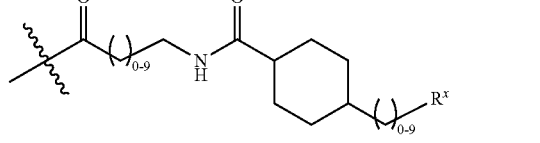

(Vf)

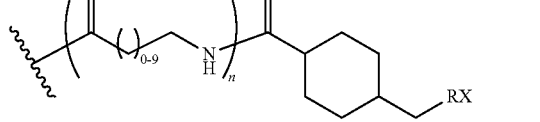

or salts thereof, wherein: $R^a$ is selected from hydrogen, alkyl, sulfonate and methyl sulfonate; $R^x$ is a reactive moiety including a functional group capable of covalently linking the linker to an antibody or antigen-binding fragment thereof; and ⌇ represents the point of attachment of the linker to an immune-stimulatory compound.

Exemplary embodiments of linkers according to structural formula (Va)-(Vf) that may be included in the conjugates described herein include the linkers illustrated below (as illustrated, the linkers include a group suitable for covalently linking the linker to an antibody or antigen-binding fragment thereof, and ⌇ represents the point of attachment of the linker to an immune-stimulatory compound:

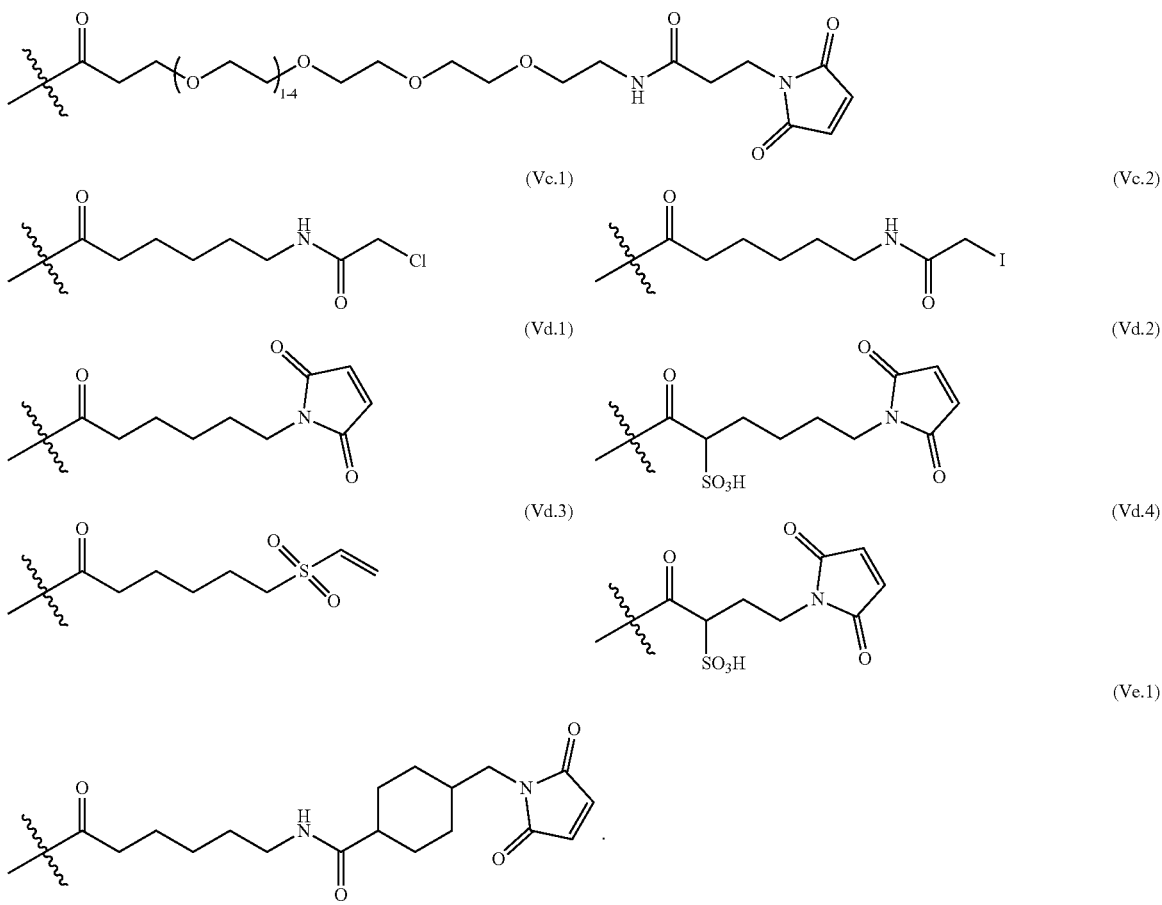

In some embodiments, a linker is represented by formula (V):

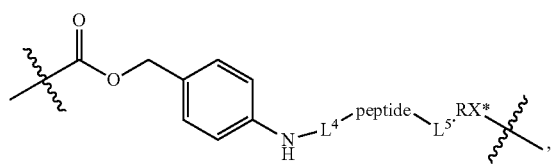

wherein:

L⁴ represents the C-terminus of the peptide;

L⁵ is selected from a bond, alkylene and heteroalkylene, wherein L⁵ is optionally substituted with one or more groups independently selected from $R^{32}$;

RX* comprises a bond, a succinimide moiety, or a hydrolyzed succinimide moiety bound to a residue of a polypeptide, such as an antibody, wherein

on RX* represents the point of attachment to the residue of the polypeptide, such as the antibody, and the other

represents the point of attachment to the myeloid cell agonist, such as a TLR8 or TLR7 agonist; and $R^{32}$ is independently selected at each occurrence from halogen, —OH, —CN, —O— alkyl, —SH, =O, =S, —NH₂, —NO₂; $C_{1-10}$ alkyl, $C_{2-10}$ alkenyl, and $C_{2-10}$ alkynyl, each of which is optionally substituted with one or more substituents independently selected from halogen, —OH, —CN, —O-alkyl, —SH, =O, =S, —NH₂, and —NO₂.

Attachment groups that are used to attach the linkers to an antibody or antigen-binding fragment thereof can be electrophilic in nature and include, for example, maleimide groups, alkynes, alkynoates, allenes and allenoates, activated disulfides, active esters such as NHS esters and HOBt esters, haloformates, acid halides, alkyl, and benzyl halides such as haloacetamides. There are also emerging technologies related to "self-stabilizing" maleimides and "bridging disulfides" that can be used in accordance with the disclosure.

Maleimide groups are frequently used in the preparation of conjugates because of their specificity for reacting with thiol groups of, for example, cysteine groups of the antibody or antigen-binding fragment thereof of a conjugate. The reaction between a thiol group of an antibody or antigen-binding fragment thereof and a drug with a linker including a maleimide group proceeds according to the following scheme:

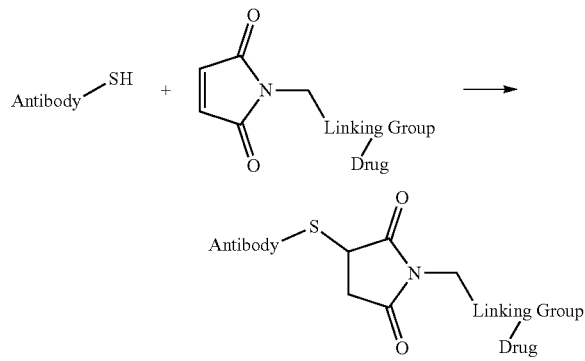

The reverse reaction leading to maleimide elimination from a thio-substituted succinimide may also take place. This reverse reaction is undesirable as the maleimide group may subsequently react with another available thiol group such as other proteins in the body having available cysteines. Accordingly, the reverse reaction can undermine the specificity of a conjugate. One method of preventing the reverse reaction is to incorporate a basic group into the linking group shown in the scheme above. Without wishing to be bound by theory, the presence of the basic group may increase the nucleophilicity of nearby water molecules to promote ring-opening hydrolysis of the succinimide group. The hydrolyzed form of the attachment group is resistant to deconjugation in the presence of plasma proteins. So-called "self-stabilizing" linkers provide conjugates with improved stability. A representative schematic is shown below:

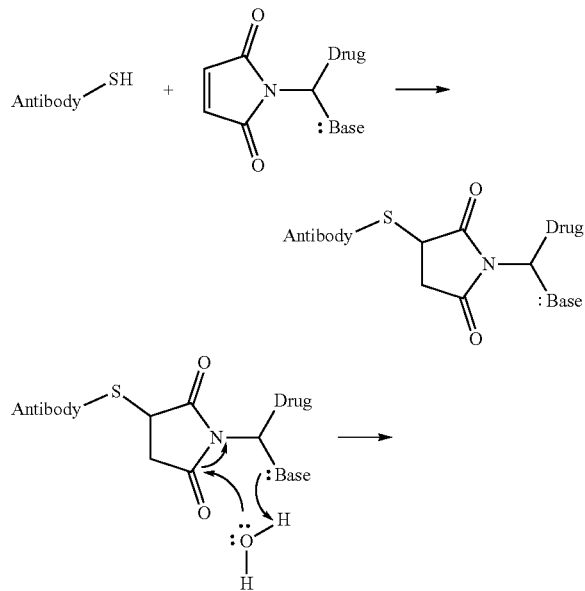

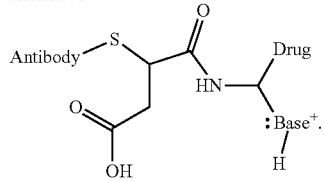

The hydrolysis reaction schematically represented above may occur at either carbonyl group of the succinimide group. Accordingly, two possible isomers may result, as shown below:

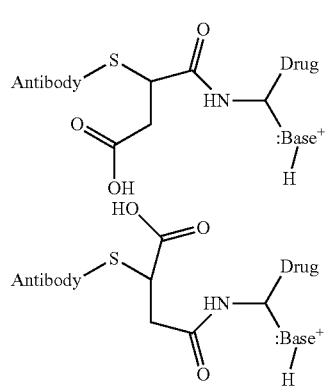

The identity of the base as well as the distance between the base and the maleimide group can be modified to tune the rate of hydrolysis of the thio-substituted succinimide group and optimize the delivery of a conjugate to a target by, for example, improving the specificity and stability of the conjugate.

Bases suitable for inclusion in a linker described herein, e.g., any linker described herein with a maleimide group prior to conjugating to an antibody or antigen-binding fragment thereof, may facilitate hydrolysis of a nearby succinimide group formed after conjugation of the antibody or antigen-binding fragment thereof to the linker. Bases may include, for example, amines (e.g., —N($R^{26}$)($R^{27}$), where $R^{26}$ and $R^{27}$ are independently selected from H and $C_{1-6}$ alkyl), nitrogen-containing heterocycles (e.g., a 3- to 12-membered heterocycle including one or more nitrogen atoms and optionally one or more double bonds), amidines, guanidines, and carbocycles or heterocycles substituted with one or more amine groups (e.g., a 3- to 12-membered aromatic or non-aromatic cycle optionally including a heteroatom such as a nitrogen atom and substituted with one or more amines of the type —N($R^{26}$)($R^{27}$), where $R^{26}$ and $R^{27}$ are independently selected from H or $C_{1-6}$ alkyl). A basic unit may be separated from a maleimide group by, for example, an alkylene chain of the form —$(CH_2)_m$—, where m is an integer from 0 to 10. An alkylene chain may be optionally substituted with other functional groups as described herein.

A linker described herein with a maleimide group may include an electron withdrawing group such as, but not limited to, —C(O)R, =O, —CN, —$NO_2$, —$CX_3$, —X, —COOR, —$CONR_2$, —COR, —COX, —$SO_2R$, —$SO_2OR$, —$SO_2NHR$, —$SO_2NR_2$, $PO_3R_2$, —P(O)($CH_3$)NHR, —NO, —$NR_3^+$, —CR=$CR_2$, and —C≡CR, where each R is independently selected from H and $C_{1-6}$ alkyl and each X is independently selected from F, Br, Cl, and I. Self-stabilizing linkers may also include aryl, e.g., phenyl, or heteroaryl, e.g., pyridine, groups optionally substituted with electron withdrawing groups such as those described herein.

Examples of self-stabilizing linkers are provided in, e.g., U.S. Patent Publication No. US 2013/0309256, the linkers of which are incorporated by reference herein. It will be understood that a self-stabilizing linker useful in conjunction with immune-stimulatory compounds may be equivalently described as unsubstituted maleimide-including linkers, thio-substituted succinimide-including linkers, or hydrolyzed, ring-opened thio-substituted succinimide-including linkers.

In certain embodiments, a linker comprises a stabilizing linker moiety selected from:

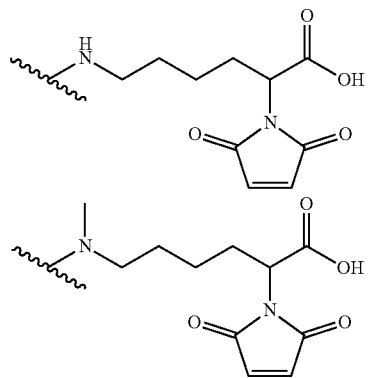

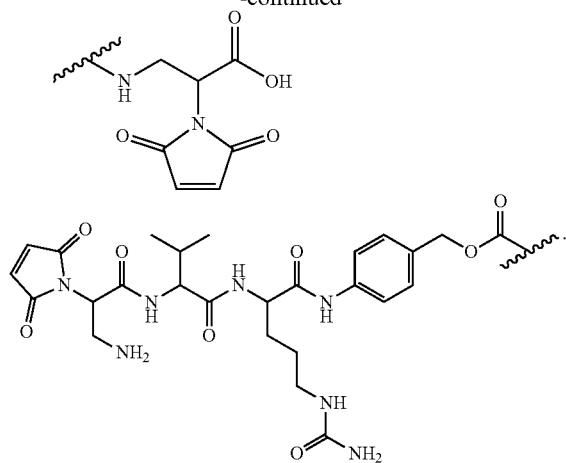

In the scheme provided above, the bottom structure may be referred to as (maleimido)-DPR-Val-Cit-PAB, where DPR refers to diaminopropinoic acid, Val refers to valine, Cit refers to citrulline, and PAB refers to para-aminobenzylcarbonyl. ⌇ represents the point of attachment to an immune-stimulatory compound.

A method for bridging a pair of sulfhydryl groups derived from reduction of a native hinge disulfide bond has been disclosed and is depicted in the schematic below. An advantage of this methodology is the ability to synthesize homogenous DAR4 conjugates by full reduction of IgGs (to give 4 pairs of sulfhydryls from interchain disulfides) followed by reaction with 4 equivalents of the alkylating agent. Conjugates containing "bridged disulfides" are also claimed to have increased stability.

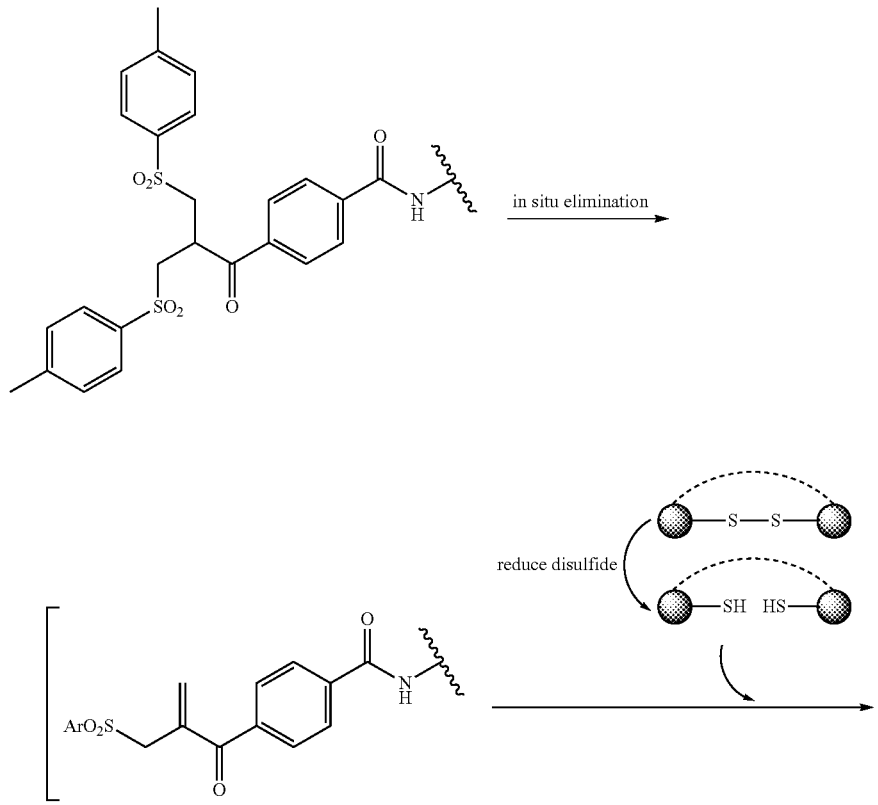

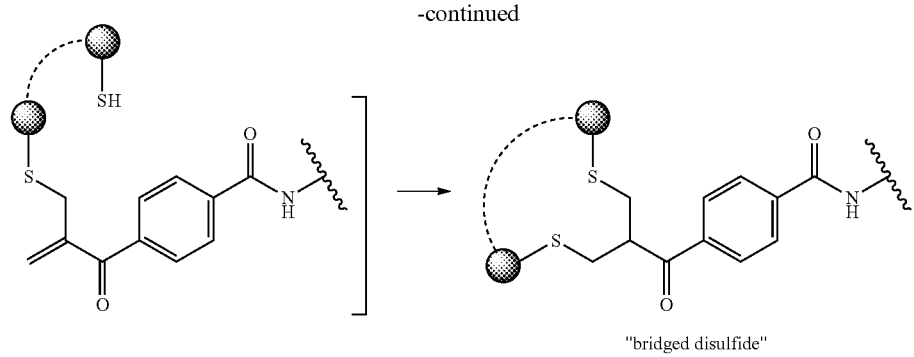

"bridged disulfide"

Similarly, as depicted below, a maleimide derivative that is capable of bridging a pair of sulfhydryl groups has been developed.

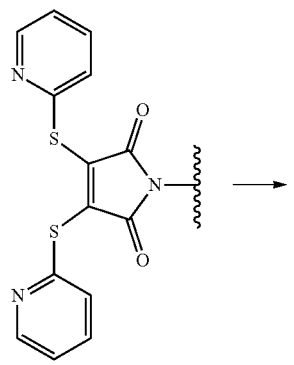

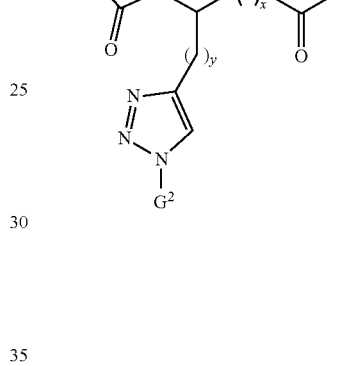

A linker can contain the following structural formulas (VIa), (VIb), or (VIc):

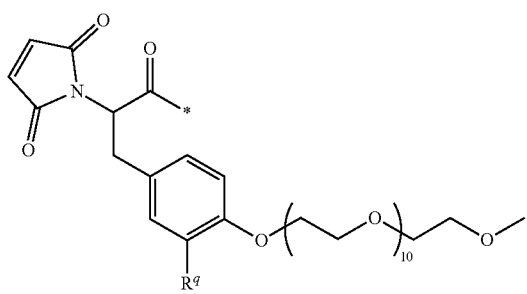

(VIa)

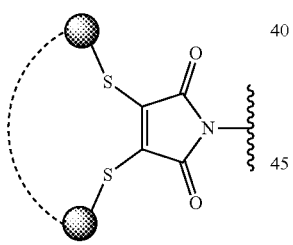

(VIb)

(VIc)

or salts thereof, wherein: $R^q$ is H or —O—$(CH_2CH_2O)_{11}$—$CH_3$; x is 0 or 1; y is 0 or 1; $G^2$ is —$CH_2CH_2CH_2SO_3H$ or —$CH_2CH_2O$—$(CH_2CH_2O)_{11}$—$CH_3$; $R^w$ is —O—$CH_2CH_2SO_3H$ or —NH(CO)—$CH_2CH_2O$—$(CH_2CH_2O)_{12}$—$CH_3$; and * represents the point of attachment to the remainder of the linker.

Exemplary embodiments of linkers according to structural formula (VIa) and (VIb) that can be included in the conjugates described herein can include the linkers illustrated below (as illustrated, the linkers can include a group suitable for covalently linking the linker to an antibody or antigen-binding fragment thereof):

261 262
(VIa.1)
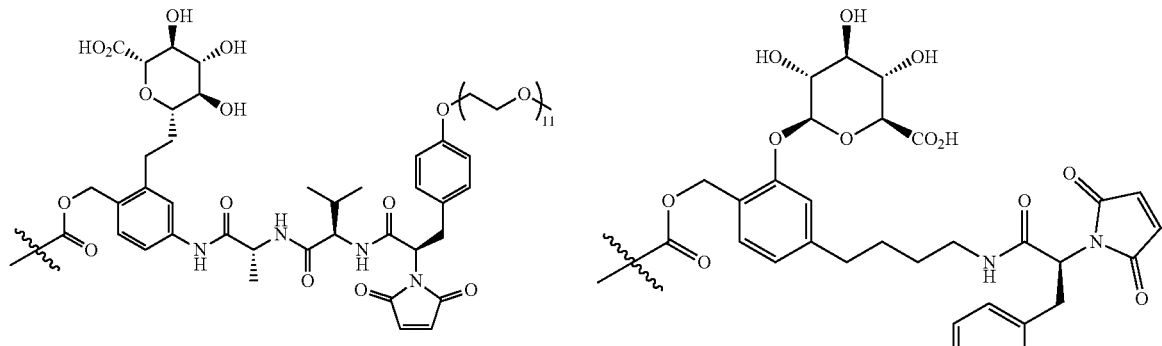
(VIa.2)
(VIa.3)
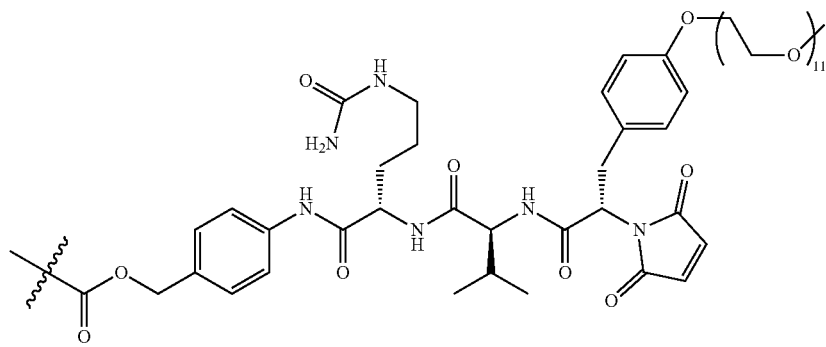
(VIa.4)
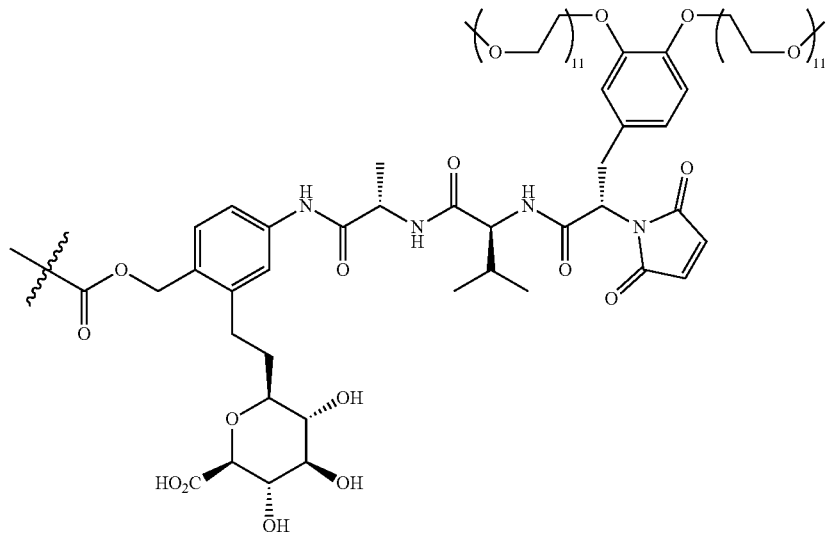
(VIb.1) (VIb.2)
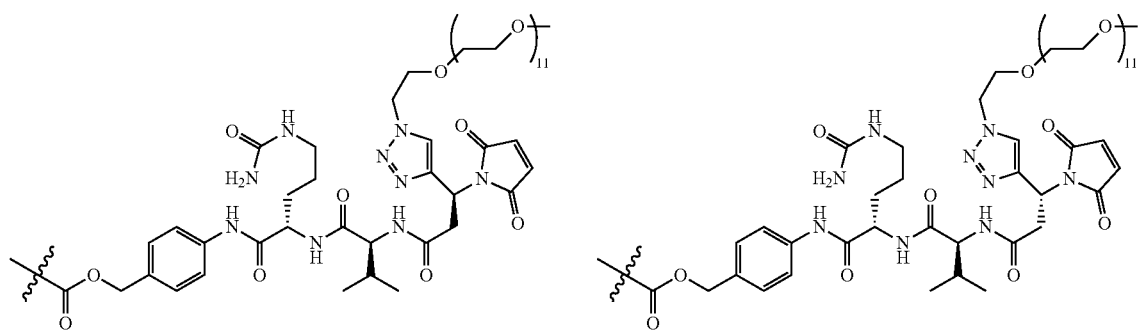

-continued

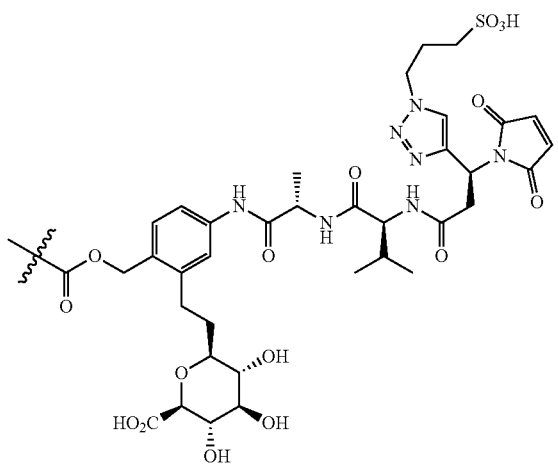
(VIb.3)

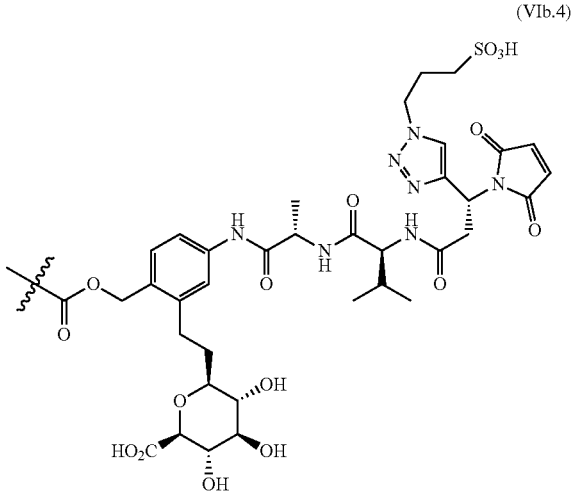
(VIb.4)

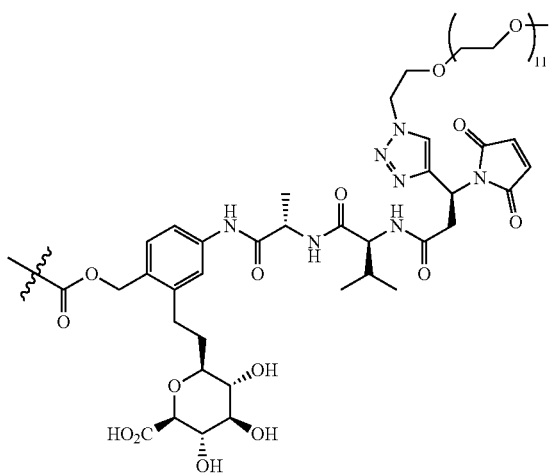
(VIb.6)

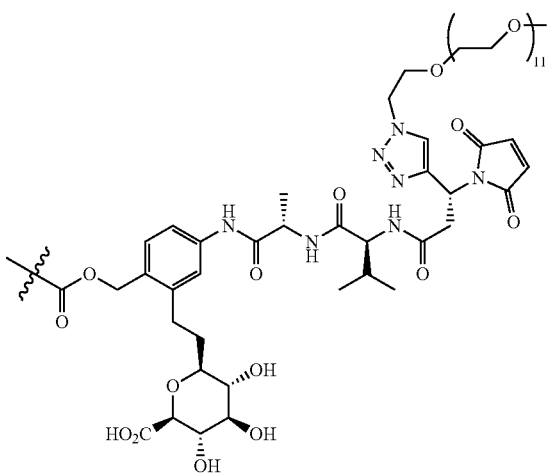
(VIIb.7)

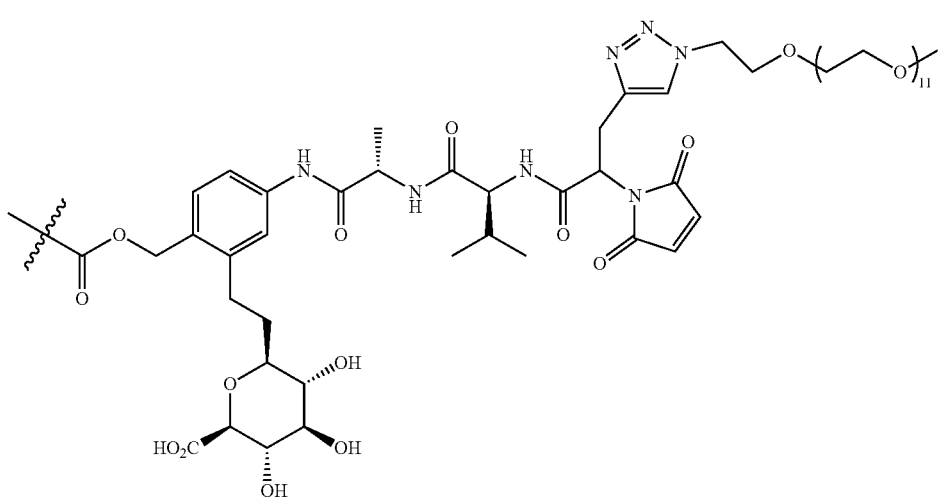
(VIIb.8)

wherein ⌇N represents the point of attachment of the linker to an immune-stimulatory compound.

Exemplary embodiments of linkers according to structural formula (VIc) that can be included in the immune-stimulatory conjugates described herein can include the linkers illustrated below (as illustrated, the linkers can include a group suitable for covalently linking the linker to an antibody or antigen-binding fragment thereof):

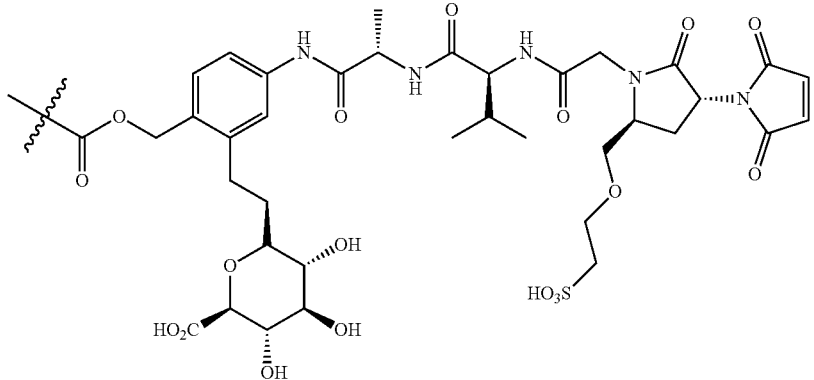
(VIc.1)
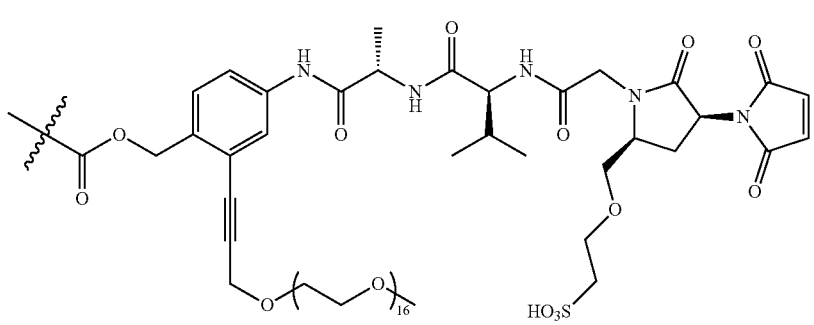
(VIc.2)
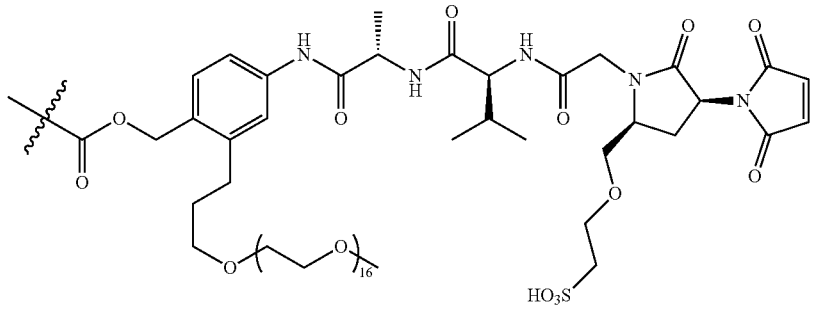
(VIc.3)
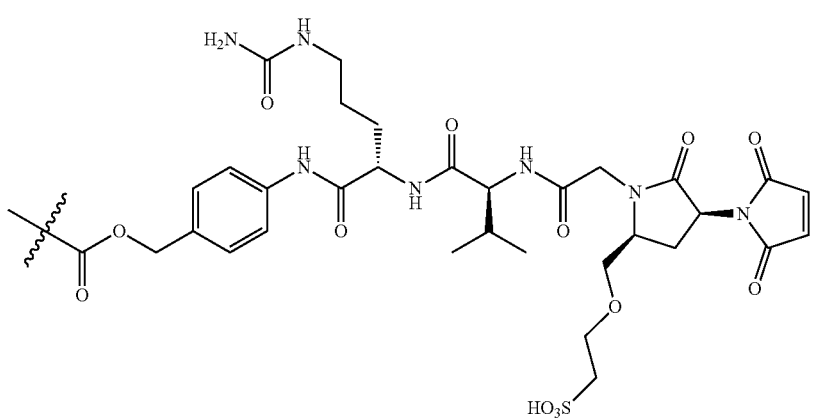
(VIc.4)

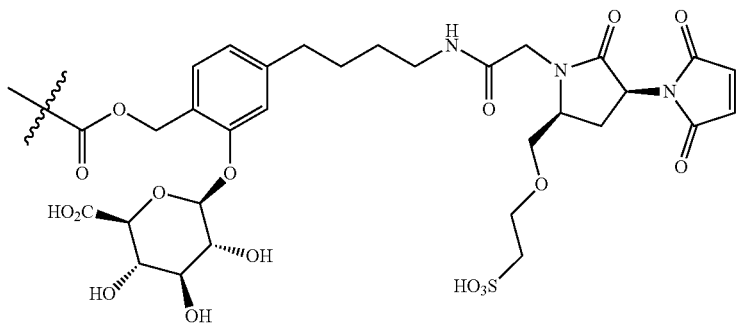

(VIc.5)

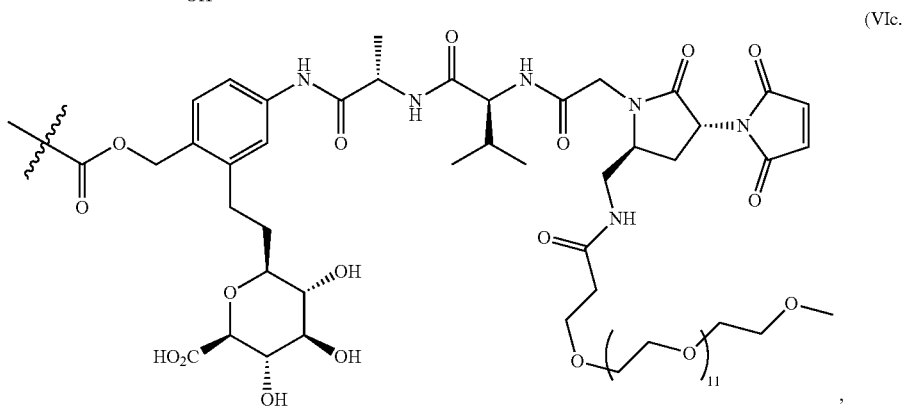

(VIc.6)

wherein ⌇ represents the point of attachment of the linker to an immune-stimulatory compound.

A linker can be attached to an antibody or antigen-binding fragment thereof at any suitable position. Factors to be considered in selecting an attachment site include whether the linker is cleavable or non-cleavable, the reactive group of the linker for attachment to the antibody or antigen-binding fragment thereof, the chemical nature of the immune-stimulatory compound and compatibility with reactive sites on the linker and the antibody or antigen-binding fragment thereof, and the effect of the attachment site on functional activities of the Fc domain. A linker may be attached to a terminus of an amino acid sequence of an antibody or antigen-binding fragment thereof or can be attached to a side chain of an amino acid of an antibody or antigen-binding fragment thereof, such as the side chain of a lysine, serine, threonine, cysteine, tyrosine, aspartic acid, glutamine, a non-natural amino acid residue, or glutamic acid residue. A linker may be bound to a terminus of an amino acid sequence of an Fc domain or Fc region of an antibody or antigen-binding fragment thereof, or may be bound to a side chain of an amino acid of an Fc domain of an antibody or antigen-binding fragment thereof, such as the side chain of a lysine, serine, threonine, cysteine, tyrosine, aspartic acid, glutamine, a non-natural amino acid residue, or glutamic acid residue.

In some embodiments, a linker is attached to a hinge cysteine of an antibody Fc domain. A linker can be attached to an antibody or antigen-binding fragment thereof at a light chain constant domain lysine. A linker can be attached to an antibody or antigen-binding fragment thereof at an engineered cysteine in the light chain. A linker can be attached to an antibody or antigen-binding fragment thereof at an engineered light chain glutamine. A linker can be attached to an antibody or antigen-binding fragment thereof at an unnatural amino acid engineered into the light chain. A linker can be attached to an antibody or antigen-binding fragment thereof at a heavy chain constant domain lysine. A linker can be attached to an antibody or antigen-binding fragment thereof at an engineered cysteine in the heavy chain. A linker can be attached to an antibody or antigen-binding fragment thereof at an engineered heavy chain glutamine. A linker can be attached to an antibody or antigen-binding fragment thereof at an unnatural amino acid engineered into the heavy chain. Amino acids can be engineered into an amino acid sequence of an antibody or antigen-binding fragment thereof as described herein or as known to the skilled artisan and can be connected to a linker of a conjugate. Engineered amino acids can be added to a sequence of existing amino acids. Engineered amino acids can be substituted for one or more existing amino acids of a sequence of amino acids.

A linker can be attached to an antibody or antigen-binding fragment thereof via a sulfhydryl group. A linker can be attached to an antibody or antigen-binding fragment thereof via a primary amine. A linker can be a link created between an unnatural amino acid on an antibody by reacting with oxime bond that was formed by modifying a ketone group with an alkoxyamine on an immune stimulatory compound.

As is known by skilled artisans, the linker selected for a particular conjugate may be influenced by a variety of factors, including but not limited to, the site of attachment to the antibody or antigen-binding fragment thereof (e.g., lys, cys or other amino acid residues), structural constraints of the drug pharmacophore and the lipophilicity of the drug. The specific linker selected for a conjugate should seek to balance these different factors for the specific antibody/drug combination.

For example, conjugates have been observed to effect killing of bystander antigen-negative cells present in the vicinity of the antigen-positive tumor cells. The mechanism of bystander cell killing by conjugates has indicated that metabolic products formed during intracellular processing of the conjugates may play a role. Neutral cytotoxic metabolites generated by metabolism of the conjugates in antigen-positive cells appear to play a role in bystander cell killing while charged metabolites may be prevented from diffusing across the membrane into the medium, or from the medium across the membrane, and therefore cannot affect bystander killing. In certain embodiments, the linker is selected to attenuate the bystander effect caused by cellular metabolites of the conjugate. In certain embodiments, the linker is selected to increase the bystander effect.

The properties of the linker, or linker-compound, may also impact aggregation of the conjugate under conditions of use and/or storage. Typically, conjugates reported in the literature contain no more than 3-4 drug molecules per antibody molecule. Attempts to obtain higher drug-to-antibody ratios ("DAR") often failed, particularly if both the drug and the linker were hydrophobic, due to aggregation of the conjugate. In many instances, DARs higher than 3-4 could be beneficial as a means of increasing potency. In instances where an immune-stimulatory compound is more hydrophobic in nature, it may be desirable to select linkers that are relatively hydrophilic as a means of reducing conjugate aggregation, especially in instances where DARs greater than 3-4 are desired. Thus, in certain embodiments, a linker incorporates chemical moieties that reduce aggregation of the conjugates during storage and/or use. A linker may incorporate polar or hydrophilic groups such as charged groups or groups that become charged under physiological pH to reduce the aggregation of the conjugates. For example, a linker may incorporate charged groups such as salts or groups that deprotonate, e.g., carboxylates, or protonate, e.g., amines, at physiological pH.

In particular embodiments, the aggregation of the conjugates during storage or use is less than about 40% as determined by size-exclusion chromatography (SEC). In particular embodiments, the aggregation of the conjugates during storage or use is less than 35%, such as less than about 30%, such as less than about 25%, such as less than about 20%, such as less than about 15%, such as less than about 10%, such as less than about 5%, such as less than about 4%, or even less, as determined by size-exclusion chromatography (SEC).

Conjugates

A conjugate as described herein comprises an anti-Nectin-4 antibody or an antigen-binding fragment thereof and at least one linker attached to at least one immune-stimulatory compound, such as a myeloid cell agonist or other agonist (e.g., TLR8 agonist, TLR7 agonist, other TLR agonist, STING agonist, RIG-I-Like receptor agonist, c-type lectin receptors agonist, or cytosolic DNA Sensors agonist). In some aspects, the present disclosure provides a conjugate represented by Formula I:

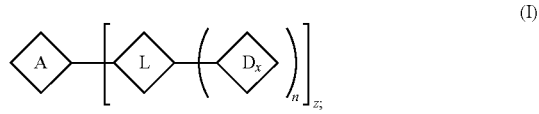

(I)

wherein. A is the anti-Nectin-4 antibody or an antigen-binding fragment thereof, L is the linker; $D_x$ is the immune-stimulatory compound; n is selected from 1 to 20; and z is selected from 1 to 20.

In some embodiments, the immune-stimulatory compound is a myeloid cell agonist. In some embodiments, the immune-stimulatory compound is a TLR8 agonist. In some embodiments, the immune-stimulatory compound is a TLR7 agonist. In some embodiments, the immune-stimulatory compound is a TLR3 agonist. In some embodiments, the immune-stimulatory compound is a TLR4 agonist. In some embodiments, the immune-stimulatory compound is a TLR5 agonist. In some embodiments, the immune-stimulatory compound is a TLR9 agonist. In some embodiments, the immune-stimulatory compound is a STING agonist. Exemplary STING agonist compounds include RG7854, ADU-S100, MK-1454, MK-2118, BMS-986301, GSK3745417, SB-11285, and IMSA-101. In some embodiments, the immune-stimulatory compound is a RIG-I-Like receptor agonist. In some embodiments, the immune-stimulatory compound is a c-type lectin receptors agonist. In some embodiments, the immune-stimulatory compound is a cytosolic DNA Sensors agonist.

In some aspects, the present disclosure provides a conjugate comprising at least one immune-stimulatory compound (e.g., a compound or salt thereof), an anti-Nectin-4 antibody or an antigen-binding fragment thereof, and at least one linker, wherein each immune-stimulatory compound is linked, i.e., covalently bound, to the anti-Nectin-4 antibody or an antigen-binding fragment thereof through a linker. The linker can be selected from a cleavable or non-cleavable linker. In some embodiments, the linker is cleavable. In other embodiments, the linker is non-cleavable. Linkers are further described in the present application in the preceeding section, any one of which can be used to connect an antibody or antigen-binding fragment thereof to an immune-stimulatory compound.

In a conjugate, the drug loading is represented by z, the number of immune-stimulatory compound-linker molecules per antibody, or the number of immune-stimulatory compounds per antibody, depending on the particular conjugate. Depending on the context, z can represent the average number of immune-stimulatory compound(-linker) molecules per antibody, also referred to the average drug loading, z can range from 1 to 20, from 1-50 or from 1-100. In some conjugates, z is preferably from 1 to 8. In some preferred embodiments, when z represents the average drug loading, z ranges from about 2 to about 5. In some embodiments, z is about 2, about 3, about 4, or about 5. The average number of immune-stimulatory compounds per antibody in a preparation of conjugate may be characterized by conventional means such as mass spectroscopy, liquid chromatography/mass spectrometry (LC/MS), HIC, ELISA assay, and HPLC.

A number of conjugates are consistent with the disclosure herein. The conjugates generally comprise an immune-stimulatory compound covalently bound to an anti-Nectin-4 antibody or an antigen-binding fragment thereof that localizes the conjugate to a target tissue, cell population or cell. The anti-Nectin-4 antibody or an antigen-binding fragment thereof is covalently attached to each immune-stimulatory compound, either directly or through a linker that tethers the immune-stimulatory compound to the anti-Nectin-4 antibody or an antigen-binding fragment thereof. Anti-Nectin-4 antibodies or an antigen-binding fragments thereof listed herein as well as are consistent with the conjugates as disclosed herein.

Some exemplary conjugates are as follows. A conjugate can comprise an anti-Nectin-4 antibody or an antigen-binding fragment thereof of this disclosure, at least one immune-stimulatory compound, and optionally at least one linker. A conjugate can comprise an anti-Nectin-4 antibody or an antigen-binding fragment thereof of this disclosure, at least one TLR7 agonist, and at least one linker. A conjugate can comprise an anti-Nectin-4 antibody or an antigen-binding fragment thereof of this disclosure, at least one TLR8 agonist, and at least one linker. A conjugate can comprise an anti-Nectin-4 antibody or an antigen-binding fragment thereof of this disclosure, at least one compound of Category A (TLR8 agonists), and at least one linker. A conjugate can comprise an anti-Nectin-4 antibody or an antigen-binding fragment thereof of this disclosure, at least one compound of Category B (TLR7 agonists), and at least one linker. A conjugate can comprise an anti-Nectin-4 antibody or an antigen-binding fragment thereof of this disclosure, at least one compound of Category C (TLR8 agonists), and at least one linker. A conjugate can comprise an anti-Nectin-4 antibody or an antigen-binding fragment thereof of this disclosure, at least one TLR3 agonist, and at least one linker. A conjugate can comprise an anti-Nectin-4 antibody or an antigen-binding fragment thereof of this disclosure, at least one TLR4 agonist, and at least one linker. A conjugate can comprise an anti-Nectin-4 antibody or an antigen-binding fragment thereof of this disclosure, at least one TLR5 agonist, and at least one linker. A conjugate can comprise an anti-Nectin-4 antibody or an antigen-binding fragment thereof of this disclosure, at least one TLR9 agonist, and at least one linker. A conjugate can comprise an anti-Nectin-4 antibody or an antigen-binding fragment thereof of this disclosure, at least one STING agonist, and at least one linker. A conjugate can comprise an anti-Nectin-4 antibody or an antigen-binding fragment thereof of this disclosure, at least one RIG-I agonist, and at least one linker. A conjugate can comprise an anti-Nectin-4 antibody or an antigen-binding fragment thereof of this disclosure, at least one c-type lectin receptor agonist, and at least one linker. A conjugate can comprise an anti-Nectin-4 antibody or an antigen-binding fragment thereof of this disclosure, at least one cytosolic DNA Sensors agonist, and at least one linker.

Exemplary Conjugates

In certain embodiments, the disclosure provides an immune-stimulatory conjugate (or conjugate) of an anti-Nectin-4 antibody or an antigen-binding fragment thereof and at least one compound of any one of Category A Formulas (IA), (IB), (IIA), (IIB), (IIC), (IIIA), (IIIB), (IVA), (IVB), and (IVC), each compound optionally attached to the antibody or an antigen-binding fragment via a linker. In certain embodiments, the disclosure provides an immune-stimulatory conjugate of an anti-Nectin-4 antibody or an antigen-binding fragment thereof and at least one compound of any one of Category B Formulas (IA), (IB), (IC), (IIA), (IIB), and (IIC), each compound optionally attached to the antibody or an antigen-binding fragment via a linker. In certain embodiments, the disclosure provides an immune-stimulatory conjugate of an anti-Nectin-4 antibody or an antigen-binding fragment thereof of this disclosure and at least one compound of any one of Category C Formulas Ia-Ih each compound optionally attached to the antibody or an antigen-binding fragment via a linker. In certain embodiments, the average Drug-to-Antibody Ratio (DAR) of the pharmaceutical composition comprising a conjugate of an anti-Nectin-4 antibody or an antigen-binding fragment thereof of this disclosure is selected from 1 to about 8, 2 to about 6, about 3 to about 5, or about 4.

In certain embodiments, the disclosure provides a pharmaceutical composition suitable for intravenous or subcutaneous administration, comprising an immune stimulatory compound of any one of Category A Formulas (IA), (IB), (IIA), (IIB), (IIC), (IIIA), (IIIB), (IVA), (IVB), and (IVC) conjugated to an anti-Nectin-4 antibody or an antigen-binding fragment thereof of this disclosure, and a pharmaceutically acceptable excipient. In certain embodiments, the disclosure provides a pharmaceutical composition suitable for intravenous or subcutaneous administration, comprising an immune stimulatory compound of any one of Category B Formulas (IA), (IB), (IC), (IIA), (IIB), and (IIC) conjugated to an anti-Nectin-4 antibody or an antigen-binding fragment thereof of this disclosure, and a pharmaceutically acceptable excipient. In certain embodiments, the disclosure provides a pharmaceutical composition suitable for intravenous or subcutaneous administration, comprising an immune stimulatory compound of any one of Category C Formulas Ia-Ih conjugated to an anti-Nectin-4 antibody or an antigen-binding fragment thereof of this disclosure, and a pharmaceutically acceptable excipient. In certain embodiments, the average Drug-to-Antibody Ratio (DAR) of a pharmaceutical composition of the aforementioned conjugates is selected from 1 to about 8, 2 to about 6, about 3 to about 5, or about 4.

In certain embodiments, the disclosure provides a method for the treatment of a disease treatable by a TLR agonist (e.g., cancer) comprising subcutaneously administering an effective amount of a conjugate of a compound of any one of Category A Formulas (IA), (IB), (IIA), (IIB), (IIC), (IIIA), (IIIB), (IVA), (IVB), and (IVC), or a pharmaceutical composition thereof suitable for intravenous or subcutaneous administration to a subject in need thereof. In certain embodiments, the disclosure provides a method for the treatment of cancer (e.g., bladder, breast, lung, head and neck, cervical), comprising intravenously or subcutaneously administering an effective amount of the conjugate of a compound of any one of Category B Formulas (I A), (IB), (IC), (IIA), (IIB), and (IIC), or a pharmaceutical composition thereof suitable for subcutaneous administration to a subject in need thereof. In certain embodiments, the disclosure provides a method for the treatment of cancer (e.g., bladder, breast, lung, head and neck, cervical), comprising intravenously or subcutaneously administering an effective amount of the conjugate of a compound of any one of Category C Formulas Ia-Ih, or a pharmaceutical composition thereof suitable for subcutaneous administration to a subject in need thereof. In any of the embodiments herein, the conjugate may be administered by slow infusion.

The disclosure provides a method of preparing an antibody conjugate of the formula:

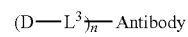

wherein:

n is selected from 1 to 20;

$L^3$ is a linker; and

D is selected from a compound or salt of a compound of any one of Category A Formulas (IA), (IB), (IIA), (IIB), (IIC), (IIIA), (IIIB), (IVA), (IVB), and (IVC); Category B Formulas (IA), (IB), (IC), (IIA), (IIB), and (IIC); and Category C Formulas (Ia), (Ib), (Ic), (Id), (Ie), (If), (Ig) and (Ih), comprising contacting D-$L^3$ with an anti-Nectin-4 antibody or an antigen-binding fragment thereof.

The disclosure provides a method of preparing an anti-Nectin-4 antibody or an antigen-binding fragment thereof conjugate of the formula:

$(D-L^3)_n$—Antibody wherein: n is selected from 1 to 20; $L^3$ is a linker; and D is selected from a compound of any one of Category A Formulas (IA), (IB), (IIA), (IIB), (IIC), (IIIA), (IIIB), (IVA), (IVB), and (IVC); Category B Formulas (IA), (IB), (IC), (IIA), (IIB), and (IIC); and Category C Formulas (Ia), (Ib), (Ic), (Id), (Ie), (If), (Ig) and (Ih), comprising contacting $L^3$ with the anti-Nectin-4 antibody or an antigen-binding fragment thereof to form $L^3$-anti-Nectin-4 antibody or antigen-binding fragment thereof and contacting $L^3$-anti-Nectin-4 antibody or an antigen-binding fragment thereof with D to form the conjugate.

In certain embodiments, the present disclosure provides a myeloid cell agonist conjugate or salt thereof represented by the formula:

$(D-L^3)_{1\text{-}8}$ Antibody, wherein Antibody is an anti-Nectin-4 antibody comprising:

(a) a light chain CDR1, CDR2 and CDR3 set forth in the light chain variable region amino acid sequence of SEQ ID NO: 14 or 13, a light chain constant region comprising SEQ ID NO:20, heavy chain CDR1, CDR2 and CDR3 set forth in the heavy chain variable region amino acid sequence of SEQ ID NO: 10, and a heavy chain constant region comprising SEQ ID NO: 18, or (b) a light chain comprising the amino acid sequence of SEQ ID NO:28 and a heavy chain comprising the amino acid sequence of SEQ ID NO:24, or (c) a light chain comprising the amino acid sequence of SEQ ID NO:27 and a heavy chain comprising the amino acid sequence of SEQ ID NO:24; and $L^3$-D is a linker-TLR8 agonist and has the structure:

,

, or wherein RX s a bond, a succinimide moiety, or a hydrolyzed succinimide moiety bound to a residue of the antibody construct, wherein i

on RX* represents the point of attachment to a cysteine residue of the antibody construct. In certain embodiments, L³-D has the structure:

In certain such embodiments, RX* is a succinamide moiety or a hydrolyzed succinamide moiety.

The compounds disclosed herein, in some embodiments, are used in different enriched isotopic forms, e.g., enriched in the content of ²H, ³H, ¹¹C, ¹³C and/or ¹⁴C. In particular embodiments, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the

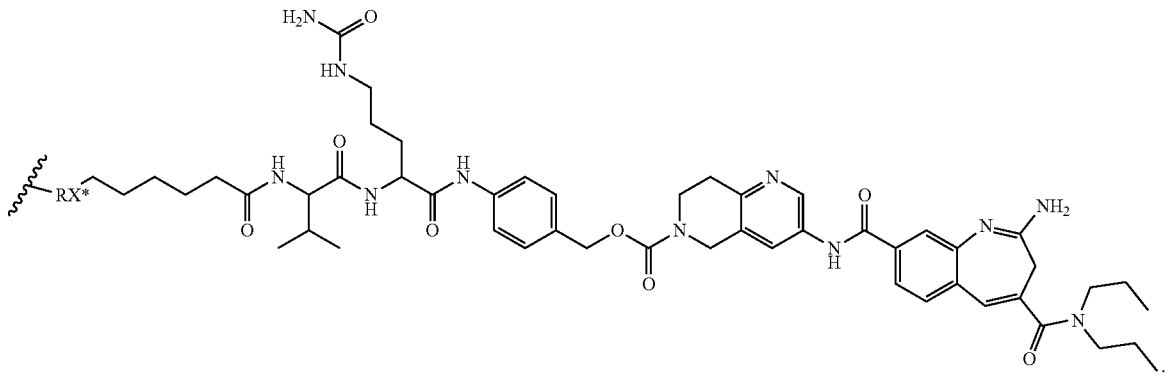

In other embodiments, L³-D has the structure:

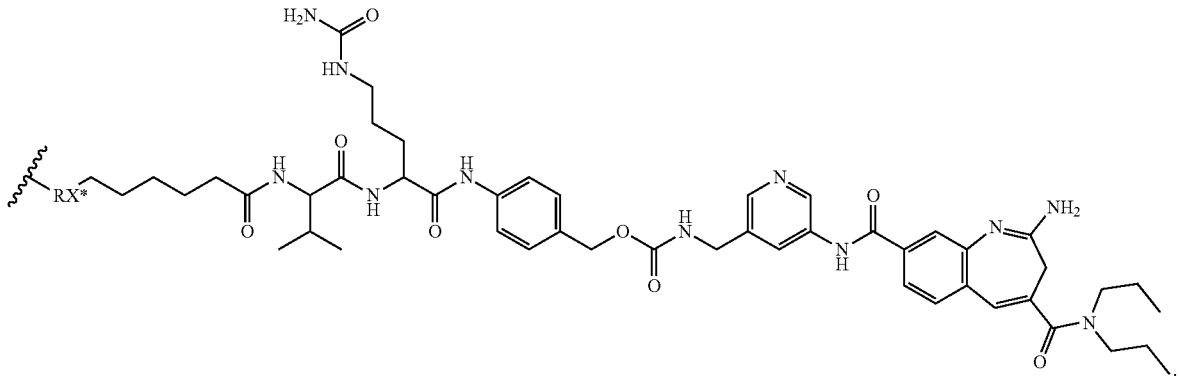

In still other embodiments, L³-D has the structure:

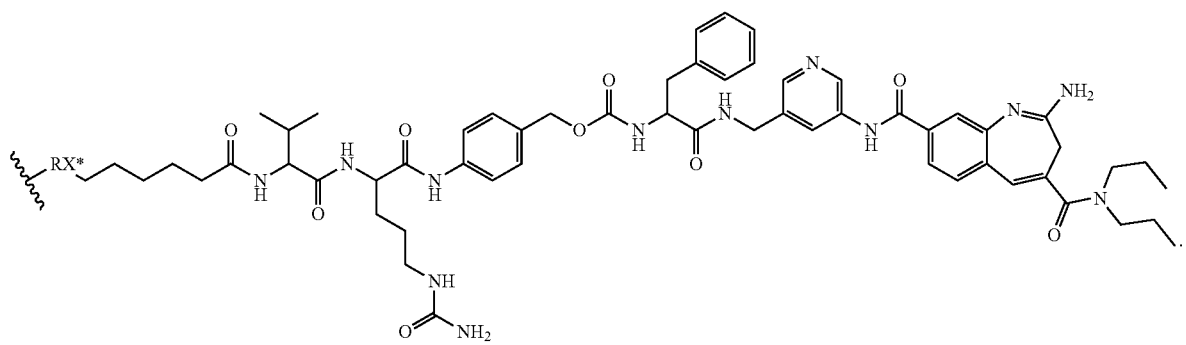

presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds.

For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present disclosure, whether radioactive or not, are encompassed within the scope of the present disclosure.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr. Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley and Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds described herein may be prodrugs attached to anti-Nectin-4 antibodies to form conjugates. The term "prodrug" is intended to encompass compounds which, under physiologic conditions, are converted into active compounds, e.g., TLR8 agonists, TLR7 agonists, other TLR agonists, STING agonist, RIG-I-Like receptor agonists, c-type lectin receptors agonists, or cytosolic DNA Sensors agonists. One method for making a prodrug is to include one or more selected moieties which are hydrolyzed or otherwise cleaved under physiologic conditions to reveal the desired molecule. In other embodiments, the prodrug is converted by an enzymatic activity of the host animal such as specific target cells in the host animal.

Prodrug forms of the herein described compounds, wherein the prodrug is metabolized in vivo to produce a compound described herein are included within the scope of the claims. In some cases, some of the herein-described compounds may be a prodrug for another derivative or active compound.

In certain embodiments, an immune-stimulatory compound, such as a TLR8 agonist or TLR7 agonist, is modified as a prodrug with a masking group, such that the TLR8 agonist, TLR7 agonist or other agonist, has limited activity or is inactive until it reaches an environment where the masking group is removed to reveal the active compound. For example, a TLR8 agonist or TLR7 agonist can be covalently modified at an amine involved in binding to the active site of a TLR8 receptor such that the compound is unable to bind the active site of the receptor in its modified (prodrug) form. In such an example, the masking group is removed under physiological conditions, e.g., enzymatic or acidic conditions, specific to the site of delivery, e.g., intracellular or extracellular adjacent to target cells. Masking groups may be removed from the amine of the compound or salt described herein due to the action of lysosomal proteases, e.g., cathepsin and plasmin. These proteases can be present at elevated levels in certain tumor tissues. The masking group may be removed by a lysosomal enzyme. The lysosomal enzyme can be, for example, cathepsin B, cathepsin S, β-glucuronidase, or β-galactosidase.

In certain embodiments, an amine masking group inhibits binding of the amine group of the compound with residues of a TLR8 receptor. The amine masking group may be removable under physiological conditions within a cell but remains covalently bound to the amine outside of a cell. Masking groups that may be used to inhibit or attenuate binding of an amine group of a compound with residues of a TLR8 receptor include, for example, peptides and carbamates.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M.

Fieser, *Fieser and Fieser's Reagents for Organic Synthesis* (1994); and L. Paquette, ed., *Encyclopedia of Reagents for Organic Synthesis* (1995).

Exemplary TLR8 and TLR7 agonists are provided herein. In some embodiments, a myeloid cell agonist-linker compound (Linker-Payload) is selected from any of Linker-Payloads provided herein. Examples of TLR8 agonist linker-compounds are provided in Table 2 and their stereoisomers. Examples of TLR7 agonist linker-compounds are provided in Table 4 and their stereoisomers. It is understood that for the compounds provided in Tables 2 and 4, salts of the compounds are also contemplated.

TABLE 2

TLR8 agonist Linker-Compounds 2.1-2.22

| Linker-Compound | Structure |
|---|---|
| 2.1 | 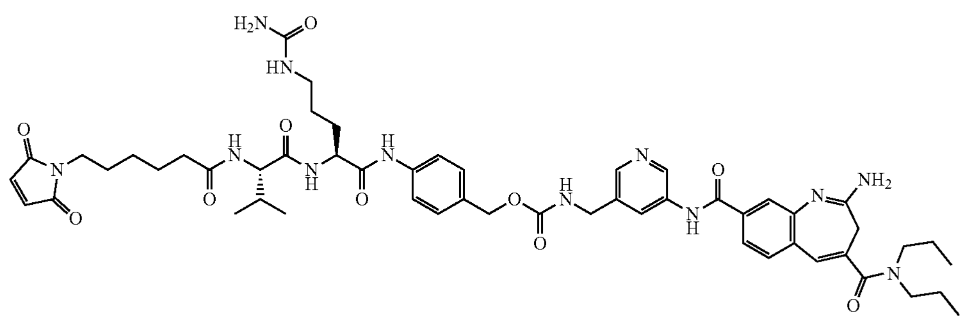 [SMILES: CCCN(CCC)C(=O)C1=Cc2ccc(C(=O)Nc3cncc(CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1] |
| 2.2 | 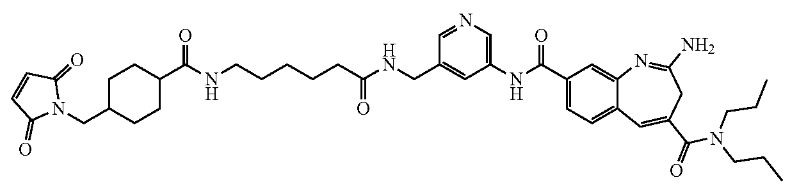 [SMILES: CCCN(CCC)C(=O)C1=Cc2ccc(C(=O)Nc3cncc(CNC(=O)CCCCCNC(=O)C4CCC(CN5C(=O)C=CC5=O)CC4)c3)cc2N=C(N)C1] |
| 2.3 | 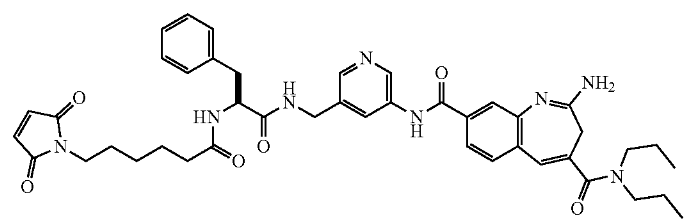 |
| 2.4 | 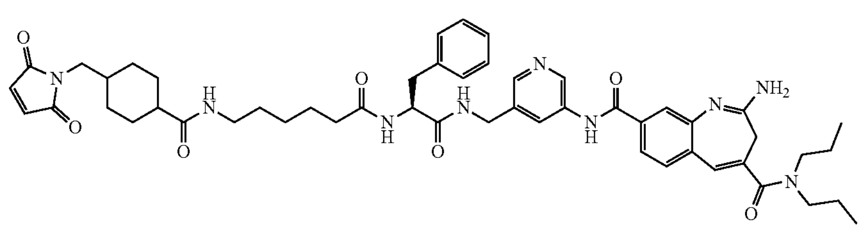 [SMILES: CCCN(CCC)C(=O)C1=Cc2ccc(C(=O)Nc3cncc(CNC(=O)[C@H](Cc4ccccc4)NC(=O)CCCCCNC(=O)C4CCC(CN5C(=O)C=CC5=O)CC4)c3)cc2N=C(N)C1] |
| 2.5 | 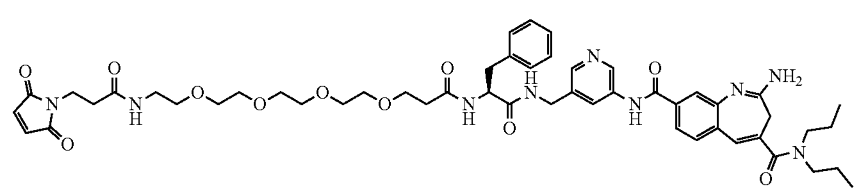 [SMILES: CCCN(CCC)C(=O)C1=Cc2ccc(C(=O)Nc3cncc(CNC(=O)[C@H](Cc4ccccc4)NC(=O)CCOCCOCCOCCOCCNC(=O)CCN4C(=O)C=CC4=O)c3)cc2N=C(N)C1] |

TABLE 2-continued

TLR8 agonist Linker-Compounds 2.1-2.22

| Linker-Compound | Structure |
|---|---|
| 2.6 | 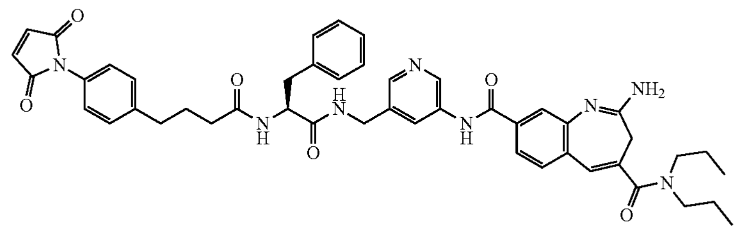 [SMILES: CCCN(CCC)C(=O)C1=Cc2ccc(C(=O)Nc3cncc(CNC(=O)[C@H](Cc4ccccc4)NC(=O)CCCc4ccc(N5C(=O)C=CC5=O)cc4)c3)cc2N=C(N)C1] |
| 2.7 | 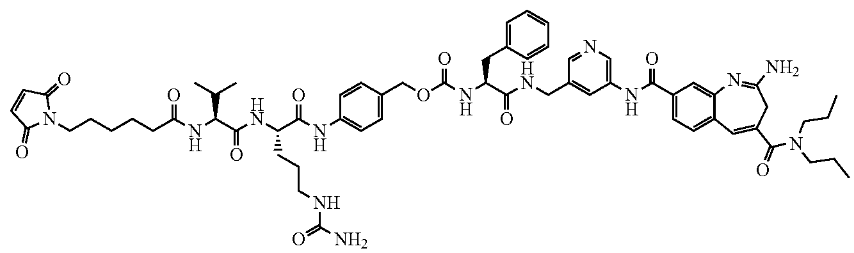 [SMILES: CCCN(CCC)C(=O)C1=Cc2ccc(C(=O)Nc3cncc(CNC(=O)[C@H](Cc4ccccc4)NC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1] |
| 2.8 | 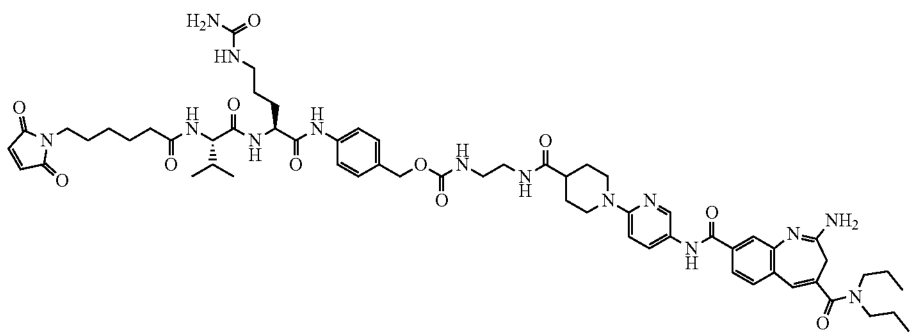 [SMILES: CCCN(CCC)C(=O)C1=Cc2ccc(C(=O)Nc3ccc(N4CCC(C(=O)NCCNC(=O)OCc5ccc(NC(=O)[C@H](CCCNC(N)=O)NC(=O)[C@@H](NC(=O)CCCCCN6C(=O)C=CC6=O)C(C)C)cc5)CC4)nc3)cc2N=C(N)C1] |
| 2.9 | 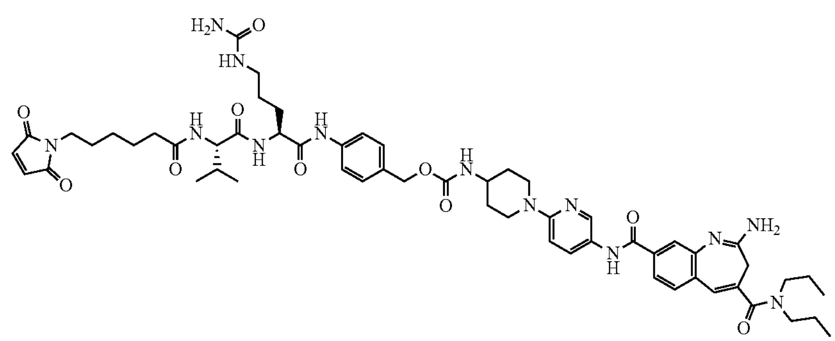 [SMILES: CCCN(CCC)C(=O)C1=Cc2ccc(C(=O)Nc3ccc(N4CCC(NC(=O)OCc5ccc(NC(=O)[C@H](CCCNC(N)=O)NC(=O)[C@@H](NC(=O)CCCCCN6C(=O)C=CC6=O)C(C)C)cc5)CC4)nc3)cc2N=C(N)C1] |
| 2.10 | 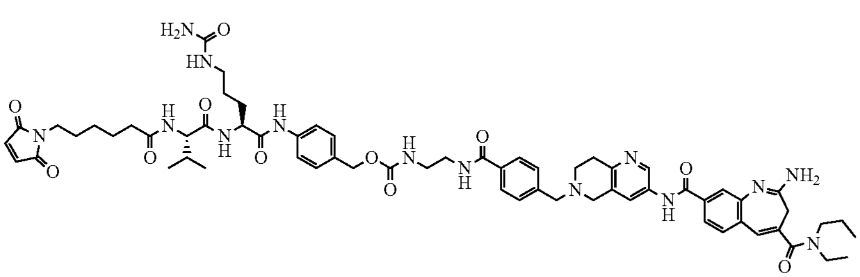 [SMILES: CCCN(CC)C(=O)C1=Cc2ccc(C(=O)Nc3cnc4c(c3)CN(Cc3ccc(C(=O)NCCNC(=O)OCc5ccc(NC(=O)[C@H](CCCNC(N)=O)NC(=O)[C@@H](NC(=O)CCCCCN6C(=O)C=CC6=O)C(C)C)cc5)cc3)CC4)cc2N=C(N)C1] |

TABLE 2-continued

TLR8 agonist Linker-Compounds 2.1-2.22

| Linker-Compound | Structure |
| --- | --- |
| 2.11 | 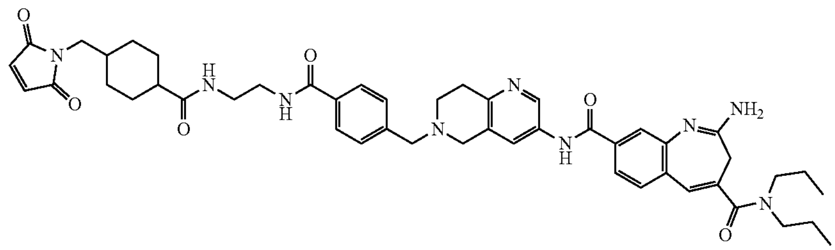 [SMILES: CCCN(CCC)C(=O)C1=Cc2ccc(C(=O)Nc3cnc4c(c3)CN(Cc3ccc(C(=O)NCCNC(=O)C5CCC(CN6C(=O)C=CC6=O)CC5)cc3)CC4)cc2N=C(N)C1] |
| 2.12 | 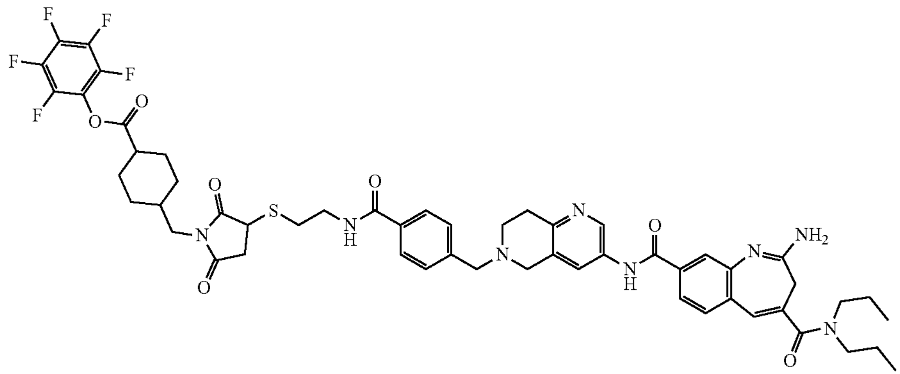 [SMILES: CCCN(CCC)C(=O)C1=Cc2ccc(C(=O)Nc3cnc4c(c3)CN(Cc3ccc(C(=O)NCCSC5CC(=O)N(CC6CCC(C(=O)Oc7c(F)c(F)c(F)c(F)c7F)CC6)C5=O)cc3)CC4)cc2N=C(N)C1] |
| 2.14 | 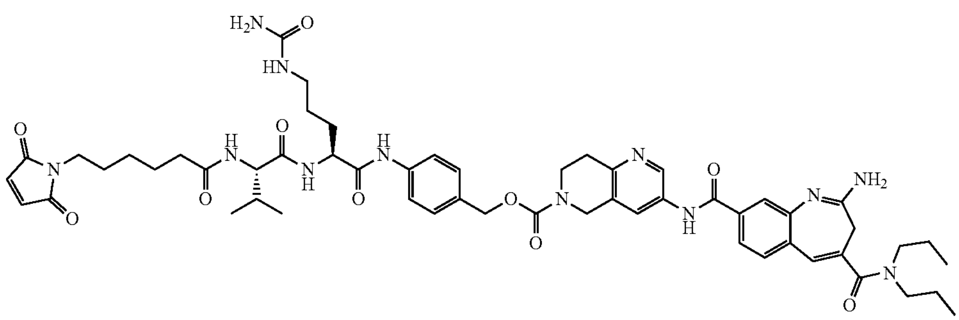 [SMILES: CCCN(CCC)C(=O)C1=Cc2ccc(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1] |
| 2.15 | 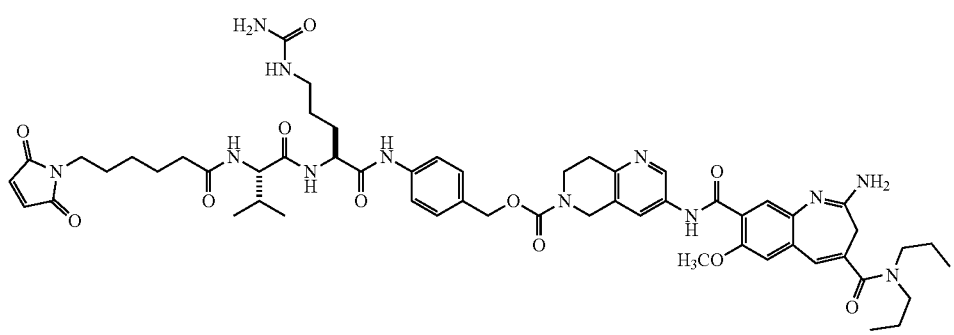 [SMILES: CCCN(CCC)C(=O)C1=Cc2cc(OC)c(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1] |

TABLE 2-continued

TLR8 agonist Linker-Compounds 2.1-2.22

| Linker-Compound | Structure |
| --- | --- |
| 2.16 | 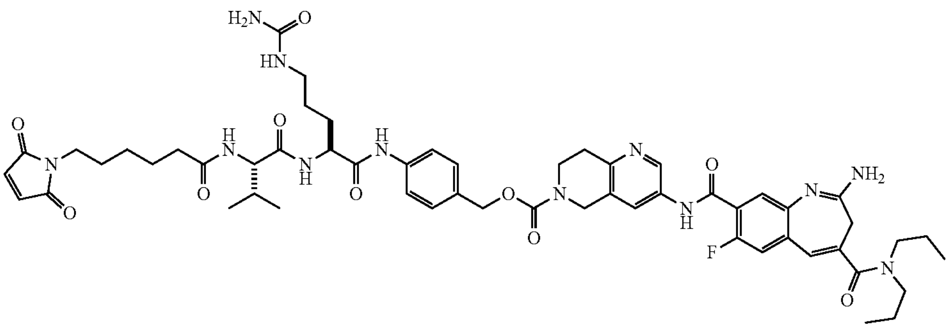 [SMILES: CCCN(CCC)C(=O)C1=Cc2cc(F)c(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1] |
| 2.17 | 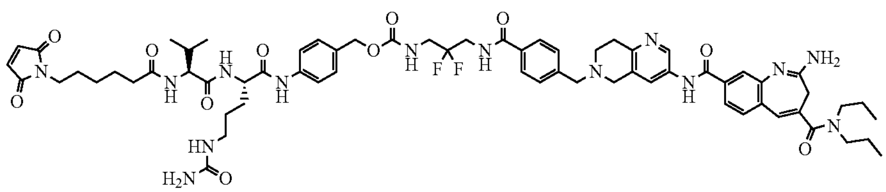 [SMILES: CCCN(CCC)C(=O)C1=Cc2ccc(C(=O)Nc3cnc4c(c3)CN(Cc3ccc(C(=O)NCC(F)(F)CNC(=O)OCc5ccc(NC(=O)[C@H](CCCNC(N)=O)NC(=O)[C@@H](NC(=O)CCCCCN6C(=O)C=CC6=O)C(C)C)cc5)cc3)CC4)cc2N=C(N)C1] |
| 2.20 | 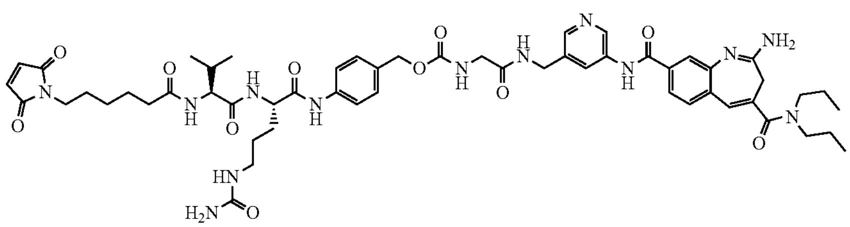 [SMILES: CCCN(CCC)C(=O)C1=Cc2ccc(C(=O)Nc3cncc(CNC(=O)CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1] |
| 2.21 | 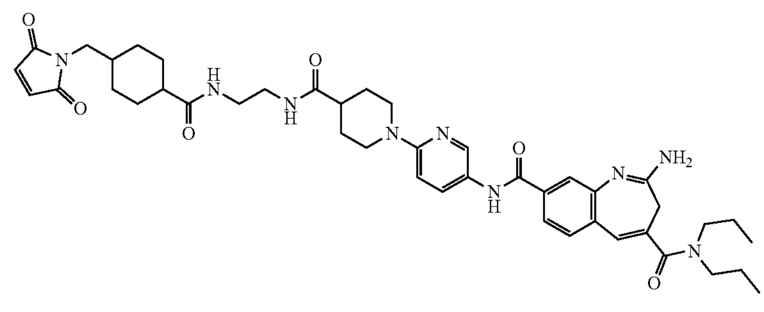 [SMILES: CCCN(CCC)C(=O)C1=Cc2ccc(C(=O)Nc3ccc(N4CCC(C(=O)NCCNC(=O)C5CCC(CN6C(=O)C=CC6=O)CC5)CC4)nc3)cc2N=C(N)C1] |
| 2.22 | 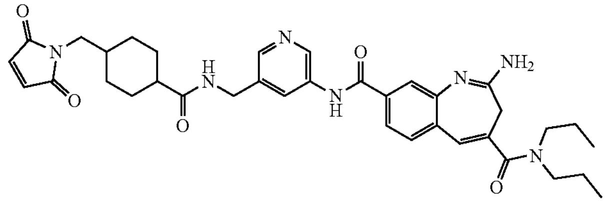 [SMILES: CCCN(CCC)C(=O)C1=Cc2ccc(C(=O)Nc3cncc(CNC(=O)C4CCC(CN5C(=O)C=CC5=O)CC4)c3)cc2N=C(N)C1] |

TABLE 4

TLR7 Agonist Linker-Compounds 4.1-4.20

| Linker-Compound | Structure |
|---|---|
| 4.1 | 4-((S)-24(S)-2-(6-(2,5-dioxo-2,5-dihydro-1H-pyrrol-1-yl)hexanamido)-3-methylbutanamido)-5-ureidopentanamido)benzyl (1-((2-((1-(4-amino-2-(ethoxymethyl)-1H-imidazo[4,5-c]quinolin-1-yl)-2-methylpropan-2-yl)oxy)ethyl)amino)-2-methyl-1-oxopropan-2-yl)carbamate |
| 4.2 | tert-butyl (2-((2-(((S)-1-((2-(((1-(1-(4-((S)-2-((S)-2-(6-(2,5-dioxo-2,5-dihydro-1H-pyrrol-1-yl)hexanamido)-3-methylbutanamido)-5-ureidopentanamido)phenyl)-5,5,11,11-tetramethyl-3,6-dioxo-2,10-dioxa-4,7-diazadodecan-12-yl)-2-(ethoxymethyl)-1H-imidazo[4,5-c]quinolin-4-yl)amino)-2-oxoethyl)amino)-1-oxo-3-phenylpropan-2-yl)amino)-2-oxoethyl)carbamate |
| 4.3 | N-(1-((2-((1-(4-amino-2-(ethoxymethyl)-1H-imidazo[4,5-c]quinolin-1-yl)-2-methylpropan-2-yl)oxy)ethyl)amino)-2-methyl-1-oxopropan-2-yl)-6-(2,5-dioxo-2,5-dihydro-1H-pyrrol-1-yl)hexanamide |

TABLE 4-continued

TLR7 Agonist Linker-Compounds 4.1-4.20

| Linker-Compound | Structure |
| --- | --- |
| 4.4 | N-(2-((1-(4-amino-2-(ethoxymethyl)-1H-imidazo[4,5-c]quinolin-1-yl)-2-methylpropan-2-yl)oxy)ethyl)-2-(3-(2,5-dioxo-2,5-dihydro-1H-pyrrol-1-yl)propanamido)-2-methylpropanamide |
| 4.5 | N-(2-((1-(4-amino-2-(ethoxymethyl)-1H-imidazo[4,5-c]quinolin-1-yl)-2-methylpropan-2-yl)oxy)ethyl)-3-(2,5-dioxo-2,5-dihydro-1H-pyrrol-1-yl)propanamide |
| 4.6 | N-(2-((1-(4-amino-2-(ethoxynnethyl)-1H-imidazo[4,5-c]quinolin-1-yl)-2-methylpropan-2-yl)oxy)ethyl)-6-(2,5-dioxo-2,5-dihydro-1H-pyrrol-1-yl)hexanamide |

TABLE 4-continued

TLR7 Agonist Linker-Compounds 4.1-4.20

| Linker-Compound | Structure |
|---|---|
| 4.7 | 4-((S)-2-((S)-2-(6-(2,5-dioxo-2,5-dihydro-1H-pyrrol-1-yl)hexanamido)-3-methylbutanamido)-5-ureidopentanamido) benzyl(2-((1-(4-amino-2-(ethoxymethyl)-1H-imidazo[4,5-c]quinolin-1-yl)-2-methylpropan-2-yl)oxy)ethyl)carbamate |
| 4.8 | (9H-fluoren-9-yl)methyl ((S)-1-(((S)-1-((1-(2-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)amino)-1-oxo-5-ureidopentan-2-yl)amino)-3-methyl-1-oxobutan-2-yl)carbamate |
| 4.9 | tert-butyl (S)-(1-((1-(2-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)amino)-3-methyl-1-oxobutan-2-yl)carbamate |

TABLE 4-continued

TLR7 Agonist Linker-Compounds 4.1-4.20

| Linker-Compound | Structure |
|---|---|
| 4.10 | 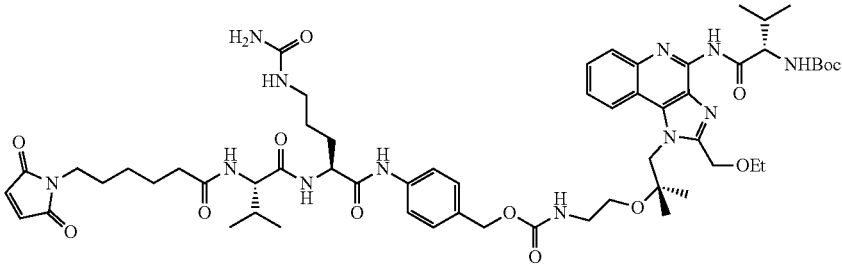<br>tert-butyl ((S)-1-((1-(2-(2-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methylpropyl)-2-(ethoxymethyl)-1H-imidazo[4,5-c]quinolin-4-yl)amino)-3-methyl-1-oxobutan-2-yl)carbamate |
| 4.11 | 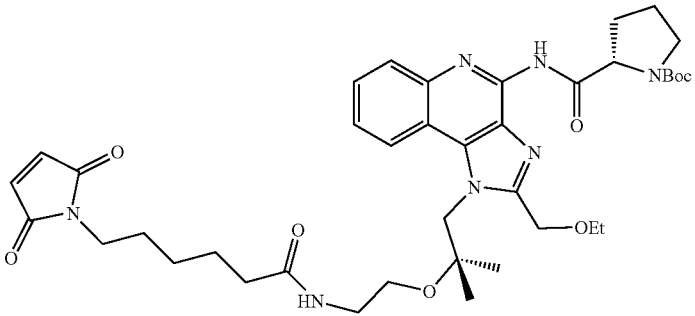<br>tert-butyl (S)-2-((1-(2-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)carbamoyl)pyrrolidine-1-carboxylate |
| 4.12 | 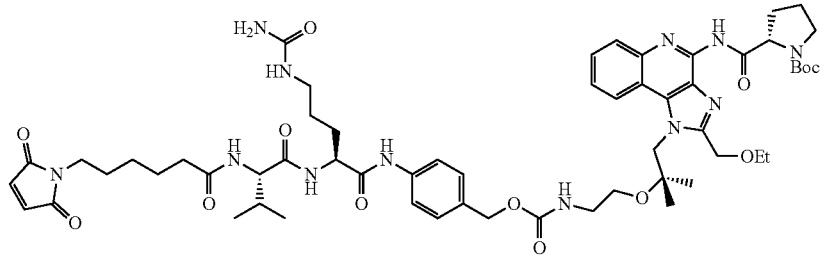<br>tert-butyl (S)-2-((1-(2-(2-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methylpropyl)-2-(ethoxymethyl)-1H-imidazo[4,5-c]quinolin-4-yl)carbamoyl)pyrrolidine-1-carboxylate |
| 4.13 | 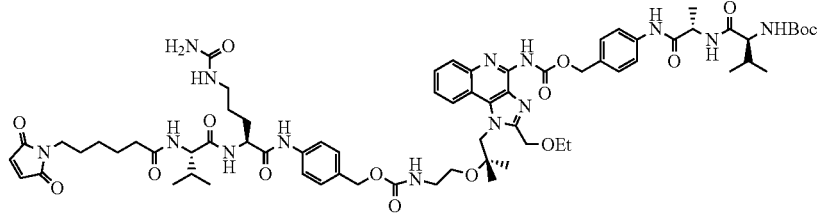<br>4-((S)-2-((S)-2-((tert-butoxycarbonyl)amino)-3-methylbutanamido)propanamido)benzyl (1-(2-(2-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methylpropyl)-2-(ethoxymethyl)-1H-imidazo[4,5-c]quinolin-4-yl)carbamate |

TABLE 4-continued

TLR7 Agonist Linker-Compounds 4.1-4.20

| Linker-Compound | Structure |
|---|---|
| 4.14 | 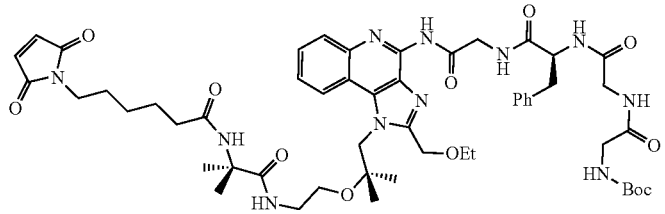<br>tert-butyl (S)-(2-((2-(((1-((2-(((1-(2-(2-(2-(6-(2,5-dioxo-2,5-dihydro-1H-pyrrol-1-yl)hexanamido)-2-methylpropanamido)ethoxy)-2-methylpropyl)-2-(ethoxymethyl)-1H-imidazo[4,5-c]quinolin-4-yl)amino)-2-oxoethyl)amino)-1-oxo-3-phenylpropan-2-yl)amino)-2-oxoethyl)amino)-2-oxoethyl)carbamate |
| 4.15 | 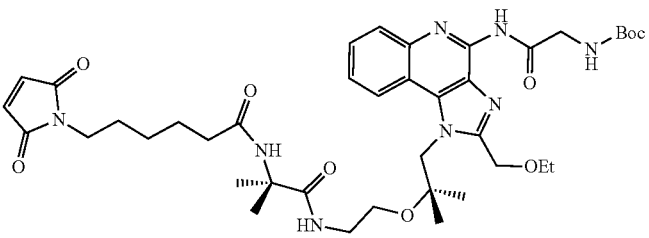<br>tert-butyl (2-((1-(2-(2-(2-(6-(2,5-dioxo-2,5-dihydro-1H-pyrrol-1-yl)hexanamido)-2-methylpropanamido)ethoxy)-2-methylpropyl)-2-(ethoxymethyl)-1H-imidazo[4,5-c]quinolin-4-yl)amino)-2-oxoethyl)carbamate |
| 4.16 | 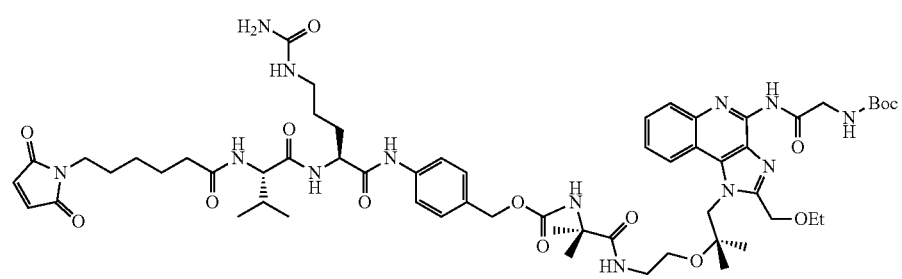<br>4-((S)-2-((S)-2-(6-(2,5-dioxo-2,5-dihydro-1H-pyrrol-1-yl)hexanamido)-3-methylbutanamido)-5-ureidopentanamido)benzyl(14(24(1-(4-(2-((tert-butoxycarbonyl)amino)acetamido)-2-(ethoxymethyl)-1H-imidazo[4,5-c]quinolin-1-yl)-2-methylpropan-2-yl)oxy)ethypamino)-2-methyl-1-oxopropan-2-yl)carbamate |
| 4.17 | 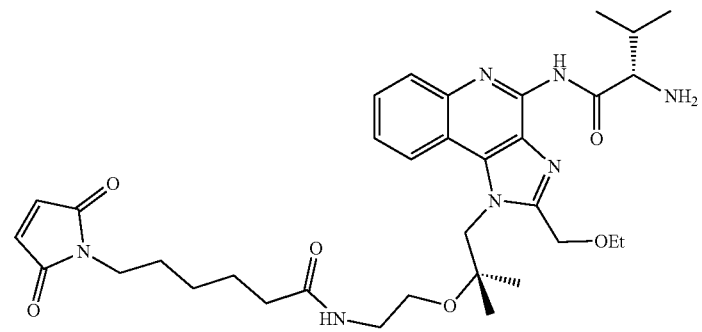<br>(S)-N-(2-((1-(4-(2-amino-3-methylbutanannido)-2-(ethoxymethyl)-1H-imidazo[4,5-c]quinolin-1-yl)-2-methylpropan-2-yl)oxy)ethyl)-6-(2,5-dioxo-2,5-dihydro-1H-pyrrol-1-yl)hexanamide |

TABLE 4-continued

TLR7 Agonist Linker-Compounds 4.1-4.20

| Linker-Compound | Structure |
|---|---|
| 4.18 | 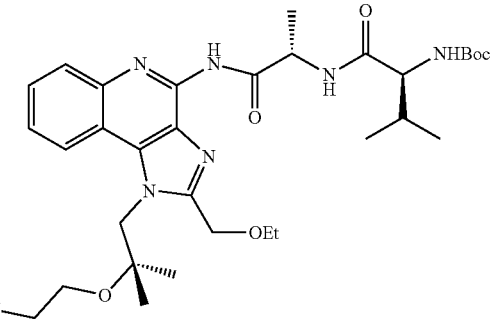<br>tert-butyl ((S)-1-(((S)-1-((1-(2-(2-(6-(2,5-dioxo-2,5-dihydro-1H-pyrrol-1-yl)hexanamido)ethoxy)-2-methylpropyl)-2-(ethoxymethyl)-1H-imidazo[4,5-c]quinolin-4-yl)amino)-1-oxopropan-2-yl)amino)-3-methyl-1-oxobutan-2-yl)carbamate |
| 4.19 | 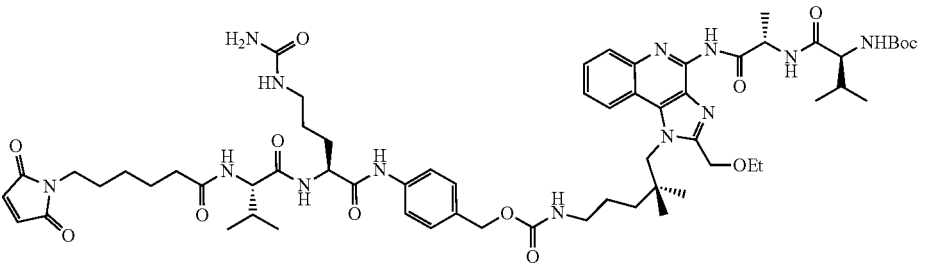<br>tert-butyl ((S)-1-(((S)-1-((1-(2-(2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethoxy)-2-methylpropyl)-2-(ethoxymethyl)-1H-imidazo[4,5-c]quinolin-4-yl)amino)-1-oxopropan-2-yl)amino)-3-mrthyl-1-oxobutan-2-yl)carbamate |
| 4.20 | 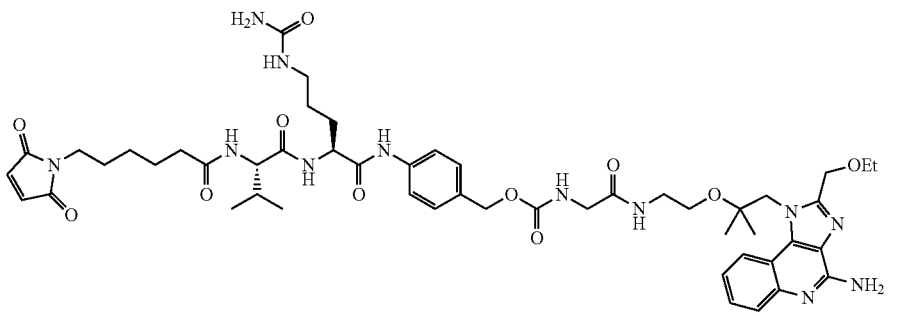 [SMILES: CCOCc1nc2c(N)nc3ccccc3c2n1CC(C)(C)OCCNC(=O)CNC(=O)OCc1ccc(NC(=O)[C@H](CCCNC(N)=O)NC(=O)[C@@H](NC(=O)CCCCCN2C(=O)C=CC2=O)C(C)C)cc1]<br>4-((S)-2-((S)-2-(6-(2,5-dioxo-2,5-dihydro-1H-pyrrol-1-yl)hexanamido)-3-methylbutanamido)-5-ureidopentanamido)benzyl (2-((2-((1-(4-amino-2-(ethoxymethyl)-1H-imidazo[4,5-c]quinolin-1-yl)-2-methylpropan-2-yl)oxy)ethyl)amino)-2-oxoethyl)carbamate |

In some embodiments, a myeloid cell agonist conjugate compound is selected from:
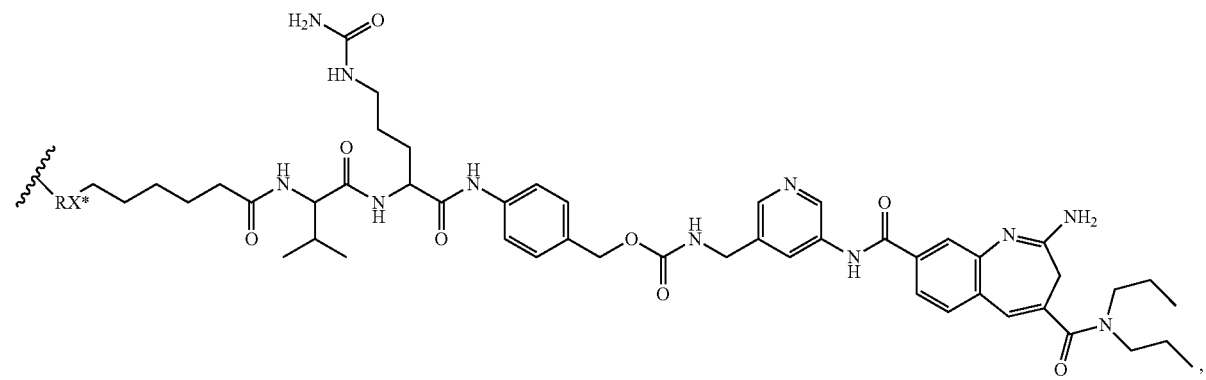
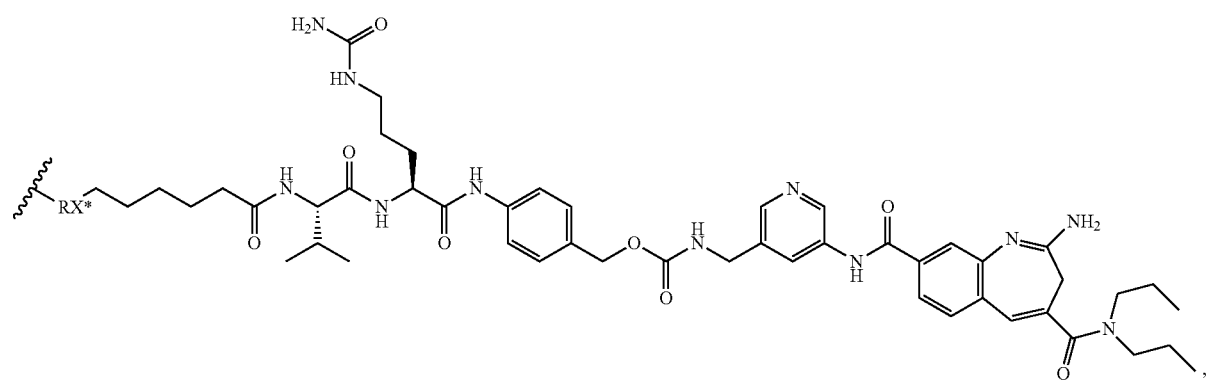
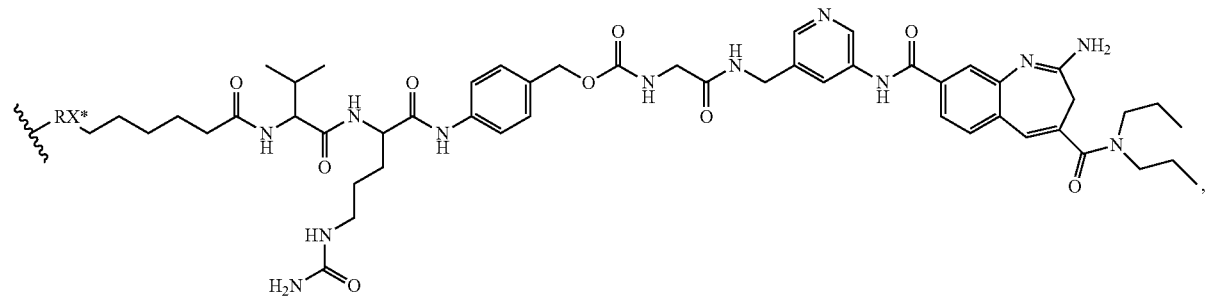
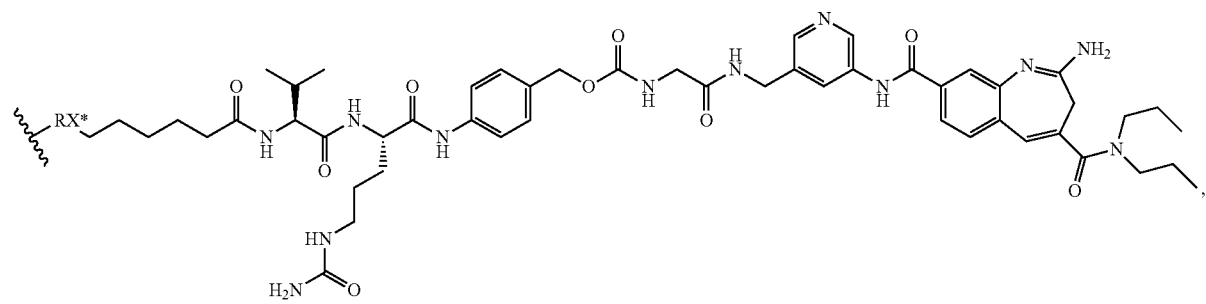

-continued
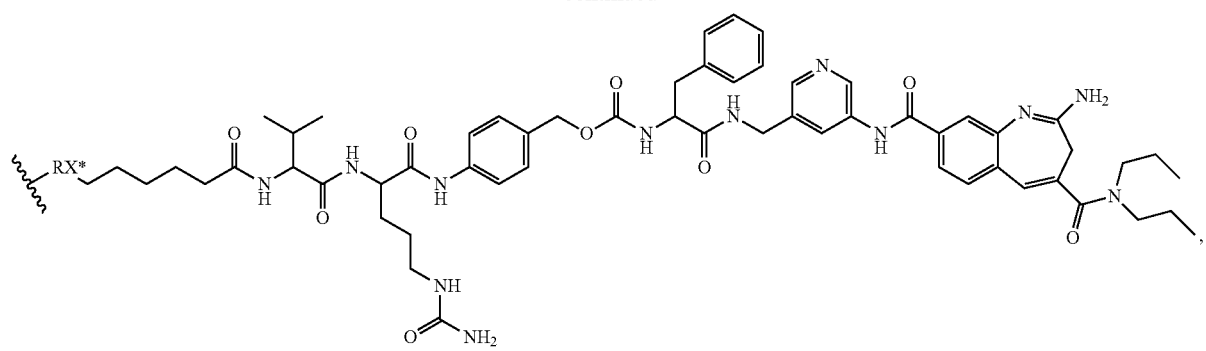
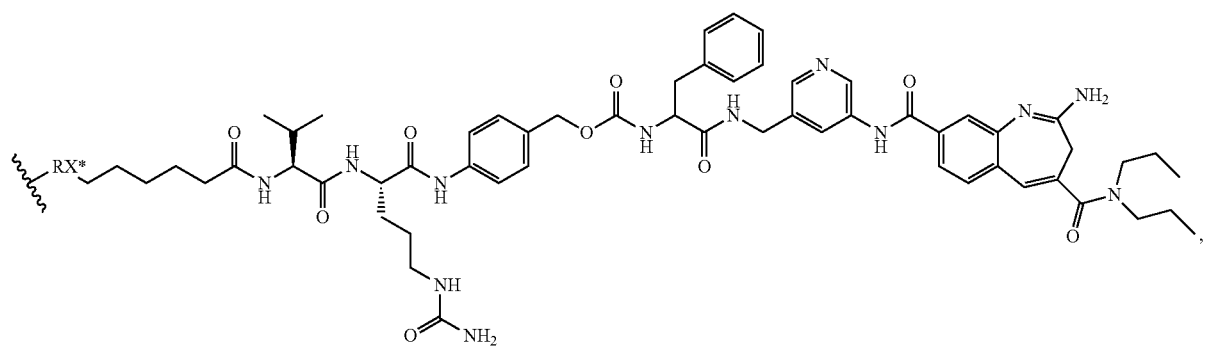
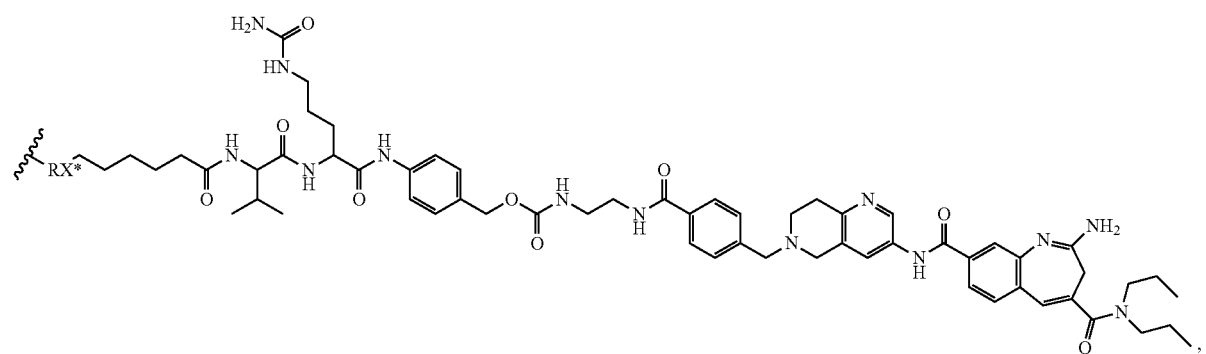
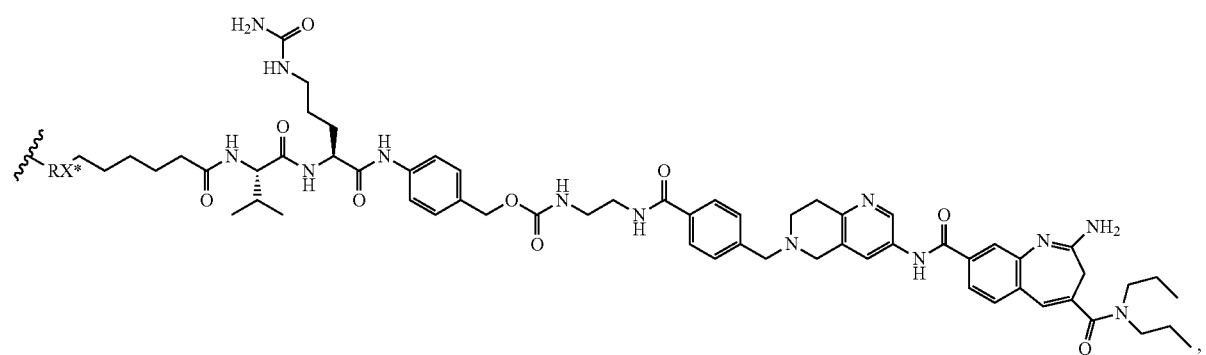

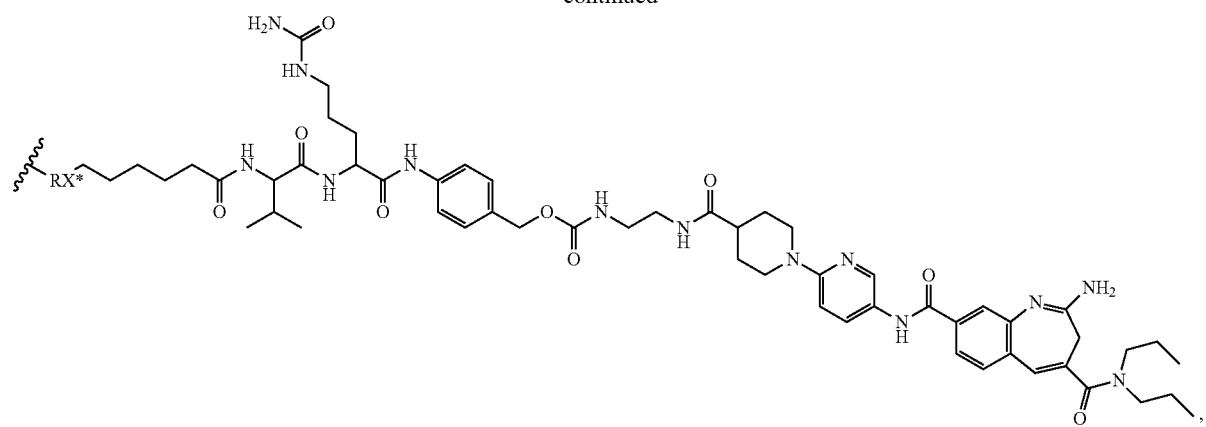
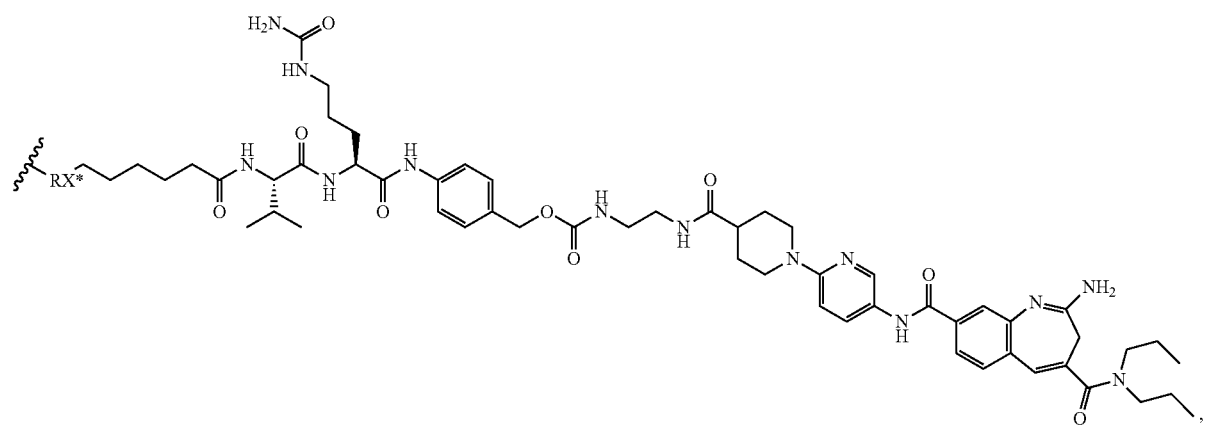
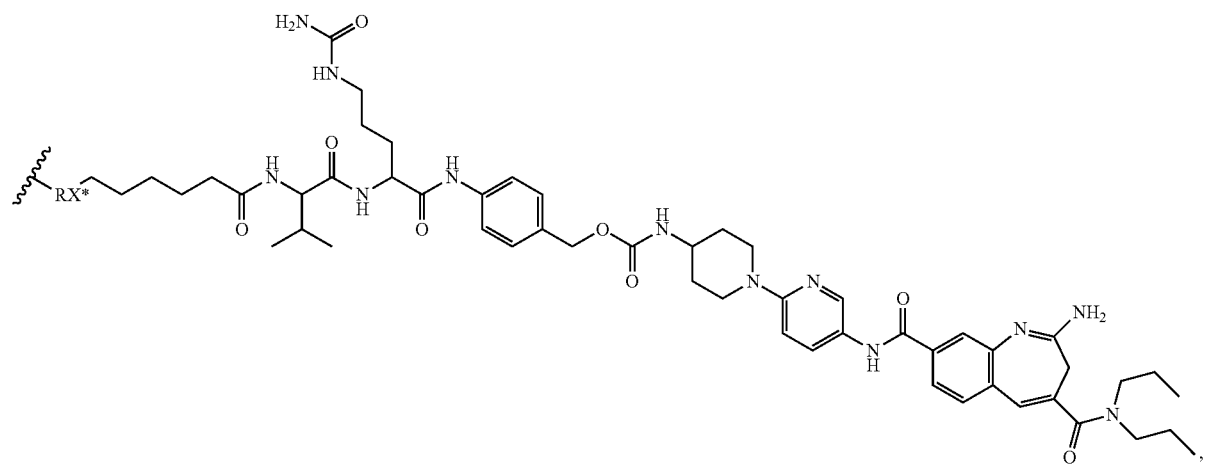

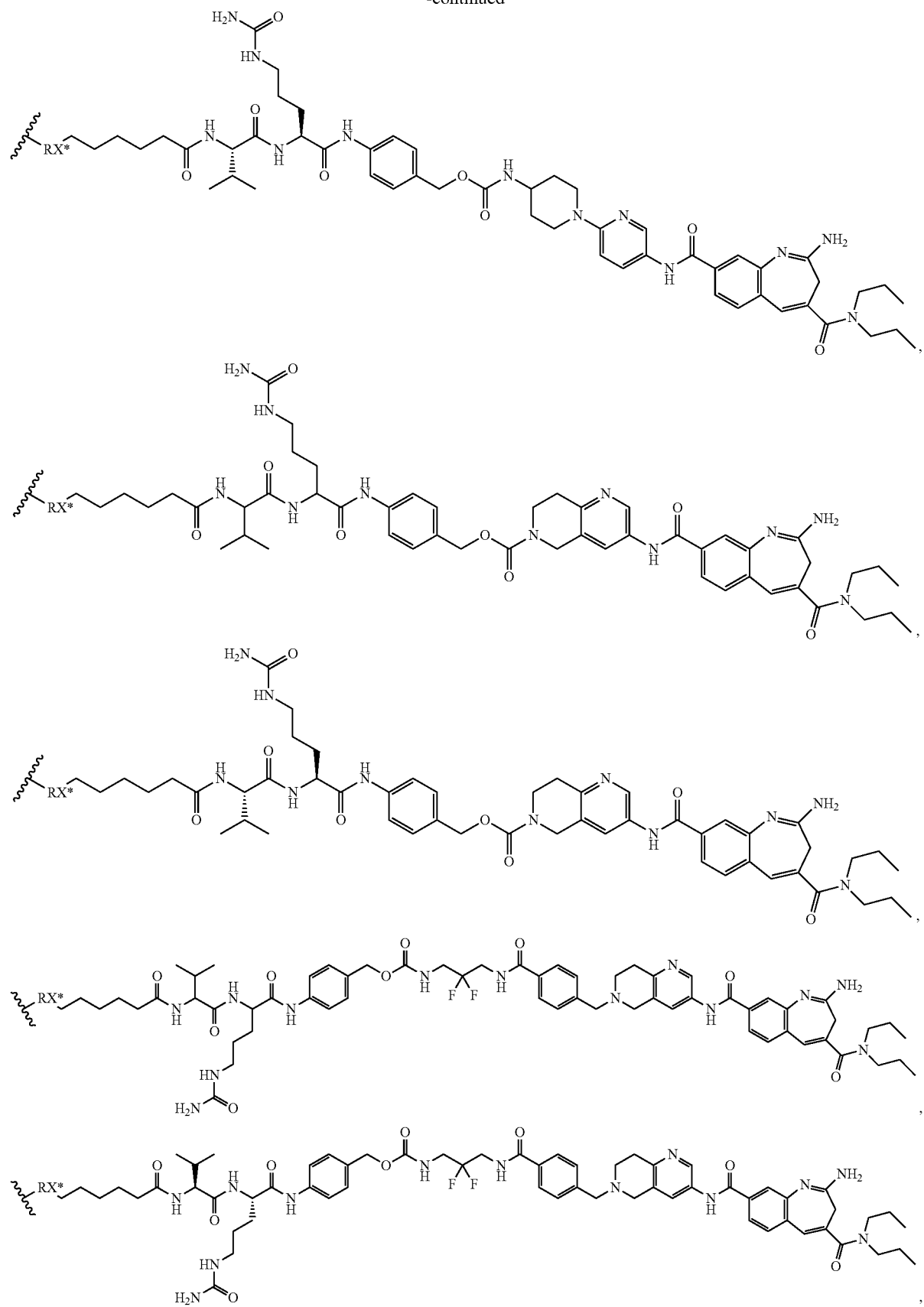

and a salt of any one thereof, wherein the RX* is a bond, a succinimide moiety, or a hydrolyzed succinimide moiety bound to a residue of an anti-Nectin-4 antibody construct, wherein

on RX* represents the point of attachment to the residue of the anti-Nectin-4 antibody construct.

The activation, stimulation or augmentation of an immune response by an immune-stimulatory conjugate, such as a myeloid cell agonist, can be measured in vitro by co-culturing immune cells (e.g., myeloid cells) with cells targeted by the conjugate and measuring cytokine release, chemokine release, proliferation of immune cells, upregulation of immune cell activation markers, and/or ADCC. ADCC can be measured by determining the percentage of remaining target cells in the co-culture after administration of the conjugate with the target cells, myeloid cells, and other immune cells. In some embodiments, an immune-stimulatory conjugate can activate or stimulate immune cell activity, as determined by in vitro assay, such as a cytokine release assay, by detection of activation markers (e.g., MHC class II markers) or other assays known in the art. In some embodiments, an immune-stimulatory conjugate has an EC50 of 100 nM or less, as determine by cytokine release assay. In some embodiments, an immune-stimulatory conjugate has an EC50 of 50 nM or less, as determine by cytokine release assay. In some embodiments, an immune-stimulatory conjugate has an EC50 of 10 nM or less, as determine by cytokine release assay. In some embodiments, an immune-stimulatory conjugate has an EC50 of 1 mM or less.

Pharmaceutical Formulations

The conjugates described herein are useful as pharmaceutical compositions for administration to a subject in need thereof. Pharmaceutical compositions can comprise the conjugates described herein and one or more pharmaceutically acceptable excipients, suitable for administration by a selected route. A pharmaceutical composition can comprise any conjugate described herein. A pharmaceutical composition can further comprise buffers, carbohydrates, and/or preservatives, as appropriate. Pharmaceutical compositions comprising a conjugate can be manufactured, for example, by lyophilizing the conjugate, mixing, dissolving, emulsifying, encapsulating or entrapping the conjugate. The pharmaceutical compositions can also include the conjugates described herein in a free-base form or pharmaceutically-acceptable salt form.

Methods for formulation of the pharmaceutical compositions can include formulating any of the conjugates described herein with one or more inert, pharmaceutically-acceptable excipients or carriers to form a solid, semi-solid, or liquid composition for intravenous or subcutaneous administration. Solid compositions can include, for example, powders, and in some aspects, the solid compositions further contain nontoxic, auxiliary substances, for example wetting or emulsifying agents, pH buffering agents, and other pharmaceutically-acceptable additives. Alternatively, the compositions described herein can be lyophilized or in powder form for re-constitution with a suitable vehicle, e.g., sterile pyrogen-free water, before use.

The pharmaceutical compositions and formulations can be sterilized. Sterilization can be accomplished by filtration through sterile filtration.

The pharmaceutical compositions described herein can be formulated for administration as an injection, e.g., an intravenous or subcutaneous injection. Non-limiting examples of formulations for injection can include a sterile suspension, solution or emulsion in oily or aqueous vehicles. Suitable oily vehicles can include, but are not limited to, lipophilic solvents or vehicles such as fatty oils or synthetic fatty acid esters, or liposomes. Aqueous injection suspensions can contain substances which increase the viscosity of the suspension. The suspension can also contain suitable stabilizers. Alternatively, the pharmaceutical compositions described herein can be lyophilized or in powder form for reconstitution with a suitable vehicle, e.g., sterile pyrogen-free water, before use.

The conjugates can be formulated for administration in a unit dosage form in association with a pharmaceutically acceptable vehicle. Such vehicles can be inherently non-toxic, and non-therapeutic. A vehicle can be water, saline, Ringer's solution, dextrose solution, and 5% human serum albumin. Nonaqueous vehicles such as fixed oils and ethyl oleate can also be used. The vehicle can contain minor amounts of additives such as substances that enhance isotonicity and chemical stability (e.g., buffers and preservatives).

In some embodiments, an aqueous formulation of a conjugate provided herein, such as for subcutaneous administration, has a pH from 4-5.2. The aqueous formulation may comprise one or more excipients, such as, for example, one or more buffering agents, one or more lyoprotectants, and the like. In some embodiments, the pH of the formulation is from 4-5.1, 4.1-5.1, 4.2-5.1, 4.3-5.1, 4.4-5.1, 4.5-5.1, 4-5, 4.1-5, 4.2-5, 4.3-5, 4.4-5, or 4.5-5. In some embodiments, the formulation comprises at least one buffer. In various embodiments, the buffer may be selected from histidine, citrate, aspartate, acetate, phosphate, lactate, tromethamine, gluconate, glutamate, tartrate, succinate, malic acid, fumarate, α-ketoglutarate, and combinations thereof. In some embodiments, the buffer is at least one buffer selected from histidine, citrate, aspartate, acetate, and combinations thereof. In some embodiments, the buffer is a combination of histidine and aspartate. In some embodiments, the total concentration of the buffer in the aqueous formulation is 10 mM to 40 mM, such as 15 mM-30 mM, 15 mM-25 mM, or 20 mM.

In some embodiments, the aqueous formulation comprises at least one lyoprotectant. In some such embodiments, the at least one lyoprotectant is selected from sucrose, arginine, glycine, sorbitol, glycerol, trehalose, dextrose, alpha-cyclodextrin, hydroxypropyl beta-cyclodextrin, hydroxypropyl gamma-cyclodextrin, proline, methionine, albumin, mannitol, maltose, dextran, and combinations thereof. In some embodiments, the lyoprotectant is sucrose. In some embodiments, the total concentration of lyoprotectant in the aqueous formulation is 3-12%, such as 5-12%, 6-10%, 5-9%, 7-9%, or 8%.

In some embodiments, the aqueous formulation comprises at least one surfactant. Exemplary surfactants include polysorbate 80, polysorbate 20, poloxamer 88, and combinations thereof. In some embodiments, the aqueous formulation comprises polysorbate 80. In some embodiments, the total concentration of the at least one surfactant is 0.01%-0.1%, such as 0.01%-0.05%, 0.01%-0.08%, or 0.01%-0.06%, 0.01%-0.04%, 0.01%-0.03%, or 0.02%.

In some embodiments, the concentration of the conjugate in the aqueous formulation is 1 mg/mL-200 mg/mL, such as 10 mg/mL-160 mg/mL, 10 mg/mL-140 mg/mL, 10 mg/mL-120 mg/mL, 20 mg/mL-120 mg/mL, or 30 mg/mL-120 mg/mL, or 40 mg/mL-120 mg/mL, or 40 mg/mL-100 mg/mL. In some embodiments, the concentration of the conjugate in the aqueous formulation is 10 mg/mL-140 mg/mL or 40 mg/mL-140 mg/mL.

Therapeutic Applications

The antibodies or antigen-binding fragments thereof, conjugates and compositions (e.g., pharmaceutical compositions) of the present disclosure can be useful for a plurality of different subjects including, but are not limited to, a mammal, human, non-human mammal, a domesticated animal (e.g., laboratory animals, household pets, or livestock), non-domesticated animal (e.g., wildlife), dog, cat, rodent, mouse, hamster, cow, bird, chicken, fish, pig, horse, goat, sheep, rabbit, and any combination thereof. In some embodiments, the subject is a human.

Anti-Nectin-4 antibodies or antigen-binding fragments thereof, conjugates, and compositions thereof of this disclosure can be useful as a therapeutic, for example, a treatment that can be administered to a subject in need thereof. A therapeutic effect of the antibodies, conjugates and compositions thereof of the present disclosure can be obtained in a subject by reduction, suppression, remission, or eradication of a disease state, including, but not limited to, a symptom thereof. A therapeutic effect in a subject having a disease or condition (e.g., cancer), or pre-disposed to have or is beginning to have the disease or condition, can be obtained by a reduction, a suppression, a prevention, a remission, or an eradication of the condition or disease, or pre-condition or pre-disease state.

A "subject in need thereof" refers to an individual at risk of, or suffering from, a disease, disorder or condition, such as cancer, that is amenable to treatment or amelioration with an anti-Nectin-4 antibody or antigen-binding fragment thereof, a conjugate of an anti-Nectin-4 antibody or antigen-binding fragment thereof with a myeloid cell agonist (e.g., TLR8 agonist), or a composition thereof as provided herein. In certain embodiments, a subject in need thereof is administered an anti-Nectin-4 antibody or antigen-binding fragment thereof, a conjugate of an anti-Nectin-4 antibody or antigen-binding fragment thereof with a myeloid cell agonist (e.g., TLR8 agonist), or a composition thereof as provided herein to treat cancer, wherein the cancer comprises a tumor having excess Nectin-4 as compared to normal tissue.

In practicing the methods described herein, therapeutically effective amounts of the antibodies or antigen-binding fragments thereof, conjugates, and pharmaceutical compositions can be administered to a subject in need thereof, often for treating and/or preventing a condition or progression thereof. The antibodies or antigen-binding fragments thereof, conjugates, or pharmaceutical compositions can affect the physiology of the subject, such as the immune system, an inflammatory response, or other physiologic affect. A therapeutically effective amount can vary depending on the severity of the disease, the age and relative health of the subject, the potency of the compounds used, and other factors.

"Treatment," "treat," and/or "treating" refer to an intervention that leads to any observable beneficial effect of the treatment or any indicia of statistically significant success in the treatment or amelioration of the disease or condition, such as ameliorating a sign, symptom, or progression of a disease or pathological condition. The beneficial effect can be evidenced by, for example, a reduction, delayed onset, or alleviation of the severity of clinical symptoms of the disease in a subject, a reduction in the frequency with which symptoms of a disease are experienced by a subject, a slower progression of the disease, a reduction in the number of relapses of the disease, an improvement in the overall health or well-being of the subject, or by other parameters that are specific to the particular disease.

A prophylactic treatment meant to "prevent" a disease or condition (e.g., tumor formation or growth, in a subject or patient) is a treatment administered to a subject who does not exhibit signs of a disease or exhibits only early signs, for the purpose of decreasing the risk of developing pathology or further advancement of the early disease. For example, if an individual at risk of developing a tumor or other form of cancer is treated with the methods of the present disclosure and does not later develop the tumor or other form of cancer, then the disease has been prevented, at least over a period of time, in that individual. A prophylactic treatment can mean preventing reccurrence of a disease or condition in a patient that has previously been treated for the disease or condition, e.g., by preventing relapse or reccurance of cancer.

As used herein, the term "effective amount" or "effective dose" refers to a quantity of a specified antibody, conjugate, or composition thereof sufficient to achieve a desired (e.g., beneficial) effect in a subject being treated with that compound, conjugate, or composition thereof, such as an amount sufficient to result in amelioration of one or more symptoms of the disease being treated in a statistically significant manner, delaying worsening of a progressive disease in a statistically significant manner, or preventing onset of additional associated symptoms or diseases in a statistically significant manner, or any combination thereof. In certain embodiments, an effective amount of an antibody, conjugate, or composition thereof is an amount sufficient to inhibit or treat the disease with minimal to no toxicity in the subject, excluding the presence of one or more adverse side effects. An effective amount or dose can be administered one or more times over a given period of time. An effective amount or dose can depend on the purpose of the treatment and can be ascertainable by one skilled in the art based on a subject's needs. When referring to an individual active ingredient, administered alone, an effective amount or dose refers to that ingredient alone. When referring to a combination, an effective amount or dose refers to combined amounts of the active ingredients that result in the therapeutic effect, whether administered serially or simultaneously.

Anti-Nectin-4 antibodies or antigen-binding fragments thereof, conjugates, and pharmaceutical compositions of this disclosure that can be used in therapy can be formulated and dosages established in a fashion consistent with good medical practice taking into account the disease or condition to be treated, the condition of the individual patient, the site of delivery of the composition, the method of administration and other factors known to practitioners.

Administration to a subject of an effective amount or dose of an anti-Nectin-4 antibody, conjugate, or composition thereof of this disclosure can be by one or more routes and can occur one or more times over a given period of time. One of ordinary skill in the art would understand that the amount, duration and frequency of administration of a compound, conjugate, or composition thereof of this disclosure to a subject in need thereof depends on several factors including, for example, the health of the subject, the specific disease or condition of the patient, the grade or level of a specific disease or condition of the patient, the additional treatments the subject is receiving or has received, or the like. Exemplary routes of administration include subcutaneous, intravenous, intraarterial, subdural, intramuscular, intracranial, intrasternal, intratumoral, or intraperitoneal. In certain embodiments, the administration is subcutaneous. Additionally, a compound, conjugate, or composition thereof of this disclosure can be administered to a subject by other routes of administration, for example, by inhalation, or oral, dermal, intranasal or intrathecal administration.

Anti-Nectin-4 antibodies or antigen-binding fragments thereof, conjugates, and compositions thereof the present disclosure can be administered to a subject in need thereof in a first administration, and subsequently in one or more additional administrations. The one or more additional administrations can be administered to the subject in need thereof minutes, hours, days, weeks or months following the first administration. Any one of the additional administrations can be administered to the subject in need thereof less than 21 days, or less than 14 days, less than 10 days, less than 7 days, less than 4 days or less than 1 day after the first administration. The one or more administrations can occur more than once per day, more than once per week or more than once per month. The administrations can be weekly, biweekly (every two weeks), every three weeks, monthly or bimonthly.

In some aspects, the present disclosure provides a method of treating cancer. In certain embodiments, the present disclosure provides a method of treating cancer comprising administering to a subject in need thereof an effective amount of: (a) an anti-Nectin-4 antibody conjugate comprising a compound of Formula (X-1)-(X-9), Category A of Formula (IA), (IB), (IIA), (IIB), (IIC), (IIIA), (IIIB), (IVA), (IVB), or (IVC), or pharmaceutically acceptable isomer, racemate, hydrate, solvate, isotope, or salt thereof; or (b) a composition of (a).

In any of the embodiments herein, an antibody conjugate composition for use in the methods of treating disease (such as cancer) has an average DAR of the conjugate ranging from about 2 to about 8, about 1 to about 3, or about 3 to about 5. In other embodiments, an antibody conjugate in a composition will have an average DAR ranging from 1 to about 10, from 1 to about 9, from 1 to about 8, from 1 to about 6, from 1 to about 3, from about 2 to about 8, from about 2 to about 6, from about 2.5 to about 5.5, from about 2.5 to about 4.5, from about 2 to about 4, from about 3.5 to about 5.5, from about 3 to about 5, from about 3.5 to about 4.5, or from about 3 to about 4. In certain embodiments, the average DAR for the conjugates of a composition used in the methods of treatment will be about 1.5, about 2, about 2.5, about 3, about 3.5, about 4, about 4.5, about 5, about 5.5, about 6, about 6.5, about 7, about 7.5, or about 8. In certain embodiments, an anti-Nectin-4 antibody conjugate of this disclosure comprises from 1-20 myeloid agonist compounds (e.g., TLR8 agonists) per antibody, preferably ranges from 1 to about 8, about 3 about 5, or 1 to about 3 myeloid agonist compounds (e.g., TLR8 agonists) per antibody.

In various embodiments, methods of treating a cancer (e.g., bladder, breast, lung, cervical, HPV+ cancer or tumor) are provided, comprising administering an effective amount of an antibody or an antigen-binding fragment thereof, a conjugate, or a pharmaceutical composition provided herein to a subject in need thereof. In some embodiments, the cancer is selected from bladder cancer, breast cancer, lung cancer, head and neck cancer, cervical cancer, pancreatic cancer, gastric cancer, esophageal cancer, and uterine cancer. In some embodiments, the bladder cancer is urothelial cancer. In some embodiments, the breast cancer is triple negative breast cancer. In some embodiments, the lung cancer is non-small cell lung cancer (NSCLC). In some embodiments, the NSCLC is squamous cell carcinoma or lung adenocarcinoma. In some embodiments, the head and neck cancer is head and neck squamous cell carcinoma (HNSCC). In some embodiments, the cervical cancer is cervical squamous cell carcinoma or endocervical adenocarcinoma. In some embodiments, the pancreatic cancer is pancreatic adenocarcinoma. In some embodiments, the esophageal cancer is esophageal adenocarcinoma. In some embodiments, the uterine cancer is uterine corpus endometrial carcinoma.

In various embodiments, methods of treating a Nectin-4-expressing cancer are provided, comprising administering an effective amount of an antibody or an antigen-binding fragment thereof, a conjugate, or a pharmaceutical composition provided herein to a subject in need thereof. In some embodiments, the cancer is selected from bladder cancer, breast cancer, lung cancer, head and neck cancer, cervical cancer, pancreatic cancer, esophageal cancer, and uterine cancer. In some embodiments, the bladder cancer is urothelial cancer. In some embodiments, the breast cancer is triple negative breast cancer. In some embodiments, the lung cancer is non-small cell lung cancer (NSCLC). In some embodiments, the NSCLC is squamous cell carcinoma or lung adenocarcinoma. In some embodiments, the cervical cancer is cervical squamous cell carcinoma or endocervical adenocarcinoma. In some embodiments, the pancreatic cancer is pancreatic adenocarcinoma. In some embodiments, the esophageal cancer is esophageal adenocarcinoma. In some embodiments, the uterine cancer is uterine corpus endometrial carcinoma.

In some embodiments, the methods of treating cancer or treating a Nectin-4-expressing cancer further comprise administering an additional therapy to the subject, such as, for example, small molecule inhibitors (including small molecule antagonists), CAR-T cells, therapeutic antibodies, antibody-drug conjugates, chemotherapeutic agents, ionizing radiation, and other anti-cancer drugs.

Examples of therapeutic antibodies contemplated as further therapeutic agents include anti-TIGIT antibodies, such as tiragolumab, vibostolimab, domvanalimab, BMS-986207, ASP8374, and BGB-A1217. In certain embodiments, an anti-TIGIT antibody may be combined with an additional antibody (e.g., an anti-PD-1 or anti-PD-L1 antibody) to be used with an anti-Nectin-4 antibody or an anti-Nectin-4 antibody conjugated to a myeloid cell agonist (such as a TLR8 agonist) as provided in this disclosure. The combination therapy using an anti-Nectin-4 antibody or anti-Nectin-4 antibody conjugated to a myeloid cell agonist provided in this disclosure, an anti-TIGIT antibody, and optionally an anti-PD-1 or anti-PD-L1 antibody may be used in treating various types of cancer, including lung cancer (e.g., small lung cell cancer and non-small cell lung cancer), gastro-esophageal junction cancer, and esophageal cancer.

Examples of small molecule antagonists contemplated as further therapeutic agents include adenosine receptor antagonist, such as AB928 (Arcus), CPI-444 (Corvus), PBF-509 (Pablobio), MK-3814 (Merck), and AZD4635 (AstraZeneca). In certain embodiments, an adenosine receptor antagonist may be combined with an additional antibody (e.g., an anti-PD-1 or anti-PD-L1 antibody) to be used with an anti-Nectin-4 antibody or an anti-Nectin-4 antibody conjugated to a myeloid cell agonist as provided in this disclosure.

Examples of chemotherapeutic agents contemplated as further therapeutic agents include alkylating agents, such as nitrogen mustards (e.g., mechlorethamine, cyclophosphamide, ifosfamide (IFEX®), melphalan (Alkeran®), and chlorambucil); bifunctional chemotherapeutics (e.g., bendamustine); nitrosoureas (e.g., carmustine (BCNU, BiCNU®; polifeprosan 20 implant (Gliadel®)), lomustine (CCNU), and semustine (methyl-CCNU)); ethyleneimines and methyl-melamines (e.g., triethylenemelamine (TEM), triethylene thiophoshoramide (thiotepa), and hexamethylmelamine (HMM, altretamine)); alkyl sulfonates (e.g., busulfan (Myleran®), busulfan injection (Busulfex®)); and triazines (e.g., dacabazine (DTIC)); antimetabolites, such as folic acid analogues (e.g., methotrexate (Folex®), trimetrexate, and pemetrexed (multi-targeted antifolate)) and capecitabine (Xeloda®); pyrimidine analogues (such as 5-fluorouracil (5-FU, Adrucil®, Efudex®), fluorodeoxyuridine, tezacitabine, gemcitabine, cytosine arabinoside (AraC, cytarabine (Cytosar-U®); cytarabine liposome injection (DepoCyt®)), 5-azacytidine, and 2,2'-difluorodeoxycytidine); purine analogues (e.g., 6-mercaptopurine (Purinethol®), 6-thioguanine, azathioprine, 2'-deoxycoformycin (pentostatin), erythrohydroxynonyladenine (EHNA), fludarabine phosphate (Fludara®), 2 chlorodeoxyadenosine (cladribine, 2-CdA)); Type I topoisomerase inhibitors such as camptothecin (CPT), topotecan (Hycamptin®), and irinotecan (Camptosar®); natural products, such as epipodophylotoxins (e.g., etoposide (Vepesid®) and teniposide (Vumon®)); vinca alkaloids (e.g., vinblastine (Velban®), vincristine (Oncovin®), and vinorelbine (Navelbine®)); anti-tumor antibiotics such as actinomycin D (dactinomycin, Cosmegan®), doxorubicin hydrochloride (Adriamycin®, Rubex®), mitoxantrone (Novantrone®), and bleomycin sulfate (Blenoxane®); radiosensitizers such as 5-bromodeozyuridine, 5-iododeoxyuridine, and bromodeoxycytidine; platinum coordination complexes such as cisplatin (Platinol®), carboplatin (Paraplatin®), and oxaliplatin (Eloxatin®); substituted ureas, such as hydroxyurea (Hydrea®); microtubule inhibitors such as paclitaxel (Taxol®) and docetaxel (Taxotere®); immunosuppressive agents such as cyclophosphamide (Cytoxan® or Neosar®); hormone-based compound such as anastrozole (Arimidex®), exemestane (Aromasin®), letrozole (Femara®), fulvestrant (Faslodex®), and bicalutamide (Casodex®) and tamoxifen citrate (Nolvadex®); an anti-inflammatory agent such as dexamethasone; an anti-androgen compound such as flutamide (Eulexin®); an anthracycline compound such as idarubicin (Idamycin®, Zavedos®) and epirubicin (Ellence®); bioreductive anticancer agent such as tirapazamine (Tirazone®); serine/threonine kinase inhibitors such as CDK4/6 inhibitors abemaciclib (Verzenio®), palbociclib (Ibrance®), and ribociclib (Kisqali®); and methylhydrazine derivatives such as N methylhydrazine (MIH) and procarbazine.

In some embodiments, wherein the disease is urothelial cancer, the additional therapeutic agent is selected from dose-dense methotrexate, vinblastine, doxorubicin, and cisplatin (ddMVAC), gemcitabine/cisplatin, gemcitabine/carboplatin, atezolizumab, pembrolizumab, nivolumab, durvalumab, avelumab, erdafitinib, and enfortumab vedotin.

In some embodiments, wherein the disease is triple negative breast cancer, the additional therapeutic agent is selected from a taxane (e.g., paclitaxel, docetaxel), anthracycline, capecitabine, gemcitabine, eribulin, a PD1/PDL1 inhibitor (e.g., nivolumab, pembrolizumab, atezolizumab), antibody-drug conjugate (ADC) (e.g., sacituzumab govitecan, ladiratuzumab vedotin), a PARP inhibitor, PTEN/AKT/PI3K inhibitor, MEK inhibitor, or any combination thereof.

In some embodiments, wherein the disease is NSCLC (squamous cell carcinoma or lung adenocarcinoma), the additional therapeutic agent is selected from a platinum-based therapeutic (e.g., carboplatinum), a taxane (e.g., paclitaxel docetaxel), radiation, a PD1/PDL1 inhibitor (e.g., nivolumab, pembrolizumab, atezolizumab), a kinase inhibitor (such as an EGFR, ALK, BRAF, MEK, NTRK, or VEGFR inhibitor; e.g., osimentinib, crizotinib, dabrafenib, tramentinib, erectinib, nintedanib), other antibody (such as anti-EGFR, anti-VEGF/anti-VEGFR; e.g., erbitux, avastin, ramucirumab), or any combination thereof.

In some embodiments, wherein the disease is pancreatic adenocarcinoma, the additional therapeutic agent is selected from radiation, a platinum-based therapy (e.g., oxaliplatin), an anti-metabolite (e.g., capecitabine, gemcitabine, irinotecan), a taxane (e.g., NAB-paclitaxel, paclitaxel, docetaxel), a kinase inhibitor (e.g., erlotinib), a PARP inhibitor (e.g., olaparib), a metabolic therapy (e.g., 5-fluorouracil (plus leucovorin), devimistat), a checkpoint inhibitor (e.g., anti-PD1, anti-PDL-1, anti-CTLA4), an oncolytic virus (e.g., pelareorep), or any combination thereof.

In some embodiments, wherein the disease is head and neck cancer, the additional therapeutic agent is selected from radiation, a platinum-based therapy (e.g., cisplatin, carboplatin), taxanes (e.g., paclitaxel, docetaxel), a metabolic therapy (e.g., 5-fluorouracil), an anti-EGFR antibody (e.g., cetuximab); a PD1/PDL-1 inhibitor (e.g., pembrolizumab, nivolumab, envafolimab), a tyrosine kinase inhibitor (e.g., erlotinib, lapatinib), an oncolytic virus (e.g., talimogene laherparepvec); a CAR T cell therapy (e.g., KITE HPV-16, KITE HPV-17), or any combination thereof.

In some embodiments, the additional therapeutic agent is an anti-TROP2 antibody-drug conjugate (e.g., sacituzumab govitecan, DS-1062, SKB264, BAT8003). In certain embodiments, such combinations of an anti-Nectin-4 antibody conjugated to a myeloid cell agonist with an anti-TROP2 antibody-drug conjugate are used to treat certain cancers, such as bladder cancer, HNSCC, or TNBC.

In some embodiments, wherein the disease is a HPV+ tumor (e.g., HNSCC and cervical cancer), the additional therapeutic agent is a CAR T cell therapy (e.g., KITE-439).

In some embodiments, wherein the disease is gastric cancer, NSCLC, or bladder cancer, the additional therapeutic agent is a PD-L1 small molecule inhibitor (e.g., GS-4224, aurigenel, BMSpep-57, BMS-103, BMS-142, BMS-1166).

In various embodiments, the method comprises administering an effective regimen that results in a T max of the conjugate of greater than 4 hours following each administration of the conjugate. In some embodiments, the effective regimen results in a T max greater than 6 hours, greater than 8 hours, greater than 10 hours, greater than 12 hours, or greater than 15 hours following each administration of the conjugate.

In certain embodiments, the methods include administration of an immune-stimulatory conjugate, or a pharmaceutical composition thereof, to a subject in need thereof in an effective regimen to activate, stimulate or augment an immune response against a disease treatable with a TLR agonist (e.g., cancer). The antibody or antigen binding fragment thereof of the conjugate recognizes an antigen associated with the disease or disease state, such as Nectin-4.

In certain embodiments, the methods include administration of a combination therapy comprising a conjugate provided herein to a subject in need thereof to activate, stimulate or augment an immune response against tumor cells of a solid tumor, such as bladder cancer, breast cancer, lung cancer, head and neck cancer, cervical cancer, pancreatic cancer, esophageal cancer, and uterine cancer. In some such embodiments, the antibody or antigen binding fragment thereof of the conjugate recognizes an antigen on the tumor cells, e.g., Nectin-4.

In some cases, treatment comprises reduced tumor growth. In some cases, treatment comprises tumor arrest.

One of ordinary skill in the art would understand that the amount, duration and frequency of administration of a conjugate or combination therapy described herein to a subject in need thereof depends on several factors including, for example but not limited to, the health of the subject, the specific disease or condition of the subject, the grade or level of a specific disease or condition of the subject, the additional therapeutics the subject is being or has been administered, and the like.

In some aspects of practicing the methods described herein, the conjugates are administered in an effective regimen of at least two or at least three cycles. Each cycle can optionally include a resting stage between cycles. Cycles of administration can be of any suitable length. In some embodiments, each cycle is a week (7 days), 10 days, every two weeks (14 days or biweekly), every three week (21 days) or every four weeks (28 days). In some embodiments, each cycle is a month. In some embodiments, at least two doses of the immune-stimulatory conjugate are administered more than 7 days apart, or more than 10 days apart. In some embodiments, at least one dose of the conjugate is administered more than 7 days, or more than 10 days, after the initial dose of the conjugate.

In certain embodiments, the total dose of the conjugate within a treatment cycle or the dose of the conjugate per administration is from about 0.1 to about 10 mg/kg. In some embodiments, the total dose within a treatment cycle or the dose of the conjugate per administration is from about 0.5 to about 7.5 mg/kg. In some embodiments, the total dose within a treatment cycle or the dose of the conjugate per administration is from about 0.5 to about 5 mg/kg. In some embodiments, the total dose of the conjugate within a treatment cycle or the dose of the conjugate per administration is from about 0.5 to about 4 mg/kg. In some embodiments, the total dose of the conjugate within a treatment cycle or the dose of the conjugate per administration is from about 0.5 to about 3.5 mg/kg. In some embodiments, the total dose of the conjugate within a treatment cycle or the dose of the conjugate per administration is from about 0.5 to about 2 mg/kg.

In certain embodiments, the total dose of the conjugate within a treatment cycle is from about 0.1 to about 100 mg/kg, such as about 0.1 to about 50 mg/kg, about 0.1 to about 25 mg/kg, about 0.1 to about 20 mg/kg, about 0.1 to about 15 mg/kg, about 0.1 to about 10 mg/kg, about 0.5 to about 100 mg/kg, about 0.5 to about 50 mg/kg, about 0.5 to about 25 mg/kg, about 0.5 to about 20 mg/kg, about 0.5 to about 15 mg/kg, about 0.5 to about 10 mg/kg, about 1 to about 100 mg/kg, about 1 to about 50 mg/kg, about 1 to about 25 mg/kg, about 1 to about 20 mg/kg, about 1 to about 15 mg/kg, or about 1 to about 10 mg/kg.

In certain embodiments, the dose of the conjugate per administration is from about 0.1 to about 100 mg/kg, such as about 0.1 to about 50 mg/kg, about 0.1 to about 25 mg/kg, about 0.1 to about 20 mg/kg, about 0.1 to about 15 mg/kg, about 0.1 to about 10 mg/kg, about 0.5 to about 100 mg/kg, about 0.5 to about 50 mg/kg, about 0.5 to about 25 mg/kg, about 0.5 to about 20 mg/kg, about 0.5 to about 15 mg/kg, about 0.5 to about 10 mg/kg, about 1 to about 100 mg/kg, about 1 to about 50 mg/kg, about 1 to about 25 mg/kg, about 1 to about 20 mg/kg, about 1 to about 15 mg/kg, or about 1 to about 10 mg/kg.

In certain preferred embodiments, the total dose of the conjugate within a treatment cycle is about 0.1 to about 25 mg/kg. In certain other preferred embodiments, the total dose of the conjugate within a treatment cycle is about 0.5 to about 20 mg/kg. In certain preferred embodiments, the total dose of the conjugate within a treatment cycle about 0.1, about 0.5, about 2, about 4, about 6, about 8, about 10, about 12, about 14, or about 16 mg/kg.

In certain preferred embodiments, the dose of the conjugate per administration is about 0.1 to about 25 mg/kg. In certain other preferred embodiments, the dose of the conjugate per administration is about 0.5 to about 20 mg/kg. In certain preferred embodiments, the dose of the conjugate per administration about 0.1, about 0.5, about 2, about 4, about 6, about 8, about 10, about 12, about 14, or about 16 mg/kg.

In certain embodiments, the conjugate is administered subcutaneously, and the total dose of the conjugate within a treatment cycle is from about 0.1 to about 100 mg/kg, such as about 0.1 to about 50 mg/kg, about 0.1 to about 25 mg/kg, about 0.1 to about 20 mg/kg, about 0.1 to about 15 mg/kg, about 0.1 to about 10 mg/kg, about 0.5 to about 100 mg/kg, about 0.5 to about 50 mg/kg, about 0.5 to about 25 mg/kg, about 0.5 to about 20 mg/kg, about 0.5 to about 15 mg/kg, about 0.5 to about 10 mg/kg, about 1 to about 100 mg/kg, about 1 to about 50 mg/kg, about 1 to about 25 mg/kg, about 1 to about 20 mg/kg, about 1 to about 15 mg/kg, or about 1 to about 10 mg/kg.

In certain embodiments, the conjugate is administered subcutaneously, and the dose of the conjugate per administration is from about 0.1 to about 100 mg/kg, such as about 0.1 to about 50 mg/kg, about 0.1 to about 25 mg/kg, about 0.1 to about 20 mg/kg, about 0.1 to about 15 mg/kg, about 0.1 to about 10 mg/kg, about 0.5 to about 100 mg/kg, about 0.5 to about 50 mg/kg, about 0.5 to about 25 mg/kg, about 0.5 to about 20 mg/kg, about 0.5 to about 15 mg/kg, about 0.5 to about 10 mg/kg, about 1 to about 100 mg/kg, about 1 to about 50 mg/kg, about 1 to about 25 mg/kg, about 1 to about 20 mg/kg, about 1 to about 15 mg/kg, or about 1 to about 10 mg/kg.

In certain embodiments, the conjugate is administered subcutaneously, and the total dose of the conjugate within a treatment cycle is about 0.1 to about 25 mg/kg. In certain other preferred embodiments, the conjugate is administered subcutaneously, and the total dose of the conjugate within a treatment cycle is about 0.5 to about 20 mg/kg. In certain preferred embodiments, the conjugate is administered subcutaneously, and the total dose of the conjugate within a treatment cycle about 0.1, about 0.5, about 2, about 4, about 6, about 8, about 10, about 12, about 14, or about 16 mg/kg.

In certain embodiments, the conjugate is administered subcutaneously, and the dose of the conjugate per administration is about 0.1 to about 25 mg/kg. In certain other preferred embodiments, the conjugate is administered subcutaneously, and the dose of the conjugate per administration is about 0.5 to about 20 mg/kg. In certain preferred embodiments, the conjugate is administered subcutaneously, and the dose of the conjugate per administration about 0.1, about 0.5, about 2, about 4, about 6, about 8, about 10, about 12, about 14, or about 16 mg/kg.

Application of immune-stimulatory conjugates described herein shows substantial benefit in directing a subject's own immune response to cells of a particular site of disease or disorder, such as cells associated with the disease or disorder. Activating or stimulating an immune response directed to targeted cells facilitates the reduction, inhibition of proliferation, inhibition of growth, inhibition of progression, inhibition of metastasis or otherwise inhibition up to and including in some cases clearance of the targeted cells. Thus, in some cases a targeted immune response activation or stimulation leads to inhibition of disease progression, or alleviation of at least one symptom of a manifest disease in a patient, up to and in some cases including complete elimination of from one symptom to an entire disease state in a subject.

In particular, the methods disclosed herein are well suited for use with immune stimulatory conjugates, such as immune stimulatory conjugates that direct an immune response in a subject to a particular disorder or disease location, cell type or cell. Accordingly, practice of some methods herein comprises selection of a suitable subject such as a subject to be subjected to or undergoing a treatment with a conjugate that directs a benzazepine or benzazepine-like compound of the conjugate to a particular disorder or disease site, cell type or cell. Often, the subject is selected for practice of the method due to having at least one symptom of a disease or disorder, or projected to develop at least one symptom of a disease or disorder (such as a subject in remission and at risk for relapse), suitable for treatment by a conjugate as disclosed herein. Some diseases are selected not based upon or not based solely on disease type, but upon detection or presence of a suitable epitope on a tumor, cell type or particular cell that facilitates localization of an immune-stimulatory conjugate to the epitope.

EXAMPLES

Example 1

Generation and Humanization of Anti-Nectin-4 Monoclonal Antibodies

Hybridomas producing monoclonal antibodies (mAbs) specific for human Nectin-4 were prepared from Balb/C and NZB/NZW mice were immunized with Nectin-4-mouse Fc (IgG2a) fusion protein and Nectin-4 transfected 3T3 cells using standard procedures. Antibody heavy and light chain sequences were obtained, amplified, and cloned. Clone supernatants containing the expressed mAbs were screened for the certain criteria, including, for example, high titer, binding to human Nectin-4 protein, binding to cells expressing Nectin-4, and cross-reactivity with *Cynomolgus macaque* cells. Based on the initial selection criteria, one mAb (D6C) was expressed and isolated.

For humanization of the D6C VH region (SEQ ID NO:9), the 3 CDR loops as defined by Kabat were grafted into the human germline sequence VH3-07 with JH6 to generate hzD6C VH (SEQ ID NO: 10).

For humanization of the D6C VL region (SEQ ID NO:11), the 3 CDR loops as defined by Kabat were grafted into the human germline sequence VKII-O1 with JK4 to generate hzD6C VL (SEQ ID NO:12). In addition, several variants of hzD6C VLv1 were constructed to contain one or more mouse back mutations in framework region 1 (FR1), CDR1, or both. Variant 1 has a FR1 mutation (hzD6.1C VL I2V, SEQ ID NO: 13), and variants 2 and 3 each contain a different CDR1 mutation to remove a potential deamidation site (hzD6.2C VL G34A (position 30d under Kabat), SEQ ID NO: 14; and hzD6.3C VL N33Q (position 30c under Kabat), SEQ ID NO: 15; respectively). Variants 4 and 5 each have a FR1 and a CDR1 mutation (hzD6.4C VL I2V N33Q (positions 2 and 30c under Kabat), SEQ ID NO: 16; and hzD6.5C VL I2V G34A (positions 2 and 30d under Kabat), SEQ ID NO: 17; respectively).

The humanized D6C VH region was combined with human IgG1 (SEQ ID NO: 18) heavy chain constant region, and each humanized D6C VL region was combined individually with the human kappa light chain constant region (SEQ ID NO:20). The humanized D6C heavy chain (SEQ ID NO:24) was co-transfected with each humanized light chain (SEQ ID NOS:26-31) individually into CHO cells in a 30 mL culture, using the parental chimeric antibody, D6C, as a benchmark. A total of 7 mAbs were generated, purified, and analyzed for titer, purity, and binding.

The highest titers were observed for hzD6.1C VL-hzD6.4C VL (481, 432, 476, and 426 mg/L, respectively), whereas the titers for chimeric D6C VL, hzD6C VL, and hzD6.5C VL were substantially lower (206, 345, and 177 mg/L, respectively). Analytical size-exclusion chromatography was used to measure the percent purity (% protein of interest, POI), which is preferably 95% or greater. There was a reduction in percent purity seen with the chimeric D6C (84%) and the CDR grafted hzD6C VL (94%). The I2V, N33Q, and G34A mutations in hzD6.1C VL (98%), hzD6.2C VL (95%), and hzD6.3C VL (96%), respectively, as well as the IV2 N33Q double mutation hzD6.4C VL (99%), resolve the purity issue. In contrast, the IV2 G34A double mutation in hzD6.5C VL significantly reduces the purity (75%). Finally, for binding, the hzD6C VL, hzD6.1C VL, hzD6.2C VL, and hzD6.5C VL showed the best binding (KD=17, 21, 32, and 44, respectively), whereas the hzD6.3C VL and hzD6.4C VL constructs showed reduces binding to human Nectin-4 (KD=286 and 204, respectively) and no binding to mouse Nectin-4. Antibody epitope binning experiments utilizing Octet® (ForteBio, Inc.) kinetic analysis revealed a competitive blocking profile similar to humanized mAb Ha2-22 (a known anti-Nectin-4 mAb; see, e.g., U.S. Pat. Publication No. 2012/0078028)

Based on these results, mAbs containing the D6C VH region and hzD6.1C VL, and containing the D6C VH region and hzD6.2C VL, were selected for further use and analysis.

Example 2

Anti-Nectin-4 Immunoconjugates Bind to Nectin-4 Expressing Cell Lines

To examine the ability of anti-Nectin-4-TLR8 agonist conjugates to bind to Nectin-4-expressing cell lines (HEK-293 cells transfected with human or cynomolgus Nectin-4, or Nectin-4 expressing tumor cell line MDA-MB-175-VII), cells were plated at about $5 \times 10^4$ cells/well and contacted with titrating concentrations of unconjugated anti-Nectin-4 antibodies (hzD6.2C, hzD6.1C, D6C and anti-Nectin-4 mAb IgG1 (a humanized mAb having CDRs from Ha22-2), anti-Nectin-4-TLR8 agonist immunoconjugates (hzD6.2C-Compound 2.14, hzD6.1C-Compound 2.14, D6C IgG1-Compound 2.14, and anti-Nectin-4 IgG1-Compound 2.14), or antibody isotype control (Digoxin IgG1) in FACS Wash (FW-PBS, 2% FBS, 1 mM EDTA) for 30 mins, at 4° C. followed by secondary anti-huIgG1-PE staining in FW for 30 mins, at 4° C. After incubations, cells were washed with FW and then analyzed on a flow cytometer.

Figure 1B:
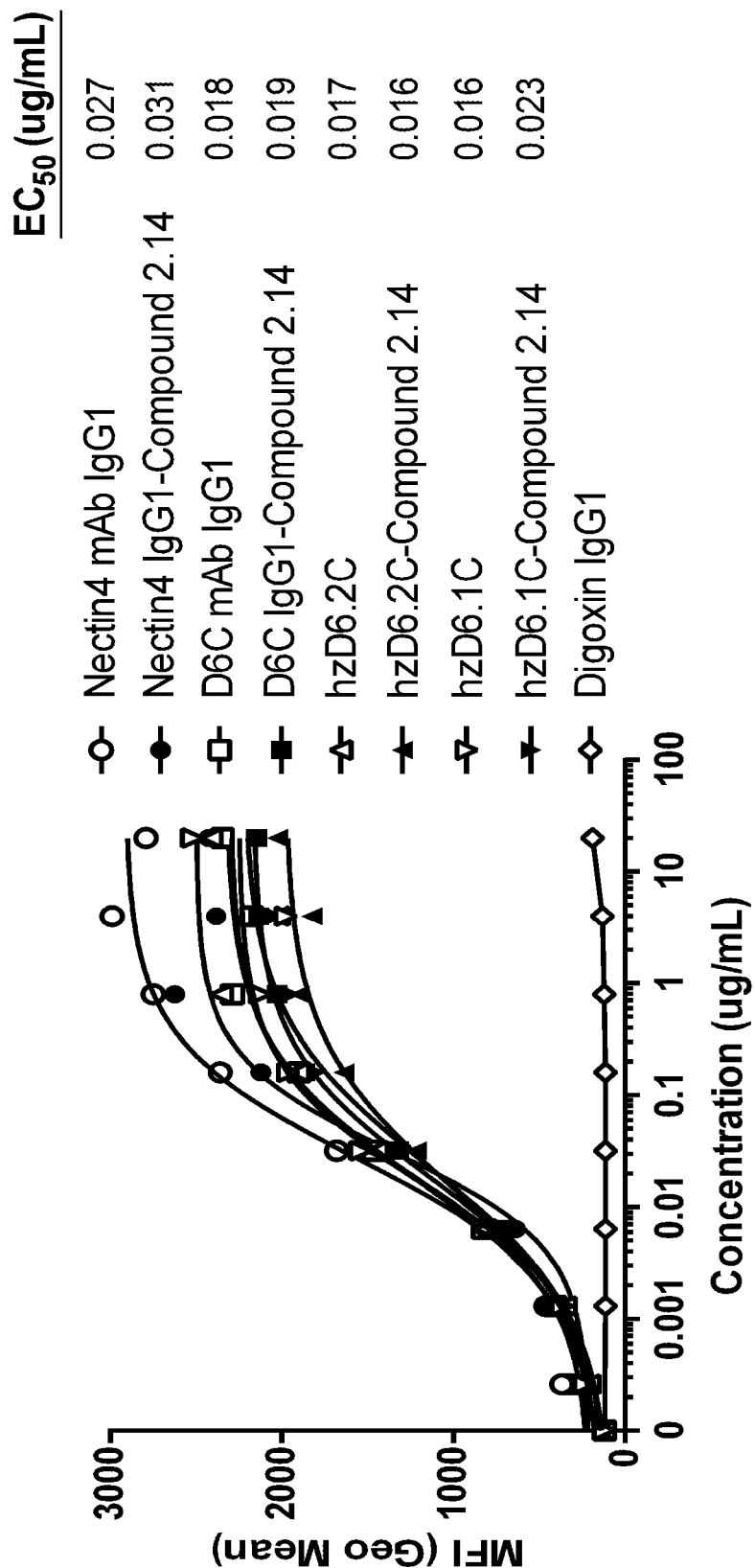
Figure 1C:
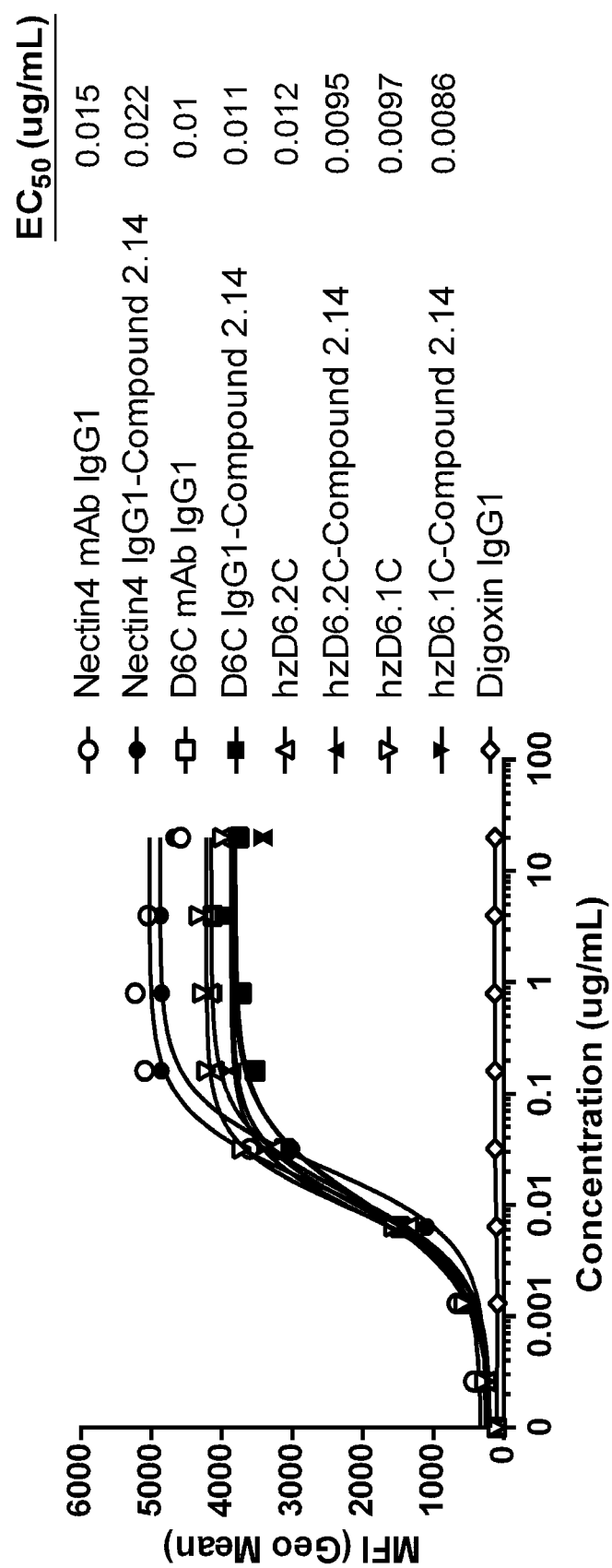
Figure 2A:
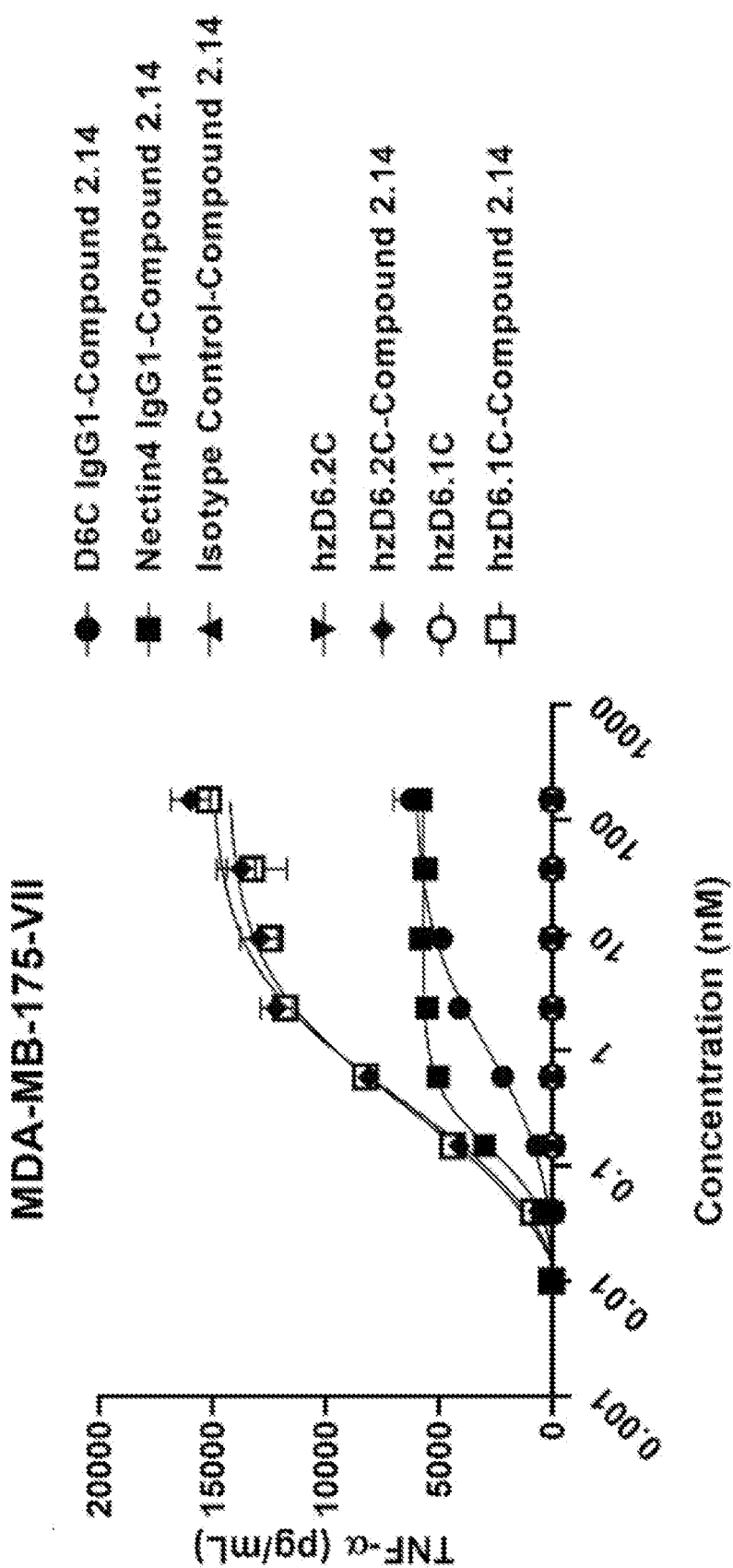
FIGS. 2A-2B show TNF-α production in PBMC-Nectin-4+ tumor cell co-cultures when contacted with anti-Nectin- 4-TLR8 agonist conjugates, but not when contacted with unconjugated Nectin-4-specific antibodies. PBMCs were cultured 24 hours with (A) Nectin-4-expressing MDA-MB-175-VII cells (FIG. 2A) or (B) Nectin-4-negative HEK-293 cells (FIG. 2B) in the presence of equivalent titrated concentrations of anti-Nectin-4-TLR8 agonist, matched unconjugated anti-Nectin-4 mAb, or isotype control antibody conjugate.
Figure 2B:
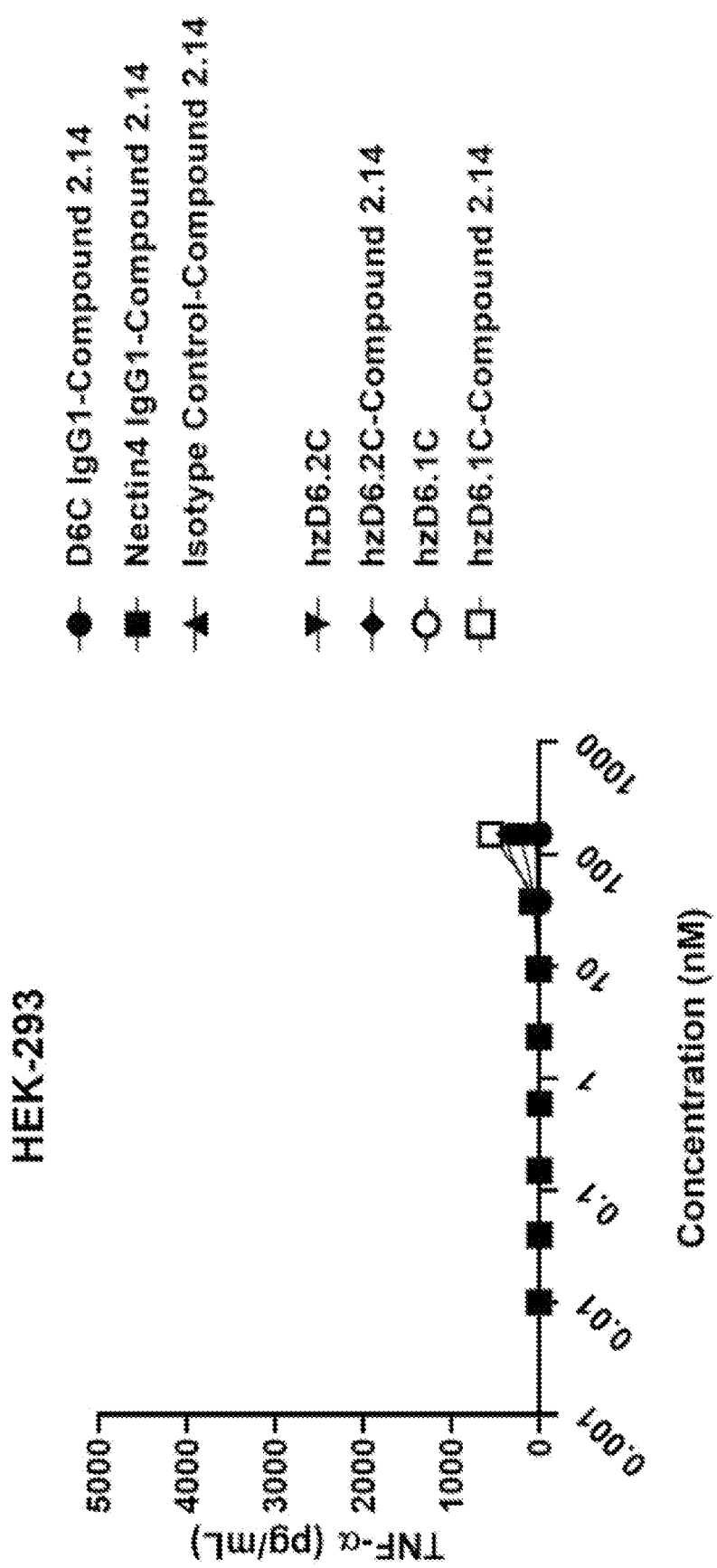
Figure 3A:
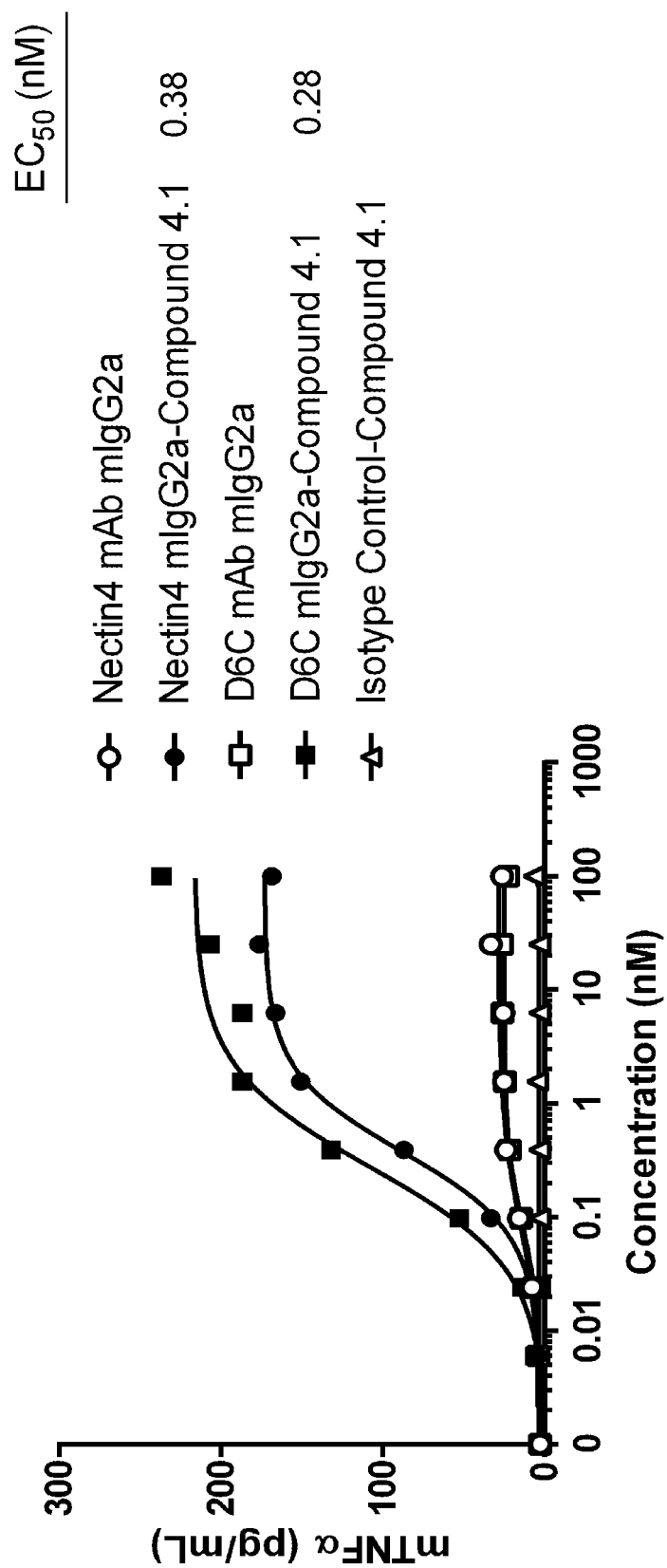
FIGS. 3A-3B show that anti-Nectin-4-TLR7 agonist immunoconjugate (a surrogate for human TLR8 agonist conjugates of this disclosure since only TLR7 (and not TLR8) is expressed in murine myeloid cells) can induce TNF-α production in murine bone marrow-derived macrophages (BMDM) when co-cultured with HEK-293 human expressing Nectin-4.
Figure 3B:
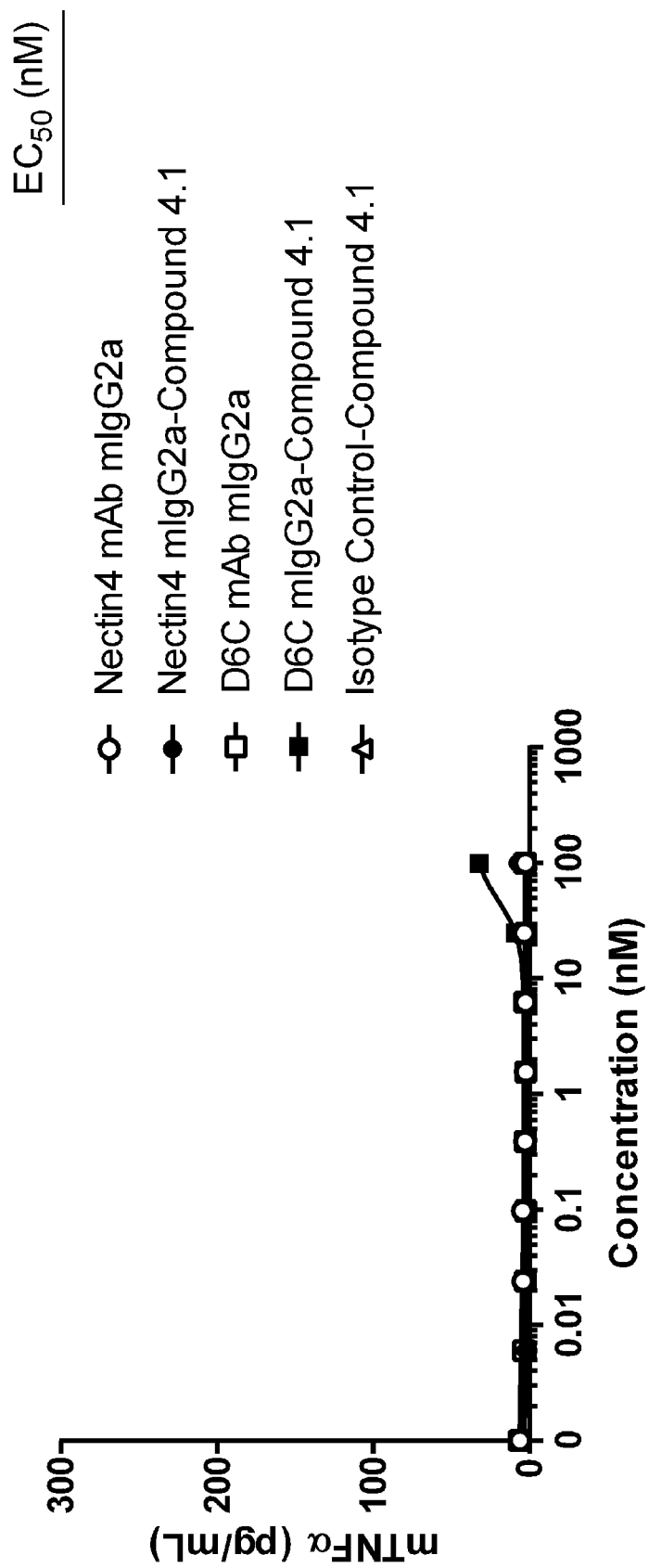

FIGS. 1A-1C show that the humanized anti-Nectin-4 immunoconjugates (hzD6.2C-Compound 2.14, hzD6.1C-Compound 2.14, and anti-Nectin-4 IgG1-Compound 2.14), as well as the parental antibody TLR8 agonist conjugate (D6C IgG1-Compound 2.14), all bind to the human and the cynomolgus Nectin-4-expressing cells with a similar $EC_{50}$ as their unconjugated anti-Nectin-4 antibody counterparts (hzD6.2C, hzD6.1C, D6C and Nectin4 mAb IgG1). Thus, the conjugation of the TLR8 agonist to the antibodies does not affect their ability to specifically bind to Nectin-4. In addition, Nectin-4 binding by the hzD6.2C-Compound 2.14, which has a mutation in CDR1, was surprisingly not affected.

Example 3

Human PBMC TNF-Alpha Production Induced by Anti-Nectin-4 TLR8 Agonist Conjugates in the Presence of Nectin-4 Expressing Tumor Cell Lines Production of TNF-α from peripheral blood mononuclear cells (PBMCs) co-cultured with Nectin-4 expressing tumor cell lines when contacted with anti-Nectin-4-TLR8 agonist conjugates was examined. Briefly, PBMCs were isolated from normal human donor peripheral blood using SepMate™-50 PBMC Isolation Tubes (STEMCELL Technologies) according to manufacturer's instructions. Isolated PBMCs were cultured with the Nectin-4 expressing tumor cell line MDA-MB-175-VII (ATCC) or the Nectin-4 negative cell line HEK-293 (ATCC) at a 5:1 ratio in the presence of titrated concentrations of anti-Nectin-4-TLR8 agonist antibody conjugates, unconjugated anti-Nectin-4 antibody controls, or an isotype control-TLR8 agonist conjugate. After 24 hours, the cell-free supernatants were collected and stored at −80° C. prior to analysis. TNF-α levels in the cell-free supernatants were quantified using the TNF-α (human) AlphaLISA® Detection Kit (Perkin Elmer) according to manufacturer's instructions.

FIGS. 2A-2B show that anti-Nectin-4-TLR8 agonist conjugates induced TNF-α production in a dose-dependent manner from human PBMCs in the presence of the Nectin-4 expressing MDA-MB-175-VII tumor cell line (FIG. 2A), but not in the presence of HEK-293 cells lacking expression of Nectin-4 (FIG. 2B). Unexpectedly, the humanized derivatives hzD6.1C-Compound 2.14 and hzD6.2C-Compound 2.14 not only showed twice the potency in inducing TNF-α production ($EC_{50}$ of 0.33 nM and 0.37 nM, respectively [average of three experiments]) compared to the parental antibody TLR8 agonist conjugate (D6C IgG1-Compound 2.14; $EC_{50}$ of 0.83 nM), but also induced about a 3-fold increase in maximal TNF-α production (see FIG. 2A). Moreover, while the humanized anti-Nectin-4 IgG1-Compound 2.14 conjugate (Ha22-2 anti-Nectin-4 antibody that cross-blocks the D6C antibodies of this disclosure) demonstrated an increased potency ($EC_{50}$ of 0.13 nM), the humanized derivatives hzD6.1C-Compound 2.14 and hzD6.2C-Compound 2.14 of this disclosure still unexpectedly induced about a 3-fold increase in maximal TNF-α production (see FIG. 2A). TNF-α production by PBMCs was not induced in the presence of the Nectin-4 expressing tumor cell line with unconjugated antibodies, which indicates that TLR8 agonism is needed for TNF-α release. Furthermore, none of the conjugated or unconjugated antibodies stimulated TNF-α production from PBMCs in the absence of Nectin-4-expressing tumor cells indicating that the activity is dependent upon Nectin-4 expression. Low level PBMC TNF-α production was observed with the Nectin-4 negative HEK-293 cell line only in cultures containing the highest concentrations of anti-Nectin-4-TLR8 conjugates tested. Similar results were observed with cynomolgus PBMC cultures from 4 separate donors (data not shown).

Example 4

Anti-Nectin-4-TLR8 Agonist Surrogate Immunoconjugates Induce TNFalpha Production in Macrophages Rodents do not express a functional homolog of TLR8 and attempts by multiple groups to generate relevant human TLR8 transgenic mice have been unsuccessful (Wang, *J. Biol. Chem.* 257:37427, 2006; Guiducci, *J. Exp. Med* 270: 2903, 2013). Like TLR8 in humans, and in contrast to TLR7 in humans, TLR7 in mice is expressed in myeloid cells, like macrophages. Thus, for murine experiments, an anti-Nectin-4-TLR7 agonist conjugate is used as a surrogate for human anti-Nectin-4-TLR8 agonist conjugates). To examine whether the anti-Nectin-4-TLR7 agonist conjugate surrogate could induce TNFα expression murine bone marrow-derived macrophages (BMDM), such cells were obtained by harvesting bone marrow cells from a Balb/c mice and differentiating in vitro into macrophages for 7 days in media supplemented with murine M-CSF.

After differentiation, murine BMDM were harvested and counted before being seeded at about $8.0\times10^4$ cells/well in 96-well flat bottom microtiter plates in assay media (RPMI, 10% Fetal Bovine Serum, 1 mM Sodium Pyruvate, IX GlutaMAX-1, 1× Non-Essential Amino Acids, 10 mM HEPES, 50 units/mL Penicillin and 50 ug/mL Streptomycin). Nectin-4-expressing HEK-293 cells were then added (about $4.0\times10^4$ cells/well) along with titrating concentrations of unconjugated anti-Nectin-4 antibodies (D6C mAb IgG2a, and anti-Nectin-4 mAb mIgG2a), anti-Nectin-4-TLR7 agonist immunoconjugates (D6C mIgG2a-Compound 4.1 and anti-Nectin-4 mIgG2a-Compound 4.1), or control TLR7 agonist immunoconjugate (Isotype Control-Compound 4.1). Mock transfected HEK-293 cells were used as a negative control. After 24 hours culture, supernatants were collected and murine TNFα levels in the supernatants were determined by ELISA.

The surrogate anti-Nectin-4-TLR7 agonist immunoconjugates (D6C mIgG2a-Compound 4.1 and anti-Nectin4 mIgG2a-Compound 4.1) were active when crosslinked with HEK-293 cells transfected with Nectin-4, stimulating production of TNFα from murine BMDM in a dose dependent manner (FIG. 3A) similar to the anti-Nectin4-TLR8 agonist immunoconjugates in the human PBMC assay system. In contrast, the unconjugated anti-Nectin-4 antibodies (D6C mAb IgG2a, and anti-Nectin-4 mAb mIgG2a) stimulated low levels of TNFα production from murine BMDM in the presence of HEK-293 cells transfected with Nectin-4. Furthermore, none of the immunoconjugates or unconjugated antibodies stimulated TNFα production from murine BMDM in the presence of HEK-293 cells lacking expression of Nectin-4 (FIG. 3B).

Example 5

In Vivo Activity of Nectin4-TLR7 Agonist Conjugate Surrogate in Mice Bearing Human Nectin-4 Expressing EMT6 Tumors To examine the in vivo efficacy of the anti-Nectin-4-TLR7 agonist conjugate surrogate (D6C mIgG2a-Compound 4.1), 7-9 week old female Balb/c mice (The Jackson Laboratory) were orthotopically implanted subcutaneously into the mammary fat pad with about $1\times10^5$ human Nectin-4-expressing EMT6 syngeneic breast cancer cells. Tumor volumes were measured using the equation: $VOL=(L\times W^2)/$ 2. Once tumors reached approximately 150 mm³ (Day 0), mice were sorted into groups of 10 and each group was individually dosed subcutaneously with 10 mg/kg of one of: (a) mouse IgG2a (mIgG2a) isotype control, (b) D6C mIgG2a (unconjugated), or (c) D6C mIgG2a-Compound 4.1, every 7 days for a total of 3 doses. The isotype control antibody was an anti-digoxin antibody. Tumor volumes were recorded 3 times per week for at least 28 days. Statistical analysis was performed using Log-rank (Mantel-Cox) test.

Figure 4:
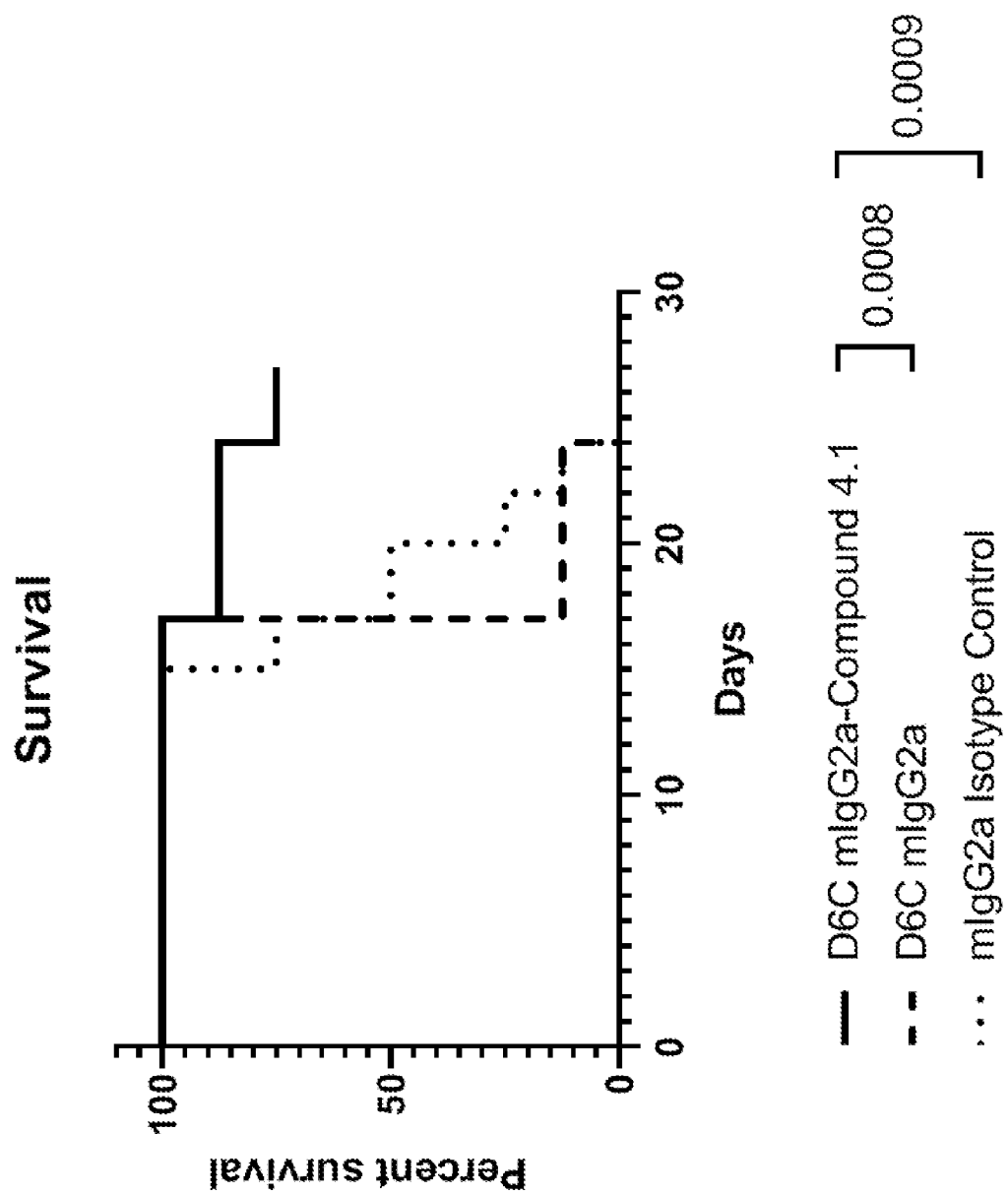
FIG. 4 is a Kaplan-Meier plot of mice bearing human Nectin-4 expressing EMT6 tumors treated with a surrogate of the Nectin-4 conjugates of this disclosure.

FIG. 4 shows that the mice treated with the surrogate of the anti-Nectin-4-TLR8 agonist conjugate resulted in delayed tumor growth and a survival advantage as compared to those treated with the unconjugated anti-Nectin-4 antibody or the isotype control.

Example 6

Intra-Tumoral Chemokines and Cytokines in Tumor-Bearing Mice Treated with a Surrogate of a Nectin4-TLR8 Conjugate To examine the effect of treating tumor-bearing mice with Nectin4-TLR7 conjugate (D6C mIgG2a-Compound 4.1), a surrogate for human Nectin4-TLR8 conjugate, chemokine and cytokine production was evaluated in the tumors. Briefly, female BALB/c mice (Jackson Laboratory) were inoculated in the mammary fat with 1×10⁵ human Nectin4-expressing EMT6 syngeneic breast cancer cells. Once tumors reached a volume of approximately 100 mm³ (Day 0), mice were sorted into groups of 6 mice and each group was individually dosed once subcutaneously with 10 mg/kg of one of: (a) D6C mIgG2a (unconjugated control) or (b) D6C mIgG2a-Compound 4.1. Two days later, tumors were excised and weighed. In a separate study, mice were inoculated, treated as described above and tumors were excised at day 5. Tumors were placed in 500 mL RPMI (Gibco) and mechanically dissociated on ice. The resulting supernatants were analyzed by Luminex (Millipore) for intra-tumoral levels of chemokines MCP-1 and IP 10 (indicators of myeloid cell activation) and cytokines IFN-γ and IL-2 (indicators of T cell and/or NK cell activation). Data is expressed as picogram of analyte per gram of starting tissue. Statistical analysis was performed using Log-rank (Mantel-Cox) test.

Figure 5A:
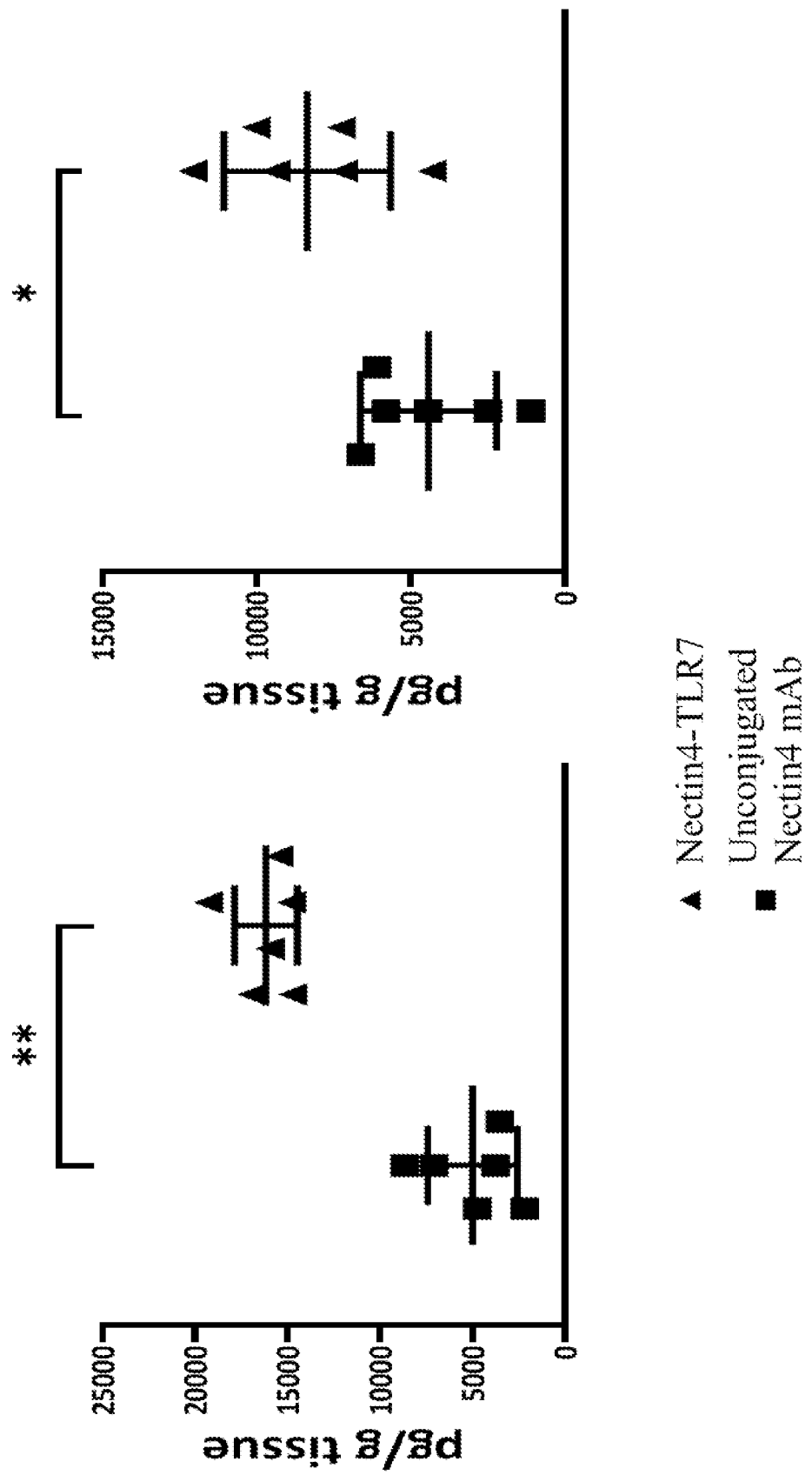
FIGS. 5A and 5B show that in vivo treatment with a surrogate for human Nectin4-TLR8 conjugate in tumor-bearing mice leads to increased intra-tumoral chemokines (FIG. 5A) and cytokines (FIG. 5B). Mice bearing Nectin4-expressing EMT6 tumors were treated with a single dose of either D6C mIgG2a (unconjugated control) or D6C mIgG2a-Compound 4.1 conjugate and tumors were: (A) harvested at Day 2 and levels of the indicated chemokines in the tumors were assessed (FIG. 5A), or (B) harvested at Day 5 and levels of the indicated cytokines in the tumors were assessed (FIG. 5B). Statistical significance was determined by Mann-Whitney test. *$p<0.001$, $p<0.01$, *$p<0.05$.
Figure 5B:
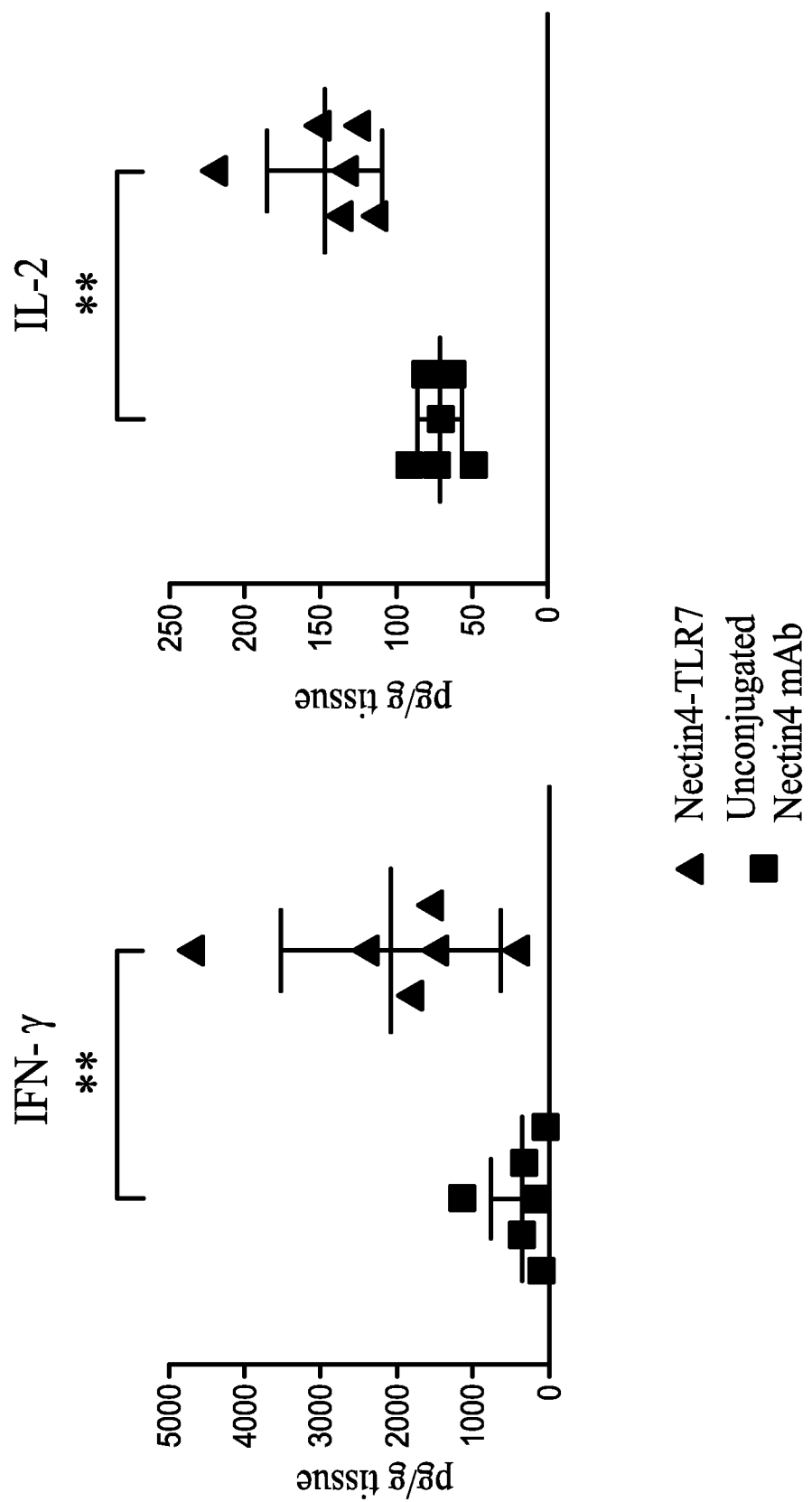

As shown in FIG. 5A, MCP-1 and IP 10 production was significantly increased by treatment with D6C mIgG2a-Compound 4.1 compared to D6C mIgG2a at day 2, indicating potent myeloid cell activation. Moreover, IFN-γ and IL-2 production was augmented at day 5 in tumors of mice treated with D6C mIgG2a-Compound 4.1 (FIG. 5B), which indicates that T cells and NK cells are being activated. Overall, these data indicate that treatment with D6C mIgG2a-Compound 4.1 conjugate can promote an enhanced innate immune response driven by myeloid cell activation, which in turn is capable of nucleating an adaptive immune response by indirectly activating T and NK cells within the tumor.

Example 7

Specificity of Anti-Nectin-4 Monoclonal Antibodies for Nectin-4

Analysis of hzD6.2C monoclonal antibody (mAb) for binding to human Nectin-1, Nectin-2, Nectin-3, and Nectin-4 extracellular domains (ECDs) was performed using Octet® Red 96 instrument (ForteBio, Inc.). Biotinylated hzD6.2C mAb was immobilized on streptavidin biosensors and incubated with hFc-tagged human Nectin-1, -2, -3, and -4 ECD dimeric proteins (Sino Biological) at varying concentrations ranging from 1.2 nM to 300 nM in PBS/1% BSA/0.2% Tween 20. The experimental measurements were performed as follows: (1) baseline acquisition (30 s); (2) biotinylated hzD6.2C mAb loading onto streptavidin biosensor (120 s); (3) second baseline acquisition (30 s); (4) association of interacting dimeric Nectin 1/2/3/4 ECD proteins for $k_{on}$ measurement (90 s); and (5) dissociation of interacting dimeric ECDs for $k_{off}$ measurement (180 s). The interacting dimeric Nectin ECD proteins were used at 5-6 concentrations of 3-fold concentration series. Data were analyzed using Octet® Data Analysis Software 9.0 (ForteBio, Inc.) and fitted to the 1:1 binding model. Equilibrium dissociation constants ($K_D$) were calculated by the ratio of $k_{on}$ to $k_{off}$. Data are provided in Table 5 below. hzD6.2C mAb showed specific binding to human Nectin-4 ECD, while no detectable binding was observed between hz3E2-4 mAb and Nectin-1, -2, and -3 ECDs.

TABLE 5

| Specificity of hzD6.2C mAb Binding to Nectin-4 | | |
| --- | --- | --- |
| Antibody | ECD | $K_D$ (with avidity) |
| hzD6.2C | huNectin-1 ECD-hFc | — |
|  | huNectin-2 ECD-hFc | — |
|  | huNectin-3 ECD-hFc | — |
|  | huNectin-4 ECD-hFc | <1 pM |

— No binding detected

Example 8

Anti-Nectin-4 Antibody Blocking of TIGIT Binding to Nectin-4 Expressing Tumor Cells Anti-Nectin-4 antibody was examined to determine whether it could block binding of TIGIT to Nectin-4 expressing T24 tumor cells. Stable Nectin-4 expression in a T24 clone was achieved by Nectin4-lentiviral transduction. Recombinant human TIGIT-Fc chimera was purchased from R & D Systems. Briefly, cell binding was examined on Nectin-4 expressing T24 cells, which were dispensed into wells of V-bottom 96-well assay plates (1×10⁵ cells/well), spun down, and the supernatant discarded. The cells were incubated with an anti-Nectin-4 antibody (hzD6.2C-mIgG2a) or an isotype control (mIgG2a) at eight different concentrations, starting with 400 nM and then 1:2 serial dilution, incubated at 4° C. for 30 min., and then rhTIGIT-Fc was added to each well at a final concentration of 40 nM. The treated cells were incubated at 4° C. for 30 min., washed three times, and then commercial PE anti-human Fc as a secondary antibody (1:200 dilution) was added and incubated at 4° C. for 20 min. The cells were washed twice and analyzed on BD Celesta™ flow cytometry. Percent of inhibition of TIGT (40 nM) binding due to anti-Nectin-4 antibody present was measured.

Figure 6:
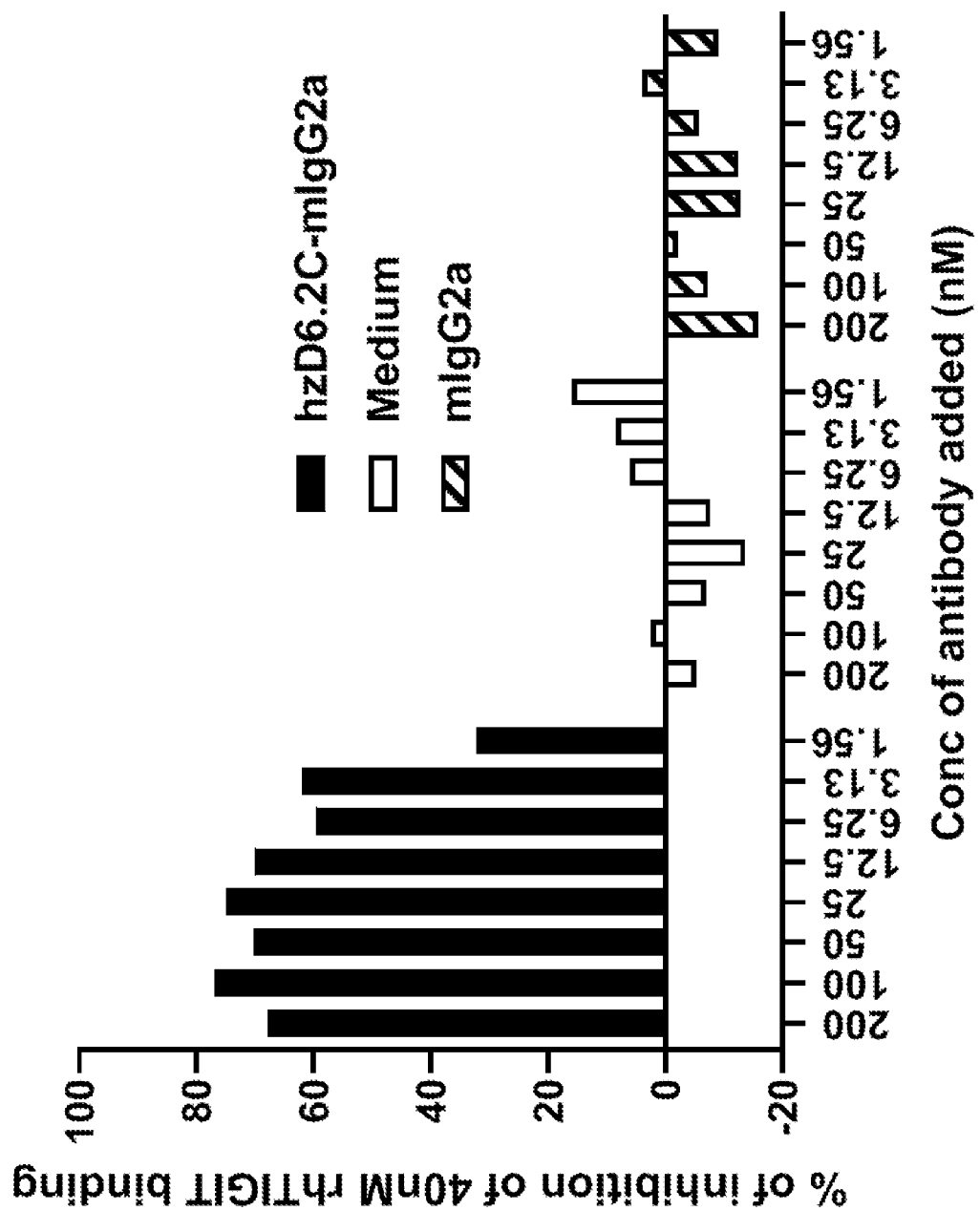
FIG. 6 shows that the binding of TIGIT-Fc to Nectin4-expressing tumor cells was blocked by the binding domain of hzD6.2C.

FIG. 6 shows that that anti-Nectin-4 antibody hzD6.2C-mIgG2a was capable of blocking more than 70% TIGIT binding at various concentrations, while mIgG2a isotype did not block TIGIT binding to Nectin-4 (the measurements slightly above or below the x-axis were within the margin of error).

Example 9

Anti-Nectin-4 Antibody Blocking of TIGIT Binding to Nectin-4 Expressing Tumor Cells To examine the in vivo efficacy of the anti-Nectin-4-TLR7 agonist conjugate surrogate (D6C mIgG2a-Compound 4.1), 7-9 week old female Balb/c mice (The Jackson Laboratory) were orthotopically implanted subcutaneously into the mammary fat pad with about $1\times10^5$ human Nectin-4-expressing EMT6 syngeneic breast cancer cells. Tumor volumes were measured using the equation: $VOL=(L\times W^2)/2$. When tumors reached approximately 90 mm$^3$ (Day 0), mice were sorted into groups of 8 mice each and dosed subcutaneously with 10 mg/kg of one of: (a) mouse IgG2a (mIgG2a) isotype control, (b) D6C mIgG2a (unconjugated control), or (c) D6C mIgG2a-Compound 4.1, every 7 days for a total of 6 doses. Tumor volume was recorded 3 times per week and mice were euthanized when tumors reached 1500 mm$^3$.

Figure 7A:
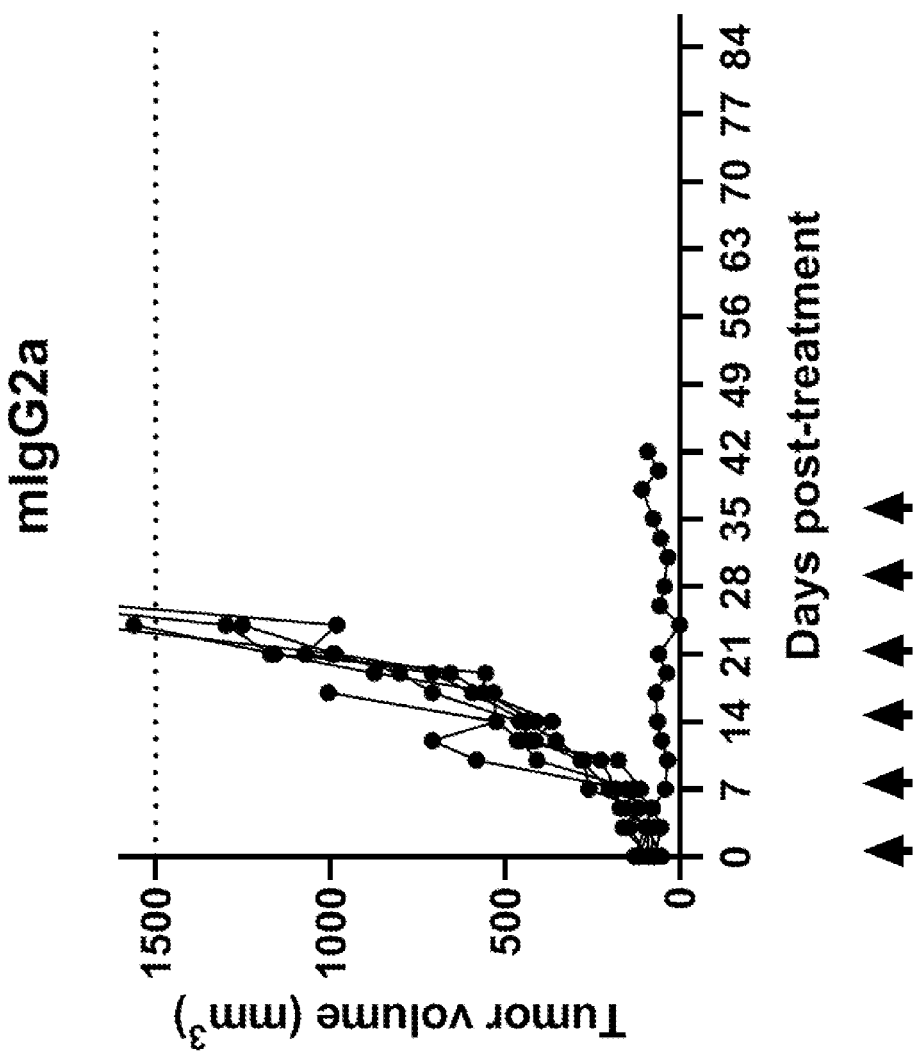
FIGS. 7A to 7C depict tumor volume (in cubic millimeters) as a function of time (measured in days post-treatment) following a subcutaneous injection into mice bearing human Nectin-4 expressing EMT6 tumors of a mouse IgG2a isotype control (mIgG2a) (FIG. 7A), an anti-Nectin-4 antibody alone (D6C mIgG2a) (FIG. 7B), or an anti-Nectin-4-TLR7 agonist conjugate surrogate (D6C mIgG2a-Compound 4.1) (FIG. 7C).
Figure 7B:
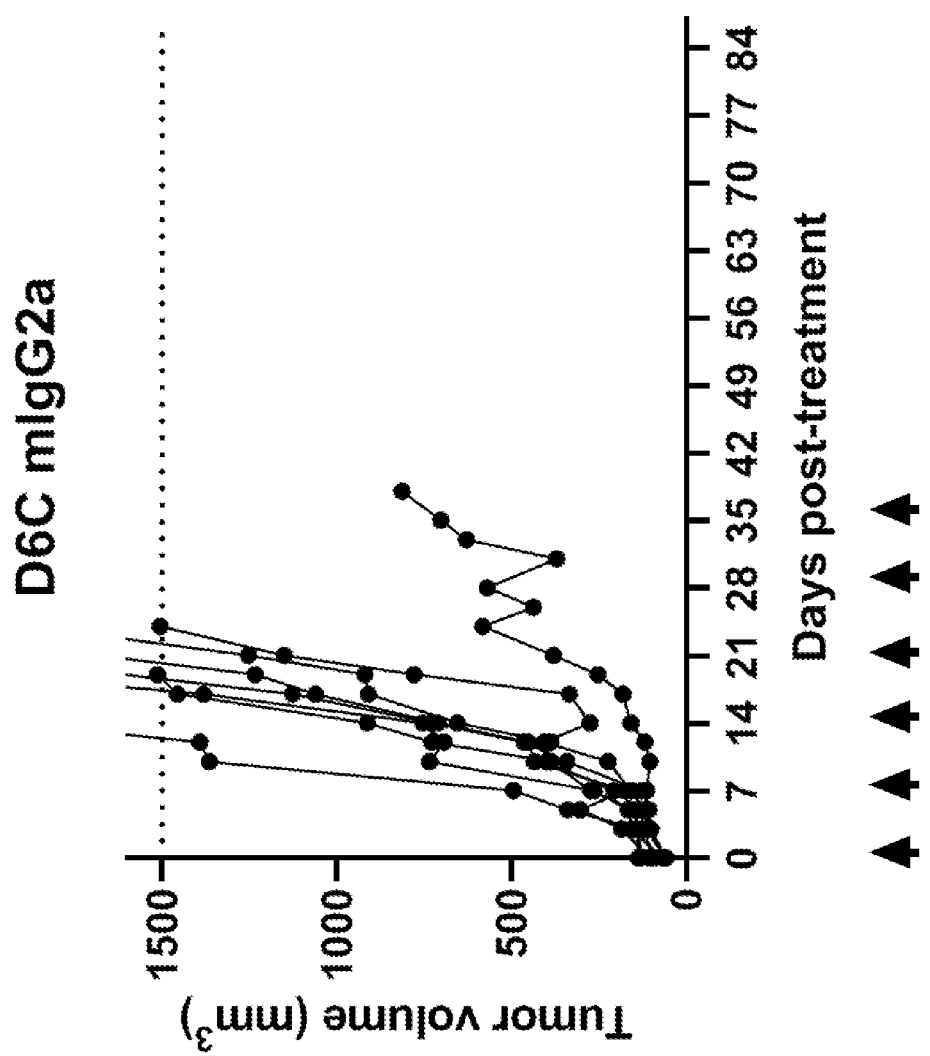
Figure 7C:
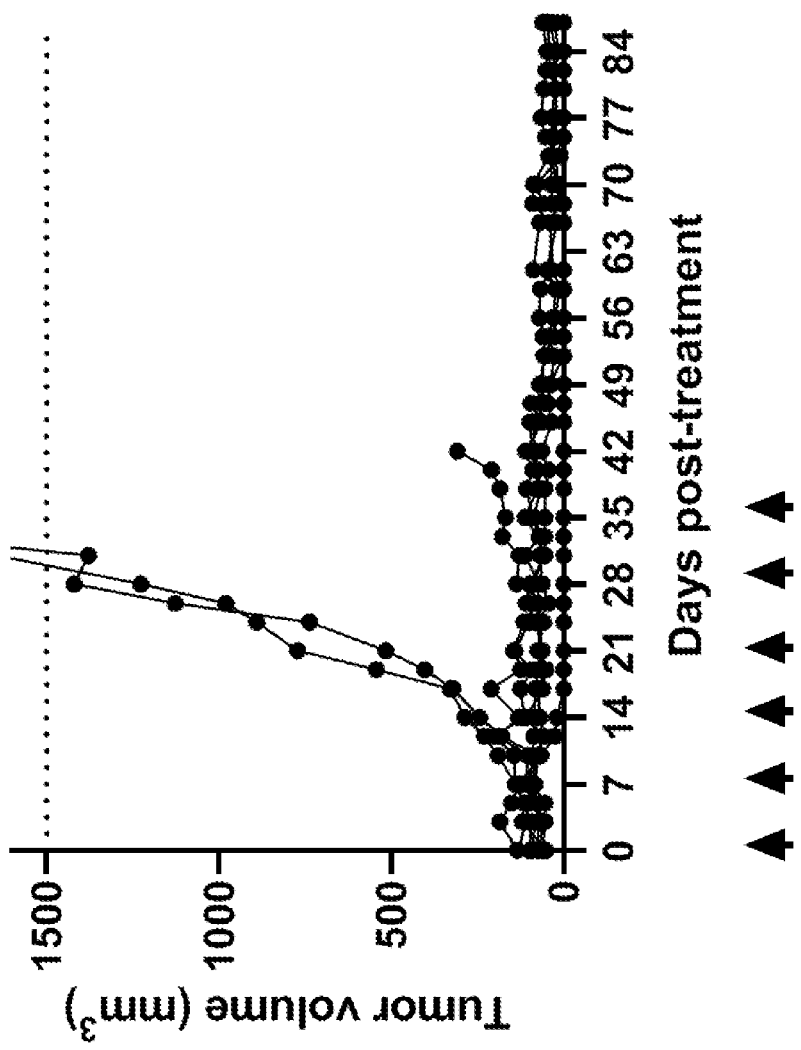

FIGS. 7A to 7C display the anti-tumor efficacy induced by single agent anti-Nectin-4-TLR7 agonist conjugate surrogate (D6C mIgG2a-Compound 4.1). This treatment inhibited tumor growth in 62.5% of mice, and durable growth control was observed to at least day 87.

Example 10

In Vivo Pharmacodynamic Activity of Anti-Nectin4-TLR8 Agonist Conjugate in Non-Human Primate (NHP)

To examine safety and tolerability, an anti-Nectin-4-TLR8 agonist conjugate was administered by subcutaneous (SC) injection to cynomolgus monkeys at dose levels ranging from 0.1 to 12 mg/kg. Blood samples were obtained prior to dosing and at 6, 24, 48, and 96 hours post-dose, and serum was recovered and stored in a freezer set to maintain −80° C. Samples were examined for chemokine serum concentrations using a multiplex immunooncology assay (Meso Scale Diagnostics, Rockville, Md.). In this study, the anti-Nectin-4-TLR8 agonist conjugate used was D6.2C IgG1-Compound 2.14.

Figure 8:
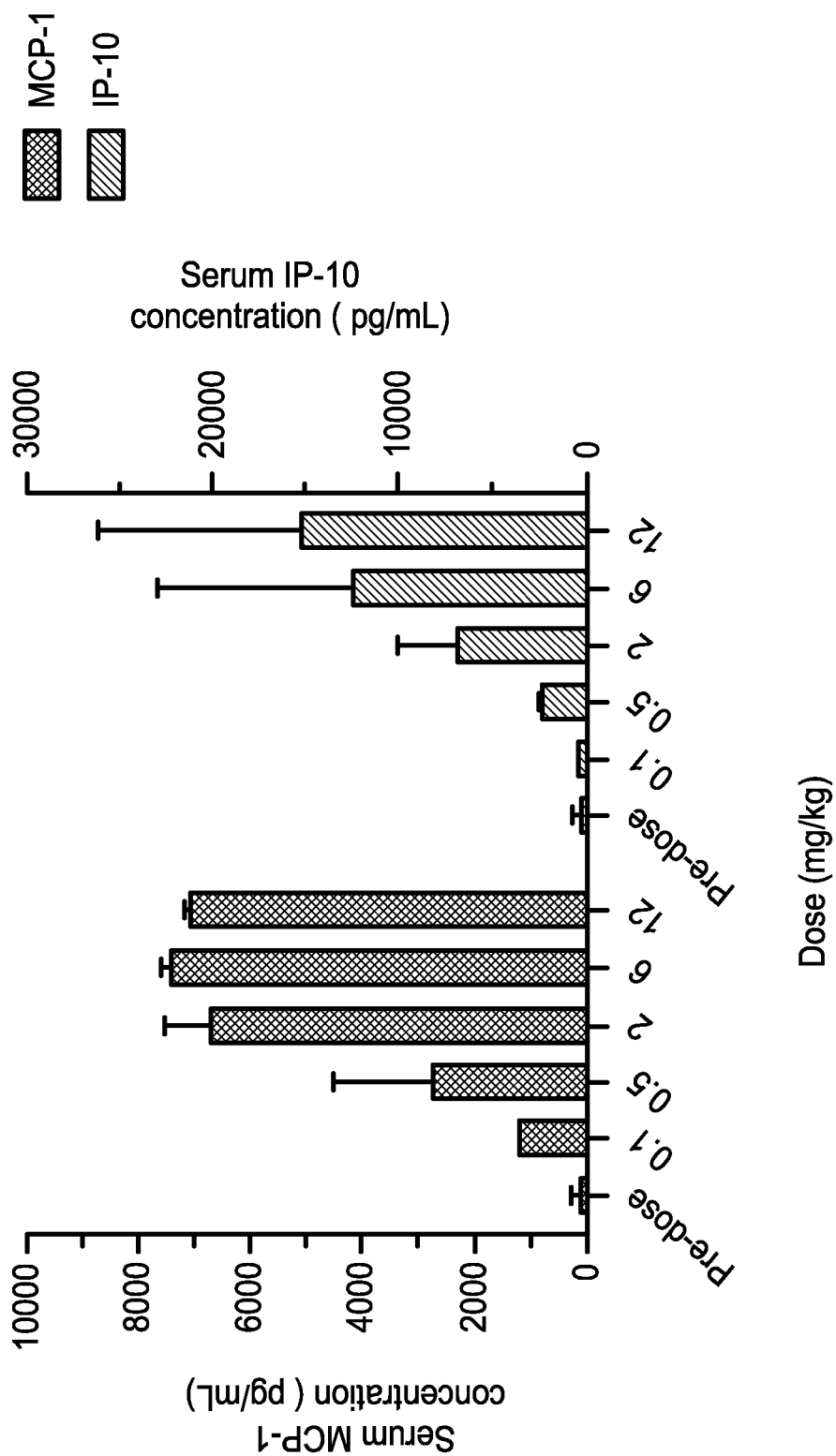
FIG. 8 depicts the mean pre-dose and peak serum MCP-1 and IP-10 concentrations as compared to dose level in monkeys following subcutaneous administration of an anti-Nectin-4-TLR8 agonist conjugate (D6.2C IgG1-Compound 2.14).

Consistent with activation of TLR8, SC doses of the anti-Nectin-4-TLR8 agonist conjugate led to transient increases in the serum concentration of markers indicative of myeloid cell activation in NHP, such as monocyte chemoattractant protein-1 (MCP-1) and interferon gamma-induced protein 10 (IP-10), which showed dose-response relationships, particularly at the lower dose levels (FIG. 8).

The data demonstrate that the anti-Nectin-4-TLR8 agonist conjugate activated myeloid cells in NHP following systemic administration via subcutaneous injection in a dose-dependent manner, and displayed a favorable safety and tolerability profile.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A myeloid cell agonist conjugate or a salt thereof, wherein the conjugate is represented by Formula (I):

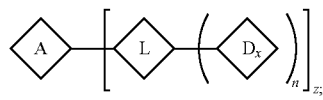

wherein:
A is an anti-Nectin-4 antibody, or an antigen-binding fragment thereof, comprising a heavy chain variable region (VH) and a light chain variable region (VL), wherein the VH comprises a CDR1 (VH-CDR1) comprising the amino acid sequence of SEQ ID NO:1, a VH-CDR2 comprising the amino acid sequence of SEQ ID NO:2, a VH-CDR3 comprising the amino acid sequence of SEQ ID NO:3; and the VL comprises a CDR1 (VL-CDR1) comprising the amino acid sequence selected from any one of SEQ ID NOS:4-6, a VL-CDR2 comprising the amino acid sequence of SEQ ID NO:7, and a VL-CDR3 comprising the amino acid sequence of SEQ ID NO:8;
L is a linker;
$D_x$ comprises a TLR8 agonist;
n is selected from 1 to 20; and
z is selected from 1 to 20.

2. The myeloid cell agonist conjugate of claim 1, wherein the anti-Nectin-4 antibody or antigen-binding fragment thereof comprises:

(a) a VH comprising an amino acid sequence that has at least 90% identity with the amino acid sequence of SEQ ID NO: 10, and a VL comprising an amino acid sequence that has at least 90% identity with the amino acid sequence of SEQ ID NO: 14; or (b) a VH comprising an amino acid sequence that has at least 90% identity with the amino acid sequence of SEQ ID NO: 10, and a VL comprising an amino acid sequence that has at least 90% identity with the amino acid sequence of SEQ ID NO: 13; or (c) a VH comprising an amino acid sequence that has at least 90% identity with the amino acid sequence of SEQ ID NO: 10, and a VL comprising an amino acid sequence that has at least 90% identity with the amino acid sequence of SEQ ID NO: 12; or (d) a VH comprising the amino acid sequence of SEQ ID NO: 10, and a VL comprising the amino acid sequence of SEQ ID NO: 14; or (e) a VH comprising the amino acid sequence of SEQ ID NO: 10, and a VL comprising the amino acid sequence of SEQ ID NO: 13; or (f) a VH comprising the amino acid sequence of SEQ ID NO: 10, and a VL comprising the amino acid sequence of SEQ ID NO: 12.

3. The myeloid cell agonist conjugate of claim 1, wherein A is an anti-Nectin-4 antibody and the antibody comprises:

(a) a heavy chain comprising an amino acid sequence that is at least 90% identity with the amino acid sequence of SEQ ID NO:24, and a light chain comprising an amino acid sequence that has at least 90% identity with the amino acid sequence of SEQ ID NO:28; or (b) a heavy chain comprising an amino acid sequence that is at least 90% identity with the amino acid sequence of SEQ ID NO:24, and a light chain comprising an amino acid sequence that has at least 90% identity with the amino acid sequence of SEQ ID NO:27; or (c) a heavy chain comprising an amino acid sequence that is at least 90% identity with the amino acid sequence of SEQ ID NO:24, and a light chain comprising an amino acid sequence that has at least 90% identity with the amino acid sequence of SEQ ID NO:26; or (d) a heavy chain comprising an amino acid sequence of SEQ ID NO:24, and a light chain comprising the amino acid sequence of SEQ ID NO:28; or (e) a heavy chain comprising an amino acid sequence of SEQ ID NO:24, and a light chain comprising the amino acid sequence of SEQ ID NO:27 or (f) a heavy chain comprising an amino acid sequence of SEQ ID NO:24, and a light chain comprising the amino acid sequence of SEQ ID NO:26.

4. The myeloid cell agonist conjugate of claim 1, wherein the TLR8 agonist is selected from any one of compounds 1.1-1.69 or a salt thereof.

5. The myeloid cell agonist conjugate of claim 4, wherein the TLR8 agonist is compound 1.36, 1.50, 1.57, 1.60, or 1.64 or a salt thereof.

6. The myeloid cell agonist conjugate of claim 1, wherein the TLR8 agonist is:

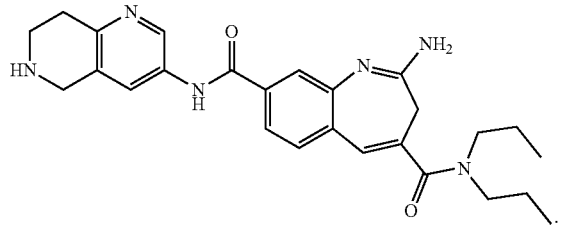 [SMILES: CCCN(CCC)C(=O)C1=Cc2ccc(C(=O)Nc3cnc4c(c3)CNCC4)cc2N=C(N)C1]

7. The myeloid cell agonist conjugate of claim 1, wherein the linker is represented by formula (V):

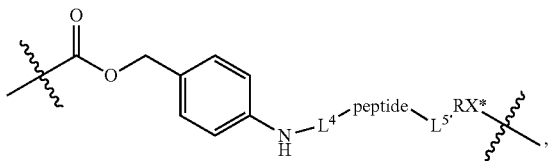

wherein $L^4$ represents the C-terminus of the peptide and $L^5$ is selected from a bond, alkylene and heteroalkylene, wherein $L^5$ is optionally substituted with one or more groups independently selected from $R^{32}$; RX* comprises a bond, a succinimide moiety, or a hydrolyzed succinimide moiety bound to a residue of the antibody, wherein

on RX* represents the point of attachment to the residue of the antibody and the other

represents the point of attachment to the TLR8 agonist; and $R^{32}$ is independently selected at each occurrence from halogen, —OH, —CN, —O—$C_{1-10}$ alkyl, —SH, =O, =S, —$NH_2$, —$NO_2$; $C_{1-10}$ alkyl, $C_{2-10}$ alkenyl, and $C_{2-10}$ alkynyl, each of $C_{1-10}$ alkyl, $C_{2-10}$ alkenyl, and $C_{2-10}$ alkynyl is optionally substituted with one or more substituents independently selected from halogen, —OH, —CN, —O—$C_{1-10}$ alkyl, —SH, =O, =S, —$NH_2$, and —$NO_2$.

8. The myeloid cell agonist conjugate of claim 7, wherein the peptide of the linker is Val-Cit or Val-Ala.

9. The myeloid cell agonist conjugate of claim 7, wherein the linker is a cleavable linker.

10. The myeloid cell agonist conjugate of claim 1, wherein L-D$_x$ has a structure selected from any one of:

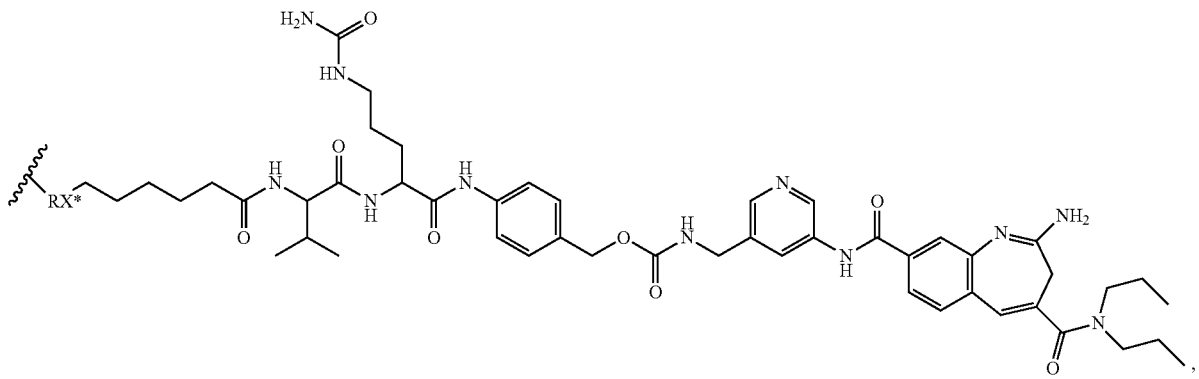

-continued
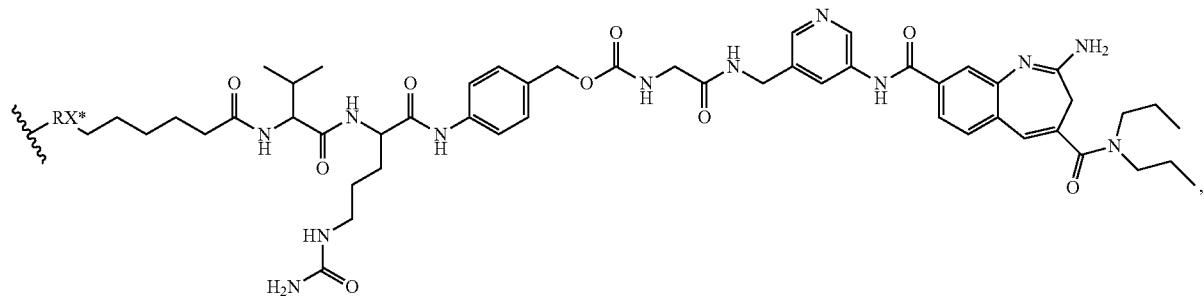
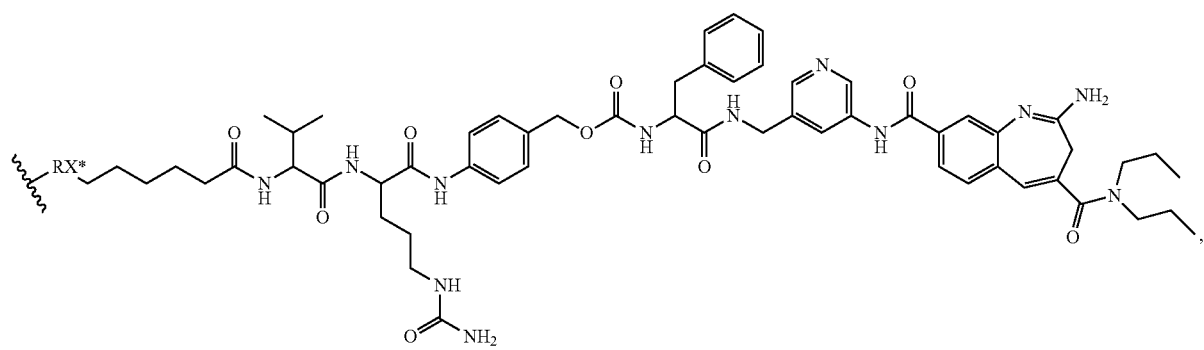
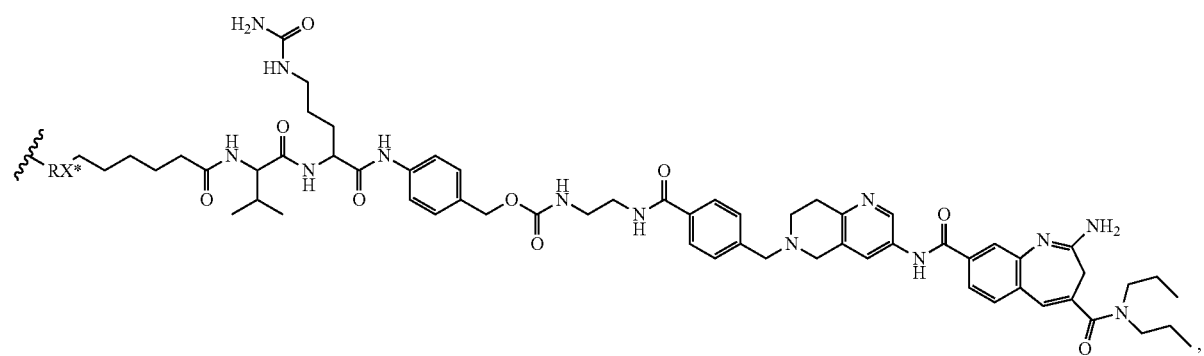
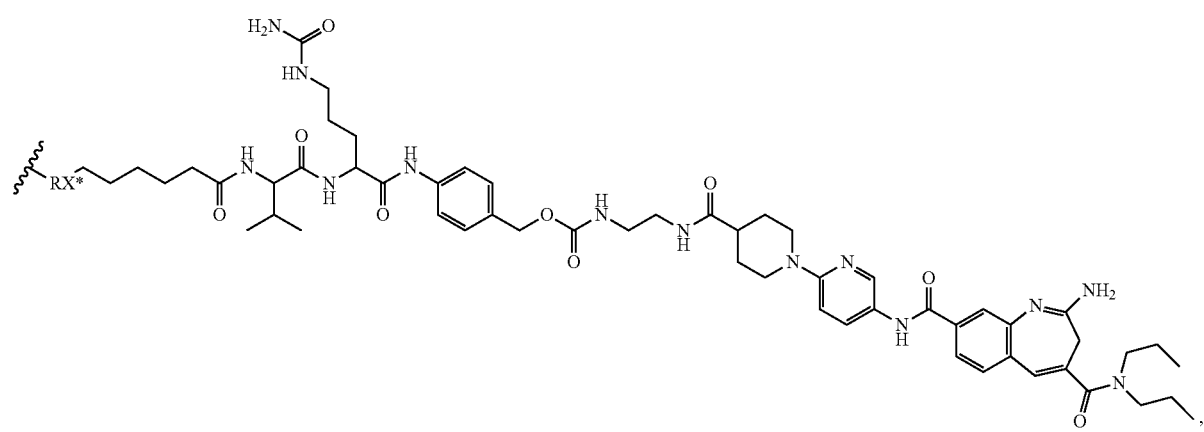

-continued

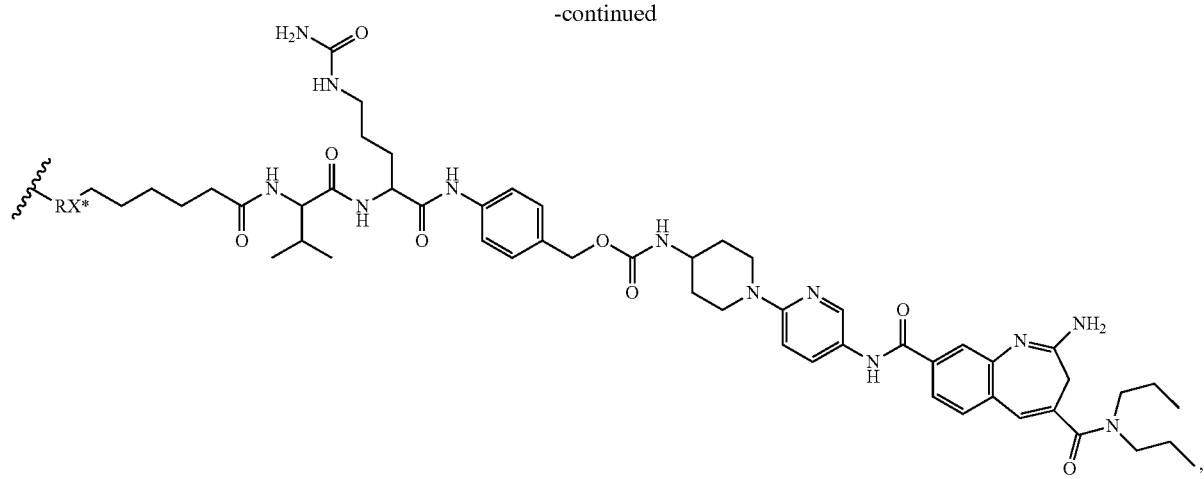

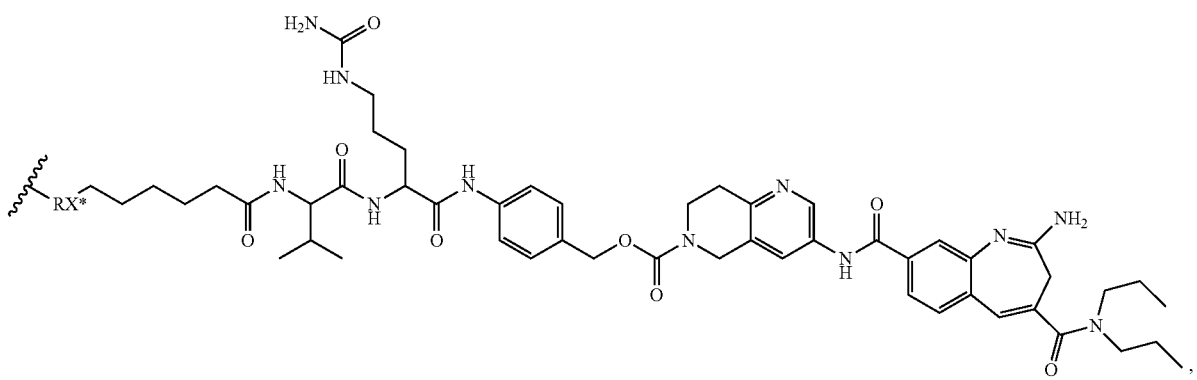

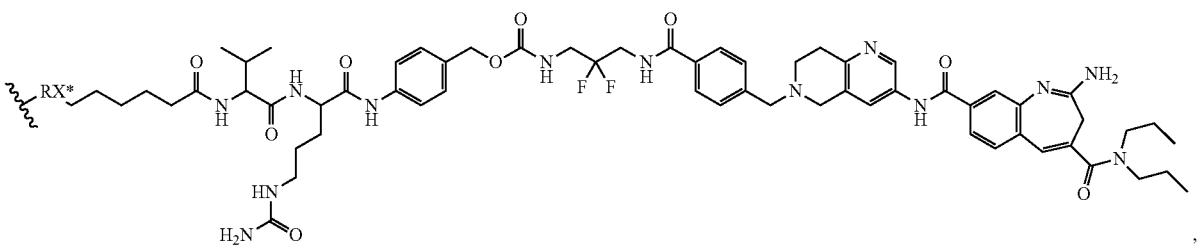

and a salt of any one thereof,
wherein the RX* is a bond, a succinimide moiety, or a hydrolyzed succinimide moiety bound to a residue of the antibody, and
wherein

on RX* represents the point of attachment to the residue of the antibody.

11. The myeloid cell agonist conjugate of claim 10, wherein:
n is an integer from 1 to about 10, or from 1 to about 5, or is 1 or 2, or is 1; and
z ranges from 1 to about 10, or from 1 to about 9, or from 1 to about 8, or 2 to about 6, or about 3 to about 5, or about 4.

12. The myeloid cell agonist conjugate or a salt thereof of claim 1, wherein:
A is an anti-Nectin-4 antibody comprising: (a) a heavy chain comprising an amino acid sequence that is at least 90% identity with the amino acid sequence of SEQ ID NO:24, and a light chain comprising an amino acid sequence that has at least 90% identity with the amino acid sequence of SEQ ID NO:28; or (b) a heavy chain comprising an amino acid sequence that is at least 90% identity with the amino acid sequence of SEQ ID NO:24, and a light chain comprising an amino acid sequence that has at least 90% identity with the amino acid sequence of SEQ ID NO:27;

L-D_x has a structure selected from any one of:
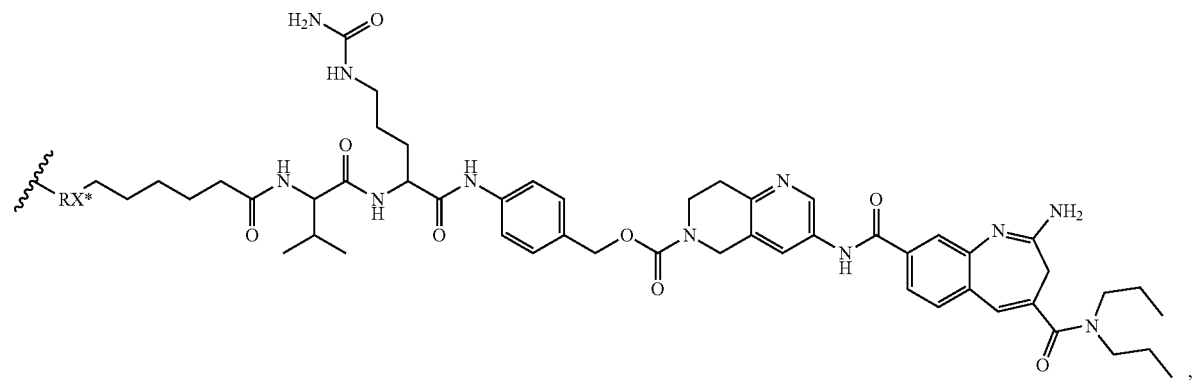
,
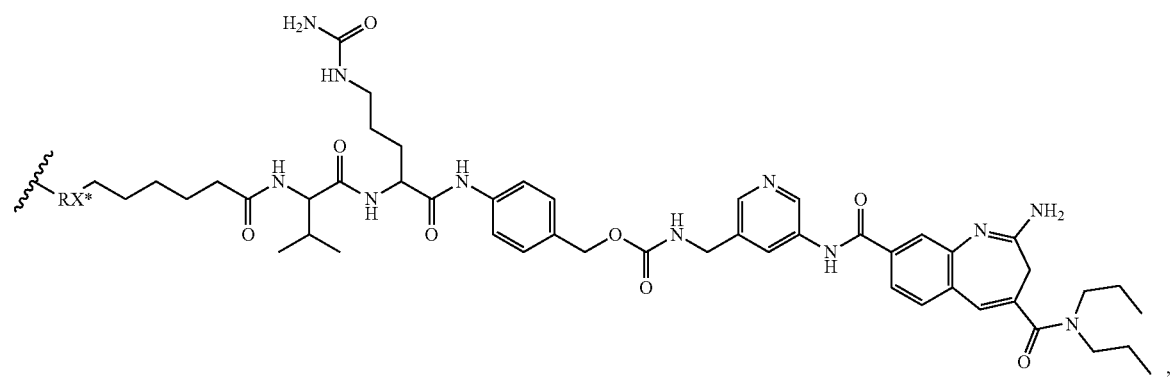
,
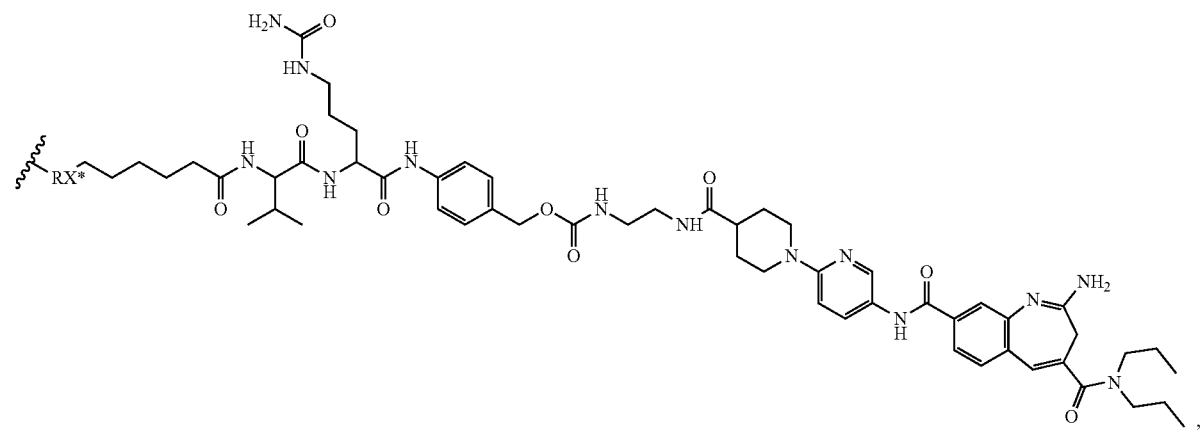
,
and
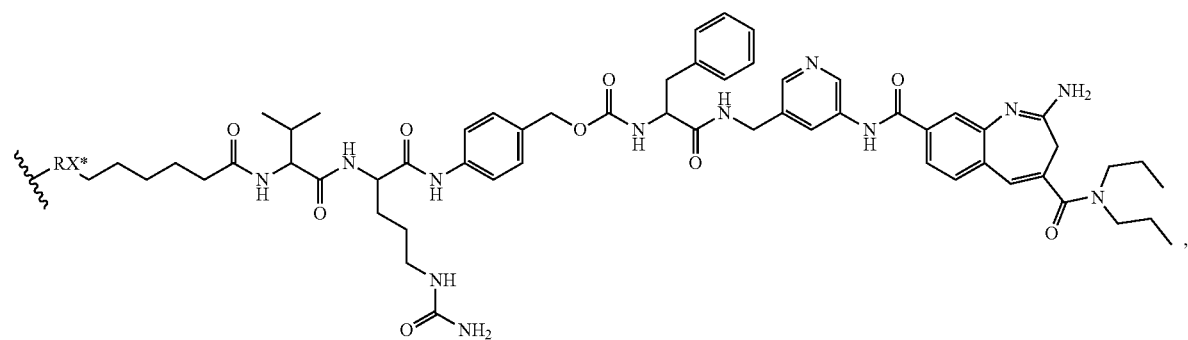
, wherein RX* is a bond, a succinimide moiety, or a hydrolyzed succinimide moiety bound to a residue of the antibody, wherein

on RX* represents the point of attachment to a cysteine residue of the antibody;
n is 1; and
z ranges from 2 to about 6.

13. The myeloid cell agonist conjugate or a salt thereof of claim 12, wherein A is an anti-Nectin-4 antibody comprising a heavy chain comprising an amino acid sequence of SEQ ID NO:24 and a light chain comprising the amino acid sequence of SEQ ID NO:28, and L-D$_x$ has a structure of:

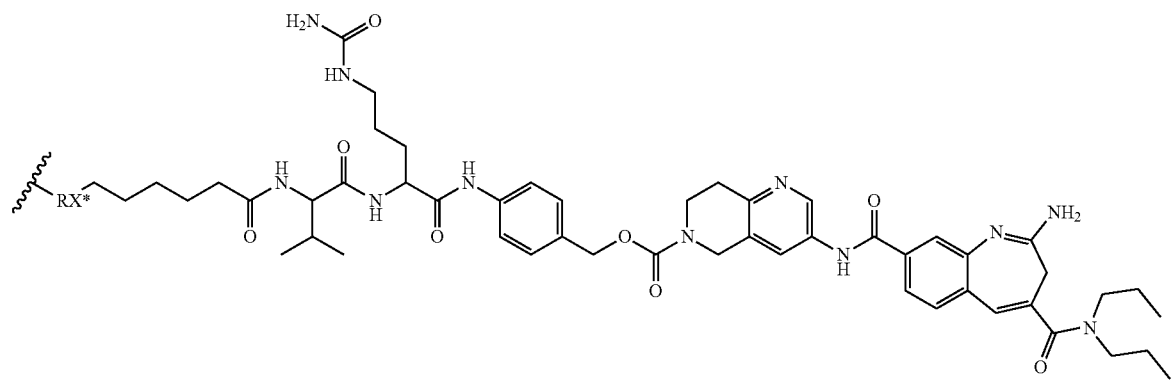

14. The myeloid cell agonist conjugate or a salt thereof of claim 12, wherein A is an anti-Nectin-4 antibody comprising a heavy chain comprising the amino acid sequence of SEQ ID NO:24 and a light chain comprising the amino acid sequence of SEQ ID NO:27, and L-D$_x$ has a structure of:

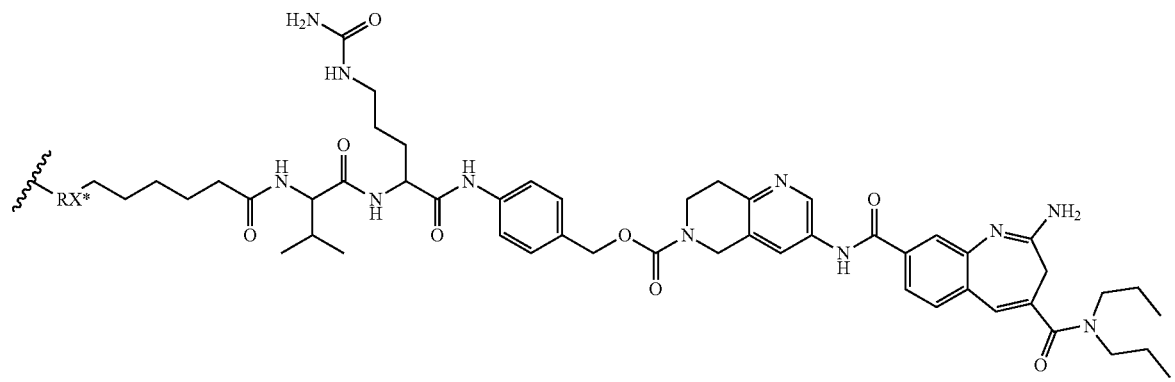

15. The myeloid cell agonist conjugate or a salt thereof of claim 12, wherein A is an anti-Nectin-4 antibody comprising a heavy chain comprising the amino acid sequence of SEQ ID NO:24 and a light chain comprising the amino acid sequence of SEQ ID NO:28, and L-D$_x$ has a structure of:

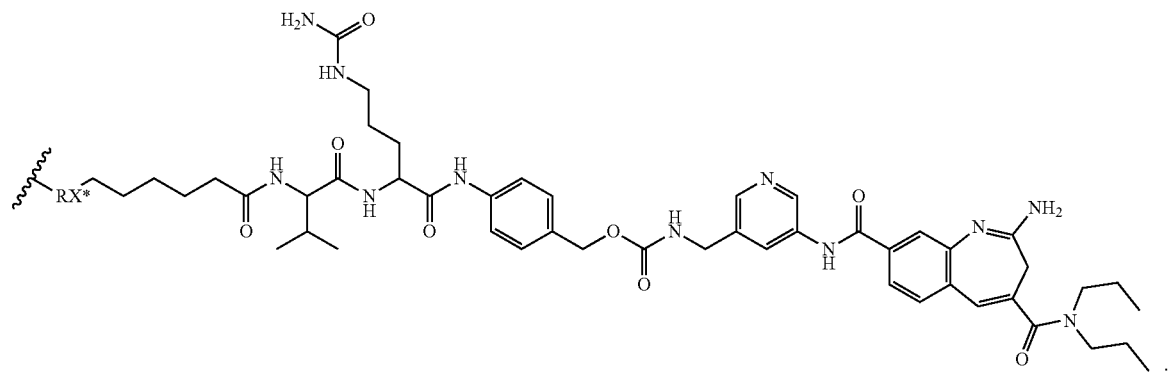

16. The myeloid cell agonist conjugate or a salt thereof of claim 12, wherein A is an anti-Nectin-4 antibody comprising a heavy chain comprising the amino acid sequence of SEQ ID NO:24 and a light chain comprising the amino acid sequence of SEQ ID NO:27, and L-$D_x$ has a structure of:

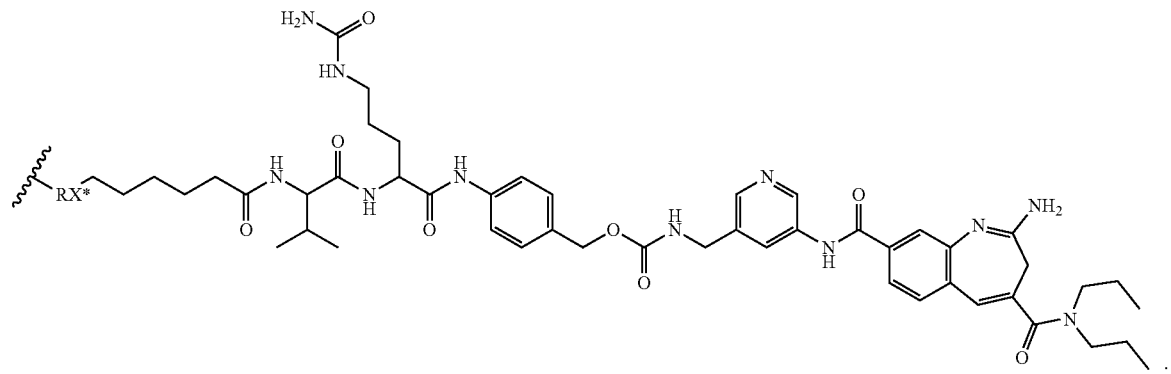

17. The myeloid cell agonist conjugate or a salt thereof of claim 12, wherein A is an anti-Nectin-4 antibody comprising a heavy chain comprising the amino acid sequence of SEQ ID NO:24 and a light chain comprising the amino acid sequence of SEQ ID NO:28, and L-$D_x$ has a structure of:

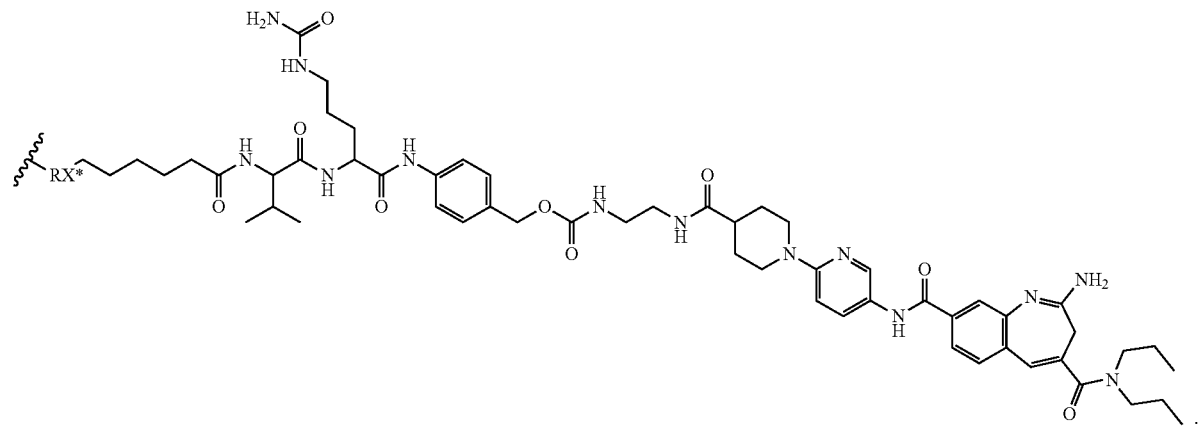

18. The myeloid cell agonist conjugate or a salt thereof of claim 12, wherein A is an anti-Nectin-4 antibody comprising a heavy chain comprising the amino acid sequence of SEQ ID NO:24 and a light chain comprising the amino acid sequence of SEQ ID NO:27, and L-$D_x$ has a structure of:

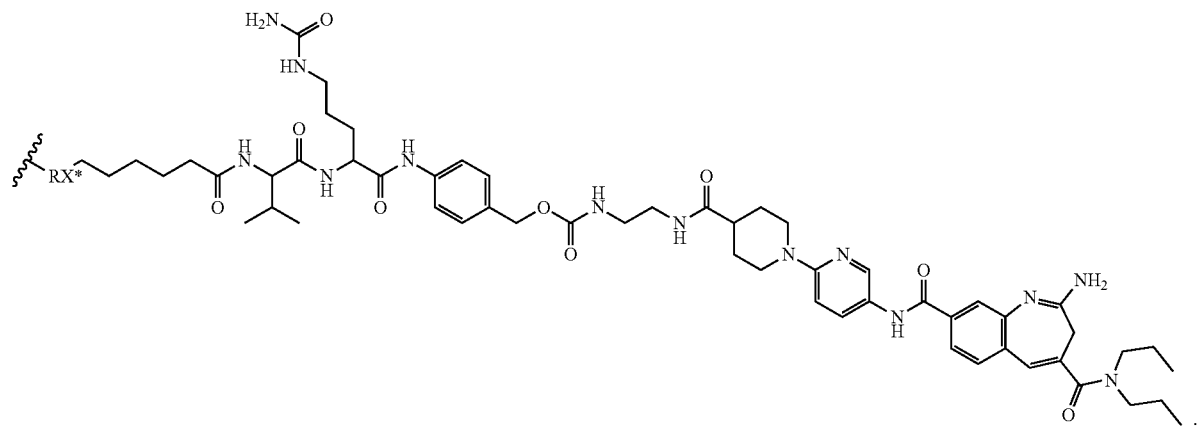

19. The myeloid cell agonist conjugate or a salt thereof of claim 12, wherein A is an anti-Nectin-4 antibody comprising a heavy chain comprising the amino acid sequence of SEQ ID NO:24 and a light chain comprising the amino acid sequence of SEQ ID NO:28, and L-D$_x$ has a structure of:

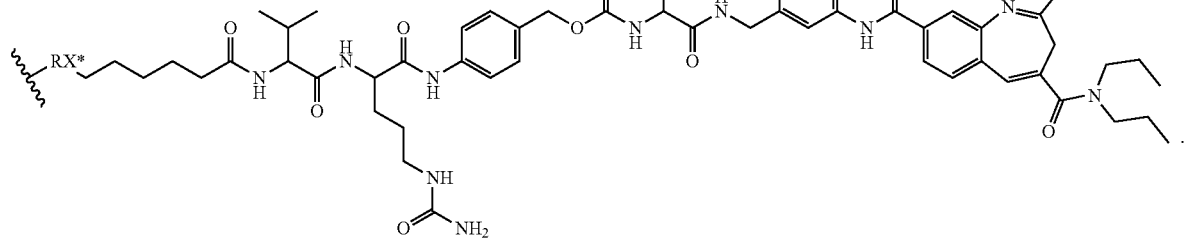

20. The myeloid cell agonist conjugate or a salt thereof of claim 12, wherein A is an anti-Nectin-4 antibody comprising a heavy chain comprising the amino acid sequence of SEQ ID NO:24 and a light chain comprising the amino acid sequence of SEQ ID NO:27, and L-D$_x$ has a structure of:

21. A pharmaceutical composition comprising the myeloid cell agonist conjugate of claim 1 and a pharmaceutically acceptable excipient.

22. The pharmaceutical composition of claim 21, wherein the average TLR8 agonist-to-antibody ratio of the conjugate ranges from about 2 to about 8, about 3 to about 8, about 3 to about 7, or about 3 to about 5.

23. A pharmaceutical composition comprising the myeloid cell agonist conjugate of claim 12 and a pharmaceutically acceptable excipient.

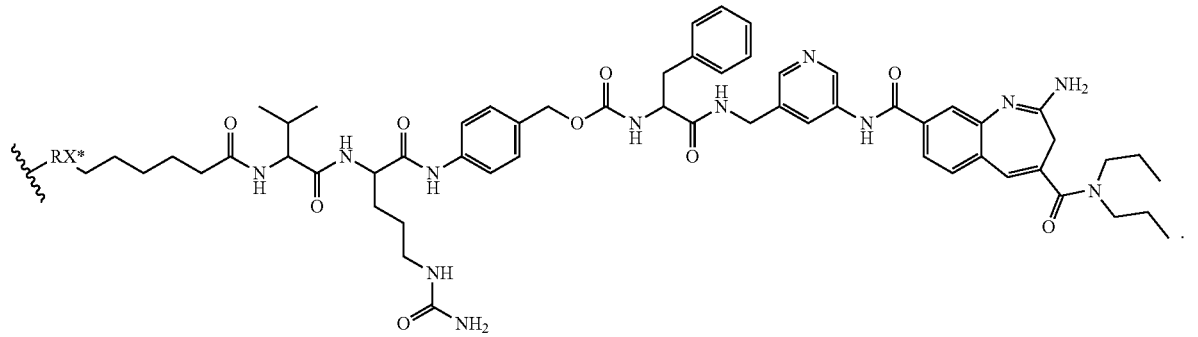

24. The pharmaceutical composition of claim 23, wherein the average TLR8 agonist-to-antibody ratio of the conjugate ranges from about 2 to about 8, about 3 to about 8, about 3 to about 7, or about 3 to about 5.

25. A method of treating a Nectin-4 expressing cancer, comprising administering to a subject in need thereof an effective amount of a myeloid cell agonist conjugate of the pharmaceutical composition of claim 23.

26. The method of claim 25, wherein the cancer is one or more of bladder cancer, breast cancer, lung cancer, head and neck cancer, cervical cancer, and pancreatic cancer.

27. The method of claim 26, wherein the bladder cancer is urothelial cancer; the breast cancer is triple-negative breast cancer; the lung cancer is non-small cell lung cancer, squamous cell carcinoma, or lung adenocarcinoma; the head and neck cancer is head and neck squamous cell carcinoma; the cervical cancer is cervical squamous cell carcinoma or endocervical adenocarcinoma; and the pancreatic cancer is pancreatic adenocarcinoma.

28. The method of claim 25, wherein the method comprises administering an additional therapeutic agent selected from a small molecule inhibitor, a CAR-T cell, a chemotherapeutic, a therapeutic antibody, and an antibody-drug conjugate.

29. The method of claim 28, wherein the additional therapeutic agent is an anti-TIGIT antibody or an adenosine receptor antagonist.

30. The method of claim 25, wherein the method further comprises administering an anti-PD-1 or anti-PD-L1 antibody.

* * * * *